US011610662B2

(12) United States Patent
Damiano et al.

(10) Patent No.: US 11,610,662 B2
(45) Date of Patent: Mar. 21, 2023

(54) MEDICAMENT PUMPS AND CONTROL SYSTEMS FOR MANAGING GLUCOSE CONTROL THERAPY DATA OF A SUBJECT

(71) Applicant: Beta Bionics, Inc., Irvine, CA (US)

(72) Inventors: Edward R. Damiano, Acton, MA (US); Firas H. El-Khatib, Allston, MA (US); Himanshu Patel, Rancho Santa Margarita, CA (US); Michael J. Rosinko, Las Vegas, NV (US); Robert James LeBourdais, Boston, MA (US)

(73) Assignee: Beta Bionics, Inc, Concord, MA (US)

( * ) Notice: Subject to any disclaimer, the term of this patent is extended or adjusted under 35 U.S.C. 154(b) by 0 days.

(21) Appl. No.: 17/653,170

(22) Filed: Mar. 2, 2022

(65) Prior Publication Data

US 2022/0257860 A1 Aug. 18, 2022

Related U.S. Application Data

(63) Continuation of application No. PCT/US2021/072742, filed on Dec. 3, 2021.
(Continued)

(51) Int. Cl.
*A61M 5/172* (2006.01)
*G16H 20/17* (2018.01)
(Continued)

(52) U.S. Cl.
CPC ......... *G16H 20/17* (2018.01); *A61B 5/14532* (2013.01); *A61B 5/4839* (2013.01);
(Continued)

(58) Field of Classification Search
None
See application file for complete search history.

(56) References Cited

U.S. PATENT DOCUMENTS 6,572,542 B1 6/2003 Houben
6,740,059 B2 5/2004 Flaherty
(Continued)

FOREIGN PATENT DOCUMENTS

WO WO 14/100557 6/2014
WO WO 15/021041 2/2015

OTHER PUBLICATIONS

Boston University, Jan. 2014, Bionic Pancreas: Introducing the iLet 1294 1000, http://sites.bu.edu/bionicpacreas/introducing-the-ilet-1294-1000/, 3 pp.
(Continued)

*Primary Examiner* — Manuel A Mendez
(74) *Attorney, Agent, or Firm* — Patnstr®, APC

(57) ABSTRACT

Glucose control systems are disclosed. An ambulatory medicament pump that is configured to wirelessly transmit one or more of a plurality of glucose control parameters and glucose control therapy data to a second ambulatory medicament pump is disclosed. A control system for transferring historical pump data from a first ambulatory medicament pump to a second ambulatory medicament pump is also disclosed. The control system can receive the historical pump data from a first ambulatory medicament pump, determine that at least one of a plurality of pairing conditions is satisfied to connect the data interface to the second ambulatory medicament pump, transmit, via the data interface, a pairing signal to the second ambulatory medicament pump, and transmit at least one of the therapy data associated with the delivery of the glucose control therapy or the glucose control parameter.

30 Claims, 84 Drawing Sheets

Related U.S. Application Data

(60) Provisional application No. 63/264,645, filed on Nov. 29, 2021, provisional application No. 63/276,481, filed on Nov. 5, 2021, provisional application No. 63/263,602, filed on Nov. 5, 2021, provisional application No. 63/249,975, filed on Sep. 29, 2021, provisional application No. 63/261,290, filed on Sep. 16, 2021, provisional application No. 63/239,365, filed on Aug. 31, 2021, provisional application No. 63/238,670, filed on Aug. 30, 2021, provisional application No. 63/216,177, filed on Jun. 29, 2021, provisional application No. 63/215,857, filed on Jun. 28, 2021, provisional application No. 63/212,521, filed on Jun. 18, 2021, provisional application No. 63/194,126, filed on May 27, 2021, provisional application No. 63/183,900, filed on May 4, 2021, provisional application No. 63/169,112, filed on Mar. 31, 2021, provisional application No. 63/168,203, filed on Mar. 30, 2021, provisional application No. 63/167,563, filed on Mar. 29, 2021, provisional application No. 63/157,541, filed on Mar. 5, 2021, provisional application No. 63/152,744, filed on Feb. 23, 2021, provisional application No. 63/152,716, filed on Feb. 23, 2021, provisional application No. 63/151,565, filed on Feb. 19, 2021, provisional application No. 63/139,210, filed on Jan. 19, 2021, provisional application No. 63/128,428, filed on Dec. 21, 2020, provisional application No. 63/122,427, filed on Dec. 7, 2020.

(51) Int. Cl.

| | |
|---|---|
| *A61M 5/142* | (2006.01) |
| *H04W 4/80* | (2018.01) |
| *G16H 40/60* | (2018.01) |
| *G16H 50/50* | (2018.01) |
| *G16H 40/67* | (2018.01) |
| *G06F 21/31* | (2013.01) |
| *G16H 20/60* | (2018.01) |
| *G06F 21/34* | (2013.01) |
| *G16H 50/20* | (2018.01) |
| *G16H 40/63* | (2018.01) |
| *A61B 5/145* | (2006.01) |
| *A61B 5/00* | (2006.01) |

(52) U.S. Cl.
CPC .... *A61M 5/14244* (2013.01); *A61M 5/14248* (2013.01); *A61M 5/172* (2013.01); *A61M 5/1723* (2013.01); *G06F 21/31* (2013.01); *G06F 21/34* (2013.01); *G16H 20/60* (2018.01); *G16H 40/60* (2018.01); *G16H 40/63* (2018.01); *G16H 40/67* (2018.01); *G16H 50/20* (2018.01); *G16H 50/50* (2018.01); *H04W 4/80* (2018.02); *A61M 2005/14208* (2013.01); *A61M 2005/14252* (2013.01); *A61M 2005/14268* (2013.01); *A61M 2005/1726* (2013.01); *A61M 2205/18* (2013.01); *A61M 2205/3386* (2013.01); *A61M 2205/3553* (2013.01); *A61M 2205/3569* (2013.01); *A61M 2205/3584* (2013.01); *A61M 2205/3592* (2013.01); *A61M 2205/502* (2013.01); *A61M 2205/505* (2013.01); *A61M 2205/52* (2013.01); *A61M 2205/609* (2013.01); *A61M 2230/201* (2013.01); *A61M 2230/63* (2013.01); *G06F 2221/2137* (2013.01); *G06F 2221/2141* (2013.01)

(56) References Cited

U.S. PATENT DOCUMENTS

| | | |
|---|---|---|
| 7,347,836 B2 | 3/2008 | Peterson |
| 7,717,903 B2 | 5/2010 | Estes et al. |
| 7,806,854 B2 | 10/2010 | Damiano et al. |
| 8,109,921 B2 | 2/2012 | Van Den Berghe et al. |
| 8,401,194 B2 | 3/2013 | Nierzwick et al. |
| 8,538,703 B2 | 9/2013 | Kovatchev et al. |
| 8,679,016 B2 | 3/2014 | Mastrototaro et al. |
| 9,215,075 B1 | 12/2015 | Poltorak |
| 9,242,038 B2 | 1/2016 | Prod'hom et al. |
| 9,317,657 B2 | 4/2016 | Breton et al. |
| 9,503,526 B2 | 11/2016 | Daoud et al. |
| 9,833,570 B2 | 12/2017 | El-Khatib et al. |
| 9,888,337 B1 | 2/2018 | Zalewski et al. |
| 9,980,140 B1 | 5/2018 | Spencer et al. |
| 10,341,866 B1 | 7/2019 | Spencer et al. |
| 10,434,253 B2 | 10/2019 | DiPerna et al. |
| 10,541,987 B2 | 1/2020 | Gillespie |
| 10,543,313 B2 | 1/2020 | Damiano et al. |
| 10,583,250 B2 | 3/2020 | Mazlish et al. |
| 10,653,834 B2 | 5/2020 | Kruse et al. |
| 10,842,934 B2 | 11/2020 | El-Khatib et al. |
| 10,960,137 B2 | 3/2021 | El-Khatib et al. |
| 10,987,032 B2 | 4/2021 | Ambrosio |
| 11,045,602 B2 | 6/2021 | Patel et al. |
| 11,135,363 B2 | 10/2021 | Rosinko et al. |
| 11,224,693 B2 | 1/2022 | Ulrich et al. |
| 11,238,133 B1 | 2/2022 | Brewer et al. |
| 11,241,537 B2 | 2/2022 | Jiang et al. |
| 11,260,174 B2 | 3/2022 | Patel et al. |
| 2004/0176667 A1 | 9/2004 | Mihai et al. |
| 2008/0154187 A1 | 6/2008 | Krulevitch |
| 2008/0312584 A1 | 12/2008 | Montgomery et al. |
| 2009/0006061 A1 | 1/2009 | Thukral et al. |
| 2009/0036753 A1 | 2/2009 | King |
| 2009/0063193 A1 | 3/2009 | Barton |
| 2009/0177154 A1 | 7/2009 | Blomquist |
| 2010/0198143 A1 | 8/2010 | Estes |
| 2011/0021898 A1 | 1/2011 | Wei et al. |
| 2011/0152756 A1 | 6/2011 | Drew |
| 2011/0152770 A1 | 6/2011 | DiPerna et al. |
| 2011/0208155 A1 | 8/2011 | Palerm et al. |
| 2012/0065894 A1 | 3/2012 | Tubb et al. |
| 2012/0266251 A1 | 10/2012 | Birtwhistle et al. |
| 2013/0102853 A1 | 4/2013 | Halvorson |
| 2013/0108046 A1 | 5/2013 | Andersen |
| 2013/0229288 A1 | 9/2013 | Alexander et al. |
| 2013/0274576 A1 | 10/2013 | Amirouche et al. |
| 2014/0039455 A1 | 2/2014 | Miller et al. |
| 2014/0058349 A1 | 2/2014 | Bazargan et al. |
| 2014/0288947 A1 | 9/2014 | Simpson et al. |
| 2015/0057518 A1 | 2/2015 | Lebel et al. |
| 2015/0095648 A1 | 4/2015 | Nix |
| 2015/0207626 A1 | 7/2015 | Neftel |
| 2015/0207796 A1 | 7/2015 | Love |
| 2015/0217053 A1 | 8/2015 | Booth |
| 2016/0224756 A1 | 8/2016 | Berger |
| 2016/0234022 A1 | 8/2016 | Motika |
| 2016/0317744 A1 | 11/2016 | Estes et al. |
| 2016/0324464 A1 | 11/2016 | Christensen |
| 2016/0331310 A1 | 11/2016 | Kovatchev |
| 2016/0342761 A1 | 11/2016 | Whiting |
| 2017/0056590 A1 | 3/2017 | DiPerna |
| 2017/0161439 A1 | 6/2017 | Raduchel et al. |
| 2017/0189614 A1 | 7/2017 | Mazlish et al. |
| 2017/0258986 A1 | 9/2017 | Tsoukalis |
| 2017/0259072 A1 | 9/2017 | Newham |
| 2017/0286614 A1 | 10/2017 | Morris |
| 2017/0296056 A1 | 10/2017 | Hresko |
| 2018/0060529 A1 | 3/2018 | Crothall |
| 2018/0103030 A1 | 4/2018 | Einberg |
| 2018/0182491 A1 | 6/2018 | Belliveau et al. |
| 2018/0185587 A1 | 7/2018 | Brauker |
| 2018/0200435 A1 | 7/2018 | Mazlish et al. |
| 2018/0235524 A1 | 8/2018 | Dunn |
| 2018/0353698 A1 | 12/2018 | Saint et al. |

(56) References Cited

U.S. PATENT DOCUMENTS

| | | |
|---|---|---|
| 2019/0019573 A1 | 1/2019 | Lake |
| 2019/0036886 A1 | 1/2019 | Wu |
| 2019/0125224 A1 | 5/2019 | Karnath |
| 2019/0132801 A1 | 5/2019 | Kamath |
| 2019/0206565 A1 | 7/2019 | Shelton, IV |
| 2019/0214124 A1 | 7/2019 | Mougiakakou |
| 2019/0247578 A1 | 8/2019 | Desborough et al. |
| 2019/0356482 A1 | 11/2019 | Nix |
| 2020/0155757 A1 | 5/2020 | Gregory et al. |
| 2021/0090705 A1 | 3/2021 | Patel et al. |
| 2021/0098105 A1 | 4/2021 | Lee et al. |
| 2021/0213200 A1 | 7/2021 | Raskin et al. |
| 2021/0378561 A1 | 12/2021 | Xu |
| 2022/0054746 A1 | 2/2022 | Patel et al. |
| 2022/0166621 A1 | 5/2022 | Kairon |
| 2022/0184307 A1 | 6/2022 | El-Khatib et al. |
| 2022/0189603 A1 | 6/2022 | Damiano et al. |
| 2022/0189604 A1 | 6/2022 | El-Khatib et al. |
| 2022/0223252 A1 | 7/2022 | Damiano et al. |
| 2022/0257860 A1 | 8/2022 | Damiano et al. |
| 2022/0277823 A1 | 9/2022 | Damiano |
| 2022/0288309 A1 | 9/2022 | Patel |

OTHER PUBLICATIONS

Brown et al., Apr. 1, 2016, "Introducing Beta Bionics: Bringing the iLet Bionic Pancreas to Market", published on Apr. 1, 2016 to https://diatribe.org/introducing-beta-bionics-bringing-iLet-bionic-pancreas-market, 3 pp.

Krugman, Aug. 25, 2018, iLet Bionic Pancreas Interface, sarakrugman.com/ilet-interface, 3 pp.

University of California, San Francisco, Diabetes Education Online, Calculating Insulin Dose, https://dtc.ucsf.edu/types-of-diabetes/type2/treatment-of-type-2-diabetes/medications-and-therapies/type-2-insulin-rx/calculating-insulin-dose/, downloaded Apr. 9, 2021, 11 pp.

International Search Report and Written Opinion dated Mar. 30, 2022 in application No. PCT/US2021/072742.

6300

| 90 Days | Saturday, January 1, 2019-Monday, March 29, 2019 |

Backup Therapy

Your glucose control system has learned your insulin needs. If your glucose control system goes offline or is temporarily unavailable, the below protocol is recommended for use for up to 72 hours.

6302

| Injections | |
|---|---|
| Usual Breakfast | 6 Units |
| Usual Lunch | 8 Units |
| Usual Dinner | 8 Units |
| Long Acting Insulin Units | 14 |
| Correction Factor mg/dL lowered per 1 Unit | 9mg/dL |

6304

| Pump Settings | |
|---|---|
| Usual Breakfast Units | 6 Units |
| Usual Lunch Units | 8 Units |
| Usual Dinner Units | 8 Units |
| Basal Rate 12:00 A.M - 6:00 A.M | .6 units per hour |
| Basal Rate 6:00 A.M - 12:00 P.M | .5 units per hour |
| Basal Rate 12:00 P.M - 6:00 P.M | .6 units per hour |
| Basal Rate 6:00 P.M - 12:00 A.M | .7 units per hour |
| Correction Factor mg/dL lowered per 1 Unit | 9 mg/dL |

Autonomous Control Summary

The autonomous control summary provides you key information about your glucose control performance during the specified time period.

6310

| 152 mg/dL Mean Glucose (CGM) | ##% Time in range 70-180 mg/dL | #.#% Time < 54 mg/dL | 4.2 Mean Meal Announcements Per Day | 45.2u Total Daily Insulin | 98% CGM Connectivity Uptime |
|---|---|---|---|---|---|
| 6.9% Estimated A1C | ##% >180 mg/dL | #.#% | | 3.2μ Total Daily Glucagon | |

FIG. 63

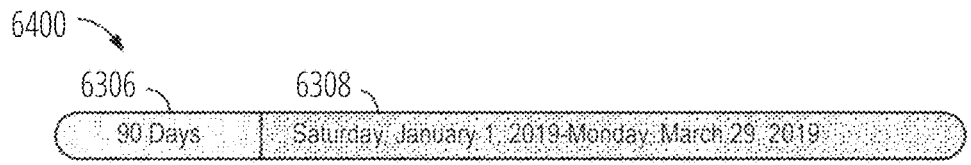

Ambulatory Glucose Profile (AGP)

AGP is a summary of glucose values from the report, with median (50%) and other percentiles shown as if occurring in a single day.

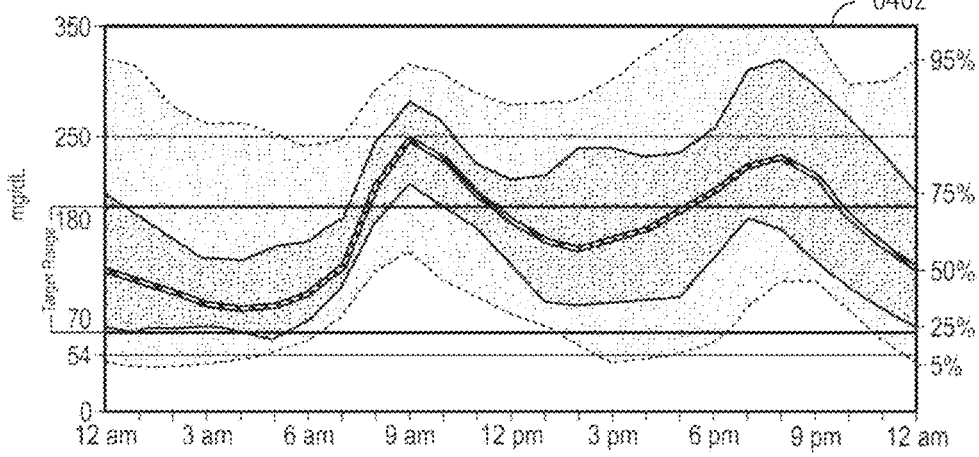

Adjustable Settings & Behavior

Settings

|  | Current Entry | Previous Entry |
|---|---|---|
| Body Weight | ### pounds | ### pounds<br>last set on DD/MM/YYYY |

| Bionic Daytime Target | % time selected |
|---|---|
| Higher | ## % |
| Usual | ## % |
| Lower | ## % |

| Bionic Nighttime Target | % time selected |
|---|---|
| Higher | ## % |
| Usual | ## % |
| Lower | ## % |

Bionic Temporary Targets: You set a temporary target ## times during the selected date range.
Pause Insulin: You paused insulin ## times during the selected date range.

FIG. 64

MEDICAMENT PUMPS AND CONTROL SYSTEMS FOR MANAGING GLUCOSE CONTROL THERAPY DATA OF A SUBJECT

INCORPORATION BY REFERENCE TO ANY PRIORITY APPLICATIONS

This application is a continuation of PCT Application No. PCT/US2021/072742, filed Dec. 3, 2021, which claims priority to U.S. Provisional Patent Application Nos. 63/122,427, filed Dec. 7, 2020; 63/169,112, filed Mar. 31, 2021; 63/151,565, filed Feb. 19, 2021; 63/261,290, filed Sep. 16, 2021; 63/128,428, filed Dec. 21, 2020; 63/152,744, filed Feb. 23, 2021; 63/157,541, filed Mar. 5, 2021; 63/152,716, filed Feb. 23, 2021; 63/168,203, filed Mar. 30, 2021; 63/212,521, filed Jun. 18, 2021; 63/139,210, filed Jan. 19, 2021; 63/276,481, filed Nov. 5, 2021; 63/215,857, filed Jun. 28, 2021; 63/183,900, filed May 4, 2021; 63/167,563, filed Mar. 29, 2021; 63/216,177, filed Jun. 29, 2021; 63/249,975, filed Sep. 29, 2021; 63/194,126, filed May 27, 2021; 63/239,365, filed Aug. 31, 2021; 63/263,602, filed Nov. 5, 2021; 63/264,645, filed Nov. 29, 2021, and 63/238,670, filed Aug. 30, 2021. The entire contents of each application referenced in this paragraph are hereby incorporated by reference herein for all purposes and made part of this specification. Any and all applications for which a foreign or domestic priority claim is identified in the Application Data Sheet as filed with the present application are hereby incorporated by reference under 37 CFR 1.57.

BACKGROUND

Technical Field

This disclosure relates to glucose control systems, including medical devices that provide glucose control therapy to a subject, glucose level control systems, and ambulatory medicament pumps that deliver medicament to the subject to control blood glucose level in the subject.

Description of Related Art

Sustained delivery, pump driven medicament injection devices generally include a delivery cannula mounted in a subcutaneous manner through the skin of the subject at an infusion site. The pump draws medicine from a reservoir and delivers it to the subject via the cannula. The injection device typically includes a channel that transmits a medicament from an inlet port to the delivery cannula which results in delivery to the subcutaneous tissue layer where the delivery cannula terminates. The delivery of medicament by the pump is controlled by a controller based on values of one or more control parameters and/or a measured glucose level in the subject. Some infusion devices are configured to deliver one medicament to a subject while others are configured to deliver multiple medicaments to a subject.

SUMMARY

Glucose control systems, such as blood glucose control systems, and ambulatory medical devices that provide therapy to a subject, such as blood glucose control, are disclosed. Disclosed systems and devices can implement one or more features that improve the user experience, such as software update techniques that avoid interrupting delivery of therapy, gesture-based control of therapy delivery, automatic resumption of therapy after a user-initiated pause, improved alarm management, display of autonomously calculated dosing recommendations, wide area network connectivity, and security features.

BRIEF DESCRIPTION OF THE DRAWINGS

The systems, methods, and devices of this disclosure each have several innovative aspects, no single one of which is solely responsible for all of the desirable attributes disclosed herein. Details of one or more implementations of the subject matter described in this specification are set forth in the accompanying drawings and the description below. The drawings are provided to illustrate certain aspects of the subject matter described herein and not to limit the scope thereof.

FIG. 63 illustrates an example backup therapy protocol in accordance with certain embodiments.

FIG. 64 illustrates an example control parameter modification report in accordance with certain embodiments.

DETAILED DESCRIPTION

Figure 1A:
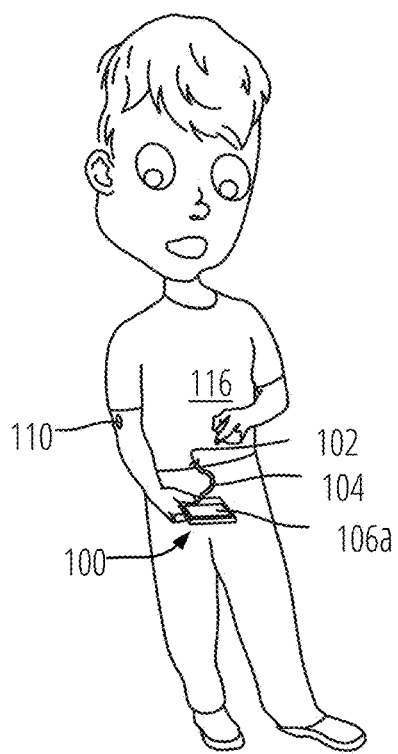
FIG. 1A illustrates an example blood glucose control system that provides blood glucose control via an ambulatory medicament pump.

Some embodiments described herein pertain to medicament infusion systems for one or more medicaments and the components of such systems (e.g., infusion pumps, medicament cartridges, cartridge connectors, lumen assemblies, infusion connectors, infusion sets, etc.). Some embodiments pertain to methods of manufacturing infusion systems and components thereof. Some embodiments pertain to methods of using any of the foregoing systems or components for infusing one or more medicaments (e.g., pharmaceutical, hormone, etc.) to a subject. As an exemplary illustration, an infusion system may include an infusion pump, which can include one or more medicament cartridges or can have an integrated reservoir of medicament. An infusion system may include medicament cartridges and cartridge connectors, but not a pump. An infusion system may include cartridge connectors and an infusion pump, but not medicament cartridges. An infusion system may include infusion connectors, a lumen assembly, cartridge connectors, an infusion pump, but not medicament cartridges or an infusion set. A blood glucose control system can operate in conjunction with an infusion system to infuse one or more medicaments, including at least one blood glucose control agent, into a subject. Any feature, structure, component, material, step, or method that is described and/or illustrated in any embodiment in this specification can be used with or instead of any feature, structure, component, material, step, or method that is described and/or illustrated in any other embodiment in this specification. Additionally, any feature, structure, component, material, step, or method that is described and/or illustrated in one embodiment may be absent from another embodiment.

Some embodiments described herein pertain to medicament infusion systems for one or more medicaments and the components of such systems (e.g., infusion pumps, medicament cartridges, cartridge connectors, lumen assemblies, infusion connectors, infusion sets, etc.). Some embodiments pertain to methods of manufacturing infusion systems and components thereof. Some embodiments pertain to methods of using any of the foregoing systems or components for infusing one or more medicaments (e.g., pharmaceutical, hormone, etc.) to a patient. As an exemplary illustration, an infusion system may include an infusion pump, which can include one or more medicament cartridges or can have an integrated reservoir of medicament. An infusion system may include medicament cartridges and cartridge connectors, but not a pump. An infusion system may include cartridge connectors and an infusion pump, but not medicament cartridges. An infusion system may include infusion connectors, a lumen assembly, cartridge connectors, an infusion pump, but not medicament cartridges or an infusion set. A glucose level control system can operate in conjunction with an infusion system to infuse one or more medicaments, including at least one glucose control agent, into a subject. Any feature, structure, component, material, step, or method that is described and/or illustrated in any embodiment in this specification can be used with or instead of any feature, structure, component, material, step, or method that is described and/or illustrated in any other embodiment in this specification. Additionally, any feature, structure, component, material, step, or method that is described and/or illustrated in one embodiment may be absent from another embodiment.

Further, certain embodiments disclosed herein relate to a glucose level control system that is capable of supporting different operating modes associated with different adaptation ranges used to generate dose control signals for delivering medicament to a subject. The different adaptation ranges may be associated with a value or a change in value of one or more control parameters used by a control algorithm that controls the administering of medicament to a subject. In some non-limiting examples, the control parameter may be associated with the quantity of medicament, a delivery rate of medicament, a step-size or graduation used to modify the quantity of medicament between administrations of the medicament, a timing of supplying medicament to the subject, a glucose absorption rate, a time until the concentration of insulin in blood plasma for a subject reaches half of the maximum concentration, a time until the concentration of insulin in blood plasma for a subject reaches a maximum concentration, or any other control parameter that can impact a timing or quantity of medicament (e.g., insulin or counter-regulatory agent) supplied or administered to a subject.

Advantageously, in certain embodiments, supporting different operating modes enables a user (e.g., a healthcare provider, parent, guardian, the subject receiving treatment, etc.) to modify the operating mode of an ambulatory medicament device. In some cases, the operating mode may be modified automatically. Moreover, modifying the operating mode enables different dosing modes to be supported. Advantageously, supporting different dosing modes enables an ambulatory medicament device to be used by different types of subjects, and/or a subject under different conditions (e.g., when exercising, before, during, or after puberty, under different health conditions, etc.).

Some embodiments described herein pertain to medicament infusion systems for one or more medicaments and the components of such systems (e.g., infusion pumps, medicament cartridges, cartridge connectors, lumen assemblies, infusion connectors, infusion sets, etc.). Some embodiments pertain to methods of manufacturing infusion systems and components thereof. Some embodiments pertain to methods of using any of the foregoing systems or components for infusing one or more medicaments (e.g., pharmaceutical, hormone, etc.) to a subject. As an exemplary illustration, an infusion system may include an infusion pump, which can include one or more medicament cartridges or can have an integrated reservoir of medicament. An infusion system may include medicament cartridges and cartridge connectors, but not a pump. An infusion system may include cartridge connectors and an infusion pump, but not medicament cartridges. An infusion system may include infusion connectors, a lumen assembly, cartridge connectors, an infusion pump, but not medicament cartridges or an infusion set. A blood glucose control system can operate in conjunction with an infusion system to infuse one or more medicaments, including at least one blood glucose control agent, into a subject. Any feature, structure, component, material, step, or method that is described and/or illustrated in any embodiment in this specification can be used with or instead of any feature, structure, component, material, step, or method that is described and/or illustrated in any other embodiment in this specification. Additionally, any feature, structure, component, material, step, or method that is described and/or illustrated in one embodiment may be absent from another embodiment.

Some embodiments described herein pertain to medicament infusion systems for one or more medicaments. Some embodiments pertain to methods of using infusion systems for infusing one or more medicaments (e.g., pharmaceutical, hormone, etc.) to a subject. Some embodiments pertain to methods of managing access to one or more therapy settings of a medicament infusion system. As an exemplary illustration, an infusion system may include an infusion pump, which can include one or more medicament cartridges or can have an integrated reservoir of medicament. An infusion system may include medicament cartridges and cartridge connectors, but not a pump. An infusion system may include cartridge connectors and an infusion pump, but not medicament cartridges. An infusion system may include infusion connectors, a lumen assembly, cartridge connectors, an infusion pump, but not medicament cartridges or an infusion set. A blood glucose control system can operate in conjunction with an infusion system to infuse one or more medicaments, including at least one blood glucose control agent, into a subject. An infusion system may include a user interface that allow modifying one or more control parameters that control medicament delivery to a subject. An infusion system may include a wireless transceiver that allows data communication between the infusion system and one or more electronic devices.

Any feature, structure, component, material, step, or method that is described and/or illustrated in any embodiment in this specification can be used with or instead of any feature, structure, component, material, step, or method that is described and/or illustrated in any other embodiment in this specification. Additionally, any feature, structure, component, material, step, or method that is described and/or illustrated in one embodiment may be absent from another embodiment.

Glucose Control System Overview

A glucose control system, such as a blood glucose control system (BGCS), may be used to control a glucose level or a blood glucose level in a subject. Blood glucose control systems can include a controller configured to generate dose control signals for one or more glucose control agents that can be infused into the subject. Glucose control agents include regulatory agents that tend to decrease blood glucose level, such as insulin and insulin analogs, and counter-regulatory agents that tend to increase blood glucose level, such as glucagon or dextrose. A blood glucose control system configured to be used with two or more glucose control agents can generate a dose control signal for each of the agents. In some embodiments, a blood glucose control system can generate a dose control signal for an agent even though the agent may not be available for dosing via a medicament pump connected to the subject.

Glucose control agents can be delivered to a subject via subcutaneous injection, via intravenous injection, or via another suitable delivery method. In the case of blood glucose control therapy via an ambulatory medicament pump, subcutaneous injection is most common. An ambulatory medicament pump (AMP) is a type of ambulatory medical device ("AMD"), which is sometimes referred to herein as an ambulatory device, an ambulatory medicament device, or a mobile ambulatory device. Ambulatory medical devices include ambulatory medicament pumps and other devices configured to be carried by a subject and to deliver therapy to the subject. Multiple AMPs are described herein. It should be understood that one or more of the embodiments described herein with respect to one AMP may be applicable to one or more of the other AMPs described herein.

In some examples, the ambulatory medical device (AMD) is an electrical stimulation device, and therapy delivery includes providing electrical stimulation to a subject. An example of an electrical stimulation device is a cardiac pacemaker. A cardiac pacemaker generates electrical stimulation of the cardiac muscle to control heart rhythms. Another example of an electrical stimulation device is a deep brain stimulator to treat Parkinson's disease or movement disorders.

Blood Glucose Control System Overview

A blood glucose control system (BGCS) is used to control blood glucose level in a subject. Blood glucose control systems can include a controller configured to generate dose control signals for one or more glucose control agents that can be infused into the subject. Glucose control agents include regulatory agents that tend to decrease blood glucose level, such as insulin and insulin analogs, and counter-regulatory agents that tend to increase blood glucose level, such as glucagon or dextrose. A blood glucose control system configured to be used with two or more glucose control agents can calculate a dose control signal for each of the agents. In some embodiments, a blood glucose control system can calculate a dose control signal for an agent even though the agent may not be available for dosing via a medicament pump connected to the subject.

Glucose control agents can be delivered to a subject via subcutaneous injection, via intravenous injection, or via another suitable delivery method. In the case of blood glucose control therapy via an ambulatory medicament pump, subcutaneous injection is most common. An ambulatory medicament pump 100 is a type of ambulatory medical device, which is sometimes referred to herein as an ambulatory device, an ambulatory medicament device, a mobile ambulatory device, or an AMD. Ambulatory medical devices include ambulatory medicament pumps and other devices configured to be carried by a subject and to deliver therapy to the subject.

In some examples, the ambulatory medical device (AMD) is an electrical stimulation device, and therapy delivery includes providing electrical stimulation to a subject. An example of an electrical stimulation device is a cardiac pacemaker. A cardiac pacemaker generates electrical stimulation of the cardiac muscle to control heart rhythms. Another example of an electrical stimulation device is a deep brain stimulator to treat Parkinson's disease or movement disorders.

Figure 1B:
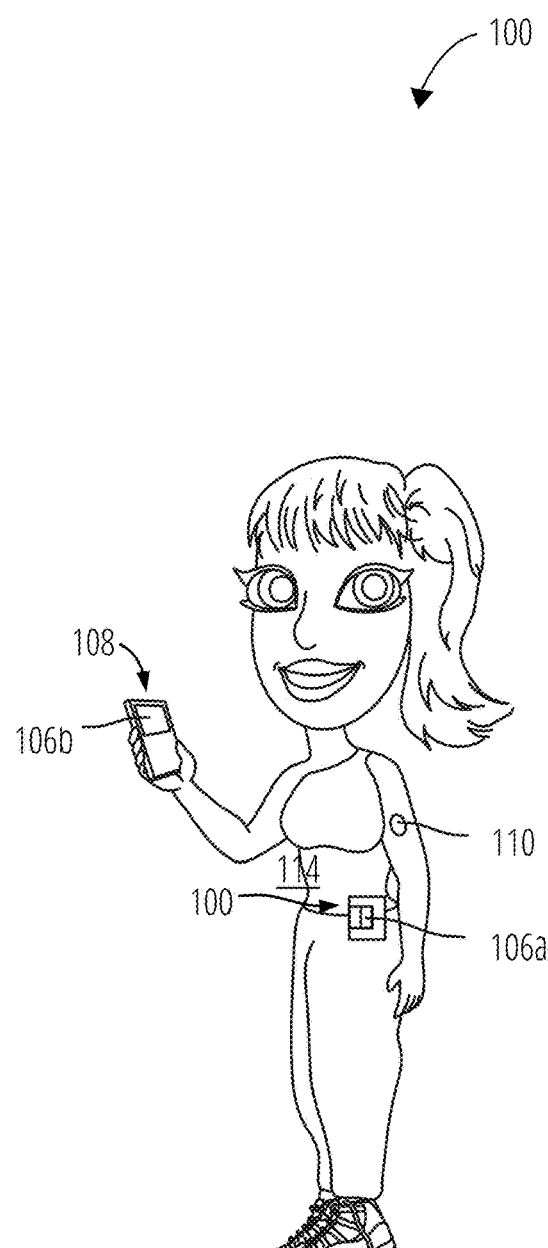
FIG. 1B illustrates another example blood glucose control system that provides blood glucose control via an ambulatory medicament pump.
Figure 1C:
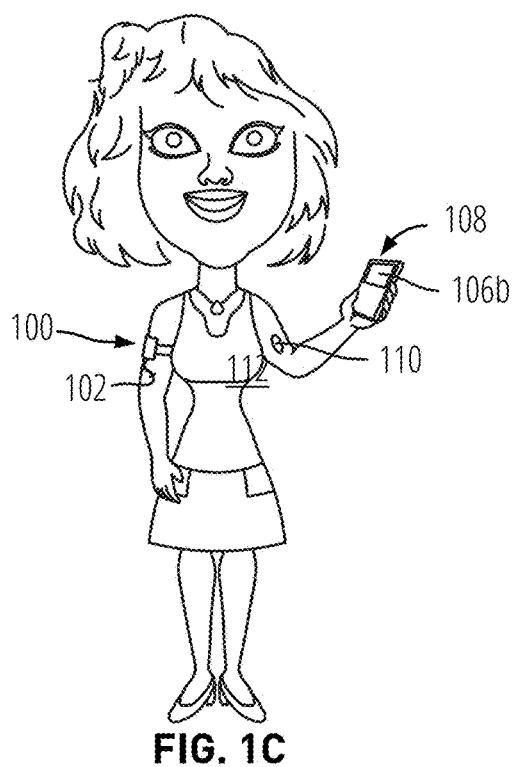
FIG. 1C illustrates a further example blood glucose control system that provides blood glucose control via an ambulatory medicament pump.

FIG. 1A-FIG. 1C show examples of blood glucose control systems that provide blood glucose control via an ambulatory medical device or AMD, such as a medicament pump connected to a subject. In FIG. 1A, the AMD 100 (medicament pump) is connected to an infusion site 102 using an infusion set 104. The AMD 100 (medicament pump) has integrated pump controls 106a that permit a user to view pump data and change therapy settings via user interaction with the pump controls 106a. A glucose level sensor 110 generates a glucose level signal that is received by the blood glucose control system.

In FIG. 1B, the medicament pump 100 communicates with an external electronic device 108 (such as, for example, a smartphone) via a wireless data connection. At least some of the pump controls 106a and 106b can be manipulated via user interaction with user interface elements of the external electronic device 108. The glucose level sensor 110 can also communicate with the AMD 100 (medicament pump) via a wireless data connection.

In FIG. 1C, the AMD 100 (medicament pump) includes an integrated cannula that inserts into the infusion site 102 without a separate infusion set. At least some of the pump controls 106b can be manipulated via user interaction with user interface elements of an external electronic device 108. In some instances, pump controls can be manipulated via user interaction with user interface elements generated by a remote computing environment (not shown), such as, for example, a cloud computing service, that connects to the AMD 100 (medicament pump) via a direct or indirect electronic data connection.

Glucose control systems typically include a user interface configured to provide one or more of therapy information, glucose level information, and/or therapy control elements capable of changing therapy settings via user interaction with interface controls. The user interface can be implemented via an electronic device that includes a display and one or more buttons, switches, dials, capacitive touch interfaces, or touchscreen interfaces. In some embodiments, at least a portion of the user interface is integrated with an ambulatory medicament pump that can be tethered to a body of a subject via an infusion set configured to facilitate subcutaneous injection of one or more glucose control agents. In certain embodiments, at least a portion of the user interface is implemented via an electronic device separate from the ambulatory medicament pump, such as a smartphone.

Figure 2A:
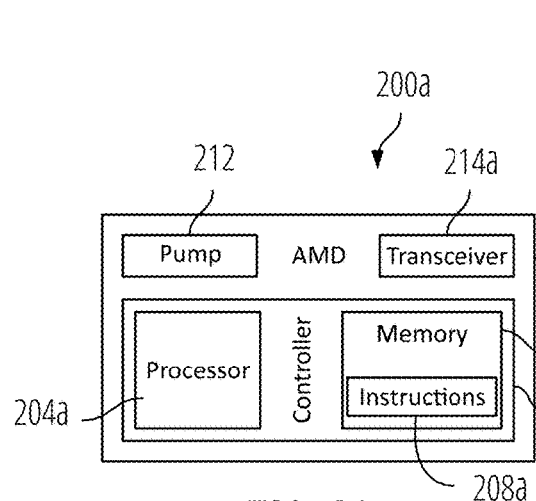
FIG. 2A shows a block diagram of an example blood glucose control system.

FIG. 2A-FIG. 2D illustrate block diagrams showing example configurations of a glucose control system 200a/200b/200c/200d. As shown in FIG. 2A, a glucose control system 200a can include a controller 202a having a hardware or an electronic processor 204a and a memory 210a that stores instructions 208a executable by the electronic processor 204a. The controller 202a and a pump 212 can be integrated into an ambulatory medical device (AMD) 100. The AMD 100 can have one or more pumps 212. The AMD 100 can include a transceiver 214a transceiver or wireless electronic communications interface 214a for wireless digital data communications with external electronic devices. When the instructions 208a stored in memory 210a are executed by the electronic processor 204a, the controller 202a can implement at least a portion of a control algorithm that generates dose control signals for one or more glucose control agents based on time-varying glucose levels of the subject (e.g., received from a glucose level sensor 110 that is in communication with the AMD 100, e.g., a medicament pump) and one or more control parameters. The dose control signals, when delivered to the pump 212, result in dosing operations that control the blood glucose of a subject. The pump 212 may be controlled by a pump controller. The pump controller receives the dose control signals and controls the operation of the pump 212 based on the received dose control signals. In some embodiments the pump controller may be integrated with the pump.

Figure 2B:
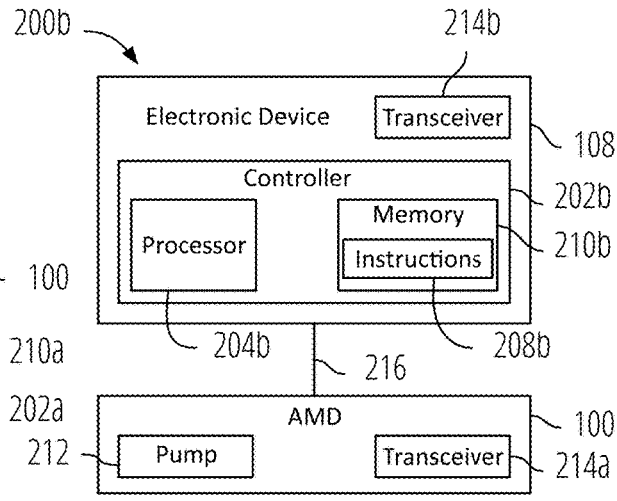
FIG. 2B shows a block diagram of another example blood glucose control system.

As shown in FIG. 2B, a glucose control system 200b can operate at least partially via execution of instructions 208b by an electronic processor 204b of an external electronic device 108 separate from the AMD 100. The external electronic device 108 can include a transceiver 214b capable of establishing a wireless digital data connection to the AMD 100, and a controller 202b can implement at least a portion of a control algorithm via execution of instructions 208b stored in memory 210b. When the instructions 208b stored in memory 210b are executed by the electronic processor 204b, the controller 202b can implement at least a portion of a control algorithm that generates dose control signals for one or more glucose control agents based on time-varying glucose levels of the subject and one or more control parameters. The dose control signals, when delivered to the pump controller of the pump 212, result in dosing operations that control the blood glucose of a subject. In some embodiments, the dose control signals are transmitted from the device transceiver 214b to the AMD transceiver 214a over a short-range wireless data connection 216. The AMD 100 receives the dose control signals and passes them to the pump 212 for dosing operations.

Figure 2C:
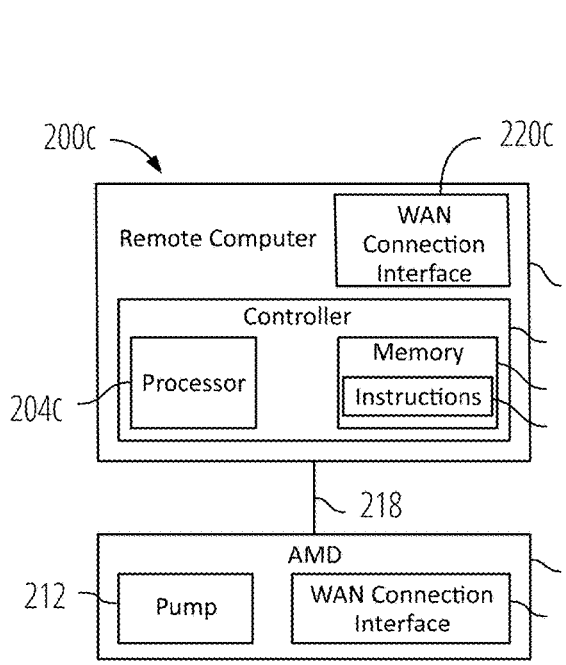
FIG. 2C shows a block diagram of another example blood glucose control system.

As shown in FIG. 2C, a glucose control system 200c can operate at least partially via execution of instructions 208c on an electronic processor 204c integrated with a remote computer 206, such as, for example, a cloud service. When the instructions 208c stored in memory 210c are executed by the electronic processor 204c, the controller 202c can implement at least a portion of a control algorithm that generates dose control signals for one or more glucose control agents based on time-varying glucose levels of the subject and one or more control parameters. The dose control signals, when delivered to the pump 212, result in dosing operations that control the blood glucose of a subject. In some embodiments, the dose control signals are transmitted from the remote computer WAN connection interface 220c to the AMD WAN connection interface 220a over an end-to-end wireless data connection 218. The AMD 100 receives the dose control signals and passes them to the pump 212 for dosing operations.

Figure 2D:
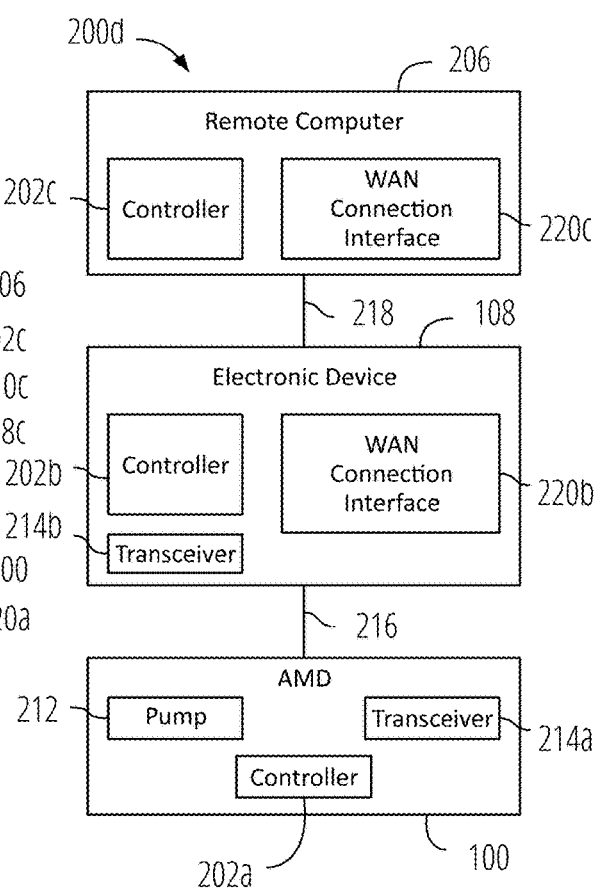
FIG. 2D shows a block diagram of another example blood glucose control system.

As shown in FIG. 2D, a glucose control system 200d can have two or more controllers 202a, 202b, 202c that cooperate to generate a dose control signal for dosing operations by the pump 212. A remote computer 206 can transmit or receive data or instructions passed through a WAN connection interface 220c via an end-to-end wireless data connection 218 to a WAN connection interface 220b of an external electronic device 108. The external electronic device 108 can transmit or receive data or instructions passed through a transceiver 214b via a short-range wireless data connection 216 to a transceiver 214a of an AMD 100. In some embodiments, the electronic device can be omitted, and the controllers 202a, 202c of the AMD 100 and the remote computer 206 cooperate to generate dose control signals that are passed to the pump 212. In such embodiments, the AMD 100 may have its own WAN connection interface 220a to support a direct end-to-end wireless data connection to the remote computer 206.

Figure 3:
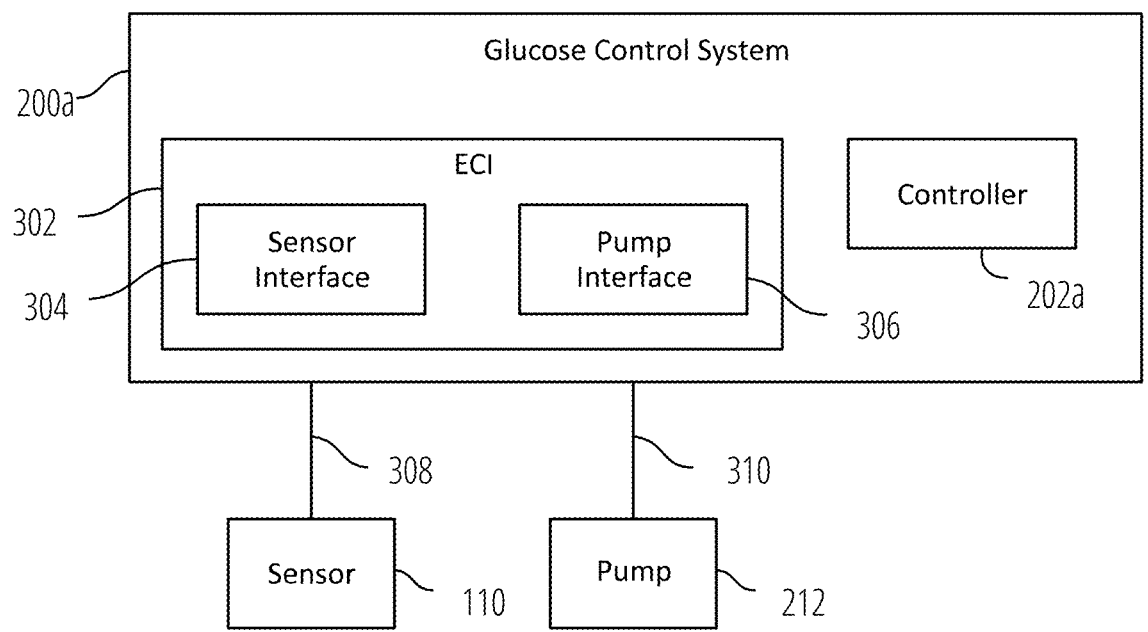
FIG. 3 is a schematic of an example glucose control system that includes an electronic communications interface.

As shown in FIG. 3, in some embodiments, the glucose control system 200a includes circuitry that implements an electronic communications interface (ECI) 302 configured to send and receive electronic data from one or more electronic devices. The ECI includes a sensor interface 304 configured to receive a glucose level signal from a glucose level sensor 110 such as a continuous glucose monitor (CGM). Some CGMs generate the glucose level signal at fixed measurement intervals, such as five-minute intervals. The glucose level sensor 110 can be operatively connected to a subject in order to generate a glucose level signal that corresponds to a blood glucose estimate or measurement of the subject. The glucose level signal can be used by the controller 202a to generate a dose control signal. The dose control signal can be provided to a pump 212 via a pump interface 306. In some embodiments, the sensor interface 304 connects to the glucose level sensor 110 via a short-range wireless connection 308. In some embodiments, the pump interface 306 connects to the pump 212 via a short-range wireless connection 310. In other embodiments, the pump interface 306 connects to the pump 212 via a local data bus, such as when the controller 202a, the ECI 302, and the pump 212 are integrated into an AMD 100.

The controller can be configured to generate the dose control signal using a control algorithm that generates at least one of a basal dose, a correction dose, and/or a meal dose. Examples of control algorithms that can be used to generate these doses are disclosed in U.S. Patent Application Publication Nos. 2008/0208113, 2013/0245547, 2016/0331898, and 2018/0220942 (referenced herein as the "Controller Disclosures"), the entire contents of which are incorporated by reference herein and made a part of this specification. The correction dose can include regulatory or counter-regulatory agent and can be generated using a model-predictive control (MPC) algorithm such as the one disclosed in the Controller Disclosures. The basal dose can include regulatory agent and can be generated using a basal control algorithm such as disclosed in the Controller Disclosures. The meal dose can include regulatory agent and can be generated using a meal control algorithm such as disclosed in the Controller Disclosures. Additional aspects and improvements for at least some of these controllers are disclosed herein. The dose control signal can be transmitted to an infusion motor via the ECI 302 or can be transmitted to the infusion motor via an electrical conductor when the controller 202a is integrated in the same housing as the infusion motor.

Figure 4A:
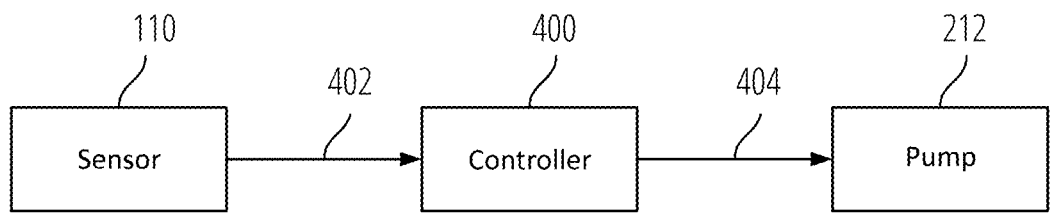
FIG. 4A shows a block diagram of an example blood glucose control system in online operation mode.

As shown in FIG. 4A, the controller 400 can be configured to operate in "online mode" during time periods when the controller receives a glucose level signal 402 from a glucose level sensor 110. In online mode, the control algorithm generates a dose control signal 404 that implements regular correction doses based on values of the glucose level signal 402 and control parameters of the control algorithm. The pump 212 is configured to deliver at least correction doses and basal doses to the subject without substantial user intervention while the controller 400 remains in online mode.

Figure 4B:
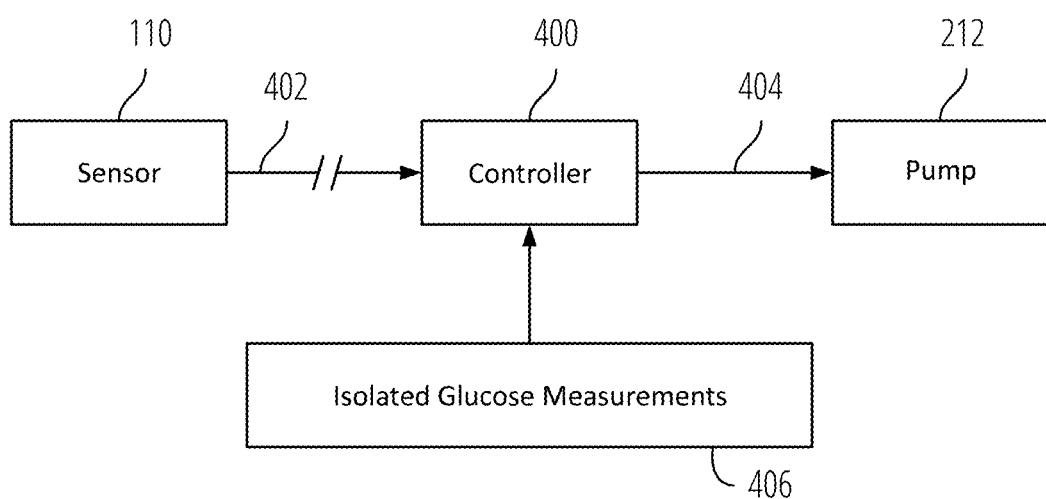
FIG. 4B shows a block diagram of an example blood glucose control system in offline operation mode.

As shown in FIG. 4B, the controller 400 can be configured to operate in "offline mode" during time periods when the controller does not receive a glucose level signal 402 from a sensor 110, at least during periods when the glucose level signal 402 is expected but not received. In offline mode, the control algorithm generates a dose control signal 404 that implements correction doses in response to isolated glucose measurements 406 (such as, for example, measurements obtained from the subject using glucose test strips) and based on control parameters of the control algorithm. The pump 212 is configured to deliver basal doses to the subject without substantial user intervention and can deliver correction doses to the subject in response to isolated glucose measurements 406 while the controller 400 remains in offline mode.

Example Ambulatory Medical Device

In some embodiments, the ambulatory medicament device (AMD) can be a portable or wearable device such as an ambulatory medicament pump (AMP) that provides life-saving treatment to a subject or subjects by delivering one or more medicaments (e.g., insulin and/or glucagon) to a subject or subjects. In some cases, the AMD includes an AMP along with other systems, such as a glucose control system and/or transceiver. Some AMDs may continuously monitor the health condition of a subject using a sensor and deliver therapy such as one or more medicaments based on the health condition of the subject. For example, an ambulatory medicament pump (e.g., an insulin pump or a bi-hormonal pump) may monitor the blood glucose level in a subject using a Continuous Glucose Monitor (CGM) and adjust the dose or frequency of the medicament delivery (e.g., insulin or glucagon) accordingly. Certain ambulatory medicament devices may be worn by subjects constantly (e.g., all day), or for a large portion of the day (e.g., during waking hours, during sleep hours, when not swimming, etc.) to enable continuous monitoring of the health condition of the subject and to deliver medicament as necessary.

Figure 5A:
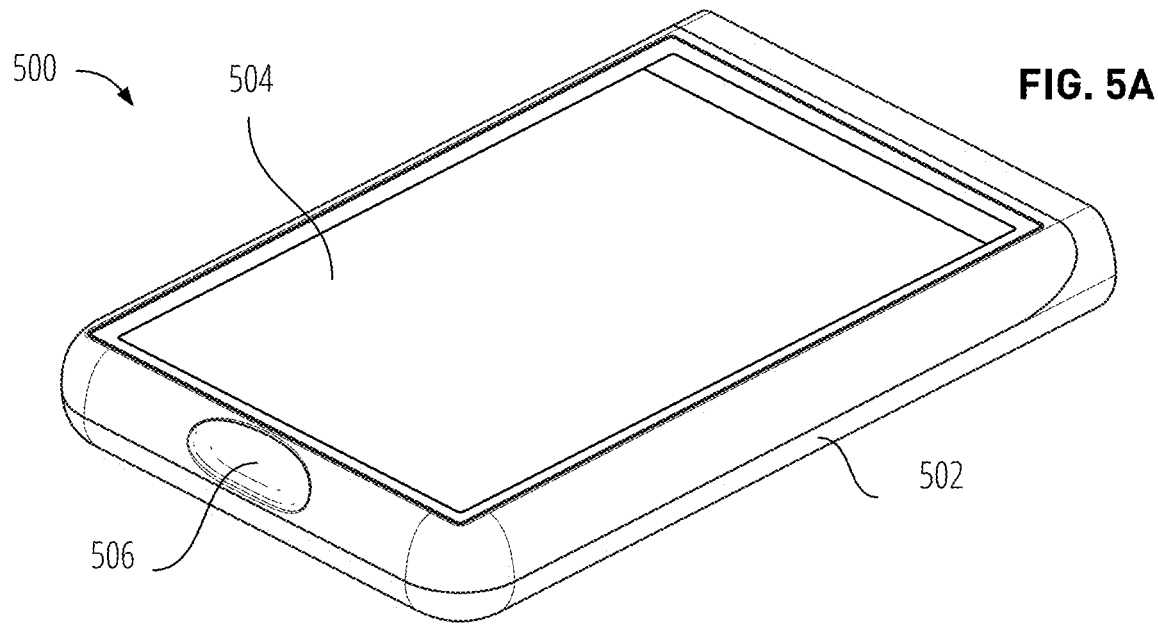
FIG. 5A illustrates a perspective view of an example ambulatory medical device.
Figure 5B:
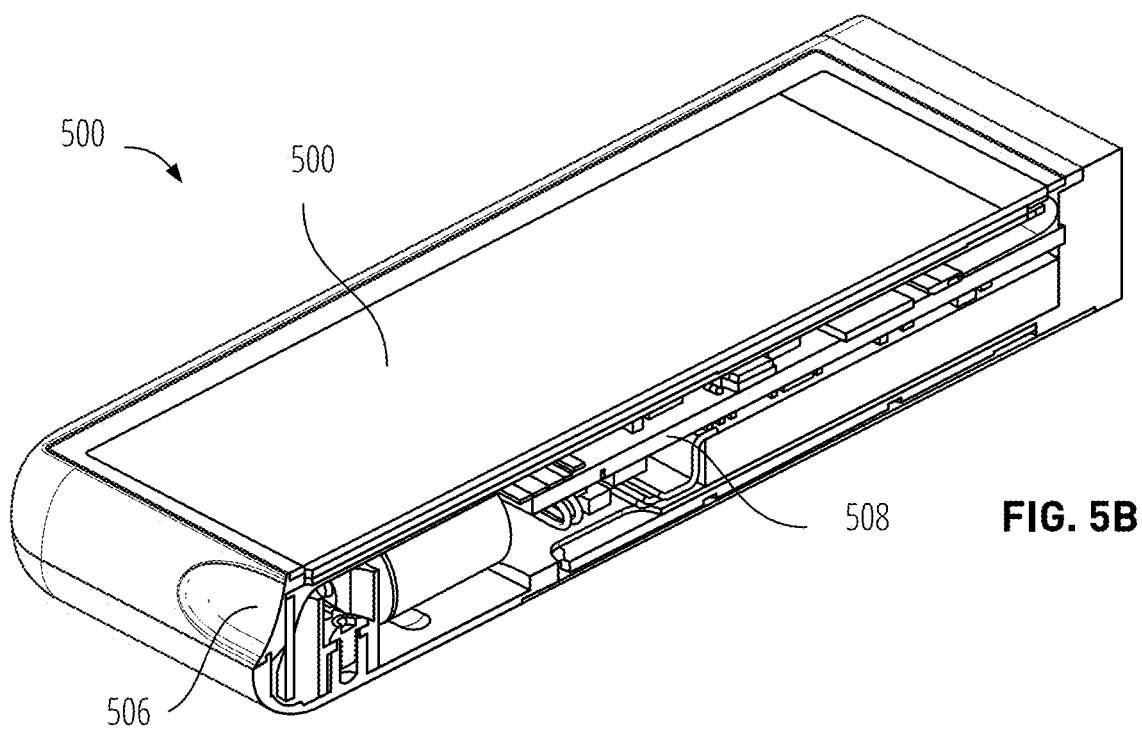
FIG. 5B illustrates a cross sectional view of the ambulatory medical device shown in FIG. 5A.

FIG. 5A illustrates a three-dimensional (3D) view of an example ambulatory medical device 500 (such as an ambulatory medicament pump) comprising a housing 502 with a wake button 506 and a touchscreen display 504. FIG. 5B is an illustration of a cross sectional view of the ambulatory medical device 500 shown in FIG. 5A. In this example, all the electronic modules 508 are included inside the housing, for example, as a single integrated electronic board. The wake button 506 may be any type of button (e.g., capacitive, mechanical) that registers an input generated by user interaction with the wake button 506 to generate a wake signal. In some embodiments, the wake signal is generated by a sensor (e.g., a biometric sensor such as a fingerprint reader or a retinal scanner, an optical or RF proximity sensor, and the like). In various embodiments, the wake signal may be generated by user interaction with the touch screen display 504 or with an alphanumeric pad (not shown). In some other examples, wake signal may be generated based on facial recognition or other biometric indicia. In yet other examples, the wake signal may be generated by a wireless signal such as RFID or Bluetooth signals or by detection of movement using one or more motion sensors such as an accelerometer. The wake button 506, if touched, pressed, or held for a certain period of time, may generate a wake signal that activates the touchscreen display 504. In some examples, touches on the touchscreen display 504 are not registered until the wake button activates the touchscreen display. In some such examples, the AMD remains locked from accepting at least certain types of user interaction or settings modification until a gesture (such as, for example, any of the gesture interactions described with reference to any of the embodiments disclosed herein) is received after the touchscreen display 504 is activated by the wake button 506. In some examples, after the touchscreen display 504 has been activated by the wake signal, a passcode may be required to unlock the touchscreen display. In some embodiments, the wake signal is generated by a sensor (e.g., a biometric sensor such as a fingerprint reader or a retinal scanner, an optical or RF proximity sensor, and the like). In various embodiments, the wake signal may be generated by user interaction with the touchscreen display 504 or with an alphanumeric pad (not shown). In some examples, a wake signal may be generated based on facial recognition or other biometric indicia. In some examples, the wake signal may be generated by a wireless signal such as a signal generated by an RFID system or Bluetooth signals received from an electronic device or by detection of movement using one or more motion sensors such as an accelerometer.

Figure 6:
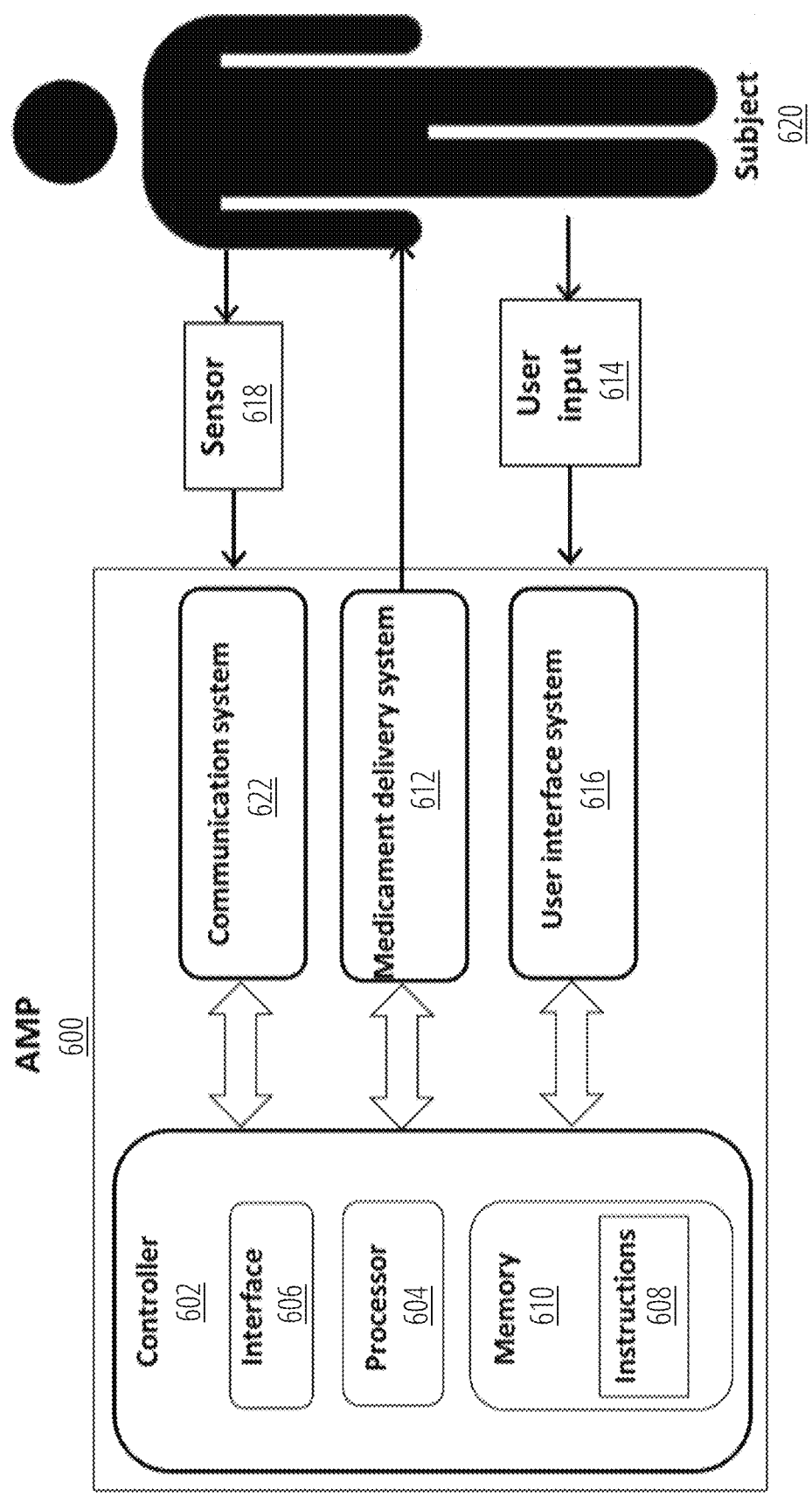
FIG. 6 illustrates different systems that may be included in an example ambulatory medical pump (AMP).

FIG. 6 illustrates different systems and sub-systems that may be included in an example AMP 600 (e.g., a blood glucose control system). As mentioned above, in some examples, the AMP may comprise glucose control system, such as a complete blood glucose control system. Further, in some cases, the AMP 600 may be an AMD that includes a medicament pump. In some implementations, the AMP may include systems and sub-systems that can enable monitoring a subject's blood glucose level, managing the subject's diabetes, tracking a condition of the AMP 600, and/or communicating with one or more computing systems. For example, the AMP 600 may include a mono-hormonal or bi-hormonal medicament pump configured to administer one or more types of insulin and, in some cases, counter-regulatory agent (e.g., glucagon or other medicaments that can reduce or address hypoglycemia). As another example, the AMP 600 may include one or more alarm generators, transceivers, touchscreen controllers, display controllers, encryption sub-systems, etc. In some examples, two or more of the systems may be integrated together inside a single housing 502 (as shown in FIG. 5A and FIG. 5B). In some examples, one or more systems or sub-systems may be individual modules contained in separate housings that can communicate with other systems and/or the main unit via a wired or wireless communication link (e.g., Bluetooth®). The AMP 600 may include a communication system 622, a medicament delivery system 612, a user interface system 616, and a controller 602 (or control system). In some embodiments, one or more systems may comprise one or more single purpose or multipurpose electronic sub-systems. In some such examples, one or more electronic sub-systems may perform procedures associated with different features of the AMP 600. In some other embodiments, one or more systems or sub-systems may comprise a non-transitory memory that can store machine readable instructions and a processor that executes the instructions stored in the memory. The memory may be a non-volatile memory, such as flash memory, a hard disk, magnetic disk memory, optical disk memory, or any other type of non-volatile memory. Further, types of memory may include but are not limited to random access memory ("RAM") and read-only memory ("ROM"). In some such examples, a system can be programed to perform different procedures each implemented based on a different set of instructions.

The controller 602 may include one or more processors 604, a memory 610 that may comprise one or more non-transitory and/or non-volatile memories and an interface 606 that enables data and signal communication between the controller 602 and other systems of the AMP (e.g., communication system 622, medicament delivery system 612 or user interface system 616). The memory 610 may be divided into two or more memory segments. The main memory 610 may exchange data with sub-systems within the controller 602 as well as other systems (e.g., via the interface 606). The memory 610 may store data while the controller 602 is powered or unpowered. The processor 604 may be any type of general-purpose central processing unit ("CPU"). In some embodiments, the controller may include more than one processor of any type including, but not limited to complex programmable logic devices ("CPLDs"), field programmable gate arrays ("FPGAs"), application-specific integrated circuits ("ASICs") or the like. The interface 606 may include data transfer buses and electronic circuits configured to support data exchange among different sub-systems within the controller 602. In some examples, in addition to data exchange between any of the systems and the controller 602, the interface 606 may support data and signal exchange among other systems of the AMP 600.

The interface 606 may include a plurality of interconnected electronic modules for signal conditioning and signal conversion (e.g., A-to-D or ADC conversion and D-to-A conversion or DAC conversion) configured to support communication and data exchange between different systems. For example, the interface 606 may convert an analog signal received from the communication system 622 and convert it to a digital signal that can be processed by the controller 602. As another example, the interface 606 may receive a digital control signal and convert it to a dose signal (e.g., an analog signal) that can be transmitted to the medicament delivery system 612, for example, to control one or more infusion pumps included in the medicament delivery system 612.

In some embodiments, the medicament delivery system 612 may comprise one or more infusion pumps configured to deliver one or more medicaments (e.g., insulin or glucagon) to a subject 620 and a pump controller that may activate the infusion pumps upon receiving does control signals. In some examples, the medicaments may be stored in one or more medicament cartridges that may be housed in or inserted into the medicament delivery system 612. In some examples, the medicament delivery system 612 may include electronic and mechanical components configured to control an infusion pumps based on signals received from controller 602 (e.g., via the interface 606).

The user interface system 616 may include a display to show status information about the AMP 600 and/or medicament. For example, the status information may include medicament type, delivery schedule, software status, and the like. The display may show graphical images and text using any display technology including, but not limited to OLED, LCD, or e-ink. In some embodiments, the AMP 600, may include a user interface (e.g., an alphanumeric pad) that lets a user provide information or interact with the AMP 600 to modify the settings of the AMP 600, respond to request for certain actions (e.g., installing a software) and the like. The alphanumeric pad may include a multitude of keys with numerical, alphabetical, and symbol characters. In different embodiments, the keys of the alphanumeric pad may be capacitive or mechanical. The user may be a subject 620 receiving medicament or therapy, or may be an authorized user, such as a clinician or healthcare provider, or a parent or guardian of the subject 620. In some other embodiments, the AMP 600 may include a touchscreen display that produces output and accepts input enabling a two-way interaction between the user and the AMP 600. The touchscreen display may be any input surface that shows graphic images and text and registers the position of touches on the input surface. The touchscreen display may accept input via capacitive touch, resistive touch, or other touch technology. The input surface of the touchscreen display can register the position of touches on the surface. In some examples, the touchscreen display can register multiple touches at once. In some embodiments, the keypad may be a display of a keypad. For example, an alphanumeric pad comprising user-selectable letters, numbers, and symbols may be displayed on the touchscreen display. In some examples, the touchscreen may present one or more user-interface screens to a user enabling the user to modify one or more therapy settings of the ambulatory medicament device.

In some examples, a user-interface screen may comprise one or more therapy change control elements (e.g., displayed on the touchscreen display) enabling a user or the subject to access therapy change controls and modify therapy settings by interacting with these control elements. For example, the user can modify the therapy settings by changing one or more control parameters using the corresponding therapy change control elements. In some embodiments, a therapy control parameter may be any parameter that controls or affects the volume, duration and/or the frequency of medicament doses delivered to the subject.

In some embodiments the communication system 622 may include one or more digital data interfaces to send or receive digital data via a wired or a wireless link. For example, the communication system may include one or more wireless transceivers, one or more antennas, and/or one or more electronic systems (e.g., front end modules, antenna switch modules, digital signal processors, power amplifier modules, etc.) that support communication over one or more communication links and/or networks. In some examples, each transceiver may be configured to receive or transmit different types of signals based on different wireless standards via the antenna (e.g., an antenna chip). Some transceivers may support communication using a low power wide area network (LPWAN) communication standard. In some examples, one or more transceivers may support communication with wide area networks (WANs) such as a cellular network transceiver that enables 3G, 4G, 4G-LTE, or 5G. Further, one or more transceivers may support communication via a Narrowband Long-Term Evolution (NB-LTE), a Narrowband Internet-of-Things (NB-IoT), or a Long-Term Evolution Machine Type Communication (LTE-MTC) communication connection with the wireless wide area network. In some cases, one or more transceivers may support Wi-Fi® communication. In some cases, one or more transceivers may support data communication via a Blue tooth or Blue tooth Low Energy (BLE) standard. In some examples, one or more transceivers may be capable of down-converting and/or up-converting a baseband or data signal from and/or to a wireless carrier signal. In some examples, the communication system 622 may wirelessly exchange data between other components of the AMP 600 (e.g., a blood glucose level sensor), a mobile device (e.g., smart phone, a laptop and the like), a Wi-Fi network, WLAN, a wireless router, a cellular tower, a Bluetooth device and the like. The antenna may be capable of sending and receiving various types of wireless signals including, but not limited to, Bluetooth, LTE, or 3G.

In some examples, the communication system 622 may support direct end-to-end communication between the AMP 600 and a server or a cloud network. In some examples the AMP 600 may communicate with an intermediary device (e.g., a smart phone or other mobile devices, a personal computer, a notebook, and the like). In some embodiments, the AMP 600 may include an eSIM card that stores information that may be used to identify and authenticate a mobile subscriber. The eSIM card may enable the AMP 600 to function as an Internet of Things (IoT) device that can communicate over a network that supports communication with IoT devices. In other embodiments, the AMP 600 may be configured to transmit data using a narrowband communication protocol such as 2G or EDGE. Using the cellular connection, the AMP 600 may be paired with a mobile device at inception and permit real-time data access to the AMP 600 by a healthcare provider. In certain implementations, the AMP 600 may include a geolocation receiver or transceiver, such as a global positioning system (GPS) receiver. As previously stated, each of the AMPs described herein may include one or more of the embodiments described with respect to the other AMPs unless specifically stated otherwise. In some embodiments the communication system 622 may include a Near Field Communication (NFC) sub-system that enables contactless data exchange between the AMP 600 and an electronic device located in the vicinity of the AMP 600.

Example Operation of the AMP

In some embodiments, the AMP 600 may continuously, periodically, or intermittently receive data related to a health condition of the subject (e.g., blood glucose level, blood glucose trend, heart rate, body movement indicia, etc.). This information may be encoded to a signal provided to AMP 600 by a sensor 618. In some such embodiments, the sensor 618 can be a continuous glucose monitor (CGM) that is connected to the AMP 600 via a wired or wireless link (e.g., a link based on or implementing the Bluetooth® standard). In some examples, a CGM may be a wearable biomedical sensor that measures a blood glucose level in the interstitial fluid. In some examples, the signal sent by the sensor 618 may be received by the communication system 622 and transmitted to the controller 602 where the signal may be analyzed to determine whether to deliver medicament to the subject 620. In some examples, a second communication system may be included in the AMP 600 to communicate with the sensor 618. If it is determined that medicament should be administered to the subject, the controller 602 may determine the dosage and/or type of medicament to administer to the subject. The determination of medicament dosage and/or type may be based at least in part on the information received from the sensor 618. The controller 602 may generate a dose control signal and send the dose control signal to the medicament delivery system 612 to initiate medicament delivery to the subject. In some examples, the dose control signal may be received by a pump controller that controls operation of an infusion pump.

In some embodiments, the controller 602 may perform one or more procedures using the processor 604 (or a plurality of processors) that execute instructions 608 stored in the memory 610 of the controller 602. These procedures may include, but are not limited to, determining the need for delivering medicament, determining the type of medicament and/or a dose size of medicament, determining the rate of delivery during a therapy session, providing information (e.g., device status, next delivery time, level of certain analytes in the subject's blood, and the like) via the user interface system 616, processing the data received from the sensor 618, or managing access to control parameters (e.g., by controlling one or more therapy change controls that may be provided by the user interface system 616).

In some embodiments, the AMP 600 may deliver multiple types of therapy. The type of therapy to be delivered may be determined automatically by the controller 602 or may be selected by the user. For example, the AMP 600 may deliver the therapy of infusing insulin into a user and may also deliver glucagon into the user. In some examples, the user interface system 616 may allow the user to select the type of medicament infused to the subject 620 during therapy (e.g., insulin, glucagon or both). In other embodiments, other hormones, medicaments, or therapies may be delivered. In some examples, the controller 602, may determine the type of medicament that is delivered to the subject 620 base at least in part on the data received from the communication system 622.

Communication and Networking

Figure 7:
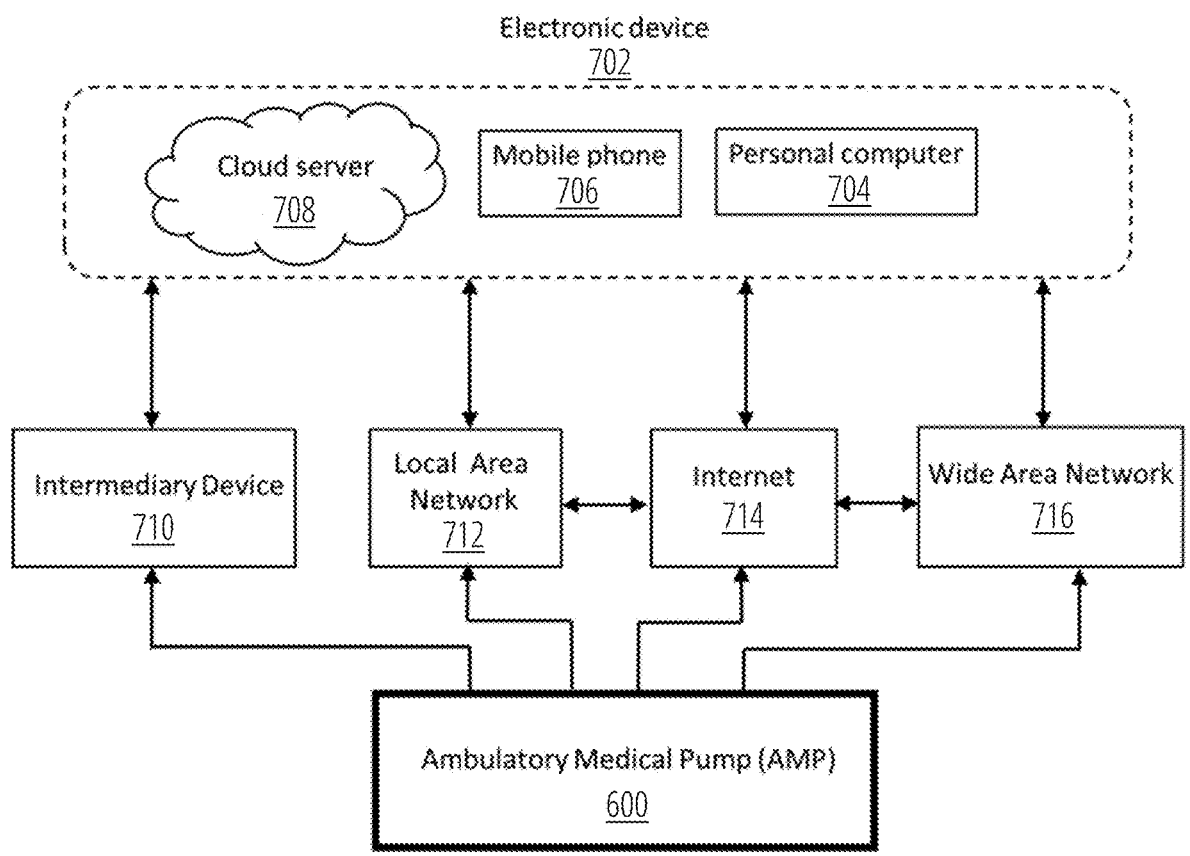
FIG. 7 illustrates various communication links that the AMP may use to establish a communication connection with an electronic device.

FIG. 7 illustrates various methods, and data links or communication paths that AMP 600 may use to communicate (e.g., exchange digital data) with an electronic device 702. The communication may include obtaining application updates, sending and/or receiving therapy data and/or therapy reports, receiving passcodes or access codes, sending a request (e.g., request for a safe access level or a request for a therapy report), receiving values of control parameters, and the like. The electronic device 702 can be a cloud server 708, a mobile phone 706 (e.g., a mobile phone of a user, the subject 620, a physician, and the like), or a personal computer 704 (e.g., a laptop, desktop, tablet, etc. of a user, the subject 620, a physician, and the like). In some examples, the cloud server 708 may be part of a data center (e.g., the data center of a healthcare provider). Further, the electronic device 102 may includes other types of devices, such as smartglasses, smartwatches, etc.

In some embodiments, the AMP 600 may establish a connection (e.g., using the communication system 622) with the electronic device 702 through an intermediary device 710 (e.g., a smart phone or other mobile device, a personal computer, a notebook or the like). In some examples, the AMP 600 may communicate with the electronic device 702 through a local area network 712 (LAN) and/or through a Wi-Fi connection. Alternatively, or in addition, the AMP 600 may establish a communication connection to the electronic device 702 via a wide area network 716 (WAN). In some examples, the communication between the AMP 600 medical device and the electronic device may be encrypted.

In some embodiments, the AMP 600 may establish a direct end-to-end communication connection over a wide area network 716 (e.g., a cellular network) with the electronic device 702. In some cases, a direct-end-to-end communication connection may be a connection that does not involve a local device, a device that is accessible by the user or the subject (besides the AMP 600), a Wi-Fi network, a short range wireless link (e.g., Bluetooth), or the like. In some such cases, the direct end-to-end communication may pass through one or more wireless systems (e.g., receivers, transmitters, transceivers, or antenna) of a wide area network 716. In some examples, the electronic device 702 may establish the end-to-end connection by receiving a public key from the AMP 600. In some examples, the public key and a private key stored in the electronic device 702 can be used to permit the electronic device 702 to decrypt data transmitted by the AMP 600. In some implementations, the electronic device 702 may establish a direct end-to-end data connection with the AMP 600 based on receiving a device identifier associated with the AMP 600. The device identifier may be a unique identifier specific to the AMP 600. In some other implementations, establishing the direct end-to-end data connection may include determining that the AMP 600 is permitted to communicate with the electronic device 702 based at least in part on the device identifier. In some examples, the device identifier may be initially provided to electronic device 702 prior to provisioning of the AMP 600 to the subject. For example, the device identifier may be initially provided to the networked-computing environment as part of a manufacturing process for manufacturing the AMP 600. In some examples, the device identifier may include or may be based on one or more of an Internet Protocol (IP) address, a Media Access Control (MAC) address, a serial number, or a subject identifier of a subject that receives therapy from the AMP 600. In some cases, the subject or a user may establish or initiate establishing the direct end-to-end data connection with the electronic device 702. In some cases, the direct end-to-end data connection may be initiated or established without any action by the subject or the user. For example, the direct end-to-end data connection may be established automatically at particular times and/or when the AMP 600 is in a particular location. In some such cases, this automatic connection may occur using information supplied to the AMP 600 at a time of manufacture, shipment, sale, or prescription to the subject. Alternatively, or in addition, a subject or other user may configure the AMP 600 to automatically connect to the electronic device 702 at particular times and/or locations. In some cases, the wide area network may include, or may communicate with, the Internet 714.

In some embodiments, the AMP 600 may be configured to communicate via the wide area network 716 during manufacture or prior to being provisioned to the subject. For example, a manufacturer can register the AMP 600 with a wireless wide-area network provider (e.g., T-Mobile or Verizon) and provide an International Mobile Equipment Identity (IMEI) number or serial number for the AMP 600 to the network provider. Moreover, fees can be negotiated between the manufacturer and the network provider or between the subject's health insurance and the network provider. Similarly, fees may be paid by the manufacturer or health insurance provider, or other entity, without subject involvement. Thus, the subject's AMP 600 may be configured to communicate via the network of the network provider without any action by the subject or the user. In some cases, the subject may be responsible for obtaining wireless service to connect the AMP 600 to a wide area network 716 (e.g., a cellular network).

In some examples, the AMP 600 may be pre-registered or authenticated with a computing network of the cloud services provider as part of the manufacturing process or before AMP 600 is provided to the subject. This enables the AMP 600 to communicate over the wide area network with the computing system of the cloud services provider from day one without any or with minimal configuration by the subject. In some cases, a user, such as a healthcare provider may register or associate the AMP 600 with the subject at the computing network of the cloud services provider.

In some embodiments, the AMP 600 may use a whitelist, or approved list, that identifies via a unique identifier (e.g., via an IP address, a MAC address, or a URL) one or more permitted cloud servers 708 or computing systems of the cloud computing system that the AMP 600 is permitted to access. By restricting access to an approved set of computing systems, the risk of malicious actors accessing the AMP 600 is reduced. Moreover, in some cases, the AMP 600 may include a blacklist, or restricted list, that identifies systems the AMP 600 is not permitted to access. The blacklist may be updated as more restricted or unsafe websites, network accessible systems, or computing systems are identified. Similarly, the whitelist may be updated over time if approved systems are added or removed.

Further, the cloud computing service may have a whitelist, or approved list, that uses unique identifiers to specify AMP 600 and/or other computing systems (e.g., remote display systems) that are permitted to communicate with the cloud computing system. Moreover, as with the AMP 600, the cloud computing service may have a blacklist or restricted list that identifies AMPs, or other computing devices, that are not permitted to access the cloud computing services. An AMP 600 may be added to the restricted list if it is decommissioned, damaged, or is no longer in possession of the subject. It may be desirable to remove an AMP's access to the cloud computing service to help protect private or personal data of a subject. Advantageously, establishing a connection based on a whitelist may enhance the security of the communication link established between AMP 600 and the cloud server 708 or other computing systems. In addition to the identifiers that identify permitted computing systems for access by the AMP 600 and/or permitted AMPs for access by a cloud or networked computing service, the whitelist may include any information that may facilitate access to the systems identified on the whitelist. For example, the whitelist may include access information (e.g., usernames, passwords, access codes, account identifiers, port identifiers, a shared secret, public keys, etc.). It should be understood that the whitelist may include different information depending on whether the whitelist is publicly accessible, accessible by only the AMP, accessible by authorized users or devices, etc. For example, a publicly accessible whitelist or a whitelist accessible by more than one authorized system or user may not include passwords or access codes.

In some cases, the AMP 600 may use a whitelist that identifies via, for example, a unique identifier (e.g., via an IP address, a MAC address, or a URL) permitted cloud servers or computing systems. In some examples, the electronic device 702 may have a whitelist that uses unique identifiers to specify AMP 600 and/or other computing systems (e.g., remote display systems) that are permitted to communicate with the electronic device 702. The whitelist may be stored in a memory of AMP 600 and/or in a memory of a trusted computing device that is accessible by the AMP 600. The trusted computing device can include any computing device that a manufacturer of the AMP 600 has identified as trusted. Alternatively, or in addition, the trusted computing device can include any computing device that a subject or user that care for the subject (e.g., parent, guardian, or healthcare provider) has identified as a trusted computing device that is designated to store the whitelist. In some examples, the whitelist may be configured during manufacture of the AMP 600. For example, the whitelist may be configured with connection information to establish communication with one or more computing systems of a networked-computing environment. In some examples, the AMP 600 may be configured to execute the specific computer-executable instructions to at least obtain an address of a computing system from the whitelist and to establish a direct end-to-end data connection to the computing (e.g., a computing system in the networked-computing environment), via a wireless wide area network using the address. In some embodiments, the AMP 600 may be configured to execute the specific computer-executable instructions to at least receive a public key from the computing system of the networked-computing environment.

In some embodiments, a portion of the communication system 622 of the AMP 600 may be enabled or disabled by the controller 602. In some cases, upon receiving a trigger, the controller 602 may maintain wireless data communication between the AMP 600 and the sensor 618 but disable wireless communication with all other electronic devices. In some examples, the trigger can be a signal received from the user interface system 616 indicating a user interaction with a user interface (e.g., a touchscreen display). For example, a user interface element may be provided on a touchscreen display to activate an "airplane mode." In some embodiments, the trigger may be a signal received from a location sensor. For example, the controller may automatically disable wireless communication signals that are not associated with the sensor 618, upon receiving a location signal from a location sensor (e.g., a GPS) indicating that the user is an airplane.

In some embodiments, the controller 602 may switch on one or more wireless communication sub-systems of the communication system 622 upon determining that a condition is satisfied by the therapy data (e.g., glucose level received from the sensor 618). In some embodiments, the controller 602 may switch on one or more wireless communication sub-systems of the communication system 622 based on a location of the user or the subject determined by a location sensor.

In some embodiments, one or more settings of the AMP 600 can be stored in an electronic device automatically or upon receiving a request from a user. For example, using a user interface of the AMP 600, the user may send a request to save one or more settings of the AMP 600 in a remote electronic device (e.g., a cloud server) via a wireless digital data link. As another examples, the AMP 600 may automatically store its current settings in a remote electronic device (e.g., a cloud server), by establishing wireless data connection with the remote electronic device. In some examples, a user may provide instructions to the AMP 600 (e.g., via user interface or a wireless link), so that the AMP 600 periodically (e.g., every week, every month) stores one or more settings of the AMP 600 in a remote electronic device.

In some embodiments, a one-time passcode may be provided to the user or the subject to enable connecting the AMP 600 to a remote electronic device (e.g., a cloud server), in order to download a device state to the AMP 600. For example, when a user obtains a new AMP, the user data and customized settings, which were previously stored in the remote electronic device, may be downloaded to the new AMP. The onetime pass code can be requested from a computer or a mobile phone, for example, using an application program configured to "set up a pump".

In some cases, the new AMP may be provided to the user with limited functionality (e.g., the pump motor may not be enabled) while the prescription verification process is proceeding. Once the prescription is verified, the required functionalities and settings associated with prescription, may be enabled.

In some, examples the eligibility of a user for downloading the personal data and/or the AMP state (e.g., therapy settings) may be confirmed based on the AMP's serial number.

Modifying Therapy Settings

In some embodiments, AMP 600 may allow a user or the subject 620, to modify a therapy setting of the AMP 600. The therapy setting may comprise values or selections related to one or more control parameters that control the dose control signal generate by the controller 602. For example, the AMP 600 may provide one or more therapy change controls in a user interface that may receive a user inputs 614 to modify one or more control parameters of the AMP 600. In some embodiments, the therapy change controls can be therapy change control elements provided in a therapy change user interface (e.g., a touchscreen display) and the user input 614 can be received in response to a user interaction with a therapy change control element.

In certain embodiments, the user may wake the AMP 600 from a sleep state or unlock the AMP 600 by, for example, interacting with a wake interface. When the AMP 600 is in a sleep state, the user interface may not receive the user input 614 or user input signals corresponding to user input. Waking the AMP 600 may include activating a touchscreen interface or presenting a lock screen to a user. Further, waking the AMP 600 may include waking the touchscreen controller such that it can receive user input or user input signals corresponding to user input. The wake interface can include one or more of the additional user interfaces mentioned above that are configured to generate and provide a wake input (or wake signal) to the controller 602 when detecting a pre-set user interaction. Alternatively, or in addition, the wake interface can be any type of wake interface element of the AMP 600 that a user can interact with to wake at least a feature (e.g., a touchscreen interface) of the AMP 600. For example, the wake interface element can be a physical button (e.g., a push button, a slide button, etc.), a capacitive element, a resistive element, or an inductive element. In some cases, the wake interface element can be or can include a biometric element, such as a fingerprint reader, an iris scanner, a face detection scanner, etc. In some cases, the AMP 600 may wake in response to detection of a movement or motion. For example, a determination that the ambulatory medicament device is being moved with a particular motion or within a line of sight or a visual range of a user may cause the AMP 600 to awaken or cause the AMP to awake the touchscreen interface of the AMP 600. The AMP 600 may determine that the AMP 600 is being moved within a line of sight of the user based on the type of motion and/or the detection of a user's eyes via, for example, an iris scanner or a camera.

In some examples, the user input 614 can be an input provided by the subject 620 to change a therapy that is currently being delivered to the subject 620. For example, the user input 614 may cause the insulin or glucagon infusion pump to start infusing an amount of insulin or glucagon into the 618. In some examples, the user input 614 provided by the user 620, may affect the therapy delivery at future time. In some examples, the user input may modify the rate of insulin or glucagon infusion into the user 620. The user input 614 may also cancel insulin or glucagon infusion into the user 620 from the insulin or glucagon infusion pump. In some cases, the user input 614 is a request to change a control parameter. The control parameter may be changed in response to the request. Alternatively, or in addition, a confirmation action (e.g., a swipe gesture or an interaction with a physical or digital button on the touchscreen) confirming the requested control parameter change may be required before the control parameter is changed.

In some cases, when a wake action is detected by the wake interface, a wake input is sent to the controller 602, which may imitate or perform a wake control procedure to wake/unlock the user interface (e.g., a touchscreen display). In some cases, the controller 602 may use the wake controller to perform the wake procedure.

When in the wake and/or unlocked state, a user may interact with a touchscreen display, alphanumeric pad or other types of user interfaces that may be provided by user interface system 616 in a the user interface, to obtain access to therapy change user interface.

The therapy change user interface may be activated by a first user interaction with the user interface (e.g., touchscreen display). When the first user interaction is detected, the user interface system 616 may send an input signal to the controller 602 to determine if the first user interaction relates to a therapy change request or a control parameter change request. In some cases, the controller 602 may determine whether the first user interaction corresponds to a request to change a control parameter, or a request to access a control parameter change interface. If it is determined that the first user interaction satisfies a set of predefined conditions, the controller 602 may send a signal to the user interface system 616 to activate the therapy change user interface.

In some embodiments, the type of therapy change user interface and/or the available therapy change selections included in the user interface may depend on the user interaction. For example, in response to one of two (or more) user interactions, the controller 602 may send one of two (or more) signals to the user interface system 616. The therapy change user interface may unlock one of two (or more) different therapy change user interfaces that may result in different options of therapy change selections for the subject 620. In an implementation of this example, a therapy change selection to make a significant therapy change, such as dramatically (e.g., more than a magnitude, or more than 3 change increments) increase the rate of insulin or glucagon infusion rate, may require a user interaction that is different from the user interaction that may be required for an insulin or glucagon infusion at a normal or prescribed rate, or a smaller change to the control parameter. In some examples, the user interaction may be a simple interaction (e.g., a simple gesture or unlock gesture interaction) that unlocks a therapy change user interface with therapy change selections that are limited in magnitude size. Another user interaction may be a complicated interaction (e.g., a series of complex gestures) that unlocks a therapy change user interface with therapy change selections that have no limits. An example of this implementation may be useful for child users. The child user may perform the first or simpler gesture that is made up of a series of simple inputs to unlock therapy change selections that are limited. An adult user may perform the second or more complex gesture that is made up of a series of complex inputs to unlock the therapy change user interface with therapy change selections that have no limits. In some cases, a simple interaction may include an interaction that is capable of being performed by a person below a particular age (e.g., a child), above a particular age (e.g., a senior citizen), or associated with a particular level of maturity or intelligence (e.g., a child or an individual with a learning disability). In contrast, a complex interaction may include an interaction that can be performed by an average adult or person that is above a particular minimum age (e.g., older than a child of a particular age), above a particular maximum age (e.g., younger than a senior citizen), or is not associated with a learning disability.

Once activated, the therapy change user interface generated by the user interface system 616 may provide one or more therapy change control elements that enable the user to modify the one or more settings of the AMP 600. In some examples, the therapy control element may include any type of user interface screen on the touchscreen, or other type of user interface in the non-touchscreen context, that enables or permits a user to change a configuration of the AMP 600. This change in configuration of the AMP 600 may relate to a change in the therapy provided or in the detection of a triggering event that causes therapy (e.g., medicament delivery) to be provided to a subject. For example, the change in configuration may include a selection between one or more hormones that regulate blood sugar level (e.g., insulin or glucagon) of a user, an amount of the one or more hormones that regulate blood sugar level of the user, a rate of delivery of the one or more hormones, a threshold for determining when to deliver the one or more hormones, a change in an estimated blood absorption rate of the one or more hormones, and the like. In some examples, the therapy control element may include any type of user interface screen on the touchscreen, or other type of user interface in the non-touchscreen context, that enables or permits a user to change one or more control parameters of the AMP 600 that control the therapy delivery. In some cases, a simple interaction may include an interaction that is capable of being performed by a person below a particular age (e.g., a child), above a particular age (e.g., a senior citizen), or associated with a particular level of maturity or intelligence (e.g., a child or an individual with a learning disability). In contrast, a complex interaction may include an interaction that can be performed by an average adult or person that is above a particular minimum age (e.g., older than a child of a particular age), above a particular maximum age (e.g., younger than a senior citizen), or is not associated with a learning disability.

In some cases, a change to the setting (e.g., control parameters or configuration of the AMP) of the AMP 600 is automatically and/or instantly recognized or implemented by the AMP 600, and/or transmitted to the AMP 600. In some cases, a confirmation of the change may be required before the setting change is implemented by or transmitted to the AMP 600.

A confirmation of the change may be received in response to a second user interaction with a user interface (e.g., touchscreen display). When the second user interaction is detected, the user interface system 616 sends an input signal to the controller 602. If it is determined that the second user interaction satisfies a set of predefined conditions, the controller 602 implements the change to the configuration of the AMP 600.

The first and/or second user interactions may include the selection of an icon, a series of taps or inputs, one or more gestures (e.g., a linear swipe, an arcuate swipe, a circular swipe, or other simple or complex movement across the touchscreen), performing a pattern or sequence on the touchscreen (e.g., drawing an image), a multi-touch or multi-input interaction, a combination of the foregoing, or any other type of interaction with a touchscreen, or portion thereof. The series of inputs may be any combination of touch movements, touch points, numerical characters, alphabetical characters, and other symbols. Gesture interactions can be guided by visual indicia displayed or printed on the AMP 600. In some embodiments, the visual indication can include animations that suggest or guide user interactions with a touchscreen. For example, the first user interaction can include an arcuate swipe around at least a portion of a generally circular icon or logo. In some examples, the first and/or second user interactions may include a predetermined sequence of numerical and/or alphabetical inputs. In some examples, a series of multiple inputs, the range of parameters for an input may be dependent on other inputs in the series. For example, required start position of a touch movement may be dependent on the position of the previous touch movement. The time that the series of inputs are entered may also be a part of the range of parameters. For example, a series of inputs may need to be entered in no less than 3 seconds or more than 3 seconds, and no more than 15 seconds or less than 15 seconds.

Further, one or more of the interactions may include interacting with a sensor, such as an optical sensor (e.g., visible light or IR sensor), biometric sensor (e.g., a fingerprint or retinal scanner), a proximity sensor, a gyroscope, or a combination of accelerometer and gyroscope, and the like. Also, in some cases, the second user interaction may be received through a wireless signal such as RFID or Bluetooth. In some embodiments, the second user interaction may include receiving a selection of a user interface element (e.g., a checkbox). Further, the second user interaction may correspond to a medicament type, such as insulin or glucagon. In some cases, the second interaction may correspond to receiving a particular sequence of numerical inputs in order to confirm the therapy change selection.

The type of user interaction that unlocks the touchscreen, provides access to a configuration screen, and/or confirms a change to the configuration of the AMP 600 may be the same or may differ.

In some examples, the system may have a time-out feature associated with a particular length time period. This particular length time period may be of any length. For example, the time period until a time-out occurs may be 30 seconds, a minute, 5 minutes, etc. Further, the length of the time period associated with a time out may be programmable. In some such cases, if no interaction occurs during the particular length time period, a time-out occurs. When a time-out occurs, a process for modifying an AMP 600 configuration may be cancelled. If the user elects to reattempt to modify the AMP 600 configuration after occurrence of a time-out, the process may be restarted. In some cases, the user interface will turn off upon occurrence of a time-out, and as stated above, the therapy change request process may be required to start again. In one implementation of the time-out, if no interaction occurs for more than 30 seconds after the system is waked/unlocked before the second user interaction is received by the user interface, the user interface will be deactivated.

In some implementations, once a change or modification to the therapy setting (e.g., a change in control parameters or configuration of the AMP 600) is confirmed, implemented, or transmitted, the AMP 600 may begin operating based on the modified setting selected and/or provided by the user.

In some cases, operating with the modified setting may include triggering therapy delivery based on the new setting or providing therapy based on the new setting. For example, the AMP 600 may generate a dose control signal based at least in part on the modified configuration or control parameter or may detect a trigger based at least in part on the modified configuration or control parameter that leads to the provisioning of therapy.

In some cases, AMP 600, or a control device that enables a user to modify a configuration of the AMP 600, may have a timeout feature. The timeout feature may cause the AMP 600 or the control device to enter a sleep or locked state after a period of inactivity by the user. In some cases, the timeout feature may cause the AMP 600 or the control device to enter a sleep or locked state after a particular period regardless of whether the user is interacting with the ambulatory medicament device or control device. In some cases, the timeout feature may cause the user interface (e.g., a touchscreen display) to become inactive or enter a lock state. Thus, a user may have a limited period to modify the configuration of the AMP 600.

In some examples, the therapy change made by a user may trigger the delivery of a medicament according to the therapy change received and confirmed by a user. This therapy change delivery may occur after a set time period from receiving the confirmation.

In some embodiments, the AMP 600 may allow the user to provide a therapy change and then cancel the therapy change. The user may provide the therapy change by modifying one or more control parameters of the AMP 600. The user may unlock a touchscreen display using a wake action and get access to a therapy change user interface (e.g., using a first gesture), where one or more therapy change control elements may be displayed. Next, an indication of a modification to a therapy control element may be received by the user interface followed by a confirmation of the modification made (e.g., a second gesture). In response to receiving an indication and confirmation of a modification to a therapy control element, the corresponding control parameter may be changed from a first setting to a second setting. In some examples, once the change is implemented, the user may decide to cancel it or revert to a prior setting. For example, the user may determine that the change is erroneous or does not provide the anticipated level of care. In some such cases, the user may provide a third gesture on the touch screen. In response to receiving the third gesture from the user interface, the therapy change procedure may restore the modified control parameter to the first setting.

In some examples, the third gesture may be a restore gesture. In some cases, the restore gesture may be a swipe gesture. In some examples the swipe gesture may be performed near or in a region of the therapy change user interface that is occupied by the therapy control element (or a particular portion thereof). An example of a restore swipe gesture may be a gesture performed from a starting swipe position to an ending swipe position located closer to a left edge of the touchscreen than the starting swipe position. For instance, a user may position a finger at a point on the touchscreen and drag the finger across at least a portion of the touchscreen towards a left edge (e.g., reminiscent of a back arrow). It should be understood that other gestures are possible to indicate a restore gesture. In some cases, a user can define the gesture to be used as a restore gesture. In some embodiments, the restore gesture is received on a different user interface screen than a therapy change user interface wherein one or more therapy control element are provided. In various examples, the restore gesture is performed in the opposite direction from a therapy change confirmation gesture that confirms the modification to the therapy control element.

In some examples, in order to cancel a therapy change request, the restore gesture has to be provided within a set time period after the confirmation gesture is received by the user interface. In some such examples, during the set time period one or more dose control signals may be provided to the medicament delivery interface resulting in one or more therapy change deliveries. In some cases, the restore gesture can be received at any time after the confirmation gesture or therapy change. In some cases, the restore gesture restores the control parameter modified during a therapy change to an immediately preceding value. In some cases, the restore gesture restores the control parameter to a value designated as a restore value (e.g., a default value or other designated restore value) or to a most recent value that maintained the subject's blood glucose level with a target setpoint range. The designated restore value may be specific to a subject or AMP 600 or may be determined based on clinical data for a set of subjects. The set of subjects may be subjects that share certain characteristics with the subject using the AMP 600. For example, the set of subjects may be of the same gender, similar age range, similar severity of diabetes, etc.

In some cases, the system may allow the user to modify a therapy change before confirmation. In these cases, the user may modify a therapy control element for a second time to change the corresponding control parameter from a second setting to a third setting.

In some examples, the third setting may be the same as the first setting. In some cases, the first setting or the third setting may be a default setting. In some cases, the first setting or the third setting may be a restore setting.

In some examples, the user may be able to cancel a therapy change delivery after confirming the therapy change and before a therapy delivery based on new settings. In some such examples, an alert may notify the user that a therapy delivery based on new settings will occur shortly.

In some examples, the user may be able to cancel a therapy change delivery triggered based on therapy change made by the user. In these examples, the user may get access to the user interface using a wake action and provide a gesture to cancel the ongoing therapy delivery based on a therapy change delivery.

Therapy Data and Therapy Report

In some examples, AMP 600 may establish a communication with an electronic device 702 to transfer therapy data to the electronic device 702.

In some examples, the therapy data comprises dose or dosage data corresponding to one or more doses of medicament provided by the AMP 600 to the subject. Further, the therapy data may comprise subject data corresponding to a medical or physiological state of the subject as determined by the AMP 600 (e.g., using the sensor 618).

In some examples, the data provided to AMP 600 may include any type of data that may be measured or obtained by the AMP 600 and may include a record of therapy provided by the AMP 600. For example, the data may include a time that therapy was provided, an amount of medicament provided as part of the therapy, a measure of one or more vital signs of the subject, a measure of blood glucose levels (e.g., measured blood glucose level) at different times for the subject, a location of the subject, and the like.

In some cases, the electronic device 702 may analyze the therapy data received from the AMP 600 and generate a therapy report. The therapy report may include data relating to the subject's disease, treatment by the AMP 600, anonymized comparisons with other subjects, statistical data relating to the subject's treatment, statistical data relating to other subjects' disease or disease management, and the like. For example, the therapy report may determine whether the subject is maintaining blood glucose levels on average or whether control parameter settings for the AMP 600 are similar to an average subject with similar physiological characteristics as the subject associated with the AMP 600.

In some examples, the data, therapy data, and/or the therapy report may be stored in a memory of the electronic device 702 and/or at a storage of the networked-computing environment.

In some examples, the therapy report or therapy data that is received and/or generated by a first electronic device may be transferred to a second electronic device via a wired or wireless digital data connection. For examples, therapy data or therapy report may be transferred from a cloud server 708 to a mobile phone 706 or a personal computer 704.

In some cases, the first electronic device may be configured to at least receive a request from the second electronic device to access the therapy report, therapy data or other data received by or stored in the first electronic device. In some cases, the second electronic device may be a computing system of a medical practitioner (e.g., such as a doctor, nurse, physician's assistant, etc.), a guardian of the subject (e.g., subject's parents), an authorized user (e.g., a user authorized by the subject such as spouse, relative, friend, and the like), a healthcare provider, or a device of the subject (e.g., mobile phone, personal computer, tablet and the like).

In some examples, the request to access the therapy data, therapy report, or other data may include an account identifier associated with a user that generated the request. In some examples, the account identifier may comprise a unique identifier associated with the subject. Alternatively, or in addition, the account identifier comprises a unique identifier associated with a user that is authorized to access the therapy report. The user may or may not be the subject. In some aspects of the present disclosure, the method may further include associating the therapy data with the account identifier at a storage of the networked-computing environment. Further, the first electronic device may be configured to determine whether an account associated with the account identifier is permitted to view the therapy report. In some examples, account permissions may be granted and/or modified by the subject. For example, the subject can access an account at a networked computing environment, for example, a cloud network provided by a cloud service provider associated with the subject, and provide one or more identifiers associated with one or more other users to give them permission to access the subject's therapy data or report stored on a cloud server 708.

Responsive to determining that the account is permitted to view the therapy report, the first electronic device may transmit the therapy report to the second electronic device over an encrypted communication channel (e.g., created by using asymmetric key pairs to encrypt the data transmitted). Alternatively, or in addition, a shared secret may be determined for the first and the second electronic device. The shared secret may be used to encrypt the therapy report.

An association between a subject, a clinic, and/or an ambulatory medical device may be performed by association of a device serial number of the AMP 600 with the subject and/or clinic. Further, a user (e.g., a subject, clinician, or parent) can access therapeutic recommendations through the cloud in case either the ambulatory medical device (e.g., an insulin pump) or the CGM sensor fails to function.

In some cases, the method may include receiving an identity or identification information of one or more users that are authorized to access therapy data stored at the networked-computing environment. For example, a user or subject may authorize a clinician or other healthcare provider, a parent or guardian, or other users that the subject desires to have access to the therapy data. The identity information of the one or more users may include any type of information that may identify the user or enable the user to be authenticated. For example, the identity information may include a name, unique identifier (e.g., social security number), an email, an address, a phone number, account information for the user at the networked-computing environment, or any other identifying information.

Managing Control Parameters in an Ambulatory Medical Device

It is often desirable to modify therapy settings of an AMP to improve a health condition of a subject who receives therapy from the AMP. A therapy setting may include values of one or more control parameters that control therapy delivery to a subject. In some AMPs, the control parameters may be changed via therapy change controls provided in a user interface of the AMP. For example, when an ambulatory medicament pump (AMP) controls the blood glucose level in a subject, modifying therapy settings may comprise changing a glucose level set point, a basal dose, a meal dose, a correction does, or type of insulin delivered to the subject. In some cases, a healthcare provider may decide to modify the therapy settings based on the results of medical examinations, blood tests, history of patient's response to therapy provided by the AMP, a combination of these factors or other reasons. In some other cases, the subject or an authorized user of the AMP may desire to modify the therapy settings during a test period in order to evaluate the outcomes of different therapy settings and/or to identify a therapy setting that results in an improvement of the subject's health condition as compared to other settings used during the test period or previously used.

Given the risks associated with selecting incorrect therapy settings by an inexperienced or untrained user, in some embodiments, access to the one or more therapy change controls of an AMP may be limited or restricted. For example, access to certain therapy change controls may be only granted to a user or a subject for a limited time and/or based on an evaluation process that takes into account the user's or the subject's knowledge, experience, level of training, age, mental health or other conditions/factors that may affect the ability of the user or the subject to modify the therapy settings without putting the subject's health at risk or while limiting the risk to the subject. In some examples, access may be only provided to certain therapy change controls required for changing control parameters that are identified based on the health condition of the subject (e.g., determined through medical tests and/or based on therapy data collected during one or more therapy periods). In some examples, the range of values that can be selected for one or more control parameters may be limited to avoid potential harmful effects that may result from setting the value of those parameters outside of the identified "safe range" for a particular subject. In some cases, access to one or more therapy change controls may be provided to a user who may use the AMP for medical research. In yet other cases, access to one or more therapy change controls may be granted to an application developer who is developing, modifying, or debugging a control software used by AMP's control system. In some embodiments, access to a plurality of therapy change controls may be granted for a limited time.

To provide user access to one or more therapy change controls of an AMP without putting the health of a subject at risk, in some embodiments, access to therapy change controls may be managed using a plurality of safe access levels for the AMP. Each of the safe access levels may correspond to one or more control parameters that can be modified by a user or a subject who is qualified to modify the one or more control parameters and/or is associated with the corresponding safe access level. In some examples, access to the selected control parameters may be allowed by enabling access to the corresponding therapy change controls in the AMP (e.g., activating or displaying one or more therapy change control elements on a touchscreen user interface).

In some embodiments, the user may be qualified for a safe access level only during a validity period of the safe access level. After the validity period, the therapy change controls associated with the safe access level may become inactive or unavailable until the user or the subject is revaluated for the same or another safe access level during another validity period. In some embodiments, the AMP may provide the user with the option of extending the validity period of the safe access level. In some embodiments, the validity period may be open ended or may expire when the subject associated with the ambulatory medicament pump changes. In some other embodiments, the validity period can be one hour, one week, one month or other time periods.

In some cases, safe access levels may be categorized based on the capacity of a user for modifying control parameters without causing harm or increasing the risk of harmful effects to the subject. For example, safe access levels may be defined based on age, training, experience, and the like. In other cases, safe access levels may be defined or categorized based on a therapy history of the subject. For example, safe access levels may be defined based on certain events or behaviors identified in the therapy data collected in the previous therapy periods when the subject was receiving therapy from the AMP. In yet other cases, one or more safe access levels may be defined based on a desire to modify therapy settings when the AMP does not provide therapy to human subjects and/or is used to perform investigative research. For example, a safe access level may be dedicated to users who use the AMP for medical research and another safe access level may be dedicated to users who develop applications for the AMP.

In one non-limiting example, four safe access levels (G0 to G3) may be defined for four groups of users where: G0 may be the safe access level for children or certain adults with diminished mental capacity. The therapy change controls available to this group may permit changing the value of one or more control parameters to preset values or back to values previously used. However, other changes to the therapy change controls or changes to other therapy change controls may be restricted. G1 may be a safe access level that is associated with adults who have little experience and/or have only received basic training for using the AMP. The therapy change controls available to this group may enable modification of few control parameters within a safe range. G2 may be s safe access level that is associated with experienced adults and/or have received advanced training. The therapy change controls available to this group may enable modification of several control parameters within a range that may include parameter values that may not be safe to use or that are only safe to use in limited circumstances. G3 may be a safe access level that can be associated with medical researchers or application developers. The therapy change controls available to this group may provide access to a larger number of therapy change controls and allow selecting a wide range of values for each of the control parameters. In some cases, the settings may include values that are unsafe for a typical subject. It should be understood that the aforementioned safe access levels is just one example set of safe access levels. Greater or fewer numbers of safe access levels may exist. Further, the safe access levels may be associated with different types of users and/or may provide different levels of control over the AMP.

For example, the AMP may be associated with three safe access levels (T1 to T3). The three access levels may comprise access levels defined based on the level of training received by a user or the subject who receives therapy from the AMP. T1 may be the safe access level associated with users who have received a basic level of training for the AMP. T2 may be the safe access level associated with users who have received an intermediate level of training for the AMP. T3 may be the safe access level associated with users who have received advanced training for the AMP. The determination of basic, intermediate, or advanced training may be made or specified by a healthcare provider and/or manufacturer of the AMP. In some examples, the therapy change controls available to each of the groups may only provide access to the control parameters that are associated with the requisite training. In some cases, the training may be provided by a healthcare provider, a physician, or a trainer who works under the supervision of the physician or the healthcare provider. In some cases, training data may be used by the healthcare provider or an electronic device to determine the training level for a user or a subject. Training data may comprise, a training certificate (e.g., a digital training certificate), a list of training courses taken or passed, AMP features and control parameters included in the training, and the like.

In some embodiments, new safe access levels may be defined by a manufacturer, healthcare provider, or other users. The new safe access level may be defined based on one or more control parameters of the AMP that are accessible to a user. Further, a new safe access level can be defined by combining existing safe access levels and/or by specifying different criteria to determine whether a user may access a control parameter. For example, three safe access levels may be defined to limit the therapy change controls accessible by different categories of users, such as children, adults who may have different training levels, and/or users who may have limited or reduced mental capacity. In one example, a safe access level may be formed by combining the aforementioned safe access levels G0 and T1, G0 and T2, and G0 and T3. These three new safe access levels may be used to provide access to selected therapy change controls to child users that have received basic, intermediate, or advanced training, respectively.

In some cases, a safe access level may permit selecting specific values of one or more control parameters. In some examples, a safe access level may enable modifying the corresponding control parameters during a set safe access period associated with the safe access level. In some examples, the safe access period for one or more control parameters associated with a safe access level can be different from the safe access period for other control parameters associated with the safe access level.

In some embodiments, a safe access level may be stored in a memory of the AMP as a safe access profile that can include a list of therapy change controls associated with the safe access level. In some examples, a safe access profile may be used by the controller of the AMP (e.g., controller 602 of AMP 600) to enable access to the corresponding therapy change controls upon receiving an indication that the subject receiving therapy from the AMP or an authorized user, is qualified for the safe access level associated with the safe access profile.

In some embodiments, the AMP can be an ambulatory medicament pump (AMP) that controls the blood glucose level in a subject by infusing doses of insulin (or insulin and a counter regulatory hormone such as glucagon) into the subject. In some such embodiments, the AMP may continuously measure the blood glucose level of the subject using a sensor and adjust the infusion time and volume of each medicament dose based at least in part on the measured glucose level. For some such AMPs, some non-limiting example control parameters may include, but are not limited to: 1) dose control parameters for autonomous delivery, such as: glucose level set point, bolus size, basal rate, duration of each therapy, 2) correction factors, 3) carbohydrate ratios, 4) control algorithm parameters such as: predicted CGM user interface, automated correction factors, Kalman filter parameters, control parameters that account for accumulation of insulin in the subject, learning factors, 5) medicament type such as: U200, U100, ultra-rapid insulin, fast-acting insulin, 6) correction doses, and 7) manual meal doses.

In some cases, a safe access level for an AMP may include access to one or more of the above-mentioned control parameters and/or may include specific safe ranges within which these parameters can be changed by the user or the subject.

In some embodiments, access to one or more therapy change controls of an AMP may be provided to the user or the subject, to facilitate identifying the values of one or more control parameters that may result in an improvement of the glycemic control of the subject. In some such embodiments access to the corresponding therapy change controls may enable the user or the subject to actively participate in the adjustment process (e.g., by systematically modifying the control parameters and carefully monitoring the therapy effects). In other embodiments, access to the corresponding therapy change controls may enable the subject (e.g., a child subject or an inexperienced subject) to revert the newly selected values for one or more control parameters to preset values or previously used values, when experiencing adverse health effects during a test period (e.g., a period used to test the therapy effects of newly selected values).

As mentioned above, in some cases the access to therapy change controls may be provided based on a health condition of the subject. As such, safe access levels for an AMP that controls the glucose level in a subject, may be categorized based on previous glycemic control of the subject by the AMP. For example, in some non-limiting cases, there may be three categories of safe access levels: a first category, H1, may be the safe access level for subjects with high risk of hypoglycemia. This access level may provide access to therapy change controls that can be used to adjust one or more control parameters that control the volume or rate of a counter regulatory hormone (e.g., glucagon), needed to avoid hypoglycemia or to increase the blood sugar level during an episode of hypoglycemia. A second category, H2, may be the safe access level for subjects with moderate risk of hyperglycemia. This access level may provide access to the same therapy change controls as the safe access level H1, however the maximum infusion rate or the maximum volume of the medicament infused during each therapy that can be selected by a user who is qualified for this safe access level, may be limited in order to reduce the probability of hypoglycemia. A third category, H3, may be the safe access level for subjects with high risk of hyperglycemia. This access level may provide access to therapy change controls that can be used to adjust control parameters that control the frequency of therapy and/or the amount of medicament delivered during each therapy (e.g., a therapy control parameter associated with accumulation of insulin in the subject), so that the user or the subject can increase the amount of infused medicament during an episode of hyperglycemia. In some embodiments, safe access levels may be categorized based on other aspects of the glycemic control of a subject by the AMP. It should be understood that the above is just one non-limiting example of safe access levels. It is possible for there to exist more or fewer safe access levels. Further each safe access level may be associated with different risk, therapy change controls, user/subject characteristics, and the like.

In some embodiments, a safe access level may be used to allow a subject or a user eligible for the safe access level to change the value of one or more control parameters beyond a normal range that can be selected by users who are not qualified for the access level. In some examples, a safe access level may be used to allow a user or the subject to enable or disable one or more features of the AMP.

As mentioned above, in some embodiments, a safe access level may be limited to a validity period (e.g., a limited or an open-ended validity period, or a validity period that expires when the subject associated with the ambulatory medicament pump changes) after which the user or the subject loses access to the corresponding therapy change controls. For example, the validity period for safe access level H1 described above may be limited to a period during which the subject is expected to have high level of physical activity (e.g., exercise, hiking, swimming and the like). In some cases, a particular user may be granted access to therapy change controls associated with a safe access level for a longer or shorter period than another user.

Method of Determining Eligibility for a Safe Access Level

In some cases, an electronic evaluation device, a healthcare provider (e.g., a physician) or a trainer who provides training for an AMP (e.g., a certified trainer who works in a physician or a healthcare provider's office and or in hospital) may determine one or more safe access levels for which a subject receiving therapy from the AMP or a user of the AMP, is eligible for. In some cases, the user may be authorized by a healthcare provider or the subject to make changes to the settings of an AMP that provides therapy to the subject. In some other cases, the electronic evaluation device, a healthcare provider or a trainer may determine the eligibility of the user or the subject for a selected safe access level. The selected safe access level may be selected by the user, the subject, the healthcare provider, or the trainer. In some examples, the electronic evaluation device, the healthcare provider or the trainer may also determine a validity period for the safe access level granted to the user. In some examples, the validity period may be longer or shorter than the safe access period associated with the safe access level. In some such examples, the AMP may use the validity period provide access to the corresponding therapy change controls. In some embodiments, the electronic evaluation device may determine whether the period during which access to one or more therapy change controls is provided is limited by the validity period (e.g., determined by the electronic evaluation device) or the safe access level period associated with the safe access level.

The electronic evaluation device can be: a cloud server, the AMP that provides therapy to the subject, a personal electronic device of the user or the subject (e.g., a desktop or laptop computer, a mobile phone), a personal electronic device of a healthcare provider or a trainer (e.g., a desktop or laptop computer, a mobile phone), an electronic device used by the healthcare provider or the trainer (e.g., a computer in a physician's or a healthcare provider's office, a compute in medical center or a clinic, and the like).

In some cases, a physician or other healthcare provider may determine a safe access level for a user and/or a validity period for the safe access level, based at least in part on evaluation data available or the user.

The evaluation data may comprise information about the user or the subject including but not limited to: age, mental condition, health condition, level of training, medical history, therapy data, therapy report, past history of managing the AMP, previous safe access levels granted, results of one or more medical tests (e.g., blood analysis, urine analysis, and the like), training data. The physician may have access to the evaluation data stored in a non-transitory memory (e.g., memory in a cloud server or an electronic device) or may receive the evaluation data from the AMP or another electronic device (e.g., through a wired or wireless digital data connection). In some examples, the therapy data may have been collected by an AMP that controls the subject's blood glucose concentration. In such examples, therapy data may include measured values of blood glucose concentration in the subject, doses of insulin (or glucagon) infused into the subject, infusion times and the like.

In some examples, a physician or healthcare provider may use the evaluation data to determine one or more safe access levels for which the subject or the user are qualified for and select a safe access level and a validity period that allow modifying the therapy change control parameters needed to improve a health condition of the subject via therapy.

In some cases, the physician or healthcare provider may provide access to a combination of therapy change controls that are not associated with a single available safe access level, that are associated with multiple safe access levels, or that are split across multiple safe access levels. For instance, in some cases, a first therapy change control may be associated with a first safe access level and a second therapy change control may be associated with a second safe access level. In such cases embodiments, the physician or healthcare provider may create a customized safe access level to enable a subject or a user access to the combination of therapy change controls. Once created, a customized safe access level may be saved and may be available for future use.

In some cases, a trainer of a user of an AMP may determine a safe access level for the user or determine the eligibility of the user for a selected safe access level (e.g., a safe access level selected by a physician or a healthcare provider or a healthcare provider) based at least in part on the level of training provided to the subject or the user. In some such cases, the trainer may use the evaluation data available for the subject or the user, to determine a safe access level for the user. In some cases, the trainer may also determine a validity period for the safe access level determined by the trainer or the selected safe access level.

In some embodiments, the electronic evaluation device may determine a safe access level for a user based on the evaluation data received from an electronic device. In some other embodiments, the electronic evaluation device may determine the eligibility of the subject or the user for a selected safe access level based on the evaluation data received from an electronic device. In some cases, the electronic evaluating device may determine a validity period for the safe access level (determined by the electronic evaluation device) or the selected safe access level.

The evaluation data may comprise information about the subject including but not limited to: age, mental condition, health condition, level of training, medical history, therapy data, therapy report, past history of managing the AMP, previous safe access levels granted, results of one or more medical tests (e.g., blood analysis, urine analysis, and the like), training data. In some cases, the evaluation data may also include one or more prescriptions of the subject (e.g., provided by a healthcare provider), a recommendation from a healthcare provider and the like.

In some examples, the evaluation data may be stored in a memory of the electronic evaluation device. In some other examples, the electronic evaluation device may receive the evaluation data from an electronic device via a wired or wireless data link. The electronic device may comprise: the AMP, a cloud server, a personal electronic device of a health care provider or a trainer, an electronic device used by a health care provider or a trainer or a personal electronic device of the subject or the user.

In some embodiments, the electronic evaluation device may determine a safe access level for a user in response to receiving a trigger. The trigger may be an access request received from an electronic device (e.g., a cloud server, a personal electronic device of the user, a healthcare provider or a trainer, or an electronic device used by the healthcare provider or the trainer), via a wired or wireless data connection. Upon receiving the access request, the electronic evaluation device may use the evaluation data available for the user to determine a safe access level for which the user may be eligible for. The validity period for the safe level access may be included in the access request or may be determined by the electronic evaluation device.

In some examples, the electronic evaluation device 802 may determine the eligibility of the user for a selected safe access level in response to receiving a trigger. In some cases, the trigger may be an eligibility request received from an electronic device (e.g., a cloud server, a personal electronic device of the user, a healthcare provider or a trainer, or an electronic device used by the healthcare provider or the trainer), via a wired or wireless data connection. In some cases, a subject who uses an AMP to control his or her blood glucose level, may send an eligibility request for a safe access level to an electronic evaluation device, in order to gain access to one or more therapy change controls associated with the safe access level. For example, the subject may need access to therapy change controls associated with changing the type of insulin received. The subject may select a safe access level, that includes therapy change controls for changing the insulin type and send an eligibility evaluation request for a safe access level to eth electronic evaluation device. After receiving the eligibility request, the electronic evaluation device may search for a prescription for a new type of insulin. If the prescription is found, the electronic evaluation device may search for other types of evaluation data (e.g., training level, age, prior safe access level granted, physician recommendation and the like), to further evaluate the eligibility of the subject for the safe access level.

In some implementations, the electronic evaluation device 802 may determine the eligibility of the user (or the subject) for a selected or requested safe access level using an interactive evaluation process. The interactive evaluation process may include an interaction with the user or the subject via one or more user interfaces of the electronic evaluation device 802 (e.g., a touchscreen display, a keyboard, a monitor, a mouse, an interactive software interface, an interactive web page and the like). For example, the interactive evaluation process may include displaying a set of queries, corresponding to one or more use cases of the AMP 600, to the user and the receiving a set of responses to the set of queries. Subsequently, the electronic evaluation device 802 may evaluate the set of responses to obtain an evaluation score and use the evaluation score to determine selected safe access level for the user.

Providing Access Based on a Safe Access Level

As described above, the access to one or more therapy change controls of an AMP may be enabled only if a safe access level that is associated with the one or more therapy change controls is granted to a user of the AMP or a subject receiving therapy are from the AMP. In some embodiments, once the safe access level is granted to the user or the subject (e.g., based on an evaluation process performed by a trainer, physician or an electronic evaluation device), the AMP may enable access to one or more therapy change controls upon receiving a passcode (e.g., a time-based passcode) via a user interface (e.g., a passcode entry interface), or receiving an access signal (e.g., from an electronic access device). The access signal can be an analog or a digital signal. In some cases, the information regarding the safe access level granted to the subject may be encoded in the access signal. For example, the granted safe access level signal, one or more therapy change controls associated with the grated safe access level, and/or a validity period of the granted safe access level may be encoded in eth access signal.

In some embodiments, the access to one or more therapy change controls of an AMP may be passcode protected. In some such embodiments, when a safe access level and a validity period are determined for a subject who receives therapy from an AMP (or an authorized user of the AMP), an electronic access device or the electronic evaluation device may generate and send a passcode (e.g., a time-based passcode), associated with the safe access level and the validity period, to the AMP. In some examples, the time-based passcode and the validity period are stored in a memory of the AMP and may be used to provide access to the therapy change controls corresponding the safe access level during the validity period. In some such examples, the time-based passcode may expire after the validity period.

In some other embodiments, when a safe access level is determined for a subject who receives therapy from an AMP (or an authorized user of the AMP), an electronic configuration device may generate a passcode (e.g., a time-based passcode), associated with the safe access level based at least in part on a public identifier received from the AMP. In some such embodiments, the passcode may be provided directly to the user or the subject by an operator or administrator of the electronic configuration device over a communication link (e.g., a wired or wireless phone line). In some examples, the operator or the administrator may provide the passcode via a voice call, voice message, or text message. In some other examples, the electronic configuration device may send the passcode via a text message to the user's phone (e.g., a smart phone).

In some cases, where a healthcare provider or a trainer determines the eligibility of the subject or the user for a safe access level, they may use an electronic access device to generate the time-based passcode and send it to the AMP. An electronic access device can be a cloud server, a personal electronic device of a healthcare provider or a trainer (e.g., a desktop, laptop computer, or a mobile phone), or an electronic device used by the healthcare provider or the trainer (e.g., a computer in a physician's or healthcare provider's office, a compute in medical center or a clinic, and the like). For example, a physician or a healthcare provider may select the safe access level and send the corresponding time-based passcode to the AMP using a user interface of the electronic access device.

In some embodiments the electronic evaluation device that has determined the safe access level and the validity period for the user or has determined the eligibility of the user for a selected safe access level, may generate the corresponding time-based passcode and automatically transmit it to the AMP using a wired or wireless data connection.

When a time-based passcode associated with a safe access level is received and stored in a memory of the AMP, the controller of the AMP may provide a passcode entry element on a user interface of the AMP where the user or the subject can provide a passcode by interacting with the user interface. In some examples, the AMP may also receive (e.g., from the electronic evaluation or access device) a validity period for the safe access level. In such examples, the passcode may expire after the validity period.

In some embodiments, the access to one or more therapy change controls of an AMP may be enabled using an access signal. In some such embodiments, when the a safe access level and a validity period are determined for a subject who receives therapy from an AMP (or an authorized user of the AMP), an electronic access device or the electronic evaluation device may generate and send an access signal, associated with the safe access level and the validity period, to the AMP. In these examples, upon receiving the access signal, the AMP may provide user access to one or more therapy change controls associated with the safe access level during the validity period.

In some embodiments, the therapy change controls associated with a safe access level may be stored in a memory of the AMP as a safe access profile. In some examples, the AMP may store a plurality of safe access profiles associated with a plurality of safe access levels (e.g., safe access-levels G0-G3 or T1-T3 described above). A safe access profile may comprise a list of therapy change controls for changing control parameters associated with the corresponding safe access level. Alternatively, or in addition, the safe access profile may include a range of values that may be selected for the control parameters. In some examples, the safe access profile may comprise a safe access period for the safe access level. In these examples, the access to the corresponding therapy change controls may be denied after the safe access period. In some example, a validity period received with the safe access level, may reduce or extend the safe access period for a safe access level.

In some embodiments, instead of generating and sending a passcode, the electronic access device or the electronic evaluation device may send an access signal to the AMP to enable access to the therapy change controls associated with a safe access level granted to a user of the AMP. The access signal may be transmitted from the electronic access device or the electronic evaluation device via a wireless data connection (e.g., via a LAN, WAN, Bluetooth, or an NFC signal). In some examples, the wireless data connection may be a direct end-to-end connection. When the access signal is received by the AMP, the AMP may provide access to the therapy change controls included in the safe access profile associated with the safe access level. In some examples, the access signal received by the AMP may enable access to the therapy change controls, associated with the granted safe access level during a validity period determined by the electronic evaluation device, a healthcare provider or a trainer.

In some examples once a safe access level is determined, it may be stored in the electronic evaluation device, electronic access device, the AMP or other electronic devices (e.g., an electronic device of the user, the subject, the healthcare provider, or the trainer). In some examples, one or more determined safe access levels that have been stored, may be used to provide access to the corresponding therapy change controls on a new AMP. In some examples, one or more determined safe access levels that have been stored, may be used to extend the safe access period or determining eligibility for the same and or another safe access level at a later time.

In some embodiments, an authorized user or a subject who has been granted a safe access level can change one or more of the corresponding control parameters to create a personalized therapy setting. A personalized therapy setting may be used for an unlimited time period or set indefinitely, expire after a set time period (as may be set, for example, by a physician), expire at the end of the safe access period (e.g., when time-based password expires), or expire after use or modification of a therapy change control (either once or a set number of times). In some cases, the user or the subject may change the personalized setting to a standard setting (e.g., shared setting) at any time or before a set period. In some cases, the personalized therapy setting may be used until a trigger occurs or until a new therapy setting is received.

In some examples, if the AMP detects that an unsafe level of therapy is delivered or may be delivered as a result of changes made based on a safe access level, the AMP may automatically change the value of the corresponding control parameters to safe values or may reject a particular change to a therapy change control. Safe values may be previously used values, values determined by the AMP based on past or present therapy data, or other values stored in a memory of the AMP. For example, if the blood glucose level of a subject who receives therapy from an AMP that provides insulin to the subject drops below a threshold value as a result of reducing the glucose set point during a safe access period, the controller of the AMP may automatically change the glucose set point back to an earlier set value.

In some embodiments, the validity period of a safe access level granted to a user or a subject receiving therapy from the AMP, may be extended by the user or the subject. For example, the user or the subject may generate a request for extension of the validity period via a user interface of the AMP. In some cases, the request for extension may be transmitted to an electronic evaluation device that determines whether the requested extension can be granted the user or the subject. Upon determining that the extension can be granted, the electronic evaluation device may send an extension signal to the AMP. Upon receiving the extension signal AMP may extend the expiration of the corresponding time-based passcode to a new ending time or enable access to the corresponding therapy change controls until the new ending time. In some examples, the ending time may be included in the request for extension. In some other examples, the ending time may be determined by the electronic evaluation device. In some embodiments, the user may send the request for extension to a healthcare provide or a trainer. In some such embodiments, the request for extension may be transmitted from the AMP to an electronic device of the trainer or the healthcare provider, directly or via an intermediary electronic device. The healthcare provider or the trainer, may approve the new ending time included in the request for extension or determine another ending time. The healthcare provider or the trainer, may use an electronic access device to extend the validity period of a granted safe access level.

In some case, after changing the values of one or more control parameters associated with a granted safe access level, a user or a subject may desire to restore previously used values of the one or more control parameters. In some such cases, the AMP may provide the user or the subject with the option of restoring previously used values of the one or more control parameters. For example, the AMP may provide a user interface (e.g., a menu on a touchscreen interface) that includes one or more restoring elements that may enable restoring the previously used values of the one or more control parameters.

As mentioned above, the validity period of a safe access level granted to a user (or the subject receiving therapy from the AMP 600), may be extended by the user or the subject. In some implementations, extending the validity period may require re-evaluating the eligibility of the user for the safe access level that was previously granted to the user based on an initial evaluation process described above. In some cases, unlike the initial evaluation process, the re-evaluation process may not involve the physician, the healthcare provider or the trainer. For example, the subject may send a validity period extension request to the electronic evaluation device 802 (e.g., via a wired or wireless connection, or a user interface), and the electronic evaluation device 802 may re-evaluate the eligibility of the user for the safe access level based on a record of the user's use of the pump during the validity period. For example, the electronic evaluation device 802 may determine whether changes made by the user to the one or more therapy control parameters resulted in increased occurrences or risk of hypoglycemia or hyperglycemia during the validity period. If the electronic evaluation device 802 determines that user's use of the pump during the validity period did not result in increased occurrences or risk of hypoglycemia or hyperglycemia during the validity period, it may extend the validity period of the safe access level and allow the user to use the corresponding control settings of the AMP during an extended validity period. In some cases, the electronic evaluation device 802 may also use the evaluation data 810, which may have been updated during the validity period, to re-evaluate the eligibility of the user for the safe access level. In some cases, the electronic re-evaluation device may use the interactive evaluation process described above to re-evaluate user's eligibility for the safe access level for an extended validity period. In some cases, if the electronic evaluation device 802 determines that user's use of the pump during the validity period resulted in periods of hypoglycemia or hyperglycemia during the validity period, it may deny the validity period extension request and notify the user (e.g., via a user interface of the AMP 600 or a user interface of the electronic evaluation device 802).

Additional Features

In some embodiments, the settings (e.g., therapy settings) of an AMP may be changed remotely using an electronic control device. For example, an electronic control device may transmit a command to the AMP via a wired or wireless digital data link to change the values of one or more control parameters of the AMP or change certain settings of the AMP. The electronic control device can be personal computer, a mobile phone a cloud server or other computing devices configured to communicate with the AMP. In some examples, the data connection between the electronic control device and the AMP may be established using one of the methods described with respect to FIG. 7.

In some embodiments, when a user or a subject obtains a new AMP, a onetime passcode may be provided to the user or the subject that can be used to download the therapy settings and subject's data from a remote electronic device, in order to activate and update the new AMP. In some such embodiments, if the new device is activated and updated during the validity period of a safe access level (previously granted to the user or the subject), the AMP may allow the user or the subject to access the corresponding therapy change controls using the previous passcode associated with the safe access level. In some examples, if the new AMP is activated and updated during the validity period of a safe access level, the AMP may automatically enable access to the corresponding therapy change controls without requesting a passcode.

EXAMPLE EMBODIMENTS

Figure 8A:
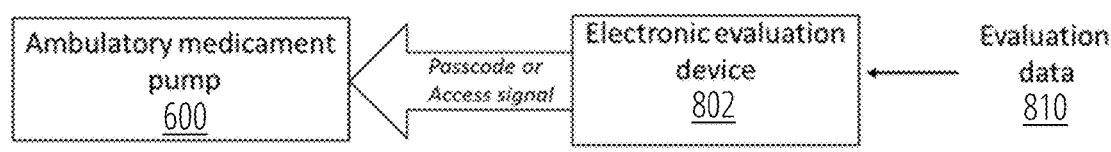
FIG. 8A shows a block diagram of an example system for managing access to therapy settings of an AMP.
Figure 8B:
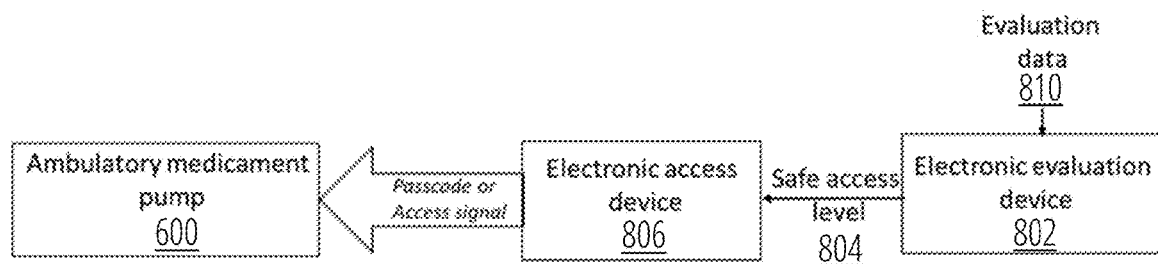
FIG. 8B shows a block diagram of another example system for managing access to therapy settings of an AMP.
Figure 8C:
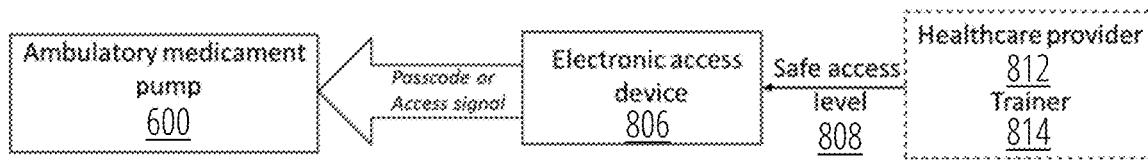
FIG. 8C shows a block diagram of another example system for managing access to therapy settings of an AMP.

FIG. 8A-FIG. 8C present three example embodiments for managing access to one or more therapy change controls of AMP 600 based on safe access levels.

In the embodiment shown in FIG. 8A, an electronic evaluation device 802 may determine a safe access level for the user or the subject based on received evaluation data 810. The evaluation data may be received via a wired or a wireless connection with: an electronic device of a trainer or a healthcare provider, the AMP 600, or a cloud server 708. In some examples, the evaluation data 810 may be stored in the electronic evaluation device 802. In some other examples, the evaluation data 810 may be received at least partially via a user interface of the electronic evaluation device 802. For example, a healthcare provider or a trainer may provide the evaluation data 810 via an interaction with the user interface.

In some examples, the electronic evaluation device 802 may determine the eligibility of the user or the subject for a selected safe access level (e.g., a safe access level selected by the user, the subject, a healthcare provider or a trainer) based on received evaluation data 810. In some examples, the selected safe access level may be included in the evaluation data 810. In some other examples the selected safe access level may be received from the AMP 600, a personal electronic device of the user, a personal electronic device of the healthcare provider or the trainer, or an electronic device used by a healthcare provider or a trainer. For example, a healthcare provider may determine that the user needs or should have access to one or more therapy change controls associated with a safe access level and the healthcare provider may select that safe access level. Subsequently, the healthcare provider may use his/her mobile phone, personal computer or computer in a health clinic, to send a request to the evaluation device 802 for determining the eligibility of the user for the selected safe access level.

Once a safe access level for which the user or the subject is eligible, or the eligibility of the user or the subject for a selected safe access level is determined, the electronic evaluation device 802 may generate and send a passcode to the AMP 600 to enable access to the corresponding therapy change controls upon receiving the same passcode from the user (e.g., via a user interface of the AMP 600). The passcode may be sent to the AMP 600 via a wired or wireless data connection. In some examples, the passcode may be a time-based passcode that can be only used to get access to the corresponding therapy change controls within a validity period. In some examples, the validity period may be determined by the electronic evaluation device 802. In some examples, the validity period may be included in the evaluation data 810. In some examples, the validity period may be included in the access request for a selected safe access level (e.g., sent by a physician or a healthcare provider or a trainer). In some examples, upon receiving the passcode the AMP 600 may notify the user that a passcode is received (e.g., by displaying an indicator in a main screen displayed on a touchscreen display). If the passcode is a time-based passcode, AMP 600 may also display the validity period of the safe access level on a display of the AMP (e.g., on a touchscreen display).

As illustrated in FIG. 8B, in some embodiments, the passcode (e.g., a time-based passcode) may be sent to the AMP 600 by an electronic access device 806 that receives a safe access level from an electronic evaluation device 802 that has determined the safe access level for which the user or the subject is eligible for, or the eligibility of the user or the subject for a selected safe access level 804. In some examples, the safe access level 804 may be transmitted via a wired or wireless data connection to the electronic access device 806. In some examples, the electronic evaluation device 802 may also send an indication of a validity period for the safe access level to the electronic access device 806.

As illustrated in FIG. 8C, a healthcare provider 812 or a trainer 814 may select a safe access level 808 and determine the eligibility of the user or the subject for a selected safe access level 808. In some such embodiments, the healthcare provider or the trainer may provide the safe access level 808 to an electronic access device 806, for example, via a user interface of the electronic access device 806. In some examples, the healthcare provider 812 or the trainer 814 may send the safe access level 808 to the electronic access device 806 using his/her personal electronic device via a wired or a wireless link. Upon receiving the safe access level 808, the electronic access device 806 may send a passcode to the AMP 600. In some examples, the passcode may be a time-based passcode that can be only used to get access to the corresponding therapy change controls within a validity period. In some such examples, the healthcare provider 812 or the trainer 814 may also determine a validity period for the safe access level 808 and provide it to the electronic access device 806 along with the safe access level.

In some cases, instead of a passcode or a time-based passcode, the electronic evaluation device 802 (in FIG. 8A) or the electronic access device 806 (in FIG. 8B and FIG. 8C) may send an access signal to the AMP 600. Upon receiving the access signal, the AMP 600 may provide access to the therapy change controls associated with the determined or the selected safe access level. For example, when an access signal is received by the AMP 600, the AMP 600 may activate one or more inactive therapy change control elements (associated with a safe access level) in a therapy change interface of the AMP 600. In some examples, upon receiving the access signal, the AMP 600 may notify the user or the subject that safe access level has been granted (e.g., by providing an indicator in a main screen displayed on a touchscreen display). If the safe access level is provided during a validity period, the AMP 600 may also display the validity period of the granted safe access level on a display of the AMP 600.

In some cases, when the eligibility of the subject or the user for a safe access level is determined or a safe access level have been determined for the subject or the user, the electronic evaluation device 802 (in FIG. 8A), electronic access device 806 (in FIG. 8B and FIG. 8C) or other remote electronic devices may send a signal or a message the AMP 600 indicating that a safe level access has been granted to the user of AMP 600 or to the subject receiving therapy from AMP 600. In some such cases, upon receiving the signal or the message, AMP 600 may establish a data connection via a digital data interface (e.g., a digital data interface of the communication system 622) with electronic evaluation device 802 or electronic access device 806, in order to receive a passcode or an access signal.

Figure 9:
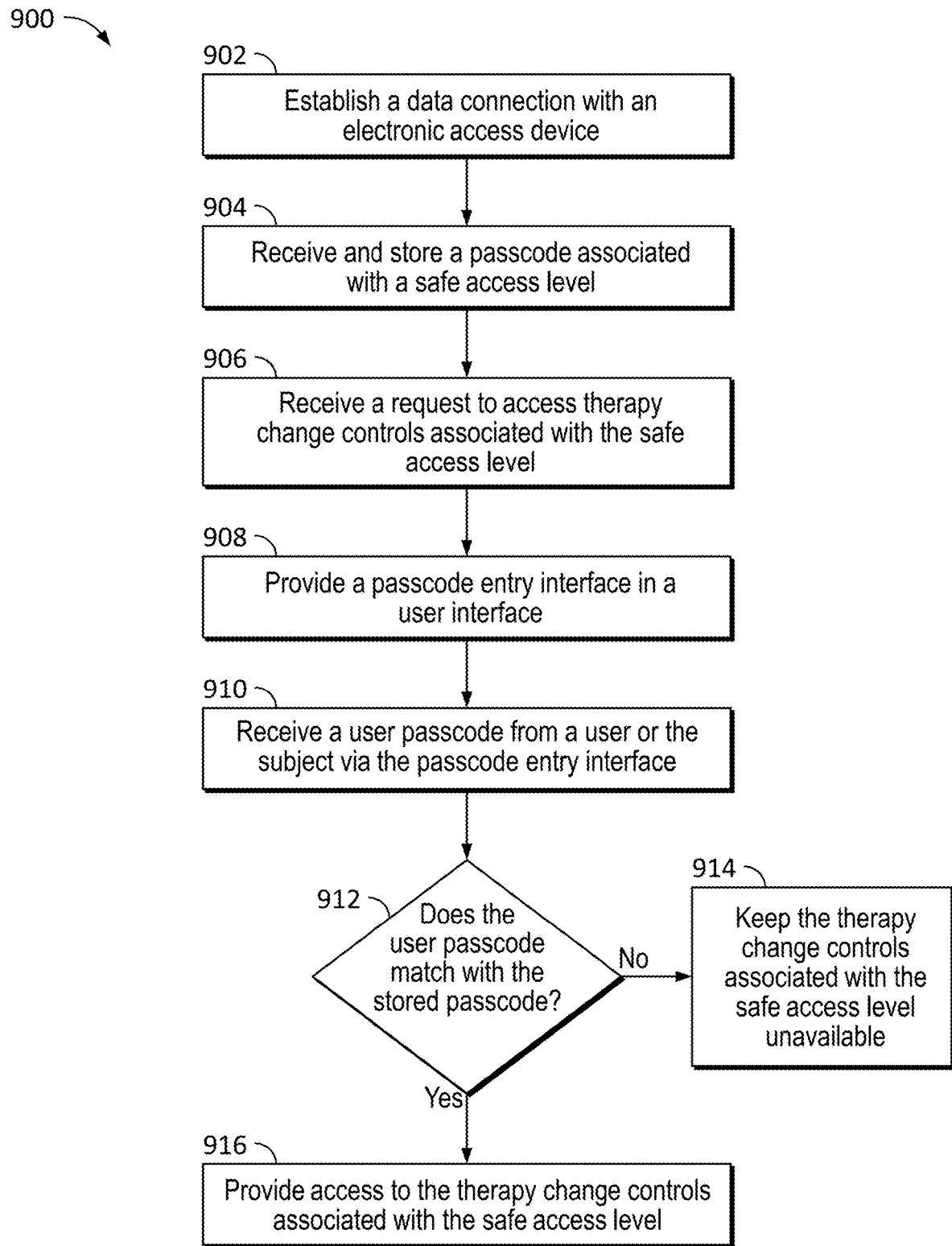
FIG. 9 is a flow diagram showing an example of a computer-implemented method that may be used by an AMP to provide access to the therapy change controls associated with a safe access level using a passcode.

FIG. 9 presents a flowchart of an example process for providing access to the therapy change controls associated with a safe access level in accordance with certain embodiments.

The process 900 may be performed by an ambulatory medicament pump (AMP), such as an AMP that provides insulin therapy to a subject, an AMD 100, or a glucose level control system. For example, the process 900 may be performed by one or more elements of the AMP 600 (e.g., the controller 602). In some cases, at least certain operations of the process 900 may be performed by a separate computing system. Although one or more different systems may perform one or more operations of the process 900, to simplify discussions and not to limit the present disclosure, the process 900 is described with respect to particular systems.

The process 900 may be performed automatically and without user interaction. In some cases, a user or the subject 620 receiving therapy from the AMP 600 may trigger the process 900 via a command or interaction with a user interface. However, once the process 900 is triggered, the process 900 may be performed automatically. In some examples, the trigger may be a command received from an electronic device (e.g., an electronic device of a healthcare provider or a trainer, a cloud server or the like). Further, the trigger may be based on the activation or first time use of the AMP 600 by the subject 620.

The process 900 begins at block 902 where the AMP 600 establishes a communication connection with an electronic access device 806 or an electronic evaluation device 802. The communication connection may be established over a wired or a wireless digital data link.

At block 904, the AMP 600 receives a passcode associated with a therapy access level from the electronic access device 806 or the electronic evaluation device 802. In some examples, the passcode may be a time-based passcode. In these examples the AMP 600 may also receive an indication of a validity period for the time-based passcode from the electronic access device 806 or the electronic evaluation device 802. In some examples, the AMP 600 may store the passcode in a memory 610 of the AMP 600.

At block 906, the AMP 600 may receive a request from the user or the subject to access one or more therapy change controls associated with the safe access level. The request may be a user interaction with a therapy change control element in a therapy change user interface menu of the AMP 600.

Once the request is received, at block 908, the AMP 600 may provide a passcode entry interface on a user interface of the AMP 600. In some examples, the passcode entry interface may be a passcode entry user interface in a main screen displayed on a touchscreen display of the AMP. In some other examples, the passcode entry interface may be a user interface in a therapy change screen displayed on a touchscreen display of the AMP 600. A user may activate the therapy change screen by interacting with another user interface, such as a user interface that references the therapy change screen.

At block 910, the AMP 600 may receive a user passcode from the user or the subject. The AMP 600 may receive the user passcode via an interaction with the passcode entry interface. In some examples, the user may provide the user passcode using a physical keyboard or a keyboard displayed on a touchscreen display.

At decision block 912, the AMP 600 may determine whether the user passcode matches with the passcode (e.g., a time-based passcode) received at block 904. Determining whether the user passcode matches the passcode received at the block 904 may include comparing the two passcodes. Comparing the passcodes may first include decrypting the user passcode and comparing it to the stored passcode. Alternatively, or in addition, the user passcode may first be hashed, and then the hashed user passcode may be compared to the stored passcode. In some cases, the use of hashing may be used to both determine that the passcodes match and to determine that the user passcode has not been corrupted or is free of errors.

If at decision block 912 it is determined that the user passcode does not match with the time-based passcode, the process proceeds to block 914 where the AMP 600 maintains the unavailability of or does not permit access to the therapy change controls associated with the safe access level. In some embodiments, at decision block 912, the AMP 600 may determine whether the user passcode is received during the validity period.

If at the decision block 912 the AMP 600 determines that the user passcode matches with the passcode (e.g., time-based passcode) received and stored at block 904 (e.g., time-based passcode), at block 916, the AMP 600 provides access to the therapy change controls associated with the safe access level. In some cases, when the passcode is a time-based passcode, at block 916 the AMP 600 may provide access to the therapy change controls if the user passcode is received during the validity period (as determined at decision block 912). If the user passcode is received after the validity period is expired, the user passcode may be ignored. Alternatively, or in addition, a warning or error message may be output indicating that the user passcode is expired or not valid.

In some examples, the access to the therapy change controls may be provided by activating one or more therapy change control elements available in a therapy change interface (e.g., a therapy change screen displayed on a touchscreen display of the AMP 600). In some other examples, the user may first activate the therapy change interface without using the user passcode. The therapy change interface may include a plurality of therapy change control elements that are inactive. Upon user's interaction with one of the inactive therapy change control elements, a passcode entry interface may be provided on the therapy change interface (block 908). In some such examples, at block 916, one or more therapy controls from the plurality of the therapy change control elements (e.g., those associated with the safe access level) may become active. In some examples, the therapy change control elements may become inaccessible (e.g., become locked or disappear from a touch screen display) after the validity period associated with the granted safe access level.

Figure 10:
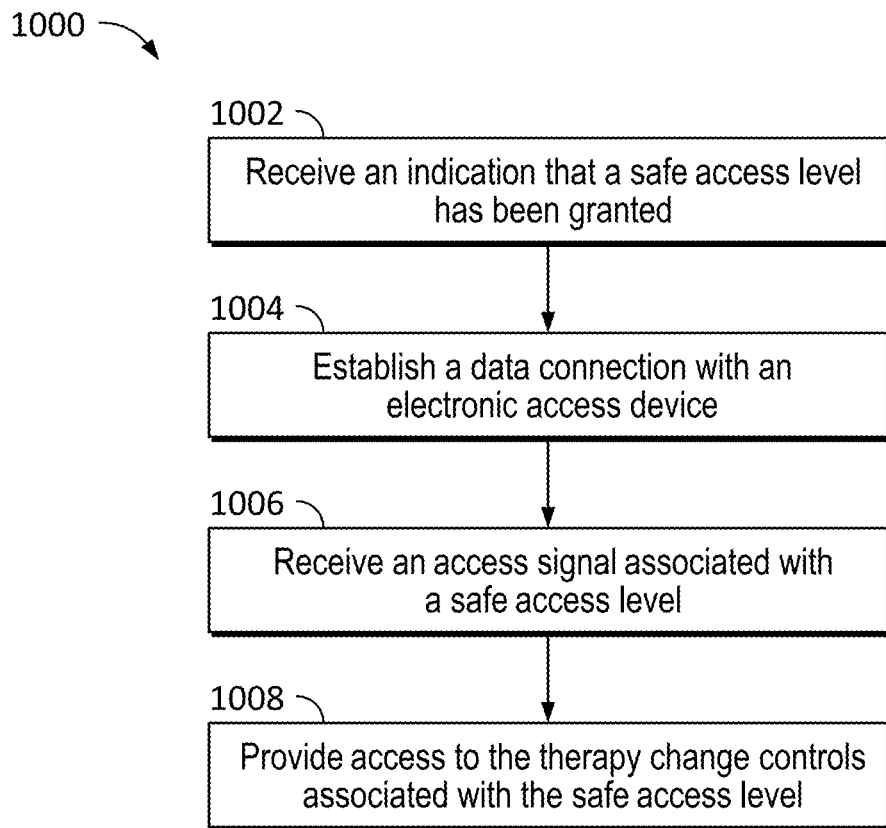
FIG. 10 is a flow diagram showing an example of a computer-implemented method that may be used by an AMP to provide access to the therapy change controls associated with a safe access level using an access signal.

FIG. 10 is a flow diagram showing an example of a computer-implemented process 1000 that may be used by an AMP 600 to provide access to one or more therapy change controls associated with a safe access level granted to a user of the AMP 600 or a subject receiving therapy from the AMP 600 using an access signal. The process 1000 may include one or more features described with respect to process 900.

The process 1000 begins at block 1002 where the AMP 600 receives an indication that a safe access level has been granted to a user of the AMP 600 or a subject receiving therapy from the AMP 600. In some examples, the granted safe access level may be a safe access level selected by a healthcare provider or a trainer. In some other examples, the granted safe access level may be a safe access level determined by an electronic evaluation device 802. The indication can be a signal, or a message received from the electronic evaluation device 802, an electronic access device 806, or another remote electronic device (e.g., an electronic device of a healthcare provider or a trainer).

Upon receiving the indication, at block 1004 the AMP 600 establishes a digital data connection with an electronic access device 806 or an electronic evaluation device 802. The digital data connection may be established over a wired or a wireless digital data link.

At block 1006 the AMP 600 receives an access signal associated with the safe access level from the electronic access device 806 or the electronic evaluation device 802. The AMP 600 may receive the access signal via a digital data interface. The digital data interface may be digital interface of the communication system 622 of the AMP 600. In some examples, in addition to the granted safe access level, the access signal may carry information about a validity period of the granted safe access level. In these examples, the validity period may be saved in a memory 610 of the AMP 600.

Upon receiving the access signal, at block 1008, the AMP 600 may provide access to the therapy change controls associated with the granted safe access level. Access to the therapy changes controls may be provided during the validity period associated with the granted safe access level. If the validity period is expired, access to the therapy change controls may be rescinded or denied. In some other examples, the access to the therapy changes controls may be provided during the safe access period associated with the granted safe access level. In yet other examples, the access signal may carry information that may be used by the AMP 600 to determine whether to limit access to the therapy control changes for a validity period or particular time period associated with the safe access level.

In some embodiments, at block 1008, the access to the therapy change controls may be provided by displaying one or more therapy change control elements on a user interface (e.g., a touchscreen interface) provided by the user interface system 616 of the AMP 600. In some other embodiments, the access to one or more therapy change controls may be provided by unlocking one or more therapy change control elements in a menu displayed on a user interface provide by the user interface system 616 of the AMP 600. The user or the subject may use the one or more therapy change control elements to change the value of one or more control parameters corresponding to the one or more therapy change controls. In some examples, the therapy change control elements may become inaccessible (e.g., become locked or disappear from a touch screen display) after the validity period associated with the granted safe access level.

Figure 11:
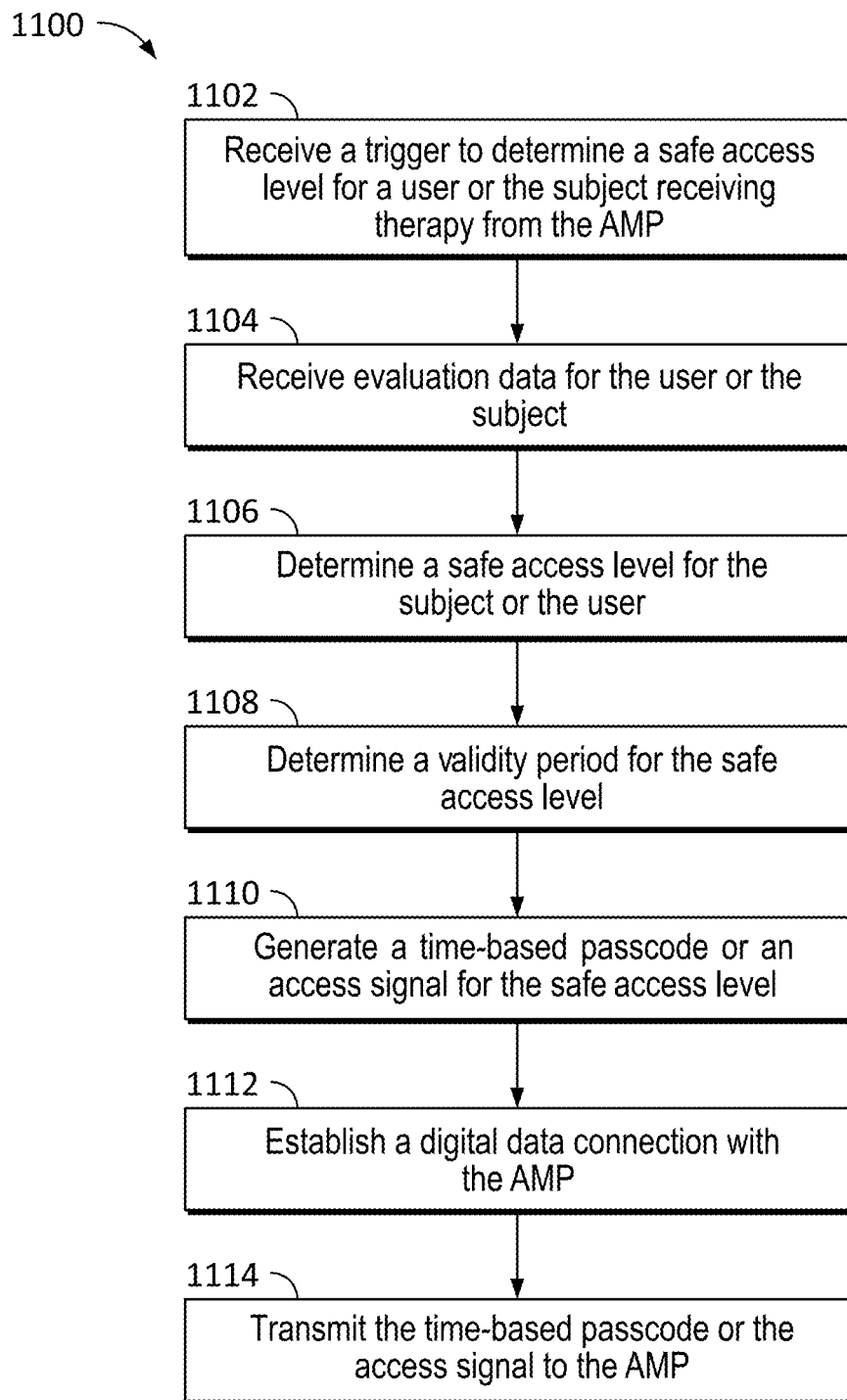
FIG. 11 is a flow diagram showing an example of a computer-implemented method that may be used by an electronic evaluation device to determine a safe access level for a user or a subject and provide access to therapy change controls associated with the determined or selected safe access level.

FIG. 11 is a flow diagram showing an example of a computer-implemented method that may be used by an electronic evaluation device to determine a safe access level for a user or a subject and provide access to therapy change controls associated with the safe access level. The process 1100 may include one or more features described with respect to embodiments presented in FIG. 8A.

The process 1100 begins at block 1102 where the electronic evaluation device 802 receives a trigger to determine a safe access level for a user of the AMP 600 or a subject receiving therapy from the AMP 600. As the described above, the trigger may be a request received from an electronic device (e.g., AMP 600, a cloud server, a personal electronic device of the user, a healthcare provides, or a trainer).

At block 1104 the electronic evaluation device 802 receives evaluation data 802 for the user and/or the subject from an electronic device (e.g., AMP 600, a cloud server, a personal electronic device of the user, a healthcare provider, or a trainer).

At block 1106, the electronic evaluation device 802 determines a safe access level for the user or the subject based on the evaluation data 802 received at block 1104.

At block 1108, the electronic evaluation device 802 determines a validity period for the safe access level during which the user may change one or more control parameters associated with the determined safe access level. In some examples, the validity period may be included in the request received at block 1102 and the process may omit the operations associated with block 1108. In some other examples, the safe access profile associated with the safe access level may include a safe access period. In some such examples, the safe access period may be used as the validity period.

At block 1110, the electronic evaluation device 802 generates a time-based passcode that expires at the end of the validity period. In some embodiments, instead of a time-based passcode, the electronic evaluation device 802 generates and access signal associated with the determined safe access level. In some examples, in addition to the determined safe access level the access signal may carry information about the validity period of the determined safe access level.

At block 1112, the electronic evaluation device 802 establishes a data communication connection with the AMP 600.

At block 1114, the electronic evaluation device 802 transmits the time-based passcode or the access signal to the AMP 600.

Figure 12:
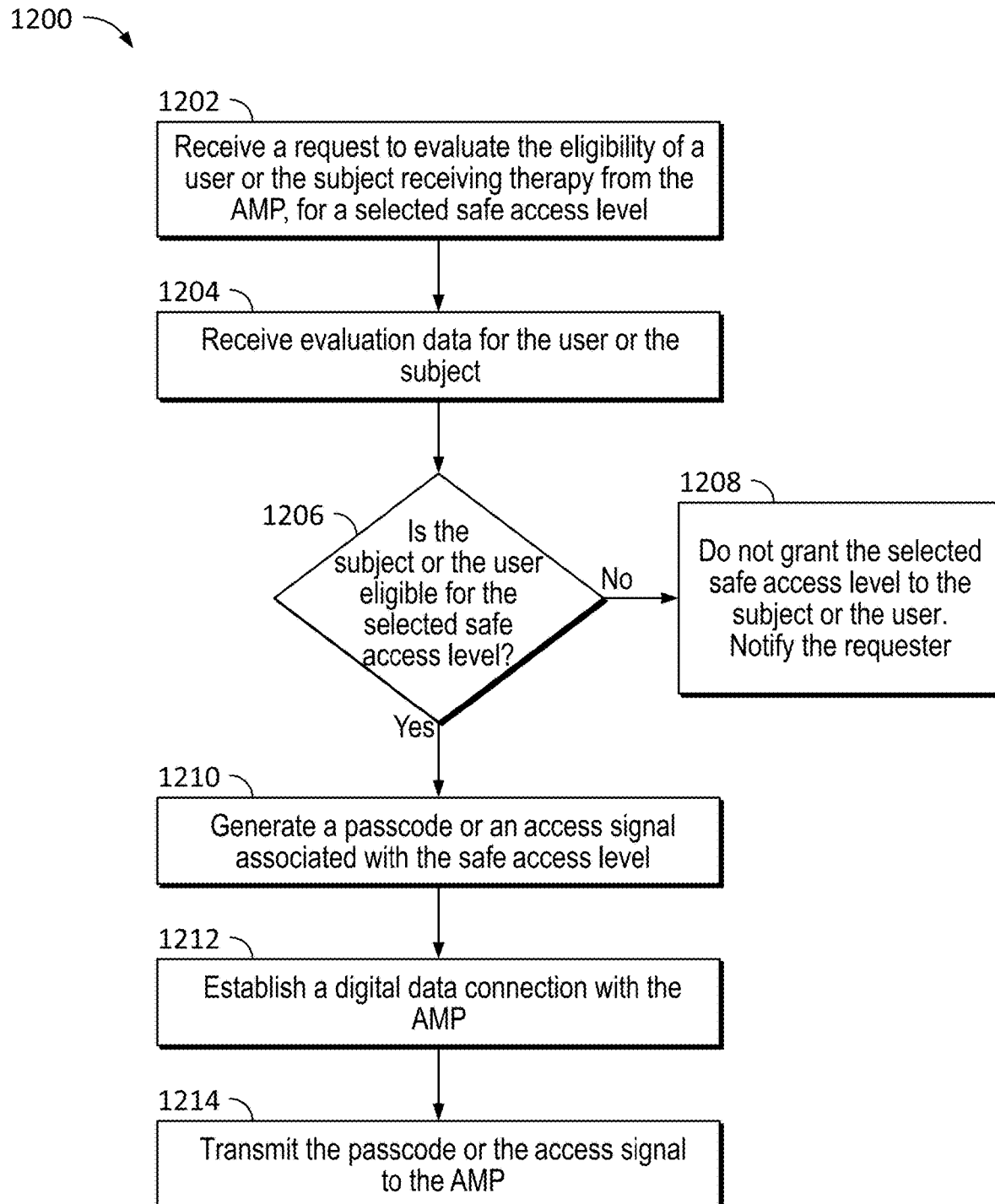
FIG. 12 is a flow diagram showing an example of a computer-implemented method that may be used by an electronic evaluation device to determine the eligibility of the user or the subject for a selected safe access level, and provide access to therapy change controls associated with the selected safe access level.

FIG. 12 is a flow diagram showing an example of a computer-implemented method that may be used by an electronic evaluation device to determine the eligibility of a user of AMP 600 or the subject receiving therapy from the AMP 600 for a selected safe access level and providing access to therapy change controls associated with the selected safe access level.

The process 1200 may include one or more methods described with respect to embodiments presented in FIG. 8A.

The process 1200 begins at block 1202 where the electronic evaluation device 802 receives a request for determining the eligibility of the user of the AMP 600 or the subject receiving therapy from the AMP 600, for a safe access level. In some cases, the request may be received from the AMP 600, a cloud server or a personal electronic device of the user, the subject, a healthcare provider or a trainer. In some other cases, the request may be received from an electronic device used by the healthcare provider or the trainer. In some examples, the request may include a validity period for the selected safe access level.

At block 1204, the electronic evaluation device 802 receives evaluation data for the user or the subject from an electronic device through a wired or wireless digital data link. In some examples, the evaluation data may be stored in the electronic evaluation device 802. In some such cases, operations associated with the block 1204 may be omitted or optional.

At block 1206, the electronic evaluation device 802 determines the eligibility of the user or the subject for the selected safe access level based at least in part on the received evaluation data at block 1204 or the evaluation data stored in the electronic evaluation device 802. If at block 1206 it is determined that the user or the subject is not eligible, the process moves to block 1208 where the electronic evaluation device 802 rejects the request by not granting the selected safe access level to the user or the subject and notifies the requester (a healthcare provider, the user, the subject or the trainer) about the rejection. For example, the electronic evaluation device 802 may send a message (e.g., a text message) to the electronic device used to send the request. In some examples, the message may include a reason for rejecting the request.

If at block 1206 it is determined that the user or the subject is eligible for the selected safe access level, the process moves to block 1210 where the electronic evaluation device 802 generates a time-based passcode or an access signal. In some examples, at block 1206, the AMP 600 may also determine a validity period for the selected safe access level based at least in part on the evaluation data received at block 1204. In some such examples, the determined validity period may be used as the expiration time of the time-based passcode. In some other examples, the validity period may be encoded in the access signal.

At block 1212, the electronic evaluation device 802 establishes a data connection with the AMP 600. In some examples the digital data connection can be a wireless connection. In some other examples, the digital data connection may be a wired connection. For examples, the user or a healthcare provider may connect the AMP 600 to the electronic evaluation device 802.

At block 1214, the electronic evaluation device 802 transmits the time-based passcode and its expiration time or the access signal to the AMP 600 over the digital data connection. In some examples, the AMP 600 may provide access to the therapy change controls associated with the selected safe access level during the validity period, based on the time-based passcode and its expiration time (e.g., using process 900) or based on the access signal (e.g., using process 1000).

Enabling a Requested Glucose Level Therapy Control Configuration

In some examples, the AMP 600 may provide access to one or more therapy change controls associated with a safe access level using a passcode generated by an electronic passcode device and provided to a subject who receives therapy from the AMP 600 or to an authorized user of the AMP 600. The safe access level may be the safe access level determined for the user or the subject. The safe access level may be determined using the method described above with respect to FIG. 8A-FIG. 8C, process 1100 or process 1200.

Figure 13A:
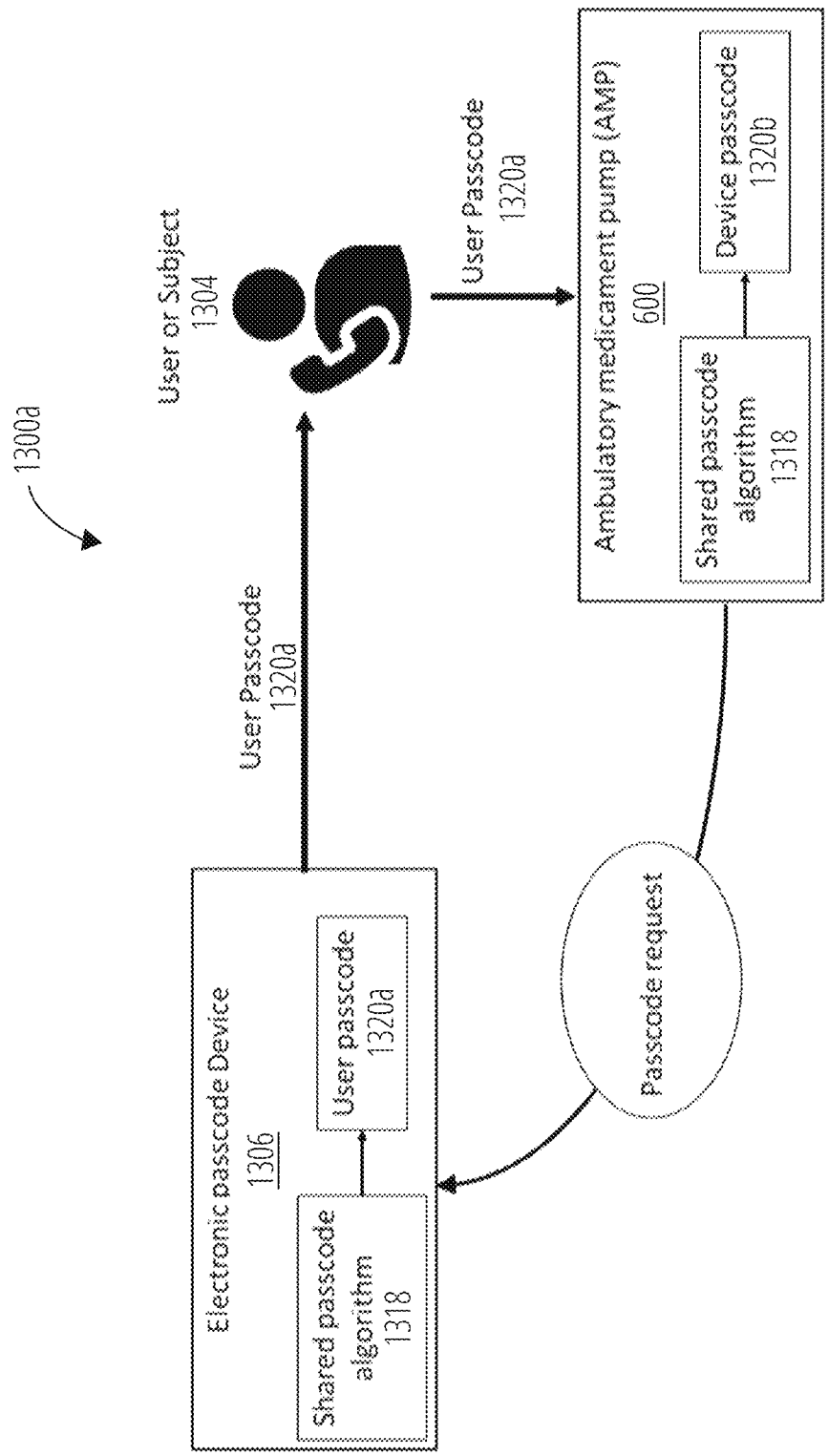
FIG. 13A shows a block diagram of an example system and method for managing to the therapy change controls of an AMP associated with a safe access level using a passcode generated by an electronic passcode device.

FIG. 13A shows a block diagram that represents an example system 1300a for proving access to the therapy change controls associated with a safe access level using a passcode generated by an electronic passcode device 1306.

In this example, the user or subject 1304 may initiate the process by requesting access to one or more therapy change controls associated with a safe access level via a therapy change control request interface of the AMP 600. The therapy change request control interface can be part of the user interface (e.g., a touchscreen display) of the AMP 600. For example, the user may access the therapy change request control interface by selecting an item on a main menu or other menus generated by the AMP 600 or by an electronic device connected to the AMP 600 (e.g., using a user-interface interaction). In some cases, the therapy change request control interface may enable the user or subject 1304 to select a group of therapy change controls associated with the safe access level or the safe access level. Selecting a therapy change control or a group of therapy change controls (or a safe access level) by the user or subject 1304 may cause the AMP 600 to generate a device passcode 1320*b* using a shared passcode algorithm 1318, establish a data connection (e.g., a wireless connection) with the electronic passcode device 1306, and send a passcode request to the electronic passcode device 1306 via the data connection. In some cases, data connection may comprise Long-Term Evolution wireless connection, a Wi-Fi network, a 5G communication network, a wide area network, a near-field communication network, or a short-range wireless electronic radio wireless communication link In some examples, the request message may comprise a device identifier. In some other examples, the message may at least comprise the device identifier and the safe access level. The device identifier may be any identifier that can be used by the electronic passcode device 1306 to uniquely identify the AMP 600. For example, the device identifier can be an IP address, a MAC address, or a serial number and the like.

Upon receiving the device identifier the electronic passcode device 1306 may generate a user passcode 1320*a* associated with the safe access level based at least in part on the passcode request received from the AMP 600. In some embodiments, the electronic passcode device 1306 may use the device identifier received with the request message and the shared passcode algorithm 1318 to generate the user passcode 1320*a*. In these embodiments, a copy of the shared passcode algorithm 1318 may be stored in a memory of the electronic passcode device.

In some cases, the electronic passcode device 1306 may generate the passcode based on the request message and eligibility data received, for example, from an electronic evaluation device (e.g., electronic evaluation device 802), a healthcare provider 812 or a trainer 814. The electronic evaluation device 802 can be the electronic device of a healthcare provider 812 or a trainer 814. In some such cases, the electronic passcode device 1306 may use the eligibility data to verify whether the user or subject 1304 is eligible for the safe access level. If the electronic passcode device 1306 verifies that the user or subject 1304 is eligible for the safe access level, it may generate the user passcode 1320*a*. The user passcode 1320*b* may be provided directly to the user or subject 1304 by an operator or administrator of the electronic passcode device 1306 over a communication link (e.g., a wired or wireless phone line). In some examples, the operator or the administrator may provide the user passcode 1320*a* via a voice call, voice message or text message. In some other examples, the electronic passcode device 1306 may send the passcode via a text message to the user's phone (e.g., a smart phone).

Upon receiving the user passcode 1320*a*, the user or subject 1304 may use enter the user passcode 1320*a* to AMP 600 using a passcode entry interface (e.g., via an interaction with the passcode entry interface). Upon receiving the user passcode 1320*a* from the user 1304, the AMP 600 may compare the user passcode 1320*a* with the device passcode 1320*b*. If the AMP 600 verifies that the user passcode 1320*a* matches with the device passcode 1320*b*, the AMP 600 may enable access to one or more therapy change controls (associated with the safe access level) using, for example, procedures described above (e.g., with respect to process 900 or process 1000).

In some embodiments, the user passcode 1320*a* may be a time-based passcode and the eligibility data received by the electronic passcode device 1306 may include a validity period associated with the eligibility data received from the electronic evaluation device, a physician or a trainer. In these embodiments, the access to the one or more therapy change controls may be enabled only if the user passcode 1320*a* (e.g., a time-base passcode), is received during the validity period. Moreover, in these embodiments, the AMP 600 may terminate the access to the one or more therapy change controls at the end of the validity period.

In some examples, a glucose level control system of an ambulatory medicament pump (AMP) or an ambulatory medicament device (AMD), may provide access to or enable a glucose level therapy control configuration that may be associated with a safe access level using an access code received from an electronic configuration device. In some implementations, the glucose control system may be a control system or a controller of an AMP that provides glucose level control therapy to a subject. For example, the glucose level control system can be the controller 602 of the AMP 600. In some implementations, a glucose level therapy control configuration may be associated with specific values of one or more control parameters of a control algorithm, a therapy control interface, a number of control parameters available in a therapy control interface, specific ranges or values associated with one or more control parameters, a type of medicament that is administered to the subject, and other features that may be used to control and monitor medicament therapy delivery to the subject.

In some cases, providing access to or enabling a glucose level therapy control configuration may enable modification of a control algorithm (e.g., modification of one or more control parameters of a control algorithm) by the subject or the user of the glucose level control system. Additionally, or alternatively, providing access to or enabling the glucose level therapy control configuration may automatically modify one or more control parameters of a control algorithm and thereby modify the execution of the control algorithm. In some cases, providing access to or enabling a glucose level therapy control configuration may generate or activate a new therapy control interface, add one or more control parameters to a therapy control interface, remove one or more control parameters to a therapy control interface, limit or expand a number of selectable options/values for one or more control parameters, or add or remove features of a therapy control interface.

The electronic configuration device may generate the access code upon receiving a unique identifier for an AMP and an identification of a requested modification or change to an initial or current glucose level therapy control configuration of the glucose level control system of the AMP. The unique identifier can include any type of identifier that can uniquely identify the AMP. For example, the unique identifier may be a serial number, unique code, or unique user account name associated with a user of the AMP. Further, the identification of the requested modification to the glucose level therapy control configuration may be received from any type of user, such as from the subject, a guardian of the subject, a trainer, a healthcare provider, and the like. Moreover, the requested modification may include an identity of one or more control parameters to modify and/or obtain access.

The safe access level may indicate or specify the glucose level therapy control configuration that the user or subject is permitted to access. This safe access level may be one of a plurality of different safe access levels with each safe access level identifying different glucose level therapy control configurations. The electronic configuration device may determine a safe access level for the user or the subject based on evaluation data received from a healthcare provider, a trainer, an electronic evaluation device 802, or any other administrative user or device capable of evaluating the ability of the user or subject to operate the AMP with a glucose level therapy control configuration associated with the safe access level. In some cases, the electronic configuration device may determine the requested glucose level therapy control configuration based at least in part on the safe access level for the user or the subject. The requested glucose level therapy control configuration may be a glucose level therapy control configuration that can be safely used by the user or the subject while managing the subject's disease and/or maintaining the subject's health within particular health parameters, such as health parameters that may be determined by the subject's healthcare provider.

In some cases, the electronic configuration device may generate the access code. The electronic configuration device may provide the access code to the subject or the user of the ambulatory medicament pump, via a direct communication channel (e.g., a phone call, text message, email, voicemail, etc.) by an administrator, a healthcare provider, or a trainer. Additionally, or alternatively, the electronic configuration device may transmit the access code to the AMP via a wired or wireless network. For example, the electronic configuration device may transmit the access code via a wireless LTE connection to the AMP.

Figure 13B:
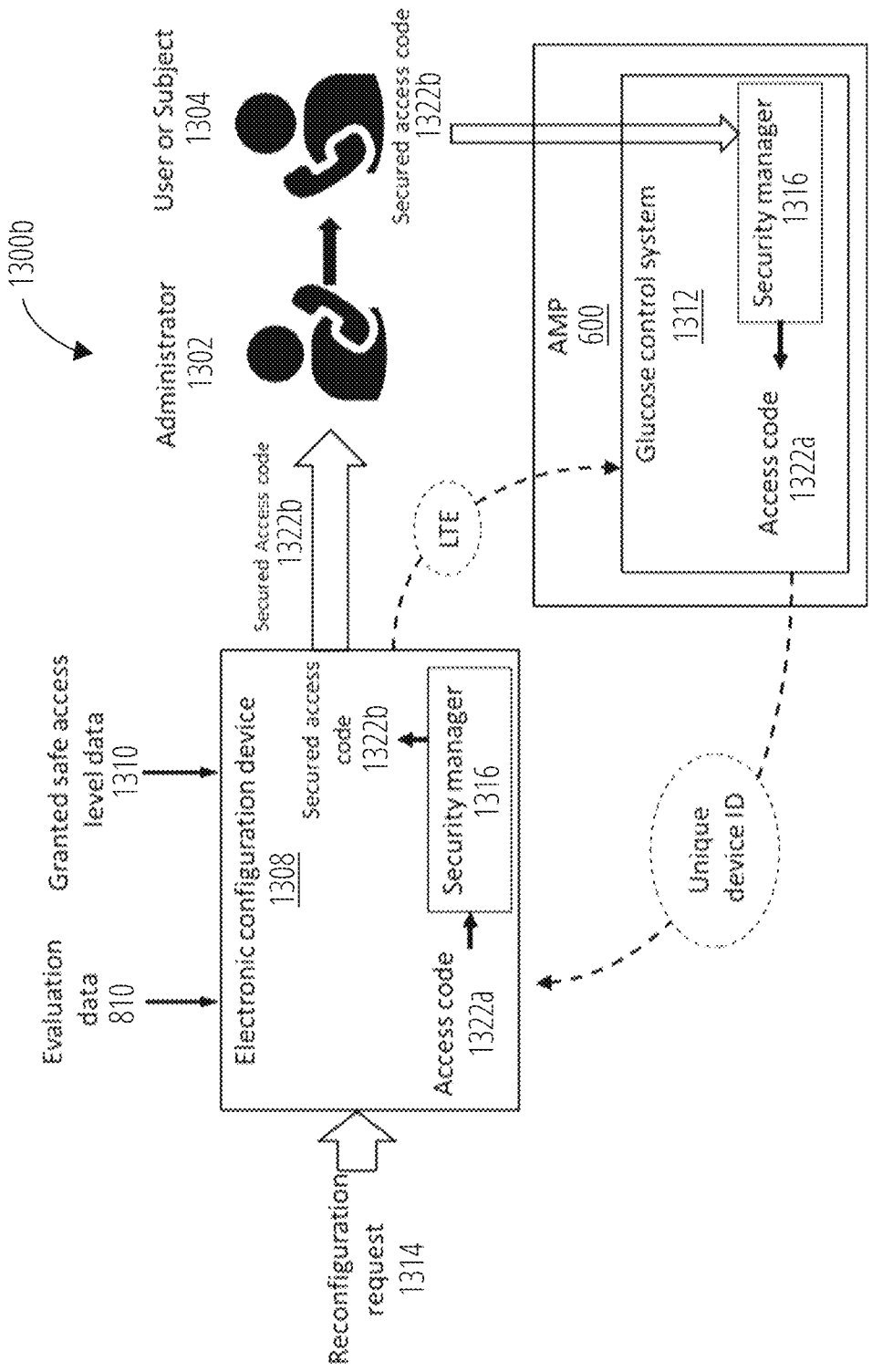
FIG. 13B shows a block diagram of an example system and method for managing access to therapy change controls of an AMP using an access code generated by an electronic configuration device.

FIG. 13B shows a block diagram that represents an example system 1300b for enabling a glucose level therapy control configuration of a glucose control system 1312 of the AMP 600. The example system 1300b includes: AMP 600 that provides medicament therapy to the subject and an electronic configuration device 1308 that may be in communication with the glucose control system 1312 of the AMP 600. Further, the electronic configuration device 1308 may communicate with the electronic evaluation device 802, one or more data repositories that may store subject's information (e.g., granted safe access level data 1310, medical history, glycemic control record, and the like), or one or more electronic devices (e.g., electronic devices of healthcare providers, or trainers). The electronic configuration device 1308 may have a user interface (e.g., a touchscreen display or a keyboard), that may be used to provide data to the electronic configuration device 1308 (e.g., subject's medical data, information related to the AMP 600 and the like), or request service from the electronic configuration device 1308 (e.g., reconfiguration request 1314).

In certain embodiments, the glucose control system 1312 may be or may include one or more of the embodiments previously described with respect to the controller 602. The AMP 600 can be modified or controlled by the user or subject 1304 via a user interface. A glucose level therapy control configuration of the glucose control system 1312 may be identified or enabled using a secured access code (or an access code) generated by an electronic configuration device 1308. In some cases, the glucose level therapy control configuration may be associated with a safe access level granted to the user or the subject by another device or authorized individual. Further, the safe access level may be determined by the electronic configuration device 1308 before generating the access code.

Figure 14:
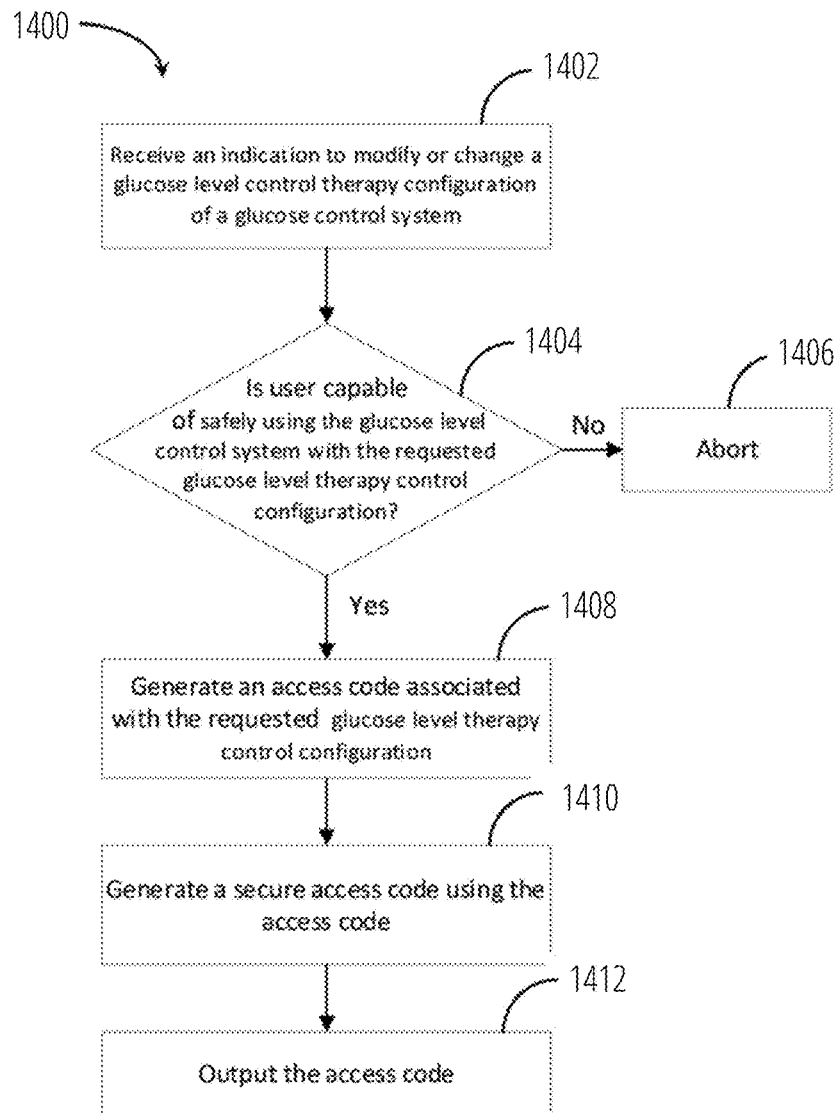
FIG. 14 shows a flow diagram showing an example of a computer-implemented method that may be used by an electronic configuration device to generate an access code usable by a glucose control system to modify or change a glucose level therapy control configuration of the glucose level control system in accordance with certain embodiments.

FIG. 14 presents a flowchart of an example process 1400 for generating an access code usable by a glucose control system 1312 of the AMP 600 to modify or change a glucose level therapy control configuration of the glucose level control system in accordance with certain embodiments.

The process 1400 may be performed by the electronic configuration device 1308. In some cases, the electronic configuration device 1308 may be a computing system of a manufacturer, a healthcare provider, a trainer, the subject, or the user (e.g., a parent or guardian of the subject). The electronic configuration device 1308 may be a cloud-based computing system, a server, a desktop computer, a tablet, a laptop, a mobile computing system (e.g., a smart phone), or any other type of computing system that can evaluate a user to determine safe access levels for the user and/or that can enable one or more glucose level therapy control configurations of the AMP 600. In various embodiments, the electronic configuration device 1308 may at least include a non-transitory memory configured to store specific computer-executable instructions, and a hardware processor in communication with the non-transitory memory and configured to execute the specific computer-executable instructions. In some cases, an electronic configuration device 1308 can be or can include one or more of the embodiments described with respect to the electronic access device 806 or the electronic evaluation device 802.

At block 1402, the electronic configuration device 1308 may receive a reconfiguration request 1314 from the user, the subject, a healthcare provider, or a trainer. The reconfiguration request 1314 may be an indication to modify a glucose therapy control configuration of the glucose control system 1312 to a requested glucose therapy control configuration. An indication to modify a glucose therapy control configuration may comprise a request to: change an initial or current glucose therapy control configuration to the requested glucose therapy control configuration, enable modification of one or more control parameters by the user or subject 1304, modify selectable values of one or more control parameters, enable or disable a control interface, modify one or more control parameters, add or enable one or more control parameters on a therapy control interface, remove or disable one or more control parameters from a therapy control interface, limit or expand a number of selectable options/values for one or more control parameters, or provide access to any other feature or configuration of the AMP that enables the user to modify therapy provided by the AMP. In some cases, the electronic configuration device 1308 may determine the requested glucose therapy control configuration based on the reconfiguration request 1314. In some cases, the reconfiguration request 1314 may include an access period associated to a period during which the user or the subject can use the requested glucose control therapy configuration.

In some cases, the electronic configuration device 1308 may receive the reconfiguration request 1314 via a user interface of the electronic configuration device 1308 (e.g., a keyboard, touch pad, touchscreen display, and the like). For example, a healthcare provider, the subject, or other authorized user may provide the reconfiguration request 1314 by interacting with a keyboard or a touchscreen display of the electronic configuration device 1308. In some other cases, the electronic configuration device 1308 may receive the reconfiguration request 1314 via a wired or wireless network connection. In some cases, the electronic configuration device 1308 may receive the reconfiguration request 1314 from the AMP 600. For example, the subject 1304 may enter the request using a user interface system 616 of the AMP 600. The request may then be transmitted by the AMP 600 to the electronic configuration device 1308.

In some cases, the reconfiguration request may include a unique identifier for the AMP 600 that enables the electronic configuration device 1308 to uniquely identify the AMP 600 or the glucose control system 1312. In some cases, the unique device identifier may be received from the AMP 600. The unique identifier may be a unique device identifier, for example, an IP address, a MAC address, a serial number, a secret manufacturer code, a user account identifier, or any other unique identifier that may be associated with the AMP 600. In some cases, the unique identifier may be stored in a database or other data structure associated with or accessible by the electronic configuration device 1308. In some such cases, the reconfiguration request 1314 may include information to identity the subject or user (e.g., a user account name or a unique user identifier). The electronic reconfiguration device may access the database to obtain a corresponding unique identifier for the AMP 600 based at least in part on the provided user identifier.

At the decision block 1404, the electronic configuration device 1308 determines or predicts the ability of the user or subject to safely use the glucose control system 1312 when configured with the requested glucose level therapy control configuration associated with the reconfiguration request 1314. For example, the electronic configuration device 1308 may determine or predict the ability of the user based on evaluation data 810 or granted safe access level data 1310 received from an external electronic device, the AMP 600 or a user interface of the electronic configuration device 1308. Alternatively, or in addition, the electronic configuration device 1308 may determine or predict the ability of the user or the subject using an interactive evaluation process via a user interface of the electronic configuration device 1308 or an intermediary electronic device.

In some cases, safe usage of the glucose control system 1312 may correspond to a usage of the glucose control system 1312 that does not result in a deviation of a subject's glycemic control from a normal glycemic control for the subject. The normal glycemic control for the subject may be a glycemic control determined by a healthcare provider or a physician. For example, a normal glycemic control may be a glycemic control where subject's glucose level stays within one or more target ranges associated with different times of the day (e.g., morning, mealtime, afternoon, sleeping time and the like). Additionally, a normal glycemic control may be a glycemic control where a rate of change of the subject's glucose level do not exceed a threshold value determined by the physician or the healthcare provider. In some cases, a safe usage of the glucose control system 1312 may correspond to a usage of the glucose control system 1312 that does not result in hyperglycemia or hypoglycemia in the subject.

In some implementations, the determination at the decision block 1404 may be based on granted safe access level data 1310 associated with the user or subject. The granted safe level access data may include data associated with a granted safe access level to the subject or the user. For example, the granted safe level access data may include a specific safe access level of a plurality of safe access levels (e.g., safe access level G0 to G3, or T1 to T3 described above), an expiration date for the granted safe access level and a unique identifier associated with AMP that provides medicament therapy to the subject or used by the user. The electronic configuration device 1308 may receive the granted safe access level data 1310, via a wired or wireless connection, from an electronic evaluation device 802, an electronic device of a healthcare provider 812, or an electronic device of a trainer 814. In some cases, the electronic configuration device 1308 may receive the granted safe access level data 1310, via a wired or wireless connection, from an intermediary electronic device. In some cases, the granted safe access level data 1310 may be received from a healthcare provider 812 or a trainer 814 via a user interface of the electronic configuration device 1308. The granted safe access level data 1310 may be associated with the user or the subject based on a unique user identifier that may be used to uniquely identify the user or the subject. Further, in some cases, the granted safe access level data 1310 may include a unique identifier (e.g., a device ID) that uniquely identifies the ambulatory medicament pump associated with the user or subject. The electronic configuration device 1308 may use the granted safe access level associated with the user or subject to determine or predict whether the user or subject 1304 can safely use the glucose level control system with the requested glucose level therapy control configuration. In some cases, the electronic configuration device 1308 may determine the requested glucose level therapy control configuration based on the granted safe access level and/or the reconfiguration request 1314.

In some implementations, the electronic configuration device 1308 may determine or predict whether the user or subject 1304 can safely use the glucose level control system with the requested glucose level therapy control configuration associated with the reconfiguration request 1314, based on evaluation data 810 received from a computing system. The computing system can be a cloud computing system, a server, a desktop, laptop, or tablet computer, a smart phone, or any other data repository that may store evaluation data. As mentioned above, evaluation data 810 may include one or more prescriptions associated with the subject, training data, historical glycemic control data of the subject, data associated with the use of the glucose level control system by the user over an evaluation time period, and the like. The evaluation data 810 may include the unique device identifier or information that uniquely identifies the ambulatory medicament pump. The evaluation data 810 may also include a unique user ID that may be used to uniquely identify the subject or the user associated with the evaluation data.

As previously described, many categories of safe access levels may be available (e.g., category G, and category T), and each category may have distinct levels (e.g., G0 to G3, or T1 to T3 described above), associated with a user's or subject's health condition and/or capability to use the therapy controls of the AMP. In some implementations, the electronic configuration device 1308 may first use evaluation data 810 to determine a specific safe access level for the user or subject 1304, and then use the safe access level, to determine or predict whether the user or subject 1304 can safely use the glucose level control system with the requested glucose level therapy control configuration. In some cases, the electronic configuration device 1308 may use the evaluation data 810 to directly analyze the user's health condition and ability to use therapy change controls based at least in part on the evaluation data 810 and determine or validate the ability of the user or subject 1304 to safely use the glucose level control system with the requested glucose level therapy control configuration, without determining a safe access level for the user or subject 1304. For example, the electronic configuration device 1308 may determine whether the training data satisfies a training threshold to validate the ability of the subject or the user to safely use the glucose level control system with the requested glucose level therapy control configuration. As another example, the electronic configuration device 1308 may use information included in the one or more prescriptions associated with the subject to validate the ability of the subject or the user to safely use the glucose level control system with the requested glucose level therapy control configuration.

In some implementations, the electronic configuration device 1308 may determine or validate the user's capability to safely use the glucose control system 1312 with the glucose level therapy control configuration associated with the reconfiguration request 1314 using an interactive evaluation process. The interactive evaluation process may include an interaction with the user or the subject via one or more user interfaces of the electronic configuration device 1308 (e.g., a touchscreen display, a keyboard, a monitor, a mouse, an interactive software interface, an interactive web page, and the like). For example, the interactive evaluation process may include displaying a set of queries, corresponding to one or more use cases of the glucose level control system, to the user and the receiving a set of responses to the set of queries. Subsequently, the electronic configuration device 1308 may evaluate the set of responses to obtain an evaluation score and use the evaluation score to determine whether the user is capable of safely using the glucose level control system with the glucose level therapy control associated with the requested glucose therapy control reconfiguration.

In some cases, the interactive evaluation process may include an interaction of the user or the subject with one or more user interfaces (e.g., a touchscreen display, a keyboard, a monitor, a mouse, an interactive software interface) of an electronic device that is in communication with the electronic configuration device 1308 (e.g., via a wired or wireless data connection). The electronic device may be the AMP 600, an electronic device of the user or the subject (e.g., a computer, or a smart phone), an electronic device of a healthcare provider or a trainer, the electronic evaluation device 802, a cloud server or any other electronic device that may support a user interface and can transfer data between the user interface and the electronic configuration device 1308. For example, the user may interact with a webpage hosted by a server or cloud computing system that is in communication with the electronic configuration device 1308. In some examples, the electronic device may transmit the user inputs collected during the interactive evaluation process to the electronic configuration device 1308. In some examples, the electronic device may determine or validate the user's capability to safely use the glucose level control system 1312, based on the interactive evaluation process, and transmit the outcome to the electronic configuration device 1308.

If at the decision block 1404 the electronic configuration device 1308 determines or predicts that user is not capable of safely using the glucose level control system when configured with the requested glucose level therapy control configuration, the process proceeds to block 1406 where the process 1400 may be terminated. Alternatively, or in addition, the electronic configuration device 1308 may notify the user or subject that the reconfiguration request 1314 has been denied. In some cases, the user may be presented with an opportunity to modify the request or provide an alternative request. The modified or alternate request may be processed using the process 1400. The notification may be a message displayed on a user interface of the electronic configuration device 1308, or a message sent to an electronic device of the user or subject 1304 via a wired or wireless network connection. The message may include a reason for the request denial and/or may provide suggested permitted alternative configurations. Moreover, in some cases, the message may indicate steps or actions the user or subject may perform to have the request accepted. For example, the message may indicate that the request is denied, but would be permitted if the user passed a particular training course.

If at the decision block 1404 the electronic configuration device 1308 determines that the user or subject 1304 is capable of safely using the glucose control system 1312 with the requested glucose level therapy control configuration, the process proceeds to block 1408 where the electronic configuration device 1308 generates an access code 1322*a* for enabling or accessing the requested glucose level therapy control configuration in the AMP 600.

The access code 1322*a* may at least comprise access level data and the unique identifier associated with the AMP 600. In some examples, the access level data may be included in the reconfiguration request 1314. In some examples, the electronic configuration device may generate the access level data based on the received or the determined requested glucose level therapy control configuration. The access level data may include data associated with the one or more control parameters of a control algorithm. As mentioned above, the unique identifier may be a unique device ID (e.g., an IP address, a MAC address, or a serial number) that uniquely identifies the AMP whose glucose level therapy control configuration is modified or changed. Additionally, the access code may include a time-based value, which is described in more detail below.

In some embodiments, the access level data, may comprise a number or a string that encodes features (e.g., protected features) that may be enabled, disabled, or modified by the glucose level therapy control configuration. In some cases, the access code may enable selecting specified values or may remove limits on accessing values for one or more control parameters. Alternatively, or in addition, the access code may modify the default values of certain control parameters. The access code may be used to configure one or more optional features.

In some non-limiting example use cases, a portion of the access level data (which may be implemented as an encoded number or string) may correspond to a feature (e.g., Manual Bolus) and another portion may correspond to a state of the feature (e.g., on or off). Alternatively, or in addition, a portion of the access level data may correspond to a control parameter and another portion may correspond to a value of the control parameter. In some non-limiting implementations, an access code may comprise a 3-digit hexadecimal value where each digit may represent 16 options or values (e.g., an off state and 15 values). In some implementations, a 3-digit hexadecimal access code can be used to enable a glucose level therapy control configuration that is configured to modify three protected features of the AMP: Manual Bolus, User Set Tmax, and Offset Targets. The first digit may be dedicated to the state of the Manual Bolus, for example, 0 may indicate the OFF state and 1 may indicate the ON state. The second digit may be dedicated to values of the User Set Tmax, where each hexadecimal symbol indicates two or more selectable values or fixed new value; for example, 0 may indicate a default value or default possible values, 1 may indicate 65 or 55, 2 may indicate 45, 55 or 65, 3 may indicate 65 or 75 and 4 may indicate all possible values. The third digit may be dedicated to Offset Targets; for example, 0 may indicate an off state, 1 may indicate +1, 2 may indicate −1, 3 may indicate +2, 4 may indicate −2 and 5 may indicate +3. It should be understood that the aforementioned example use case is just one possible implementation of encoding a glucose therapy control configuration. Other implementations for the format of the access level data and/or for the content of the access level data are possible.

In some cases, a new glucose level therapy control configuration may require a new therapy control interface to be implemented by the AMP or the controller of the AMP. In such cases, the safe access level data may include information usable by the controller to implement the new therapy control interface. For example, a digit of the hexadecimal string may be dedicated to control interface types.

Additionally, the access code 1322a may also comprise an error-detection code such as a cyclic redundancy check (CRC), a checksum, a hash value, an error correction code, or a parity bit to detect inconsistencies or errors in the transmitted access code.

In some cases, the time-based value may correspond to a time period during which the access code 1322a is valid and/or may be used to access the glucose level therapy control configuration associated with the access code (e.g., the glucose level therapy control configuration defined by the access level data). Alternatively, or in addition, the time-based value may correspond to an access period during which the requested glucose level therapy control configuration associated with the access code 1322a, is available and may be used by the user to adjust one or more control parameters or modify the setting of the AMP. In some examples, the time period associated with the time-based value may be measured from a time at which the access code is first used, generated, or provided to the AMP 600. In some cases, the time-based value can be a specific date and time. In yet other examples, the time-based value may be associated with a number of times the requested glucose level control configuration is used to adjust one or more control parameters.

In some implementations, the electronic configuration device 1308 may use granted safe access level data 1310 or evaluation data 810 to determine the time-based value for an access code corresponding to a time period during which the access code is valid. In some cases, the electronic configuration device 1308 may determine the time-based value based at least in part on a prescription received or associated with a subject, training data associated with training by the subject, or information regarding a health condition of the subject. The prescription, training data, or health information may be received by the electronic configuration device 1308 and stored in a memory of the electronic configuration device 1308. In some cases, the time-based value may be provided to the electronic configuration device as part of evaluation data 810, granted safe access level data 1310, therapy control configuration data, or a glucose therapy control configuration reconfiguration request 1314. In some cases, the electronic configuration device 1308 may generate the time-based value based on a seed value stored in the electronic configuration device 1308. The seed value may be also stored in the AMP 600 associated with the unique ID, for which the access code 1322a is generated. The seed value may include any type of value that may be used by two different devices to generate the same value independently of each other and/or without exchanging information. For example, the seed value may be a current time as determined using an agreed upon time source (e.g., a time source specified by the International Bureau of Weights and Measures). As another example, the seed value may be a synchronous counter that is shared by the electronic configuration device 1308 and the AMP 600. The seed value may be applied to an algorithm used in common by the electronic configuration device 1308 and the AMP 600 to generate a shared value (e.g., the time-based value). In some embodiments, the seed value may be a shared or negotiated value that is negotiated between the electronic configuration device 1308 and the AMP 600. In some cases, the seed value refers to a particular algorithm rather than a singular value.

At block 1410, the electronic configuration device 1308 may use the access code 1322a generated at block 1408 to generate a secured access code 1322b. In some cases, a security manager 1316 may generate the secured access code 1322b using one or more encryption or hashing algorithms. In some implementations, electronic configuration device 1308 may encrypt the access code to generate the secured access code 1322b. Various symmetric or asymmetric encryption algorithms may be used for encrypting the access code including, for example, IDEA, MD5, HMAC, TripleDES, Blowfish, Twofish, DES, 3DES, AES, RSA, ECC, and the like.

In some other implementations, the electronic configuration device 1308 may generate the secured access code by hashing the access code 1322a. Various hash algorithms may be used for hashing the access code for example, MD5, SHA-1, SHA-2, SHA-3, BLAKE2, BLAKE3, RIPEMD-160, Whirlpool, SHA1 and the like. In some cases, different portions of the access code 1322a (e.g., safe access level data, unique ID, or time-based value) may be hashed separately with different hashing algorithms.

At block 1412, the electronic configuration device 1308 may output the secured access code 1322b via a user interface. In some implementations, the secured access code 1322b may be provided to an administrator 1302, a healthcare provider, a trainer, or anyone who is authorized to help manage care of the subject (e.g., a parent or a guardian of the subject). In some examples, the electronic configuration device 1308 may provide the secured access code 1322b to the user via a wired or wireless phone line (e.g., as a voice or text message). In some cases, the electronic configuration device 1308 may directly provide the secured access code to the AMP 600 over a wired or wireless network connection.

The electronic configuration device 1308 may provide the secured access code 1322b (e.g., the encrypted or the hashed access code) by displaying it on a display of the electronic configuration device 1308. In some cases, the electronic configuration device 1308, may send the secured access code 1322b to the user or subject 1304, or other authorized individuals via a wired or wireless network connection (e.g., as an e-mail, text message or the like).

Once the secured access code 1322b (or the access code 1322a) is received by the subject or the user, the subject or the user may provide the secured access code 1322b to the glucose control system 1312 via an access code entry interface (e.g., a touchscreen display, or a keyboard) of a user interface system 616 of the AMP 600. Alternatively, or in addition, the electronic configuration device 1308, may transmit the secured access code 1322b over a wired or wireless network connection (e.g., an LTE) to the AMP 600 (to the glucose control system 1312 of the AMP 600). In some cases, the electronic configuration device 1308, may transmit the secured access code 1322b to an electronic intermediary device (e.g., a smart phone, a laptop or desktop, computer, a smartwatch, and the like) over a wired or wireless connection (e.g., LTE, 5G, Bluetooth®, etc.) and the electronic intermediary device may transmit the secured access code 1322b to the AMP 600.

In some implementations, instead of the secured access code 1322b, the electronic configuration device 1308, may provide the access code 1322a (generated at block 1408) to the subject, user, or other authorized individual using one or more of the methods mentioned above with respect to providing the secured access code 1322b. In these implementations, block 1410 in the process 1400 may be eliminated.

Figure 15:
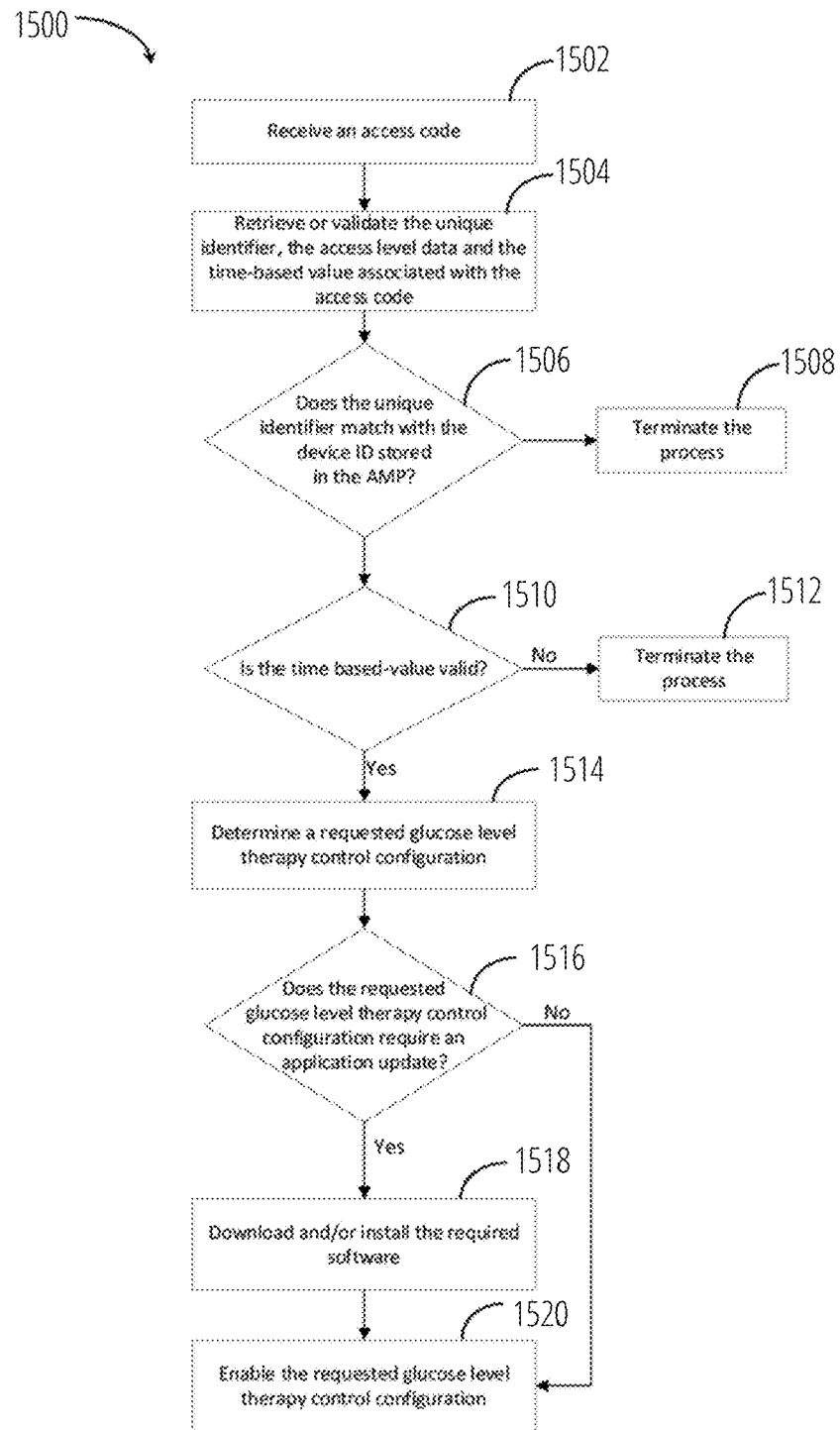
FIG. 15 shows a flow diagram showing an example of a computer-implemented method that may be used by the glucose control system of an ambulatory medicament device to enable or activate a requested glucose level therapy control configuration of the glucose control system.

FIG. 15 presents a flowchart of an example configuration activation process 1500 for enabling or activating a requested glucose level therapy control configuration of the glucose control system 1312 of the AMP 600 using a secured access code 1322b (or an access code 1322a). The activation of the requested glucose level therapy control configuration may modify or enable modification of a control algorithm of the glucose level control system based on a safe access level for a user of the AMP 600. The process 1500 may be performed by the glucose control system 1312 of the AMP 600.

At block 1502 the glucose control system 1312 may receive a secured access code from a user interface (e.g., in response to a user interacting with the user interface), or a wired or wireless connection to an electronic configuration device (e.g., via the communication system 622).

At block 1504 the glucose control system 1312 may retrieve or validate the access level data, unique identifier, and/or the time-based value encoded in the secured access code 1322b (or access code 1322a). In some cases, the glucose control system 1312 may use a security manager 1316 to retrieve the access level data, unique identifier, and/or the time-based value using the secured access code 1322b. For example, the security manager 1316 may execute a decryption algorithm to decrypt the secured access code 1322b and extract the access level data, unique identifier, and/or the time-based value. In some implementations, the secured access code 1322b is encrypted using a public key of the AMP 600 or a shared secret shared between the electronic configuration device 1308 and the AMP 600. In some such cases, the security manager 1316 may decrypt the secured access code 1322b using a private key stored in a secure memory location of the glucose control system 1312. In some examples, the security manager 1316 may use a decryption algorithm used by the electronic configuration device 1308 to encrypt the access code 1322a.

In some cases, at block 1504 the glucose control system 1312 may use the security manager 1316 to validate the secured access code 1322b using a hashing algorithm (e.g., the hashing algorithm used to generate the access code 1322b), a second access level data, a second unique identifier, and/or a second time-based value stored in the memory 610 of the controller 1312. In some cases, the second access level data and the second time-based value may be associated with the reconfiguration request 1314. For example, the second access level data may be associated with the requested glucose therapy control configuration and the second time-based value may be associated with a period during which the requested glucose therapy control configuration will be available. In some examples, the security manager 1316 may use the hashing algorithm, used to generate the secured access code 1322b, to validate the second access level data, the second unique identifier, and/or the second time-based value based on secured access code 1322b.

In some implementations, the glucose control system 1312 may use the hashing algorithm to hash the second access level data, the second unique identifier, and/or the second time-based value stored in the memory 610 of the glucose control system 1312 to generate a second hashed value. The hashing algorithm used by the glucose control system 1312 may be the same hashing algorithm used to generate the secured access code 1322b. Subsequently, the glucose control system 1312 may validate the secured access code 1322b by comparing the second hashed value and the secured access code 1322b. In some implementations, the second access level data, the second unique identifier, and/or the second time-based value are hashed separately. In some such cases, each hashed value is compared to a corresponding hashed value included as part of the secured access code 1322b. Upon validating the secured access code 1322b, the glucose control system 1312 may access the safe access level data, unique identifier, and/or the time-based value.

In some cases, the glucose control system 1312 may use an error detection code to determine whether the access code is error free. If the glucose control system 1312 determines that the access code includes errors, it may determine whether the access code can be recovered from the detected error.

At decision block 1506 the glucose control system 1312 may determine whether a unique identifier retrieved (e.g., decrypted) from the secured access code 1322b (or the access code 1322a) matches with a second unique identifier stored in the memory 610 of the glucose control system 1312. Alternatively, if at block 1504 the unique identifier is validated using the secured access code 358b (e.g., by hashing the secured access code and the second unique identifier), block 1504 may be omitted and the process moves to decision block 1510.

If at the decision block 1506 the glucose control system 1312 does not verify that the unique identifier matches with the second unique identifier, the process may proceed to block 1508 where the configuration activation process 1500 is terminated. Upon termination of the process, the glucose control system 1312, may notify the user (e.g., via a user interface of the AMP 600) or the subject that the received access code is not associated with the AMP 600 used by the user or the subject.

If at the decision block 1506 the glucose control system 1312 verifies that the unique identifier matches with the second unique identifier, the process may proceed to the decision block 1510 where the glucose control system determines whether the time-based value retrieved at block 1504, is valid or expired. In some cases, the glucose control system 1312 may determine whether the time-based value retrieved at block 1504, is valid or expired by comparing the time-based value to a second time-based value generated at the glucose level control system. Alternatively, if at the decision block 1504 the time-based value is validated using the secured access code 1322a (e.g., by hashing the secured access code and the second time-based value), block 1510 may be omitted and the process moves to block 1514.

If at the decision block 1510 the glucose control system 1312 verifies that the time-based value is not valid (e.g., it is expired or does not match with the second time-based value), the process may proceed to block 1512 where the configuration activation process 1500 is terminated. Upon termination of the process, the glucose control system 1312, may notify the user (e.g., via a user interface of the AMP 600) or the subject that the received access code is expired.

If at the decision block 1510 the glucose control system 1312 verifies that the time-based value is valid, the process may proceed to the block 1514 where the glucose control system 1312 determines a requested glucose level therapy control configuration using the access level data retrieved at block 1504 or the second access data validate at the block 1504. As mentioned above, the requested glucose level therapy control configuration may identify a new therapy control interface, a control parameter to include in a therapy control interface, the control parameter to enable in the therapy control interface, a control parameter value for the control parameter, a new control algorithm functionality for the control parameter, or any other feature that may modify therapy or control of therapy at the AMP. In some cases, implementation of the requested glucose level therapy control configuration may require an update to or a new version of the computer-executable instructions or control software associated with an existing glucose level therapy control configuration. For example, if the requested glucose level therapy control configuration identifies a new therapy control interface, a new control software may need to be installed to provide access to the new therapy control interface. As another example, if the requested glucose level therapy control configuration identifies a new control algorithm or a new control algorithm functionality, a new set of instructions (e.g., a new application, or a new software) may be needed to support the new functionality or to implement the new control algorithm.

At decision block 1516, the glucose control system 1312 may determine whether the requested glucose level therapy control configuration requires a software or application update. The glucose control system 1312 may analyze the access level data extracted from the received access code to determine the need for updating an application. The application update can be a new version of an existing application, a replacement or substitute application, or an application patch. The application update may include a binary executable file that may be executed by the processor of the glucose control system 1312.

If at the decision block 1516 the glucose control system 1312 determines that the requested glucose therapy control configuration does not require a new software update or installation, the process may move to block 1520.

If at the decision block 1516 the glucose control system 1312 determines that the requested glucose therapy control configuration requires a new application or software update or installation, the process may move to block 1518 where the glucose control system 1312 downloads and/or installs the required application update. In some cases, upon determining that an application update is needed, the glucose control system may notify the user or the subject, that an application has to be updated in order to enable the requested glucose control therapy configuration determined based on the access code (the access level data extracted from the access code). In some cases, the user notification may include an application code/name/version and/or a server or host from which the application update can be downloaded.

In some cases, the application update may be stored in a host computing system separate from the glucose control system 1312. In some cases, the application update may be stored in a memory 610 of the glucose control system 1312. In some cases, the host computing system may be the electronic configuration device 1308. In some cases, the application update may be pushed or transmitted to the host computing system by the electronic configuration device 1308. In some implementations, the glucose control system 1312 may update an application executing on the ambulatory medical device without interrupting, or while causing minimal interruption, to therapy provided by the AMP 600 to the subject. In some implementations, the glucose control system 1312 may automatically download and update an application based on one or more methods described in U.S. patent application Ser. No. 17/062,356 the contents of which are hereby incorporated by reference in its entirety herein and made a part of the present application. In some implementations, the user may download and/or install the application update using instructions included in the user notification.

In some cases, the new application or application update may be needed to enable new features of a requested glucose therapy control configuration not supported by the glucose controller prior to receiving the access code.

At block 1520, the glucose control system 1312 may enable or activate the requested glucose level therapy control configuration. Once activated, the requested glucose level therapy control configuration may allow the user or the subject to modify the values of one or more control parameters that were not previously available for the user to modify or to modify beyond a certain range before activating the requested glucose level therapy control configuration. In some cases, activation of the requested glucose level therapy control configuration may limit or stop the access to one or more control parameters of a control algorithm. In some cases, activation of the requested glucose level therapy control configuration may disable or enable a feature of glucose control system 1312. In some examples, upon activating a requested glucose therapy control configuration, the glucose control system 1312 may notify the user and show the new available features, new parameter control ranges, new parameters that can be controlled, eliminated features, parameters that can not be modified anymore and the like, on a display of the AMP 600.

In various embodiments, the glucose control system 1312 may allow the user or the subject to revert the glucose control system 1312 to a glucose therapy control configuration used before activating the requested glucose level control configuration. In some cases, the user may need a revert code to revert back the requested glucose level control configuration. The revert code may be generated and provided to the user or the subject by the electronic configuration device 1308 using one or more of the systems and methods described above with respect to FIG. 13A and FIG. 13B.

In certain embodiments, the glucose control system 1312 may revert the glucose control system 1312 to a glucose therapy control configuration used before activating the requested glucose level control configuration after an expiration condition is satisfied. In some cases, the glucose control system may determine that an expiration condition has been satisfied based on: an expiration time period measured from the time at which the requested glucose level control configuration has been activated, an expiration date, a number of administrations of medicament after activating or enabling the requested glucose level control configuration, or a number of adjustments made to one or more control parameters after activating or enabling the requested glucose level control configuration. In some cases, the expiration time period or the expiration date may be associated with the time-based value extracted from the secured access code or the access code.

In some cases, one or more features of a requested glucose therapy control configuration may have different expiration conditions. Each feature of the requested glucose therapy control configuration may cease being accessible after its corresponding expiration condition is satisfied.

In certain embodiments, the glucose control system 1312 may revert the glucose control system 1312 to a glucose therapy control configuration used before activating the requested glucose level control configuration. The glucose control system 1312 may revert the glucose control system 1312 to a prior glucose therapy control configuration upon receiving a command or signal from a remote computing system, or in response to an expiration condition. The remote computing system may be the electronic configuration device 1308 or a computing system of a healthcare provider, a manufacturer, or a trainer.

In some cases, the changes and adjustments made by the user or the subject using a newly activated requested glucose therapy control configuration may result in hypoglycemia, hyperglycemia, an abnormal behavior of the subject's glucose level, or a degradation of subject's glycemic control. In some such cases, the glucose control system 1312 may automatically revert the glucose control system 1312 to a glucose therapy control configuration used before activating the requested glucose level control configuration.

As mentioned above, upon evaluating the ability of the user to safely use the glucose level control system with a requested glucose level therapy control configuration, the electronic configuration device 1308 may change an initial glucose level therapy control configuration to the requested glucose level therapy control configuration. The electronic configuration device 1308 may allow the user to use the requested glucose level therapy control configuration during an access period with the time-based value retrieved from the access code (e.g., the secured access code 1322*b*).

In some implementations, the user may extend the access period by sending an access period extension request to the electronic configuration device 1308 (e.g., via wired or wireless connection or a user interface). In some cases, extending the validity period may require re-evaluating the ability of the user to safely use the glucose level control system with the requested glucose level therapy control configuration. In some cases, the re-evaluation process may not involve the physician, the healthcare provider or the trainer. For example, upon receiving the access period extension request from the user, the electronic configuration device 1308 may re-evaluate the user's ability to safely use the requested glucose level control system based on the user's use of one or more therapy controls associated with the requested glucose level therapy control configuration during the access period. For example, the electronic configuration device 1308 may determine whether changes made by the user to the one or more therapy control parameters, associated with the requested glucose level therapy control configuration, resulted in hypoglycemia or hyperglycemia during the access period. If the electronic configuration device 1308 determines that user's use of therapy controls associated with the requested glucose level therapy control configuration during the access period did not result in hypoglycemia or hyperglycemia, it may allow the user to use the requested glucose level therapy control configuration during an extended access period. In some cases, the electronic configuration device 1308 may also use the evaluation data 810, which may have been updated during the access period, in the re-evaluation process. In some cases, the electronic configuration device 1308 may use the interactive evaluation process described above to re-evaluate user's ability to safely use the requested glucose level control system during an extended access period. In some cases, if the electronic configuration device 1308 determines that user's use of therapy controls associated with the requested glucose level therapy control configuration during the access period resulted in periods or hypoglycemia or hyperglycemia, it may deny the access period extension request and notify the user that the access period may not be extended (e.g., via a user interface of the AMP 600 or a user interface of the electronic configuration device 1308).

In some embodiments, a user may request access to a glucose level therapy control configuration that was previously requested. Regardless of whether the prior request was granted or denied, the user may be reevaluated to determine whether user can safely operate the AMP when configured with the requested glucose level therapy control configuration. In some cases, re-evaluation of the user may be based at least in part on new evaluation data. For example, a history of operation of the AMP may be used to reevaluate the user. The history of operation may include data that was not previously available during a prior request to access the glucose level therapy control configuration. The subsequent request to access the glucose level therapy control configuration may occur during or shortly after use of the AMP with the glucose level therapy control configuration as part of a request for re-authentication to use the glucose level therapy control configuration. In some cases, the subsequent request to access the glucose level therapy control configuration may occur at some time after expiration of a prior granting of access to the glucose level therapy control configuration.

Software Update of Ambulatory Medical Device

It is often the case that a computer application is updated after it is released. In some cases, the application is updated to patch bugs or vulnerabilities. In other cases, the application is updated or replaced with a new version to introduce new features or improve existing features. Regardless of the reason, it is often the case that an application is shutdown or is not executing while the application is updated. For most applications, there is minimal to no harm in shutting down or not executing an application while it is updated or otherwise replaced. For example, it is inconsequential that a video game, word processing, or edutainment application is not executing while it is updated.

However, it can be inconvenient, harmful, or, in some cases, life-threatening to cause an application on an ambulatory medical device to cease executing while it is updated or replaced by a new version of the application. If a subject or subject that is receiving therapy from the ambulatory medical device enters a state where therapy is desired or needed while an application or control software of the ambulatory medical device is being updated or replaced, harm may occur to the subject. For example, suppose the ambulatory medical device is an insulin pump, such as those that may be used by a type-1 diabetic. If the insulin pump becomes inoperative due to a software update process occurring at a time when a subject's blood glucose level exceeds a set-point or target range, the user may not receive a necessary insulin bolus from the ambulatory medical device. Thus, it is desirable to modify reduce or eliminate disruption to subject care or therapy when updating applications, such as control software, of an ambulatory medical device.

In some embodiments, an ambulatory medical device includes a computer-implemented method of updating an application executing on the ambulatory medical device without interrupting, or while causing minimal interruption, to therapy provided by the ambulatory medical device to a subject or subject. The method may generally be performed by a hardware processor, (e.g., a controller, and the like), included in an ambulatory medical device and based on a set of instructions that may be stored, for example, in a non-transitory memory of the AMD. The application update may be a new version of the application, a replacement or substitute application, or an application patch. In some examples, the application may be an older version of the application that has been used by instances of the ambulatory medical device for more than a threshold period of time and has experienced less than a threshold number of faults. The application update may be stored in one or more host computing systems. The application update may be pushed to the host computing systems by a company that manages or manufactured the ambulatory medical device or other software company that is authorized by the manufacturer or licensee of the device.

Figure 16:
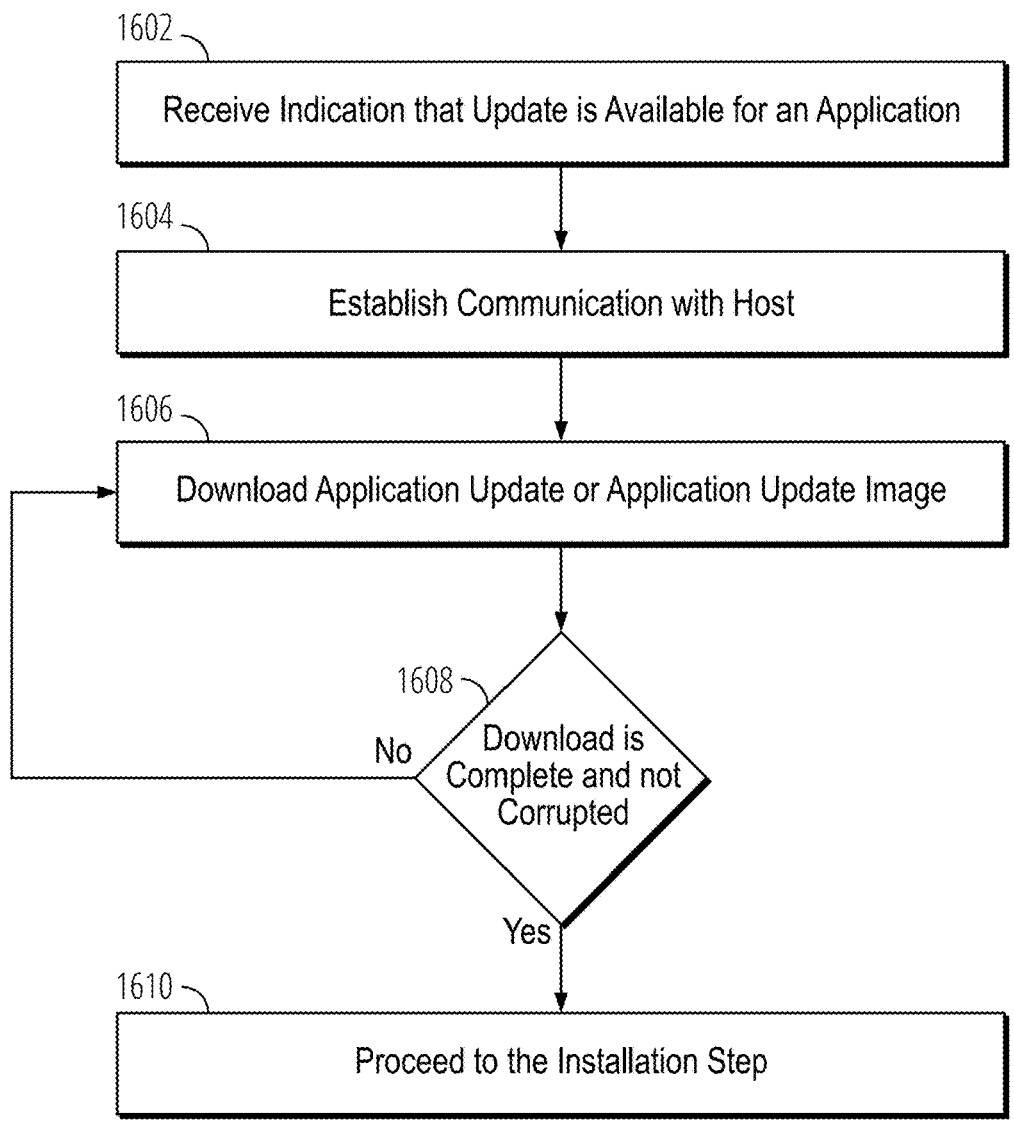
FIG. 16 is a flow diagram showing an example of a computer-implemented method that may be used by an AMD in order to detect and download an application update.

FIG. 16 is a flow diagram showing an example of a computer-implemented method that may be used by the AMD in order to detect and download an application update from a host computing system or other computer readable media in which a copy of the application update is stored. In certain aspects, an ambulatory medical device, such as a medicament delivery device or a medicament pump may receive an indication 1602 that an update is available for an application, such as control software or other software that controls or facilitates the operation of the ambulatory medical device. The software update may include a binary executable file for various processors of the ambulatory medical device. In some embodiments, the indication may be a determination made by a software or hardware module included in an ambulatory medical device of AMD. For example, the AMD may access a particular host computing system (e.g., using its communication module) to determine whether an update is available, based on set of update trigger conditions stored in a memory of AMD. The set of update trigger conditions may be defined/changed by a user and/or received by AMD from a host computing system. For example, a trigger condition may push the AMD to periodically search for an update at time intervals set by the user or received from a host computing system. Alternatively, or in addition, in response to a trigger (such as a user command, the replacement of medicament within the ambulatory medical device, the connecting to a particular network, or the connecting to a network using a particular communication transceiver (e.g., Wi-Fi) or the like), the ambulatory medical device may access a particular host computing system to determine whether an update is available to an application installed on the AMD. The software to be updated on the AMD may be currently executing on the ambulatory medical device or may be executed in future.

In some embodiments, the indication may be a query received from the host computing system that may access the AMD to read and compare the software versions and/or the hardware configuration (and/or warranty) to determine the eligibility of the ambulatory medical device for a software upgrade. The serial number, the model number, and/or the software version may be used to determine software upgrade eligibility. In some embodiments, the eligibility may be determined based on the geoposition of the device and/or whether the device is connected to a local area network (such as for example, a Wi-Fi network) or a wide area network (such as, for example, a cellular network). In various embodiments, the ambulatory medical device may have an antenna that provides the device with GPS, text or picture messaging, telephone calling, and data transfer capabilities. Software update may be provided on a limited release with test groups of varying sizes, e.g., 1-100 or 1-1000 or 1-10000. There may be a phased rollout of the software updates. In some embodiments, the AMD may respond to an upgrade eligibility request with a version of the first software or a model identification information of the ambulatory medical device or a manufacturing date of the ambulatory medical device.

If it is determined that an update is available to the application executing on the ambulatory medical device, the ambulatory medical device may establish a connection 1604 to a host computing system that hosts the update to the application. Such connection may be established via one or more links or methods discussed above, such as with reference to FIG. 7.

Once a connection is established, the ambulatory medical device may download the application update or application update from the host computing system over the connection 1606. In some examples, the ambulatory medical device may download an image of the application update from the host computing system. While the application update is being downloaded, an existing version of the application on the ambulatory medical device may continue to execute. Thus, there is little or no interruption to therapy provided by the ambulatory medical device while the application update is being obtained by the ambulatory medical device.

Once the application update is obtained, the ambulatory medical device (using its control and computing module) may perform one or more operations to confirm that the application update was successfully downloaded from the application host system and that the download was not corrupted 1608. For example, the ambulatory medical device may calculate a hash or checksum value from the downloaded application update. This hash or checksum value may be compared with one received from the application host system. If the calculated hash or checksum value matches the received hash or checksum value, then it may be determined that the download is both complete and not corrupt. Further, the ambulatory medical device may use the checksum, a tag, a payload size, or any other method to confirm that the download of the application update is complete and not corrupt. If it is determined that the download is corrupt 1608, the AMD discards the corrupt copy and downloads another copy of the update 1606. If it is determined that the download is complete and not corrupt, the AMD may proceed to the installation step 1610 wherein the application update may be installed on the AMD without interrupting the ongoing or upcoming therapy sessions.

Figure 17:
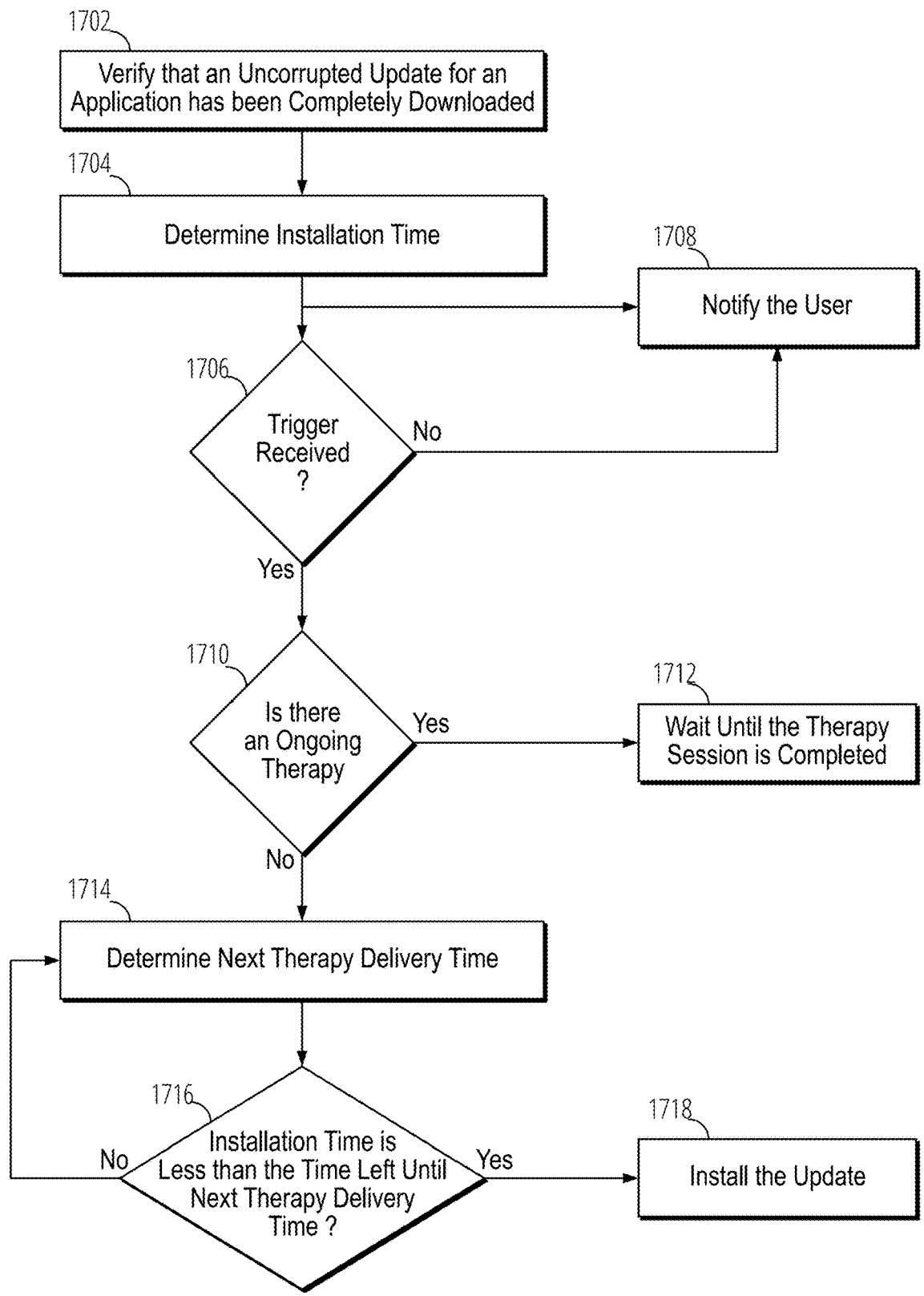
FIG. 17 is a flow diagram showing an example of a computer-implemented method that may be used by an AMD to install a down-loaded application update without interrupting the therapy provided to a subject.
Figure 18:
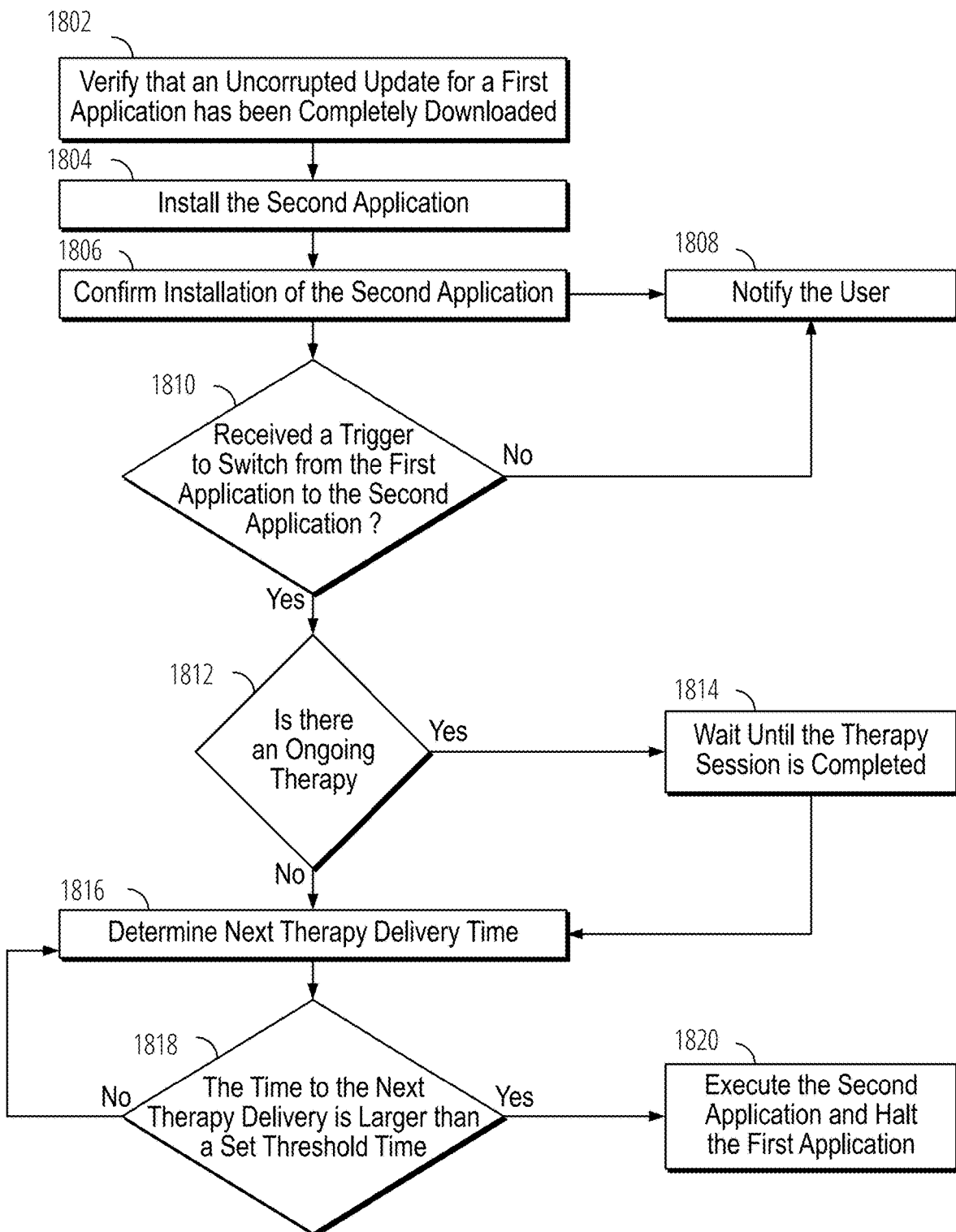
FIG. 18 is a flow diagram showing an example of a computer-implemented method that may be used by an AMD to install a second update downloaded from a host computing system and switch control of the AMD from a first application to the second application without interrupting the therapy provided to a subject.
Figure 19:
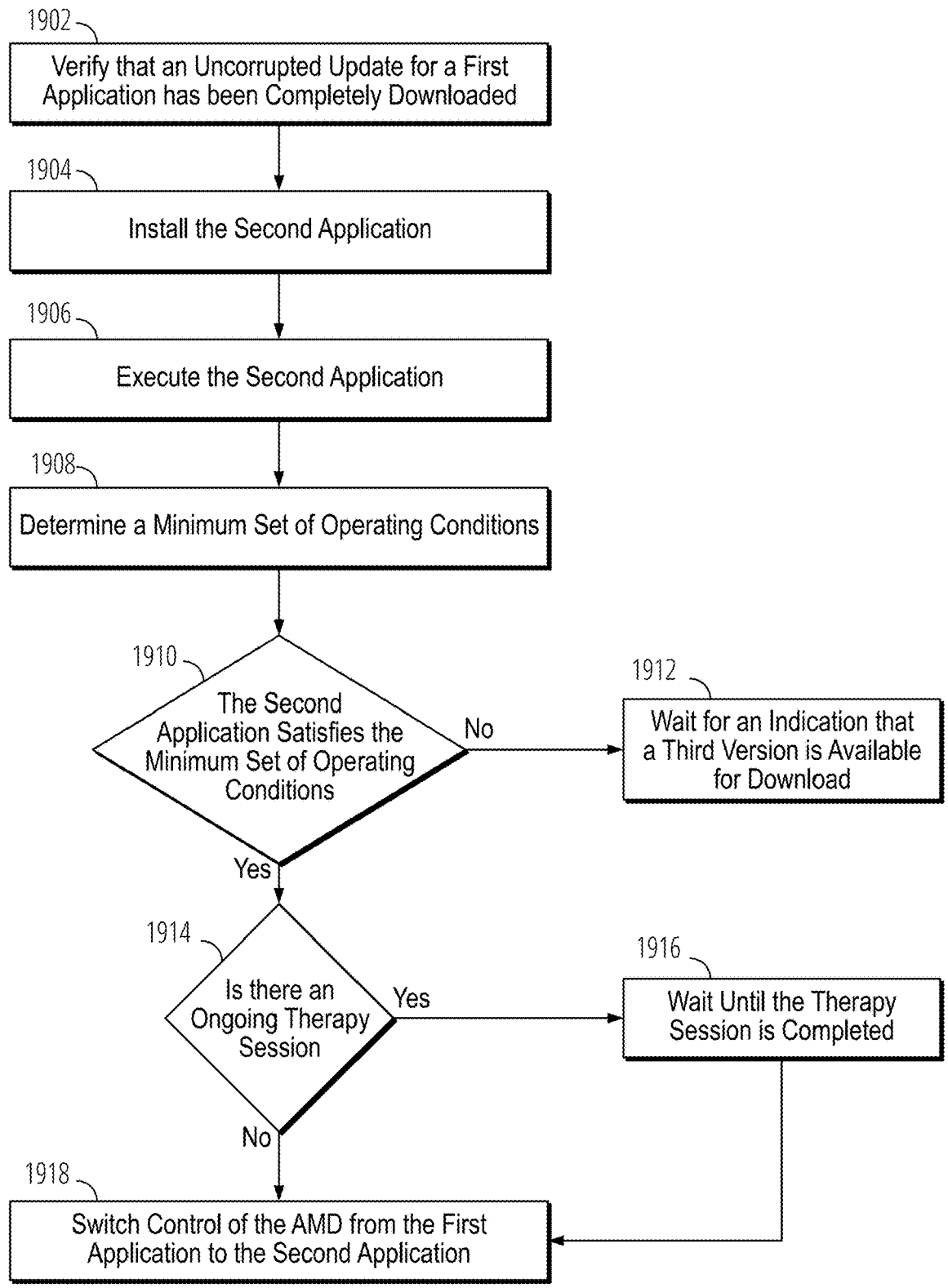
FIG. 19 is a flow diagram showing an example of a computer-implemented method that may be used by an AMD to install a second application downloaded from a host computing system, verify and switch control of the AMD from a first application to the second application without interrupting the therapy provided to a subject, only if the second application satisfies a minimum set of operation conditions.

FIG. 17-FIG. 19 are flow diagrams illustrating examples of computer-implemented methods that may be used by the AMD to install a downloaded application update without disrupting the therapy provided to a subject.

In the example method illustrated in FIG. 17, if it is verified that an uncorrupted copy of the update for an application is successfully downloaded 1702 (e.g., using the procedure described above with reference to FIG. 16), the control and computing module (CCM) of the AMD may determine the amount of time required to install the application update 1704 and wait for a trigger signal 1706 to initiate installation process. In some examples, the CCM may notify to the user 1708 through a user interface (e.g., a touchscreen display), that an update is ready for installation. The notification may include the installation time and information about the update. In such examples, if a trigger is not received, CCM may send one or more notifications to the user indicating that a new update is ready for installation. In some examples, the trigger may be the confirmation that the application was successfully downloaded. Alternatively, or in addition, the trigger may be a user command received based on an interaction by a user or subject with a user interface that is part of or that communicates with the ambulatory medical device.

The installation time may be determined by the CCM based on data or metadata provided with the downloaded application update. For example, the application update may include a file (e.g., a text file or configuration file) that includes the install time. The installation time may be determined by the manufacturer of the ambulatory medical device or the publisher of the application update. For example, the developer of the software update may average the install time across several test devices to determine the install time metadata that is provided with the software update. General purpose computers have a wide variety of configurations and the performance of a general purpose computer may vary depending on the applications executing at a particular time. Thus, the determination of install time for an application based on the measurement of install time on a test device is typically unreliable. However, as an ambulatory medical device is often a special-purpose device that is designed to perform a specific function (e.g., provide insulin to a subject), an install time determined during testing by a manufacturer may in many cases be a reliable determination of install time on an ambulatory medical device of a subject. Alternatively, or in addition, to determining the install time based on testing by a manufacturer, the install time of an application update may be determined or estimated based on a size of the application update. In some cases, the provided or estimated install time may include a buffer. In other words, an additional amount of time may be added to the install time to account for variances in operating condition of the ambulatory medical device or inaccuracies in the estimated install time.

If a trigger is received 1706, the CCM may check for any ongoing therapy session 1710. If the no therapy is currently being administered, the CCM determines the next therapy time 1714 (or the time left until the next therapy session). If therapy is currently being administered the installation will be delayed 1712 until the therapy session is compete. Once the current therapy session is complete, the CCM may determine the time remaining until next therapy session 1714 (e.g., during which medicament, such as insulin is delivered to a subject).

In some cases, the determination of the next time that therapy is to be delivered may be an estimate based on historical delivery of therapy, a present condition of the subject (e.g., when a glucose level is of a subject is at the center of a desired range, the next therapy delivery time may be estimated to be further off than when the glucose level is at the edge of the desired range), and/or an indication provided by a user or subject (e.g., an indication that the user is planning to have a meal, to exercise, or to go to sleep). Alternatively, or in addition, the determination of the next time that therapy is to be delivered may be based on a scheduled delivery of therapy (e.g., every 5 minutes or every hour).

As previously described, it is desirable to prevent disruption to therapy during the application update process. Thus, after the next therapy time is determined 1714, the estimated install time may be compared 1716 to the determined or estimated next therapy delivery time to determine whether the installation of the application update can be completed before the next therapy delivery to the subject. If it is determined that the time left until the next therapy session is sufficiently longer than the determined time for completing the installation, installation of the application updated may be initiated 1718. In some examples, the determined time to the next therapy session has to be longer than the determined installation time by a threshold value. Such threshold value may be different for different application updates and/or the type of next therapy session. If it is determined that the application installation cannot be completed before the next therapy delivery (or the time left until the next therapy is not larger than that estimated installation time by a threshold value), the installation of the application may be delayed, regardless of receipt of the trigger. In this case, the CCM may wait for the next therapy to be completed and then determine a new therapy time 1714. This process may be repeated until CCM determines that the update can be installed without interrupting an expected or scheduled therapy by the ambulatory medical device. In some examples, a new determination may be made before completion of the next therapy, to determine whether installation may be completed prior to a subsequent therapy time after the next therapy time.

In some cases, a time when the application can be installed without interrupting therapy may not be identified. In some such cases, a user (e.g., a clinician or other medical provider, or a subject) may be provided with an alert that an application update is available and/or that the application update cannot be installed without interrupting therapy. The user may be provide with an option as to whether to permit the update and/or when to install the application update. The option may include presenting the user with the estimated install time enabling the user to schedule the application update at a time when interruptions to therapy may be minimal or when an alternative source of therapy (e.g., injection therapy) can be utilized.

In some embodiments, once it is verified that an uncorrupted copy of the update for an application is successfully downloaded 1702, the AMD's control and computing module (CCM) may notify the user and wait for a trigger signal before determining the installation time. Once the trigger has been received, the CCM initiates the installation process of the downloaded copy of the application update without interrupting therapy provided by the ambulatory medical device to the subject. In such embodiments, the application update may be installed in a different memory location than the memory location where the original application is installed and executed.

FIG. 18 is flow diagram illustrating an example of a computer-implemented method that may be used by the AMD in order to install a second application that is an update to a first application executing on the ambulatory medical device, without disrupting the therapy provided to a subject. In this example, once the control and computing module (CCM) of the AMD verifies that an uncorrupted copy of the second application is successfully downloaded 1802 (e.g., using the procedure described above with reference to FIG. 16), the CCM may initiate the installation process of the second application 1804 without interrupting the execution of the first application. The CCM may confirm 1806 the successful installation of the second application and wait for a trigger signal 1810 to initiate the execution of the second application in place of the first application. In some examples, the installation of the second application may be confirmed by sending a notification the user 1808 via a user interface of the AMD. In some examples, the CCM may determine the amount of time required for switching the control of AMD to from the first application to the second application. The notification may include information about the update and the time required for switching between the applications. In some examples, the trigger may be a user command received based on an interaction by a user or subject with a user interface that is part of or that communicates with the ambulatory medical device. In such examples, if a trigger is not received the AMD may send one or more notifications to the user indicating that a new update is ready for installation. If a trigger is received, the CCM may check for any ongoing therapy session 1812. If the no therapy is currently being administered, the CCM determines the next therapy time 1816 (or the time left until the next therapy session). If therapy is currently being administered the installation will be delayed 1814 until the therapy session is compete. Once the current therapy session is complete, the CCM may determine the time remaining until next therapy session 1816. The estimated next therapy delivery time may be compared to a set threshold time to determine whether the switching from the first application to the second application can be performed without interfering with the next therapy session. If it is determined that the time left until the next therapy session is longer than the set threshold time 1818, the execution of the second application will be initiated and the execution of the first application will be halted 1820. In some examples, the set threshold time may be determined by the CCM at least partly based on the time required to execute of the second application and halt the first application. In some other examples, the set threshold time may be received from a host computing system.

In some embodiments, the performance of an application update may be tested before switching control of the AMD to the application update. FIG. 19 illustrate an example method that may be used by such embodiment. First the AMD verifies that an uncorrupted copy of the update for a first application is successfully downloaded 1902 (e.g., using the procedure described above with reference to FIG. 16). Next the AMD may install 1904 and execute 1906 the downloaded copy of the second application without interrupting the execution of the first application and therefore the therapy that might be provided by the ambulatory medical device to the subject. In some examples, the second application update may be installed to a separate portion (e.g., a separate execution space or separate memory) from the portion where the first application is installed and is being executed. The Control and computing module (CCM) of the AMD may determine that a minimum set of operating conditions 1908 are satisfied by the second application 1910, wherein the minimum set of operating conditions relate to maintaining therapy provided by the ambulatory medical device to the subject. If it is determined that the minimum set of operating conditions are not satisfied by the second application, the AMD may wait for an indication that a third application is available 1912 and repeat the procedure described above to evaluate the performance of the third application. If it is determined that the minimum set of operating conditions are satisfied by the second application, the AMD may check for an ongoing therapy session 1914. If it is determined that currently no therapy is provided to a subject, CCM may switch the control of the ambulatory medical device from the first application to the second application 1918. If currently therapy is provided to a subject, the CCM may wait until the therapy session is competed 1916 and then switch the control of the AMD from the first application to the second application.

In some cases, the ambulatory medical device may be updated (or downgraded) to add (or remove) features from the ambulatory medical device. For example, the ambulatory medical device may initially provide only insulin therapy. At some point in time, the ambulatory medical device may be upgraded to include bi-hormonal control (e.g., to provide both insulin therapy and counter-regulatory agent (e.g., Glucagon) therapy). The upgrade may be based on newly available features and/or based on a decision by a user to purchase or otherwise obtain additional features. Similarly, a user may opt to downgrade therapy from bi-hormonal to insulin-only therapy. Alternatively, the upgrade or downgrade may be made based on the availability of medicament. In some examples, a first update can be a first application version comprising a first feature set (e.g., providing insulin therapy) and a second update can be a second application version comprising a second feature set (e.g., provide both insulin therapy and Glucagon therapy). In some such examples the first feature set may comprise a subset of the second feature set. In some other examples, the first feature set may comprise a partially overlapping set of features with the second feature set.

In some examples a computer-implemented method that may be used by the AMD in order to detect, download and install an update to an application executing on the ambulatory medical device wherein the application comprises one of a first application version comprising a first feature set or a second application version comprising a second feature set. In some examples, the first feature set may comprise partially overlapping set of features with the second feature set. In some other examples, the first feature set may comprise partially overlapping set of features with the second feature set. The AMD may receive an indication of availability of the application update, download the application update and verify that an uncorrupted image of the application update is successfully downloaded (e.g., using the procedure described above with reference to FIG. 16). Next, the control and computing module (CCM) of the AMD may initiate the installation process of the application update image without interrupting the execution of the application. In some examples, the indication received by the AMD 1602 (with reference to FIG. 16), may include information about application update being an update to the first application version or to the second application version. In some such examples, the CCM may determine the version of the application update and download the application update image based on the determined version In some embodiments, any downloaded application update may be installed to a separate portion (e.g., a separate execution space or separate memory) from a currently executing version of the application. Once installation of the application is complete and the application is verified as being successfully installed, the active version of the application can be switched. For example, control of the ambulatory medical device can be provided to the updated application, the previously executing application can be ceased or halted. The old application can then be removed, or kept as backup. Determining when to switch which version of the application is active may follow a similar process as previously described for identifying a next therapy delivery time and selecting a time to switch active versions of the application when there will not be an interruption to the therapy provided by the ambulatory medical device.

In some embodiments, the ambulatory medical device may be configured to store multiple instances of an application (e.g., ambulatory medical device control software). For example, the ambulatory medical device may have a current, or first, version of the application that it is installed in a first memory location (e.g., in the memory 610) and is executing to, for example, control therapy provided by a subject. Further, the ambulatory medical device may include an updated, or second version of the application installed in a second memory location (e.g., in the memory 610). The update of the second version may have been downloaded and installed (e.g., in a prior to detection of the fault). In such embodiments, when a fault is detected during execution of the first version of the application, the ambulatory medical device may initiate the execution of the second version of the application and then switch control of the AMD to the second version of the application to maintain therapy to the subject.

Figure 20:
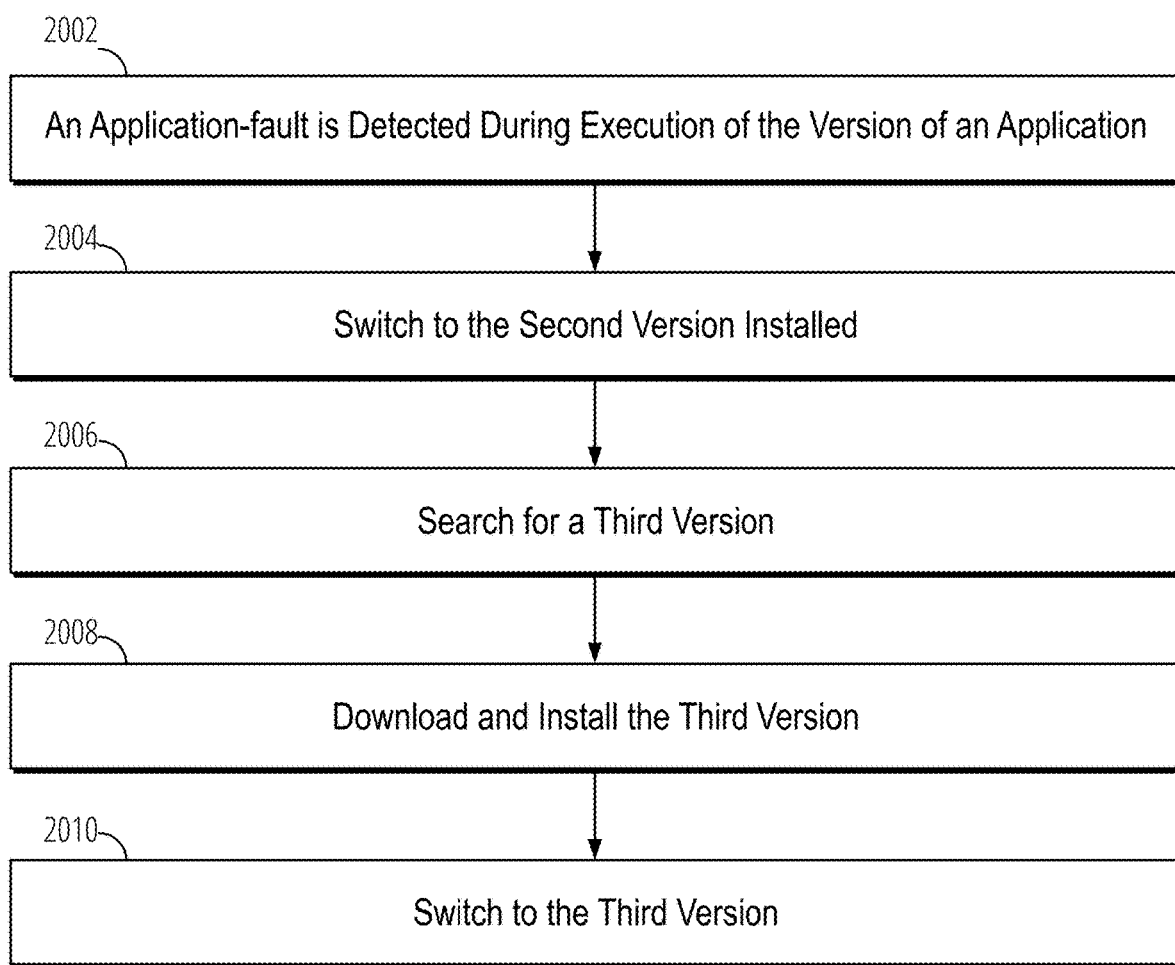
FIG. 20 is a flow diagram showing an example of a computer-implemented method that may be used to respond to detection of an application fault during the execution of a first version of an application and switching control of the AMD to a second version an application installed on the AMD.

In some examples, the second version of the application installed on the AMD may be a version older than the first version, or version that may not have track a record of stability and reliability. FIG. 20 is a flow diagram for such examples. Once an application-fault is detected during execution of the first version 2002, the control and computing module (CCM) of the AMD may switch the control of the AMD to the second version of the application 2004 while establishing a connection with a host computing system configured to host a third update and download the third update 2006. The third version of the application may be a new version, a version prior to the first version, an update to the first application that addresses the detected application-fault or an older version that satisfies the conditions to be classified as a "safe version" (e.g., less than a threshold number or rate of faults over a minimum period of time). The second version (installed in the device) may control the AMD while the third version is being downloaded and installed 2008 without interrupting the therapy. Once the download of the third version is complete, the CCM may initiate the installation process of the downloaded copy of the third application and switch control of the ambulatory medical device form the second application to the third application 2010 without interrupting therapy provided by the ambulatory medical device to the subject In yet other embodiments, a "safe version" of the application may have been installed on the ambulatory medical device prior to detection of a fault. The safe version of the application may include a version of the application that has been used by instances of the ambulatory medical device for more than a threshold period of time and has experienced less than a threshold number of faults. For example, the safe version of the application may be a two-year old version of the application that has demonstrably had less than a threshold number of faults occur over the period of two years. This safe version of the application may have less features than the first or second version of the application. However, when a fault is detected during execution of the first or second version of the application, the ambulatory medical device may switch control of the device to the safe version of the application to maintain therapy to the subject.

In some cases, if there is an issue installing an updated version of the application, the ambulatory medical device may revert to the current version or a safe version installed on the AMD.

In some other examples, the AMD may be triggered to establish a connection with the host computing system and search for the second version once a fault is detected during execution of the first version. In these examples, the ambulatory medical device may revert to the safe version (installed in the device) while downloading and installing the second version without interrupting the therapy.

Figure 21:
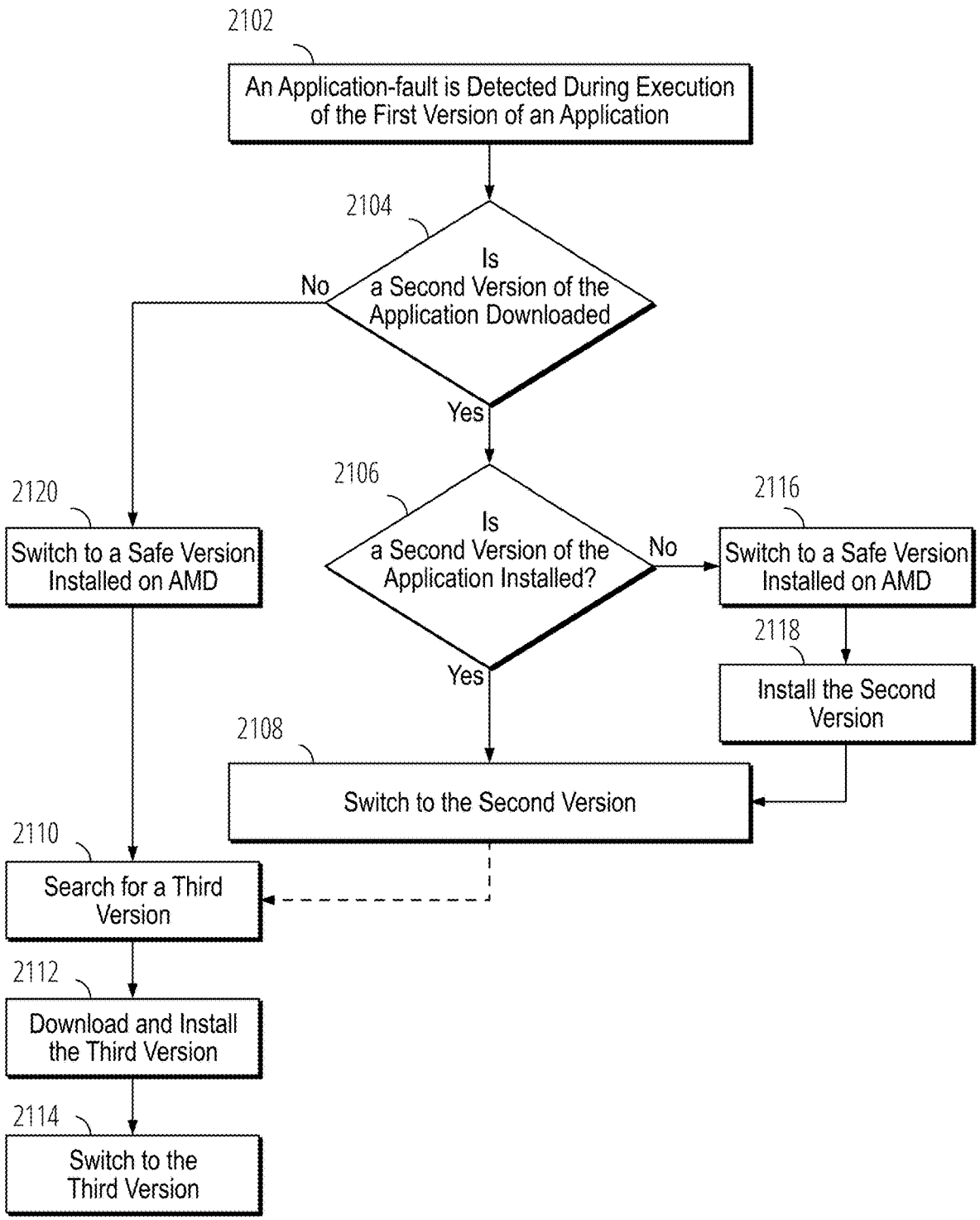
FIG. 21 is a flow diagram showing an example of a computer-implemented method that may be used to respond to detection of an application fault during the execution of a first version of an application and switching control of the AMD to a second version an application installed on the AMD and/or downloading a third version of the application.

FIG. 21 is a flow diagram illustrating yet another example of a method of responding to a fault detection by the AMD. In this example, once an application-fault is detected during execution of the first version of an application 2102, the control and computing module (CCM) of the AMD may look for a second version of the application 2104 in the main memory or the storage. If it is determined that the second version has been already downloaded, the CCM will determine 2106 whether the second version of the application is installed in a memory location and is ready to be executed. If it is determined that the second version of the application is installed, the control of the AMD will be switched to the second version of the application 2108. With reference to block 2106, if CCM determines that the second version exists in the memory but it is not installed, it will switch the control of the AMD to a safe version that may be already installed 2116 and then initiates the installation 2118 of the second version. Once the installation of the second version is complete, the CCM may switch control of the AMD from the safe version of the application to the second version of the application. In some embodiments, after the control of the AMD is switched to the second version of the application, the CCM may search for a third version of the application 2110 that may be an update to the previously downloaded second version. If a third version is found, the CCM may download and install the third version 2112 and switch the control of the AMD to the third version 2114. With reference to block 2104, if the CCM cannot find a second version of the application in a memory or storage location, it will switch the control of the AMD to a safe version of the application 2120 that may be installed in a memory location (e.g., in the main memory or in the storage) and then search for a third version of the application 2110. If a third version is found, the system may download and install the third version 2112 and switch the control of the device to the third version 2114.

In some embodiments, when an application-fault of an application executing on the ambulatory medical device is detected, the AMD may transmit an indication of the application-fault to the host computing system of a manufacturer or maintenance service of the ambulatory medical device. In some other embodiments, the AMD may notify the user when an application-fault occurs through a user interface of the AMD or user interface communicating with the AMD.

Direct Network-Connected Medical Device Communication and Remote Viewing

An ambulatory medical device, such as an ambulatory medicament device (e.g., blood glucose control system (e.g., an insulin pump or a bi-hormonal pump that includes insulin and a counter-regulatory agent), a pacemaker, or any type of medical device that may be connected to a subject to provide therapy to the subject, can generate a significant amount of data related to therapy provided to a subject (therapy data). This therapy data may be useful for the subject, a healthcare provider, or other users (e.g., parent or guardian) to actively manage the subject's health condition. For example, the therapy data may be useful to determine whether a modification to therapy may be desirable or to confirm that intended therapy is being delivered at the right time. In other examples the data may be used to generate an alerts about the health condition of the subject when therapy data indicates that immediate attention is needed with regards to subject' health condition.

Various aspects of accessing the therapy data or other types of data stored in a memory of the AMD needs proper management in order to provide uninterrupted, secure and easy access to authorized users. As described above, the procedures and task performed by an AMD, including those associated with data transfer management, may be associated with certain computer-executable instructions stored and executed by a control and computing module of the AMD. As such, different AMD configurations used for various data transfer management tasks, may be configurations of the control and computing module of the AMD.

Accessing the data from the ambulatory medical device can be problematic in some cases. For example, accessing the data may require a user to connect the ambulatory medical device to a computer to upload the data. This places a burden on the user to remember to connect the ambulatory medical device. Further, during the period when the device is connected to the computer, the subject may not be receiving therapy from the ambulatory medical device. In some cases, the subject may not be capable of connecting the device to the computer (e.g., when the AMD is not within range of the local device) and may not have someone available to assist the subject. Thus, a direct end-to-end connection to a computing system that (e.g., computing system of a healthcare provider) can safely share data (e.g., therapy data) with authorized users may facilitate data management and access.

Figure 22:
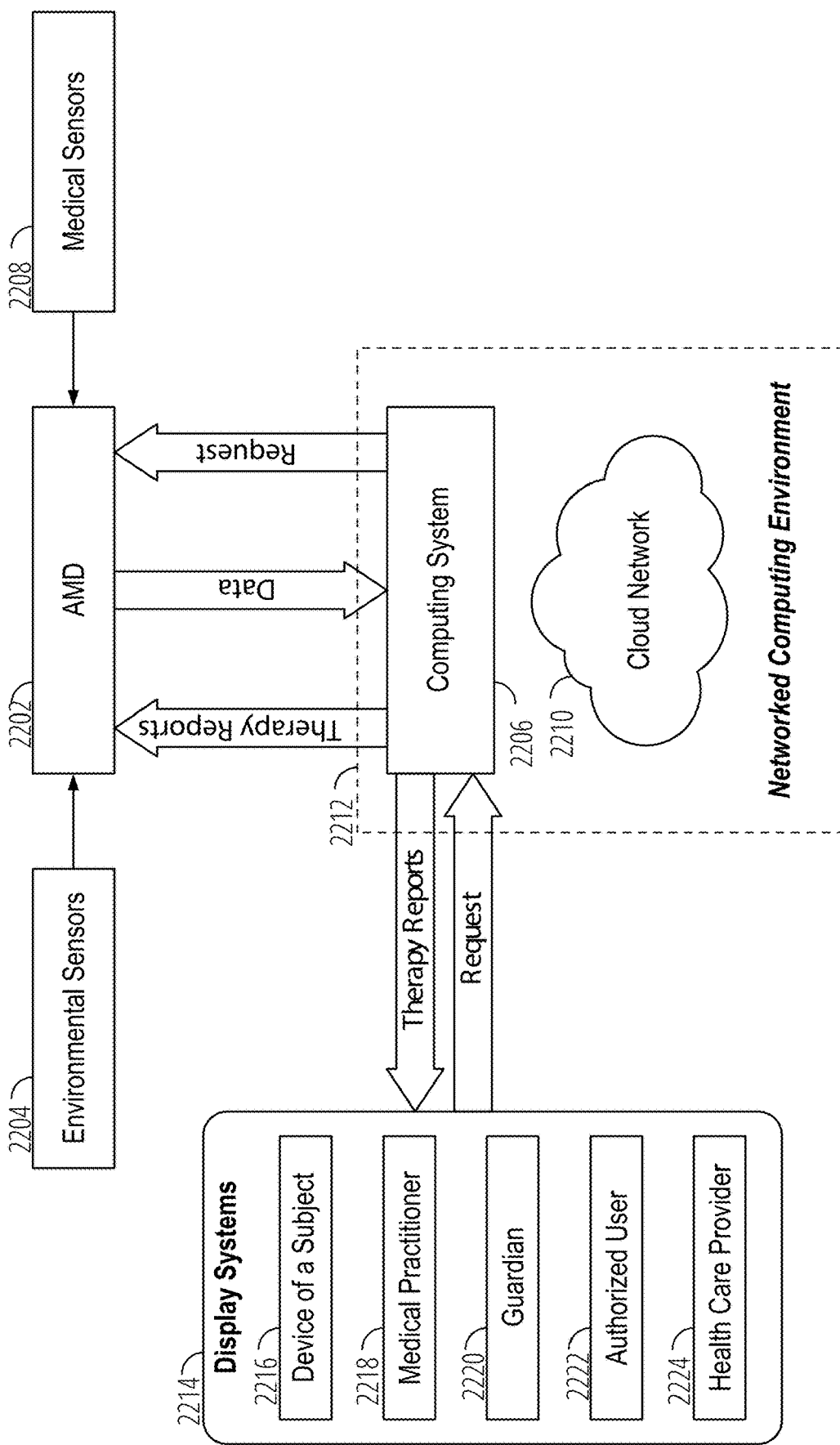
FIG. 22. is a block diagram, illustrating an example network configuration wherein the AMD is directly connected to a computing system and the computing system shares the therapy reports with one or more display systems and the AMD.

FIG. 22 is a block diagram illustrating an example network configuration wherein the AMD 2202 is directly connected to a computing system 2206 in addition to environmental sensors 2204 and medical sensors 2208. The computing system 2206 may be part of networked computing environment 2212 (e.g., a data center, networked computing system), or cloud network 2210 or cloud computing system of a cloud service provider. The computing system may include one or more non-transitional memories and one or more hardware processors configured to execute the computer-executable instructions stored in one or more non-transitional memories. In some such examples, the procedures performed by the computing system may be associated with the execution of certain computer-executable instructions stored in a memory of the computing system by a hardware processor of the computing system.

In some examples, the direct end-to-end data connection may be supported by one or more transceivers in a communication module of the AMD (e.g., the communication system 622 of FIG. 6). For example, a direct connection may be established between the AMD 2202 and the computing system 2206 over a wide area network (e.g., a cellular network) without using an intermediary system using various wireless standards and technologies (e.g., 4G, 5G and the like). In some examples, the transceiver may support communication via communication standards, including but not limited to, low power wide area network (LPWAN), Narrowband Long-Term Evolution (NB-LTE), Narrowband Internet-of-Things (NB-IoT), or Long-Term Evolution Machine Type Communication (LTE-MTC). In some cases, the transceiver is always on, and in other cases, the transceiver may be activated when a data transfer is scheduled, requested or activated. In some cases, the capability of the ambulatory medical device 2202 to communicate with the computing system may be activated during manufacture or before providing the device to a subject.

In some cases, the subject or a user establishes or initiates establishing the direct end-to-end data connection with the computing system. For example, the subject may interact with a user interface to cause the ambulatory medical device to communicate with the cloud computing service. In other cases, the direct end-to-end data connection may be initiated or established without action by the subject or the user. For example, the direct end-to-end data connection may occur automatically at particular times or when the ambulatory medical device is in particular locations. This automatic connection may occur using information supplied to the ambulatory medical device at a time of manufacture, shipment, sale, or prescription to the subject. Further, in some cases, the ambulatory medical device can communicate with the computing system without having access to a wifi network or a local area network (LAN). For example, the ambulatory medical device may communicate using a cellular or other wide area network. Further, in some cases, the interaction by the user with the ambulatory medical device may be relatively minimal or simple compared to traditional network communication. For example, a user may push a single button (e.g., an "upload" button) to trigger establishing of a connection with the cloud computing service and causing data to be provided from the ambulatory medical device to the cloud computing service.

In some cases, the ambulatory medical device may be turned on and paired with the wireless wide area network (e.g., a cellular network) at the time of manufacture, or prior to being provided to a subject. Further, the ambulatory medical device may be authenticated with the networked-computing environment as part of the manufacturing process Further, establishing the direct end-to-end data connection may include determining that the ambulatory medical device is permitted to communicate with the computing system based at least in part on the device identifier.

In some implementations, establishing the direct end-to-end data connection may include determining that the ambulatory medical device is permitted to communicate with the computing system based at least in part on a device identifier associated with the ambulatory medical device. The device identifier may be a unique identifier specific to the ambulatory medical device. The device identifier may include or may be based on one or more of an Internet Protocol (IP) address, a Media Access Control (MAC) address, a serial number, or a subject identifier of a subject that receives therapy from the ambulatory medical device.

Further, establishing the direct end-to-end data connection may include determining that the ambulatory medical device is permitted to communicate with the computing system based at least in part on the device identifier. The device identifier may be initially provided to the networked-computing environment prior to provisioning of the ambulatory medical device to the subject. For example, the device identifier may be initially provided to the networked-computing environment as part of a manufacturing process for manufacturing the ambulatory medical device. The request may include a device identifier associated with the ambulatory medical device.

The ambulatory medical device may be configured to at least identify a computing system 2206 of a networked computing environment 2212 based on a whitelist of one or more approved computing systems. The whitelist may be stored in a memory of the AMD 2202 (e.g., a memory in the control and computing module of the AMD). Further, the whitelist may be configured during manufacture of the ambulatory medical device. For example, the whitelist may be configured with connection information to establish communication with one or more computing systems of a networked-computing environment. Further, the ambulatory medical device may be configured to at least obtain an address of the computing system from the whitelist and to establish a direct end-to-end data connection to the computing system of the networked-computing environment via a wireless wide area network using the address. The whitelist may include unique identifiers, such as MAC addresses or static IP addresses that are associated with computing systems of the cloud services provider.

To enhance security, the ambulatory medical device may use a whitelist that identifies via a unique identifier (e.g., via an IP address, a MAC address, or a URL) permitted cloud servers or computing systems in networked computing environment. Further, the cloud computing service may have a whitelist that uses unique identifiers to specify ambulatory medical devices and/or other computing systems (e.g., remote display systems) that are permitted to communicate with the cloud computing system.

When the AMD communicates data over a network, there is a risk of a data breach. Thus, to improve security, all communication between the ambulatory medical device and the computing may be based on a secure data transmission method. For example, the ambulatory medical device may encrypt all data using an asymmetric key.

In some examples, the therapy data may be encrypted before being transferred to the computing system. In these examples, AMD may have a public key and a private key stored in one of its memories permitting the AMD to encrypt data communications transmitted by the ambulatory medical device to the computing system. In these examples, AMD may transmit the public key along with the therapy data to the computing system. The public key provided by the AMD and a private key stored on the computing system may permit the computing system to decrypt the data received from the ambulatory medical device. In some such cases, the public key may timeout and a new public key may be obtained from the ambulatory medical device to facilitate decrypting subsequent communications from the ambulatory medical device. In some cases, the public key may be associated with a time-to-live (TTL) value. In some such cases, the public key may timeout and a new public key may be obtained from the ambulatory medical device to facilitate decrypting subsequent communications from the ambulatory medical device.

Moreover, the secure data transmission may include generating a shared secret based at least in part on the public key and the private key. In some such cases, decrypting the encrypted data comprises using the shared secret to decrypt the encrypted data. In some examples, shared secret may be established using public key exchange algorithm (e.g., Diffie-Hellman key exchange algorithm).

In some cases, the computing system may be configured to transfer the data after receiving a request to transfer data stored on the ambulatory medical device to the computing system over the direct end-to-end data connection via the wireless wide area network. Responsive to receiving the request to transfer data stored on the ambulatory medical device to the computing system, the computing system may be configured to receive, via the direct end-to-end data connection.

Once a connection is established and the therapy data is transferred to the computing system, the computing system may analyze the therapy data received from the ambulatory medical device and generate a therapy report. Further, the computing system may detect an alarm condition, based on therapy data analysis, and generate an alarm that may be provided to the subject, authorized user (e.g., healthcare provider). In some cases, the therapy data may trigger an automatic response by the computing system. For example, the AMD may determine that a medicament or another disposable is running low based on the received data and may automatically reorder the medicament or the disposable.

In some cases, the computing system may periodically receive data from the ambulatory medical device based on a regular schedule. Alternatively, or in addition, the data may be received in response to a command or when the ambulatory medical device determines it is within a certain location. For example, when the ambulatory medical device determines it is within a subject's home or at a healthcare provider's office based on a local area network connection or based on a geolocation system (e.g., a global positioning system (GPS)). In some implementations, additional encrypted data is received from the ambulatory medical device on an intermittent basis. Alternatively, or in addition, additional encrypted data is received from the ambulatory medical device on a continuous basis for at least a time period. The ambulatory medical device may be configured to transmit data as it is generated, or shortly thereafter, (e.g., in real or near real-time (e.g., within a few millisecond, seconds, or minutes of the data being generated)), or in bulk at specified periods of time. Transmitting the data in bulk at particular time periods may extend battery life, but may provide for less up-to-date analysis. Data can be made available on-demand by keeping the transceiver always on, but this may consume more power. Thus, the scheduling of data transfer may be balanced based on different considerations, such as: (1) power consumption and (2) need to share information with authorized users or systems.

In some cases, the computing system may be used as a backup for the ambulatory medical device. For example, the ambulatory medical device can backup data to the computing system every night, when it is charging, or when it is in proximity to home or a physician's office (e.g., when subject is in waiting room, the device may upload data that the physician can then access). Moreover, if the ambulatory medical device is replaced (e.g., for a new model or to replace a damaged device), the device can automatically synchronize with the computing system to obtain subject-specific configuration or therapy control data.

Therapy Data and Therapy Report

In some examples, the therapy data comprises dose or dosage data corresponding to one or more doses of medicament provided by the ambulatory medical device to the subject. Further, the therapy data may comprise subject data corresponding to a medical or physiological state of the subject as determined by the ambulatory medical device.

In other examples, the data provided to computing system may include any type of data that may be measured or obtained by the ambulatory medical device and may include a record of therapy provided by the ambulatory medical device. For example, the data may include a time that therapy was provided, an amount of medicament provided as part of the therapy, a measure of one or more vital signs of the subject, a measure of blood glucose levels at different times for the subject, a location of the subject, and the like.

In some cases, the therapy data may be used to track the use of disposables, such as insulin or other medicament, or insulin pump site kits. In some cases, the computing system may automatically order or reorder disposables at a particular time based on tracking the use of the disposable. Alternatively, or in addition, the reordering of the disposables may be initiated or performed from the ambulatory medical device (e.g., via a wireless wide area network or via a local connection through a separate electronic device).

In some cases, the data transferred to the computing systems may comprise operation data corresponding to operation of the ambulatory medical device. Alternatively, or in addition, the data may further comprise error data corresponding to an error in operation of the ambulatory medical device.

In some examples, the data, therapy data and/or the therapy report may be stored in a memory of the computing system and/or at a storage of the networked-computing environment.

In some cases, the method may include converting the therapy data from one format to another format. For example, the method may include converting the therapy data from a format used to store and/or present data on ambulatory medical device to a format that can be stored or processed on the computing system. In some cases, the therapy data is converted from a machine-readable format to a human-readable format. The data may be stored in a more easily interpreted format that can be understood by different types of users. For example, the data may be presented in one format for a healthcare provider (e.g., sensor readings), a simplified format for a subject or parent of a subject, other data formats for displaying data to different types of users.

In some examples, the therapy data collected from different AMDs associated with plurality of subjects may be aggregated for a group of subjects based on their association with an institution or organization (e.g., a clinic, an insurance company, and the like)

In some other examples, a therapy report based at least in part on the therapy data may be generated by the computing system. The therapy report may comprise time-series therapy data relating to the therapy delivered by the ambulatory medical device over a particular time period.

In some examples, the therapy report may be sent to AMD wherein the subject can see the report via a user interface (e.g., a touchscreen display).

In some cases, the ambulatory device data and/or data generated by the computing system based on the ambulatory device data can be viewed on a secondary display system from the computing system. For example, a clinician or parent can access the data from their personal device. The communication between the computing systems and the viewing device may be encrypted. Moreover, permission for sharing of end user data with a 'follower' (e.g., family member) or clinician may be granted or controlled by the end user (e.g., the subject or a guardian).

An association between a subject, a clinic, and/or an ambulatory medical device may be performed by association of a device serial number of the ambulatory medical device with the subject and/or clinic. Further, a user (e.g., a subject, clinician, or parent) can access therapeutic recommendations through the cloud in case either the ambulatory medical device (e.g., an insulin pump) or the CGM sensor fails to function.

In some cases, the computing system may be configured to at least receive a request from one or more display systems 2214 that are separate from the networked computing environment to access the therapy report, therapy data or other data received by or stored in the AMD. In some cases, the display system may be a computing system of a medical practitioner 2218 (e.g., such as a doctor, nurse, . . . ), a guardian of the subject 2220 (e.g., subject's parents), an authorized user 2224 (e.g., a user authorized by the subject such as spouse, relative, friend, and the like), a health care service provider 2222, or a device of the subject 2216 (e.g., cell phone, personal computer, tablet and the like).

In some examples, the display system can be a therapy data management system that analyses a therapy data associated with a specific type health problem (e.g., data associated with managing diabetes) and provides useful information to the subject or an authorized user to monitor and manage the corresponding ailment.

The request may comprise an account identifier associated with a user that generated the request. In some examples, the account identifier may comprise a unique identifier associated with the subject. Alternatively, or in addition, the account identifier comprises a unique identifier associated with a user that is authorized to access the therapy report. The user may or may not be the subject. In some aspects of the present disclosure, the method may further include associating the therapy data with the account identifier at a storage of the networked-computing environment. Further, the computing system may be configured to determine whether an account associated with the account identifier is permitted to view the therapy report. In some examples, account permissions may be granted and/or modified by the subject. For example, the subject can access an account at a networked computing environment 2212, for example, a cloud service provider associated with the subject, and provide one or more identifiers associated with one or more other users to give them permission to access the subject's therapy data or report stored on the computing system.

Responsive to determining that the account is permitted to view the therapy report, the hardware processor may be configured to transmit the therapy report to the display system over an encrypted communication channel.

In some cases, the method may include receiving an identity or identification information of one or more users that are authorized to access therapy data stored at the networked-computing environment. For example, a user or subject may authorize a clinician or other healthcare provider, a parent or guardian, or other users that the subject desires to have access to the therapy data. The identity information of the one or more users may include any type of information that may identify the user or enable the user to be authenticated. For example, the identity information may include a name, unique identifier (e.g., social security number), an email, an address, a phone number, account information for the user at the networked-computing environment, or any other identifying information.

Figure 23:
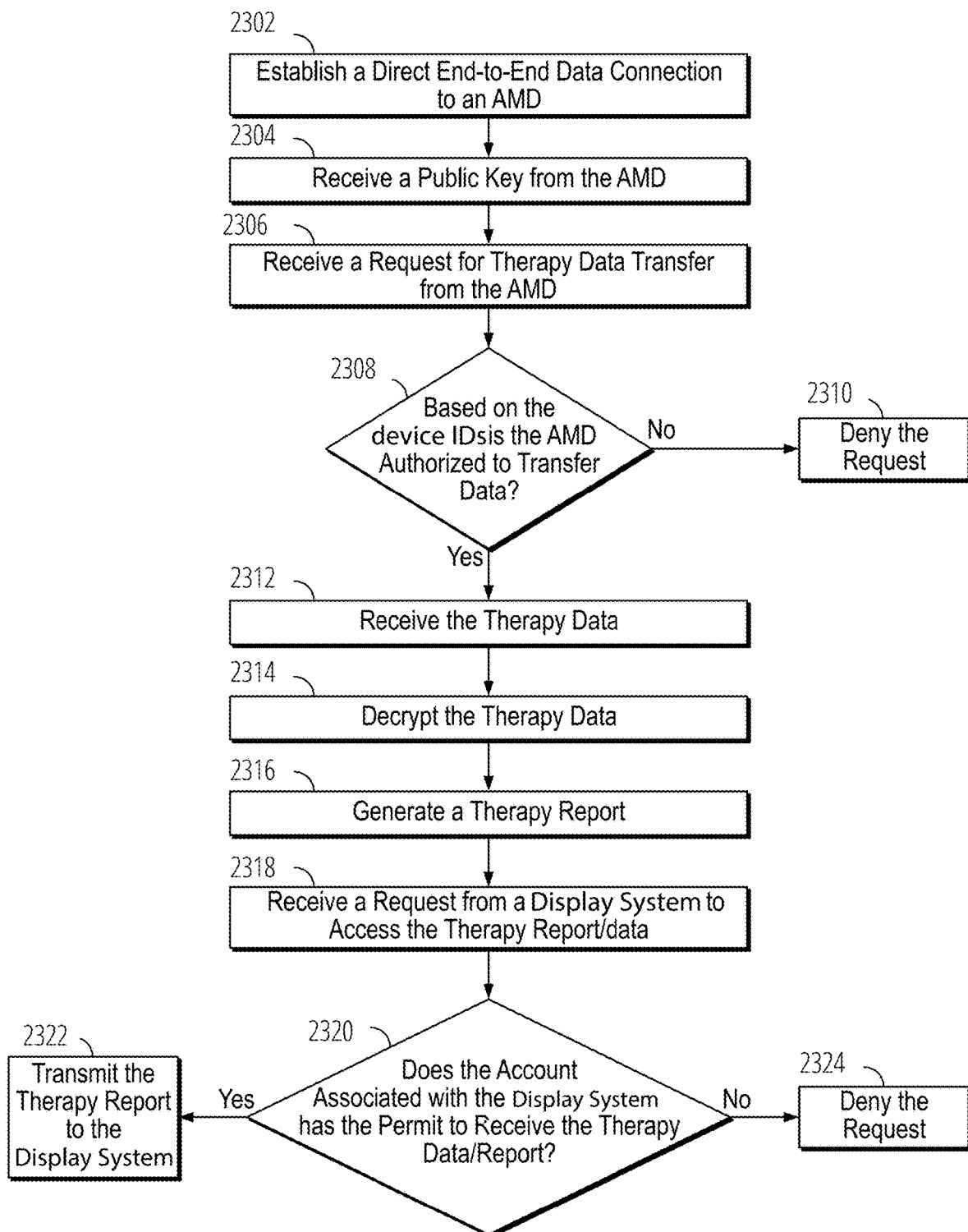
FIG. 23 is a flow diagram illustrating an example method that may be used by a computing system, to generate and share a therapy report based on encrypted therapy data received from an AMD.

FIG. 23 is a flow diagram that illustrates an example method that may be used by computing system 2206, to generate and share a therapy report based on encrypted therapy data received from an AMD 2202. In some examples, the AMD 2202 may generate the encrypted therapy data using a public key and a private key. The method may include establishing a direct end-to-end data connection 2302 to an ambulatory medical device, for example, via a wireless wide area network (WAN) using a Narrowband Long-Term Evolution (NB-LTE) transceiver included in the AMD 2202. Once a direct end-to-end data connection between the AMD 2202 and the computing system 2206 is established, the computing system may receive a public key 2304 (e.g., associated with encrypted data), from the AMD 2202 over the established connection. Next, the computing system may receive a request from the AMD 2306 to transfer data (e.g., therapy data) stored on the AMD 2202 to the computing system 2206 over the direct end-to-end data connection. In some examples, the computing system 2206 may use the device ID associated with the AMD 2202 to determine whether the AMD 2202 is authorized to transfer data to the computing system 2308. If, based on the device ID, it is determined that the AMD 2202 is authorized to transfer data to the computing system, the encrypted therapy data may be transferred 2312 to the computing system. If, based on the device ID, it is determined that the AMD 2202 is not authorized to transfer data to the computing system, the request may be denied 2310. The computing system may decrypt the encrypted therapy data 2314 using a private key (e.g., stored in a memory of the computing system) and a public key received from the AMD 2202. In some examples, the therapy data may be used to generate a therapy report 2316. In some examples, the decrypted therapy data and/or therapy report may be stored in a memory of the computing system 2206.

The example method may further include receiving a request from a display system 2214 that is separate from the networked computing environment, to access the therapy report 2318. The request may comprise an account identifier associated with a user that generated the request. The method may include determining using the account identifier to determine whether the account associated with the account identifier is permitted to view the therapy report 2320. In the computing system determines that the account associated with the received account identifier does not have the required permission, the request will be denied 2324. Responsive to determining that the account is permitted to view the therapy report, the method may include transmitting the therapy report to the display system 2322 over an encrypted communication channel.

In certain implementations, the method may further include determining that the therapy data or other data received from the AMD satisfy an alert threshold condition. In these implementations, it is determined that the therapy data or other data received from the AMD satisfy an alert threshold condition, the computing system may send an alert to one or more display systems designated to receive alerts from the computing system.

In some examples, alert threshold condition may be associated with the health condition of the subject. For example, alert threshold condition may include subject's blood sugar level is above or below a set value (hyperglycemia or hypoglycemia). In some other examples the alert threshold condition may be associated with the operation of the AMD. For example, alert threshold condition may include the rate of therapy (e.g., the rate at which insulin is provided to a subject) being above or below a set value.

In some other examples, alert threshold condition may be associated with the temporal behavior of therapy data over a period of time. For example, the alert threshold condition may include the fluctuations or variations of the subject's blood sugar level being above a set value.

In some examples, the alert threshold condition may be defined or set by health provider. In some such examples, the health provider may change one or more alert threshold conditions based on the health condition of the subject.

Figure 24:
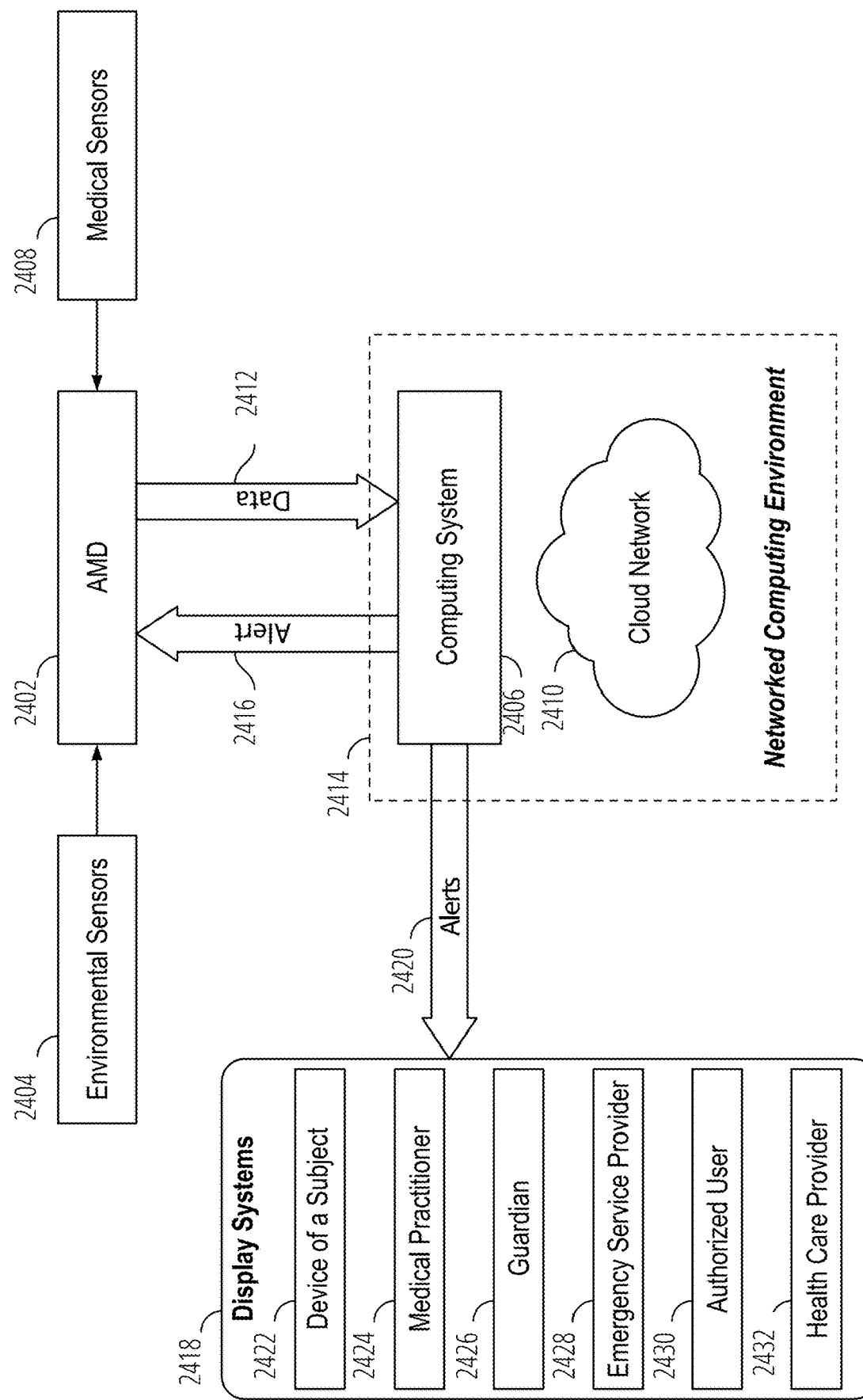
FIG. 24. is a block diagram, illustrating an example network and data flow configuration wherein the AMD is directly connected to a computing system and the computing system generates and sends alerts to one or more display systems and the AMD.

FIG. 24 is block diagram, illustrating an example network and data flow configuration where an AMD 2402, which is directly connected to a computing system 2406 (e.g., computing system within a cloud network 2410), may generate and send alerts 2416 (e.g., alert messages, alert signals and the like) upon determining that data 2412 received from the AMD satisfies a threshold condition. The computing system 2406 may be part of networked computing environment 2414 (e.g., a data center, networked computing system), or cloud network 2410 or cloud computing system of a cloud service provider. The computing system may include one or more non-transitional memories and one or more hardware processors configured to execute the computer-executable instructions stored in one or more non-transitional memories. The AMD may receive data from one or more medical sensors 2408 (e.g., analyte sensor, temperature sensor, heart beat sensor, and the like) and/or one or more environmental sensors (e.g., geolocation receiver, motions sensor, accelerometer and the like.). These sensors may be included in the AMD unit or may be connected to the AMD via a wired or wireless link.

In some cases, the display systems receiving the alert 2420, may be display systems that have already received therapy reports from the computing system 2406. In other examples, a group of display systems may be selected and authorized by the subject, who is receiving therapy from the AMD, to receive alerts 2420. The display systems that may receive alerts 2420 from the AMD may include: a medical practitioner 2424 (e.g., such as a doctor, nurse, . . . ), a guardian of the subject 2426 (e.g., subject's parents), an emergency service provider 2428, an authorized user 2430 (e.g., a user authorized by the subject such as spouse, relative, friend, and the like), a healthcare provider 2432, or a device of a subject 2422 (e.g., cell phone, personal computer, tablet and the like). In some examples, when it is determined that received data 2412 the AMD satisfies a threshold condition, in addition to sending a alerts to one or more display systems 2418, the computing system 2406 may send an alert 2416 to the AMD 2402.

In some examples, the AMD 2402 may be configured to establish a connection to support continuous data transfer to the computing system 2406 for a given period of time (e.g., provided to the AMD by the subject), in order to capture any data that is generated over that period and satisfies an alert threshold condition. For example, the subject may request a continuous connection between AMD and the computing system when going for hike alone to make sure that if his/her health condition deteriorate during the hike, an alert is sent to authorized display systems.

In some examples, a geolocation sensor (e.g., a Global Positioning System (GPS) receiver) and/or a proximity sensor can be used to enable location-activated features such as automatic upload of data at certain locations.

In some cases, the ambulatory medical device may include or be connected to an accelerometer or a geolocation system. This velocity of the ambulatory medical device may be determined based at least in part on the accelerometer or geolocation system. Using the data obtained 2412 from the ambulatory medical device 2402 including the location and/or velocity information, the computing system 2406 can provide intelligent alerts. For example, if the data indicates that a user is travelling at a high rate of speed (e.g., likely in a car) and the user's blood glucose level is low (e.g., below 55 mg/dl), the computing system may automatically alert emergency service providers 2428 that a subject is at risk of hypoglycemia and may be driving. Further, the computing system can provide a location of the subject to the emergency service provider 2428.

In some examples, the computing system can generate alerts based on a trend of the aggregated therapy data or based on therapy data that is an outlier to the aggregate therapy data or an outlier to a time-based average of the therapy data.

Further, the geolocation sensor and/or a motion sensor (e.g., an accelerometer) can be used to detect velocity of a subject to enable intelligent motion-sensitive alerts. For example, if the subject is moving at 60 mph and experiences low blood glucose, the system may enable a set of driving alerts and schedule possibly therapy in the future. The driving alerts may inform the subject to pull over immediately due to a risk of a hypoglycemic event. Further, an emergency responder may be informed of a subject location using based on information obtained from the geolocation sensor. If the subject is moving at 6-7 mph, exercise alerts may be enabled to, for example, alert the user to pause exercising and attend to low blood sugar. If the subject hasn't moved for 3 hours and has low blood sugar, the system can enable automatic notification to emergency services. Further, a determination of the subject's motion can be used to automatically adjust setpoint (e.g., raise setpoint during exercise). The activity level of the subject can be sensed and use to improve alerts and therapy.

Additionally, the cloud server can send a text message or call to a follower's and/or end user's phone or smart device in case the therapy data satisfies an alert threshold. These messages may be provided from the cloud computing system to a third-party device in case roaming or disabling of the data plan on the ambulatory medical device occurs (e.g., no TCP/IP available). Further, the cloud computing service may send a text message or call 911 in case of a detected emergency. The cloud server can track, for example, via GPS, the end user's most recent location and share that information with a follower and/or emergency personnel. Moreover, the cloud computing system may enable an end user to order and reorder medical supplies directly from the viewing device.

Moreover, the computing system can generate notifications (e.g., generate a message when there is a risk of hypoglycemia). Further, more detailed processing in the cloud can result in improved recommendations (e.g., Tmax, setpoint, or other control parameters)

Figure 25:
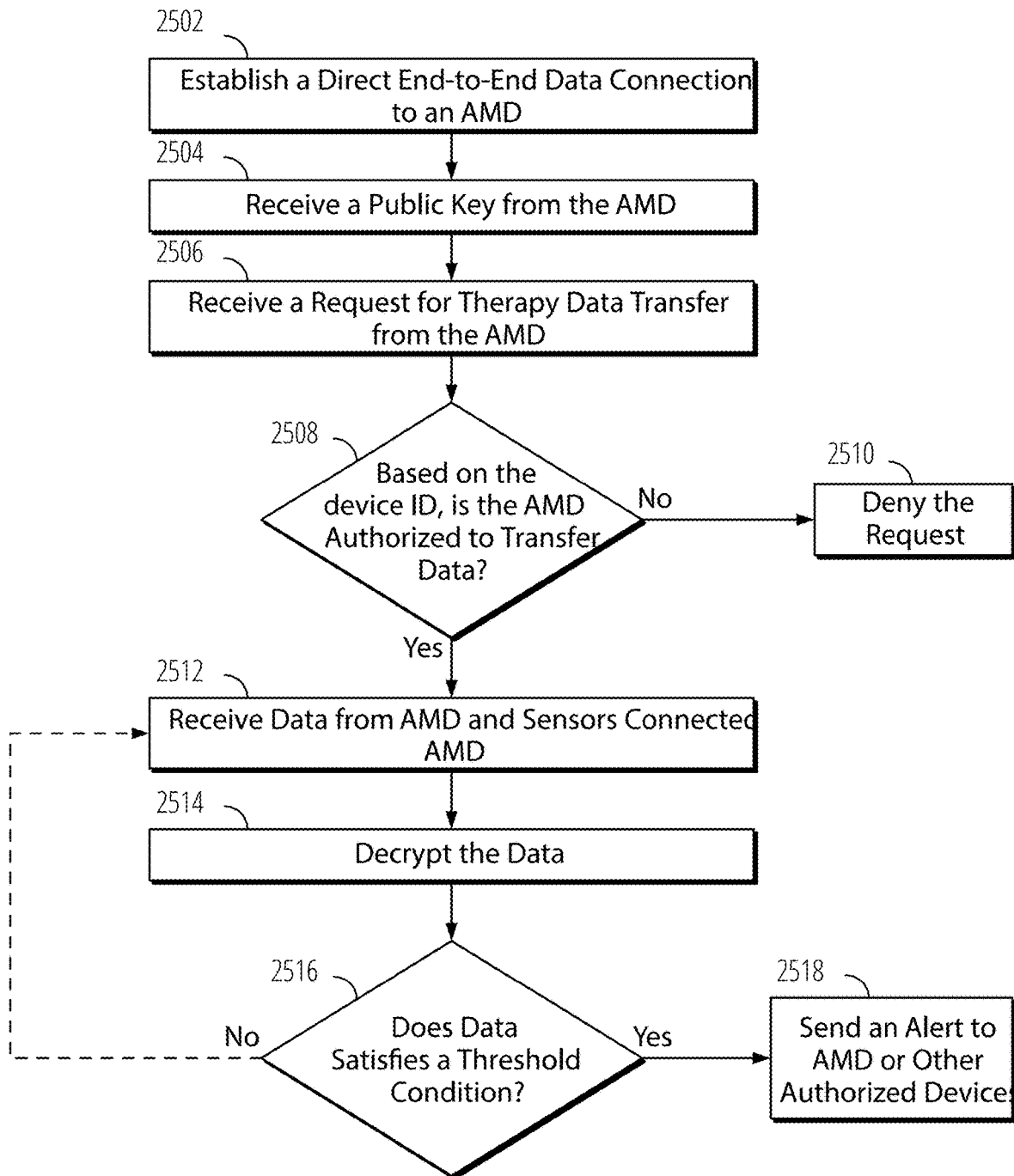
FIG. 25 is a flow diagram illustrating an example method that may be used by a computing system, to generate and send an alert to one or more authorized devices.

FIG. 25 is a flow diagram illustrating an example method that may be used by computing system 2406, to generate and send alerts (e.g., alert messages, alert signals and the like) to one or more authorized devices and to the AMD. The method may include establishing a direct end-to-end data connection 2502 to an ambulatory medical device, for example, via a wireless wide area network (WAN) using a Narrowband Long-Term Evolution (NB-LTE) transceiver included in the AMD 2402. In some examples, the direct end-to-end connection may be established for a given period of time set by the subject or an authorized user (e.g., a guardian of the subject). Once a direct end-to-end data connection between the AMD 2402 and the computing system 2406 is established, the computing system may receive a public key 2504, from the AMD 2402 over the established connection. Next, the computing system may receive a request from the AMD 2506 to transfer data (e.g., therapy data, medical sensor data or environmental sensor data) generated by the AMD 2402 to the computing system 2406 over the direct end-to-end data connection. In some cases, the request may include a time period during which AMD continuously transmits any data generated by the AMD 2402 or obtained from one or more sensors (e.g., environmental sensors 2404 or medical sensors 2408), to the computing system 2406. In some such cases, the time period for continuous data transfer from the AMD 2402 to the computing system 2406, may be provided by the subject or a guardian of the subject to the AMD. In some examples, the computing system 2406 may use the device ID associated with the AMD 2402 to determine whether the AMD 2402 is authorized to transfer data 2508 to the computing system 2406. If, based on the device ID, it is determined that the AMD 2402 is authorized to transfer data to the computing system 2406, the encrypted therapy data may be transferred 2512 to the computing system 2406. If, based on the device ID, it is determined that the AMD 2402 is not authorized to transfer data to the computing system, the request may be denied 2510. The computing system 2406 may decrypt the received data 2514 using a private key (e.g., stored in a memory of the computing system 2406) and a public key received 2502 from the AMD 2402. In some examples, the computing system 2406 may determine whether the received data (e.g., therapy data, medical sensor data or the environmental sensor data), satisfies a threshold condition 2516. In some cases, the threshold condition may be provided to the AMD by the subject or an authorized user (e.g., a guardian of the subject). In some other examples, the threshold condition may be provided by a healthcare provider. In some such examples, the threshold condition may be stored in a memory of the AMD. If it is determined that the data satisfies a threshold condition, an alert may be generated and sent 2518 to one or more display systems 2418 that are authorized (e.g., by the subject or a guardian of the subject) to receive alerts. In some examples, the subject or the guardian may authorize one or more display systems 2418 to receive alerts by providing the account IDs of the one or more displays systems to the computing system 2406 or the networked computing environment 2414.

Preventing Inadvertent Therapy Changes

As described above, the ambulatory medicament device may include a user interface (e.g., touchscreen interface or a non-touchscreen interface) that may present one or more user-interface screens to a user enabling the user to modify one or more therapy settings of the ambulatory medicament device, such as a quantity of medicament delivered when a condition is met or the condition that triggers the delivery of medicament to a subject. The user may be a subject receiving medicament or therapy, or may be another user, such as a clinician or healthcare provider, or a parent or guardian. For ambulatory medicament devices that include a user interface, there is a risk that a setting is accidentally modified or is modified (intentionally or unintentionally) by a user that does not fully comprehend his or her action (e.g., a child or a user with a reduced mental capacity). Further, ambulatory medicament devices may accidentally have settings modified by inadvertent interactions with a user interface, such as may occur when an ambulatory medicament device is worn against the body of a subject.

This section relates to an ambulatory medicament device (AMD) to prevent an inadvertent modification in medicament deliver, for example, in the event of a setting of the AMD being accidentally modified by a user or inadvertent interactions with a user interface.

As mention above, in some embodiments the user may modify the control or configuration the AMD using a user interface. There is a possibility that the control or configuration of the AMD is accidentally modified through the user interface. For example, as the user may transport the ambulatory medical device, there is a danger that the user will inadvertently activate input in the ambulatory medical device that initiates a therapy change input (e.g., by applying pressure on the ambulatory medical device that may be placed in the jacket pocket of the user).

Figure 26:
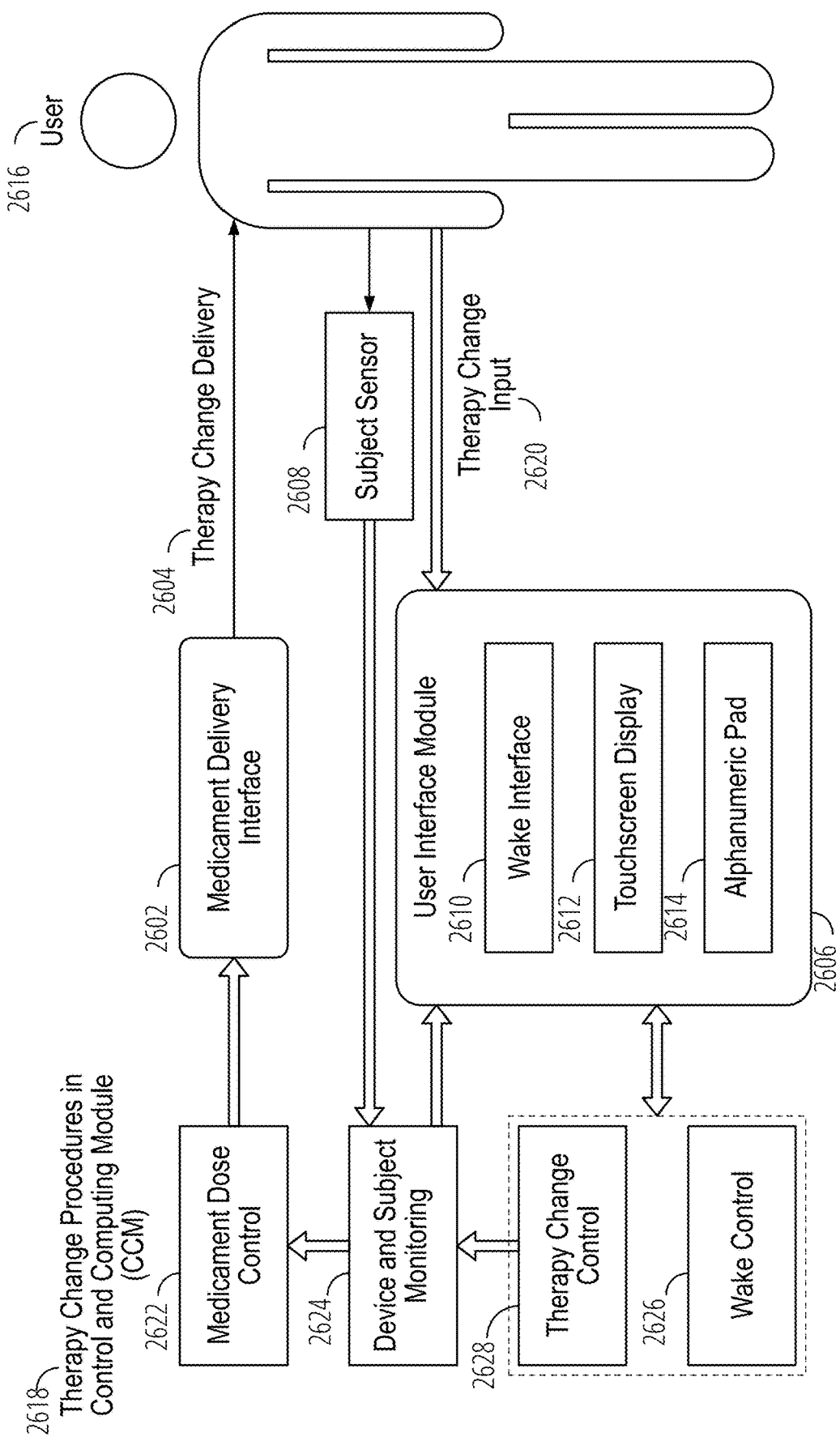
FIG. 26 illustrates the interconnection among modules and procedures in AMD involved in receiving, accepting and/or canceling therapy change request.

With reference to FIG. 26, in some such embodiments, the control and computing module (CCM) of the AMD may include a set of therapy change procedures 2618 implemented to prevent therapy change inputs 2620 that are inadvertent. The therapy change procedures 2618 may be implemented as instructions stored in a memory of CCM and executed by the processor. The therapy change input 2620, received from a user 2616, may be verified by the therapy change procedures 2618 before the ambulatory medical device provides the therapy change delivery 2604. All the user interactions with the user interface module 2606 may be controlled and analyzed by the control and computing module (CCM) via one or more therapy change procedures 2618.

In these embodiments, the user 2616 may wake or unlock the AMD by interacting with a wake interface 2610. The wake interface 2610 can be any of the additional user interfaces mentioned above, configured to generate a wake input to the CCM when detecting a pre-set user interaction.

The therapy change input 2620 can be an input provided by the user 2616 to change a therapy that is currently being delivered to the user 2616. In some embodiments, the therapy change input 2620 may cause the insulin or glucagon infusion pump to start infusing an amount of insulin or glucagon into the user 2616. Alternatively, the therapy change input 2620 may modify the rate of insulin or glucagon infusion into the user 2616. The therapy change input 2620 may also cancel insulin or glucagon infusion into the user 2616 from the insulin or glucagon infusion pump.

When a wake action is detected by the wake interface 2610, a wake input is sent to the control and computing module wherein it imitates a wake control procedure 2626 that generates a wake signal to wake/unlock the user interface (e.g., a touch screen display).

When in the wake and/or unlocked state, a user may interact with the touchscreen display 2612, alphanumeric pad 2614 or other types of user interfaces that may be included in the user interface module 2606, to obtain access to therapy change user interface.

The therapy change user interface may be activated by a first user interaction with the user interface (e.g., touchscreen display 2612). When the first user interaction is detected, the user interface module user interface module 2606 sends an input signal to the control and computing module wherein it is analyzed by a therapy change control procedure 2628. If it is determined that the first user interaction satisfies a set of predefined conditions, the therapy change control procedure 2628 generates a signal to the user interface module user interface module 2606 to activate the therapy change user interface.

In some embodiments, the therapy change user interface may be limited based on the first user interaction. For example, the therapy change control procedure 2628 may send one of two signals to the user interface module user interface module 2606. The therapy change user interface may then unlock one of two different therapy change user interfaces that result in different options of therapy change selections for the user 2616. In an implementation of this example, a therapy change selection to make a significant therapy change, such as dramatically increase the rate of insulin or glucagon infusion rate, requires a first user interaction that is different from the first user interaction that would be required for an insulin or glucagon infusion at a normal or prescribed rate. In some examples, the first user interaction may be a simple interaction (e.g., a simple gesture) that unlocks a therapy change user interface with therapy change selections that are limited. Another first user interaction may be a complicated interaction (e.g., a series of complex gestures) that unlocks a therapy change user interface with therapy change selections that have no limits. An example of this implementation may be useful for child users. The child user may perform the first gesture that is made up of a series of simple inputs to unlock therapy change selections that are limited. An adult user may perform the first gesture that is made up of a series of complex inputs to unlock the therapy change user interface with therapy change selections that have no limits.

Once activated, the therapy change user interface that may provide one or more control or configuration elements that enable the user to modify the control or configuration of the ambulatory medicament device. The control or configuration element may include any type of user interface screen on the touchscreen, or other type of user interface in the non-touchscreen context, that enables or permits a user to change a configuration of the ambulatory medicament device. This change in configuration of the ambulatory medicament device may relate to a change in the therapy provided or in the detection of a triggering event that causes therapy (e.g., medicament) to be provided to a subject. For example, the change in configuration may include a selection between one or more hormones that regulate blood sugar level (e.g., insulin or glucagon) of a user, an amount of the one or more hormones that regulate blood sugar level of the user.

In some cases, a change to the configuration of the ambulatory medicament device is automatically and/or instantly recognized or implemented by the ambulatory medicament device, and/or transmitted to the ambulatory medicament device. In other cases, a confirmation of the change may be required before the change is implemented by or transmitted to the ambulatory medicament device.

This confirmation may be entered based on a second user interaction with a user interface (e.g., touchscreen display 2612). When the second user interaction is detected, the user interface module user interface module 2606 sends an input signal to the control and computing module wherein it is analyzed by a therapy change control procedure 2628. If it is determined that the second user interaction satisfies a set of predefined conditions, the therapy change control procedure 2628 implements the change to the configuration of the AMD.

The first and/or second user interactions may include the selection of an icon, a series of taps or inputs, one or more gestures (e.g., a linear swipe, an arcuate swipe, a circular swipe, or other simple or complex movement across the touchscreen), performing a pattern or sequence on the touchscreen (e.g., drawing an image), a multi-touch or multi-input interaction, a combination of the foregoing, or any other type of interaction with a touchscreen, or portion thereof. The series of inputs may be any combination of touch movements, touch points, numerical characters, alphabetical characters, and other symbols. Gesture interactions can be guided by visual indicia displayed or printed on the AMD. In some embodiments, the visual indicia can include animations that suggest or guide user interactions with a touchscreen. For example, the first user interaction can include an arcuate swipe around at least a portion of a generally circular icon or logo. In some examples, the first and/or second user interactions may include a predetermined sequence of numerical or alphabetical inputs. In some examples, a series of multiple inputs, the range of parameters for an input may be dependent on other inputs in the series. For example, required start position of a touch movement may be dependent on the position of the previous touch movement. The time that the series of inputs are entered may also be a part of the range of parameters. For example, a series of inputs may need to be entered in no less than 3 seconds or more than 3 seconds, and no more than 15 seconds or less than 15 seconds.

Further, one or more of the interactions may include interacting with a sensor as an optical sensor (e.g., visible light or IR sensor), biometric sensor (e.g., a fingerprint or retinal scanner), a proximity sensor, a gyroscope, or a combination of accelerometer and gyroscope, and the like. Also, in an exemplary embodiment, the second user interaction may be made through a wireless signal such as RFID or Bluetooth. In some embodiments, the second user interaction may include receiving a selection of an indicator box that correspond to either insulin or glucagon and receiving a predetermined sequence of numerical inputs in order to deliver the therapy change selection.

The type of user interaction that unlocks the touchscreen, provides access to a configuration screen, and/or confirms a change to the configuration of the ambulatory medicament device may be the same or may differ.

In an exemplary embodiment, the system may have a time-out such that if no interaction occurs for a set period of time, the user interface will turn off and the therapy change request process has to start again. In one implementation of the time-out, if no interaction occurs for more than 30 seconds after the system is waked/unlocked before the second user interaction is received by the user interface, the user interface will be deactivated.

Once the configuration change is confirmed, implemented, or transmitted, the ambulatory medicament device may begin operating with the changed configuration.

This operation may include triggering therapy based on the new configuration or providing therapy based on the new configuration. For example, the ambulatory medicament device may generate a dose control signal based at least in part on the modified configuration or control parameter, or may detect a trigger based at least in part on the modified configuration or control parameter that leads to the provisioning of therapy.

With reference to FIG. 26, in some embodiments, the changes made through the therapy change user interface are sent to CCM wherein the therapy change control procedure 2628 in CCM transfers the changes to the device and subject monitoring procedure 2624. The device and subject monitoring procedure 2624 may be implemented in the CCM to monitor the status of the AMD (e.g., therapy delivery configuration) and the health condition of the user 2616 (or a subject). For example, the subject monitoring procedure 2624 may receive information about a therapy change requested by a user 2616 through a user interface (a touchscreen display 2612 or alphanumeric pad 2614) or information about glucose level in subject's blood from the subject sensor 2608. Subsequently, the device and subject monitoring procedure 2624 may transmit the information pertaining a health condition of the subject and/or the AMD configuration, to the medicament dose control procedure 2622. In some examples, the parameters in the medicament dose control procedure 2622 may be adjusted based on the changes and/or information captured by the device and subject monitoring procedure 2624. The medicament dose control procedure 2622, controls the medicament delivery interface 2602 by providing a medicament dose signal. The medicament does control may be generated based on detected conditions or physiological characteristics of the subject (e.g., provided by the readings of the subject sensor 2608) and according to parameter values received from the therapy change control procedure 2628. The medicament delivery interface 2602 may provide a therapy change delivery to the user according to the information received by device and subject monitoring procedure 2624.

In some examples, the dose control signals may be produced based on time (e.g., medicament may be delivered on a periodic basis), one or more a command, indication that the subject is planning to engage or is engaging in a particular activity (e.g., eating a meal, exercising, sleeping, fasting, etc.), or any other factor that may relate to or cause the triggering of therapy (e.g., medicament delivery).

Figure 27:
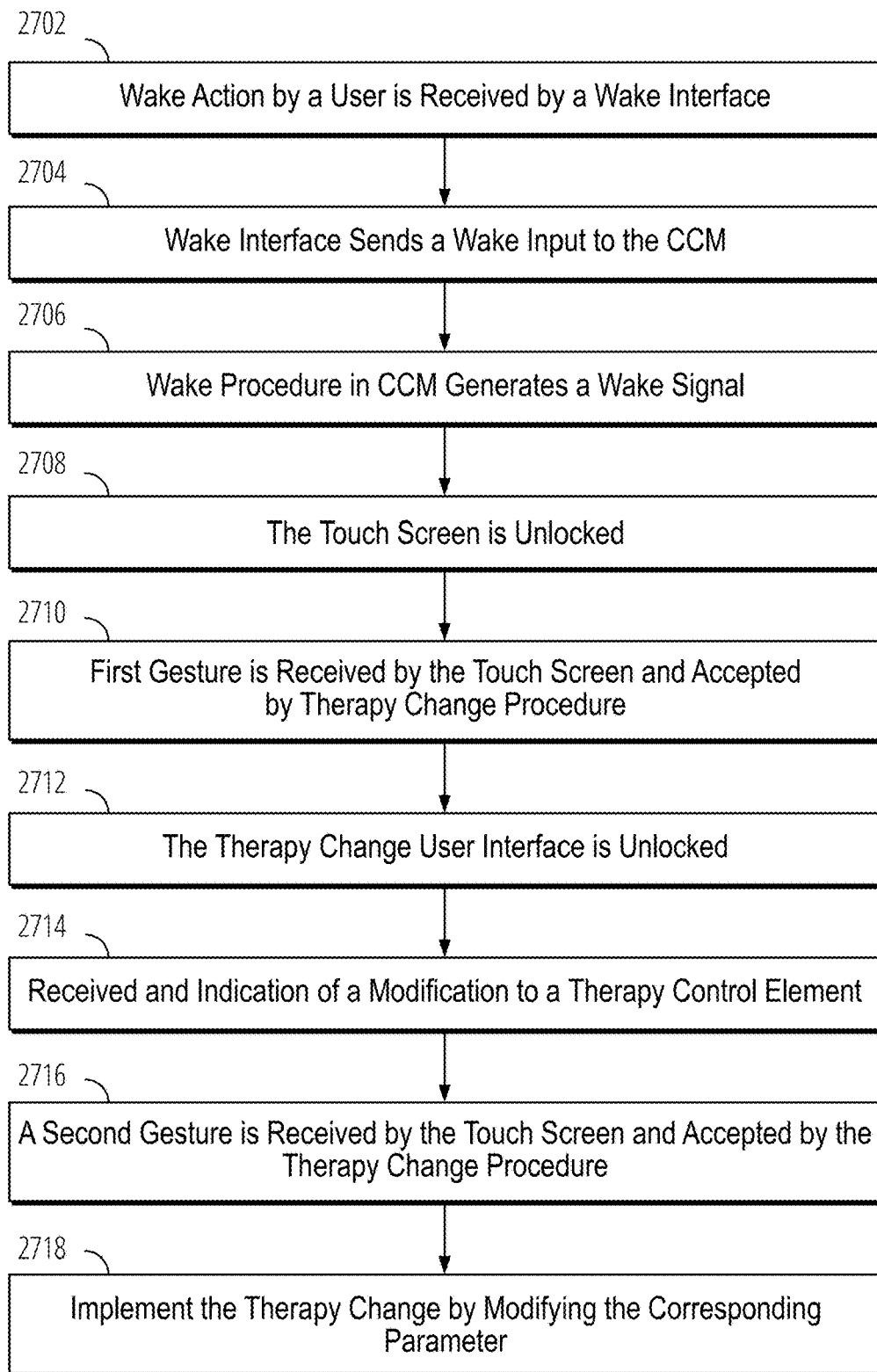
FIG. 27 is a flow diagram illustrating an example method that may be used by an AMD to allow a user to change the configuration of the ambulatory medicament device using a touch screen user interface.

FIG. 27 is a flow diagram illustrating an example method that may be used by an AMD to allow a user to change the configuration of the ambulatory medicament device using a touch screen user interface. The user may initiate the configuration change process by waking/unlocking the touch screen using a wake action. Once the wake action is received by the wake interface 2702, the wake interface sends a wake input to CCM 2704. Within CCM, the wake procedure generates a wake signal 2706 that unlocks the touch screen 2708. Next, in response to receiving a first gesture by the user 2710, the therapy change user interface is unlocked 2712. Using one or more therapy control or configuration elements provided in the therapy change user interface, the user may change the therapy configuration 2714. The user may confirm the changes made, by providing a second gesture on the touch screen 2716. Once the confirmation is received 2716 the requested changes will be implemented 2718, and the ambulatory medicament device may begin operating with the changed configuration. In some examples, once the user confirms the changes made, a dose control signal may be sent to the medicament delivery interface 2602 that triggers a therapy change delivery to the subject.

In some cases, the ambulatory medicament device, or a control device that enables a user to modify a configuration of the ambulatory medicament device, may have a timeout feature. The timeout feature may cause the ambulatory medicament device or the control device to enter a sleep or locked state after a period of time of inactivity by the user. In some cases, the timeout feature may cause the ambulatory medicament device or the control device to enter a sleep or locked state after a particular period of time regardless of whether the user is interacting with the ambulatory medicament device or control device. Thus, a user may have a limited period of time to modify the configuration of the ambulatory medicament device.

In some examples, the therapy change made by a user may trigger the delivery of a medicament according to the therapy change received and confirmed by a user. This therapy change delivery may occur after a set time from period from receiving the confirmation.

In some embodiments of the AMD, an alarm status indicator may be presented to the user via the user interface. The alarm status indicator, can be an alert message or an alert symbol. The alarm status indicator may be related to a configuration change made by a user, a change in the status of the AMD not related to a user input, or the condition of the subject (e.g., detected by the subject sensor).

Figure 28A:
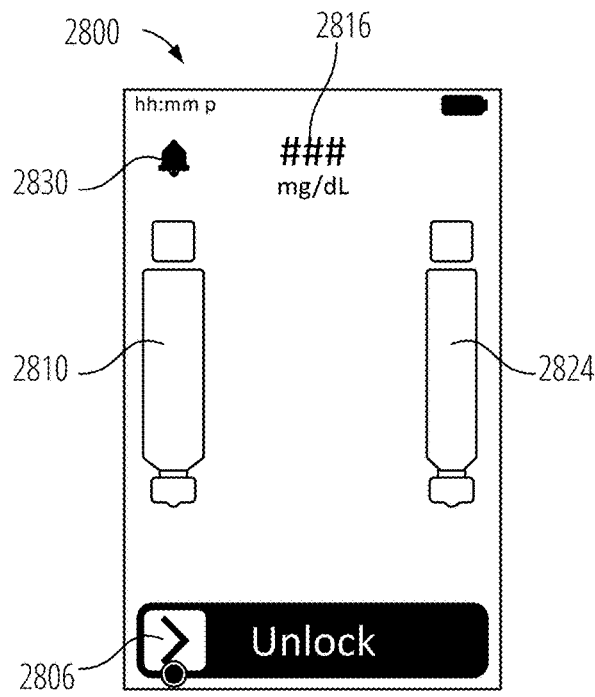
FIG. 28A is an illustration of the touchscreen display of an example AMD after the touch screen is waked/unlocked by a wake action of a user and before the first user gesture is received.

FIG. 28A is an illustration of the touchscreen display 2800 of an example AMD after the touch screen is waked/unlocked by a wake action of a user and before the first user gesture is received. Even while the touchscreen display is locked, the touchscreen display 2800 may display any images, animations, text, or other graphics. The first gesture prompt 2806 displays to the user 2616 the input required to unlock the therapy change user interface. Here, the first gesture prompt 2806 shows the user 2616 that a touch movement that begins at the greater-than symbol and moves right across the "Unlock" text is the acceptable first gesture. In addition to the first gesture prompt, the refill status of the AMD is shown in a graphic representation 2810. Here, the graphic representation 2810 shows that the insulin cartridge in the AMD is almost full. A current blood sugar level 2816 is shown at the top of the touchscreen display 2800, which can inform the user 2616 of the need for a hormone that regulates blood sugar levels. The touchscreen display 2800 also shows a graphic representation of a cartridge of glucagon 2824. The graphic representation of an alarm 2830 in the touchscreen display 2800 shows that an alert is set on the AMD.

Figure 28B:
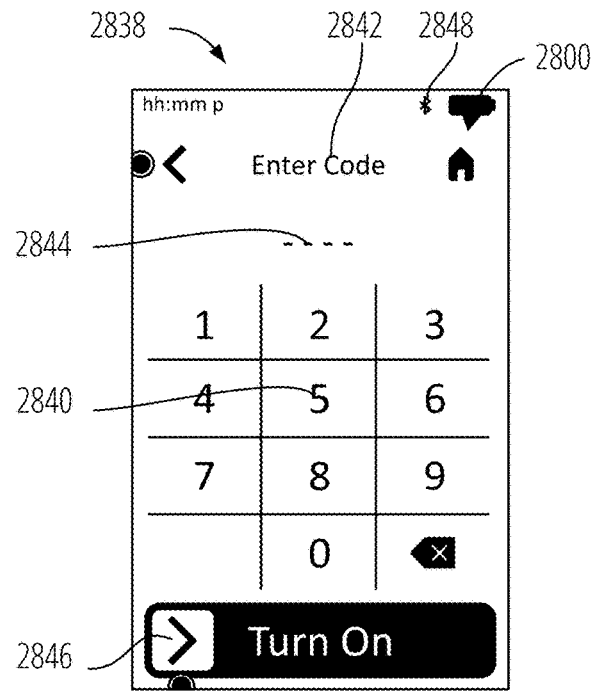
FIG. 28B is an illustration of an example touchscreen display that may prompt the user to enter a predetermined series of inputs for the first gesture or second gesture.

FIG. 28B is an illustration of an example touchscreen display 2838 that may prompt the user to enter a predetermined series of inputs for the first gesture or second gesture. In various embodiments, such as the embodiment shown in FIG. 28B, the touchscreen display 2838 may display touchable number keys 2840. In various embodiments, the touchscreen display 2838 prompts the user 2616 to enter the series of inputs that complete the first gesture or second gesture. The text Enter Code 2842 prompts the user 2616 to enter a predetermined or preselected numerical sequence as part of the first gesture or second gesture. The numerical sequence being typed by the user 2616 is displayed in field 2844 as it is entered as an aid to the user 2616. The input 2846 of the touchscreen display 2838 shows that a touch movement of a swipe right across the bottom of the screen is required to complete the predetermined series of inputs for the first gesture or second gesture. A Bluetooth connection symbol 2848 shows that the ambulatory medical device 1600 is paired or can be paired to another electronic device.

Figure 28C:
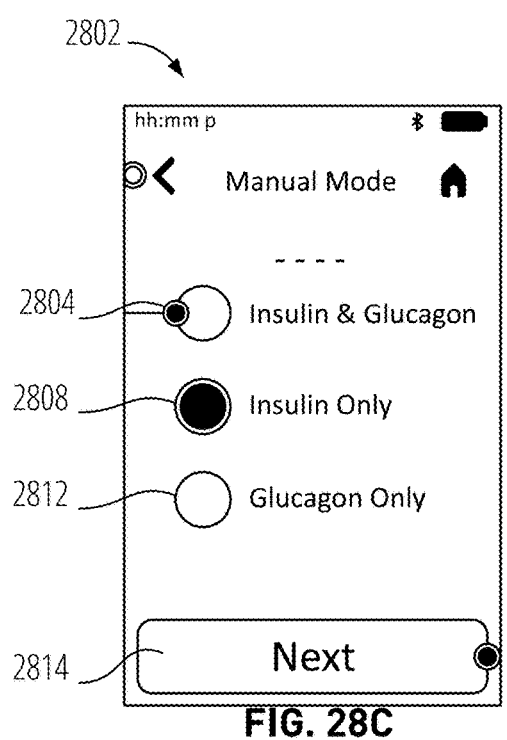
FIG. 28C is an illustration of an example therapy change user interface.

FIG. 28C is an illustration of an example therapy change user interface (in this case a touchscreen display 2802). The touch screen display may the user 2616 prompt to select a hormone that regulates blood sugar level. The touchscreen display 2802 presents the user 2616 with an option to select between two hormones. The touchscreen display 2802 aids the user 2616 by showing the selected hormone 2808 for the user 2616. The selected hormone 2808 is "insulin Only". The user 2616 is also given the options of selecting the hormone Glucagon Only button 2812 or both Insulin & Glucagon button 2804 to regulate blood sugar level. Once the user 2616 selects between the one or more hormones that regulate blood sugar level. The Next button 2814 may be selected to complete the therapy change selection or select more options. In one embodiment, to select more options, the therapy change user interface prompts the user 2616 to select an amount of the one or more hormones that regulate blood sugar level of the user 2616. In other embodiments, the user 2616 may be prompted to select a blood sugar level and the ambulatory medical device 200 may choose the hormone and the amount of the hormone.

Figure 28D:
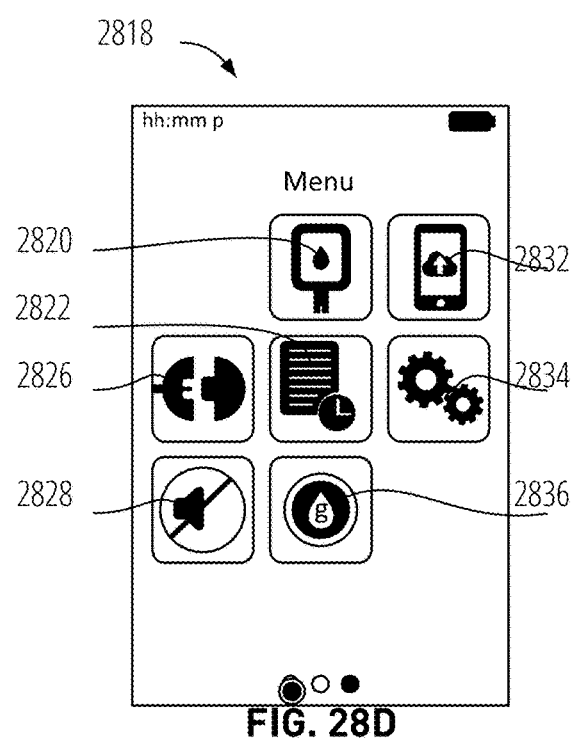
FIG. 28D is an illustration of another therapy change user interface on a touchscreen display.

FIG. 28D is an illustration of another therapy change user interface on a touchscreen display 2818. Here, the user 2616 is given a multitude of options. One or more options in the therapy change user interface allow the user 2616 to make a therapy change selection. Other options are related to the therapy change selection. A Deliver Hormone button 2836 allows the user 2616 to select a therapy change that delivers a hormone that regulates blood sugar to the user 2616. A Test Blood Sugar button 2820 allows the user 2616 to test the blood sugar level of the user 2616. A Generate Report button 2822 generates a document that reports the therapy changes that have been delivered to the user 2616. A Refill Cartridge button 2826 allows the user 2616 to fill a cartridge in the ambulatory medical device 1600 with medicament. An Upload to Cloud button 2832 allows the user 2616 to transmit therapy change information to a cloud-based server. A Sound Control button 2828 allows the user 2616 to control the sounds emitted by the ambulatory medical device 1600. A Settings button 2834 allows the user 2616 to manipulate other settings of the ambulatory medical device 1600.

As mentioned above, in some embodiments of the AMD, an alarm status indicator may be presented to the user via the user interface to alert the user about a change made or occurred in the AMD configuration.

For example, with reference to FIG. 26, the user 2616 may make a therapy change input 2620 using the user interface and based on the procedure illustrated in FIG. 27. Once therapy change control procedure 2628 implements the therapy change, the AMD may alert the user that a therapy change is implemented. The alert message or symbol may be presented on a user interface (e.g., touch screen display) before and/or during the therapy change delivery 2604. For example, alarm indicator may inform the user 2616 that a therapy change is about to occur. Any number of details of the therapy change may be displayed as part of the alert message or symbol. In some cases the alarm status indicator may appear after the user unlocks or wakes the user interface using a wake action.

Figure 29:
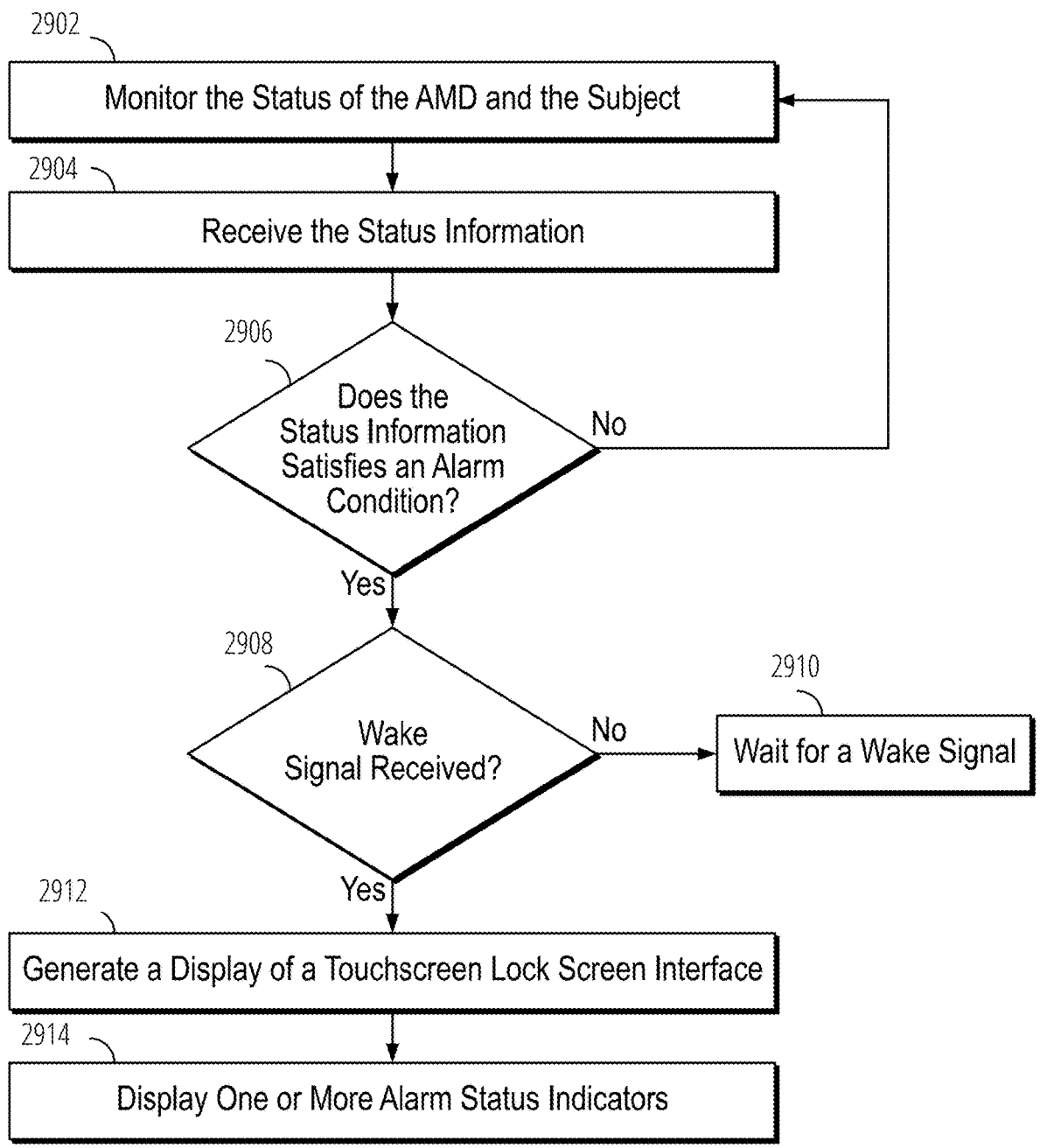
FIG. 29 is a flow diagram illustrating an example method that may be used by an AMD to generate an alarm status indicator.

FIG. 29 is a flow diagram illustrating an example method that may be used by an AMD to generate an alarm status indicator. In some embodiments the device and subject monitoring procedure (excused within CCM), may continuously monitor the status of the AMD (e.g., the user interface, different modules of the AMD and the like) as well as the health condition of a subject (e.g., using various subject sensors such as analyte sensors) 2902. Once a status information is received 2904, the device and subject monitoring procedure may determine whether the received status information satisfies an alarm condition 2906. If the received status information does not satisfy an alarm condition, no cation will be taken and device and subject monitoring procedure continuous monitoring the AMD and the subject. If it is determined that the received status information satisfies an alarm condition, the system search for a wake signal 2908. If no wake signal is detected, the systems waits for a wake signal to be received 2910. Once a wake signal is received via one or more user interfaces or sensors, the CCM may generate a display of a touchscreen lock screen interface 2912 and display one or more alarm status indicators 2914, corresponding to the detected alarm condition, on the lock screen.

Figure 30:
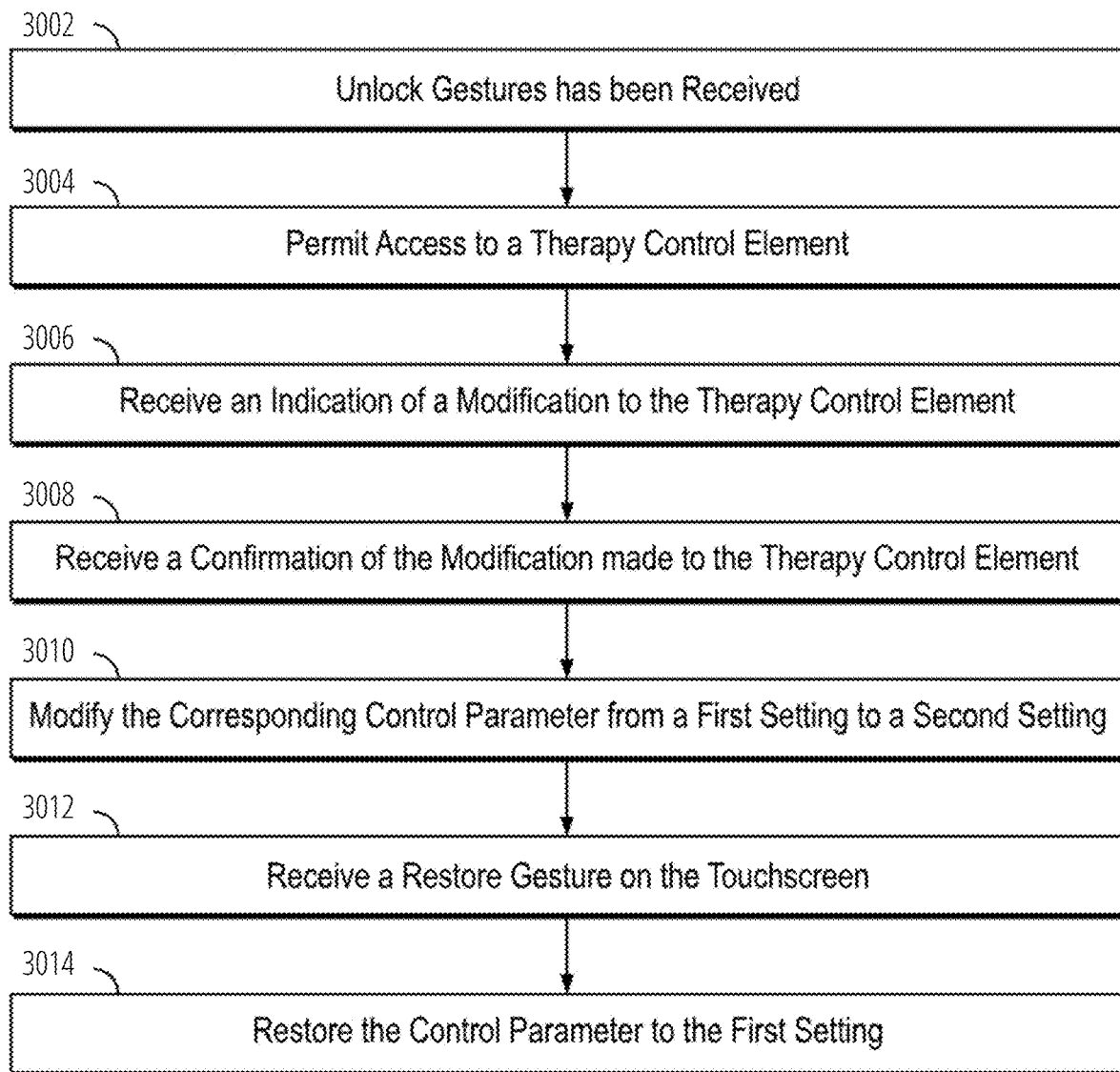
FIG. 30 is a flow diagram illustrating an example method that may be used to cancel a therapy change using a touchscreen interface.

In some embodiments, the AMD may allow the user to provide a therapy change and then cancel the therapy change. FIG. 30 is a flow diagram illustrating an example method that may be used to cancel a therapy change using a touchscreen interface. The user may unlock the touchscreen display 3002 using a wake action and get access to a therapy change user interface 3004 (e.g., using a first gesture), where one or more therapy control elements may be displayed. Next, an indication of a modification to a therapy control element may be received 3006 by the user interface followed by a confirmation of the modification made 3008 (e.g., a second gesture). In response to receiving an indication and confirmation of a modification to a therapy control element, the corresponding control parameter may be changes from a first setting to a second setting 3010. In some examples, once the change is implemented 3010, the user may decide to cancel it, for example, after realizing that requested change is erroneous. In these examples the user may provide a third gesture 3012 on the touch screen. In response to receiving the third gesture from the user interface the therapy change procedure may restore the modified control parameter to the first setting 3014. In some examples the third gesture may a restore gesture. In some cases, the restore gesture may be a swipe gesture. In some examples the swipe gesture may be performed near or in a region of the therapy change user interface that is occupied by the therapy control element. An example of a restore swipe gesture may be performed from a starting swipe position to an ending swipe position located closer to a left edge of the touchscreen than the starting swipe position. In some embodiments, the restore gesture is received on a different user interface screen than a therapy change user interface wherein one or more therapy control element are provided. In various examples, the restore gesture is performed in the opposite direction from a therapy change confirmation gesture that confirms the modification to the therapy control element.

In some examples, in order to cancel a therapy change request, the restore gesture has to be provided within a set time period after the confirmation gesture is received by the user interface. In some such examples, during the set time period one or more dose control signals may be provided to the medicament delivery interface resulting in one or more therapy change deliveries.

In some cases, the system may allow the user, to modify a therapy change before confirmation. In these cases, the user may modify a therapy control element for a second time to change the corresponding control parameter from a second setting to a third setting.

In some examples, the third setting may be the same as the first setting. In some cases the first setting or the third setting may be a default setting. In some other cases, the first setting or the third setting may be a restore setting.

Figure 31:
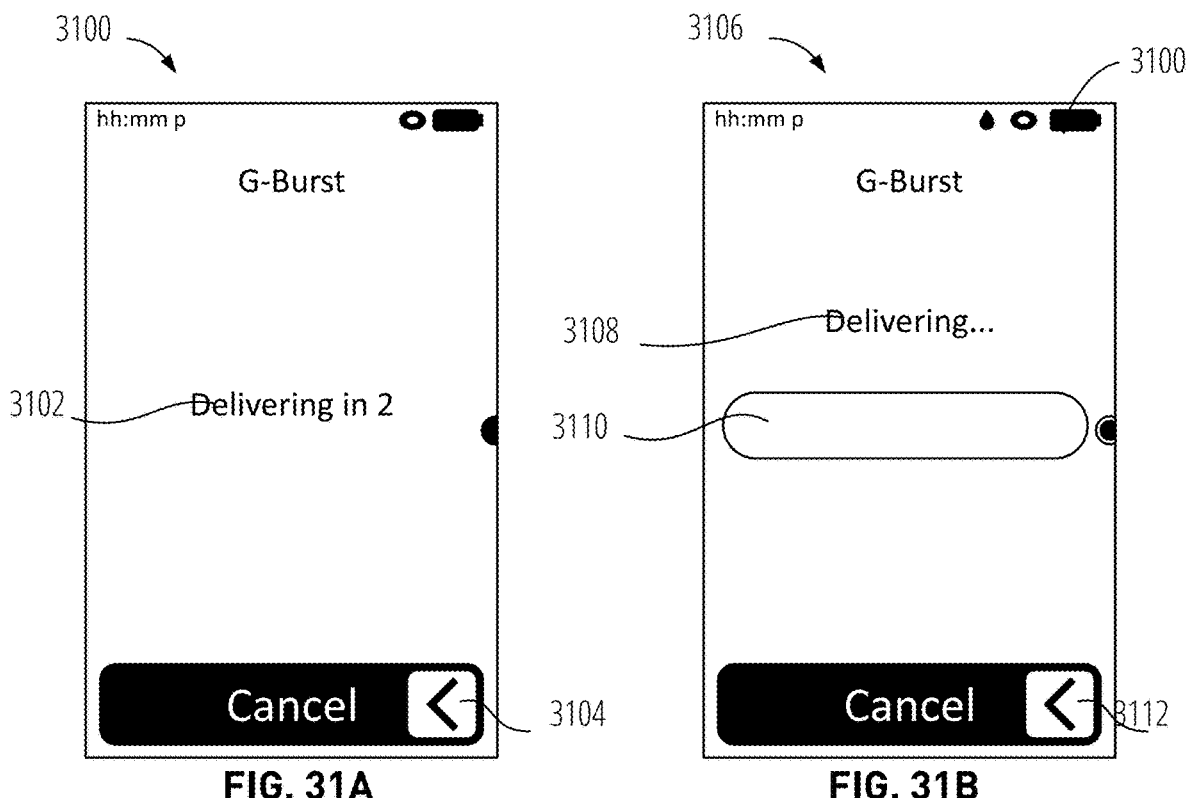
FIG. 31A is an illustration of a touchscreen display alerting the user that the delivery of one or more medicaments will occur.
FIG. 31B is an illustration of a touchscreen display showing that a medicament is being delivered to the user.

FIG. 31A is an illustration of a touchscreen display 3100 alerting the user that the delivery of one or more medicaments will occur. The alert may be accompanied by sound or vibration effects. Here, the alert informs the user 2616 a delivery of medicament will occur in 2 seconds 3102. The touchscreen display 3100 is further allowing the user 2616 to perform a gesture to cancel the therapy change. The gesture to cancel the delivery is a touch movement that starts at the less-than symbol 3104 and swipes left across the "Cancel" text. In the embodiment shown in FIG. 31A, a single gesture by the user 2616 may cancel the therapy change. In an exemplary embodiment, input of the wake signal, the first gesture, the therapy change selection, and the second gesture are all required to cancel a therapy that is being delivered.

In some examples, the user may be able to cancel a therapy change delivery triggered based on therapy change made by the user. In these examples, the user may get access to the user interface using a wake action and provide a gesture to cancel the ongoing therapy corresponding to a therapy change delivery.

FIG. 31B is an illustration of a touchscreen display 3106 showing that a medicament is being delivered to the user 2616. The text Delivering 3108 informs the user 2616 that a medicament is currently being delivered to the user 2616. The progress bar 3110 is a graphic representation of the progress of the delivery. As shown in FIG. 31B, the delivery is only starting and zero progress has been completed. The touchscreen display 3106 is allowing the user 2616 to perform a gesture to cancel the delivery, which includes interrupting and discontinuing the delivery if it had already begun but has not yet been completed. The gesture to cancel the delivery is a touch movement that starts at the less-than symbol 3112 and swipes left across the "Cancel" text. In an exemplary embodiment that is shown in FIG. 31B, the therapy change delivery 2604 may be canceled by an input by the user 2616. The input to cancel a therapy change delivery 2604 may be any input such as a wake signal input or a series of touch inputs such as a gesture.

Additional embodiments relating to interacting with an ambulatory medicament device that can be combined with one or more embodiments of the present disclosure are described in U.S. Provisional Application No. 62/874,950, which was filed on Jul. 16, 2019 and is titled "PREVENTING INADVERTENT THERAPY CHANGES ON AN AMBULATORY MEDICAL DEVICE," the disclosure of which is hereby incorporated by reference in its entirety herein for all purposes, and in U.S. Provisional Application No. 62/874,954, which was filed on Jul. 16, 2019 and is titled "CAPACITIVE TOUCH WAKE BUTTON FOR AN AMBULATORY MEDICAL DEVICE," the disclosure of which is hereby incorporated by reference in its entirety herein for all purposes.

Automatic Resumption of Medicament Delivery Following Manual Suspension

In some cases, it may be desirable to suspend operation of the ambulatory medicament device or to suspend at least the delivery of medicament by the ambulatory medicament device for a period of time. For example, it may be desirable to suspend an operation associated with the delivery of medicament when the medicament reservoir or cartridge in the ambulatory medicament device is empty or needs replacing. As another example, it may be desirable to suspend delivery of medicament when the ambulatory medicament device is removed or is being moved to another site on the subject. In yet another example, it may be desirable to suspend delivery of the medicament when the subject is taking or ingesting another medicament that may produce a contraindication with the medicament provided by the ambulatory medicament device. In some cases, when a subject suspends the treatment delivered by a medical device, the subject may forget to resume the treatment delivered by the medical device. In other cases, the health condition of the subject may deteriorate during the suspension period requiring therapy delivery prior to end of the suspension period. As such, there is a need for AMDs that allows subjects to safely suspend treatment for temporary amounts of time.

In some embodiments, the AMD may support a therapy suspension and resumption procedure allowing a user to suspend all therapies or a subset of therapies for a period of time defined by the user as well as automatic resumption of one or more therapies at the end of the requested suspension period or when a threshold condition is met (e.g., a threshold condition associated with the health condition of the subject).

In AMDs that support therapy suspension, inadvertent activation and/or resumption of therapy delivery can be dangerous (e.g., when the AMD is an insulin and/or glucagon infusion device). In some examples to mitigate this risk, the AMD may be configured to avoid inadvertent suspension or resumption of therapies. For example, inadvertent activations of suspensions of medicament delivery may be prevented by requiring a user to perform gestures to activate suspension on the ambulatory medical device. The gestures must be entered at a particular prompt to activate a therapy suspension.

One particular application of the therapy suspension with automatic resumption feature in an AMD can be in the field of diabetes drug delivery. For example, the may need the ability to suspend delivery of insulin during situations such as exercise, which has a blood glucose lowering effect. Suspension of insulin delivery can prevent a subject from entering a hypoglycemic state (extreme low blood glucose), which carries severe complications. Once the therapy is suspended the user many at the risk of entering a hyperglycemic state (high blood glucose that may result in complications such as diabetic ketoacidosis or neurovascular complications), if the user forgets to reactivate the drug delivery after exercise. Further, the subject's blood glucose level may raise above or below a dangerous level during the period of exercise. In these situations, the automatic medicament delivery resumption may improve the health of the subject.

In certain cases, the AMD may suspend one or more therapy deliveries when the AMD receives an indication that therapy (e.g., delivery of medicament) is to be suspended. The indication that therapy is to be suspended may be a command from a user. Often the user is the subject, but the user may also include other users that may have a say or interest in the care of the subject. For example, the user may be a clinician or other healthcare provider, or a parent or guardian.

In some examples, the indication that the therapy or medicament delivery is to be suspended may be a command received via an interface of the ambulatory medicament device or from another device that provides the user with an interface to request that medicament delivery be suspended. For example, the device may be a smartwatch, smartphone, laptop or desktop, or other control device that can communicate via a wired or wireless connection with the ambulatory medical device.

In some cases, the indication that the therapy or medicament delivery is to be suspended may be received from the ambulatory medicament device itself. For example, if the quantity of medicament available to the ambulatory medicament device drops below a threshold (e.g., the cartridge or reservoir is empty or below a minimum dosage amount), a signal may be generated to suspend medicament delivery. In some embodiments, suspension of therapy occurs based on a loss of a sensor signal, such as the loss of a glucose level signal.

Figure 32:
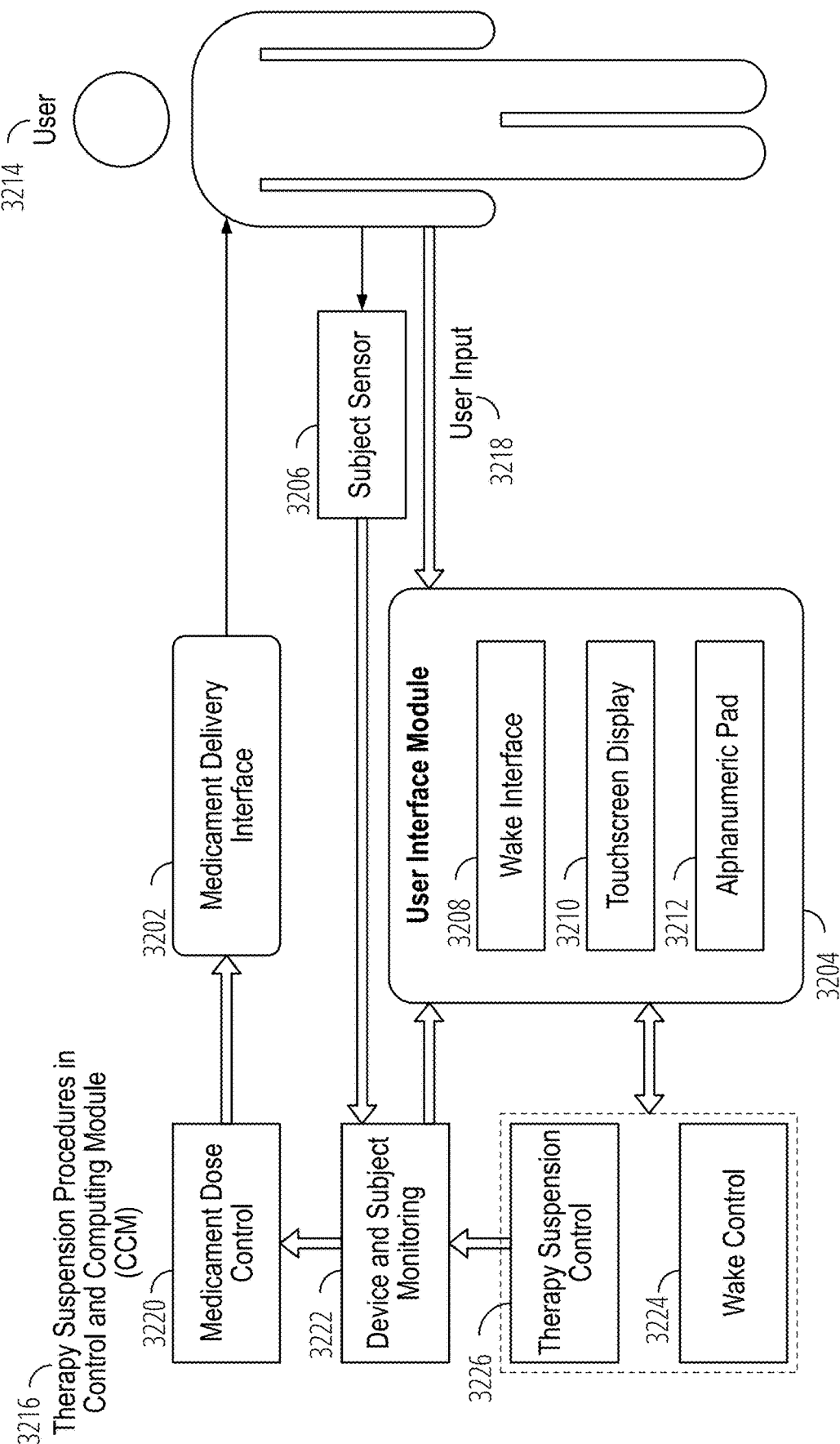
FIG. 32 is a block diagram illustrating the interconnection among modules and procedures in AMD involved in receiving, accepting and/or canceling a therapy suspension request.

FIG. 32 illustrates the interconnection among modules and procedures involved in receiving, accepting and/or canceling a therapy suspension request, in an example AMD. In some embodiments, a request for suspending one or more therapies (e.g., delivery of one or more medicament to the subject) can be made by a user 3214 by providing a user input 3218 (e.g., the start and stop time for therapy suspension, selecting the type of therapy that should be suspended, and the like), through a therapy suspension user interface provided by the user interface module 3204. The therapy suspension user interface sends the suspension request along with the corresponding information to CCM wherein the therapy suspension control procedure 3226 implemented in CCM, processes and sends a therapy suspension signal to the device and subject monitoring procedure 3222. To prevent therapy suspension request user inputs 3218 that are inadvertent, the therapy suspension control procedure may include a therapy suspension request verification procedure to verify the therapy suspension request.

The device and subject monitoring procedure 3222 may be implemented in the control and computing module 3216 to monitor the status of the AMD (e.g., therapy delivery configuration) and the health condition of the user 3214 (or a subject). For example, when the device and subject monitoring procedure 3222 receives the request for therapy suspension, it may send a signal to the medicament dose control procedure 3220 indicating that no does control signal should be send to the medicament delivery interface 3202 during the period request by the user 3214. In some cases, if during the suspension period, certain pre-set conditions are satisfied, the device and subject monitoring procedure 3222 automatically resumes the therapy delivery by sending a signal to the medicament dose control procedure 3220. For example, if during the suspension period the subject sensor 3206 detects an elevation of the level of one or more analytes in subject's blood and/or interstitial fluid beyond a set threshold, it may resume the medicament delivery to the user 3214 by a sending a dose control signal to the medicament delivery interface 3202.

In order to prevent inadvertent activation of a suspension, the user may initiate a therapy suspension request starting with a wake action (e.g., received by the wake interface 3208 and processed by the wake control procedure 3224), that activates the user interface module 3204. Using a first interaction with a user interface (e.g., a touchscreen display 3210 or alphanumeric pad 3212) the user may unlock a therapy suspension user interface where the information pertaining therapy suspension is provided. Next, the user may confirm the requested therapy suspension using a second interaction with the user interface. In some examples, the system may allow access to the therapy suspension user interface and accept the suspension request, only if the first and second interaction with the user interface are verified by the therapy suspension control procedure 3226.

In some examples, the therapy suspension control procedure 3226 may receive the request for suspension and suspension information from another device connected to the ambulatory medical device 1600 (e.g., through the communication module).

The suspension information provided by the user may include a set of parameters needed for a suspension. For example, the suspension information may include the dates and/or times for starting and ending the therapy suspension, threshold values needed to define a threshold condition that may trigger an early resumption of the therapy delivery, and the like. In some other examples, suspension information may indicate that the suspension of therapy should happen at a particular time or after a particular event (e.g., after the next dose of medicament is delivered or after the condition of the subject reaches a particular state, such as the middle of a desired blood glucose range). In some examples, the threshold values may be associated with input provided by the subject sensor 3206 or other types of sensors that may be used to monitor one or more parameters associated with the health condition of the user 3214.

The parameters for a suspension may include the start and stop conditions for a suspension. The start condition for a suspension may be a condition that, when met, activates a suspension. In some such examples, the start condition is met when a timer runs out. Similarly, the stop condition is a condition that, when met, ends the suspension. In one example, the stop condition is met when a timer runs out. In another example, the stop condition is met when a threshold is met. A threshold may be related to a measurement taken by ambulatory medical device (e.g., by a subject sensor 3206), such as a glucose concentration of the blood of a user. The threshold may be met if the glucose concentration goes above, goes below, or matches a set concentration. Multiple conditions may be set by the suspension request interface component. For example, a time condition and a threshold condition may be set simultaneously. A user may specify that a suspension will end after a set time. However, the suspension may end sooner than the set time if the glucose concentration of the user meets a threshold.

In some cases, the request to suspend therapy may include an indefinite suspension period. In other words, the request may not include a time period specified by a user or an identity of a resumption condition. In some other cases, the indication may include a request to temporarily suspend delivery of therapy for a defined period of time or until a further interaction or event occurs. Thus, the resumption condition can include an expiration of time or an active event (e.g., a command or a determined condition of a subject). Further, the therapy to be suspended may include any type of therapy. For example, the therapy to be suspended may be the suspension of the delivery of medicament, which may include insulin, counter-regulatory agent (e.g., Glucagon), or both insulin and a counter-regulatory agent. In some cases, the ambulatory medicament device may be capable of and/or configured to administer multiple medicaments (e.g., both insulin and a counter-regulatory agent). In some such cases, the request to suspend therapy may include a request to suspend one (e.g., insulin or the counter-regulatory agent) or both of the medicaments.

The interactions with the user interface may include the selection of an icon, a series of taps or inputs, one or more gestures (e.g., a swipe or other simple or complex movement across the touchscreen), performing a pattern or sequence on the touchscreen (e.g., drawing an image), a multi-touch or multi-input interaction, a combination of the foregoing, or any other type of interaction with a touchscreen, or portion thereof. The series of inputs may be any combination of touch movements, touch points, numerical characters, alphabetical characters, and other symbols. In some examples, the first and/or second user interactions may include a predetermined sequence of numerical or alphabetical inputs. In some examples, a series of multiple inputs, the range of parameters for an input may be dependent on other inputs in the series. For example, required start position of a touch movement may be dependent on the position of the previous touch movement. The time that the series of inputs are entered may also be a part of the range of parameters. For example, a series of inputs may need to be entered in no less than 3 seconds or more than 3 seconds, and no more than 15 seconds or less than 15 seconds. In some cases, a visual guide may assist the user in generating the user interaction. For example, one or more arrows or images may be presented to the user to guide the user in providing the command to suspend the delivery of therapy.

Further, one or more of the interactions may include interacting with a sensor as an optical sensor (e.g., visible light or IR sensor), biometric sensor (e.g., a fingerprint or retinal scanner), a proximity sensor, a gyroscope, or a combination of accelerometer and gyroscope, and the like. Also, in an exemplary embodiment, the second user interaction may be made through a wireless signal such as RFID or Bluetooth. In some embodiments, the second user interaction may include receiving a selection of an indicator box that correspond to either insulin or glucagon and receiving a predetermined sequence of numerical inputs in order to deliver the therapy change selection.

The type of user interaction that unlocks the touchscreen, provides access to a therapy suspension user interface or confirms a suspension request may be the same or may differ.

In an exemplary embodiment, the system may have a time-out such that if no interaction occurs for a set period of time at each step during the therapy suspension request process, the user interface will turn off and the therapy suspension request process has to start again. In one implementation of the time-out, if no interaction occurs for more than 30 seconds after the system is waked/unlocked before the second user interaction is received by the user interface, the user interface will be deactivated.

Figure 33:
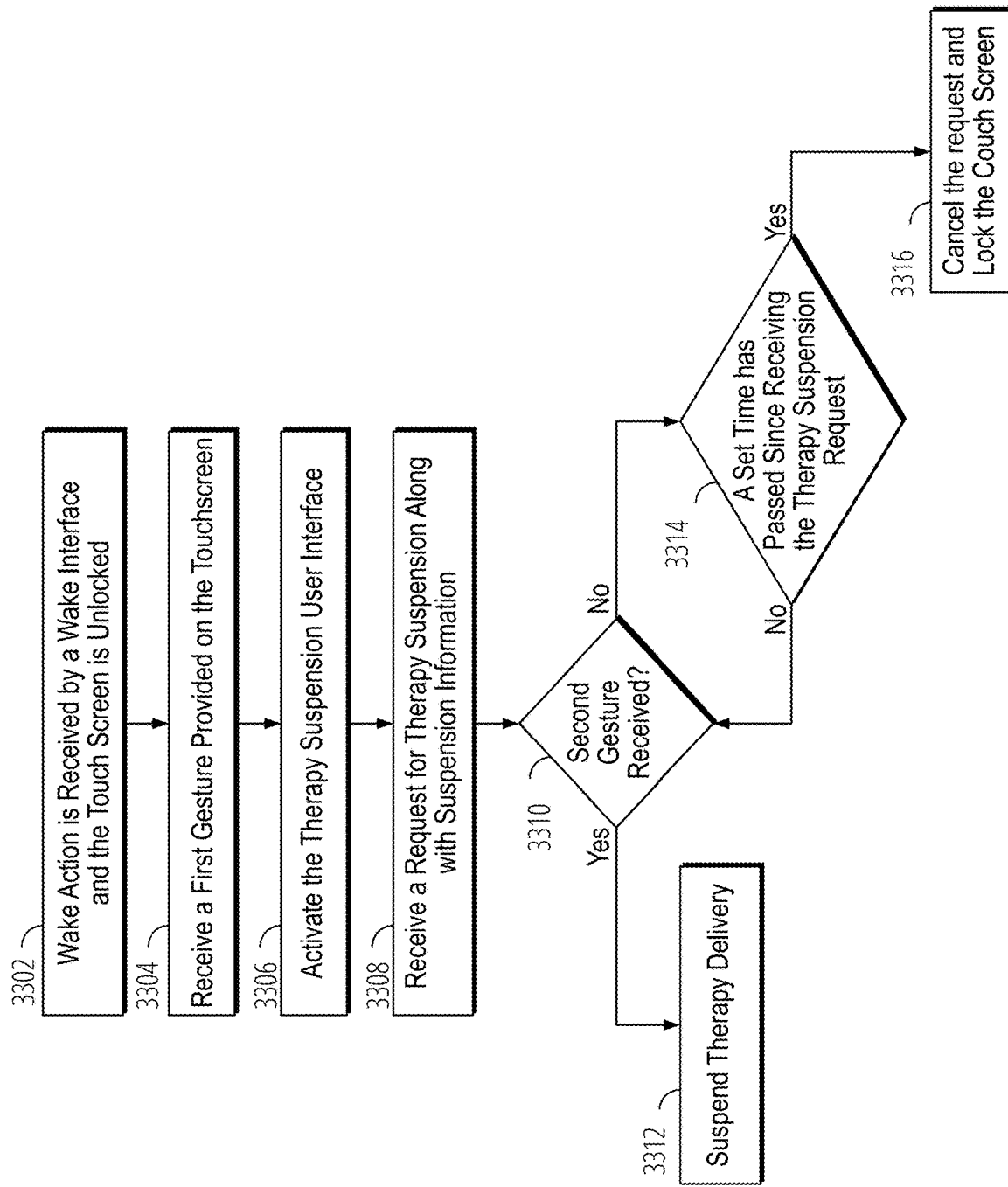
FIG. 33 is a flow diagram illustrating an example method for receiving and implementing a suspension request, which may be implemented by an AMD

FIG. 33 is a flow diagram illustrating an example method for receiving and implementing a suspension request, which may be implemented by an AMD. In this example the user may use a touchscreen interface to request and confirm a therapy suspension. Once the user activates the touchscreen using a wake action 3302, the AMD may wait for a first gesture on the touchscreen. After the user provides the first gesture and the gesture is verified by the therapy suspension control procedure 3226, a therapy user interface may be activated 3306 where the user can request a therapy suspension and provide 3308 the suspension information (e.g., a start day/time and stop day/time and/or a resumption condition). Next, the AMD may wait for second gesture on the user interface 3310. If the second gesture is received and verified by the therapy suspension control procedure 3226, the therapy delivery will be suspended 3312. If the second gesture is not received or not verified by the therapy suspension control procedure 3226, the therapy suspension control procedure 3226, may determine if a set time has passed since receiving the therapy suspension request 3314. If it is determined that a set time has passed since receiving the therapy suspension request, the request will be canceled and the touch screen will be locked 3316. If it is determined that time from receiving the therapy suspension is less than a set time the AMD may wait for the second gesture to be received.

In some examples, once a wake action is received 3302, the AMD may automatically activate a therapy suspension user interface 3306, without the need for a first gesture 3304. In these examples, once the request for therapy suspension is received 3308, a gesture (e.g., a first gesture) may be required to verify the request. In some such examples, once the therapy delivery is suspended, a second gesture may stop a suspension before any of the conditions of the stop parameter are met. This allows the user the versatility of being able to modify a suspension that has been activated.

Figure 34:
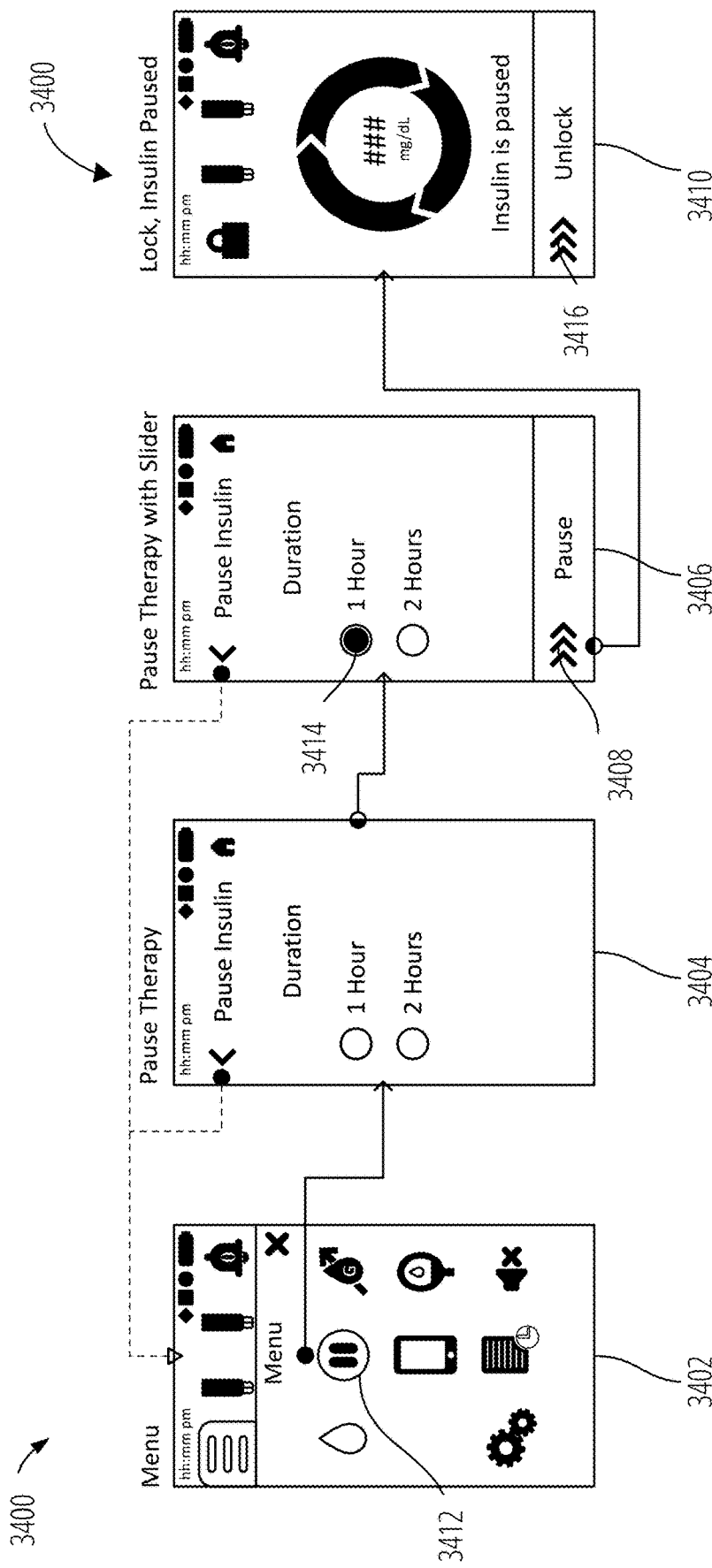
FIG. 34 illustrates a plurality of user interface screens that the ambulatory medical device may display when a user pauses therapy.

FIG. 34 is an illustration of a plurality of screens 3400 that the ambulatory medical device may display when a user activates a therapy suspension user interface. Screen 3402 shows a user interface that an ambulatory medical device may display to a user 3214. The display may be a touchscreen display 3210 that can accept input that includes the first and second gestures. The therapy suspension system of the ambulatory medical device is not limited to the displays shown in FIG. 34. Various displays may communicate, to the user 3214, the same information shown in FIG. 34. The screen 3402 allows the user 3214 to select various functions. The pause button 3412, shown on screen 3402 is a function that suspends the delivery of a medicament to the user 3214. When the pause button 3412 is selected, the user 3214 is treated to the pause screen 3404. The pause screen 3404 allows the user 3214 to select a duration of the medicament suspension. The ambulatory medical device may display various interfaces to allow the user 3214 to select a duration of the medicament suspension. The pause screen 3404 shows a simple interface, giving the user 3214 one of two duration options.

When the user 3214 has made a duration selection on the pause screen 3404, the pause screen 3406 shows the user 3214 the duration 3414 that the user 3214 selected (e.g., in the figure the user 3214 selected 1 hour. Thus the medicament delivery is suspended for 1 hour after the suspension begins). The pause screen 3406 has a prompt 3408 for the user to make a gesture to confirm the requested suspension before the medicament suspension begins. As shown by the prompt 3408, the user 3214 is being prompted to swipe right across the bottom of the screen. Once the user 3214 performs the gesture to begin the medicament suspension, the suspension screen 3410 is displayed on the touchscreen. The suspension screen 3410 informs the user 3214 that the medicament is paused. The user 3214 has the option of performing another gesture to unlock the ambulatory medical device. The prompt 3416 for the user 3214 to unlock the device forces the user to perform another swipe to execute more functions on the ambulatory medical device 1600.

Suspending the medicament delivery may occur by not generating a dose control signal to deliver a dose of medicament. Alternatively, or in addition, suspending the medicament delivery may occur by sending a signal to the medicament pump to cease providing therapy or medicament to the subject.

In some cases, the ambulatory medicament device may not immediately suspend therapy upon receiving a command to suspend therapy. For example, if the ambulatory medicament device is in the process of delivering medicament or determines that a condition of the subject indicates that medicament may soon be required to maintain the subject's condition (e.g., blood glucose) within a particular state (e.g., within a desired blood glucose range), the suspension of therapy may be delayed until at least such time that medicament is not being delivered, is predicted to not be required during the suspension period, or the next therapy has been delivered. In some such cases, the ambulatory medicament device may inform that user that the suspension of therapy is being delayed. Further, the ambulatory medicament device may indicate the reason for the delay. In some cases, the user may be able to override the delay and request immediate suspension of therapy. For example, if the user is replacing the medicament cartridge, the user may override an indication that the suspension of therapy should be delayed. In some cases, the requested start time may be overridden by a determined condition of the subject.

The suspension of therapy or the suspension of the delivery of medicament may continue until a resumption condition occurs. In certain cases, when a resumption condition is met, the suspension period may automatically end without action by the user or subject.

The resumption condition may include the expiration of a time period, a command from a user (e.g., the subject), detection that the ambulatory medicament devise satisfies a condition (e.g., that medicament has been refilled), that the condition of the subject meets certain criteria (e.g., the subject's blood glucose level drops below a threshold range or rises above a threshold range), or any other condition that may satisfy the reason for suspension of therapy or that overrides the request for suspension of therapy. For example, the drug delivery device may be configured to automatically resume drug delivery when a glucose threshold is reached or exceeded. This threshold could be set to 300 mg/dl for example. The resumption condition may include detection of an impending risk of hypoglycemia or hyperglycemia, or a hypoglycemia or hyperglycemia event. Further, the resumption condition may include a meal announcement, or an "exercise concluded announcement," a motion sensing event, a pause of other administered medicament, a conclusion of an undefined suspension length (e.g., during cartridge change), a speed-based resumption event, a location-based resumption, a remote resumption in case of an emergency (e.g., commanded from caregiver admin software or clinician), or any other type of resumption event. In some cases, the resumption condition can include a combination of criteria.

In some cases, automatically resuming therapy may include discontinuing the suspension of therapy before the expiration of the suspension period. For example, if a condition that caused therapy to be suspended is resolved prior to the expiration of the suspension period, therapy may be resumed.

In some cases, when a resumption condition (provided by the user) is met, the ambulatory medicament device may confirm that one or more additional condition of the ambulatory medicament device are satisfied before therapy is resumed. For example, if the ambulatory medicament device determines that medicament has not been refilled or if there is a problem with the refill (e.g., cartridge is incorrectly installed), the ambulatory medicament device may continue to maintain the suspension of therapy despite the trigger to resume therapy.

In some examples, a therapy suspension may be ended if a third interaction with a user interface (e.g., a gesture) is detected. The third user interface interaction may be detected by the user interface module 3204 and sent to the therapy suspension control procedure 3226. If the therapy suspension control procedure 3226 verifies that third interaction with the user interface is a predetermined third user interface interaction, it may send a signal to the device and subject monitoring procedure 3222 to activate the medicament dose control procedure 3220. This allows the user the versatility of being able to end a suspension that has been activated, during the suspension period set by the user before the confirmation (second interface with the user interface). In some cases, a user may decide to end a therapy suspension to modify one or more suspension conditions set prior to activation of the current therapy suspension. In some other examples, user may decide to end a therapy suspension due to change in user's health condition not included in one or more therapy resumption conditions provided before activating the current therapy suspension.

Figure 35:
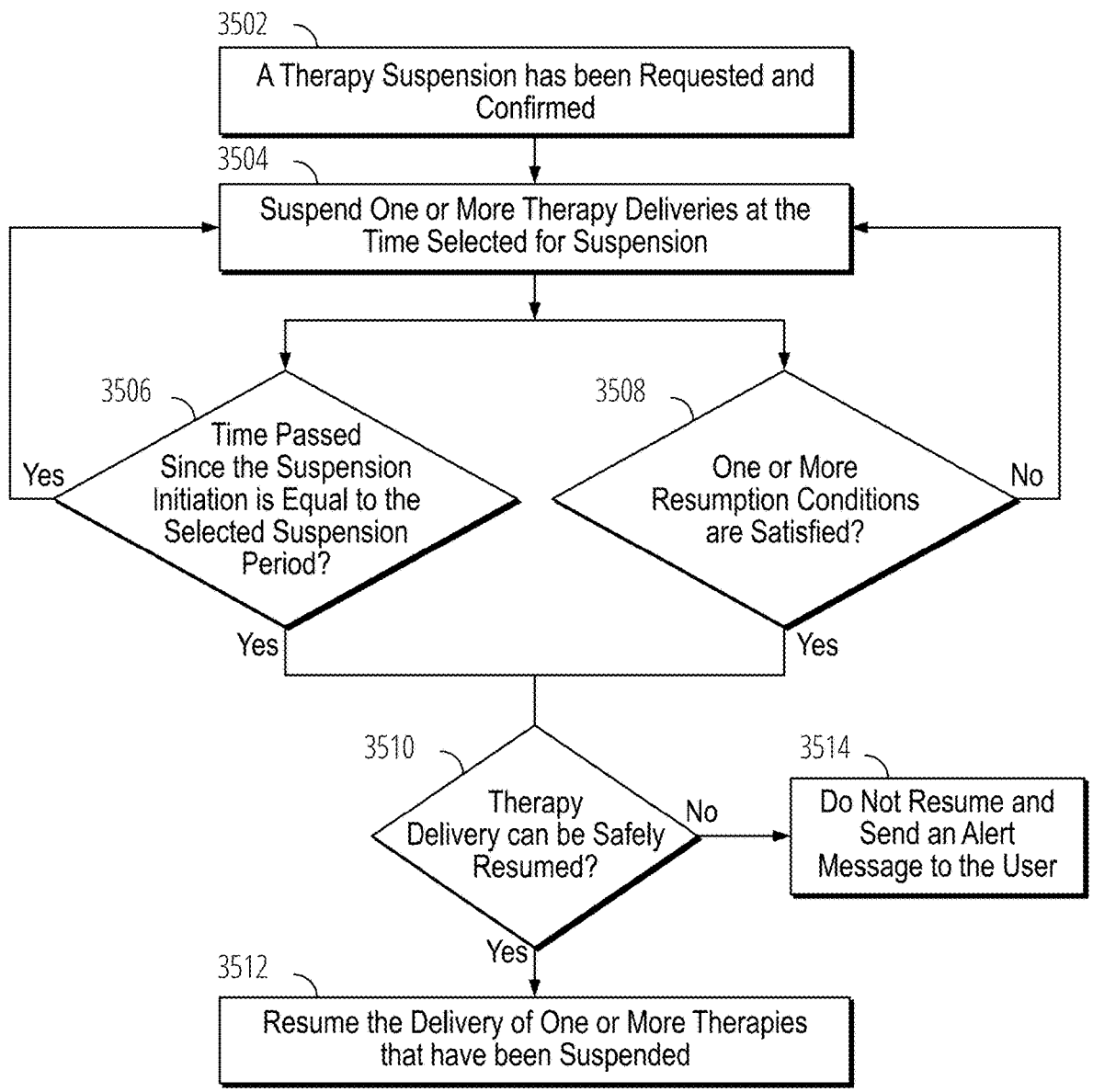
FIG. 35 is a flow diagram illustrating an example method of resuming a suspended therapy that may be implemented by an AMD.

FIG. 35 is a flow diagram illustrating an example method of resuming a suspended therapy that may be implemented by an AMD. Once a therapy suspension has been requested and confirmed by a user (e.g., using the procedure illustrated in FIG. 18) 3502, the AMD suspends one or more therapies selected for suspension 3504 at suspension initiation time received as part of the suspension information. For example, therapy suspension control procedure 3226 deactivates the medicament dose control procedure 3220 using the device and subject monitoring procedure 3222. During the suspension period, the therapy suspension control procedure 3226 continuously monitors the system clock and the subject and device condition (e.g., using medicament dose control procedure 3220).

If the therapy suspension control procedure 3226 determines that the time passed since the suspension initiation is less than the requested suspension time period 3506 and none of condition for resumption has been met 3508, the therapy suspension continues.

If the therapy suspension control procedure 3226 determines that the time passed since the suspension initiation is equal to the requested suspension time period 3506, or one or more resumption conditions have been met 3508, it may check other AMD or subject conditions (not included in the therapy suspension information), in order to determine whether the therapy delivery can be safely resumed 3510. If it is determined that the therapy delivery cannot be safely resumed, an alert message will be send to the user interface to inform the about the reason for such determination 3514. If it is determined that the therapy delivery can be safely resumed, the one or more suspended therapies will be resumed 3512.

Figure 36:
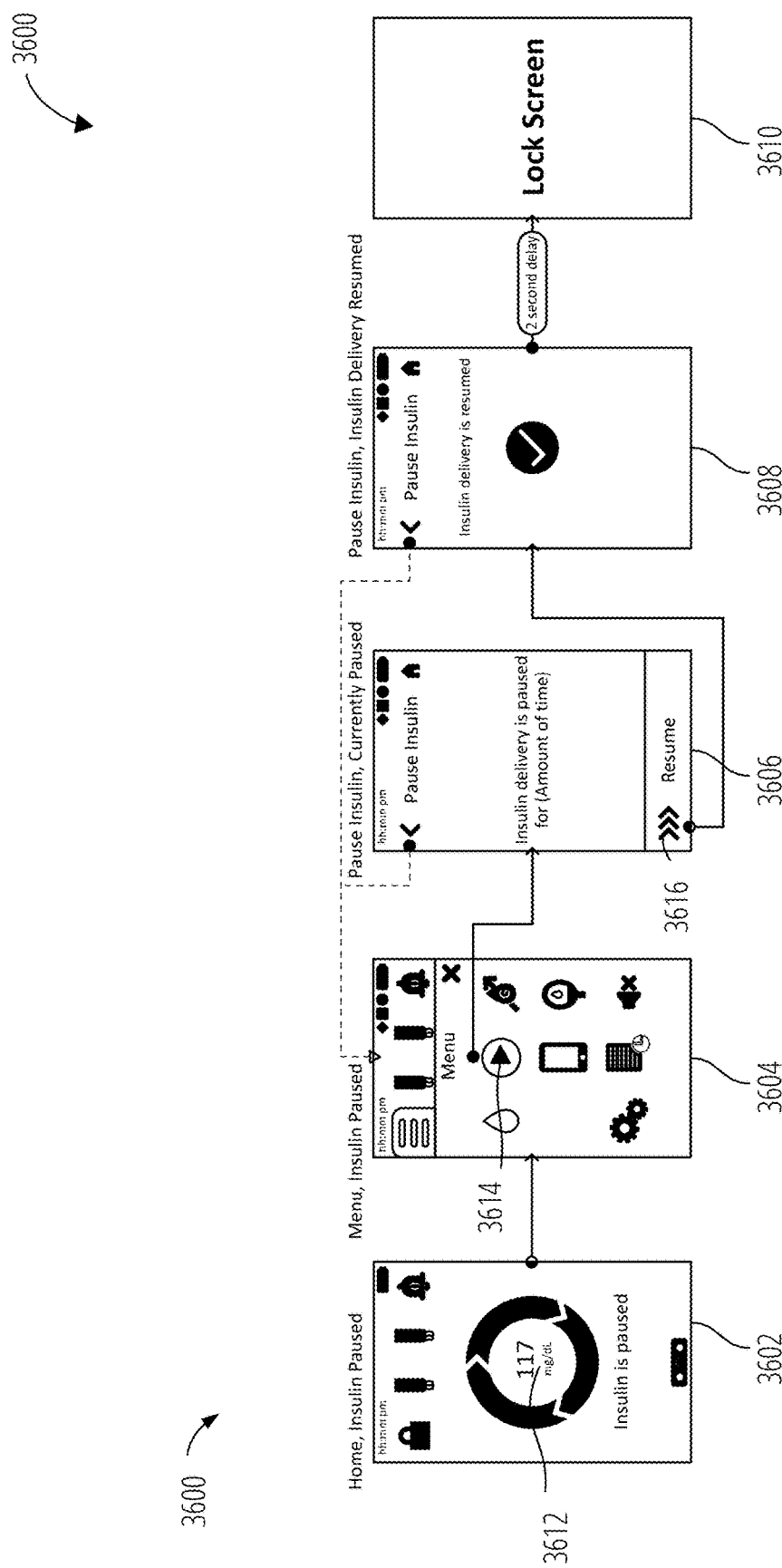
FIG. 36 illustrates a plurality of user interface screens that the ambulatory medical device may display when a user resumes therapy.

FIG. 36 is an illustration 3600 of a plurality of screens that may be displayed, for example, on a touchscreen display when a user 3214 resumes a suspended therapy. Screen 3602 informs the user that the delivery of medicament is currently in a suspended mode. The screen 3612 also shows the user 3214 the current glucose concentration of the blood of the user 3214. The ambulatory medical device may display various vital measurements that are useful to the user 3214. In one implementation, the medicament suspension ends if the glucose concentration of the blood of the user meets or passes a threshold.

The interface screen 3604 allows the user 3214 to select and execute various functions on the ambulatory medical device. The resume button 3614 is a function that ends a medicament suspension. When the resume button 3614 is selected, the ambulatory medical device displays a resume screen 3606. The resume screen 3606 has a prompt 3616 that prompts the user 3214 to perform a gesture. In the examples shown, the user 3214 receives a prompt 3616 in the resume screen to swipe right across the bottom of the resume screen 3606. The requirement to perform the gesture to resume medicament delivery prevents the user 3214 from inadvertently resuming medicament delivery in the ambulatory medical device.

Once the user 3214 performs the gesture to resume medicament delivery, the medicament suspension ends. The resumption screen 3608 shows the user 3214 that the regular medicament delivery has resumed. Once the resumption screen 3608 has been displayed to the user 3214 for a sufficient amount of time to inform the user 3214 that the suspension is ending, the ambulatory medical device may display a lock screen 3610. The lock screen 3610 prevents the user 3214 from inadvertently executing more functions on the ambulatory medical device.

In one embodiment, the ambulatory medical device must receive a second gesture to end the suspension before the one or more conditions to end the suspension are met. The purpose of the second gesture is to ensure that the user 3214 does not inadvertently end the suspension. Like the first gesture, the second gesture may be simple or complex.

With reference to FIG. 32, once the AMD device is instructed to resume therapy and/or determines that therapy is to be resumed, the ambulatory medicament device may determine whether a dose of medicament should be supplied to the user based on a control algorithm used by the ambulatory medicament device to control the provisioning of medicament to the subject. For example, the therapy suspension control procedure 3226 may determine a resumption condition has been satisfied or receive a user input from the user interface module 3204 (a third interaction with a user interface) indicating that therapy suspension should be ended. Subsequently the therapy suspension control procedure 3226 may send a signal to the device and subject monitoring procedure 3222 to activate the medicament dose control procedure 3220. If medicament is to be supplied, the medicament does medicament dose control procedure 3220 may generate and send a dose control signal to the medicament delivery interface 3202.

In some cases, the ambulatory medicament device may alert the user and/or the subject that therapy is being resumed. This alert may occur before generating a dose control signal and/or after a resumption condition is satisfied (e.g., a suspension time expires). In some cases, the user may request that the suspension of therapy end early. The user may request the early resumption of therapy be interacting with the aforementioned user interface using one or more of the previously described interaction methods (e.g., gestures or taps).

Additional embodiments relating to suspending medicament delivery to a subject that can be combined with one or more embodiments of the present disclosure are described in U.S. Provisional Application No. 62/910,970, which was filed on Oct. 4, 2019 and is titled "METHOD FOR SUSPENDING DELIVERY OF A DRUG INFUSION DEVICE WITH AUTOMATIC RESUMPTION OF DELIVERY," the disclosure of which is hereby incorporated by reference in its entirety herein for all purposes.

AMD with Security Functionality

An ambulatory medicament device (AMD), such as, but not limited to, an insulin pump, that provides life-saving treatment to subjects or subjects based on the condition of the subject, may include a user interface (e.g., a touchscreen display) that lets a user to modify the settings of the ambulatory medicament device. The setting may include, but not limited to, a condition that triggers the delivery of medicament to a subject, the quantity of medicament delivered when a condition is met, type of the medicament and the like. The setting may also include features of the AMD that may not be directly related to the medicament delivery (e.g., the screen brightness, an alarm sound, and the like). In some examples, it is desirable to manage access to various settings of AMD in order to avoid inadvertent changes while enabling changes that may be necessary for uninterrupted and proper operation of the AMD. For example, it may be desirable to limit the access to some settings to certain authorized users (e.g., a healthcare provider) while enable access to some other settings other authorized users (e.g., the subject, a guardian or parent of the subject).

In many cases, a healthcare provider can modify the settings of the ambulatory medicament device. However, it is often desirable that a non-healthcare provider modify at least some settings of the ambulatory medicament device. For example, when the ambulatory medicament device runs out of or has below a threshold amount of medicament, it is often desirable that a user be able to refill or change a medicament cartridge without visiting a healthcare provider. In some cases, changing the medicament cartridge may include interacting with a user interface and/or one or more settings of the ambulatory medicament device. Another example of when it is desirable for a non-healthcare user (e.g., a subject, parent, or guardian) to modify settings of the ambulatory medicament device is when the initial settings of the ambulatory medicament device are not providing the desired effect (e.g., sufficient medicament, too much medicament, providing the medicament too slowly or too fast, etc.). In some cases, normal maintenance of the ambulatory medicament device and/or subject may require interaction with the ambulatory medicament device settings and/or controls. For example, negative consequences may being to occur when an ambulatory medicament device remains connected to a subject at the same site for more than a threshold period of time (e.g., for more than 2-3 days, more than 5 days, more than a week, etc.). Thus, the ambulatory medicament device may need to be periodically moved from one site on the subject to another site on the subject (e.g., from left-side to right-side, from arm to leg, from stomach to back, etc.). The change in site location may require interaction with settings of the ambulatory medicament device (e.g., pausing operation until the site change is completed).

Although, as explained above, there are a number of reasons it is desirable to enable a user other than a healthcare provider (e.g., the subject receiving therapy, a parent, or a guardian) to have access to at least some user settings of an ambulatory medicament device, it is also desirable to regulate access to at least some of the ambulatory medicament device settings. For example, it is generally undesirable that a child (subject or otherwise), or a user below a particular age, have access to ambulatory medicament device settings that could cause harm to the subject if modified. Further, it may be undesirable for certain subjects who have diminished mental capacity regardless of age to have access to at least some ambulatory medicament settings.

The user may be a subject receiving medicament or therapy, or may be another user, such as a clinician or healthcare provider, or a parent or guardian of the subject. In some examples, the passcode required for changing one or more setting via an intermediary device may be different that the passcode required for changing the same settings directly using the AMD's user interface.

One solution to regulating access to settings of the ambulatory medicament device is to implement a lock feature to require that a user provide a passcode, a passcode, or other information before the user is permitted to modify a setting of the AMD, such as a control parameter. To simplify discussion, the disclosure will describe using a passcode. However, it should be understood that the passcode can be substituted for a passcode or any other type of secret or semi-secret information. In some examples, when the AMD is in the locked state, it may continue delivering therapy to the subject at the same rate as unlocked state.

The lock feature may be activated by default, or may be activated by a user. In some examples, the lock feature can be enabled through a setting in a control menu of the AMD device provided on a user interface (i.e., touchscreen display). The setting may include an on/off toggle (e.g., a software interface element or a hardware interface element) so when the toggle is on, a passcode (e.g., 4 to 8 numeric digits) may be required. In some cases, if the lock feature is on, the passcode (e.g., a 4 to 8 numeric digit code) may be required to turn the lock feature off. When the lock feature is activated, the user may program the ambulatory medicament device with a user passcode selected by the user. Alternatively, or in addition, the user passcode may be set in response to a passcode change request. In some cases, a user passcode may expire. In such cases, a user may be required to generate a new passcode after the previous passcode expires or before the previous passcode is permitted to expire. In other cases, the ambulatory medicament device may periodically generate a new passcode (e.g., an override passcode), or may generate the passcode at a time when a user supplies the passcode.

In some cases, the user interface element used for accessing a user interface that enable changing one or more settings of the AMD may differ from the a user interface for modifying the control parameters associated with that setting. For example, a keypad may be used to enter a passcode for unlocking a user interface for changing a control parameter and a touchscreen may be used to modify the control parameter.

When the lock feature is enabled, the user interface screen may look and function the same as if the lock feature were not enabled. If the lock feature is enabled, when a visual guide for unlocking the device (such as, for example, a linear unlock slider, an arcuate unlock slider, or another unlock user interface element) is activated, a passcode entry interface (e.g., a keypad user interface element) may be displayed. If either the user passcode or the global override passcode is entered, the user interface may proceed as normal. Otherwise, the user interface may revert back to the original lock screen.

In some examples, the user action that permits a user to change one or more settings of the AMD may be different from the wake action that activates a user interface. For example, a wake action may be used to activate a touchscreen display that may display a plurality of user selectable elements some of which may be accessible without a passcode. In such examples, a subset of the user selectable elements, for example those allowing the user to change therapy control parameters, may require a passcode. In some cases, access to each user parameter control element may require a different passcode. In some other examples, providing a passcode may to an AMD in locked state, may directly enable access to a subset of control parameter elements.

To help recall the passcode, the passcode may be set by the user enabling the user to select a passcode the user is more likely to remember. However, regardless of who sets the passcode, there is a risk that the user will not remember the passcode. Due to the nature of the device (e.g., a device that may provide life-saving treatment), it is desirable that certain user's not be restricted from accessing particular settings of the ambulatory medicament device, and be able to quickly (e.g., within seconds, minutes, prior to a next therapy event, or before harm may occur to the subject) obtain access to the particular settings when required. Thus, while some non-medical devices may implement lockout periods or other restrictions to prevent a malicious user from trying to brute-force determine a passcode for a device, such features are generally undesirable for an ambulatory medicament device. Accordingly, embodiments disclosed herein include an ambulatory medicament device that includes an override passcode that enables access to the ambulatory medicament device (or control settings thereof) regardless of whether the user passcode is provided.

In some examples the passcode or the override passcode can be a series of taps, series of inputs, a complex or a simple gesture (e.g., a swipe or other movement across the touchscreen), The series of inputs may be any combination of touch movements, touch points, numerical characters, alphabetical characters, and other symbols. In some examples, the time that the series of inputs are entered may also be a part of the range of parameters. For example, a series of inputs may need to be entered in no less than 3 seconds or more than 3 seconds, and no more than 15 seconds or less than 15 seconds. One example of the complex gesture is a swipe.

In some other examples the passcode or the override passcode can be a complex or a simple gesture (e.g., a swipe or other movement across the touchscreen), performing a pattern or sequence on the touchscreen (e.g., drawing an image), a multi-touch interaction, a combination of the foregoing, or any other type of interaction with a touchscreen, or portion thereof. Another example of a complex gesture is entering a predetermined sequence of touches. In some cases, the passcode may include a quiz or set of questions, In some examples, the ambulatory medicament device may be configured to receive therapy settings or modifications to therapy settings from an intermediary device via a communication connection. In some cases, this feature may be supported in addition to providing the user with option of modifying one or more settings with a user interface of the AMD. The communication connection between the intermediary device and the AMD may be a direct connection via, for example, Bluetooth®, or a connection via a network, such as over a local area network or a wide area network. In some such cases, the ambulatory medicament device may include a wireless transceiver, such as an NB-LTE transceiver, a Wi-Fi transceiver, or a Bluetooth transceiver. The intermediary device, that provides the user with a user interface to modify settings of the AMD, include any type of device (e.g., a computing device) that can communicate with an ambulatory medicament device. For example, the intermediary device may be a laptop or desktop computer, a smartwatch, a smartphone, or a hardware control device that may be configured to interact with the ambulatory medicament device. Embodiments disclosed herein are applicable regardless of whether the user interface for modifying therapy settings or the configuration of the ambulatory medicament device is generated or presented by the ambulatory medicament device to the user or via another device. In some such cases, a user may provide a user-generated passcode or an override passcode via an interface of the computing device. The computing device may then provide the user-generated passcode or the override passcode to the ambulatory medicament device via the network connection between the devices.

In some examples, even if the AMD is in locked state, certain intermediary devices may have access to user interfaces that may be used to change one or more settings (e.g., therapy settings) of the AMD. For example, the smart phone of a guardian or a parent of the subject may be used to change one or more settings of the AMD while the AMD is in the locked state.

In some examples, the AMD may be configured to receive a passcode from or via a computing systems (e.g., a cloud computing system). In these examples, the AMD may receive passcode through a direct end-to-end connection (e.g., a wireless connection over a wide area network) stablished with the computing system. In some such examples, another computing device (e.g., a smartphone, a laptop, a personal computer, and the like) connected to the computing system, may send a passcode to the AMD and be able to change one or more settings of the AMD if the passcode is validated by the AMD.

In cases where the user cannot recall the user passcode, the user can obtain access to the user interface that permits modification of the control parameter by supplying an override passcode. In some examples, the override passcode may be a universal fixed passcode (e.g., an 8-digit override passcode) that can be used instead of the user set passcode. The override passcode can be stored in the ambulatory medicament device at the time of manufacture and may be shared among multiple ambulatory medicament devices (e.g., a global override passcode), or may be unique to a particular ambulatory medicament device. The override passcode may be managed by the manufacturer or by a third-party service. To obtain the override passcode, the user may contact the manufacturer or passcode managing service. Generally, enabling the passcode may exist to prevent a user with a diminished mental capacity (e.g., a child) from modifying settings of the ambulatory medicament device. Thus, security may be less of a concern and any user can contact the manufacturer or passcode managing service to obtain the override passcode. In some such cases, a single global override may be used for all devices produced by the manufacturer. However, in some cases, a level of security may be desired. In some such cases, it may be necessary for the user to authenticate him or herself. Further, the user may be required to provide a serial number of the ambulatory medicament device. In some cases, each model or each unit of the ambulatory medicament device may have a different override passcode. The user may provide authorization information and a serial number of the ambulatory medicament device to the manufacturer or passcode managing service to obtain the override passcode.

In some examples, may periodically generate a new override passcode or may generate an override passcode at a time when a user supplies the passcode. In these examples, the ambulatory medicament device may use the same parametric values to generate the override passcode as another device may use thereby ensuring a match between the override passcodes. Advantageously, in some cases, by using an algorithm to generate the override passcode, the override passcode can be obtained regardless of whether a user is able to contact a manufacturer or other passcode managing service. In some cases, the user may generate the override passcode without access to a network or phone using, for example, a computing device that can access a common parameter value as the ambulatory medicament device.

In some cases, the override passcode may change over time or be a rotating passcode. For example, in some cases, the override passcode may change every thirty seconds, every minute, every hour, etc. In some such cases, the override passcode may be determined from an algorithm executed by an application. The ambulatory medicament device may store a copy of the algorithm in a memory of the ambulatory medicament device and may execute the algorithm to determine the override passcode that is currently valid. A copy of the algorithm may be executed by another computing device accessible by the user. The output of the algorithm may be based on a value that is commonly accessible by the ambulatory medicament device and the copy of the algorithm accessible by the computing device. For example, the output of the algorithm may be generated based on a time, a user identifier, a provided value, or any other factor that may be used to repeatedly generate the same output. In some cases, the override passcode may be calculated based on a combination of factors. For example, the override passcode may be calculated based on a portion of a serial number or model number for the ambulatory medicament device and the time. The determination of the override passcode may be calculated by the ambulatory medicament device, a computer server, and/or an application on a user device.

In some cases, the override code can be automatically received by the ambulatory medicament device. Thus, a user may not need to see or enter the override code. In some cases, the override code may be transmitted to another device of the user (e.g., a smartphone or laptop). For example, the override code can be texted to a user's smartphone. In some cases, the override code may be received in a coded manner that may not be understandable by a child or user with diminished mental capacity.

In some cases, the override passcode may be linked to a location. For example, the override passcode may only be enterable at a healthcare provider's office or at the subject's place of residence. The determination of the location of the ambulatory medicament device may be based on a geolocation system (e.g., a Global positioning System (GPS)) available to the ambulatory medicament device.

In some examples, at least for a subset of therapy settings, the passcode may provide a second level of security in addition to other interactions with the user interface (e.g., a first and a second gesture on a touchscreen display) that may be used to change the therapy settings and/or accept the change made to a therapy setting. In some other examples, at least for a subset of settings, the passcode may be used instead of other interactions with the user interface (described above).

As mentioned above, interacting with the user interface may cause the ambulatory medicament device, or other device that can modify a control of the ambulatory medicament device, to present a passcode input screen to the user. The user may enter the passcode to unlock additional user interface features including, for example, a user interface that enables the user to modify at least one control parameter of the ambulatory medicament device. The control parameter can be modified based on an interaction with a parameter control element of the user interface. Further, modification of the control parameter may cause modification of the generation of a dose control signal that is generated by a control algorithm based at least in part on the control parameter.

In some embodiments, the ambulatory medicament device may have an advanced therapy screen, or other user interface, that permits a healthcare provider, or other user, to obtain additional details relating to therapy provided by the ambulatory medicament device. Although the advanced therapy screen may generally be intended for a knowledgeable user, such as a clinician, in some cases, any user may obtain access to the advanced therapy screen. The advanced therapy screen may permit the healthcare provider to modify control parameters that may not be modifiable by other users. For example, the healthcare provider may be able to control parameters that relate to the calculation of a rate of insulin accumulation, the rate the insulin diminishes within the blood of the subject, the setting of a glucose setpoint, an aggression level or factor of therapy relating to an amount of insulin provided when the subject's glucose level is outside the setpoint range, or when the insulin reaches a point of maximum concentration within the blood of the subject (e.g., Tmax).

Access to the advanced therapy screen may be limited by requirement of a passcode, which may be referred to as a clinician passcode to distinguish it from the user-generated passcode and/or the override passcode. This clinician passcode may or may not be user-generated. However, the clinician passcode may be a separate passcode from the user-generated passcode that permits access to the non-advanced therapy screen interface. Further, the clinician passcode may be separate from the override passcode that permits a user to override the user-generated passcode to obtain access to the non-advanced therapy screen interface. In some cases, the clinician passcode may be used as an override passcode. In some example the clinician passcode can be valid for period of time (e.g., set by a subject or another authorized user such as the guardian or apparent of the subject). For example, the clinician passcode may be valid for a day, a week or a month. In some examples, the AMD may allow certain authorized users to terminate the clinician access at any time.

In some cases, access to the advanced therapy screen may be limited to a particular period of time. After the time period expires, the ambulatory medicament device may automatically restrict access to the advanced therapy screen. In some cases, the user interface of access may be extended. For example, if the healthcare provider is continuing to interact with the advanced therapy screen, the screen may remain accessible.

In some cases, the advanced therapy screen may provide additional features. For example, while a user may be able to indicate that an amount of insulin provided for a meal or as a correction factor should be higher or lower, the healthcare provider may be able to specifically adjust the amount of insulin. Moreover, while a user's direction may or may not be followed depending, for example, if the request exceeds a threshold or may cause blood glucose to not satisfy a setpoint range, an indication provided via the advanced therapy screen may be followed regardless, or may have a wider range or different threshold that may control whether the instruction is followed. Further, the advanced therapy screen may be used to temporarily pause therapy and/or may prevent subject access.

In some cases, the manufacturer of the ambulatory medicament device may provide a remote unlock signal that can be used to unlock access to the ambulatory medicament device and/or to an advanced therapy screen of the ambulatory medicament device.

As described above, the passcode may be desired to prevent particular users from inadvertently changing certain control parameters of the ambulatory medicament device. However, features of the ambulatory medicament device that do not affect therapy may remain accessible to a user when the ambulatory medicament device is in a locked state. For example, a user may be able to access therapy history, screen brightness settings or colors, or any other feature that is unlikely to harm a subject if modified in a particular manner. Further, as the passcode feature is generally to prevent control parameter changes, the ambulatory medicament device may provide therapy and continue to provide therapy at the same rate and under the same condition, whether or not the ambulatory medicament device is locked or unlocked.

When the ambulatory medicament device receives the user passcode or the override passcode, the ambulatory medicament device validates the passcode. The passcode may be validated by comparing the received passcode to a passcode stored in a memory of the ambulatory medicament device or generated by the ambulatory medicament device. If the passcode received from the user is successfully validated, the user may be granted access to a user interface to modify one or more control parameters. In some cases, the user may be requested to re-enter a passcode to confirm a change to a control parameter. In some other examples, the user may be requested to provide a gesture on a touchscreen to confirm a change to a control parameter.

If the passcode is not validated, the ambulatory medicament device, or other control device that can provide access to control parameters of the ambulatory medicament device, may prevent access to the user interface to modify the one or more control parameters. In some cases, the user interface that presents the user with the ability to enter the passcode may permit the user a particular number of tries or a particular number of tries within a particular time period to enter the user passcode. If the correct user passcode is not entered within the provided number of tries or within the particular time period, the user interface may enter a lock state (e.g., the screen will be turned off) and prevent further attempts to enter a passcode for at least a period of time. In some cases, the user passcode option may be indefinitely locked or blocked. In some such cases, the control parameters of the ambulatory medical device may only be accessible if the override passcode is provided. Alternatively, or in addition, a user passcode of a different user may be used to provide access to the control parameters of the ambulatory medical device. In some examples, if the correct override passcode is not entered within the provided number of tries or within the particular time period, the user interface may block any attempt to change the override passcode for at least a period of time.

In some cases, once the passcode is successfully entered or validated, a user may deactivate the passcode feature of the ambulatory medicament device. Deactivating the passcode feature may require use of a separate passcode or the override passcode in addition to the user passcode.

In some cases, the passcode may be optional or omitted based on the computing device connected to the ambulatory medicament device. For example, if the end-to-end connection is established between a smartphone registered to a particular user (e.g., a parent of the subject), the ambulatory medicament device may unlock automatically without requiring a passcode. In other cases, the smartphone, or other computing device, may automatically provide the user-generated passcode or the override passcode to the ambulatory medicament device upon establishing a connection. In some cases, the ambulatory medicament device may automatically be unlocked when connected to a charger or when in a particular geographic area. For example, a geo-fence may be configured in one or more locations, such as the subject's house or the clinician's office. When the ambulatory medicament device determines it is within the geo-fence, the ambulatory medicament device may automatically be unlocked. Similarly, when the ambulatory medicament device determines that it is not within the geo-fenced region, it may automatically be locked. The determination of the location of the ambulatory medicament device may be made based on a geo-location system, such as the Global Positioning System (GPS).

Figure 37:
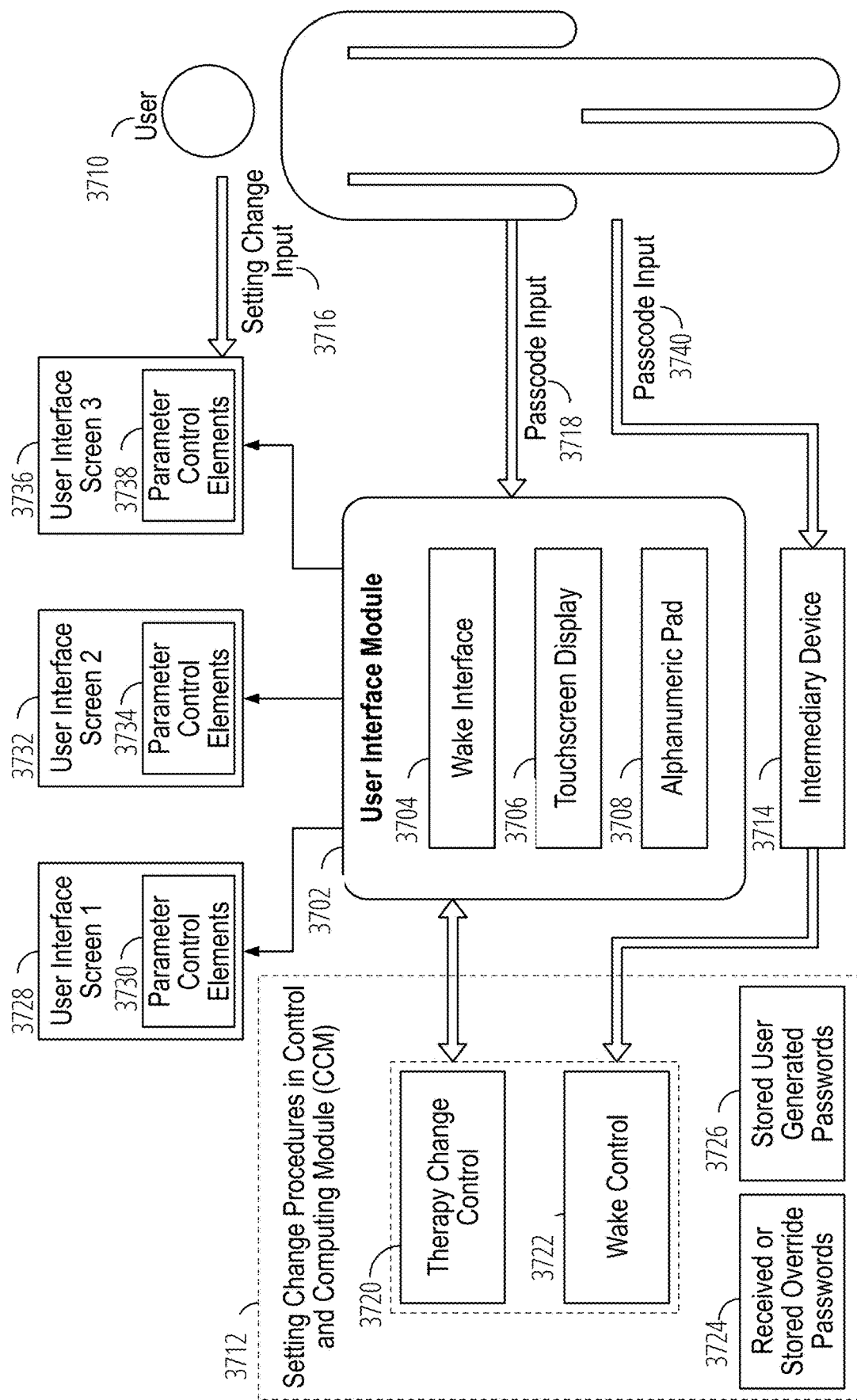
FIG. 37 is a block diagram illustrating the interconnection among modules and procedures in AMD involved in changing the settings of the AMD.

In some cases, after a certain number of unsuccessful passcodes are entered (e.g., after 5 tries), the user interface screen may be turned off or may accept only the global override passcode Example AMD with Security Codes FIG. 37 is a block diagram illustrating the interconnection among modules and procedures in AMD involved in changing the settings of the AMD. In some cases, one or more settings of the AMD may be changed using a setting change input 3716 to one or more parameter control element parameter control elements 3730/3734/3738 presented on one or more setting user interface screens 3728/3732/3736 provided by the user interface module 3702. In some examples, when the lock feature is activated, access to one or more setting control screens 3728/3732/3736 and/or one or more parameter control element 3730/3734/3738, may be protected by a passcode. In order to change a parameter control element 3730/3734/3738, the user may provide a passcode input 3718 (e.g., a user generated passcode or an override passcode), via the user interface module 3702 (e.g., using a touchscreen display 3706 or alphanumeric pad 3708). Alternatively or in addition the user 3710 may provide a passcode 3740 using an intermediary device (e.g., a laptop, a smart phone and the like) that is connected to the AMD (e.g., via a wireless link). In some examples, the access to one or more setting user interface screens 3728/3732/3736 and/or parameter control element parameter control elements 3730/3734/3738, may be managed by setting change procedures 3712 stored in a memory in the control and computing module of the AMD. A hard processor may execute the machine readable instructions associated with the setting change procedures 3712.

In some examples, the option to provide a passcode may become available, when the user 3710 performs a wake action on a wake interface 3704. In these examples if the wake control procedure 3722 of the CCM determines that a valid wake action is performed, it may present selectable elements associated with the setting user interface screens 3728/3732/3736, for example, on a touchscreen display. In some other examples, the first screen presented on the touchscreen display, may provide other selectable elements including an element to change the settings of the AMD. In such examples, selecting element associated with settings change may activate a second screen that presents selectable elements associated with the setting user interface screens 3728/3732/3736. When the lock feature is activated, access to any of the setting user interface screens 3728/3732/3736 and/or parameter control element 3730/3734/3738 may require a passcode. In some examples, each one of the user interface screens 3728/3732/3736 and/or parameter control element 3730/3734/3738 may require a different passcode. In some other examples, one or more user interface screens 3728/3732/3736 and/or parameter control element 3730/3734/3738 may not require a passcode. For example, access to the first user interface screen 3728 may require a first passcode, the access to the second user interface screen 3732 may require a second passcode and the access to the third user interface screen 3736 may not need a passcode. In yet another examples, all the user interface screens 3728/3732/3736 may be presented without the need for providing a passcode, but access to the one or more control elements in a control screen may require a passcode. For example, the user may select the second user interface screen 3732 without entering a passcode but in order to select one or more parameter control element 3734 on that screen, the user may need to enter one or more passcodes.

In some examples, once a passcode or override passcode received from the intermediary device 3714 or the user interface module 3702, the passcode may be transmitted to the control and computing unit of the AMD where the setting change procedures 3712 (therapy change control procedure 3720 and wake control procedure 3722) determine the validity of the passcode by comparing it to the one or more stored user generated passwords 3726 or received or stored override passwords 3724 stored in a memory of the CCM.

Figure 38:
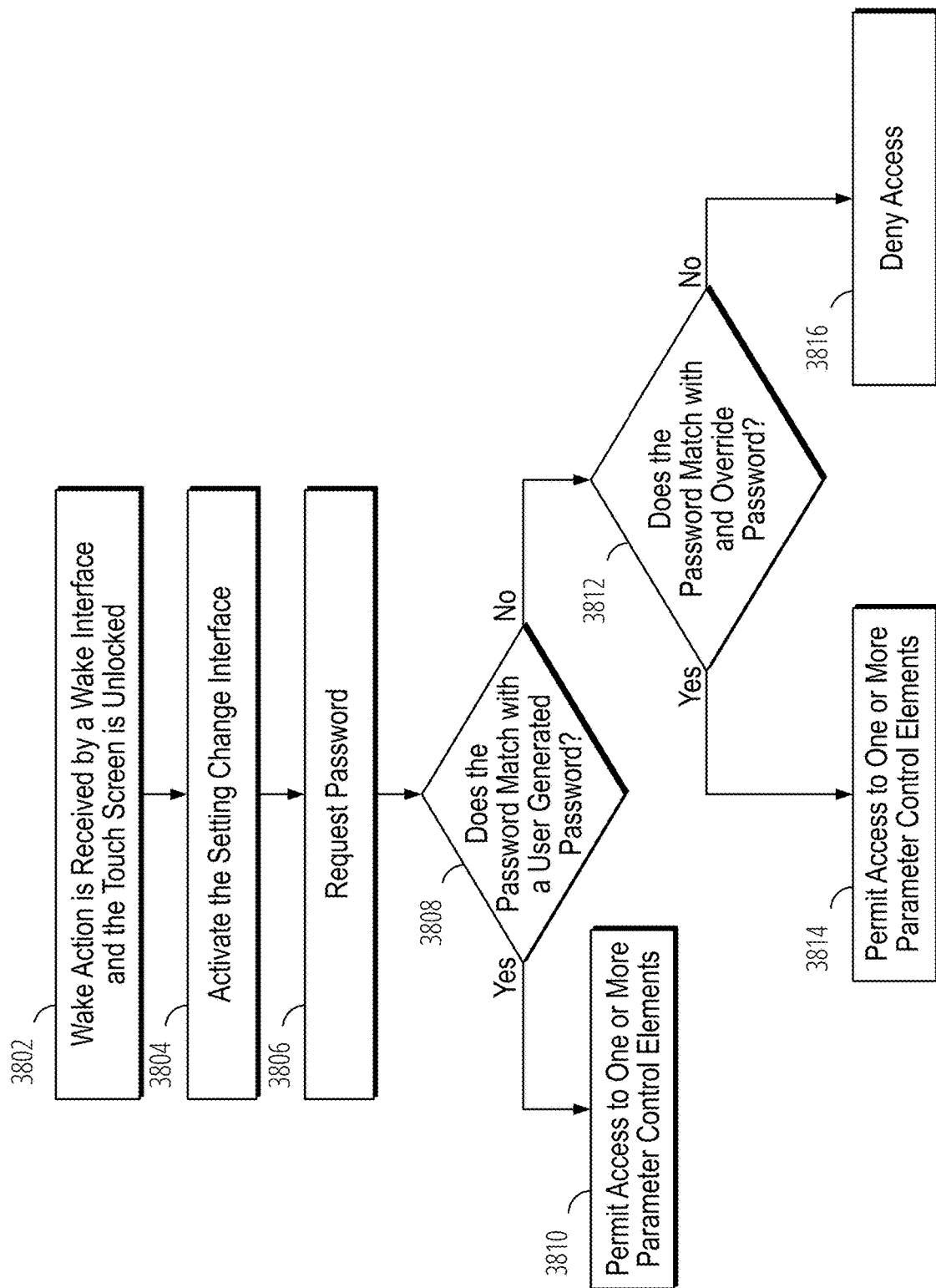
FIG. 38 is a flow diagram illustrating an example method that may be used by an AMD to allow a user to change a setting of the AMD using a user generated passcode or an override passcode.

FIG. 38 is a flow diagram illustrating an example method that may be used by an AMD to allow a user to change a setting of the AMD using a user generated passcode or an override passcode. Once the AMD (e.g., the wake action procedure in the CCM) receives a valid wake action 3802, a user interface may be activated. In some example, the wake action may directly activate a setting change interface 3804 (e.g., a setting change screen presented on a touchscreen display). In some examples, a specific wake action may activate the setting change interface. On the setting change interface 3806, the AMD (e.g., the setting change procedure in the CCM) may request a passcode (e.g., by presenting a user interface to enter a passcode). Once a passcode is received, the AMD (e.g., the setting change procedure in the CCM) may determine whether the passcode matches a user generated passcode 3808. If it is determined the passcode matches with a user generated passcode, the AMD may provide access 3810 to one or more control parameter elements associated with the received passcode. If the received passcode dose not match with any of the stored user generated passcode, the AMD may determine whether the passcode matches with an override passcode 3812. If it is determined the passcode matches an override passcode stored in a memory of AMD or a memory of an authorized computing device, the AMD may provide access 3814 to one or more control parameter elements associated with the received override passcode. If it is determined the passcode does not matches an override passcode, the AMD denies access 3816 to one or more passcode protected control elements.

Figure 39:
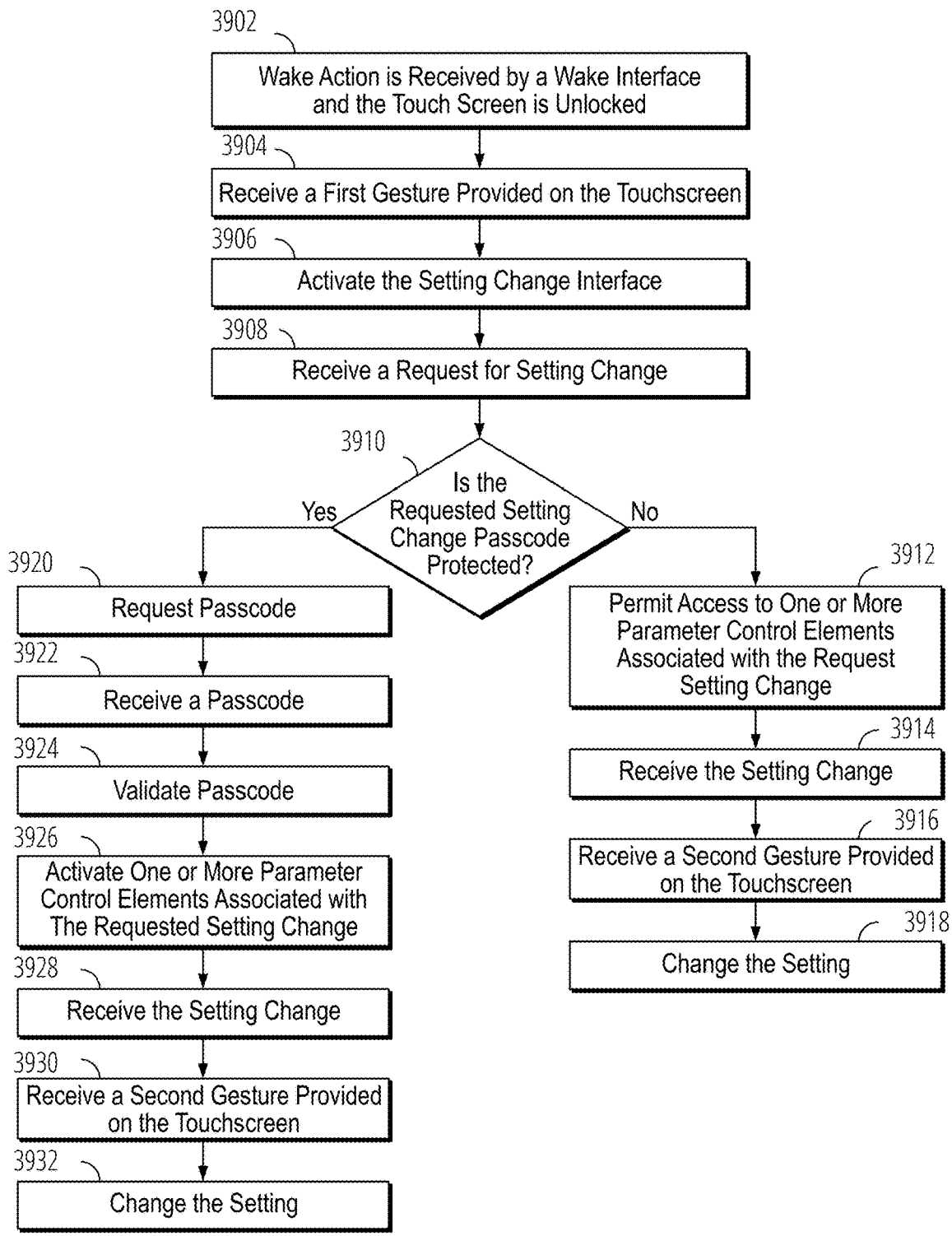
FIG. 39 is a flow diagram illustrating an example method that may be used by an AMD to allow a user to change a setting of the AMD using a user generated passcode or an override passcode.

FIG. 39 is a flow diagram illustrating another example method that may be used by an AMD to allow a user to change a setting of the AMD using a user generated passcode or an override passcode. Once the AMD (e.g., the wake action procedure in the CCM) receives a valid wake action 3902, the AMD may provide a user interface (e.g., a touchscreen display) on which the user can provide a first gesture to activate a setting change interface or screen. When a first gesture is received from a user or subject 3904, the AMD may activate a setting change interface 3906 or a screen. In some examples, the setting change interface or a screen may include one or more parameter control elements associated with one or more settings of the AMD. In some other examples, the setting change interface or a screen may include one or more selectable elements each associated with a setting change screen (e.g., a screen provided on a touchscreen display) that may include one or more control parameters. When a request for setting change is received

3908, the AMD may determine whether the requested setting change is passcode protected or not 3910. In some examples, the request for setting change may include selecting a parameter control element. In some other examples, the request for setting change may include selecting a list of parameter control elements (e.g., included in a separate screen provided on a touchscreen display).

If the AMD determines that the requested setting change is not protected by a passcode, it may permit access to one or more parameter control elements associated with the requested setting change 3912. In some examples, once the changes are received via parameter control elements 3914, the user may need to provide a second gesture on the user interface (e.g., touchscreen display) to confirm the changes made. In response to receiving the second gesture 3916, the AMD may change one or more settings 3918 according to the requested and confirmed changes.

If the AMD determines that the requested setting change is protected by a passcode, it may request a passcode 3920 via a passcode display (e.g., provided on a touchscreen display). In some examples, the request for the passcode may be presented on a display but the passcode may be received via a physical keypad. Once a passcode is received 3922 from the user or subject, the AMD may validate the passcode 3924 by comparing it with one or more user generated passcodes or an override passcode. If it is determined that the passcode matches with a user generated passcode or an override passcode, the AMD may activate 3926 one or more parameter control elements associated with the requested setting change. Subsequently, the AMD may receive a setting change via the selected control parameter element 3928. In some examples, the user may need to provide a second gesture on the user interface (e.g., touchscreen display) to confirm the changes made. In response to receiving the second gesture 3930, the AMD may change one or more settings according to the requested and confirmed changes 3932.

AMD with Alarm System

In some cases, a condition may occur that impacts the operation of the ambulatory medicament device. This condition may be associated with the ability of the ambulatory medicament device to operate as intended by the manufacturer, a subject receiving therapy from the ambulatory medicament device, and/or user (e.g., healthcare provider, parent, or guardian of the subject). In some cases, the ambulatory medicament device may be operating as intended, but the condition of the subject may not satisfy a desired level of health. In either case, it is generally desirable to generate an alarm to inform the subject and/or one or more users of the condition of the ambulatory medicament device and/or the subject. Moreover, it is desirable to track the alarm until the condition that caused the alarm is resolved. Further, it is desirable to issue different types of alarms for different conditions to enable a subject or user to easily distinguish the severity of the condition that triggered the alarm. The user may be a subject receiving medicament or therapy, or may be another user, such as a clinician or healthcare provider, or a parent or guardian.

This section of the disclosure relates to an ambulatory medicament device, such as an insulin pump or a combined insulin and counter-regulatory agent (e.g., Glucagon) pump, configured to generate a dose control signal configured to cause a medicament pump to infuse medicament into a subject. Moreover, the present disclosure relates to an ambulatory medicament device configured to detect a condition of the ambulatory medicament device and/or the subject, and to generate an alarm when it is determined that the detected condition satisfies an alarm condition.

As mention above, an ambulatory medicament device may include an alarm system configured to monitor the ambulatory medicament device and/or the subject, and to generate an alarm when it is determined that a condition has been detected that satisfies an alarm condition. In some examples, the alarm system that may organize a list of alarms, notifying a user of these alarms, and allowing the user to acknowledge alarms.

In some embodiments, the alarm system may comprise a plurality of sensors that monitor the AMD or the subject, a monitoring system interface that receives the data from sensors, and alarm generation module that process the received data and generate alarms if an alarm condition is met. In some examples, the monitoring system interface and the alarm generation module are implemented using one or more hardware processors and machine readable. In some other examples, the monitoring system interface and the alarm generation module are separate hard ware modules.

Figure 40:
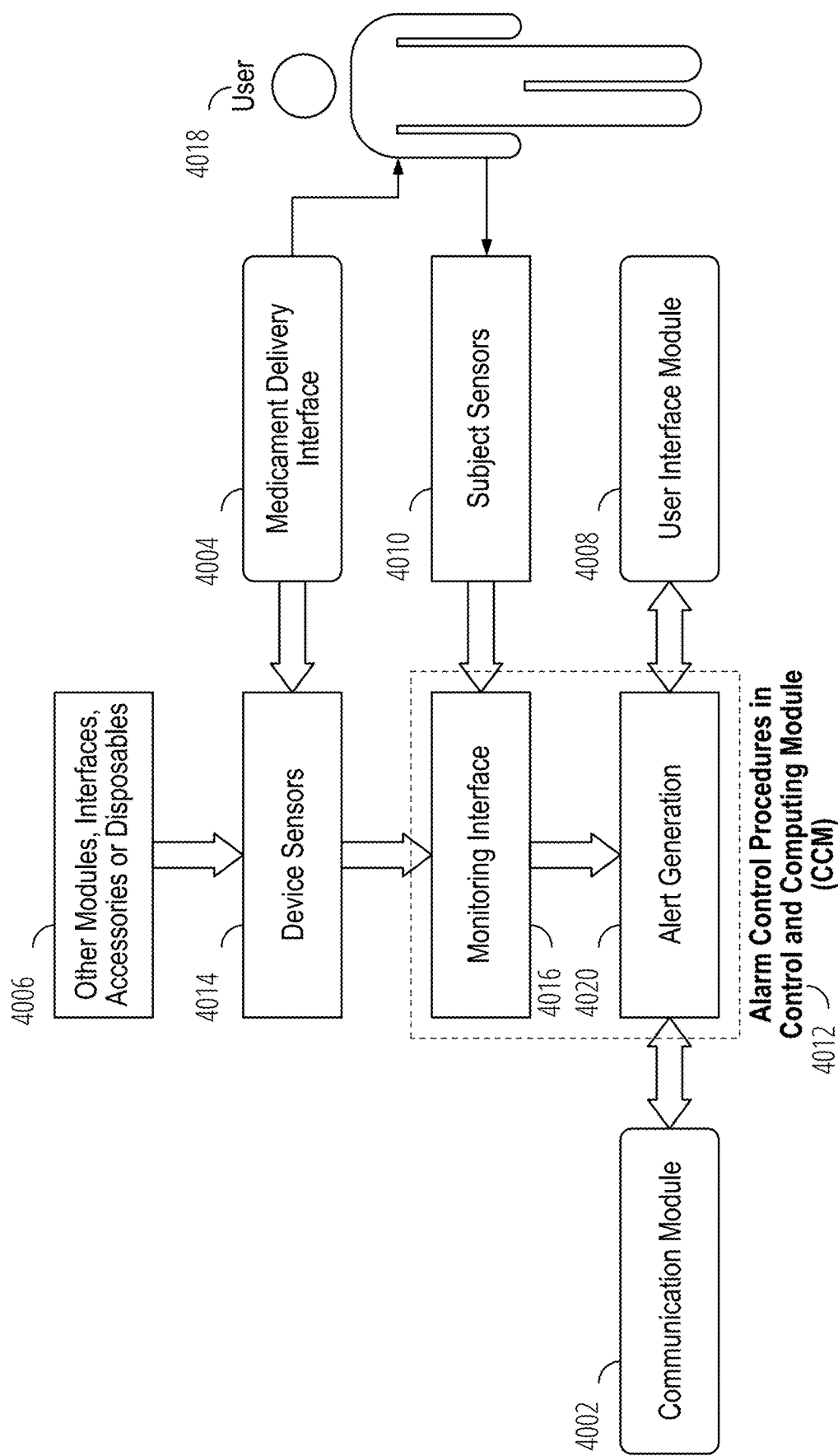
FIG. 40 is a schematic diagram illustrating the interconnection among modules and procedures in AMD involved in monitoring the status of the AMD and/or the subject and generate alarms when an alarm condition is met.

With reference to FIG. 40, in some embodiments, an alarm control procedure 4012 implements alarm control procedures in the control and computing module (CCM) of the AMD. The alarm control procedure 4012 can be implemented as instructions stored in a memory of the CCM and executed by a hardware processor to generate an alarm upon detection of a condition of the ambulatory medicament device and/or the subject. In some cases, the hardware processor of the monitoring system is a hardware processor of the ambulatory medicament device that controls medicament delivery. In other cases, the hardware processor of the monitoring system may be a separate hardware processor.

In some examples, the alarm control procedure 4012 includes a monitoring interface 4016 and an alert generation 4020 system. The monitoring interface 4016 monitors the condition or status of the AMD and/or the subject at least partially based on signals or status values received form a set of device sensors 4014 and a set of subject sensors 4010. In some examples, the device sensors may be configured to track the status of the components or the elements of the ambulatory medicament device, and the subject sensors can be configured to obtain measurements of one or more physiological characteristics of the subject In some examples, a device sensor 4014 is a sensor that generates a signal or status value associated with the condition of modules, interfaces, accessories, other modules, interfaces, accessories, or disposables 4006 of the AMD. In some examples, a device sensor 4014 may generate a signal that corresponds to a parameter associated with a component in a module or interface. For example, one device sensor may record the voltage of a battery and another device sensor may record the follow rate of a pump the medicament delivery interface 4004.

In some examples, a subject sensor 4010 may be any sensor that generates a signal or status value associated with one or more physiological indicators (or parameters) of a subject (e.g., heart rate, blood pressure, body temperature, level of blood sugar, serum levels of various hormones or other analytes). The device and subject monitoring interface 4016 can include continuously receiving and analyzing signals received from device sensors 4014 and subject sensors 4010 to determine the condition of the ambulatory medicament device, the subject, a sensor, and/or other accessories.

In some cases, a single sensor may be used to monitor both the condition of the subject and the ambulatory medicament device or accessories and sensors connected to AMD. For example, a continuous glucose monitoring CGM sensor may be used to monitor the condition of the subject, and may also be monitored to determine whether the condition of the CGM satisfies an alarm condition (e.g., to alarm a user that the CGM should be replaced).

Although described as sensors of the ambulatory medicament device, one or more of the sensors may be accessories that may or may not be part of the ambulatory medicament device, but that may communicate with the ambulatory medicament device.

In some examples, alarm control procedure 4012 implements procedures for allowing a user 4018 or the subject to change the alarm settings and/or acknowledging an alarm annunciation via the user interface module 4008. In some examples, the user 4018 may be able to see one or more alarms annunciated on a user interface (e.g., as a list of alarms), even if the AMD is in locked state. In these examples, the user may not be able to acknowledge or respond to alarm when the AMD is in locked state.

In some such examples, a user 4018 or the subject may get access to an alarm setting screen or acknowledge an alarm annunciation by providing a wake signal and a first gesture (e.g., on a touchscreen display). In some cases, the first gesture may be created by entering predetermined characters on the alphanumeric pad. In some such examples, the alarm control procedure 4012 distinguishes inadvertent alarm control inputs from intentional alarm control inputs. An inadvertent alarm control input is an alarm acknowledgment input that was made without the intent of the user 4018 to acknowledge the alarm that the ambulatory medical device is delivering to the user 4018.

In some examples, the alarm control procedure 4012 implements processes for determination and categorization of an alarm condition based on its severity level (e.g., a severity level between 0 and 5), according to the information received through the monitoring interface 4016.

In some other examples, the alarm control procedure 4012 implements procedures for controlling the annunciation of alarm conditions via the user interface module 4008, at least partially, based on their severity level. In some such examples, a user interface (e.g., a touchscreen display) may be configured to allow the user 4018 to navigate directly to the issue or fault for which an alarm is being delivered. This capability provides the user 4018 with access to address the fault causing the alarm so that it could be corrected thereby stopping the alarm.

Alarm Conditions

In some examples, the device and subject monitoring interface 4016 may provide the status information received from the device sensor 4014 and/or subject sensors 4010 to the alert generation 4020 system. In some examples, the status information may comprise one or more status values. In some such examples, the alert generation 4020 system is configured to determine based at least in part on the status information received from the subject monitoring interface 4016, whether an alarm condition is satisfied.

Determining whether the alarm condition is satisfied may include comparing one or more status values associated with the ambulatory medicament device and/or the subject to one or more alarm thresholds or alarm conditions. In some cases, each alarm threshold or alarm condition may be associated with an alarm profile. In some such cases, determining whether the alarm condition is satisfied may include comparing the status information to one or more alarm thresholds or alarm conditions included in one or more alarm profiles. In some examples, the alarm profile may be stored in a storage of the control and computing module. In some such examples, at least some of the alarm profiles may be provided to the CCM by an authorized user or the subject via a user interface or directly transferred from another device to the storage (e.g., from USB drive, a laptop, smart phone, PC and the like). In some other examples, at least some of the alarm profiles may be stored in the storage 218 at the time of manufacture, Each of the alarm profiles may indicate the characteristics or status of the ambulatory medicament device and/or subject that triggers an alarm corresponding to the alarm profile. For example, at least some alarm profiles may indicate the threshold status values below of above which an alarm should be triggered. For example, one alarm profile may indicate that when a blood glucose level of the subject exceeds a particular threshold, a particular alarm is to be generated and/or annunciated. As another example, an alarm profile may indicate that when an available amount of medicament is below a particular threshold, a particular alarm is to be generated and/or annunciated. The type of alarm and/or the alarm frequency or intensity associated with the medicament level may differ from the alarm triggered based on the blood glucose level. Although the previous examples, described a single condition associated with a single alarm profile, it should be understood that multiple conditions may be associated with an alarm profile. For example, a blood glucose level that exceeds an upper threshold or is below a lower threshold may be associated with different alarm profiles or the same alarm profile. As another example, a blood glucose level that is above an upper threshold or a medicament pump that is unable to supply insulin may be associated with the same alarm profile. On the other hand, a medicament pump that is unable to supply insulin due to an empty insulin cartridge may be associated with a different alarm profile than if the medicament pump is unable to supply insulin due to damage to the medicament pump.

Some non-limiting examples of conditions of the ambulatory medicament device or of the subject that may be associated with an alarm profile include conditions relating to a battery capacity (e.g., below a threshold charge capacity or below a capacity associated with a particular amount of operating time (e.g., one day)), a battery condition (e.g., high temperature or low voltage), a medicament or drug delivery condition (e.g., medicament is empty or below a threshold, motor is stalled, catheter is occluded, etc.), subject sensor condition (e.g., blood glucose sensor is expiring, or signal was not received from sensor), calibration failure, high or low glucose levels, network (e.g., Bluetooth® or BN-LTE) communication errors, haptic interface errors (e.g., motor non-responsive), speaker errors (e.g., noise or low volume), medicament cartridge errors (e.g., empty cartridge, cartridge detection error, etc.), and the like. As explained below, each of these errors or conditions may be associated with different severity levels that cause the annunciation of different alarms.

In some cases, each alarm profile may be associated with a severity level of the alarm. The severity level may be associated with how urgently the condition that triggered the alarm should be addressed or resolved. Further, the severity level may be associated with an amount of harm that may be caused to a subject if the condition that triggered the alarm is not resolved or is not resolved within a particular time period. The number of severity levels may vary based on the type of ambulatory medicament device. Generally, there is no limit to the number of severity levels. However, there may be a point of diminishing returns as the number of severity levels exceeds a particular number because, for example, it may be difficult for a user to distinguish between the different numbers of severity levels or to identify with which severity level a particular alarm is associated. Thus, the number of severity levels may be limited to a particular number, such as 3, 5, 6, 9, or some number in between. However, it is possible for there to be more than 9 severity levels.

There may be multiple alarm profiles associated with the severity level. Or each condition of the ambulatory medicament device and/or subject that is associated with the same severity level may be associated with the same alarm profile.

The ambulatory medicament device may determine a severity of an alarm condition based on the condition of the ambulatory medicament device and/or the subject that triggered the alarm condition. In some cases, the ambulatory medicament device may determine the severity of the alarm condition based at least in part on an alarm profile associated with the alarm condition.

Generally, if the alarm condition does not prevent the ambulatory medicament device from providing therapy, the ambulatory medicament device may continue to provide therapy. However, if the alarm condition interferes with the delivery of therapy, operation of the ambulatory medicament device may be suspended or partially suspended. Generally, alarm conditions that interfere with the provisioning of therapy may be associated with a higher severity level. However, some alarm conditions that interfere with the provisioning of therapy may be associated with lower severity levels. For example, a determination that the ambulatory medicament device cannot supply insulin may normally be associated with a highest severity alarm. But if a user indicates that the site location is currently in process of being changed, the alarm condition may be associated with a lower severity level (e.g., an informational alarm reminding the user that insulin cannot be delivered during site change).

Alarm Annunciation

The alert generation 4020 system can implement an annunciation pattern selected based at least in part on the status information generated by and received from the monitoring interface 4016, whether an alarm condition is satisfied. Determining whether the alarm condition is satisfied may include comparing one or more status values associated with the ambulatory medicament device and/or the subject to one or more alarm thresholds or alarm conditions associated with an alarm profile.

Upon verifying that an alarm condition associate with an alarm profile is satisfied, the alert generation 4020 system annunciates the alarm condition.

In some examples, the alarm system may generate a list of pending alarm conditions and store it in a memory of the AMD. In these examples, any time an alarm condition associated with an alarm profile is satisfied, the alarm system may update the list of pending alarm condition by adding the new alarm condition to the list of pending alarm conditions.

In some examples, the list of pending alarm conditions may be sorted according to the severity level associated with the alarm conditions.

In some examples, the alarm system may annunciate the alarm conditions via the user interface module 4008 of the ambulatory medical device 1600. For example, the alarm condition may be annunciated via one or more user interfaces (e.g., a display, a speaker, and the like). In some such examples, an alarm may comprise an audio alarm, a text message, a graphical message, a text or graphical message with audio, vibrations, flashing light and any combination of these.

In some other examples, the alarm conditions may be transmitted to other devices, via the communication module 4002 of the AMD where, for example, an authorized user 4018 (e.g., guardians or parents of the subject), the subject or an emergency provider can view the alarm condition. In yet other examples, the alert generation 4020 system, may establish a direct end-to-end connection with a computing system (e.g., a cloud computing system) using the communication module 4002 and send the alarm condition to the computing system through the end-to-end connection.

Based on the severity of the alarm condition and/or the alarm profile corresponding to the alarm condition, an alarm may be generated and/or annunciated that is associated with the severity of the alarm condition and/or the type of alarm condition. Different alarm conditions and/or alarm profiles may result in different types of alarms or different annunciations of the alarm. For example, an alarm associated with the highest severity level may include an audible alarm with a loudness that exceeds a particular decibel level (e.g., above 70 or 80 decibels), a visible alarm (e.g., a flashing or steady light) with a luminance above a particular luminance value (e.g., a luminance between $10^5$ or $10^6$ candelas per square meter), and/or a vibrational alarm. Further, the alarm associated with the highest severity level may not be snoozed or dismissed. Alternatively, the alarm associated with the highest severity level may be snoozed for a shorter time period than alarms of lower severity levels (e.g., for 5 minutes, for 10 minutes, etc.). An alarm associated with a different severity level than the highest severity level may include a different combination of audible, visible, and vibrational alarms. Not only may the existence of audible, visible, and vibrational alarms differ for different severity levels, but so may the characteristics of each of the alarm types. For example, audible alarms may have different sound patterns, loudness, frequencies, etc. Visible alarm may be of different intensity, color, pattern, etc. Vibrational alarms may be of different pattern, intensity, etc. Further, an alarm with a different severity level than the highest severity level may be permitted to be snoozed or dismisses, or snoozed for a longer period of time. In some examples, the severity of the alarm condition may determine the type of type of the alarm generated (e.g., audio, text, graphical, or any combination of these).

Further, the display of alarm conditions on the user interface may include an icon for each type of alarm condition. The user interface may display the number of alarm conditions and/or the number of alarm conditions of a particular type or severity level. In some cases, a duplicate alarm may be omitted from the list of alarms. In other cases, a count of the occurrence of alarms may be increased to reflect the duplicate alarm. In some cases, a duplicate alarm may result in the annunciation of the duplicate alarm. In other cases, the duplicate alarm is ignored. In some cases, the occurrence of a duplicate alarm may cause an escalation of the existing alarm. For example, if an alarm condition that causes an annunciation of an alarm with a first severity level is detected as occurring a second time, the alarm may be annunciated with a second severity level that indicates a greater degree of severity that the first severity level. It should be understood that an alarm occurring after an alarm condition is resolved may not be considered a duplicate alarm, but instead may be a reoccurrence of the alarm condition and/or an indicator that the resolution for the alarm condition failed (e.g., an insulin cartridge replacement is faulty or is empty).\

In some cases, the list of alarms may be accessed when the ambulatory medicament device is locked. Further, details about the alarms may be accessible when the ambulatory medicament device is locked.

Each of the alarm conditions, or information associated therewith, may be added to an indicator or user interface (e.g., a list, or other data structure or user interface element) that may be accessed by a user. This user interface may maintain the alarm condition on the user interface until the alarm condition is resolved. Further, the alarm conditions may be sorted or ranked based on the severity level of the alarm condition, the time that the alarm condition occurred, whether the alarm condition relates to the subject or the ambulatory medicament device, any combination of the foregoing, or any other factor for sorting or ranking the alarm conditions.

In some cases wherein the alarm is presented on a display, the displayed information may include details about what caused the alarm, the severity of the alarm, how to respond to or address the alarm, or any other information that may be informative regarding why the alarm was generated and/or how to respond to the alarm. In some cases, the information may provide a workflow or instructions on how to respond to the alarm. The instructions may include a link to a workflow provided by a manufacturer of the ambulatory medicament device or of another entity, such as an entity that provides medicament or site changing kits.

In some cases, different views of an alarm or different information associated with the alarm may be provided based on an identity of the user, or a role of the user, viewing the alarm. For example, a child may be instructed to contact a parent to address an alarm. But a parent may be provided with information to resolve the alarm. The parent may receive simplified information (e.g., blood glucose level is high) about what caused the alarm, but a healthcare provider may receive more detailed information regarding the alarm (e.g., internal control parameter values, insulin flow rates, curvature of insulin diminishment predictions, etc.) that facilitates the healthcare provider caring for the subject.

The alarm conditions may be displayed on a display of the ambulatory medicament device. Alternatively, or in addition, the alarm conditions may be displayed on a remote display that is separate from the ambulatory medicament device. The remote display may be a display that is authenticated or associated with a computing device that is authenticated to access data, such as alarm conditions, from the ambulatory medicament device. In some cases, the list of alarms may be presented on a mobile device (e.g., a smartwatch or smartphone) or on a computing device (e.g., a laptop or desktop) that can obtain data directly or indirectly from the ambulatory medicament device.

In some cases, annunciating the alarm may include contacting a manufacturer and/or user (e.g., a healthcare worker, a parent or guardian, or other registered user). Further, the alarm may include instructions on repairing the ambulatory medicament device and/or on addressing the alarm condition. For example, the alarm may provide a user with instructions to replace the insulin cartridge and how to replace the insulin cartridge. As another example, the alarm may provide instructions on how to change the battery of the device or on how to change a site where the insulin pump connects to the subject. In some cases, the alarm may include one or more operations associated with the alarm. For example, the alarm may trigger reordering of insulin or may request that the user confirm a reorder request to reorder insulin.

A user may be able to acknowledge and/or snooze alarms. Certain alarms, such as informational alarms, may be dismissible. However, generally the alarm may remain on the alarm list until the condition that caused the alarm is resolved.

Resolving the alarm may include any action that addresses the condition that caused the alarm to be generated. For example, resolving the alarm may include replacing an insulin cartridge, changing a site where the ambulatory medicament device is connected to the subject, charging a battery of the ambulatory medicament device, providing insulin or a counter-regulatory agent to the subject and/or the ambulatory medicament device, or any other action that may be performed to address an alarm condition. In some cases, the resolution action may be acknowledging the alarm. For example, if the alarm is informational (e.g., to inform the user that more insulin has been ordered), acknowledging the alarm may be a sufficient resolution action.

In some cases, whether the alarm condition is resolved may depend on an identity of the user. For example, if a child interacts with an alarm related to reordering of insulin, the alarm may remain until a parent or guardian acknowledges the alarm. However, the child may be able to snooze the alarm. In some cases, a user interface that displays alarms may differ based on who is viewing the alarm. For example, a child may view the alarms, but may not be able to interact with the alarms. However, a parent or guardian may be able to snooze or dismiss an alarm. Further, a child may be instructed to bring the device to a parent or adult to address an alarm. In some cases, the child may be informed of how urgently to contact the parent (e.g., contact a parent immediately, within a day, within a week, etc.). Moreover, a designated adult may separately be alarmed (e.g., via a text or email alarm). The parent or guardian may receive additional information not provided to the child or subject (e.g., a link to repair instructions or a workflow to address the alarm condition).

In some cases, certain conditions may self-resolve over time. For example, a low battery alarm may resolve as the battery is charged. In such cases, the alarm may be cancelled automatically as the battery charge level exceeds a particular threshold. Further, in some cases, one or more alarms and/or the alarm list can be viewed and/or accessed on a home screen, a main screen, or other non-alarm based user interface screen in addition to a user-interface screen designated for display alarms. The alarm list may be accessed from the ambulatory medicament device and/or a computing system in communication with the ambulatory medicament device.

However, in some cases, the alarm condition may or may not be resolvable when the ambulatory medicament device is locked.

A user may interact with the alarms generated based on the alarm condition. In some cases the user can only interact with the alarms when the ambulatory medicament device is unlocked. In other cases, the user can interact with the alarms to snooze them or to obtain further information. However, the user may not be able to dismiss the alarm without unlocking the ambulatory medicament device. Interacting with the alarms may include providing information associated with the alarm to a user in response to the user interacting with the alarm, or an indicator representative of the alarm.

Example AMD with Alarm Management System

Figure 41:
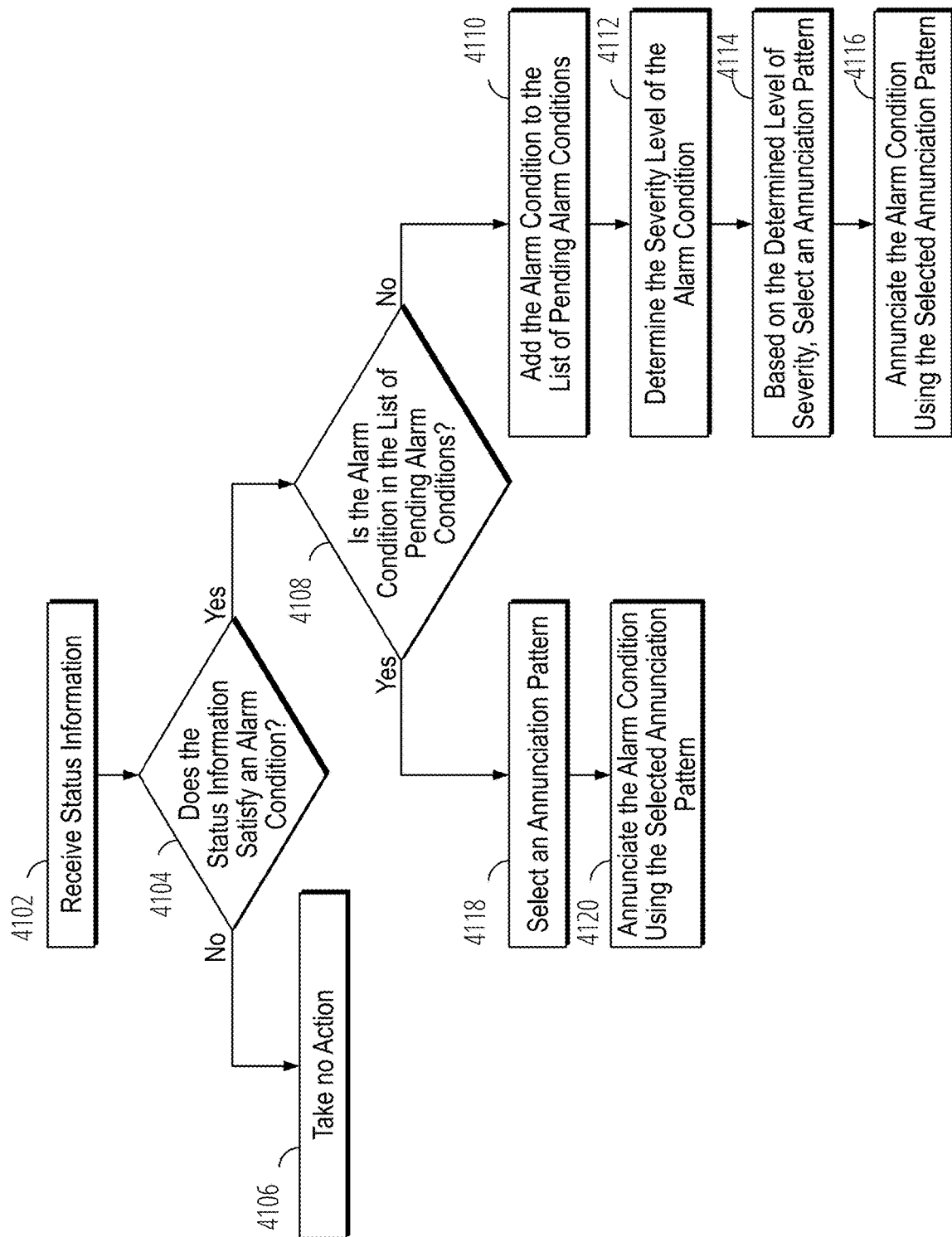
FIG. 41 is a flow diagram illustrating an example procedure that may be used by the alarm system of an AMD to annunciate an alarm condition upon receiving a status information that satisfies an alarm condition.

FIG. 41 shows a flow diagram illustrating an example procedure that may be used by the alarm system of an AMD to annunciate an alarm condition upon receiving a status information that satisfies an alarm condition. In some examples, the alert generation 4020 system implements an annunciation process by execution of instructions by a processor in CCM of the AMD, where the instructions can be stored in the main memory, storage of the AMD, or in a memory of a connected electronic device or computing system.

The alarm system may receive status information 4102 using the device and subject monitoring interface 4016, one or more device sensors and/or one or more subject sensors. In some examples, the alert generation 4020 system determines whether the received status information satisfies an alarm condition 4104. In some examples, the alarm condition may be an alarm condition in an alarm profile. If the received status information does not satisfy an alarm condition, no action may be taken 4106. If the received status information satisfies an alarm condition, the alarm system may determine whether the alarm condition is already present in the list of pending alarm conditions or not 4108. If the alarm condition is not present in the list of pending alarm conditions, the alarm system may add the alarm condition to the list of pending alarm conditions 4110. Next the alarm system, may determine the severity of the alarm condition 4112. Based on the determined level of severity, the alert generation 4020 system can select an annunciation pattern 4114 and annunciate the alarm condition using the selected annunciation pattern 4116. If the alarm condition is present in the list of pending alarm conditions, the alarm system may select an annunciation pattern 4118 and annunciate the alarm condition using the selected annunciation pattern 4120. In some examples, the annunciation pattern selected at block 4118, may be an annunciation pattern that is different than the previously used annunciation patterns for the alarm condition. In some such examples, the annunciation pattern selected at block 4118, may be selected based on number of times that the same alarm condition is satisfied by a received status information. The process of the alarm detection and control function may repeat each processing cycle so long as the ambulatory medical device is in use. In some examples, after an alarm is annunciated, the alarm system may wait for user acknowledgment of the alarm. If the user acknowledges the alarm, the system proceeds to perform alarm processing. However, if the user fails to acknowledge the alarm, the annunciation continues and may escalate depending on the level of the alarm.

As mentioned above, the alarm conditions may be categorized based and annunciated based on their severity level. In some examples, the alarms are categorized numerically in descending order with the highest priority fault displayed at the top of the list.

In some examples, a level 0 severity, may be for a trivial fault that does not require any action by the user thus not warranting an alarm notification. In some other examples, a level 1 severity may be an informational type notification that repeats at a certain frequency (e.g. every 30 minutes) until acknowledged by user which results in it being reset. The annunciation may include a brief vibration and a beep, for example. In some examples, a level 2 severity, may be one relating to an imminent loss of system function. Thus, such an annunciation may include two brief vibrations and two beeps, for example, and repeating at a certain frequency (e.g. every 30 minutes). Thus, the user would still need to address the situation creating the fault to completely stop the annunciation. In some other examples, a level 3 fault may be for when the system is no longer fully functional thus requiring user intervention to correct the issue. The annunciation may begin with a base level intensity with three brief vibrations and three audio beeps, for example, and repeating at a certain frequency (e.g. every 5 minutes). The annunciation escalates at a second frequency, e.g. every 30 minutes, up to a maximum intensity level. The escalation may be a change in vibration intensity and/or audio level, for example. The escalation may be cleared to base level when the user acknowledges the fault; however, the base alarm remains if underlying condition persists. Thus, the user would still need to address the situation creating the fault to completely stop the annunciation. In some examples, a level 4 severity, may be for when the system is no longer functional and not correctable by the user. The annunciation may begin with a base level intensity with three audio beeps, for example, and repeating at a certain frequency (e.g. every 5 minutes). The annunciation escalates at a second frequency, e.g. every 30 minutes, up to a maximum intensity level. The escalation may be a change in audio level, for example. The escalation may be cleared when the user acknowledges the fault; however, the base alarm remains because the underlying condition persists. In some other examples, a level 5 severity, may be for high priority alarms per IEC 60601-1-8. The annunciation when activated may be cleared only when the underlying issue is resolved, e.g. glucose level is raised.

Additional embodiments relating to determining a severity of an alarm condition and annunciating the alarm based at least in part on the severity of the alarm condition that can be combined with one or more embodiments of the present disclosure are described in U.S. Provisional Application No. 62/911,017, which was filed on Oct. 4, 2019 and is titled "ALARM SYSTEM AND METHOD IN A DRUG INFUSION DEVICE," the disclosure of which is hereby incorporated by reference in its entirety herein for all purposes.

Non-Critical AMD Condition Management

In some cases, a condition may occur that impacts the operation of the ambulatory medicament device. This condition may be associated with the ability of the ambulatory medicament device to operate as intended by the manufacturer, a subject receiving therapy from the ambulatory medicament device, and/or user (e.g., healthcare provider, parent, or guardian of the subject). In some cases, the condition or malfunction of the ambulatory medical device may prevent the ambulatory medical device from providing therapy to the subject. In other cases, the condition or malfunction may permit, at least for a period of time, the ambulatory medical device to continue providing at least partial therapy to the subject. In either case, it is generally desirable to generate an alert to inform the subject and/or one or more users of the condition of the ambulatory medical device and/or the subject. Moreover, it is desirable to track the alert until the condition that caused the alert is resolved. Further, it is desirable to issue different types of alerts for different conditions to enable a subject or user to easily distinguish the severity of the condition that triggered the alert.

In many cases, if the nature of the alert is non-critical, it may be safer to continue the underlying therapy and notify the user of the condition than to cease therapy. In some such cases, the best response to a problem with the device for a subject is to notify the device manufacturer, or other user that can address the problem, while the subject continues to receive therapy until a replacement device can be obtained or a repair can be made.

Additionally, alert fatigue can be an issue with medical devices due to excessive alerts which do not necessarily require user interaction. Alert fatigue can be dangerous because it can lead users to ignore serious alerts or alerts that require action in the short term.

The method described herein may be performed by an AMD (e.g., by one or more processor of the AMD) to detect device malfunctions for the AMD and that can generate alerts corresponding to the ambulatory medical device and prioritize the alerts to enable the subject or user to quickly and easily determine whether the device malfunction will impact therapy, should be addressed in the short-term (e.g., immediately, in 1-2 hours, within the day, etc.), and/or can be addressed at the subject's convenience (e.g., within a month, or more). In some cases, the method may be used by other systems.

In certain embodiments, the system disclosed herein can detect a condition in which the ambulatory medical device does not meet a manufacturer's specification (e.g. a failure of a haptic annunciator, a Bluetooth® radio malfunction, glucagon or insulin runs out, there is a medicament delivery malfunction, a touchscreen failure, etc.). In some cases, there can be several tiers of critical and/or non-critical faults. If it is determine that the underlying condition is not sufficient to stop therapy (e.g., delivery of insulin is not stopped), the fault may be deemed non-critical. In some cases, the fault may not be a fault of the device, but may be indicative of required maintenance (e.g., recharge battery indicator, order more medicament indicator, etc.). The condition may be annunciated to the user with appropriate instructions (e.g., call manufacturer for replacement medicament or parts) for addressing the fault or issue.

After the annunciation is acknowledged, the alert may be re-annunciated as a reminder at some later period in time (e.g. the alert may be re-annunciated daily at 4:00 PM or on Saturdays at noon). The length of time between annunciations may depend on the severity of the fault. In some cases, the re-annunciation cannot be stopped by the user, but may only cease if the underlying condition is resolved.

The method may include detecting a condition of the ambulatory medical device. The condition of the ambulatory medical device may be determined by one or more sensors of the ambulatory medical device. Further, the condition of the ambulatory medical device may be determined by the presence or absence of one or more errors when performing one or more functions of the ambulatory medical device. For example, if the ambulatory medical device fails to establish a communication connection with a control system or a data storage system, it may be determined that there is a possible malfunction with the ambulatory medical device. As another example, if the ambulatory medical device fails to deliver medicament or detects an error when attempting to deliver medicament, there may be a malfunction with the medicament pump. In some cases, the condition of the ambulatory medical device may be determined based on one or more configuration values being outside a normal operating range. For example, if the speed of delivery of medicament is faster or slower than a configured operating range, then it may be determined that there is a malfunction with the medicament pump or a connection with a medicament delivery tube (e.g., a catheter).

The method may include comparing the detected condition of the ambulatory medical device to a set of normal operating parameters. The set of normal operating parameters may be the specifications set by the manufacturer for when the ambulatory medical device is operating as intended by the manufacturer. In some cases, the normal operating parameters may be associated with a range of values. For example, the operating parameter for a speed of medicament delivery may be associated with a range of speeds, which may vary based on user settings, medicament type, site location of medicament delivery, or manufacturing tolerances, among other parameters. Comparing the detected condition of the ambulatory medical device to the set of normal operating parameters may include comparing each operating parameter in the specification to a corresponding detected operating parameter of the ambulatory medical device. The ambulatory medical device may generate a user alert based on the determined condition of the ambulatory medical device. For example, the AMD may generate an alert when the detected condition of the ambulatory medical device does not satisfy a set of normal operating parameters.

The method may further include determining whether the detected condition satisfies a minimum set of operating parameters. In some cases, the minimum set of operating parameters may match the normal operating parameters. However, typically the minimum set of operating parameters differ from the normal operating parameters. The minimum operating parameters may include the minimum specifications, minimum parameters, or minimum condition required by the ambulatory medical device to maintain or continue providing therapy to the subject. In other words, the minimum operating parameters are the operating parameters sufficient to provide therapy. However, the minimum operating parameters may not be sufficient to enable all features of the ambulatory medical device. For example, the minimum operating parameters may permit the ambulatory medical device to deliver insulin to the subject, but may not be sufficient to deliver the insulin at a normal delivery speed for the particular ambulatory medical device. As another example, the minimum operating parameters may permit the delivery of therapy, but may not be sufficient to track a log of therapy or to transmit a therapy log to another computing system. In some cases the normal operating parameters and/or minimum operating parameters may be specified by a subject or healthcare provider (e.g., the minimum amount of medicament that is to be provided in each bolus may be specified by a healthcare provider). In some cases, the normal or minimum operating parameters may be modified.

When it is determined that the condition of the ambulatory medical device satisfies at least the minimum operating parameters, the ambulatory medical device may be configured to maintain delivery of therapy to the subject. Maintaining delivery of therapy may include maintaining therapy at the same rate, at a reduced rate (e.g., providing only basal therapy and therapy responsive to a meal announcement), or at a minimum maintenance rate (e.g., providing only basal insulin). Advantageously, the ability of the ambulatory medical device to distinguish between a minimum set of operating parameters and a normal set of operating parameters enables an ambulatory medical device with a malfunction to continue providing therapy, which sometimes includes life-saving treatment, to a subject until the ambulatory medical device can be repaired or until the condition of the device worsens to a point where the minimum operating parameters cannot be maintained. In some cases, the ambulatory medical device may temporarily maintain delivery of therapy. Temporarily maintaining therapy may provide a subject time to address the issue that caused the ambulatory medical device to not satisfy the normal operating parameters before the subject loses access to therapy. In some cases, the ambulatory medical device temporarily maintains therapy until the device condition makes it no longer possible to maintain therapy.

Figure 42:
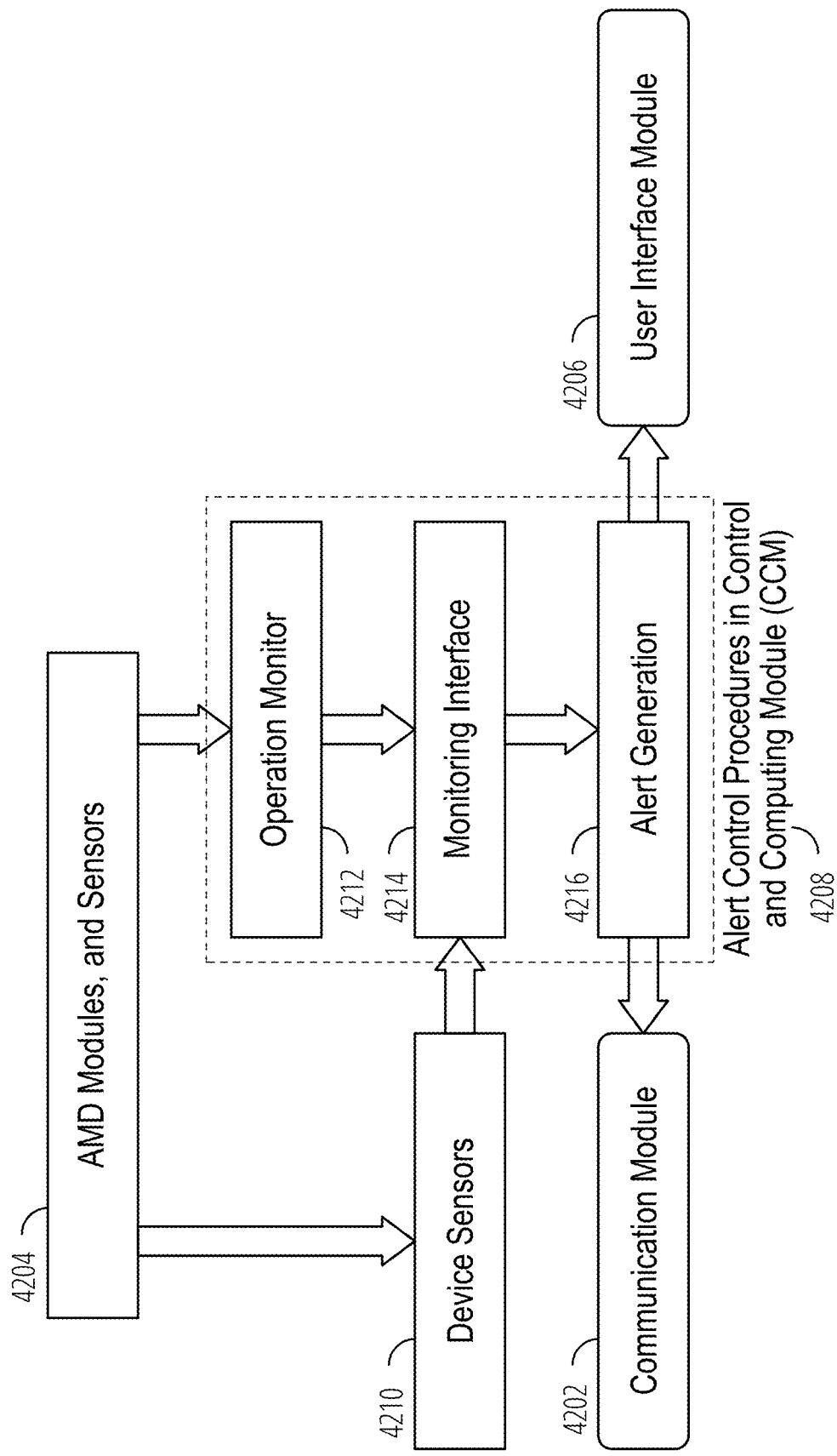
FIG. 42 is a block diagram illustrating the interconnection among modules and procedures in AMD involved in monitoring the condition of the AMD and generating alerts when a device malfunction is detected.

FIG. 42 is a block diagram illustrating the interconnection among modules and procedures in AMD involved in monitoring the condition of the AMD and generating an alert when a device malfunction is detected. In some examples, the condition of AMD may include the status of the modules and components of the AMD, such as AMD modules and sensors 4204 and/or operation of modules and procedures of the AMD. In some embodiments, the alert system may be implemented as a set of alert control procedures 4208 in the control and computing module (CCM) of the AMD. The alert control procedures 4208, may be implemented as instructions stored in a memory of CCM and executed by a hardware processor to generate an alert upon detection of a malfunction of the ambulatory medicament device. In some cases, the hardware processor may be a hardware processor of the ambulatory medicament device that controls medicament delivery. In other cases, the hardware processor of the monitoring system may be a separate hardware processor.

In some examples, the alert control procedures 4208 may include a monitoring interface 4214, an operation monitoring procedure 4212 and alert generation procedure 4216. The monitoring interface 4214 may monitor and evaluate the condition of the AMD and/or the subject at least partially based on the information received from the operation monitoring procedure 4212 and device sensors 4210. In some examples, the device sensors may be configured to track the status of the components or the modules of the ambulatory medicament device and the operation monitoring procedure 4212 may be configured to monitor the operation of the modules and other procedures. In some examples, the detected of the AMD may be provided to the alert generation procedure monitoring interface. The alert generation procedure 4216 may compare the detected condition of the AMD with a set of normal operating parameter. In some examples, the alert generation procedure may also determine whether the detected condition of the AMD satisfies a minimum set of operating parameters. In some examples, if it is determined that the detection condition of the AMD does not satisfy the normal operating parameters, the alert generation procedure may generate an alert. In some examples, the alert may be transmitted to the user interface module 4206 and displayed on a display of the AMD (e.g., a touchscreen display). In some other examples, once an alert is generated the AMD may establish a connection (e.g., a wireless connection) with another device. This other device may include a local device (e.g., a laptop, smartphone or smartwatch of the user) or a computing system of a cloud-based service. In some such examples, the alert may be transmitted by the communication module 4202 to the computing systems where it may be displayed on user interface associated with the computing system. In some cases, the additional device may receive data from the ambulatory medical device enabling it to monitor the condition of the ambulatory medical device.

The type of the alert, and the frequency at which the alert is repeated, or whether an alert is dismissible or not, may be determined by the alert generation procedure based on the detected condition of the AMD and the alert information stored in a memory of the AMD. In some examples, the alert information may be provided by the subject, an authorized user or a healthcare provider. In some other examples, the alert information may be stored in the AMD at time of manufacturing.

In some examples, upon determination that the detected AMD condition does not satisfy a set of normal operating parameters, the alert generation procedure may cause the medicament delivery interface to stop therapy delivery or modify one or more delivery parameters (e.g., therapy delivery rate). In some examples, upon determination that the detected AMD condition does not satisfy a set of normal operating parameters, but satisfies a set of minimum operating parameters, the therapy delivery may be maintained at a normal rate.

The alert may include any type of alert. For example, the alert may be a visual alert (e.g., a light or changing light), an audible alert (e.g., a beep or series of beeps), a haptic or vibration alert, an email alert, a text alert, or any other type of alert. Different device conditions may be associated with or may trigger different alerts. Thus, the user alert may enable the user to determine the device condition of the ambulatory medical device based on the alert. For example, an indication that the ambulatory medical device failed to deliver a medicament may trigger one type of alert while an indication that the ambulatory medical device has below a particular level of medicament available may trigger a different alert. In some cases, the user alert is dismissible and/or may be snoozed by the user. In other cases, such as when the ambulatory medical device fails to satisfy a set of minimum operating parameters, the user alert may not be dismissible or cannot be snoozed.

A dismissible alert may be scheduled to repeat on a particular schedule until an alert modification condition occurs. The frequency with which the dismissible alert repeats may depend on the severity of the condition or the particular operating parameters that do not satisfy normal or minimum operating parameters. More urgent device conditions may result in alerts that repeat more frequently. Further, alerts may vary based on when the condition was detected, the time of day, or the detected activity of a subject (e.g., sleep, abnormal activity, or elevated activity, such as exercise). Similarly, the snooze options may vary for different alerts or any of the aforementioned conditions. In some cases, the ambulatory medical device may escalate an alert if it detects that the condition of the ambulatory medical device has become more critical.

The alert frequency may be for a static time period (e.g., every 5 hours) or may ramp towards more frequency (e.g., every 5 hrs for 1 to 3 reminders, every 4 hours for 3 to 6 reminders, etc.), or may change based on time of day (e.g., snooze alerts during sleeping hours for non-urgent alerts), etc.

The alert modification condition may include any action that causes the operating parameters of the ambulatory medical device to return to normal operating parameters. For example, the alert modification condition may be a repair or replacement of a faulty component. In some cases, the alert modification condition may comprises an acknowledgement of the alert. In other cases, the alert modification condition may include a worsening of the ambulatory medical device condition. In such cases, the modification to the alert may include the substitution of the alert to a different alert that indicates a different or more serious condition of the ambulatory medical device. For example, an urgent condition may become critical if the detected malfunction is addressed after generating certain number of alerts. When an urgent condition becomes critical, it may trigger a different alert type (e.g., a louder sound, or brighter image) and/or escalation in the alert frequency. For example, the audible alert may become louder and may be combined with a vibration alert from a haptic annunciator. Moreover, if the condition reaches a critical state, the ambulatory medical device may cease providing therapy to the subject.

In some cases, generating the alert may further include contacting a manufacturer and/or healthcare provider (e.g., clinician). Further, generating the alert may include ordering replacement parts. In some cases, the alert may instruct a subject or user on how to repair the ambulatory medical device.

Once the malfunction is addressed, the ambulatory medical device is repaired, or the condition that caused the alert is resolved, a user may permanently (or until the next time a device condition triggers the alert) dismiss the alert. Alternatively, or in addition, the ambulatory medical device may automatically dismiss the alert if it senses that the device condition that caused the alert has been resolved. In some cases, the ambulatory medical device may periodically recheck the device condition to determine whether the alert condition has been resolved.

In some cases, the manufacturer or healthcare provider may remotely clear or stop an alert using, for example, an NB-LTE connection. In some cases, only the manufacturer and/or healthcare provider can clear or stop the alert. Further, in some cases, a manufacturer and/or a healthcare provider may notify a user (e.g., a subject, or parent or guardian) of an issue or impending issue with the ambulatory medical device. The notification may be received by the ambulatory medical device via the NB-LTE connection. Alternatively, or in addition, the notification may be received via a computing device, such as a smartphone or laptop.

Figure 43:
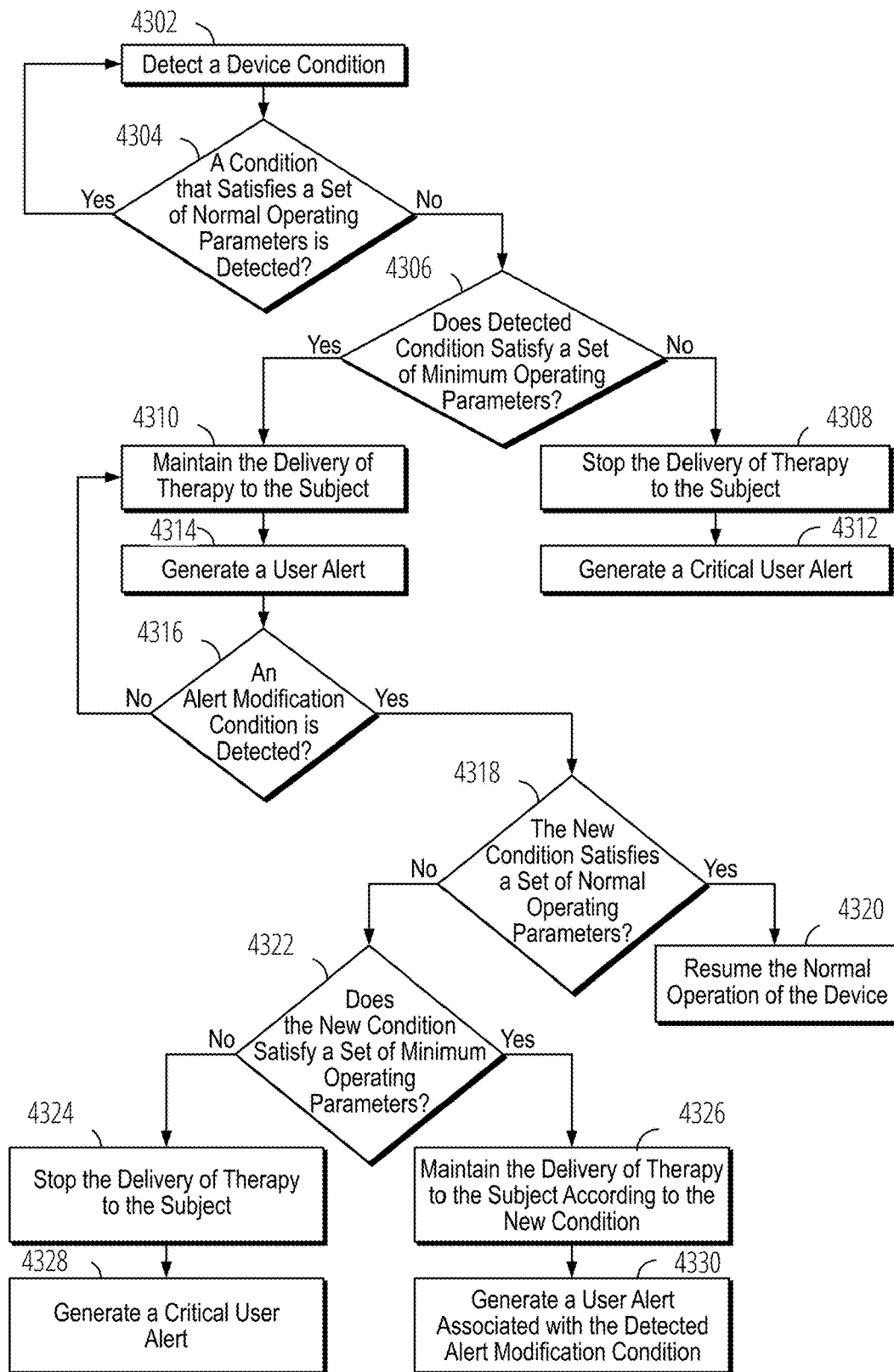
FIG. 43 is a flow diagram illustrating an example procedure that may be used by the alert system of an AMD to monitor the operation of an AMD and generate alerts when a device malfunction is detected.

FIG. 43 is a flow diagram illustrating an example procedure that may be used by the alert system of an AMD to monitor the operation of an AMD and generate alerts when a device malfunction is detected. In some examples, the alert system continuously monitors the status of all modules and components associated with AMD as well as the operation of all modules and procedures of the AMD. When a device condition is detected 4302, the alert system may determine whether the detected device condition satisfies a set of normal operating parameters 4304. If it is determined that the detected device condition satisfies a set of normal operating parameters, the alert system takes no action and continuous monitoring the AMD. If it is determined that the device condition does not satisfy a set of normal operating parameters, the alert system determines whether the detected device condition satisfies a set of minimum operating parameters. If, at block 4306, it is determined that the device condition does not satisfy a set of minimum operating parameters, the alert system may send a signal to the therapy delivery module to stop delivery of therapy to the subject 4308, and immediately generate a critical user alert 4312 indicating that immediate action is required. In some examples, upon generation of a critical alert the alarm system of the AMD, may contact a healthcare provider or certified user (e.g., parent or guardian of the subject) and also send the critical alert to one or more computing devices (e.g., laptop, cell phone, personal computer, and the like) of the healthcare provider or certified user. If, at block 4306, it is determined that the device condition satisfies a set of minimum operating parameters, the alert system may maintain the delivery of therapy to the subject 4310 and generate a user alert 4314. In some such examples, the alert system may maintain the delivery of the therapy at rate associated with the detected condition of the AMD (e.g., normal rate or minimum maintenance rate) until an alert modification condition is detected 4316. Upon detection of an alert modification condition 4316, the alert system may determine whether the new device condition satisfies a normal set parameters 4318. If, at block 4318, it is determined that the new device condition satisfies a set of normal operating parameters, the alert system may resume the normal operation of the AMD 4320 (e.g., deliver the therapy at a normal rate). If at block 4318, it is determined that the new device condition does not satisfy a set of normal operating parameters, the alert system may determine whether the new device condition satisfies a minimum set parameters 4322. If, at block 4322, it is determined that the new device condition satisfy a set of minimum operating parameters. The alert system may maintain or modify the rate of therapy delivery according to the new device condition 4326 and generate a user alert 4330 according to the according to the new device condition. If, at block 4322, it is determined that the new device condition does not satisfy a set of minimum operating parameters, the alert system may send a signal to the therapy delivery module to stop delivery of therapy to the subject block 4324, and immediately generate a critical user alert 4328 indicating that immediate action is required. In some examples, upon generation of a critical alert the alarm system of the AMD, may contact a healthcare provider or certified user (e.g., parent or guardian of the subject) and also send the critical alert to one or more computing devices (e.g., laptop, cell phone, personal computer, and the like) of the healthcare provider or certified user.

Managing Doses of Glucose Control Agents

Ambulatory medical devices allow subjects the freedom to treat themselves while being mobile. Self-managed medical treatment comes with inherent risks to the subject.

An automated blood glucose control system may automatically provide insulin and/or a counter-regulatory agent (e.g., Glucagon) to a subject to help control the blood glucose level of the subject. Generally, a control algorithm is implemented by an automated blood glucose control system (BGCS) to determine when to deliver one or more glucose control agents and how much agent to provide to the subject. Further, the control algorithm may control both an ongoing or periodic delivery of insulin (e.g., a basal dose), and a correction bolus that may be provided to adjust a subject's blood glucose level to within a desired range. The control algorithm may use blood glucose level readings obtained from a sensor, such as a continuous glucose monitoring (CGM) sensor, that obtained automated blood glucose measurements from the subject. Moreover, in some cases, the control algorithm may deliver a bolus of insulin in response to an indication of a meal to be consumed or being consumed by the subject.

Insulin may be administered subcutaneously into blood of a subject. There is often a delay between when the insulin is provided and when the amount of insulin in the subject's blood plasma reaches maximum concentration. This amount of time may vary based on the type of insulin and on the physiology of the particular subject. For example, with a fast-acting insulin, it may take approximately 65 minutes for a bolus of insulin to reach maximum concentration in the blood plasma of the subject. For some other types of insulin, it may take anywhere from 3-5 hours to reach maximum concentration in the blood plasma of the subject. Accordingly, the blood glucose control system may implement a predictive algorithm that implements a bi-exponential pharmacokinetic (PK) model that models the accumulation of insulin doses in the blood plasma of the subject. The blood glucose control system may modify its predictions based on the type of insulin, one or more blood glucose readings, and/or characteristics of the subject.

In some cases, a subject may receive a manual bolus of insulin or medicament. For example, a user (e.g., healthcare provider, parent, or guardian) or subject may inject a dose of insulin into the subject. As another example, the user or subject may manually direct the automated blood glucose control system to provide a bolus of insulin to the subject.

It is generally undesirable to have too much insulin. An excess of insulin can lead to Hypoglycemia. As described above, it may take time for insulin to reach maximum concentration in the blood plasma of the subject. Thus, a blood glucose level reading from a sensor may not immediately, or even after a particular period of time, reflect the amount of insulin within a subject. Thus, a manual bolus of insulin may not be detected by the automated blood glucose control system. As a result, if the automated blood glucose control system is operating during delivery of a manual bolus, or is configured to operate on the subject prior to blood glucose level readings reflecting the effect of the manual bolus on the subject, the automated blood glucose control system may unnecessarily administer additional insulin to the subject potentially leading to hypoglycemia.

The present disclosure relates to an automated blood glucose control system configured to provide automatic delivery of glucose control therapy to a subject and receive information about manual glucose control therapy provided to the subject. Using the received information about the manual glucose therapy, the automated blood glucose control system can adjust the blood glucose control algorithm to account for the manual dosing of insulin (or counter-therapy agents). The manual glucose control therapy may be provided by injection therapy, or it may be provided by an insulin pump.

In some cases, the automated blood glucose control system may receive an indication of insulin or medicament to administer to a subject in place of an automatically calculated dose of insulin. For example, the automated blood glucose control system may receive an indication that a subject is consuming or will consume a meal. The indication may include a type of meal to be consumed (e.g., breakfast, lunch, or dinner) and an estimate of the quantity of food or carbohydrates to be consumed (e.g., less than usual, a usual amount, more than usual, 30-40 grams of carbohydrates, 45-60 grams of carbohydrates, etc.). Based on the indication, or meal announcement, the automated blood glucose control system may calculate an amount of insulin to administer to the subject. The calculation may be based on an insulin to carbohydrate ratio provided by a clinician and/or determined by the automated blood glucose control system. Moreover, the calculation may be based at least in part on a history of blood glucose level measurements for the subject when consuming particular meals.

The calculated amount of insulin for the meal announced by the user may be presented to the user. The user (e.g., the subject) may modify the amount of insulin to administer. For example, the user may determine that for the size meal the subject is consuming or planning to consume, more or less insulin should be administered. In such cases, the user may modify the calculated insulin dosage to match the user's determination of the amount of insulin to administer. In some cases, the automated blood glucose control system may modify its control algorithm based on the user's input. Thus, future meal announcements may result in a calculation of insulin that satisfies the subject's insulin needs and/or preferences.

In some cases, the indication of an amount of a manual bolus may be received by a user entering a numerical value (e.g., an amount of insulin, a number of carbohydrates, or another calculation) associated with administering insulin. As described above, the automated blood glucose control system may automatically-calculate a meal dose of insulin and present it to a user via a user interface where a user may enter the manual bolus information. At the time of making the meal announcement, the user may have an option to enter the manual bolus. The meal controller of the blood glucose pump can provide a recommendation against the manual entry if there is a prior history of online operation or a basis for making the recommendation.

The information may be received from a user via a user interface. This user interface may be provided by the automated blood glucose control system. Alternatively, or in addition, the user interface may be generated by another device, such as a laptop or desktop, a smartphone, a smartwatch, or any other computing device that can communicate via wired or wireless communication with the automated blood glucose control system. The information may include one or more of: an indication of delivery of a manual bolus (e.g., via injection therapy), an amount of the manual bolus, a type of the insulin (or other medicament), a time when the manual bolus was delivered, a general location that the manual bolus was administered to the subject (e.g., back, stomach, arm, leg, etc.), a reason for the manual bolus (e.g., a meal, a maintenance dose, a blood glucose level reading, in advance of exercise, etc.), and any other information that may be useable by the blood glucose control system in controlling the blood glucose level of the subject.

Advantageously, in certain embodiments, providing manual dosing information to the automated blood glucose control system can help the blood glucose control system maintain the blood glucose level of the subject within a desired range when the automated features of the blood glucose control system are active or operational. For example, if the automated blood glucose control system determines from a CGM sensor reading that a subject's blood glucose level is high, the automated blood glucose control system might normally administer a bolus of insulin. However, if the automated blood glucose control system receives an indication that a manual bolus of insulin was administered recently (e.g., within the past thirty minutes), the automated blood glucose control system may reduce or not administer a bolus of insulin, thereby preventing a Hypoglycemic event. In some such cases, the automated blood glucose control system may continue monitoring the blood glucose level of the subject and may administer additional insulin at a later time if the blood glucose level readings do not reflect an expected blood glucose level based on the reported manual bolus of insulin.

In some cases, it may be unnecessary to receive an indication of the manual bolus because, for example, a user may cause the automated blood glucose control system to provide the manual bolus. In such cases, the automated blood glucose control system may track the amount of insulin delivered and the timing of the administering of the bolus. To track the manual bolus, the automated blood glucose control system may store the information associated with the manual bolus in a therapy log. Accordingly, when the automated blood glucose control system is operating in an automatic mode, the automated blood glucose control system can access the therapy log to determine whether any manual bolus were administered and, if so, the timing and amount of the manual bolus.

In some cases, the automated blood glucose control system may model the diminishing of insulin, or other medicament, in the blood plasma over time based on the information associated with the manual bolus. Modeling the diminishing of medicament over time may be used to estimate a future effect of the medicament previously administered. In some cases, the model may account for previously administered medicament by the automated blood glucose control system. Further, in some cases, the model may account for physiological characteristics of the subject, such as the subject's weight or an input parameter related to the subject's weight (e.g., body mass index). Moreover, the model may account for perfusion over time of the medicament bolus from a subcutaneous infusion site into the blood plasma of the subject. Further, the automated blood glucose control system may model an accumulation of insulin, model time course of activity of insulin, or model a finite rate of utilization of insulin.

Based on the model, the automated blood glucose control system may adjust the automated administering of insulin, or other medicament when operating in an automatic mode. Further, the automated blood glucose control system may operate the administering of medicament (e.g., by controlling a medicament pump) based on a glucose level of the subject and the modeled concentration of medicament in the subject.

In some cases, the automated blood glucose control system may confirm that the manual bolus was delivered to the subject. The confirmation may be determined based at least in part on whether blood glucose level readings by the CGM sensor match or are within a threshold level anticipated by the automated blood glucose control system based on the manual dosing information. Alternatively, or in addition, the automated blood glucose control system may request, via a user interface, that a user confirm that the manual bolus was delivered. In cases where the manual bolus in delivered by the automated blood glucose control system, a user may be requested to confirm the administering of the manual bolus by using a particular gesture or sequence of interactions with a user interface (e.g., a touchscreen) of the automated blood glucose control system or of a device (e.g., laptop or smartphone, etc.) that communicates with the automated blood glucose control system.

As previously described, in some cases, the information relating to the manual bolus may include an amount of insulin and a reason the manual bolus was administered (e.g., for a meal of a particular size). In some such cases, the automated blood glucose control system may determine an amount of insulin the automated blood glucose control system would administer in an automatic operating mode based on the manual dosing information if the manual bolus had not been supplied. If the automated blood glucose control system determines it would have supplied a different quantity of the medicament, and if the difference exceeds a threshold, the automated blood glucose control system may adjust a blood glucose control algorithm to account for the difference. For example, the automated blood glucose control system may change the operating setpoint or range of insulin the automated blood glucose control system attempts to maintain in the subject. As another example, the automated blood glucose control system may supplement the manual bolus with additional insulin to account for an under-administering of insulin, or may reduce a subsequent dosage of insulin to account for an over-administering of insulin.

As previously indicated, the automated blood glucose control system may maintain a therapy log of manual insulin therapy. This therapy log may be maintained based on the use of the automated blood glucose control system to provide a manual bolus, or based on information provided by the user based on manual administering of insulin (e.g., via injection). The manual boluses may be supplied when the automated blood glucose control system is not operating, is not operating in an automatic mode, or is not connected to the subject. Once the automated blood glucose control system is connected to the subject and is configured in automatic mode, the automated blood glucose control system may determine therapy, if any, to provide to the subject based on a combination of the therapy log and the glucose control algorithm implemented by the automated blood glucose control system.

The automated blood glucose control system may generate a dose control signal based on the determined therapy. This dose control signal may be supplied to a medicament pump, which may control delivery of the medicament (e.g., insulin) to the subject.

In some cases, a user may control whether the automated blood glucose control system is operating in a manual mode or an automatic mode by interacting with a user interface of the automated blood glucose control system or of a device that communicate with the automated blood glucose control system. The user interaction may include any type of user interaction with a user interface. For example, the user interaction may include interaction why physical buttons or interactions with a touchscreen including gestures or taps on the touchscreen.

Additional embodiments relating to managing meal medicament doses and manual dosing that can be combined with one or more embodiments of the present disclosure are described in U.S. Provisional Application No. 62/911,143, which was filed on Oct. 4, 2019 and is titled "SYSTEM AND METHOD OF MANAGING MEAL DOSES IN AN AMBULATORY MEDICAL DEVICE," the disclosure of which is hereby incorporated by reference in its entirety herein for all purposes.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method including: providing an option to a user to select between receiving medicament using a manual delivery component or an automated delivery system. The method also includes receiving, by the automated delivery system, subjective information regarding the activity or action that may alter the blood-glucose level. The method also includes receiving, by the manual delivery component, an amount of the medicament to be infused. The method also includes storing a time and the amount of medicament that is infused into the automated delivery system that controls blood glucose level. Other embodiments of this aspect include corresponding computer systems, apparatus, and computer programs recorded on one or more computer storage devices, each configured to perform the actions of the methods.

Implementations may include one or more of the following features. The method where the automated delivery system modifies medicament delivery based on the time and the amount of medicament that was received from either the manual delivery component or the automated delivery system. The method where the manual delivery component includes a keypad which allows the user to type in the dosage amount of the desired medicament. The method where providing the option to select is provided prior to a user performing the activity that may alter the blood-glucose level. The method where the activity that may alter the blood-glucose level includes of consuming food or exercising. The method where the subjective information regarding the activity of consuming food includes the approximate relative size of the food that is to be digested. The method where the approximate relative size of the food is compared to the recommended meal doses for the user, and depending on whether the approximate relative size is the same, larger, or smaller than the recommended doses, the model predictive control component is able to determine the actions that is required to regulate the glucose level of the blood. The method where the subjective information regarding the activity of exercising includes the intensity and the duration of the exercise. The method where the intensity and the duration of the exercise is compared to the recommended intensity and duration, and depending on whether it is the same, larger, or smaller than the recommended intensity and duration, the automated delivery system is able to determine the actions that is required to regulate the glucose level of the blood. Implementations of the described techniques may include hardware, a method or process, or computer software on a computer-accessible medium.

One general aspect includes a system having a medical device configured to provide an option to a user to select between receiving medicament using a manual delivery component or an automated delivery system. The system also includes automated delivery system configured to receive subjective information regarding the activity that may alter the blood-glucose level. The system also includes a manual delivery component configured to receive an amount of the medicament to be infused. The system also includes where the medical device storing a time and the amount of medicament that is infused into an automated delivery system that controls blood glucose levels. Other embodiments of this aspect include corresponding computer systems, apparatus, and computer programs recorded on one or more computer storage devices, each configured to perform the actions of the methods.

Upon utilizing an ambulatory medical device to request for a therapy change, users may have different preferences. Therefore, it is desirable for modern technology, specially the ambulatory medical devices to be equipped with optionality features. These optionality features may fulfill the different preferences of the users and subjects. The optionality features may allow users to control the therapy changes more closely and may allow them to be more engaged with the medical assistance of the ambulatory medical device.

In order to fulfill the variety of preferences, an ambulatory medical device needs to provide options which allows the user to either manually request the amount of the desired medicament or chose an automated delivery system that automatically delivers the right amount of the medicament at the right time without further assistance. For the manual component, the user may personally input the desired amount on a keypad that is provided by the medical device. The medical device further confirms and delivers the requested medicament. After the medicament is infused through a manual delivery component, the data is stored into a model predicative control component which is further used to control and regulate the blood glucose level. However, if the user decides to use the automated delivery system, the user must provide subjective information regarding the activity or the action that may alter the blood-glucose level. For example, if the blood-glucose level changing activity is consuming food, the user must provide the time and the dosage amount of the food that is going to be digested. This information is tied to the automated delivery system, and the subjective information is further stored into a model predicative control component.

Embodiments described herein include an ambulatory medical device that has a keypad which allows a user to type in a dose of insulin or glucagon to be administered to a user. A user may wish to receive a single dose of insulin prior to consuming food and decide how much insulin need to be administered. In other embodiments, the user may choose to receive a burst of glucagon due to low blood sugar because of physical activities. Embodiments may include the options for manual inputs of medicament and automated delivery system of medicament. In various implementations, the automated delivery system of medicament is driven by the blood glucose level or related trends. Embodiments herein address a problem that may arise when the user has just received a manual dose and has switched on the automated delivery system. In such cases, the automated delivery system may be made aware of all manual medicament infusion amounts and the timing of such infusions. Accordingly, the manual delivery component may inform the automated delivery system upon delivering any medicament the type of medicament delivered, the amount of medicament and the timing of the medicament delivered. By having the above information, the automated delivery system may determine the amount of medicament that is the user's blood stream and adjust the automated delivery of medicament and the timing of the automated delivery. Accordingly, embodiments are directed to allows for a risk free transition from the manual delivery component and the automated delivery system.

Differences from other system may include that the manual delivery may be tied to an automated delivery system, the dose input from the user is then stored into the MPC algorithm (Model Predictive Control) instead of the meal delivery algorithm and is handled by the MPC algorithm. Other embodiments may include selection being able to have a relativistic algorithmically tuned value. Other embodiments may include a learning algorithm that includes a usual size meal or larger size meal or small size meal. Embodiments may include correlating the manual inputs to asking the user what was the size of the meal and learning how the insulin affects the user. Embodiments may include correlating the manual inputs to asking the user what activity the user performed and learning how the glucagon affects the user for a particular activity.

BGCS with Manual Dose Management

Figure 44:
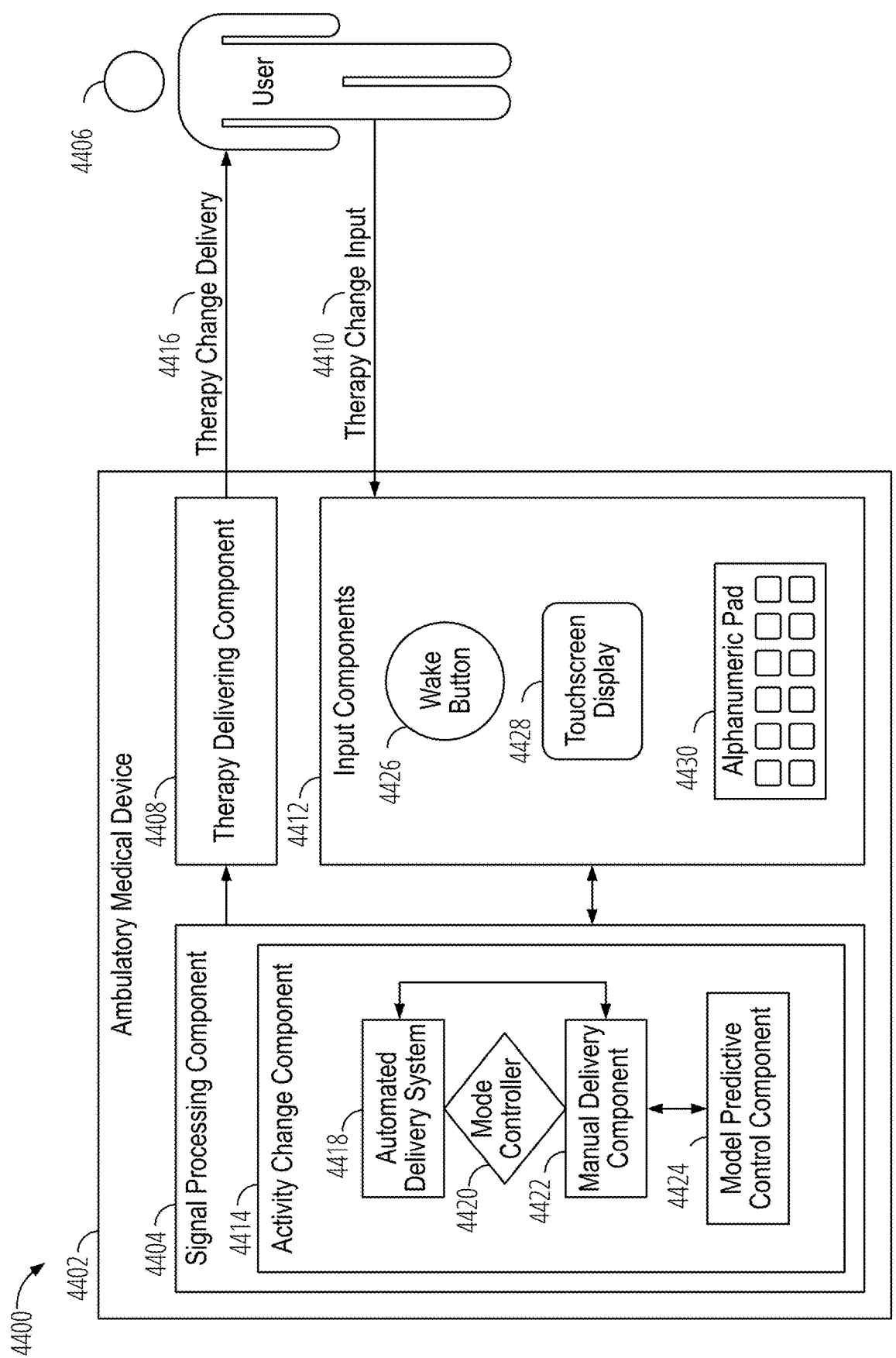
FIG. 44 is a schematic diagram illustrating an ambulatory medical device that provides the user with various options for providing medicament.

FIG. 44 illustrates a schematic of the therapy change delivery system 4400 in an ambulatory medical device 4402 that allows the user the choice of receiving manual delivery of medicament or automated delivery of medicament. Moreover, the therapy change delivery system 4400 allow the user to transition between the manual mode and the automated mode with ease. The therapy change delivery system 4400 includes the ambulatory medical device 4402, a signal processing component 4404, a user 4406, a therapy delivering component 4408, a therapy change input 4410, input components 4412, activity change component 4414, and a therapy change delivery 4416. When the user intends to receive a therapy from an ambulatory medical device 4402, the user 4406 may initiate a therapy change input 4410 to request the manual or automated medicament.

The ambulatory medical device 4402 is any medical device that a user 4406 may carry around and use with the approval of a medical professional. There are many different types of ambulatory medical devices 4402. In one embodiment, the ambulatory medical device 4402 is an insulin and/or glucagon infusion device for user 4406 that have type I diabetes. Ambulatory medical devices 4402 allow users 4406 the freedom to receive medical care in any setting at their convenience. However, the drawback of using an ambulatory medical device 4402 could be the user 4406 making mistakes when the user is away from the medical professionals. One possible issue may be caused the user 4406 switches from a manual delivery mode to an automated delivery mode when the automated delivery mode is unable to determine the amount of medicament in the user's blood stream. Embodiments are directed to the manual medicament delivery information being provided to the automated medicament delivery system so that it can adjust its operations based on the current and future medicament in the user's blood stream. In some cases, such as the embodiment where the ambulatory medical device 4402 is an insulin and/or glucagon infusion device, doing automated delivery of medicament can be problematic.

The ambulatory medical device 4402 includes a signal processing component 4404, a therapy delivering component 4408, and input components 4412. The signal processing component 4404, therapy delivering component 4408, and input components 4412 may be physically connected, wirelessly connected, connected via a cloud-based computer system, or connected in any other way.

The signal processing component 4404 is a computing system that performs the computing functions for the ambulatory medical device 4402. The signal processing component 4404 includes a processor, memory, and storage. The signal processing component 4404 may be a single computing system or may be made up of several computing systems. The signal processing component 4404 may perform the computing functions for a single ambulatory medical device 4402 or many ambulatory medical device 4402. The signal processing component 4404 receives signals from the therapy delivering component 4408 and from the input components 4412. The signal processing component 4404 also transmits signals to the therapy delivering component 4408 and the input components 4412. Signals of the therapy change input 4410, the therapy change delivery 4416, and all steps of the activity change component 4414 may be received or transmitted by the signal processing component 4404.

The user 4406 is any individual that uses the ambulatory medical device 4402. In one embodiment the user 4406 is an individual with diabetes that requires a periodic infusion of insulin or glucagon to maintain healthy blood sugar levels. In various embodiments, the ambulatory medical device 4402 infuses insulin or glucagon into the user 4406. The user 4406 may transport the ambulatory medical device 4402. Thus, as the user 4406 moves around, there is a danger that the user 4406 will inadvertently activate input in the ambulatory medical device 4402 that initiates a therapy change input 4410.

The therapy delivering component 4408 provides medicaments to the user 4406. Signals received from the signal processing component 4404 are executed by the therapy delivering component 4408 to change therapy such as starting, modifying, or stopping a therapy. The therapy delivering component 4408 may have a computing component for interpreting and executing instructions from the signal processing component 4404. Thus, the therapy delivering component 4408 can follow a program that is controlled by the signal processing component 4404. In one embodiment, the therapy delivering component 4408 is one or more infusion pumps. An infusion pump is capable of delivering fluids at varying rates to a user 4406. The infusion pump may deliver any fluid, including medicaments. The infusion pump may be connected to a user 4406 through any means. In one example, the infusion pump is connected to the body through a cannula. In an exemplary embodiment, the therapy delivering component 4408 is an insulin infusion pump. Also, in an exemplary embodiment, the therapy delivering component 4408 is an insulin and glucagon infusion pump. Signals received from the signal processing component 4404 may be interpreted by an insulin and glucagon pump to start, stop, or change the rate of insulin and glucagon being delivered into a user 4406.

In an exemplary embodiment, the therapy delivering component 4408 is an electrical stimulation device. An example of an electrical stimulation device is a cardiac pacemaker. A cardiac pacemaker stimulates the cardiac muscle to control heart rhythms. Instructions received from the signal processing component 4404 may be interpreted by a cardiac pacemaker to start stimulating a cardiac muscle, stop stimulating a cardiac muscle, or change the rate of stimulation of a cardiac muscle. Another example of an electrical stimulation device is a deep brain stimulator to treat Parkinson's disease or movement disorders. Instructions received from the signal processing component 4404 may be interpreted by the deep brain stimulator to start, stop, or modify the stimulation of the brain.

The therapy change input 4410 is an input provided by the user 4406 to change a therapy that is currently being delivered to the user 4406. The change of therapy may be to start a therapy, modify a therapy, or cancel a therapy. There are many types of possible therapy changes, and the types of therapy changes are dependent on the type of ambulatory medical device 4402. In one embodiment, the ambulatory medical device 4402 is an insulin or glucagon infusion device. However, there are many possible embodiments of ambulatory medical devices 4402 for the disclosed subject matter. The therapy change input 4410 in an insulin or glucagon infusion device may be an instruction, that when executed, causes the insulin or glucagon infusion device to start infusing an amount of insulin or glucagon into the user 4406. Alternatively, the therapy change input 4410 may be an instruction to modify the rate of insulin or glucagon infusion into the user 4406. The therapy change input 4410 may also be an instruction to cancel insulin or glucagon infusion into the user 4406 from the insulin or glucagon infusion device. In an exemplary embodiment, the ambulatory medical device 4402 is an electrical implant, that when operated, stimulates a part of the body. An example is an electrical brain implant for users 4406 with Parkinson's disease or for pain management. The implementation of the therapy change can be to modify the rate of electrical stimulation to the body.

Figure 51:
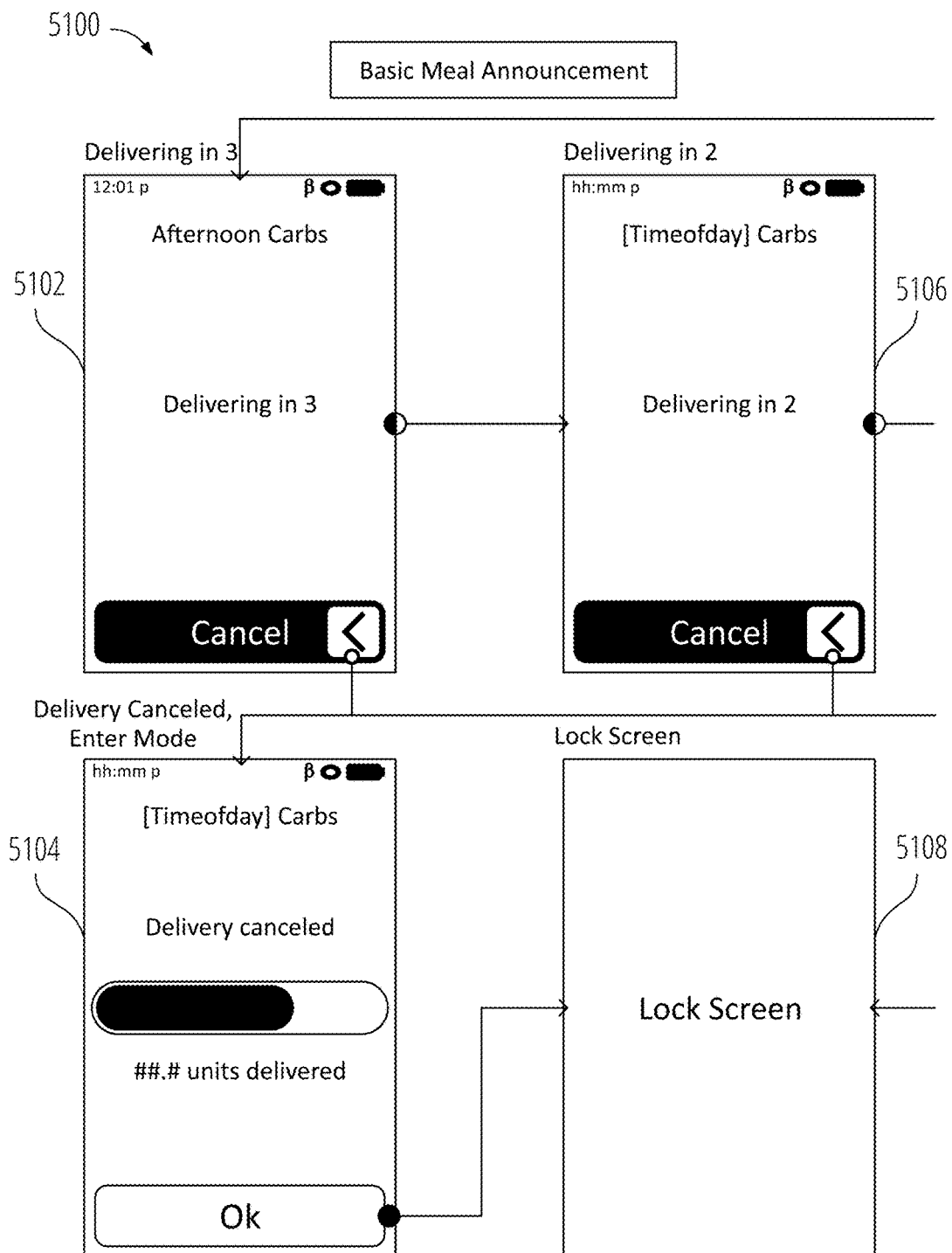
FIG. 51 is a series of user interface screen displays showing an ambulatory medical device delivering the units and cancelling the delivery of the units.

The therapy change delivery 4416 is the performance, by the ambulatory medical device 4402, of the therapy change input 4410 that was verified by the 4414. The therapy change that is delivered by the therapy change delivery 4416 corresponds to the therapy change selection made by the user 4406. In one embodiment, the ambulatory medical device 4402 alerts the user 4406 that it is performing a therapy change delivery 4416. In an example of various embodiments, the ambulatory medical device 4402 displays the therapy change during the therapy change delivery 4416. Any number of details of the therapy change may be displayed during the therapy change delivery 4416. As shown in FIG. 51, a simple message of "Delivering" may be displayed during the therapy change delivery 4416. Alternatively, more exact details, such as "Delivering 2 units of insulin" or "Delivering insulin at 2 units per minute" may be displayed. In another example, the ambulatory medical device 4402 plays a sound effect during the therapy change delivery 4416. In an exemplary embodiment that is shown in FIG. 51, the therapy change delivery 4416 may be canceled by an input by the user 4406. The input to cancel a therapy change delivery 4416 may be any input such as a wake signal input or a series of touch inputs such as a gesture.

The input components 4412 allow the user 4406 to interact with and control the ambulatory medical device 4402. The amount of control that a user 4406 has may vary based on the type of ambulatory medical device 4402 and the user 4406. For example, an ambulatory medical device 4402 that delivers pain medication may allow the user more control than an ambulatory medical device 4402 that controls heart rhythms. In another example. a user 4406 that is a young child (less than about 10, 11 or 12 years) may be allowed less control over an ambulatory medical device 4402 than a user 4406 that is a teen or an adult. The input components 4412 include a wake button 4426, a touchscreen display 4428, and an alphanumeric pad 4430.

The wake button 4426 is activated by a user 4406 to create a wake signal input to unlock an ambulatory medical device 4402. The wake button 4426 may be any input button. In one embodiment, the wake button 4426 is a capacitive button that detects a change in capacitance. The wake button 4426 may have a computing component for interpreting and executing instructions from the signal processing component 4404. Thus, the wake button 4426 can follow a program that is dictated by the signal processing component 4404.

The touchscreen display 4428 may display a therapy change user interface for the user 4406 and receive user 4406 inputs on the touchscreen display 4428 input surface. Inputs on the touchscreen display 4428 may be registered by any touch technology including, but not limited to capacitive and resistive sensing. The touchscreen display 4428 may be a part of a mobile computing device, such as a cellular phone, tablet, laptop, computer or the like. The touchscreen display 4428 may have a computing component for interpreting and executing instructions from the signal processing component 4404. Thus, the touchscreen display 4428 can follow instructions that are directed by the signal processing component 4404. To receive input, the touchscreen display 4428 may display buttons, alphanumeric characters, symbols, graphical images, animations, or videos. The touchscreen display 4428 may display an image to indicate when the ambulatory medical device 4402 is locked or inaccessible via the touchscreen display 4428. The touchscreen display may receive the series of inputs that make up the first gesture and the second gesture.

The alphanumeric pad 4430 registers numerical inputs, alphabetical inputs, and symbol inputs. The alphanumeric pad 4430 includes a multitude of keys corresponding to numerical, alphabetical, and symbol inputs. The alphanumeric pad 4430 may have a computing component for interpreting and executing instructions from the signal processing component 4404. Thus, the alphanumeric pad 4430 can follow instructions that are dictated by the signal processing component 4404. The alphanumeric pad 4430 may be configured to provide haptic feedback from its keys. The alphanumeric pad or pads 4430 may have any number of keys and any number of characters and may span multiple screens that the user 4406 can toggle between in order to find all of their sought-after characters. In one embodiment, the wake button 4426 is incorporated into the alphanumeric pad 4430. In various embodiments, the wake button 4426 may be any one or more keys of the alphanumeric pad 4430. In an exemplary embodiment, the alphanumeric pad 4430 is displayed as part of the touchscreen display 4428. Characters from the alphanumeric pad 4430 may be used as input for the wake signal input, first gesture, therapy change selection, and second gesture. In an exemplary embodiment, the first gesture and/or second gesture are created by entering predetermined characters on the alphanumeric pad 4430.

The activity change component 4414 may be part of a specialized software that is executed on an ambulatory medical device or include a specialized hardware that performs the various functions described here. The activity change component 4414 may receive inputs from the user regarding weather the user is about to conduct activities that will change the blood glucose of the user. For example, the user may provide input using the input components 4412 that the user is about to perform exercise that may lower their blood sugar or eat a meal that will increase their blood sugar. Upon receiving the activity change from the input components 4412, the activity change component 4414 offers the user the option via the mode controller 4420 to select between the automated delivery system 4418 or the manual delivery component 4422. As shown in FIG. 44, the manual delivery system may inform the automated delivery system 4418 and the model predictive control component 4424 regarding any manual medicament deliveries of insulin or glucagon.

In various embodiments, the user may choose the dosage amount, the drug type (insulin or glucagon; fast or slow acting) and the time of the delivery and the manual delivery component 4422 may receive such information and deliver the medicament(s) accordingly. In one embodiment, the manual delivery component 4422 may inform the automated delivery system 4418 and the model predictive control component 4424 regarding the drug type (insulin or glucagon; fast or slow acting) and the time of the delivery.

When the user activates the automated delivery system 4418, the data from previous manual medicament infusions can be readily available so that the automated delivery system 4418 may be able to determine how much medicament is still in the user's blood stream. The automated delivery system 4418 may make that determination by tracking the finite rate of utilization of infused insulin by the subject based on the time and amount of any manual medicament infusions reported to the automated delivery system 4418.

Figure 45:
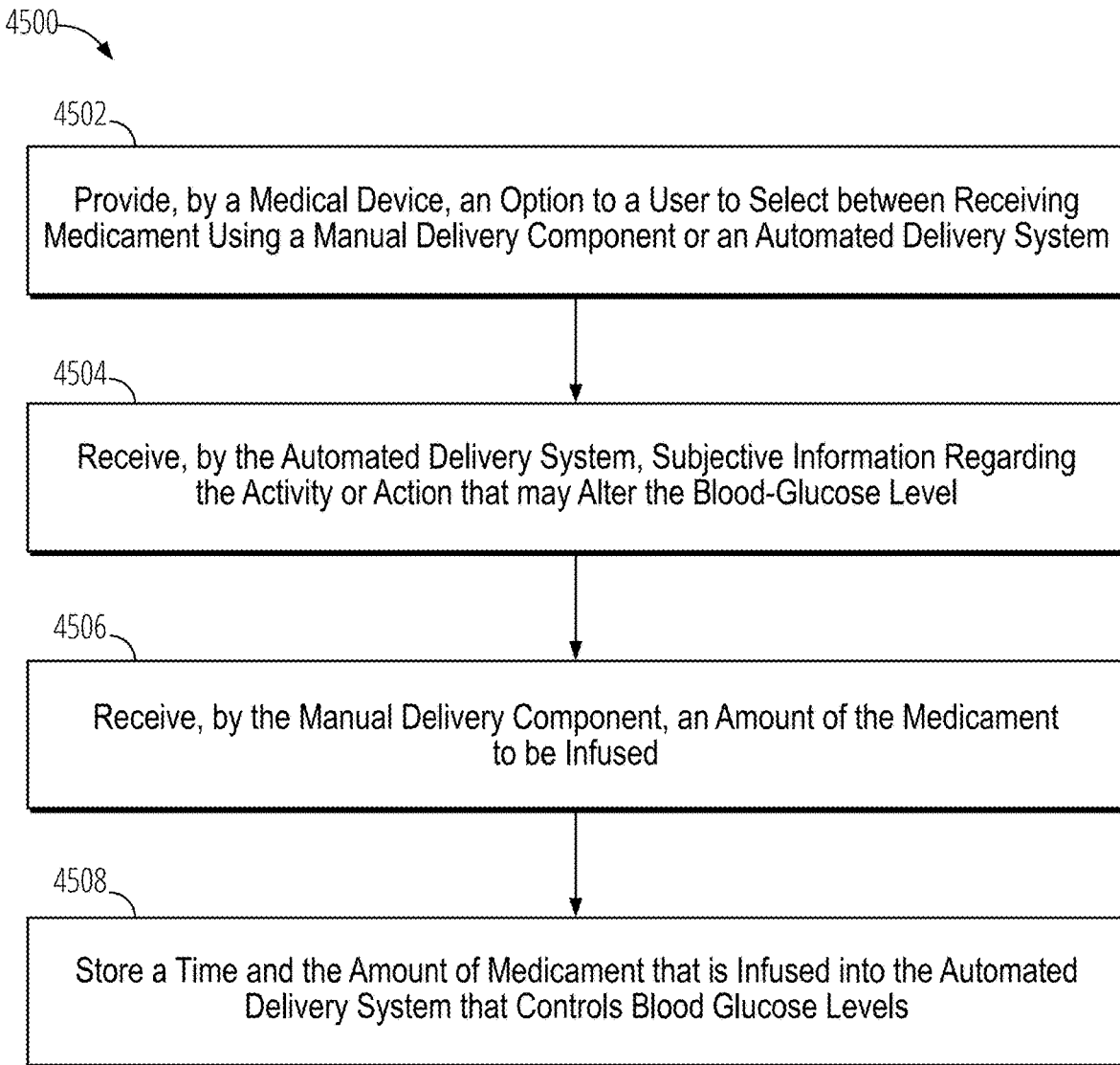
FIG. 45 is a flow diagram of a process for providing options for meal dosage selection on an ambulatory device.

FIG. 45 is a flow chart of a process 4500 detailing a medicament selection process, according to an exemplary embodiment. In step 4502, the medical device provides an option to a user to select between receiving medicament using a manual delivery component or an automated delivery system. By using the mode controller 113, the user can select the method for the therapy change request between manual delivery component and the automated delivery system.

In step 4504, the medical device may receive subjective information regarding the activity or action that may alter the blood-glucose level. Subjective information may include the size of the meal and/or the type of physical activity. In step 4506, the manual delivery component may receive an amount of the medicament to be infused. The medicament may be a plurality of hormones, including but not limited to, glucagon or insulin. At step 4508, the medical device may store a time and the amount of medicament that was infused into the automated delivery component that controls the blood glucose level. The systems that are disclosed in FIG. 44 will be utilized to accomplish each and every step from steps 4502, 4504, 4506 and 4508.

Figure 46:
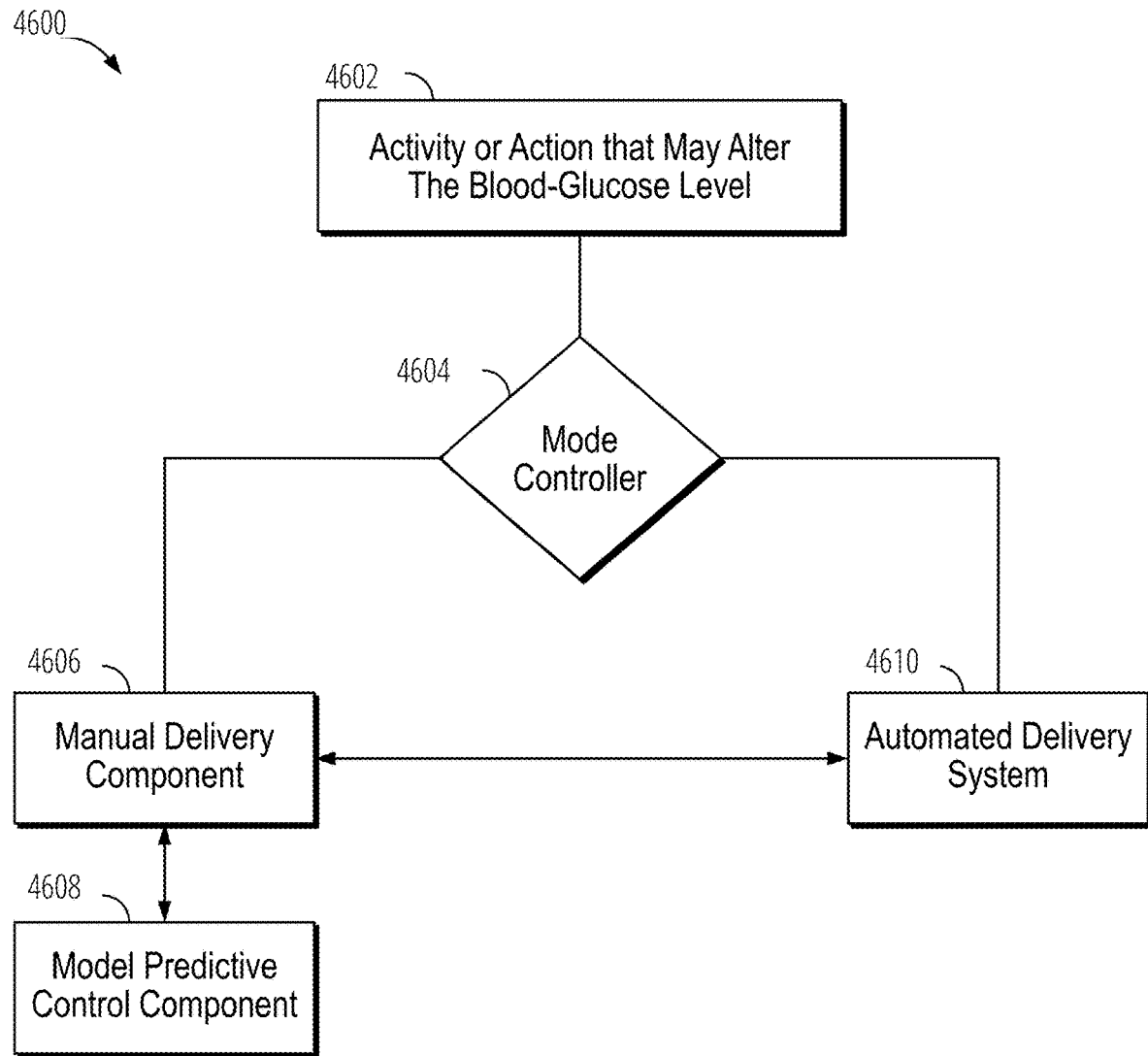
FIG. 46 is another flow diagram of a process for providing options for meal dosage selection on an ambulatory device.

FIG. 46 is another flow diagram of a process 4600 for providing options for meal dosage selection or physical activity of the user on an ambulatory device. Embodiments described herein include an ambulatory medical device that has a keypad which allows a user to type in a dose of insulin or glucagon to be administered to a user. A user may wish to receive a single dose of insulin prior to consuming food and decide how much insulin need to be administered. In other embodiments, the user may choose to receive a burst of glucagon due to low blood sugar because of physical activities. Embodiments may include the options for manual inputs of medicament and automated delivery system of medicament. In various implementations, the automated delivery system of medicament is driven by the blood glucose level or related trends. Embodiments herein address a problem that may arise when the user has just received a manual dose and has switched on the automated delivery system. In such cases, the automated delivery system may be made aware of all manual medicament infusion amounts and the timing of such infusions. Accordingly, the manual delivery component may inform the automated delivery system upon delivering any medicament the type of medicament delivered, the amount of medicament and the timing of the medicament delivered. By having the above information, the automated delivery system may determine the amount of medicament that is the user's blood stream and adjust the automated delivery of medicament and the timing of the automated delivery. Accordingly, embodiments are directed to allows for a risk free transition from the manual delivery component and the automated delivery system.

At block 4602, the user may inform the activity change component 4414 that the user is about to engage in activities that may alter the blood-glucose level of the user. The mode controller 4420 may be activated at decision block 4604 and ask whether the user wants to use the manual delivery component 4606 or the automated system 4610. If the user chooses to use the manual delivery component 4606 and the user provides an input to infuse medicament, the ambulatory device 4402 may delivery the medicament to the user. Upon the manual delivery process completion, the manual delivery component 4606 may inform at least one of the model predictive control component 4608 and the automated delivery system 4610 regarding the type of medicament, amount of medicament and the time when the medicament was delivery. The predictive control component 4608 and automated delivery system 4610 may track these manual infusions of medicament and determine that based on the rate of decay or the half-life of the medicament the total amount of medicament that remains in the user's blood stream at a particular time or a period of time. Accordingly, when the automated delivery system 4610 is activated by the user, the automated delivery system 4610 may change its medicament infusion based on the medicament that remains in the user's blood stream after a manual infusion by the user.

Differences from other system may include that the manual delivery may be tied to an automated delivery system, the dose input from the user is then stored into the MPC algorithm (Model Predictive Control) instead of the meal delivery algorithm and is handled by the MPC algorithm. Other embodiments may include selection being able to have a relativistic algorithmically tuned value. Other embodiments may include a learning algorithm that includes a usual size meal or larger size meal or small size mean. Embodiments may include correlating the manual inputs to asking the user what was the size of the meal and learning how the insulin affects the user. Embodiments may include correlating the manual inputs to asking the user what activity the user performed and learning how the glucagon affects the user for a particular activity.

Figure 47:
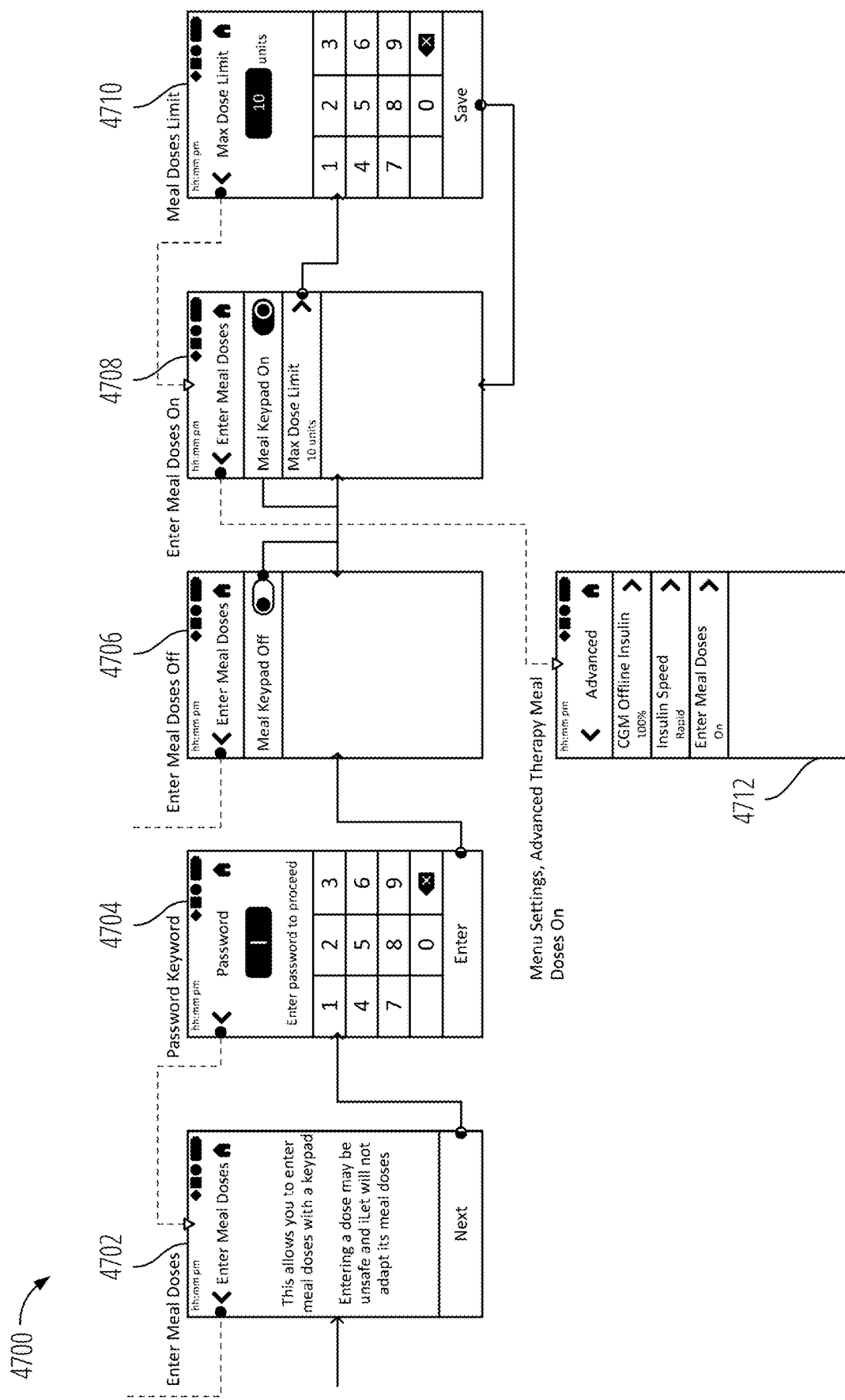
FIG. 47 is a series of user interface screen displays showing a user initiating the activation of meal dosage on an ambulatory device.

FIG. 47 illustrates a plurality of screens 4700 that may be produced by the ambulatory medical device 102. The plurality of screens 4700 demonstrates a process that a user may take in order to enter meal doses. When the mode controller 4420 is activated, the enter meal doses screen 4702 may be displayed. Once the screen 4702 is displayed, a warning text may be displayed for the user to ensure safety. The warning text states that entering a dose may be unsafe and the device will not adapt its meal doses. This warning text cautions the user of the risks that may be involved in the process of using the ambulatory medical device 4402. After a user acknowledges the warning sign and choses to proceed, a password screen 4704 may be displayed. Once the password screen 4704 is displayed, a keypad is provided for the user to enter a predetermined sequence of numbers to ensure that the user is the actual registered user of the ambulatory medical device 4402. When the ambulatory medical device 4402 receives the correct predetermined password from the user, the enter meal doses official screen 4706 and meal doses official screen 4708 may be displayed. The user may decide to access the advanced screen 4712, and upon doing so, the advanced screen 4712 will allow the user to double check the CGM Insulin levels and change the speed of the of the insulin pump. In screen 4706 and screen 4708, the user is provided the option to have the meal keypad on or off. If the user selects to have the keypad on, then an option may be provided for the user to choose the max dose limit. If the user decides to choose the max dose limit, the official max dose limit screen 4710 is displayed, where the user may enter up to 10 units of the dose. The provided number of units is then stored in the model predictive control component 116 for further regulation of the blood glucose level.

Figure 48:
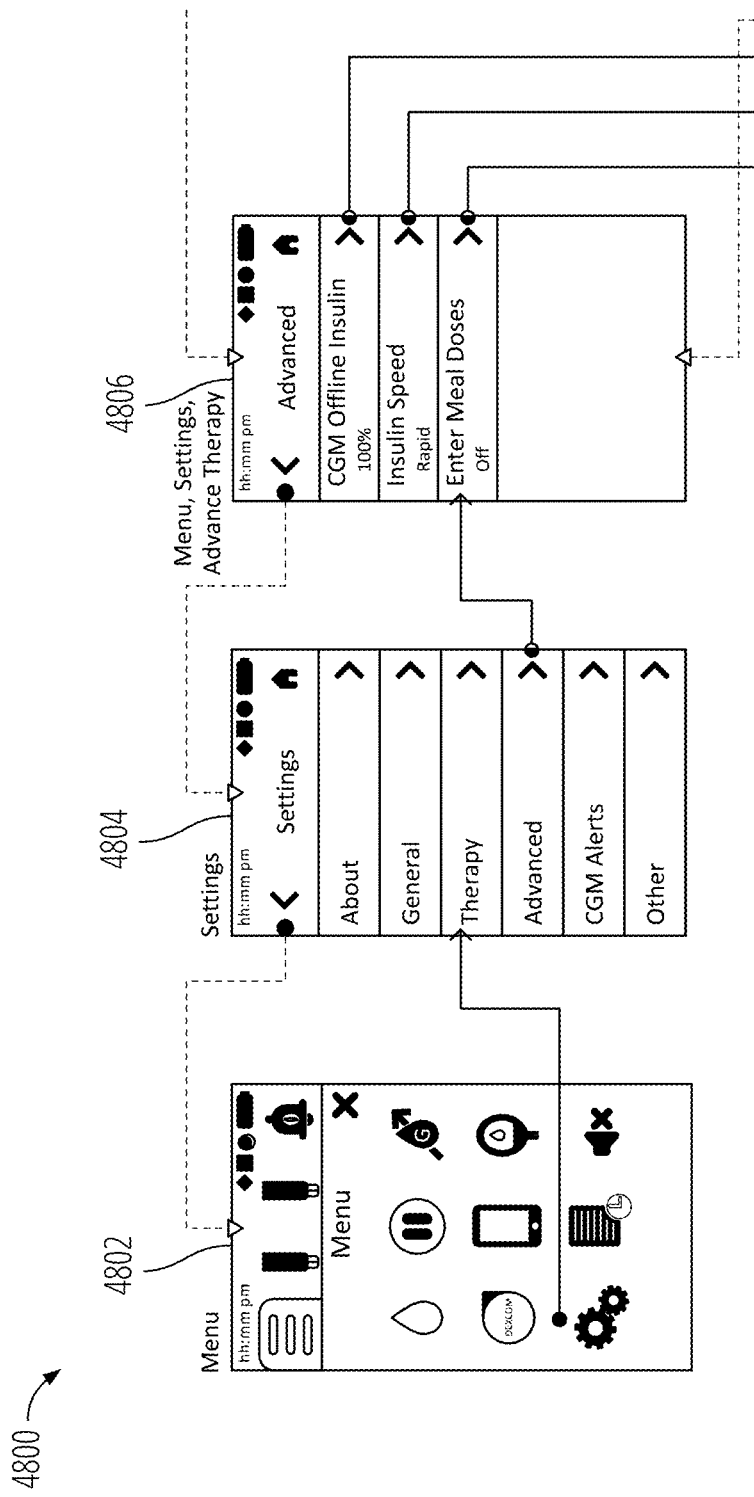
FIG. 48 is a series of user interface screen displays showing a user activating meal dosage on an ambulatory device.

FIG. 48 illustrates a plurality of screens 4800 that may be produced by the ambulatory medical device 4402. Upon activating the ambulatory medical device 4402, the initial menu screen 4802 may be displayed. In the menu screen 4802, options regarding functionalities of the ambulatory medical device 4402 is provided. The list of functionalities may cover all the aspects of the ambulatory medical device 4402. The user may access and control many aspects of the device by choosing the setting option. The setting option will allow the user to further assess and regulate the adjustable functionalities of the ambulatory medical device 4402. Upon selecting the setting option, the setting screen 4804 may be displayed and the user may select the advanced setting option. Upon selecting the advanced option, the advanced setting screen 4806 is displayed, and the user is provided the option to double check the CGM insulin levels and change the speed of the of the insulin pump. The user may speed up the process or slow down the process depending on the regulation stats that are provided by the model predictive control component 4424.

Figure 49:
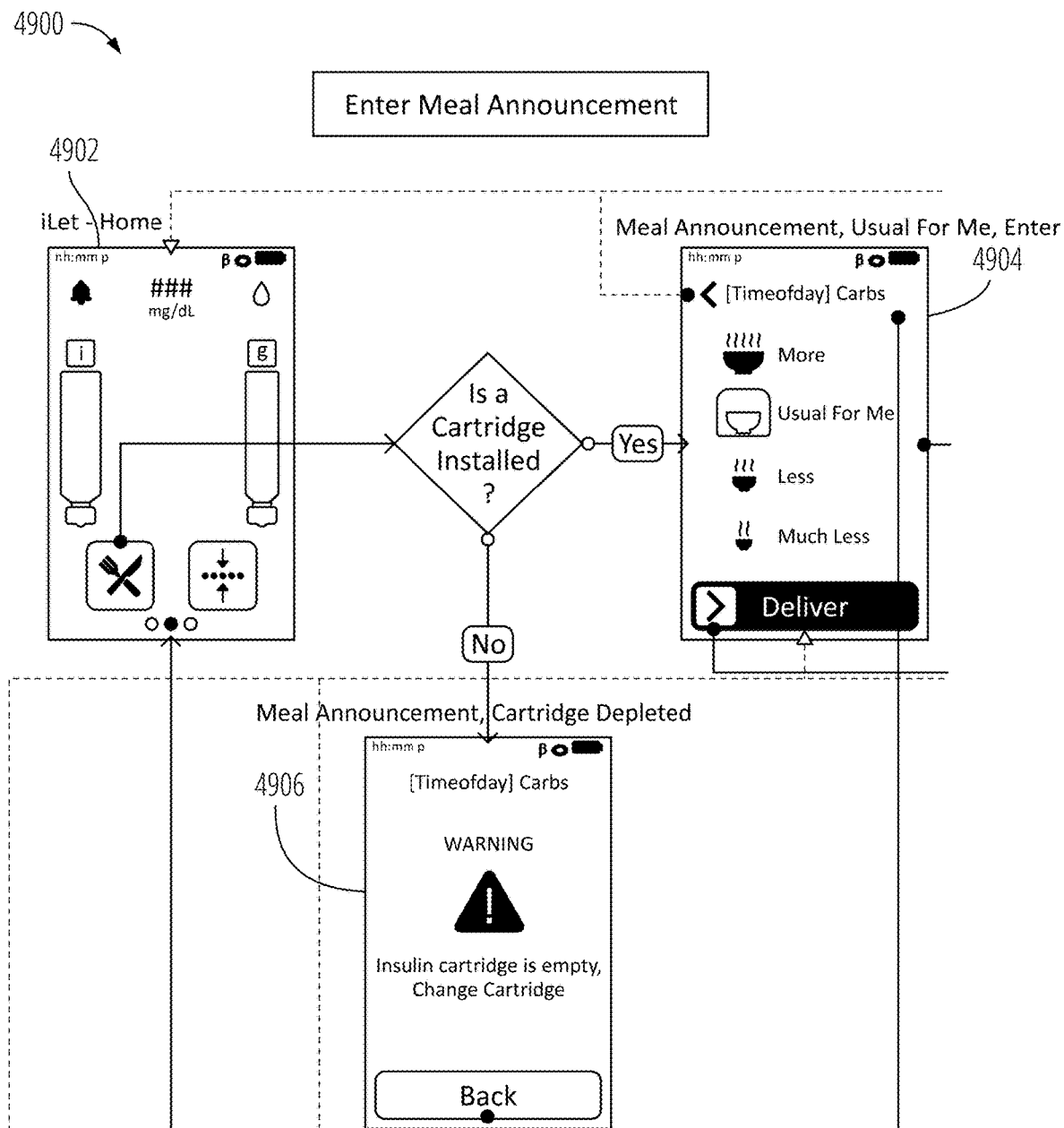
FIG. 49 is a series of user interface screen displays showing a user activating meal announcement on an ambulatory device.

FIG. 49 illustrates a plurality of screens 4900 that may be produced by the ambulatory medical device 4402. The plurality of screens 4900 is the process that a user may take in order to enter meal announcements. The home screen 4902 provides information and stats regarding the cartridge of the ambulatory medical device 4402. The user may select the meal button with or without an installation of a new cartridge. If a user selects the meal button without installing a new cartridge, the ambulatory device 4402 will display the warning screen 4906, where the user is warned that the insulin cartridge is empty, and the device further advises the user to change the cartridge. However, if a new cartridge is already installed and the food button is pressed, the ambulatory medical device 4402 will display the carbs screen 4904, where the user is provided the option to choose a meal dose option. The carbs screen 4904 allows the user to provide subjective information regarding the food that is to be digested. This subjective data provided by the user is further stored in the model predictive control component 4424 for further regulation of the blood glucose level.

Figure 50:
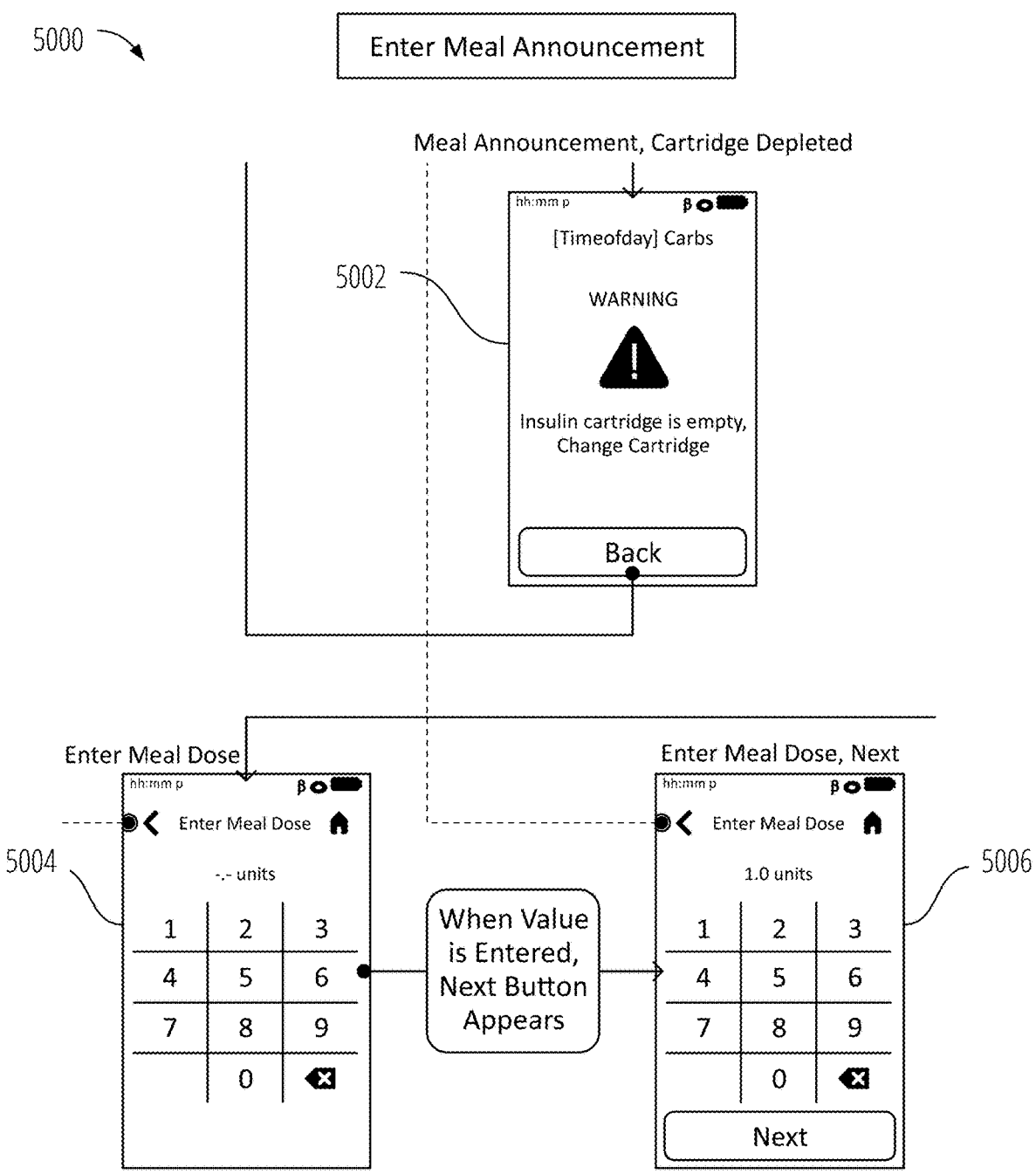
FIG. 50 is a series of user interface screen displays showing a user inputting the total number of units on an ambulatory device.

FIG. 50 illustrates a plurality of screens 5000 that may be produced by the ambulatory medical device 4402. The plurality of screens 5000 demonstrates the process of the user being alerted about the empty cartridge and having the option to replace the cartridge and further enter the meal doses. Warning screen 5002 alerts the user that the insulin cartridge is empty and the fact that it needs to be replaced. Upon replacing the cartridge, screens 5004 and 5006 will be displayed. Screen 5004 is initially displayed, and a user may enter a specified dose for each meal on a numerical pad. Upon inserting a numerical specified dose, screen 5006 is displayed where a next button is provided for the user to further complete the therapy change. The numerical specified dose is further stored in the model predictive control component 4424 for further regulation of the blood glucose level.

FIG. 51 illustrates a plurality of screens 5100 that may be produced by the ambulatory medical device 4402. Upon selecting the delivery request, a user may cancel the delivery of the medicaments prior to the completion of the delivery. The ambulatory medical device 4402 displays a countdown prior to delivery. The initial countdown screen 5102 is proceeded by the secondary countdown screen 5106. During these countdown screens, a cancel button is provided for the user to cancel the therapy change. During the initial countdown screen 5102 or the secondary countdown screen 5106, the user may cancel the delivery at any time. By swiping the cancel button, the user may officially stop the delivery of the therapy change. If the user does not cancel, the therapy change may be delivered successfully. Furthermore, the time and the amount of the therapy change delivery is stored in the model predictive control component 4424 for further regulation of the blood glucose level. However, if the user decides to cancel the delivery, the delivery will be canceled and the screen 5104 will be provided. Once the delivery cancelation is requested and the screen 5104 is displayed, upon pressing the ok button, the ambulatory medical device 4402 will display a lock screen 5108 and take the time to officially cancel the therapy change request.

Figure 52:
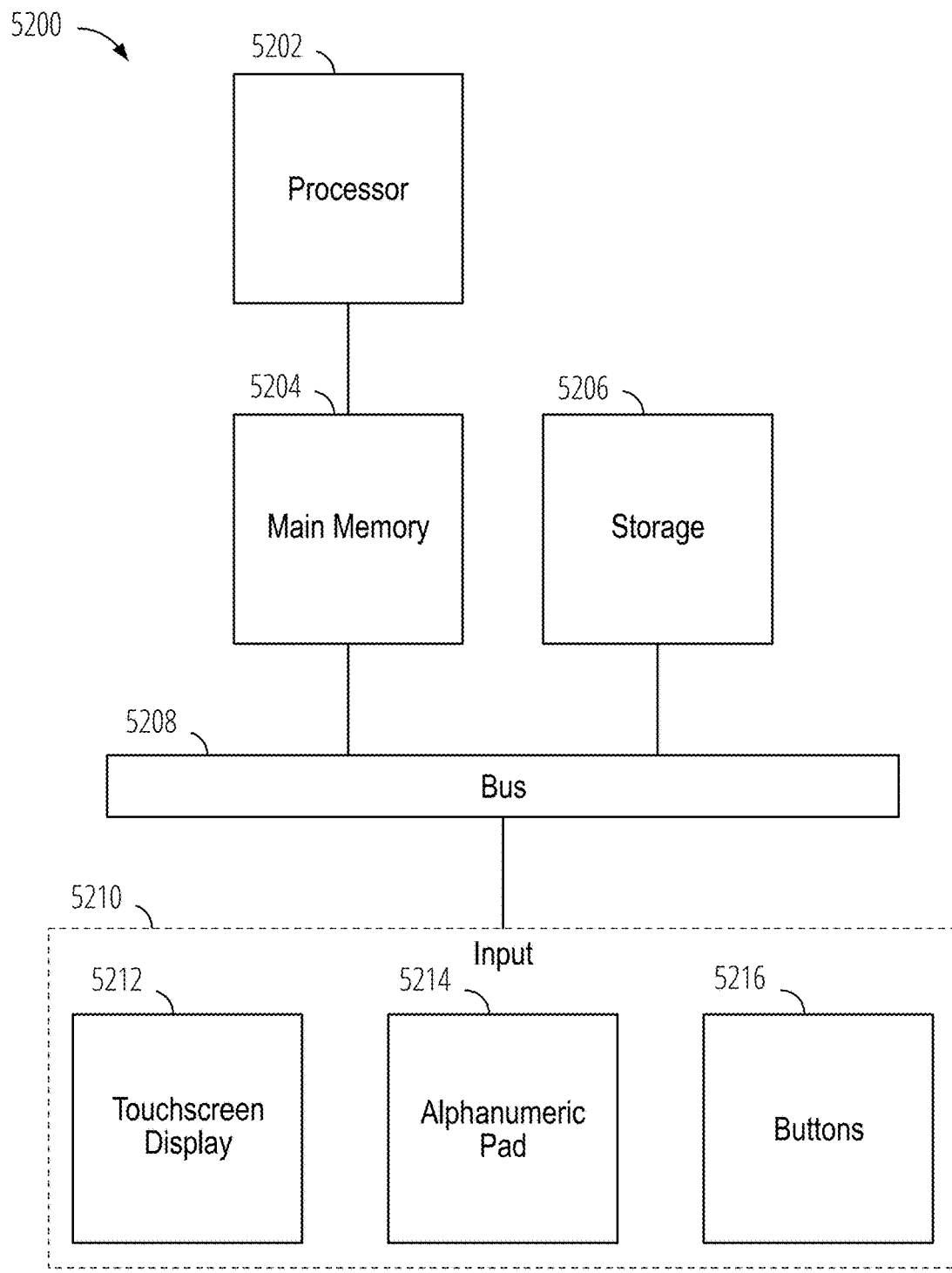
FIG. 52 is a schematic illustrating a computer system that can be implemented in various embodiments of the described subject matter.

FIG. 52 is a block diagram illustrating a computer system 5200 that may be implemented in the various embodiments in the described subject matter. The computer system 5200 includes a processor 5202, main memory 5204, storage 5206, a bus 5208, and input 5210. The processor 5202 may be one or more processors. The processor 5202 executes instructions that are communicated to the processor through the main memory 5204. The main memory 5204 feeds instructions to the processor 5202. The main memory 5204 is also connected to the bus 5208. The main memory 5204 may communicate with the other components of the computer system through the bus 5208. Instructions for the computer system 5200 are transmitted to the main memory 5204 through the bus 5208. Those instructions may be executed by the processor 5202. Executed instructions may be passed back to the main memory 5204 to be disseminated to other components of the computer system 5200. The storage 5206 may hold large amounts of data and retain that data while the computer system 5200 is unpowered. The storage 5206 is connected to the bus 5208 and can communicate data that the storage holds to the main memory 5204 through the bus 5208.

The processor 5202 may be any type of general purpose processor including, but not limited to a central processing unit ("CPU"), a graphics processing unit ("GPU"), a complex programmable logic device ("CPLD"), a field programmable gate array ("FPGA"), or an application-specific integrated circuit ("ASIC"). One embodiment of the computer system 5200 in the ambulatory medical device 102 features a CPU as the processor 5202. However, embodiments may be envisioned for the computer system of the ambulatory medical device 102 that incorporate other types of processors 5202.

The main memory 5204 can be any type of main memory that can communicate instructions to the processor 5202 and receive executed instructions from the processor 5202. Types of main memory 5204 include but are not limited to random access memory ("RAM") and read only memory ("ROM"). In one embodiment, the computer system 5200 incorporates RAM as the form of main memory 5204 to communicate instructions to the processor 5202 and receive executed instructions from the processor 5202. Other embodiments may be envisioned that incorporate other types of main memory 5204 in the computer system 5200.

The storage 5206 can be any type of computer storage that can receive data, store data, and transmit data to the main memory 5204 via the bus 5208. Types of storage 5206 that can be used in the computer system 5200 include, but are not limited to, magnetic disk memory, optical disk memory, and flash memory. In one embodiment, flash memory is used as the storage 5206 in the computer system 5200 of the ambulatory medical device 102. Other embodiments that use other types of storage 5206 for the computer system 5200 may be envisioned.

The bus 5208 connects the internal components of the computer system 5200. The bus 5208 may include a multitude of wires that are connected to the components of the computers system 5200. The wires of the bus 5208 may differ based on the components of the computer system 5200 to which the bus 5208 connects. In various embodiments, the bus 5208 connects the processor 5202 to the main memory 5204. In various embodiments, the processor 5202 is directly connected to the main memory 5204.

The input 5210 of the computer system 5200 includes a touchscreen display 5212, an alphanumeric pad 5214, and buttons 5216. The touchscreen display 5212 both produces output and accepts input. The bus 5208 may be coupled to the touchscreen display 5212 to produce visual output. The touchscreen display 5212 may also accept input via capacitive touch, resistive touch, or other touch technology. The input surface of the touchscreen display 5212 can register the position of touches on the surface. Some types of touchscreen display 5212 can register multiple touches at once. The alphanumeric pad 5214 includes a multitude of keys with numerical, alphabetical, and symbol characters. Signals from the alphanumeric pad 5214 are communicated by the bus 5208 to the main memory 5204. Keys of the alphanumeric pad 5214 may be capacitive or mechanical. In some embodiments, the alphanumeric pad 5214 is displayed on the touchscreen display 5212. Buttons 5216, such as the wake button 120, may be capacitive, mechanical, or other types of input buttons.

Control Systems for Managing State Data

Glucose control therapy, such as blood glucose control therapy, generally requires the coordination of many elements within a system. For example, a glucose control therapy system can broadly include one or more medicament delivery systems (e.g., a medicament pump, a patch pump, a medicament pen, a hospital infusion pump), a control system, and/or a glucose sensor (e.g., a continuous glucose monitor (CGM)). Each of those elements may include one or more sub-elements. In order for data, such as state data, to be properly managed among the various elements of the system, the various elements must be able to properly communicate with one another. For example, a system involving a plurality of medicament pumps (e.g., ambulatory medicament pumps) must be able to provide proper communication among the various devices and properly store and manage the relevant data. This need to properly manage the relevant state data, such as historical state data, often demands that the data be properly received, stored, and/or transmitted at appropriate times and in an appropriate manner. Modern systems do not generally allow for proper data management that satisfy these needs. However, systems and methods described herein help solve this deficiency in the art.

Running an AID (Automated Insulin Dosing) algorithm often requires the management of state data, such as insulin on board (IOB), learned basal rates, meal sizes, aggressiveness factors, etc. Since these data can often take several days to learn and refine, it is beneficial to be able to transfer these data to a new pump when changing out a disposable pump.

The state data is generally precious and/or private and so should generally be stored in a location and manner to be safely transferred to a new pump. The state data can be stored on the original pump, a mobile device and/or a remote server. As described in more detail below, the pump and/or control system can use near-field communication (NFC) or another wireless interface to transfer data from the old pump to a new pump. Such transfers may not even require power to successfully occur. For example, writeable NFC tags may be written-to without power of their own, using energy received via the NFC signal. In some cases, an NFC-enabled fob may be swappable and may not need a power source.

During a pump transition, the state data may be transferred from a storage media to the new pump. State data can include a variety of data described herein, such as a latest dosing history, an amount of IOB, recent CGM history, recent meal announcements, algorithm-specific control parameters (see above related to the PK model), pump settings, dose-related parameters, alarm history, alarm acknowledgement status, user preferences, estimated correction factors and carb ratios, basal rates, meal dose sizes, and physiological model state (subject model).

The user interface for these connections may be such that when the new pump is paired, the state data is transmitted and the communication is monitored for errors. If errors are detected, one or more retries can be attempted. If these fail, the state data may be reset to a safe state.

Managing and storing the data as described herein may involve advanced data security and integrity protocols. For example, during transmission of data between devices, the data may be encrypted. The transmitting and/or receiving device may execute one or more cyclic redundancy checks (CRCs), which may include repeatable calculations to better confirm that data is not corrupted during transmission. Additionally or alternatively, a private/public key system may be employed. The public key may be used to transfer data, and each receiving device (e.g., control system, medicament pump, remote computing environment, etc.) may have a private key for encryption/decryption. Additionally or alternatively, a digital signature may be required for successful transmission. Each medicament pump can include a key pair. A remote electronic device (e.g., a remote computing environment) can hold a registry of public keys to confirm that data transfer is going to the target receiving device.

In some embodiments, the medicament device can be manufactured with a digital certificate that confirms that the medicament device is certified by the manufacturer and has the correct key pair. The digital certificate can include a signed public key and/or private key that exists in a secured enclave (e.g., in a remote computing environment). The digital certificate may be passed from an old medicament device to a new (replacement) medicament device to confirm that the medicament devices are properly certified.

As described below, a control system may be configured to connect to one or more medicament pumps. Each medicament pump may be assigned a specific user account. For example, a medicament pump can already be linked to a user when the medicament pumps is shipped by the manufacturer to the user. Additionally or alternatively, the user account can be associated between the user and the medicament pump during a pairing process. Unique identifiers may be stored on the control system so that a user may indicate her/his identity via a variety of methods, such as using a biometric identifier (e.g., fingerprint, retina scan) or a digital key identifier (e.g., username/pas sword).

Although any medicament delivery system may be used in the systems and methods described herein, for convenience reference will be made to a medicament pump below. A modular control system can provide communication among a plurality of medicament pumps and/or a glucose sensor.

One way to allow interoperability among a plurality of medicament pumps is to use a control system that manages the storage and/or flow of data among the medicament pumps. In some examples, a first medicament pump is configured to store data therein (e.g., in non-transitory memory, on a removable data module, etc.) and to allow transmission of that data to a second medicament pump.

The control system may be configured to be operated on a separate device from the plurality of medicament pumps. Additionally or alternatively, the control system can be self-contained within a small modular component, such as within a chip, of a medicament pump. The system can comprise a system on a module (SOM), which can allow the module to be disposed within a number of medical devices, such as a medicament pump (e.g., an ambulatory medicament pump) or other medical device. The control system can include a data interface to communicate with other electronic devices, such as a remote network (e.g., cloud, server), one or more medicament pumps, a glucose sensor, and/or a computing device (e.g., a laptop, cell phone, smartphone, Personal Diabetes Manager (PDM), tablet, wearable electronic device, etc.). The data interface can include a wired data interface and/or a wireless data interface. The data interface may refer to a plurality of data interfaces. In some examples, each data interface of the plurality of data interfaces is configured to communicate with a different electronic device.

In some examples, the control system can include one or more algorithms stored thereon, such as the control algorithm described above. The system may be able to output a dosing recommendation to a pump controller via a wired and/or wireless data interface. The system can integrate cellular wireless and/or GPS radio module(s) as well. The dosing recommendation can include a command or instruction to the pump controller. Additionally or alternatively the recommendation may include a displayed recommendation but no command for some reason (e.g., that the medicament pump or a component thereof), and feedback can be accepted (e.g., in case the user performs a manual injection).

The control system can receive historical pump data from a first medicament pump and decode encoded data of the historical pump data to obtain therapy data associated with the delivery of the glucose control therapy (e.g., an amount of a medicament delivery, a time of the medicament delivery) and/or one or more glucose control parameters. The one or more glucose control parameters can include a variety of parameters. Example of glucose control parameters include an insulin decay rate constant associated with a decay rate of insulin at a subcutaneous depot of the subject, a clearance time associated with an estimate of an amount of time for a bolus of insulin to be utilized by the subject, an insulin rise rate constant associated with a rise rate of insulin in blood of the subject after a bolus of insulin, a half-life value associated with when a concentration of insulin in blood plasma of the subject reaches half of a maximum concentration in the blood plasma, a weight of the subject, an age of the subject, demographic information associated with the subject, a sensitivity constant (e.g., an indication of a date of diagnosis, which may indicate a newly diagnosed diabetic) associated with the subject's sensitivity to a glucose level or bolus of medicament, a health state the subject (e.g., subject is pregnant or sick), an activity level of subject, a diet of the subject, a basal rate of medicament delivery associated with the subject, a correction factor, a carbohydrate ratio, a glucagon control parameter, and/or any other parameter described herein.

The control system can determine that at least one of a plurality of pairing conditions is satisfied to connect the data interface to the second medicament pump. Example pairing conditions include a user request to pair the control system to a second medicament pump, a user input initiating a replacement process for a first medicament pump, an indication that the second medicament pump is operatively connected to deliver medicament to the subject, a sensory alarm configured to alert a user that stored historical pump data is ready for transmission, an alert indicating a malfunction associated with the first medicament pump, a determination that a level of medicament in a medicament reservoir of the first medicament pump is below a threshold level, a signal received from a remote electronic device (e.g., a remote server, a user device) requesting transmission of the stored data, and/or any other pairing condition described herein.

The control system can transmit a pairing signal to the second medicament pump. In some embodiments, the control system receives a confirmation signal from the second medicament pump. The may transmit, in response to receiving the confirmation signal, the stored data. In some examples, the control system can estimate one or more glucose control parameters based on stored data, such as therapy data associated with the delivery of the glucose control therapy. In some embodiments, the control system can receive a glucose level signal from a glucose sensor operatively coupled to the subject and estimate one or more glucose control parameters based on the glucose level signal received from the glucose sensor. The control system can include a graphical user interface and may transmit to the graphical interface the stored data. In some examples, the control system can transmit the stored data to a remote electronic device, such as a mobile device, a remote computing environment, or some other remote device.

In some embodiments, the control system can receive data from the first medicament pump, such as an therapy data associated with the delivery of the glucose control therapy, one or more glucose control parameters, and or any other state data.

The control system can include one or more computing components, including a microprocessor, a Bluetooth Low Energy (BLE) wireless modem, a clock, and/or non-volatile memory to independently operate and maintain a wireless connection and/or calculate dosing results. As described in more detail below, the system can save and restore state data and/or other data on the module. Additionally or alternatively, the system can receive remote software upgrade services and provide them to a target pump controller or other associated medical device. Because of the benefits of the system where applicable (e.g., interconnectivity among medicament pumps, a small form factor, etc.), the system can be part of a digital infrastructure that provides interactivity among multiple electronic devices, such as a mobile device, wearable device (e.g., smart watch), cloud network, and/or third-party services. The system may include a hardware and/or software validation package that satisfies public standards, such as, for example, FCC, EMC/EMI, IEC 62304, or other validation standard. In some examples, the system can be coupled directly to an infusion pump, such as a pump in a hospital room.

The control system may receive one or more inputs from a user and/or from another device. For example, the system may receive one or more glucose control parameters or other state data from the user. These data may be received via a graphical user interface or other user control element coupled to the control system.

The modular system can receive various details related to a subject receiving therapy. For example, the system may receive a body weight and/or glucose control parameters from a remote device and/or from a directly coupled medical device. In some embodiments, the modular system can receive meal announcement requests and/or a pump status.

The control system can receive indications of the status of a pump controller of one or more medicament pumps. For example, the modular system can receive an indication that the pump controller of a first medicament pump is available and/or that it is not available for delivery of therapy. In some embodiments, the modular system may receive a delivery report. The delivery report may indicate how much therapy was delivered since a previous time (e.g., since a most recent status request) or how much therapy was delivered at some historical point. The delivery report can include a recommendation for future therapy. The recommendation may include a command to deliver the recommended therapy.

The control system may determine one or more glucose control parameters by learning the glucose control parameters during online operation of an automated glucose control system. For example, the modular system may generate the glucose control parameters by calculating a size of a correction bolus of insulin of the regular correction boluses at a time of receiving an isolated glucose measurement (e.g., from a glucose sensor). Additionally or alternatively, the system may generate the glucose control parameters by calculating a size of a meal bolus of insulin. The glucose control parameters may be determined by use of the control algorithm described above.

The control system can receive historical pump data from one or more ambulatory medicament pumps. The historical pump data can include encoded data. For example, the historical pump data can include encoded data corresponding to therapy data (e.g., glucose control therapy data) associated with delivery of glucose control therapy delivered by an ambulatory medicament pump to the subject. The therapy data can include one or more of an amount of insulin on board, a value used in a pharmacokinetic (PK) model of a control algorithm, a time of a delivery of medicament, an amount of delivery of medicament, and/or another parameter associated with therapy delivery. In some examples, the therapy data includes version data. The version data can include a timestamp corresponding to a time associated with an update of the therapy data. For example the timestamp can indicate when the last recorded delivery of therapy occurred. Additionally or alternatively, the version data may include an indicator of an ordering within a sequence of delivery of the glucose control therapy. For example, the version data may indicate where in the sequence a particular delivery of therapy occurred. The version data may include a version code comprising encoded time data associated with delivery of the glucose control therapy. The version code may be encoded to identify a time of day of delivery of medicament, a time within a session of multiple deliveries of medicament, an ordering within the session, or some other indicator of when therapy was delivered.

Additionally or alternatively, the historical pump data can include second encoded data corresponding to one or more glucose control parameters used by an ambulatory medicament pump in calculating a dose control signal. There are many examples of glucose control parameters. A non-exhaustive list of such glucose control parameters includes, but is not limited to: an insulin decay rate constant associated with a decay rate of insulin at a subcutaneous depot of the subject, a clearance time associated with an estimate of an amount of time for a bolus of insulin to be utilized by the subject, an insulin rise rate constant associated with a rise rate of insulin in blood of the subject after a bolus of insulin, a half-life value associated with when a concentration of insulin in blood plasma of the subject reaches half of a maximum concentration in the blood plasma, a weight of the subject, an age of the subject, a learned parameter (e.g., via a control algorithm described herein, such as a learned basal rate), glucose level data of the subject, a model parameter associated with a pharmacokinetic (PK) model, a health state of the subject (e.g., sick, pregnant, etc.), a parameter associated with an activity level of the subject, an aspect of a diet of the subject (e.g., smoker), a basal rate of insulin delivered to the subject, a correction factor, a carbohydrate ratio associated with the subject, a glucagon control parameter, demographic information associated with the subject, a sensitivity constant (e.g., date of diagnosis) associated with the subject's sensitivity to a glucose level or bolus of medicament, or any other parameter that may be used in calculating a dose control signal, such as those described herein.

The control system can decode the encoded data of the historical pump data to obtain the corresponding decoded data. These data may be transmitted to and/or stored in a memory of the control system.

It can be advantageous to maintain continuity of glucose control therapy to a subject, especially when changing pumps. Thus, the control system can be configured to be paired with a plurality of medicament pumps and to receive, store, and/or transmit glucose control therapy data to/from one or more of the medicament pumps. Thus, the control system can determine when a pairing with a medicament pump is initiated. The control system can determine that at least one of a plurality of pairing conditions is satisfied to connect the control system to a medicament pump. For example, the control system may pair with a new/replacement pump so that the control system can transmit stored glucose control therapy data to the replacement pump. A variety of pairing conditions can exist. A non-exclusive list of example pairing conditions includes, but is not limited to, a user request to pair the control system to the medicament pump (e.g., to the replacement medicament pump), a user input initiating a replacement process for a medicament pump (e.g., an old medicament pump to be replaced), an indication that the medicament pump (e.g., the replacement medicament pump) is ready to deliver medicament to the subject, a sensory alarm configured to alert a user that the historical pump data is ready for transmission, an alert indicating a malfunction (e.g., an occlusion, a low battery power, an electrical malfunction, a controller malfunction, a pump malfunction) associated with the medicament pump, a determination that a level of medicament in a medicament reservoir of the medicament pump is below a threshold level, a signal received from a remote electronic device requesting transmission of at least one of the therapy data associated with the delivery of the glucose control therapy or a glucose control parameter, or any other pairing condition.

In response to determining that the pairing condition is satisfied, the control system can transmit a pairing signal to the medicament pump. In some examples, the control system can receive a confirmation signal from the medicament pump. Additionally or alternatively, the control system may transmit the therapy data and/or the one or more glucose control parameters in response to receiving the confirmation signal. The control system may turn off a ready state of a medicament pump (e.g., the medicament pump to be replaced) in response to receiving the confirmation signal. Turning off a ready state can include discontinuing the control algorithm (described herein) on the medicament pump.

In some examples, the control system generates a dose control signal that causes a pump controller of one or more medicament pumps to deliver the medicament to the subject. For example, the control system may generate a dose control signal in the old/original medicament pump and in the replacement pump. The dose control signal may be based on one or more factors, such as the therapy data associated with the delivery of the glucose control therapy and/or one or more glucose control parameters. Generating the dose control signal may include calculating regular correction boluses of glucose control agent, e.g., in response to the one or more glucose control parameters.

The control system may further receive and be configured to decode other encoded data, such as data corresponding to a glucose level of a subject. Additionally or alternatively, the control system can receive and decode data corresponding to an indication of a glucose trend. The glucose trend may indicate a predicted change in the glucose level of the subject.

In some embodiments, the control system can estimate current data based on the historical data. The estimated data may not be exact but may be useful in approximating glucose control therapy data to avoid significant lapses in therapy, such as between switching from an old medicament pump and a replacement pump. The control system can estimate the glucose control parameter based on at least one of an amount of glucose control therapy, a time of the glucose control therapy, and/or an amount of insulin on board. These estimated data may be slightly inaccurate data based on historical data, but they may rely on one or more of a trend and/or a snapshot in a subject's glucose control therapy that has been measured. For example, previously obtained historical data may show a higher amount of insulin on board at a first time than at a second time. This may indicate that the subject has received additional therapy between the first and second times. As another example, a measured glucose level at a first time may have been higher than at a second time, which may indicate that an amount of insulin on board may be higher at the second time than at the first time. The actual (e.g., measured) data may be transmitted to and/or stored by the control system, which can use the actual data to make the estimation. The data may be received from a medicament pump, from a glucose sensor (e.g., a continuous glucose monitor (CGM)), and/or from another remote electronic device (e.g., a remote computing environment).

The control system may be configured to transmit various data to a graphical user interface. The control system may include the graphical user interface or the graphical user interface may be operatively coupled to the control system. The control system can transmit the data to a remote electronic device, such as a medicament pump, a user device, and/or a remote computing environment.

It may be advantageous for the control system to periodically connect with a medicament pump to obtain the therapy data. Because of physical or electronic restrictions in the medicament pump (e.g., short battery life, limited processing power, limited memory, etc.), it may not be practical to be in continuous communication with the medicament pump, such as a pump that is to be replaced soon. In some embodiments, the control system can connect with a medicament pump in response to satisfaction of a data retrieval condition. The control system can determine that at least one of a plurality of data retrieval conditions is satisfied. If the data retrieval condition is satisfied, the control system may connect to the medicament pump to connect the data interface to the medicament pump. In response to determining that the at least one of a plurality of data retrieval conditions is satisfied, the control system can receive the therapy data and/or the glucose control parameter.

There are a variety of data retrieval conditions that can be satisfied. Generally, the data retrieval condition indicates a practical and/or convenient time for which data may be transmitted to/from the control system. A non-exhaustive list of such conditions includes, but is not limited to, an occurrence of a scheduled time, a transmission of a meal announcement (e.g., input by a user), a user request to pair the system to the first ambulatory medicament pump, a user input initiating a replacement process for the first ambulatory medicament pump, an indication that the medicament pump is to be replaced, an indication that another medicament pump is ready to deliver medicament to the subject (e.g., is operatively connected to the subject), a sensory alarm configured to alert a user that the historical pump data is ready for transmission, an alert indicating a malfunction associated with the medicament pump, a determination that a level of medicament in a medicament reservoir of the first ambulatory medicament pump is below a threshold level, a determination that an amount of available medicament of the first ambulatory medicament pump is insufficient for a subject's medicament needs, a signal received from a remote electronic device requesting transmission of at least one of the therapy data or the glucose control parameter, and/or any other data retrieval condition. Reference will now be made to some of the figures.

Figure 53:
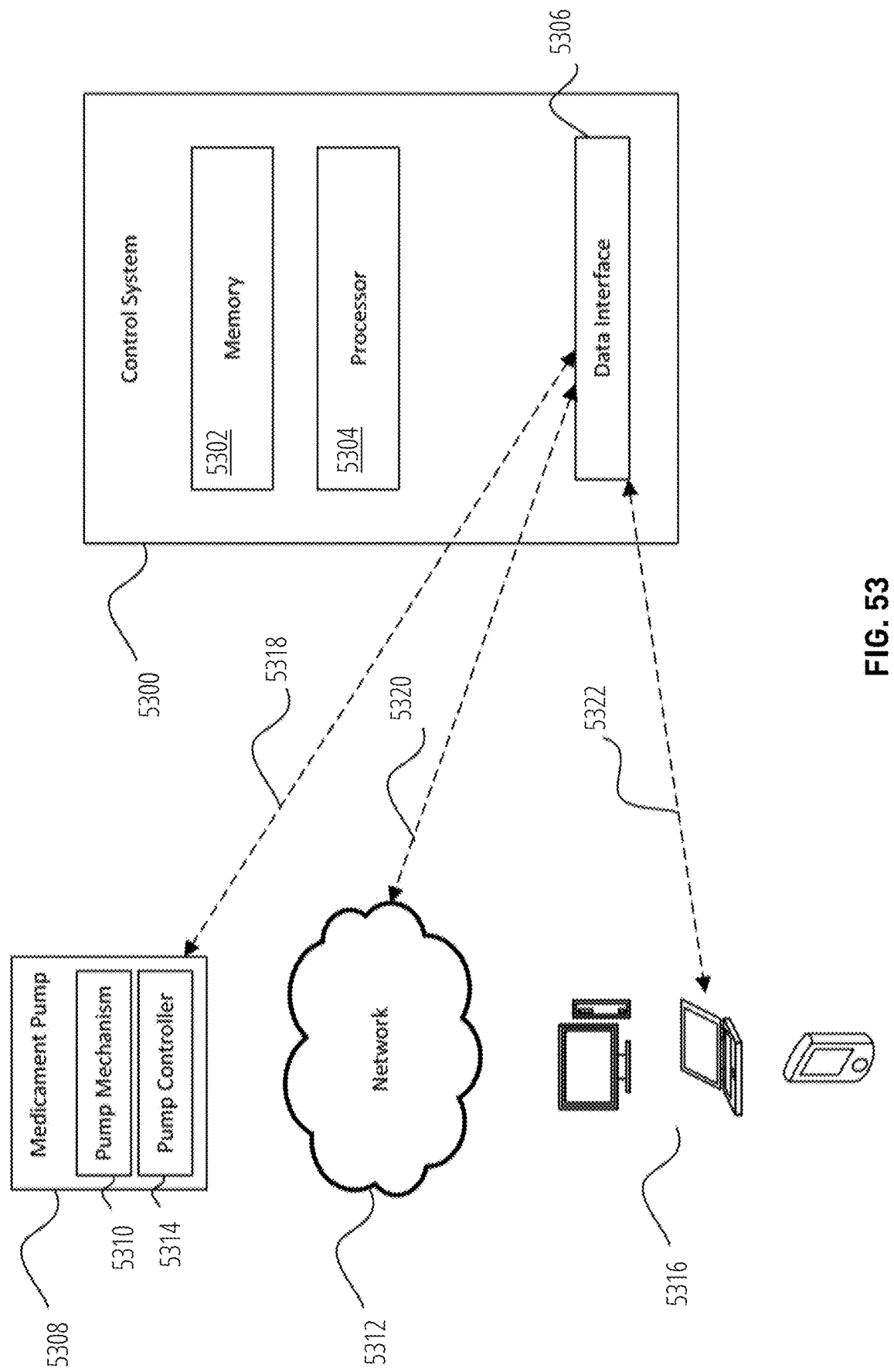
FIG. 53 shows an example control system configured to transfer historical pump data from a first ambulatory medicament pump to a second ambulatory medicament pump.

FIG. 53 shows an example control system 5300 configured to transfer historical pump data from a first ambulatory medicament pump to a second ambulatory medicament pump. The control system 5300 includes a non-transitory memory 5302, an electronic hardware processor 5304, and a data interface 5306. The data interface 5306 may include a wireless and/or wired data interface. The data interface 5306 can include a short-range wireless data interface.

The data interface 5306 may be in communication (e.g., wired, wireless) with one or more of a medicament pump 5308 (e.g., via a medicament pump connection 5318), with a network 5312 (e.g., via a network connection 5320), and/or a user device connection 5322 (e.g., via a user device connection 5322). Each of the connections 5318, 5320, 5322 may be one-way or two-way. The data interface 5306 may also be in communication with other elements of the medicament pump 5308, such as the pump mechanism 5310 and/or the pump controller 5314. The communication with the other elements of the medicament pump 5308 may be via a wired connection. The control system 5300 can represent one or a plurality of medicament pumps. In some embodiments, for example, the control system 5300 is in communication with a medicament pump that is to be replaced as well as an additional pump to replace that pump. However, for simplicity, reference to the medicament pump 5308 will represent one or a plurality of medicament pumps.

The medicament pump 5308 may be any medicament pump described herein, such as the pump 100 and/or pump 212. The pump controller 5314 is configured to direct medicament from a medicament reservoir to the subject using the pump mechanism 5310.

The data interface 5306 may be able to communicate (e.g., wirelessly, via wired connection) with a medicament pump 5308, a network 5312, and/or a user device 5316 via respective connections 5318, 5320, 5322. The data interface 5306 can communicate with the medicament pump 5308, such as via a wireless connection. The medicament pump 5308 can include a pump mechanism 5310 and a pump controller 5314. In some embodiments, the data interface 5306 communicates with the pump controller 5314 of the medicament pump 5308.

The network 5312 may include any wired network, wireless network, or combination thereof. For example, the network 5312 may be a personal area network, local area network, wide area network, over-the-air broadcast network (e.g., for radio or television), cable network, satellite network, cellular telephone network, or combination thereof. As a further example, the network 5312 may be a publicly accessible network of linked networks, possibly operated by various distinct parties, such as the Internet. In some implementations, the network 5312 may be a private or semi-private network, such as a corporate or university intranet. The network 5312 may include one or more wireless networks, such as a Global System for Mobile Communications (GSM) network, a Code Division Multiple Access (CDMA) network, a Long Term Evolution (LTE) network, or any other type of wireless network. The network 5312 can use protocols and components for communicating via the Internet or any of the other aforementioned types of networks. For example, the protocols used by the network 5312 may include Hypertext Transfer Protocol (HTTP), HTTP Secure (HTTPS), Message Queue Telemetry Transport (MQTT), Constrained Application Protocol (CoAP), and the like. Protocols and components for communicating via the Internet or any of the other aforementioned types of communication networks are well known to those skilled in the art and, thus, are not described in more detail herein. The network 5312 may comprise the "cloud." The network 5312 may include a remote computing environment.

Various example user devices 5316 are shown in FIG. 53, including a desktop computer, a laptop, and a mobile phone, each provided by way of illustration. In general, the user devices 5316 can be any computing device such as a desktop, laptop or tablet computer, personal computer, tablet computer, wearable computer, server, personal digital assistant (PDA), PDM, hybrid PDA/mobile phone, mobile phone, smartphone, set top box, voice command device, digital media player, and the like. A user device 5316 may execute an application (e.g., a browser, a stand-alone application) that allows a user to access and interact with interactive graphical user interfaces as described herein.

The control system 5300 may be configured to store a plurality of pump controller decoding profiles corresponding to respective pump controllers. The control system 5300 can be configured to select a pump controller decoding profile from a plurality of pump controller decoding profiles. The pump controller profile can be configured to operate with a particular pump, with a brand of pump, and/or with a different grouping of pump.

The control system 5300 can be configured to determine a status of the medicament pump 5308, such as a status of the pump controller 5314. The control system 5300 can receive, via the data interface 5306, an encoded pump status signal from the pump controller 5314. The encoded pump status signal can include data corresponding to an availability of the ambulatory medicament pump to deliver medicament to the subject. For example, the pump status signal can indicate that the medicament pump 5308 is ready to deliver glucose control therapy to a subject (e.g., that the medicament pump 5308 is operatively connected to the subject). The control system 5300 can additionally or alternatively receive an encoded medicament delivery signal from the pump controller pump controller 5314. The encoded medicament delivery signal can include data corresponding to an amount of medicament dosed to the subject.

Each pump controller decoding profile can be configured to decode various data from the medicament pump 5308. For example, the decoding profile can be configured to decode an encoded pump status signal, an encoded medicament delivery signal, encoded therapy data (e.g., glucose control therapy data), encoded glucose control parameter data, an encoded glucose level of the subject, encoded data indicating a glucose trend, and/or other encoded data. The glucose trend can indicate a predicted change in the glucose level of the subject over a time period and/or at a given time. The encoded therapy data can contain therapy data, such as described herein. The glucose control parameter data can include one or more glucose control parameters, which may include any glucose control parameter described herein. The selected pump controller decoding profile can correspond to the pump controller 5314 that is operatively coupled to the medicament pump 5308. Using the selected pump controller decoding profile(s), the control system 5300 can decode the corresponding encoded data. In some embodiments, the control system 5300 can calculate the dose control signal using a control algorithm (described above) that is configured to calculate regular correction boluses of glucose control agent in response to at least the glucose level of the subject.

In some embodiments, in order to properly transmit the decoded data to the pump controller 5314 (e.g., for instructions on delivering glucose control therapy) of the corresponding medicament pump 5308, the control system 5300 can proceed to encode the data so that it can be read by the corresponding pump controller 5314. Note that the control system 5300 may receive encoded data from a first medicament pump and may transmit encoded data to a second medicament pump. Like with the pump controller decoding profiles, the control system 5300 may have stored thereon one or more of a plurality of pump controller encoding profiles. The control system 5300 can select a pump controller encoding profile from the plurality of pump controller encoding profiles. The selected pump controller encoding profile can correspond to the respective pump controller 5314. The pump controller encoding profile can be configured to encode the therapy data, the glucose control parameter data, the dose control signal, and/or any other data that may be transmitted to the pump controller 5314.

The control system 5300 may determine that the medicament pump 5308 is ready to deliver medicament to the subject. In some embodiments, the control system 5300 can encode a dose control signal for commanding the medicament pump 5308 to administer glucose control therapy (e.g., using the pump mechanism 5310) via infusion of glucose control agent into the subject.

The control system 5300 may be configured to communicate with a plurality of pump controllers, store and transmit historical data stored on the control system 5300 (e.g., in the memory 5302) in response to a triggering condition. In this way, the data may not be lost and can be preserved for another medicament pump 5308. For example, a first medicament pump may be disposed of or intended to be disposed or replaced, and a user or other individual may be interested in the stored historical data in the control system 5300. The historical data may be data received from the first medicament pump, from the network 5312, from the user device 5316, from a glucose sensor, and/or from another electronic device. Such historical data can include a therapy delivery history, one or more glucose control parameters, and/or other data that may be stored over time on the control system 5300. In some embodiments, the control system 5300 can calculate a dose control signal for use in the medicament pump 5308. Over time, the generated dose control signal(s) may be stored on the control system 5300. Additionally or alternatively, the control system 5300 may receive periodic and/or regular updated data from the medicament pump 5308 or other electronic device. These data may include therapy data or other state data and may be stored in the memory 5302.

Once stored, the control system 5300 may be configured to transmit the stored data to a remote electronic device (e.g., a glucose sensor (not shown), the network 5312, the user device 5316) once a triggering condition is satisfied. The triggering condition can include one or more of a variety of triggering conditions. These conditions may indicate or reflect a change that is occurring on the medicament pump 5308 and/or on the control system 5300. The triggering condition may include a pairing condition. For example, the pairing condition may include a user request to pair the control system to the medicament pump 5308 (e.g., a replacement medicament pump 5308), a user input initiating a replacement process for the medicament pump 5308 (e.g., the pump to be replaced), and/or an indication that the medicament pump 5308 is ready to deliver medicament to the subject. Additionally or alternatively, the pairing condition can include a sensory alarm configured to alert a user that the historical pump data is ready for transmission. The sensory alarm may prompt a user to cause the control system 5300 to transmit the data to the remote electronic device. The pairing condition can include an alert indicating a malfunction associated with the first ambulatory medicament pump 5308. The malfunction may include any problem with the medicament pump 5308, such as a problem that may raise a potential concern of the ability of the medicament pump 5308 to properly deliver medicament. The malfunction can include, for example, an occlusion, a low battery power, an electrical malfunction, a controller malfunction, a pump malfunction, and/or any other malfunction in the proper operation of the medicament pump 5308.

It may be advantageous to bring to a user's attention that a medicament pump 5308 is predicted not to be able to deliver adequate medicament to the subject. For example, a user may want to replace the medicament pump 5308 in such conditions. Accordingly, the pairing condition may include a determination that a level of medicament in a medicament reservoir of the first ambulatory medicament pump 5308 is below a threshold level, a signal received from a remote electronic device requesting transmission of stored data, and/or any other indication that attention should be drawn to the medicament delivery capability of the medicament pump

5308. The medicament reservoir may be included in the medicament pump 5308 (not shown in FIG. 53). Other pairing or triggering conditions are possible and these are listed by way of illustration only.

In embodiments where the pairing condition includes a sensory alarm, the sensory alarm may be configured to regularly and/or periodically alert the user and/or subject until the glucose control parameters are transferred to the remote electronic device (e.g., to the replacement medicament pump). For example, the sensory alarm can include a visual, audible, haptic, and/or other alarm. in some embodiments, the sensory alarm includes a beep, a tone, and/or other audible alarm. The alarm may include a vibration and/or flashing light. The sensory alarm may be configured to be annoying to a user so that the user is motivated to provide instructions for the control system 5300 to send the stored data to the remote electronic device.

The control system 5300 may monitor the data transfer for errors. If an error is detected, the control system 5300 may automatically or manually attempt to retransfer the data. If the number of failed attempts exceeds a threshold number (e.g., 2, 3, 4, 5, 6), the state data may be reset to a safe state. In the safe state, the data may be restricted (e.g., can only be transferred via a wired connection, requires special credentials to request further transfer, etc.). The safe state data may be valuable because it describe the latest reliable state data even if it does not describe the latest state data stored on the control system 5300 and/or on the medicament pump 5308.

In some embodiments, the control system 5300 can transmit via the data interface 5306 data to a graphical user interface. For example, the control system 5300 may transmit a glucose level of the subject, glucose control therapy data (e.g., a time and/or amount of delivered medicament), one or more glucose control parameters, an indication of the glucose trend of the subject, and/or other similar data to the graphical user interface for display. Additionally or alternatively, the data may be transmitted to a remote device, such as a user device 5316 and/or the network 5312, via a corresponding connection 5320, 5322.

As noted above, the control system 5300 can receive, store, and/or transmit one or more glucose control parameters to the one or more devices illustrated, such as the medicament pump 5308 (e.g., the medicament pump to be replaced, a replacement medicament pump), the user device 5316, and/or the network 5312. As described above, example glucose control parameters can include a variety of parameters. A non-exhaustive list of such glucose control parameters includes, but is not limited to: an insulin decay rate constant associated with a decay rate of insulin at a subcutaneous depot of the subject, a clearance time associated with an estimate of an amount of time for a bolus of insulin to be utilized by the subject, an insulin rise rate constant associated with a rise rate of insulin in blood of the subject after a bolus of insulin, a value (e.g., half-life value) associated with when a concentration of insulin in blood plasma of the subject reaches a threshold concentration (e.g., half, maximum) in the blood plasma, a weight of the subject, an age of the subject, a learned parameter (e.g., via a control algorithm described herein), glucose level data of the subject, a model parameter associated with a pharmacokinetic (PK) model, a health state of the subject (e.g., sick, pregnant, etc.), a parameter associated with an activity level of the subject, an aspect of a diet of the subject (e.g., smoker), a basal rate of insulin delivered to the subject, a correction factor, a carbohydrate ratio associated with the subject, a glucagon control parameter, demographic information associated with the subject, a sensitivity constant associated with the subject's sensitivity to a glucose level or bolus of medicament, or any other parameter that may be used in calculating a dose control signal, such as those described herein. Other parameters may be included, such as those with reference to the control algorithm above.

The control system 5300 can receive various data related to an amount of insulin on board and/or a value used in a pharmacokinetic (PK) model of the control algorithm described above. The control system 5300 may be configured to execute the control algorithm in some embodiments. The glucose control therapy data may include the amount of insulin on board and/or the value used in the PK model.

Figure 54:
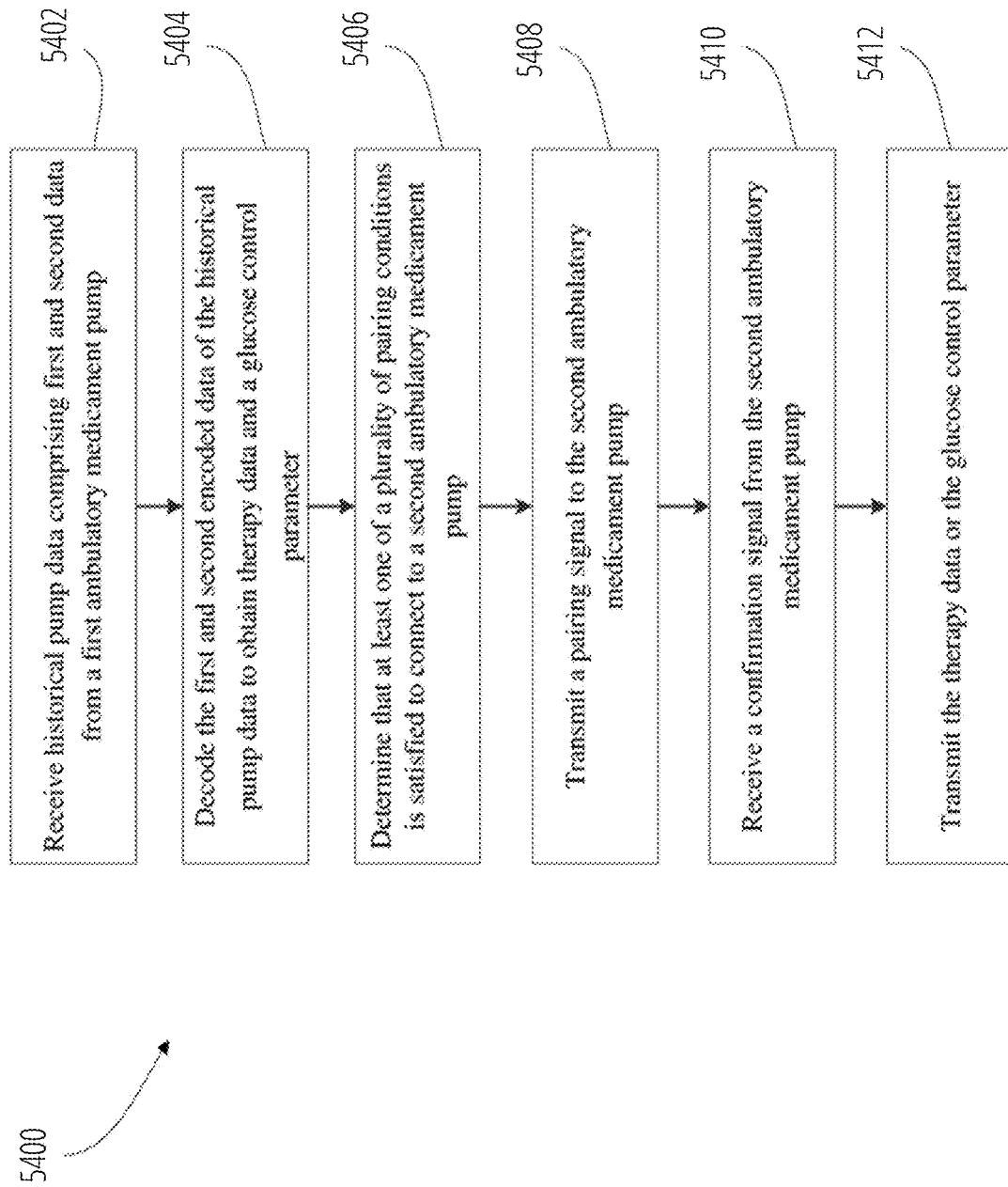
FIG. 54 shows a flow diagram illustrating an example method that may be used by a control system to transfer historical pump data from a first ambulatory medicament pump to a second ambulatory medicament pump.

FIG. 54 shows a flow diagram illustrating an example method 5400 that may be used by a control system (e.g., the control system 5300) to transfer historical pump data from a first ambulatory medicament pump to a second ambulatory medicament pump. The system can receive the historical pump data comprising first and second encoded data from the first ambulatory medicament pump at block 5402. At block 5404 the system decodes (e.g., automatically) first and second encoded data of the glucose level signal to obtain therapy data and a glucose control parameter. The glucose control parameter can include one or more of the glucose control parameters described above. At block 5406, the system determines that at least one of a plurality of pairing conditions is satisfied to connect to a second ambulatory medicament pump. The pairing conditions may be any of the pairing conditions described herein. At block 5408, the system transmits a pairing signal to the second ambulatory medicament pump. At block 5410 the system receives a confirmation signal from the second ambulatory medicament pump. At block 5412, the system transmits, based on the confirmation signal, the therapy data or the glucose control parameter to an electronic device, such as the second ambulatory medicament pump. In some embodiments, the system transmits the data additionally or alternatively to a remote electronic device, such as a remote server. In some embodiments, the method 5400 includes turning off a ready state of the first ambulatory medicament pump in response to receiving the confirmation signal. Turning off a ready state can include discontinuing running or executing an algorithm (e.g., a control algorithm described herein) on the target medicament pump.

In some embodiments, the method 5400 can include additional steps. For example, the system may generate, based on at least the therapy data and the glucose control parameter, a dose control signal that is configured to cause a pump controller of the first ambulatory medicament pump to deliver the medicament to the subject. The method 5400 may further include receiving additional encoded data corresponding to a glucose level of a subject and to an indication of a glucose trend. The glucose trend can indicate a predicted change in the glucose level of the subject. Additionally or alternatively, the system may estimate a second glucose control parameter based on at least one of the an amount of glucose control therapy received by the subject, a time of the medicament glucose control therapy received, an amount of insulin on board, a glucose level signal, or another parameter. In some embodiments, the system can transmit to a remote electronic device (e.g., a graphical user interface, a mobile device, a remote computing environment) one or more of the therapy data or the glucose control parameter. Additionally or alternatively, the system can receive at least one of an amount of insulin on board or a value used in a pharmacokinetic (PK) model of a control algorithm. In some embodiments, the method 5400 includes receiving from the first ambulatory medicament pump, in response to determining that the at least one of a plurality of data retrieval conditions is satisfied at least one of the therapy data or the glucose control parameter.

Medicament Pumps for Managing State Data

As noted above, glucose control therapy may require the coordination of a plurality of elements within a system. Providing consistent glucose control therapy from one medicament pump to another requires significant coordination of the various devices as well as proper management of the state data that is generated during a course of therapy provided to the subject. Complicating matters further, a user may switch among a variety of medicament pumps each with different operating parameters, encoding/decoding profiles, and/or other aspects. A medicament pump may include any ambulatory medicament pump, such as a patch pump, but a medicament pump can include a medicament pen or a hospital infusion pump.

In order for data, such as state data, to be properly managed across the variety of medicament pumps, the medicament pumps involved must be able to properly communicate with one another. For example, each medicament pump must be able to provide proper communication among the other medicament pump(s) and/or with other devices to properly store and manage the relevant data. This need to properly manage the relevant state data, such as historical state data, often demands that the data be properly received, stored, and/or transmitted at appropriate times and in an appropriate manner. Modern systems do not generally allow for proper data management that satisfy these needs. However, systems and methods described herein help solve this deficiency in the art. As noted above, although any medicament delivery system may be used in the systems and methods described herein, for convenience reference will be made to a medicament pump below.

Managing state data among a plurality of medicament devices can require extensive care and coordination. One way to manage (e.g., store, transmit) the data among the variety of medicament pumps is to include a removable data module. A removable data module can include one or more different data storage devices, such as a data chip, a data card, a microchip, a SIM card, a memory card or cartridge, or any other removable hardware memory. A first medicament pump can house or otherwise be operatively coupled to the removable data module. The removable data module can record and store state data obtained by the first medicament pump. At some point, the removable data module may be removed from the first medicament pump to have the state data thereon read by another electronic device, such as a second medicament pump.

Another way to manage the state data is to transmit the data wirelessly to the second medicament pump. This transmission may be directly (e.g., via a short-range wireless connection) or indirectly through an intermediate electronic device (e.g., via a computing device connected to a wide-area network connection).

The medicament pump be configured to execute one or more algorithms, such as the control algorithm described above. Using the one or more algorithms, the medicament pump may be able to generate some or all of the state data described herein.

Figure 55A:
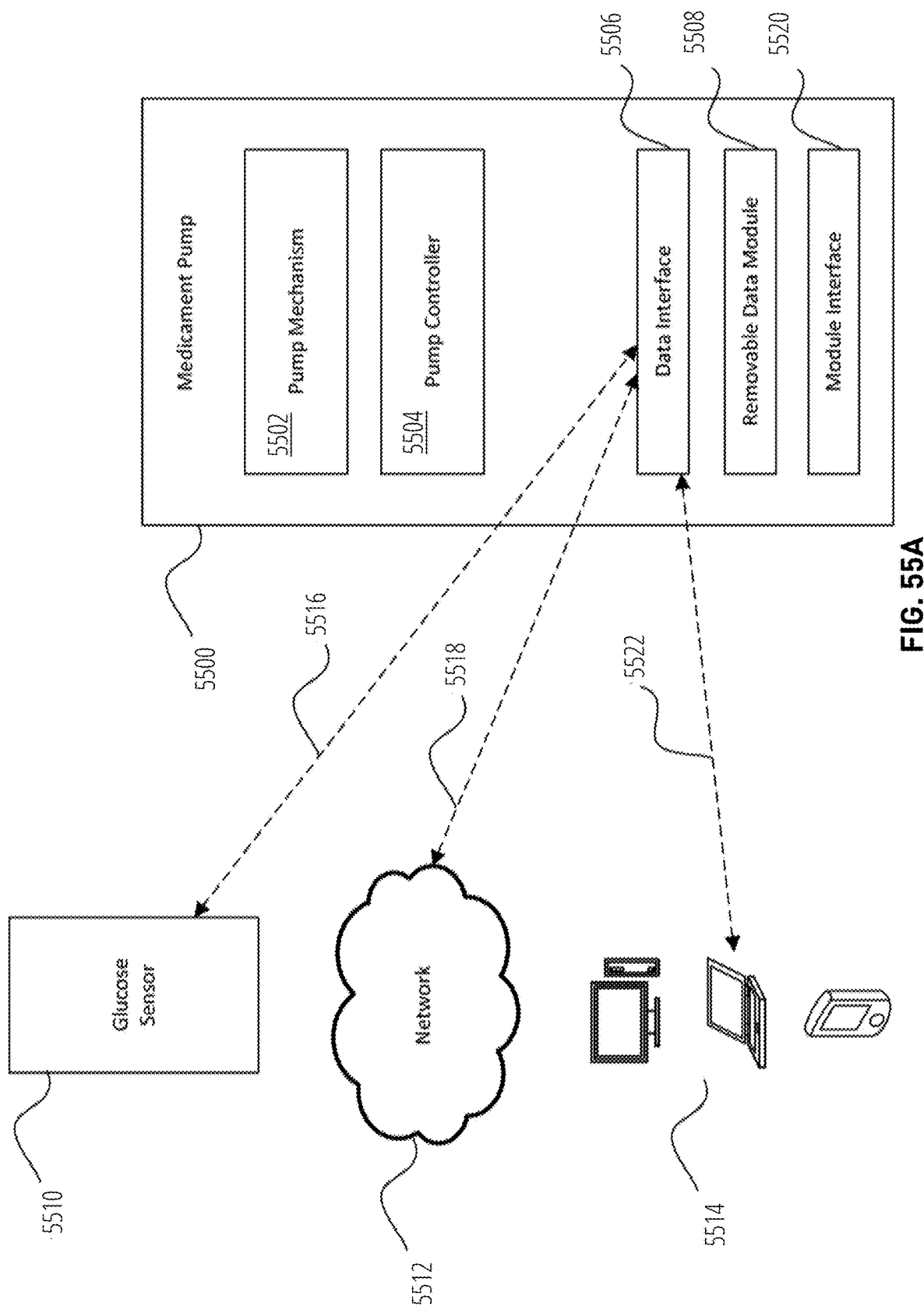
FIG. 55A shows an example medicament pump that is configured to store data on a removable data module configured to be readable by a second ambulatory medicament pump.

Another way to manage state data is by transferring data among a plurality of medicament pumps. FIG. 55A shows an example medicament pump 5500 that is configured to store data on a removable data module 5508 configured to be readable by a second ambulatory medicament pump. The medicament pump 5500 includes a pump mechanism 5502, a pump controller 5504, and may include additional elements. The data interface 5506 may include one or more data interfaces, such as a wireless and/or wired data interface.

The medicament pump 5500 may be any medicament pump described herein, such as the pump 100, the pump 212, and/or the medicament pump 5308. The pump controller 5504 is configured to direct medicament from a medicament reservoir to the subject using the pump mechanism 5502.

The data interface 5506 may be in communication (e.g., wired, wireless) with one or more of a glucose sensor 5510 (e.g., via a glucose sensor connection 5516), with a network 5512 (e.g., via a network connection 5518), and/or with a user device 5514 (e.g., via a user device connection 5522). Each of the connections 5516, 5518, 5522 may be one-way or two-way. The data interface 5506 may also be in communication with other elements of the medicament pump 5500, such as the pump mechanism 5502 and/or the pump controller 5504. The communication among one or more of the elements of the medicament pump 5500 may be via a wired connection.

The network 5512 may include any network described above with respect to the network 5312 in FIG. 53. Additionally or alternatively, the user device 5514 may include any user device described above with regard to the user device 5316 in FIG. 53.

In some embodiments, the medicament pump 5500 includes a module interface 5520 that is configured to receive the removable data module. The module interface 5520 can include a hardware receptacle. The hardware receptacle can be shaped and/or otherwise adapted to fit the removable data module therein. The module interface 5520 may be configured to allow access to the removable data module from an outside of the medicament pump 5500. Additionally, or alternatively, the module interface 5520 may be configured to house the removable data module within the medicament pump 5500. For example, the removable data module may only be accessed by opening up the medicament pump 5500 in some embodiments. The module interface 5520 can retain the removable data module via an interference fit, a clamp or other retaining structure, and/or any other coupling means.

The medicament pump 5500 can include an electronic processor that is configured to execute instructions stored on a non-transitory memory to perform various functions, such as some of the ones described below. The medicament pump 5500 can determine various state data, such as therapy data (e.g., glucose control therapy data), that is related to delivery of glucose control therapy delivered to a subject. The therapy data can include one or more of an amount of insulin on board, a value used in a pharmacokinetic (PK) model of a control algorithm, a time of a delivery of medicament, an amount of delivery of medicament, and/or another parameter associated with therapy delivery. In some examples, the therapy data includes version data. The version data can include a timestamp corresponding to a time associated with an update of the therapy data. For example, the timestamp can indicate when the last recorded delivery of therapy occurred. Additionally, or alternatively, the version data may include an indicator of an ordering within a sequence of delivery of the glucose control therapy. For example, the version data may indicate where in the sequence a particular delivery of therapy occurred. The version data may include a version code comprising encoded time data associated with delivery of the glucose control therapy. The version code may be encoded to identify a time of day of delivery of medicament, a time within a session of multiple deliveries of medicament, an ordering within the session, or some other indicator of when therapy was delivered.

As noted above, the medicament pump 5500 can generate one or more of a plurality of glucose control parameters. These parameters can include a variety of parameters, such as those described above, such as an insulin decay rate constant associated with a decay rate of insulin at a subcutaneous depot of the subject, a clearance time associated with an estimate of an amount of time for a bolus of insulin to be utilized by the subject, an insulin rise rate constant associated with a rise rate of insulin in blood of the subject after a bolus of insulin, a half-life value associated with when a concentration of insulin in blood plasma of the subject reaches half of a maximum concentration in the blood plasma, a weight of the subject, an age of the subject, a learned parameter, glucose level data of the subject, a model parameter associated with a PK model, a health state of the subject, a parameter associated with an activity level of the subject, an aspect of a diet of the subject, a basal rate of insulin delivered to the subject, a correction factor, a carbohydrate ratio associated with the subject, a glucagon control parameter, demographic information associated with the subject, a sensitivity constant associated with the subject's sensitivity to a glucose level or bolus of medicament, or any other parameter that may be used in calculating a dose control signal, such as those described herein.

The medicament pump 5500 can determine that the removable data module 5508 has been removed from the module interface. The medicament pump 5500 may determine this in a variety of ways. For example, the medicament pump 5500 may detect that the removable data module 5508 is no longer in electronic communication with the medicament pump 5500 (e.g., the removable data module 5508 is not coupled to the module interface). Additionally, or alternatively, the medicament pump 5500 may receive an indication from a user or from an electronic device that the removable data module 5508 has been removed.

In response to determining that the removable data module 5508 has been removed, the medicament pump 5500 can transmit an indication that the data module has been removed. For example, the medicament pump 5500 may transmit an internal indication that the removable data module 5508 is no longer coupled to the medicament pump 5500. The indication may automatically trigger execution of a pump deactivation process that is configured to deactivate the first medicament pump. Deactivation can include shutting off (e.g., permanently, temporarily), conserving battery, deleting stored data, transmitting an indication to a remote electronic device (e.g., the network 5512, the user device 5514), transmitting an indication to a graphical user interface, generating a user alert, and/or any other deactivation step. This may protect the privacy of the data stored on the medicament pump 5500.

In some embodiments, the medicament pump 5500 can receive a glucose level signal from the glucose sensor 5510. The glucose level signal may include encoded data, such as data corresponding to a glucose level of the subject and/or data corresponding to an indication of a glucose trend in the subject. The glucose trend may indicate a predicted change in the glucose level of the subject. The medicament pump 5500 can decode the encoded data obtain the glucose level of the subject and the indication of the glucose trend.

The medicament pump 5500 may be able to transmit to a user control element (e.g., a user device 5514) an indication that the removable data module is ready for removal. In response to transmitting the indication (or prior to transmitting), the medicament pump 5500 may be configured to automatically or manually be deactivated.

In some embodiments, the medicament pump 5500 may be configured to generate, a dose control signal configured to cause the pump controller 5504 of the medicament pump 5500 to deliver medicament to the subject. This generation of the dose control signal can include calculating regular correction boluses of glucose control agent. The medicament pump 5500 may generate the dose control signal based on at least one or more of the plurality of glucose control parameters and/or other state data stored thereon.

Additionally or alternatively, the medicament pump 5500 may be configured to wirelessly transmit the glucose control therapy data, one or more of the plurality of glucose control parameters, and/or other state data to a remote electronic device (e.g., the network 5512, the user device 5514). The medicament pump 5500 may receive and/or estimate an amount of insulin on board, a value used in a pharmacokinetic (PK) model of a control algorithm (see above), or other state data In some embodiments, the medicament pump 5500 can transmit data to a graphical user interface. For example, the medicament pump 5500 may transmit the state data that it has stored thereon. The medicament pump 5500 may regularly and/or periodically store the determined/received state data as needed. For example, data received from the glucose sensor 5510 or other electronic device may be stored at or near the time that the data is received. Additionally or alternatively, data that is calculated by the medicament pump 5500 may be stored at or near the time of calculation. Over time, the medicament pump 5500 may catalogue this data on the local memory and/or on the removable data module 5508 for access later by the medicament pump 5500 and/or by a second (e.g., replacement) medicament pump.

In some embodiments, the data may be stored in response to a triggering condition. The triggering condition can include one or more of a variety of triggering conditions. These conditions may indicate or reflect a change that is occurring in the medicament pump 5500. For example, the triggering condition may include a user request to store the data, a user indication of an intent to discard or otherwise dispose of the medicament pump 5500, and/or a user input initiating a replacement process for the medicament pump 5500. The triggering condition can include an alert indicating a malfunction associated with the medicament pump 5500. The malfunction may include any problem with the medicament pump 5500, such as a problem that may raise a potential concern of ability of the medicament pump 5500 to properly deliver medicament. The malfunction can include any defect or malfunction described herein.

Figure 55B:
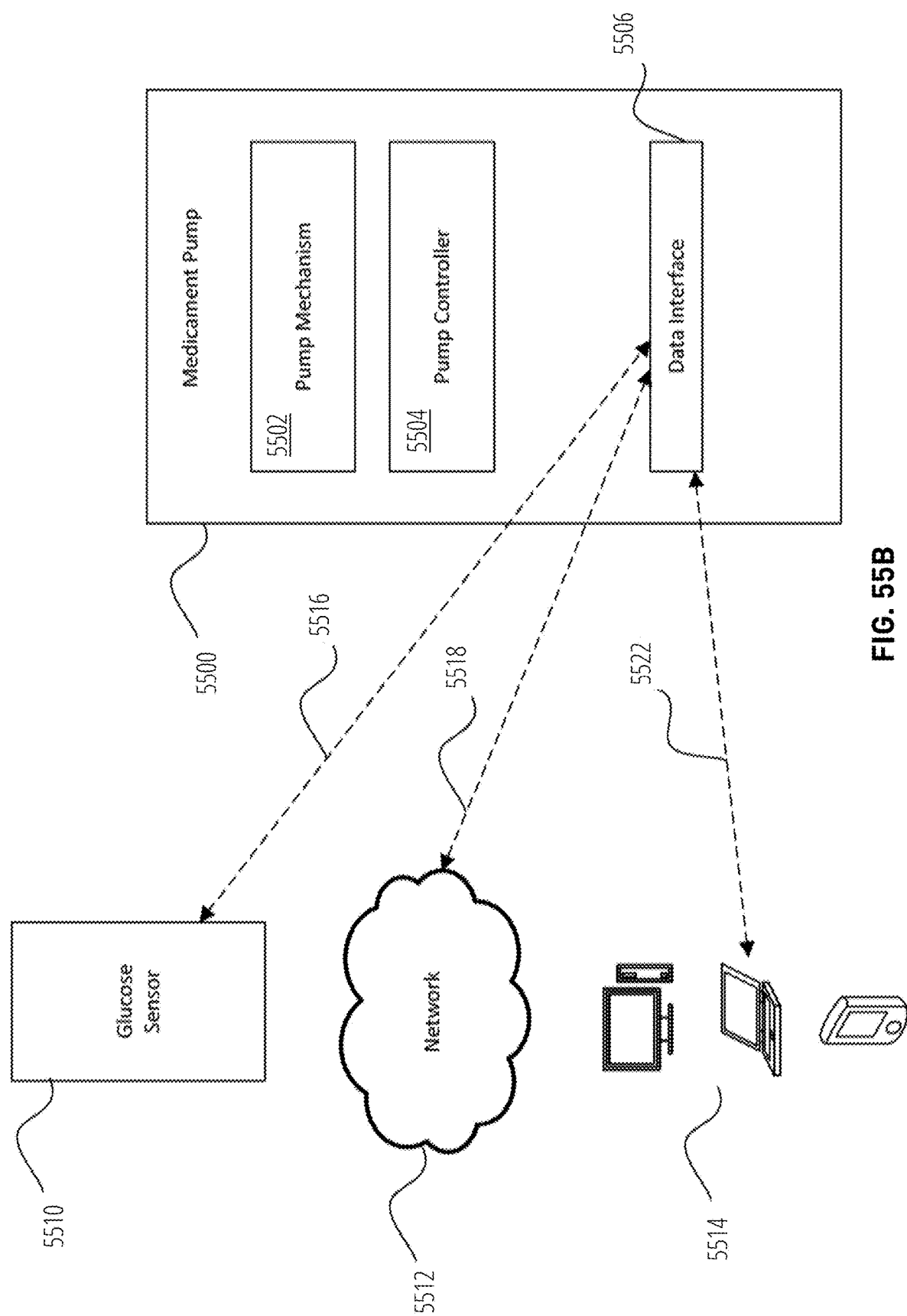
FIG. 55B shows another example medicament pump that is configured to wirelessly transmit state data to a second ambulatory medicament pump.

It may be advantageous to be able to wirelessly transmit data from a first medicament pump to a second medicament pump. This may not only be more convenient for a user but may better ensure that the data is transferred timely or at all. FIG. 55B shows another example medicament pump 5500 that is configured to wirelessly transmit state data to a second medicament pump. The medicament pump 5500 shown in FIG. 55B may share one or more features of the medicament pump 5500 shown in FIG. 55A, and vice versa.

As noted above, the medicament pump 5500 may be configured to determine therapy data (e.g., glucose control therapy data) that includes an amount of insulin on board, a time of a delivery of glucose control therapy, and/or an amount of delivery of glucose control therapy. Additionally or alternatively, the medicament pump 5500 can generate one or more glucose control parameters, such as those described herein.

The medicament pump 5500 may determine that the medicament pump 5500 is ready to pair with a second medicament pump. This determination may be automatic or manual and may be in response to the satisfaction of one or more pairing conditions. The pairing conditions may include an occurrence of a scheduled time, a transmission of a meal announcement (e.g., input by a user), a user request to pair the medicament pump to a remote electronic device, a user input initiating a replacement process for the medicament pump, an indication that the second medicament pump is ready to deliver medicament to the subject (e.g., is operatively connected to the subject), a sensory alarm configured to alert a user that the historical pump data is ready for transmission, an alert indicating a malfunction associated with the medicament pump, a determination that a level of medicament in a medicament reservoir of the first medicament pump is below a threshold level, a determination that an amount of available medicament of the medicament pump is insufficient for a subject's medicament needs, a signal received from a remote electronic device requesting transmission of at least one of the therapy data or the glucose control parameter, and/or any other pairing condition.

In response to determining that at least one pairing condition is satisfied, the medicament pump 5500 can wirelessly transmit one or more glucose control parameters and/or glucose control therapy data to a second medicament pump (e.g., a replacement pump). In some embodiments, before transmitting the data, the medicament pump 5500 can first transmit a pairing request signal to the second medicament pump. Additionally or alternatively, the medicament pump 5500 may receive a pairing confirmation signal from the second medicament pump. In some embodiments, the medicament pump 5500 transmits to a user control element (e.g., user device 5514) an indication that the second (e.g., replacement) medicament pump is ready to be paired with the medicament pump 5500.

The medicament pump 5500 may monitor the data transfer for errors. If an error is detected, the medicament pump 5500 may automatically or manually attempt to retransfer the data. If the number of failed attempts exceeds a threshold number, the state data may be reset to a safe state. In the safe state, the data may be restricted as described above.

The medicament pump 5500 may be able to transmit the data via short-range and/or wide-area transmission technology. For example, it may be advantageous for a user to quickly transmit the data to the replacement medicament pump via short-range data transfer technology. Such transfer may be via radiative data transfer (e.g., via Bluetooth Low Energy (BLE)) or inductive data transfer (e.g., near-field communication (NFC)). In some embodiments, power transfer may be possible from one medicament pump to another. For example, the medicament pump 5500 or the replacement medicament pump may not need to be powered for the data transfer to take place. Thus, it may not always be necessary to receive a confirmation signal from one of the medicament pumps to initiate data transfer. In some embodiments, the data may be transferred wirelessly using LTE. In some embodiments, the data may be transferred via a wired connection.

As noted above, in some embodiments the medicament pump 5500 can execute, in response to transmitting data to the second ambulatory medicament pump, a pump deactivation process configured to deactivate the medicament pump 5500.

Figure 56:
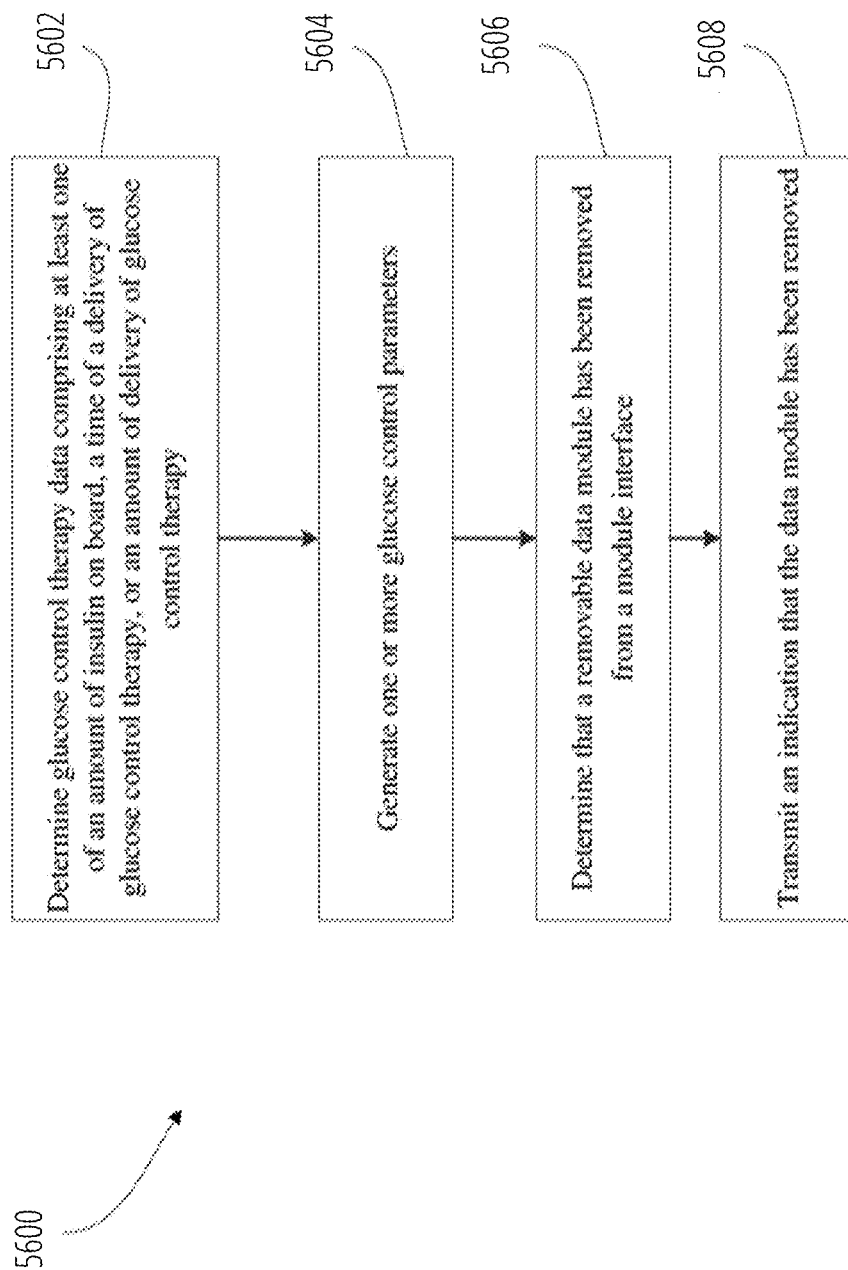
FIG. 56 shows a flow diagram illustrating an example method that may be used by a medicament pump to store data on a removable data module of a first ambulatory medicament pump configured to be readable by a second ambulatory medicament pump.

FIG. 56 shows a flow diagram illustrating an example method 5600 that may be used by a medicament pump (e.g., the medicament pump 5500, pump 100, pump 212) to store data on a removable data module of a first ambulatory medicament pump configured to be readable by a second ambulatory medicament pump. At block 5602, the medicament pump can determine glucose control therapy data comprising at least one of an amount of insulin on board, a time of a delivery of glucose control therapy, or an amount of delivery of glucose control therapy. At block 5604, the medicament pump generates one or more of a plurality of glucose control parameters, such as those described above. At block 5606, the medicament pump determines that the removable data module has been removed from the module interface. At block 5608, the medicament pump transmits an indication that the data module has been removed. In some embodiments, the medicament may execute, in response to transmitting the indication that the data module has been removed, a pump deactivation process configured to deactivate the medicament pump. Additionally or alternatively, the medicament pump may transmit one or more of the received/generated data to a remote electronic device.

In some embodiments, the method 5600 incudes one or more additional steps. For example, the medicament pump may receive (e.g., from a control system, from a glucose sensor, from another medicament pump) and/or decode data corresponding to one or more of a glucose level of the subject or an indication of a glucose trend of the subject. The medicament pump may generate (e.g., based on one or more glucose control parameters) a dose control signal configured to cause the pump controller of the medicament pump to deliver medicament to the subject.

Figure 57:
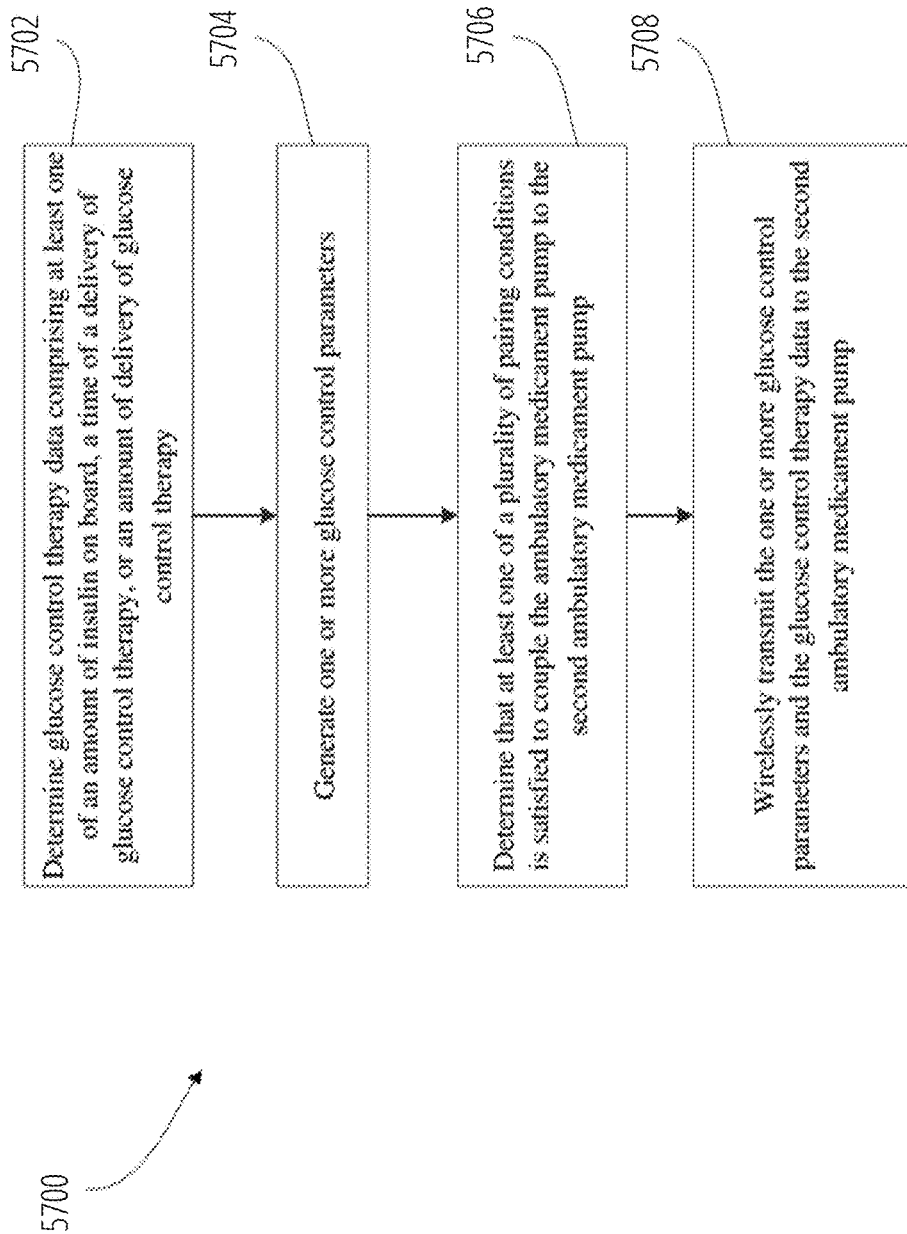
FIG. 57 shows a flow diagram illustrating an example method that may be used by a medicament pump to wirelessly transmit from the medicament pump one or more of a plurality of glucose control parameters and glucose control therapy data to a second ambulatory medicament pump.

FIG. 57 shows a flow diagram illustrating an example method 5700 that may be used by a medicament pump (e.g., the medicament pump 5500, pump 100, pump 212) to wirelessly transmit from the medicament pump one or more of a plurality of glucose control parameters and glucose control therapy data to a second ambulatory medicament pump.

At block 5702, the medicament pump can determine glucose control therapy data comprising at least one of an amount of insulin on board, a time of a delivery of glucose control therapy, or an amount of delivery of glucose control therapy. At block 5704, the medicament pump generates one or more of a plurality of glucose control parameters, such as those described above. At block 5706, the medicament pump determine that at least one of a plurality of pairing conditions is satisfied to couple the ambulatory medicament pump to the second ambulatory medicament pump. At block 5708, the medicament pump wirelessly transmit the one or more glucose control parameters and the glucose control therapy data to the second ambulatory medicament pump, in response to determining that the at least one of the plurality of pairing conditions is satisfied. Additionally or alternatively, in response to determining that the at least one of the plurality of pairing conditions is satisfied, the medicament pump may receive from a remote electronic device at least one glucose control parameter.

In some embodiments, the medicament pump transmits a pairing request signal to the second ambulatory medicament pump and/or receives a pairing confirmation signal from the second ambulatory medicament pump. In response to determining that at least one of the plurality of pairing conditions is satisfied, the medicament pump may transmit to the second ambulatory medicament pump at least one of an amount of insulin on board or a value used in a pharmacokinetic (PK) model of a control algorithm.

Example Implementation of Glucose Level Control System

Figure 58:
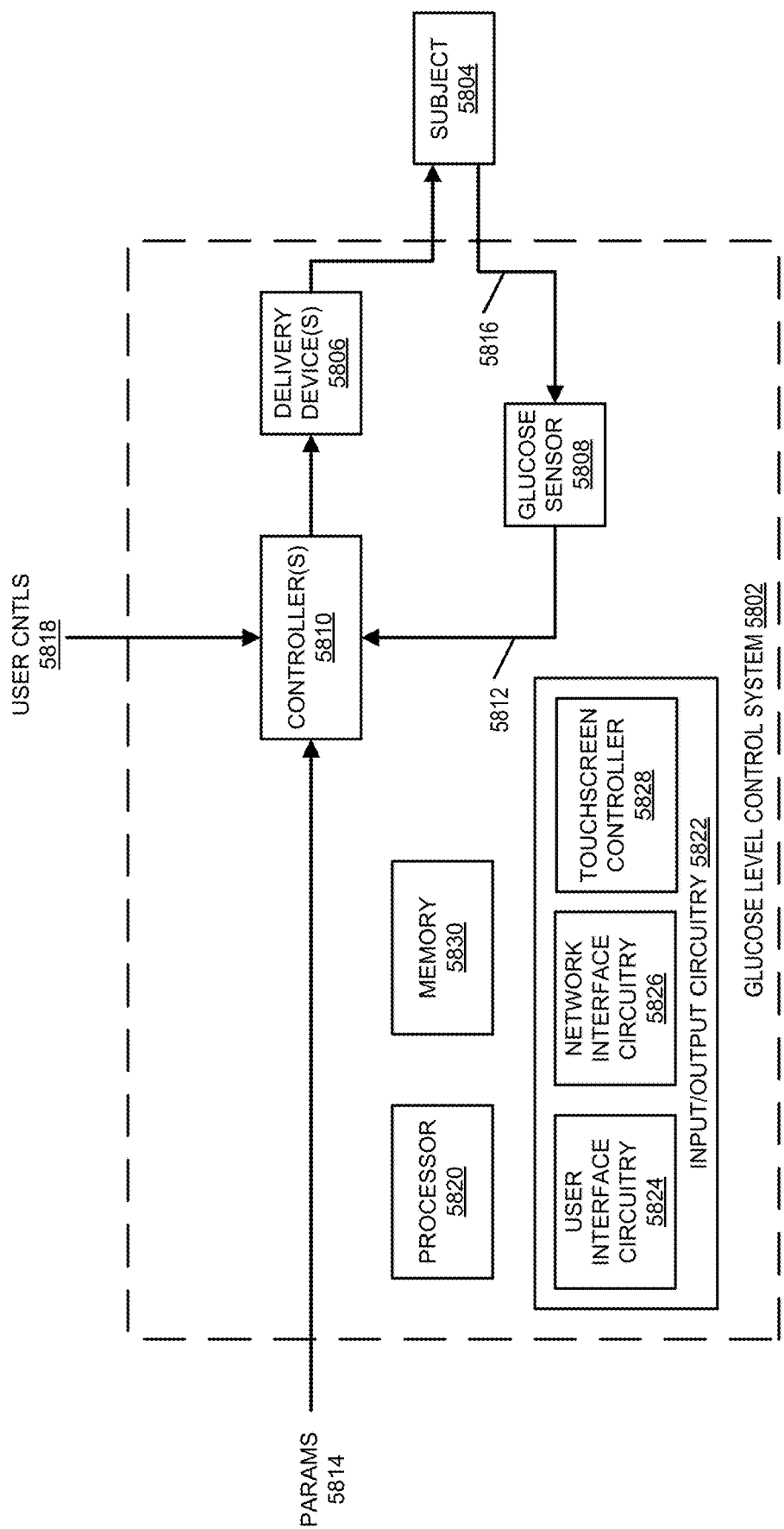
FIG. 58 illustrates a block diagram of a glucose level control system in accordance with certain embodiments.

FIG. 58 illustrates a glucose level control system 5802 for regulating the blood glucose level of an animal subject (subject 5804), which may be a human. The glucose level control system 5802 is an example of a medicament infusion system and may include any of the embodiments previously described above with respect to medicament infusion systems.

The subject 5804 may receive doses of insulin from one or more delivery device(s) 5806, for example infusion pump(s) coupled by catheter(s) to a subcutaneous space of the subject 5804. As described below, the delivery device(s) 5806 may also deliver a counter-regulatory agent or hyperglycemic agent, such as glucagon or dextrose, for control of the blood glucose level under certain circumstances. For the delivery of both insulin and a counter-regulatory agent (e.g., glucagon), the delivery device(s) 5806 may be mechanically driven infusion mechanisms having dual cartridges for insulin and the counter-regulatory agent, respectively. In the present description, reference is made to glucagon specifically, but it is to be understood that this is for convenience only and that other counter-regulatory agents (e.g., dextrose) may be used. Similarly, the term "insulin" herein is to be understood as encompassing all forms of insulin-like substances including natural human or animal insulin as well as synthetic insulin in any of a variety of forms (commonly referred to as "insulin analogs").

For online or autonomous operation, a glucose sensor 5808 is operatively coupled to the subject 5804 to continually sample a glucose level of the subject 5804. In some cases, the glucose sensor 5808 may be referred to as a continuous glucose monitoring (CGM) sensor, which may continuously or periodically measure or sense blood glucose levels of the subject 5804 for at least a period of time. Sensing may be accomplished in a variety of ways, generally involving some form of physical coupling 5816 between the subject 5804 and the glucose sensor 5808. A controller 5810 may control operation of the delivery device(s) 5806 as a function of a glucose level signal 5812 from the glucose sensor 5808 and subject to programmed input parameters (PARAMS) 5814 which may be provided by a user such as the subject 5804, a parent or guardian of the subject 5804, or a healthcare provider (e.g., a clinician or doctor). One input parameter for automatic operation may include the weight of the subject 5804. In some cases, the glucose level control system 5802 can provide effective automated control without receiving explicit information regarding either meals that the subject 5804 has ingested or any other "feedforward" information, which is achieved in part by an adaptive aspect to operation of the controller 5810. In other cases, the glucose level control system 5802 can use received information regarding either meals that the subject ingested, or plans to ingest, or other "feedforward" information to modify control of blood glucose and/or delivery of insulin or counter-regulatory agent.

The controller 5810 is an electrical device with control circuitry that provides operating functionality as described herein. In one embodiment, the controller 5810 may be realized as a computerized device (e.g., a hardware processor) having computer instruction processing circuitry that executes one or more computer programs each including respective sets of computer instructions. In some cases, the processing circuitry will generally include one or more separate processors 5820 along with memory 5830 and input/output circuitry 5822 coupled to or in communication with the separate processor 5820 (or separate processors 5820), where the memory 5830 stores computer program instructions and data, and the input/output circuitry 5822 can provide interface(s) to external devices such as the glucose sensor 5808 and delivery device(s) 5806. In some cases, the input/output circuitry 5822 may provide a user interface, or may operate with one or more processors (e.g., the controller 5810 or a separate processor 5820 included in the glucose level control system 5802 or in a separate computing system, such as a smartphone, a laptop computer, a desktop computer, a smartwatch, and the like) to provide a user interface to a user (e.g., the subject 5804, a parent or guardian, or a clinician). In some cases, the input/output circuitry 5822 may include a touchscreen and/or a touchscreen controller 5828 configured to control a touchscreen (not shown).

In some cases, the controller 5810 may perform all of the functionality of the glucose level control system 5802. In such cases, the processor 5820 may be optional or omitted. In other cases, the controller 5810 may perform at least automated glucose control of the subject 5804, and one or more separate processors 5820 may perform one or more additional operations of the glucose level control system 5802 (or medicament pump), such as tracking occurrences of hyperglycemic or hypoglycemic events or risk events, outputting data to a user, controlling or initiating communication with another computing system, regulating access to the glucose level control system 5802, or other operations unrelated to operation of a medicament pump or the delivery device(s) 5806.

The input/output circuitry 5822 may control communication with one or more other computing systems and/or with a user. In some cases, the input/output circuitry 5822 may include one or more separate interface circuits or controllers to facilitate user interaction and/or communication. For example, the input/output circuitry 5822 may include user interface 5824, network interface 5826, and/or a touchscreen controller 5828.

The user interface 5824 may include any circuitry or processors that may output a user interface to a user and/or receive user input from the user via the user interface. The user interface 5824 may receive one or more signals from a separate processor 5820 corresponding to a user interface. The user interface 5824 may control a display to present the user interface to a user based on the one or more signals received from the separate processor 5820. Further, the user interface 5824 may include any circuitry that can receive a signal corresponding to an interaction by a user with a user interface and can provide the signal to the separate processor 5820 and/or controller 5810 for further processing. In some cases, the user interface circuitry may be replaced by a touchscreen controller 5828 that can control a touchscreen interface. In other cases, the touchscreen controller 5828 may be in addition to the user interface 5824.

The network interface 5826 may include any circuitry that enables communication with a wired or wireless network. The network interface 5826 may include one or more network interface cards and/or wireless radios (e.g., a Bluetooth radio, a Bluetooth Low Energy (BLE) radio, a 4g LTE radio, a 5G radio, a ND-LTE radio, and the like).

The memory 5830 can include non-volatile memory and/or volatile memory. The non-volatile memory may include flash memory or solid-state memory.

The glucose level control system 5802 is also able to operate in an offline manner in which it is used to provide delivery of insulin (and potentially glucagon as well), independent of or without receipt of glucose levels reported by the glucose sensor 5808. For example, in cases where the glucose sensor 5808 needs replacing, is not properly connected to the subject 5804, or is defective, the glucose level control system 5802 may operate in an offline manner without input from the glucose sensor 5808. Thus, overall operation may be divided between online periods each including a succession of sampling intervals when a glucose level signal 5812 is available, and offline periods each including a succession of sampling intervals when the glucose level signal 5812 is either completely or intermittently unavailable. The description below uses the terms "online" and "offline" for these periods. Also, offline operation may be user-selected for some reason even when a glucose level signal 5812 is available for use.

User control inputs (user control inputs 5818 or USER CNTLs) may be provided via a local or remote user interface of some type. In some embodiments, the user interface may resemble that of conventional insulin pumps or similar devices, e.g., by including control buttons for commanding the delivery of a bolus and perhaps a small display. In other embodiments, the system may have a wired or wireless interface to a remote device that may incorporate a fuller-function user interface, such as a smartphone, smartwatch, laptop computer, desktop computer, cloud computing service, or other wearable device or computing device. In some cases, the wireless interface may provide access to a local area network, such as a personal home network, a company network, or otherwise. Alternatively, or in addition, the wireless interface may provide a direct connection between local devices available to a user (e.g., via Bluetooth or other near field communication technologies). In some cases, the wireless interface may provide access to a wide area network, such as, but not limited to, the Internet. For example, the wireless interface may include a cellular interface that permits access to a network via a 4G or 5G cellular connection. In some cases, the cellular interface may be a low power interface, such as narrowband LTE or other Internet of Things (IoT) interfaces.

In offline mode, the glucose sensor 5808 may be absent, non-functioning, or not coupled to the subject 5804. As such, in offline mode, the blood glucose level signal 5812 may not be available to control automatic operation. In some cases, a user may provide one or more blood glucose measurements to the glucose level control system 5802 to facilitate automatic operation of the control system 5802. These measurements may be provided over a particular time period. Alternatively, or in addition, the glucose level control system 5802 may use a therapy history and/or a history of prior glucose control measurements to facilitate automatic operation of the glucose level control system 5802 for at least a particular time period.

The description herein refers to a "user" as the source of the user control inputs 5818. The "user" as used herein may be the subject 5804, a parent or guardian of the subject 5804, a healthcare provider (e.g., a clinician, doctor, or other person who may provide medical care to the subject), or any other user who may be authorized to help manage therapy of the subject 5804. In certain implementations, the glucose level control system 5802 is a personal device worn by a subject 5804 for continual glucose control. In some such implementations, the user and subject 5804 may be the same person. In other implementations, there may be another person involved in the care of the subject 5804 and providing control input, and in such implementations, that other person has the role of user.

Example Controllers for a Glucose Level Control System

Figure 59:
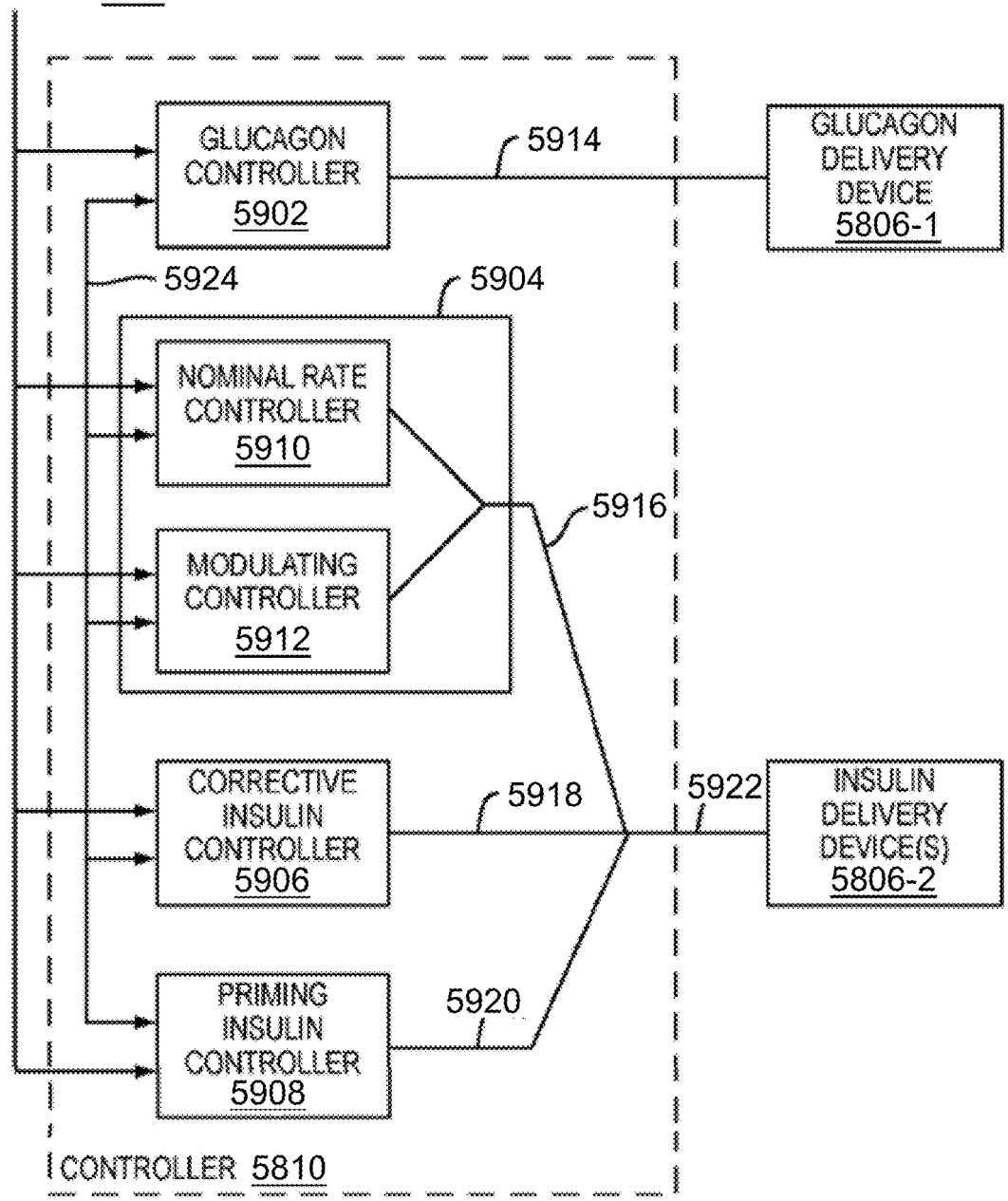
FIG. 59 illustrates a block diagram of a controller system in accordance with certain embodiments.

FIG. 59 shows an example structure of the controller 5810 in accordance with certain embodiments. The controller 5810 illustrated in FIG. 59 may represent a physical structure with different controllers or processors, or a logical structure that is implemented by one or more physical processors. In other words, a single processor may be used to implement each of the controllers illustrated in FIG. 59, each controller may be implemented by its own processor, or certain processors may implement multiple, but not necessarily all, of the controllers illustrated in FIG. 59 as part of the controller 5810. Moreover, although the controllers of FIG. 59 are illustrated as part of the controller 5810, in some implementations, one or more of the controllers may be separate from the controller 5810.

The controller 5810 may include four separate controllers, namely a glucagon (or counter-regulatory agent) glucagon controller 5902, a basal insulin controller 5904, a corrective insulin controller 5906 (or model predictive controller), and a priming insulin controller 5908 (or meal controller). The basal insulin controller 5904 includes a nominal rate controller 5910 and a modulating controller 5912. As shown, the glucagon controller 5902 generates a glucagon dose control signal 5914 provided to a glucagon delivery device 5806-1. Respective outputs 5916, 5918, and 5920 from the controllers 5904, 5906, and 5908 may be combined to form an overall insulin dose control signal 5922 provided to insulin delivery device(s) 5806-2. As shown, the output signal 5916 from the basal insulin controller 5904 may be formed by a combination of respective outputs of the nominal rate controller 5910 and a modulating controller 5912. The insulin delivery device(s) 5806-2 may include devices tailored to deliver different types and/or quantities of insulin, and the exact configuration may be known to and/or under the control of the controllers 5904-5908. For ease of description, the collection of one or more insulin delivery device(s) 5806-2 is referred below to in the singular as an insulin delivery device 5806-2.

Also shown in FIG. 59 are input/output signals of the various controllers, including the glucose level signal 5812, programmed input parameters (PARAMS)s 5814 and user control inputs 5818 as well as a set of inter-controller signals 5924. The inter-controller signals 5924 enable communication of information from one controller, where the information is developed or generated, to another controller where the information may be used for that controller's control function.

The controllers 5902-5908 may be operated in either the online/automatic mode or in the offline mode. In the automated mode, the corrective insulin controller 5906 regulates glucose level using a control scheme such as described in U.S. Pat. No. 7,806,854, the contents of which are hereby incorporated by reference in its entirety herein. The basal insulin controller 5904 and priming insulin controller 5908 may perform adaptive automated control as described in International Patent Application Publication WO 2012/058694 A2, the contents of which are hereby incorporated by reference in its entirety herein. The controllers 5902-5908 generally employ control methods or algorithms that include control parameters that are mathematically combined with reported glucose values to generate an output value that is converted (either directly or via additional conditioning) into the dose control signals 5914, 5922. For example, the control scheme described in U.S. Pat. No. 7,806,854 includes a generalized predictive control (GPC) method that incorporates a variety of control parameters. The control algorithms are generally adaptive, meaning that control parameters are dynamically adjusted during operation to reflect changing operating circumstances and a "learning" aspect—by monitoring its own operation, the algorithm adjusts its operation to be more specifically tailored to the individual user, enhancing the algorithm's effectiveness and reducing or avoiding a need for additional explicit input information about the user. It should be noted that the programmed input parameters (PARAMS)s 5814 may form part of the control parameters used by the control algorithm. Other control parameters are internal parameters according to the specifics of the algorithm, and selected ones of those internal control parameters are dynamically adjusted to realize the adaptation of the control algorithm.

One feature of operation is the ability of the controllers to learn from recent past periods of online operation and to use that learning during offline operation. U.S. Pat. No. 10,543,313, the contents of which are hereby incorporated by reference in its entirety herein, describes two methods that are usable independently or together in offline operation. A first method automatically calculates the correct size of a correction bolus of insulin at a time of receiving an isolated glucose measurement, the correction bolus then being administered by the system in response to a user control input. A second method automatically calculates the correct size of a meal bolus of insulin and administers it in response to a user control input. Both methods utilize information obtained during past periods of online operation to automatically calculate correct values, freeing the user of a need to make the calculation or provide a correction factor.

Carbohydrate Therapy Equivalence Tracking

Hyperglycemia is a condition that occurs when the levels of sugar or glucose in the blood exceeds a particular level (e.g., 180 mg/dL). This condition may occur in diabetics. To help reduce the occurrence of hyperglycemia, a subject may use an automated glucose level control system, which may automatically provide insulin to a subject using a medicament pump. The administered insulin may help control the blood glucose level of the subject by consuming glucose in the subject.

Hypoglycemia is a condition that occurs when the levels of sugar or glucose in the blood are below a particular level (e.g., 70 mg/dL). This condition may have adverse consequences including loss of consciousness, seizures, and death. The levels of blood sugar that lead to hyperglycemia and hypoglycemia may vary from patient to patient. To reduce the risk of hypoglycemia, a subject may consume carbohydrates to increase blood sugar. Because of the severe consequences associated with a hypoglycemic event, subjects usually consume carbohydrates that metabolize quickly. These carbohydrates are often unhealthy but are preferable to the occurrence of a hypoglycemic event. For example, the carbohydrates may include candy bars with a lot of refined sugar.

A bihormonal glucose-control system may reduce the risk of occurrence of hypoglycemia by including, in addition to insulin, a counter-regulatory agent (e.g., Glucagon) that can be administered to a subject when the blood glucose level drops too low (e.g., below 50 mg/dL). For subjects who do not have a bihormonal glucose-control system, it may be useful to understand the reduction in carbohydrate therapy, or the consumption of carbohydrates to address hypoglycemic events or potential hypoglycemic events, that can be achieved by switching to a bihormonal glucose-control system. Further, it may be useful for subjects who do have a bihormonal glucose-control system to understand the reduction in carbohydrate therapy obtained by having the bihormonal glucose-control system. For example, understanding the amount of carbohydrate therapy consumed or avoided can be important in monitoring the subject's nutrition intake. While monitoring nutrition in take is important for all people, it is particularly important for diabetics because diabetics must balance eating healthy with ensuring that their blood sugar is maintained in a particular range to avoid both hyperglycemia and hypoglycemia.

The present disclosure relates to a system that can perform a computer-implemented method of generating an indication of total carbohydrate therapy over a time period in a subject using a medicament pump configured to deliver at least insulin therapy to the subject. The system may be an automated glucose level control system (e.g., the glucose level control system 5802) that includes a hardware processor (e.g., controller 5810) for determining dose control signals to provide the medicament pump (e.g., delivery device(s) 5806). In some cases, the medicament pump may be configured to deliver both insulin therapy and counter-regulatory agent (e.g., Glucagon) therapy. Alternatively, the system may be separate from the glucose level control system but may receive blood glucose information from the glucose level control system. For example, the system may be personal computing system or a cloud computing system that can received blood glucose information from the glucose level control system.

The system may receive or determine a glucose level of a subject (e.g., subject 5804). The glucose level of the subject may be determined based on a signal (e.g., a glucose level signal) received from a continuous glucose monitoring (CGM) sensor (e.g., glucose sensor 5808) that corresponds to the glucose level of the subject. In some cases, the glucose level may be determined from an isolated glucose measurement, such as may be obtained using a glucose measurement kit and/or glucose paper.

Using at least the glucose level of the subject, the system can determine whether a triggering event for raising the subject's blood glucose level has occurred. The triggering event may include a blood glucose level that indicates an occurrence of a hypoglycemic event or a risk of the occurrence of a hypoglycemic event exceeding a risk threshold within a particular period of time. A risk of a hypoglycemic event may be determined when a glucose level of the subject falls below a glucose threshold. This glucose threshold may vary for different subjects and may, in some cases, be specified by the subject or a caregiver (e.g., healthcare provider, parent, or guardian). Thus, in some cases, different triggering events may be defined based on a risk tolerance of a subject to an occurrence of hypoglycemia or to possible different preferences for an amount of blood glucose to be present in the subject. Different subjects may prefer that blood glucose be maintained, or attempt to be maintained, at different levels due, for example, to differences in activity levels or metabolism by different subjects. Determining the risk of the occurrence of a hypoglycemic event may include receiving an indication of a risk of hypoglycemia from a glucose sensor or a prediction of a glucose level at a future time. For example, a determination of an imminent risk of hypoglycemia may comprise a determination that the subject's blood glucose level is expected to be below 60 mg/dl within the next 5-15 minutes.

Responsive to the triggering event, the system may determine an amount of counter-regulatory agent to administer, or an amount of counter-regulatory agent that would be administered if the glucose level control system included the capability of administering a counter-regulatory agent. In some cases, the counter-regulatory agent is administered by, for example, the automated glucose level control system. In other cases, the counter-regulatory agent is not administered. For example, the automated glucose level control system may not be capable of delivering the counter-regulatory agent. As another example, the automated glucose level control system may be capable of delivering the counter-regulatory agent but may not have a dose of the counter-regulatory agent available.

The system can use the indication of the counter-regulatory agent that is administered or that would be administered to determine a corresponding amount of carbohydrates. The corresponding amount of carbohydrates may be indicative of the amount of carbohydrates that were consumed to prevent the hypoglycemic event, to reduce the risk of the hypoglycemic event, or in response to an occurrence of a hypoglycemic event. Alternatively, or in addition, the corresponding amount of carbohydrates may be indicative of the amount of carbohydrates that would have been consumed if the counter-regulatory agent were not available.

The corresponding amount of carbohydrates may be obtained from a mapping between amounts of a counter-regulatory agent and amounts of carbohydrates. In some cases, the mapping may be based on a measured equivalency between carbohydrates and a counter-regulatory agent. Alternatively, or in addition, the mapping may be between a determined amount of counter-regulatory agent and an amount of carbohydrate a subject indicates he or she normally consumes when determining that a hypoglycemic event may occur.

The mapping may be implemented by a lookup table that maps different amounts of counter-regulatory agent to different corresponding amounts of carbohydrates. In some cases, a single quantity of counter-regulatory agent may map to different amounts of carbohydrates depending on the type of carbohydrate consumed (e.g., simple vs complex carbohydrates, or the type of candy bar consumed, etc.). Alternatively, the mapping may be based on a formula that converts an amount of counter-regulatory agent to an amount of carbohydrates based on a correspondence between the amount of counter-regulatory agent and the amount of carbohydrates. The determination of a relationship between the counter-regulatory agent and carbohydrates may be based on clinical tests comparing carbohydrates to the counter-regulatory agent (e.g., Glucagon, dextrose, etc.). Further, the mapping may be based at least in part on a subject's preferred carbohydrate source and/or characteristics of the subject (e.g., weight).

In some cases, the system can track a number of hypoglycemic events or a number of occurrences of a trigger indicating an impending risk of a hypoglycemic event within a particular time period. The time period may be days, weeks, months, years, or any other period of time over which it is desirable to determine a relationship between carbohydrates consumed or avoided based on the lack of availability or availability of a counter-regulatory agent. In some cases, the tracking of carbohydrate therapy may be based on a number of hypoglycemia events or hypoglycemia risk events instead of or in addition to a time period.

For each occurrence of a hypoglycemic event or occurrence of a trigger indicating an impending risk of a hypoglycemic event, the system can determine an estimate of the carbohydrate therapy saved or that would have been saved by having access to the counter-therapy agent. The system can generate a report for the time period that indicates the total carbohydrate saved or that would have been saved with access to counter-regulatory agent. The report may include an aggregate or sum of the carbohydrate therapy required or saved during the time period. This time period may be days, weeks, months, years, or since a particular time (e.g., since the subject starting using the system). Further, the report may indicate the type of carbohydrates typically consumed by the subject when responding to a hypoglycemic event or a risk of an impending hypoglycemic event. This report can be presented to the subject, a healthcare provider, and/or a parent or guardian of the subject. The healthcare provider can use this report to help care for the subject. For example, the healthcare provider can use the report to generate a nutrition plan for the subject that accounts for the carbohydrates consumed to maintain the blood glucose level within a desired or setpoint range.

The report may include a range of carbohydrate therapy avoided or likely consumed to address the risk of hypoglycemia events. Further, the report may include an amount of calories saved or not consumed, an amount of sugar avoided, an amount of food not consumed, a likely weight gain avoided, etc. based on the use of a counter-regulatory agent in place of carbohydrate therapy.

Carbohydrate Therapy Equivalence Tracking Process

Figure 60:
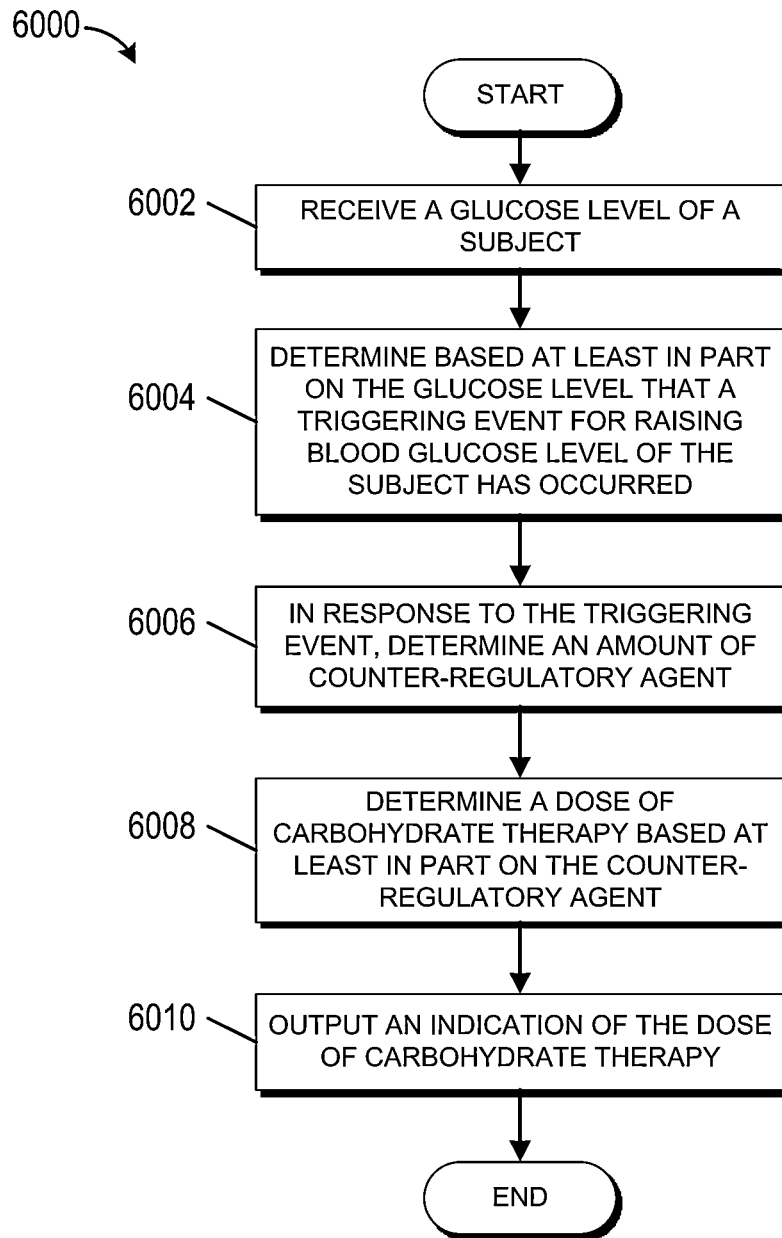
FIG. 60 presents a flowchart of an example carbohydrate therapy equivalence tracking process in accordance with certain embodiments.

FIG. 60 presents a flowchart of a carbohydrate therapy equivalence tracking process 6000 in accordance with certain embodiments. The process 6000 may be performed by any system that can track the glucose level of a subject over time and identify hypoglycemic events, or occurrences when a risk of a hypoglycemic event satisfies a threshold (e.g., when the risk of the hypoglycemic event matches or is above a particular probability). For example, the process 6000 may be performed by one or more elements of the glucose level control system 5802. In some cases, at least certain operations of the process 6000 may be performed by a separate computing system that receives indications of blood glucose levels of the subject 5804 from the glucose level control system 5802 and/or indications of hypoglycemic events (or identified above threshold hypoglycemic risk events). Although one or more different systems may perform one or more operations of the process 6000, to simplify discussions and not to limit the present disclosure, the process 6000 is described with respect to particular systems.

The process 6000 begins at block 6002 where the glucose level control system 5802 receives a glucose level of a subject 5804. Receiving the glucose level may include receiving a glucose level signal corresponding to a glucose level of the subject. The glucose level signal may be received from the glucose sensor 5808 (e.g., a CGM sensor). Alternatively, or in addition, the glucose level may be received from a user that provides the glucose level to the glucose level control system 5802 via a user interface, such as a user interface generated by the separate processor 5820 that may be output on a touchscreen by the touchscreen controller 5828. The glucose level received from the user may be a glucose level measured using an alternative sensor or measurement mechanism (e.g., diabetes measurement strips) that may be used in place of the glucose sensor 5808.

At bock 6004, the glucose level control system 5802 determines based at least in part on the glucose level that a triggering event for raising the blood glucose level of the subject 5804 has occurred. The triggering event may include a determination that a hypoglycemic event or an episode of hypoglycemia is present or is occurring in the subject 5804. Alternatively, or in addition, the triggering event may include a determination that there is an impending risk of hypoglycemia in the subject 5804, or an impending risk that a hypoglycemic event will occur within a particular amount of time in the subject 5804. The determination of the hypoglycemic event or the risk of a hypoglycemic event occurring may be determined by comparing the glucose level of the subject to a glucose threshold. Alternatively, or in addition, the determination of the hypoglycemic event or the risk of a hypoglycemic event occurring may be determined by comparing a trend and/or rate of change (e.g., rate of decrease) in the glucose level to a threshold. In some cases, the particular blood glucose level and the trend in the blood glucose level may be combined to determine a risk of hypoglycemia. For example, if the glucose level is low (e.g., below a particular threshold, such as 60 mg/dL), but a determined trend in the glucose level is upwards, then a risk of hypoglycemia may be lower than if the glucose level is above the threshold, but the determined trend in the glucose level is downwards towards a threshold. In some cases, the threshold(s) used to determine whether a hypoglycemic event is occurring or to determine that there is an above threshold risk of hypoglycemia occurring may vary based on physiological characteristics of the subject 5804. The physiological characteristics may be based on physiological characteristics associated or shared among groups of patients (e.g., gender, age, weight) or may be specific to the particular subject 5804. For example, thresholds associated with a risk of hypoglycemia may be determined based on determined glucose levels of the subject 5804 during prior occurrences of hypoglycemia as determined by the glucose level control system 5802 or based on clinical data specific to the subject 5804.

In response to the triggering event at the block 6004, the glucose level control system 5802 determines an amount of counter-regulatory agent at block 6006. The glucose level control system 5802 may determine the amount of counter-regulatory agent based at least in part on the blood glucose level of the subject 5804, the amount or percentage of risk of hypoglycemia occurring (e.g., a 99% risk or probability of hypoglycemia may trigger a larger counter-regulatory agent dose than a 75% risk or probability of hypoglycemia), physiological characteristics of the subject 5804, a trend in the blood glucose level of the subject 5804, or a type of counter-regulatory agent.

In some cases, the glucose level control system 5802 may use a delivery device 5806-1 to deliver the determined amount of counter-regulatory agent to the subject 5804. The counter-regulatory agent may be delivered to the subject 5804 in response to the impending risk of hypoglycemia or the episode of hypoglycemia, and/or in response to the glucose level satisfying or falling below a threshold glucose level. The threshold glucose level or the determination of whether to deliver the counter-regulatory agent may be based on physiological characteristics of the subject 5804 and/or the risk tolerance of the subject 5804 to a hypoglycemic event. It should be understood that, in the present context, risk tolerance generally does not refer to a user's subjective propensity for risk. Instead, the risk tolerance is typically an objective determination of how likely the subject 5804 is to have a hypoglycemic event, or for symptoms of hypoglycemia to occur, when the blood glucose level of the subject 5804 is at a particular level. This risk tolerance may be determined based on a history of hypoglycemia, or lack thereof, in the subject 5804 at particular blood glucose levels and/or based on clinical data obtained for the subject 5804.

In other cases, the glucose level control system 5802 may not deliver counter-regulatory agent to the subject 5804 because, for example, the glucose level control system 5802 may not be capable of delivering counter-regulatory agent or because the cartridge holding the counter-regulatory agent may be empty or have less than a threshold amount of counter-regulatory agent remaining.

At block 6008, the glucose level control system 5802 determines a dose of carbohydrate therapy based at least in part on the counter-regulatory agent. The carbohydrate therapy may refer to carbohydrates consumed to prevent or respond to an occurrence of hypoglycemia. The carbohydrates may include any type of carbohydrate that the subject 5804 may consume to prevent or respond to an occurrence of hypoglycemia, and typically includes fast-acting carbohydrates, which may include sugary foods that are easily converted into sugars in the human body. For example, the carbohydrate may be a candy bar, soda, fruit juice, or other foods that may have a lot of sugar or refined sugars.

Determining the dose of carbohydrate therapy may include accessing a mapping between the counter-regulatory agent and carbohydrates. This mapping may be stored in, and accessed from, the memory 5830 and/or may be accessed from another computing device. The glucose level control system 5802 may determine the dose of carbohydrate therapy based at least in part on the mapping and the amount of the counter-regulatory agent. In some cases, the mapping may vary based on the type of counter-regulatory agent and/or the type of carbohydrates. The type of counter-regulatory agent may be identified by a user or may automatically be determined based on a medicament cartridge installed or inserted into the glucose level control system 5802. Further, the type of carbohydrates may be specified by a user and may include an identity of the type of carbohydrates usually consumed by the subject 5804 when responding to an occurrence or a risk of an occurrence of hypoglycemia. For example, the user may specify, via a user interface, whether the subject usually consumes a candy bar or fruit juice, or the size of the carbohydrate usually consumed when responding to an occurrence or a risk of an occurrence of hypoglycemia.

In some cases, the mapping between the counter-regulatory agent and carbohydrates may be generated based on a clinical comparison of the counter-regulatory agent to the carbohydrates. Alternatively, or in addition, the mapping may be based at least in part on a physiological characteristic of the subject 5804.

The mapping may be stored in a lookup table or other data structure that can store relationships between different carbohydrates and counter-regulatory agents. The mapping may be between different quantities and/or types of carbohydrates and different quantities and/or types of counter-regulatory agent. Alternatively, or in addition, the mapping may be a formula that relates the carbohydrates to the counter-regulatory agent or vice versa. For example, the glucose level control system 5802 may use the determined amount of counter-regulatory agent as an index to a lookup table to determine a corresponding quantity of carbohydrates. Alternatively, the glucose level control system 5802 may apply the determined amount of counter-regulatory agent to a formula to calculate a corresponding quantity of carbohydrates. This formula may be generated based on the type of counter-regulatory agent and/or carbohydrates, physiological characteristics of the user, and/or clinical data.

In some cases, the mapping may vary based on the glucose level control system 5802. For example, the glucose level control system 5802 may include a first mapping when the glucose level control system 5802 (or medicament pump thereof) is a bi-hormonal pump configured to deliver insulin and counter-regulatory agent therapy to the subject, and may include a second mapping when the glucose level control system 5802 is not configured to deliver the counter-regulatory agent therapy to the subject 5804. In some cases, the glucose level control system 5802 may store both mappings in the memory 5830. For example, the glucose level control system 5802 may use the first mapping when counter-regulatory agent is available and may use the second mapping when counter-regulatory agent is not available. The mappings may vary for a number of reasons including because a bi-hormonal glucose level control system 5802 may more precisely control the occurrence of hypoglycemic events due to the availability of counter-regulatory agent, which may therefore alter the frequency and type of carbohydrates that a subject may consume.

At block 6010, the glucose level control system 5802 outputs an indication of the dose of carbohydrate therapy. Outputting the indication of the dose of carbohydrate therapy may include outputting an indication of the dose of carbohydrate therapy on a display for presentation to a user. Further, the indication of the dose of carbohydrate therapy may be transmitted to another computing system for display or aggregation with other therapy data associated with the subject 5804, such as therapy data used by a clinician to help manager the subject's 5804 care. In some cases, the indication of the dose of carbohydrate therapy may be included in a report corresponding to care of the subject 5804.

In certain embodiments, the operations of the process 6000 are performed or repeated over a period of time. For example, the operations associated with the block 6002-6008 may be repeated one or more times over the period of time. In such cases, the determined doses of carbohydrate therapy may be aggregated for the period of time to determine a total carbohydrate therapy for the period of time. Further, the block 6010 may include outputting an indication of the dose of carbohydrate therapy for each individual time that a dose of carbohydrate therapy is determined and/or the aggregated determined doses of carbohydrate therapy for the period of time. The period of time may be any time period. For example, the period of time may be a day, week, month, year, since the subject 5804 began using the glucose level control system 5802, since a user obtained or ceased obtaining access to a counter-regulatory agent, or any other period of time. In some cases, the period of time is defined by the occurrences of hypoglycemic events or occurrences of the risk of hypoglycemia satisfying a threshold. For example, the period of time may be the time associated with 5, 10, 15, 100, or any other number of hypoglycemic events or occurrences of the risk of hypoglycemia satisfying a threshold.

The indication of total carbohydrate therapy may correspond to a reduction in carbohydrates consumed by the subject 5804 because, for example, of the availability of counter-regulatory agent to the glucose level control system 5802, and consequently, the subject 5804. Thus, the indication of total carbohydrate therapy may correspond to a reduction in carbohydrates achievable by an availability to the subject 5804 of the counter-regulatory agent. Further, the indication of total carbohydrate therapy may correspond to an amount of counter-regulatory agent provided or that can be provided to the subject as a substitute for carbohydrates.

The particular carbohydrates consumed, or the amount of carbohydrates consumed by each subject or during each hypoglycemic event, may vary. For example, a subject 5804 may consume a particular candy bar when the subject's 5804 measured blood sugar level is too low or when the subject feels that the blood sugar level is likely low (e.g., begins to feel some hypoglycemic effects). The subject may consume the whole candy bar or may consume a portion. Some of the candy bar may be lost to the subject (e.g., fall on the ground). In other cases, the subject may have different candy bars available, or other refined sugar sources, during different hypoglycemic events. Thus, even though there may be an objective mapping between carbohydrates and counter-regulatory agent, the amount of carbohydrates consumed or avoided due to the availability of counter-regulatory agent may vary for each hypoglycemic event. Accordingly, the indication of total carbohydrate therapy avoided, or that could be avoided if counter-regulatory agent were available, may indicate a range of carbohydrates that may potentially be replaced by the availability of counter-regulatory agent.

In some cases, the indication of carbohydrate therapy or total carbohydrate therapy may include one or more of an indication of calories, an indication of carbohydrates, an indication of a measure of sugar, an indication of a quantity of food, or an indication of weight of the subject attributable to the carbohydrate therapy. The indications may be associated with what is consumed due to a lack of counter-regulatory agent, or what is avoided based on the availability of counter-regulatory agent. For example, the indication of calories may be the number of calories not consumed because of the presence of the counter-regulatory agent. Advantageously, the availability of therapy information relating to the carbohydrate therapy or avoided carbohydrate therapy can assist in patient care. For example, a subject can reduce refined sugar consumption that can have a number of health consequences. Further, a healthcare provider can better help a subject control his or her weight based on the carbohydrate information.

The indication of carbohydrate therapy may be presented to a user in any presentable form. For example, the indication of carbohydrate therapy may be presented as a table, a chart, a graph, a histogram, or other data presentation tool for indicating the reduction in carbohydrates over time that is achieved by the presence of counter-regulatory agent or that could be achieved by the use of counter-regulatory agent for the particular subject 5804. It should be understood that the indication of carbohydrate therapy data may vary for different users due to differences in physiological characteristics of the users, differences in the diabetes of each user, differences in lifestyle of each user, among other factors. Advantageously, by using the glucose level control system 5802 to track the carbohydrate therapy of the subject 5804 or to determine the carbohydrate therapy avoided or avoidable associated with counter-regulatory agent, management of the subject's 5804 blood glucose level can be personalized.

Additional Carbohydrate Therapy Equivalence Tracking Embodiments

People with diabetes often consume oral carbohydrates for the purpose of treating or preventing hypoglycemia. Such extra carbohydrates can have unhealthy consequences, contributing to weight gain being one of them. Having a bihormonal glucose-control system that infuses a counter-regulatory agent (e.g., Glucagon) to reduce the frequency, extent, and duration of hypoglycemia can significantly reduce the amount of oral carbohydrates that are needed "medicinally" to treat or prevent hypoglycemia.

Certain embodiments of the present disclosure relate to a method for translating an amount of online counter-regulatory dosing (e.g. glucagon) computed by an autonomous glucose-control system to an amount of carbohydrates that the user is estimated to have been spared from needing by virtue of the counter-regulatory dosing, or that the user would be spaced from needing if the user had access to the counter-regulatory agent. In a bihormonal autonomous glucose-control system that infuses both insulin and a counter-regulatory agent/hormone, the method may include a mapping between the online counter-regulatory dosing, which was delivered to treat or prevent low glucose levels, and oral carbohydrates that are estimated to have otherwise been required to achieve a comparable safe control situation (had the counter-regulatory dosing not been delivered). In an insulin-only autonomous glucose-control system, where doses of a counter-regulatory agent/hormone are not delivered, but are still computed online, the method may include a mapping between the computed online counter-regulatory dosing and an estimated amount of oral carbohydrates that the subject will likely have been spared from needing to consume to treat or prevent low glucose levels had the counter-regulatory agent been available and its doses actually delivered.

Without loss of generality, embodiments disclosed herein include an autonomous glucose-control system where the counter-regulatory agent is glucagon. However, other medicaments and/or counter-regulatory agents may be utilized. The method may include relating computed online glucagon dosing with consumed oral carbohydrates for the treatment or prevention of low glucose levels ("treatment carbs") as observed in real use (e.g., during clinical studies) in the insulin-only configuration, and relating the relationship between the counter-regulatory agent and carbohydrates to a similar relationship between delivered online glucagon doses (or other counter-regulatory agent) and similarly consumed oral carbohydrates in the bihormonal (insulin-glucagon) configuration.

Using data gathered from real use (e.g., clinical studies), a relationship between the consumed treatment carbs in an insulin-only configuration, $C_{io}$, and the online computed (but not delivered) glucagon dosing, Gc, can be described by the relationship $C_{io}=R_{io}(x)*Gc$, where $R_{io}(x)$ may be a relating factor that can be a function of several dependencies that are included in vector x. Such dependencies can include the specific insulin and/or glucagon being used (e.g., their clinical properties), and/or the pharmacokinetic settings assumed by the control system in relation to insulin and/or glucagon. The dependencies can also include the user's body mass and the glucose target used by the glucose-control system. In some embodiments, $R_{io}(x)$ may be a constant, or $R_{io}(x)=R_{io}$, for a system exhibiting limited variation in the relationship between $C_{io}$ and $G_c$ (e.g., due to limited effect, or limited or no variation in the associated dependencies).

Similar to the insulin-only configuration, from real-use data, a relationship between the consumed treatment carbs in a bihormonal (insulin-glucagon) configuration, $C_{bh}$, and the online delivered glucagon dosing, $G_d$, can be described by the relationship $C_{bh}=R_{bh}(x)*G_d$, where $R_{bh}(x)$ may be described in a similar fashion to $R_{io}(x)$ above. In some cases, the quantities $C_{io}$, $G_c$, $C_{bh}$, and $G_d$ can refer to daily amounts, as averaged over some period of use (e.g., a week). In some cases, the quantities $C_{io}$, $G_c$, $C_{bh}$, and $G_d$ can refer to average daily amounts per body mass of the user, in which case dependency on body mass can be eliminated from x.

In cases where $G_c$ is computed, but no glucagon is actually delivered in an insulin-only system, $G_c$ has no effect on glucose insofar as treating or preventing low glucose levels, which in turn is generally expected to invoke further computed glucagon dosing (e.g., goes towards increasing the magnitude of $G_d$ for a given situation). By contrast, since $G_d$ is delivered in a bihormonal system, it is expected to have an effect in preventing or reducing the frequency, extent, or duration of low glucose levels, which in turn is expected to limit the overall magnitude of glucagon dosing (e.g., limits $G_d$ for a given situation). As such, for a given set of dependencies, it is generally expected that $G_c > G_d$ between the two system configurations. Likewise, since $G_c$ has no effect in combating low glucose levels while $G_d$ does have such an effect, it is expected that treatment carbohydrates $C_{io} > C_{bh}$, when comparing the two system configurations.

If one can ideally relate, for a given real-use case of an insulin-only system with Gc, what the corresponding $C_{io}$ would have been for the same real-use scenario, had the computed online glucagon dosing actually been delivered as $G_d$, one can project an estimate that the user would have required "$C_{io}-C_{bh}$" less treatment carbs (e.g., would have saved that much), had they instead been using a bihormonal system (with the same insulin controller), where glucagon would have been delivered. Conversely, if one can ideally relate, for a given real-use case of a bihormonal system with $G_d$, what the corresponding $C_{bh}$ would have been for the same real-use scenario, had the delivered online glucagon dosing not been delivered but only computed as $G_c$, one can project an estimate that the user had actually avoided the need to take "$C_{io}-C_{bh}$" additional treatment carbs, had they been instead using an insulin-only system (with the same insulin controller), where glucagon would not have been delivered. It should be understood that the above calculations are an estimate in an ideal situation as, in practice, it is not possible to have a re-run of a past real-use scenario to obtain such ideal relationships.

For practical implementation, real-use cases where the insulin-only system is used can be re-simulated while assuming a bihormonal system is available, where glucagon is assumed to be delivered. Since the control system may take delivered doses into account when issuing subsequent nearby glucagon doses, the simulated glucagon dosing may exhibit a reduction relative to the original $G_c$ of the insulin-only system. With the glucose profile kept unaltered in a simulation, the simulation may lack reflecting any resulting glucose excursions in response to the assumed delivered glucagon dosing. The simulation in turn may lack reflecting the full reduction in glucagon dosing down to $G_d$ that may have been observed if the glucose excursions had in fact benefited from glucagon being delivered. Thus, the reduced glucagon dosing that is observed in the simulation, pseudo delivered glucagon $a_d$, may arguably be exaggerated in magnitude relative to what would have been the "real $\hat{G}_d$". As described above, based on prior analyses $G_c$ can be mapped to a corresponding amount $C_{io}$ in the insulin-only configuration, and $\hat{G}_d$ can be mapped to a corresponding amount $\hat{C}_{bh}$ in the bihormonal configuration. The simulation results, therefore, can map the reduction "$G_c-\hat{G}_d$" to an estimate "$C_{io}-\hat{C}_{bh}$" of treatment carbs that the user would spare had they been using the bihormonal system. The estimates may be conservative estimates. Repeating the simulation analyses across a variety of real-use cases that span the range of $G_c$ observed in practice provides a global mapping between them and the associated range of (in some cases, conservative) estimates "$C_{io}-\hat{C}_{bh}$" of treatment carbs that the user would likely not need to consume had they been using the bihormonal system. Conversely, the mapping can be utilized when a bihormonal system is being used, where the observed dosing $G_d$ is mapped back to a pseudo glucagon $\hat{G}_c$ and the resulting associated difference "$\hat{C}_{io}-C_{bh}$" provides a (in some cases, conservative) estimate of the treatment carbs that the user had likely saved by virtue of being on the bihormonal system.

Certain embodiments includes a system that comprises a controller for automatic control of a blood glucose level of a subject. The controller may be operative to generate an insulin dose control signal based on time-varying glucose levels of the subject as represented by a glucose level signal over time. The glucose level signal can be generated by a glucose sensor operative to continually sense a glucose level of the subject. The insulin dose control signal may control the delivery of doses of insulin by a delivery device. Further, the controller can operate at a regular frequency to generate an insulin dose control signal to regulate the glucose levels in the subject. During online operation, the controller can employ a control algorithm that generates a glucagon dosing signal, which may be mapped to an associated amount of oral carbohydrates.

The oral carbohydrates may be associated with the prevention or treatment of low glucose levels. Further, the mapping between the glucagon dosing signal and the oral carbohydrates may be derived from analysis of clinical data. The glucagon dosing signal may be computed, but not delivered in an insulin-only system configuration. In contrast, the glucagon dosing signal can be computed, and glucagon can be delivered in an insulin-glucagon system configuration. The computed glucagon dosing in an insulin-only system configuration can be mapped to an amount of oral carbohydrates that is estimated to have been saved had glucagon dosing been delivered if an insulin-glucagon system configuration had instead been used. The delivered glucagon dosing in an insulin-glucagon system configuration can be mapped to an amount of oral carbohydrates that is estimated to have been saved if an insulin-only system configuration had instead been used. The mapping may be dependent on the clinical properties of the insulin and glucagon being used, and settings in the control system related to the action and effect of insulin and glucagon. Further, the mapping may be dependent on the subject's body mass.

Backup Therapy Protocol Generation

An ambulatory medicament device, such as a glucose level control system (e.g., an insulin pump or a combined insulin and counter-regulatory agent (e.g., Glucagon) pump), can provide personalized therapy to a subject. In other words, the ambulatory medicament device may provide medicament that is specific to a subject's physiology, condition, activity, and the like. Further, some ambulatory medicament device's monitor a condition of the subject to determine when to provide therapy, what type of therapy to provide (e.g., insulin or counter-regulatory agent therapy), and/or how much therapy to provide. The therapy provided by the ambulatory medicament device may be ongoing and, in some cases, lifesaving. Thus, it is important that ambulatory medicament device function uninterrupted.

Despite best efforts, sometimes therapy by the ambulatory medicament device is interrupted. For example, the ambulatory medicament device may break, a subject may run out of or not have access to a necessary disposable (e.g., a replacement insulin cartridge, a site kit for changing the site of the ambulatory medicament device, a replacement battery, and the like), or the subject may forget to charge a battery of the ambulatory medicament device or not be in a location where a power source is available to charge the ambulatory medicament device. Thus, there are occasions when the ambulatory medicament device may not be available or may need replacing.

When the ambulatory medicament device is not available, or when a replacement (temporary or permanent) ambulatory medicament device is being used, it may be desirable to have an indication of the therapy settings from the ambulatory medicament device. For example, if a user (e.g., a subject, healthcare provider, parent, or guardian) is providing alternative therapy (e.g., injection therapy) while the ambulatory medicament device, it may be necessary to know the quantity of therapy to provide under particular circumstances or at particular times.

In some cases, a healthcare provider may have access to therapy information that may have been previously determined, for example, via clinical testing. This therapy information may include any type of information that can be used to determine therapy to provide to a subject at a particular time or under particular conditions. For example, the therapy information may indicate a setpoint insulin range for the subject, a quantity of insulin to provide to the user to adjust glucose levels, an amount of time for insulin to reach max concentration in the subject, or any other information that might impact the timing or amount of dosing of a medicament.

The therapy information available to the healthcare provider may be insufficient. For example, the subject may not be able to reach the healthcare provider to obtain the therapy information at a point in time when the information is needed. Further, in some cases the information may be outdated because, for example, the ambulatory medicament device may have refined the therapy over time. If the refinements have occurred recently, it is possible that the outdated values of the healthcare provider may be sufficient until a replacement ambulatory medicament device can repeat the refinement process of the original ambulatory medicament device. In other cases, the outdated therapy information may be insufficient because, for example, the refinements were significant or the subject may have had physiological changes (e.g., weight gain or weight loss, or metabolism changes) since the last time a clinical test was performed. Using outdated therapy information may be less effective and may cause discomfort or harm to a subject.

Certain embodiments of a system disclosed herein can generate backup therapy data. Using the backup therapy data, a subject (or user) can perform injection therapy or configure a replacement ambulatory medicament device if the subject's current device malfunctions. By using the backup therapy data, the subject can maintain a level of therapy care that matches or more closely matches what was being provided by the ambulatory medicament device than clinical data, which may be outdated if available at all.

The system can include an automated glucose level control system (e.g., the glucose level control system 5802) configured to generate a backup therapy protocol comprising insulin therapy instructions derived from autonomously determined doses of insulin. During normal operation, the system may receive glucose level signals from a sensor operatively configured to determine glucose levels in a subject. The sensor can include any type of sensor that can determine glucose levels. For example, the sensor may be a Continuous Glucose Monitoring (CGM) sensor.

Using the determined glucose levels, the system may autonomously determine and/or generate a dose control signal using a control algorithm. The determination and/or generation of the dose control system may be performed without any user action or interaction with the glucose control signal. In some cases, the lack of user action or interaction with the glucose level control system refers to conscious action and may exclude sensor measurements of physiological characteristics of the subject. The control algorithm may autonomously determine doses of insulin to be infused into the subject for the purpose of controlling blood glucose of the subject based at least in part on the glucose level signal. The control algorithm may include any type of control algorithm.

For example, the control algorithm may be a bi-exponential pharmacokinetic (PK) model that models the accumulation of insulin doses in the blood plasma of the subject. The automated blood glucose system may control delivery or administering of insulin or a counter-regulatory agent based on the bi-exponential PK model and one or more blood glucose measurements of the subject. The bi-exponential PK model may model the absorption of subcutaneously administered insulin into blood and/or a rate of diminishing glucose in the blood. The bi-exponential PK model over time may be represented by the following equation:

$$p(t)=KU_0(e^{-\alpha_1 t}-e^{-\alpha_2 t}) \quad (1)$$

where $U_0$ is the subcutaneous dose in units (U), K is a scaling constant, and $\alpha_1$ and $\alpha_2$ are time constants.

As an alternative example, the control algorithm may include a linear algorithm that models diminishing glucose or the accumulation of glucose in the subject based on a linear reduction rate. For example, the control algorithm may determine that a particular dose, D, of insulin is to be administered to the subject. The control algorithm may then estimate that 0.25*D of the insulin is absorbed into the blood plasma per hour over 4 hours. Similarly, the control algorithm may estimate that the insulin diminishes at a rate of 0.33*D per hour over three hours upon the insulin reaching maximum concentration within the blood plasma.

Regardless of the control algorithm used, the automated glucose level control system may administer insulin and, in some cases, a counter-regulatory agent one or more times over a particular time period. There may be multiple reasons and/or triggers that cause the automated glucose level control system to supply insulin. For example, the automated glucose level control system may provide a basal does of insulin on a periodic basis in an attempt to maintain a steady blood glucose level in the blood plasma of the subject. As another example, the automated glucose level control system may supply mealtime boluses of insulin to account for an expected amount of glucose to be consumed as part of a meal. The mealtime bolus may be an amount specified by a user or may be an amount of insulin administered in response to an indication of meal size by the subject. This indication of meal size may be subjective. In some cases, the size of the bolus of insulin for an identified meal size may be a fixed or constant value. In some other cases, the size of the bolus of insulin for an identified meal size may vary over time as the automated glucose level control system learns or refines the amount of insulin to administer to a subject to keep the subject's blood glucose within a target setpoint. The automated glucose level control system may learn or refine the optimal insulin to administer based on a comparison of expected blood glucose level measurements to actual blood glucose level measurements when the subject (or other user) makes a subjective identification of meal size. In addition to basal and mealtime boluses of insulin, the automated glucose level control system may also supply correction doses of insulin to the subject based on the glucose level signal. The correction doses of insulin may be supplied in response to a model predictive controller (MPC) determining or estimating that a user's level of insulin is expected to fall below a threshold in some future period of time based on blood glucose level readings. The MPC may execute a control algorithm that can regulate glucose concentration to a reference setpoint while simultaneously minimizing both the control signal aggressiveness and local insulin accumulation. A mathematical formulation describing the subcutaneous accumulation of administered insulin may be derived based on nominal temporal values pertaining to the pharmacokinetics of insulin in the subject. The mathematical formulation may be in terms of the insulin absorption rate, peak insulin absorption time, and/or overall time of action for the insulin (or another medicament). Examples of an MPC controller that may be used with embodiments of the present disclosure are described in U.S. Pat. No. 7,806,854, issued on Oct. 5, 2010, the disclosure of which is hereby incorporated by reference in its entirety herein for all purposes.

The automated glucose level control system may track insulin therapy administered to the subject over a tracking period. Although the tracking period is not limited in length and may generally be any period of time, typically the tracking period is at least a minimum period of time sufficient for the automated glucose level control system to learn or refine the amount of medicament (e.g., insulin) to administer to the subject under particular conditions (e.g., when particular blood glucose levels are detected or when particular meal sizes are identified). For example, the automated glucose level control system may initially administer 6 units of insulin for lunch and 10 units of insulin for dinner. These initial values may be set be a healthcare provider and/or a subject based, for example, on clinical data for the subject. However, over time (e.g., 3-5 days), the automated glucose level control system may determine that providing 7 units of insulin for lunch and 8 units of insulin for dinner maintains the subject's blood glucose level closer to the median of the setpoint range than did the initial configuration. Although not limited as such, generally each unit of insulin is $\frac{1}{100}^{th}$ of a milliliter of insulin.

As indicated, the tracking period can be any length of time. For example, the tracking period could be 1 day, 3 days, 5 days, 7 days, anything in between, or more. Typically, the tracking period is at least long enough to provide sufficient time to learn or refine initial settings of the automated glucose level control system for the subject. In some cases, the tracking period may be 1 or 2 days. In other cases, the tracking period may be from a particular time period until a current time period. For example, the tracking period may be from the start of therapy until a current point in time. In other cases, the tracking period may be a moving or shifting window. For example, the tracking period may be the least week, two weeks, month, or year. Further, for non-blood glucose systems, the tracking period may differ based on the amount of time sufficient to determine or refine medicament control values for the subject. In some cases, the tracking period may a window of a particular length. This window may be a moving window. For example, the window may be the previous 7 days. As time passes, the window moves to continue to encompass the previous 7 days.

Tracking the insulin therapy may include storing the autonomously determined doses of insulin delivered to the subject. These autonomously determined doses of insulin may include one or more of basal insulin doses, mealtime insulin boluses, or correction insulin doses. Moreover, tracking the insulin therapy may including tracking the type of insulin used. The type of insulin may include any type of insulin, such as fast-acting insulin (e.g., Lispro, Aspro, or Glulisin), regular or short-acting insulin (e.g., Humulin R, Novolin R, or Velosulin R), intermediate-acting insulin (e.g., Humulin N, Novolin N, ReliOn), long-acting insulin (e.g., detemir (Levemir), and glargine (Basaglar, Lantus)), or Ultra long-acting insulin (e.g., degludec (Tresiba), glargine u-300 (Toujeo)). Further, tracking the insulin therapy may include tracking counter-regulatory agent (e.g., Glucagon) therapy.

In some cases, tracking the insulin therapy may include calculating average therapy provided over a period of time (e.g., over the tracking window). For example, the tracking the insulin therapy may include determining a moving average of the past 7 days of nominal basal doses during each dosing interval. Assuming basal therapy is provided every five minutes, the moving average may be calculated based on the previous 288 doses (e.g., over 1 day) or 2016 doses (e.g., over 7 days). This calculation can be used to obtain a basal rate profile for backup therapy. In some cases, the time period may be broken up into different time segments that may be associated with different rates of therapy. For example, there may be 4 basal therapy periods (e.g., 10 pm-4 am, 4 am-10 am, 10 am-4 pm, and 4 pm-10 pm). Thus, a separate moving average may be calculated for each of the basal therapy periods over a day, or over some other time period (e.g., 7 days). The calculated averages may be used to calculate a backup basal rate that can be used to program an automated glucose level control system. Further, the basal rate profile may include aggregating the doses across the day to determine a dose of long-acting insulin that can be used for injection therapy.

Similar to the basal therapy, a moving average of correction doses can be calculated to determine a correction bolus of insulin to supply via a pump or injection therapy. Alternatively, or in addition, the moving average of correction doses in combination with measurements of blood glucose of the subject over time may be used to determine a rate of change of blood glucose from a unit of insulin provided during correction therapy.

Mealtime boluses may also be calculated using a moving average. Further, a separate moving average may be calculated for each meal (e.g., breakfast, lunch, and dinner) dose over some period of time (e.g., 7 previous days of mealtimes). In some cases, each of the moving averages may be calculated using different windowing functions. For example, the moving average may be calculated using a Hann window or a Hamming window. In some cases, different levels of dosing may be determined for different meal sizes and different doses may be determined for different meals. In some cases, different meals (e.g., breakfast vs lunch) may have different dosing despite similarity in size due, for example, to differences in the subject's blood glucose levels when they wake up versus when they usually have lunch, or because differences in types of foods consumed at breakfast versus lunch. Further, in some cases, differences in metabolisms of different subjects may result in different mealtime boluses.

The insulin therapy may be stored in a therapy log, or any other type of data structure. Further, the insulin therapy may be stored in a memory of the automated blood glucose system, on a companion device, on a computing device of the subject or user (e.g., a laptop or desktop), in a cloud computing environment, or in any other storage system capable of receiving the insulin therapy information from the automated glucose level control system.

Using the therapy log or tracked insulin data, the automated blood glucose system, or a computing system with access to the therapy log or tracked insulin data, may generate a backup insulin therapy protocol. The backup insulin therapy protocol may include a backup injection therapy protocol or a backup pump therapy protocol. The backup injection therapy protocol may include one or more amounts of insulin (or other medicament) to administer using injection therapy (e.g., manually provided shots) at one or more times to help maintain the subject's condition within a normal or desired physiological range or condition. The backup pump therapy protocol may include data and/or instructions for a replacement medicament pump of the same type or of a different type to supply therapy to the subject. The replacement medicament pump may be a permanent replacement or a temporary replacement.

The backup pump therapy protocol may be the same as and/or include the same type of information as the backup injection therapy protocol. Alternatively, or in addition, the backup pump therapy protocol may include different values than the backup injection therapy protocol. For example, the backup pump therapy protocol may include an indication of basal therapy to provide periodically on relatively short increments (e.g., every 5 minutes, every half hour, every hour, etc.). Because an insulin pump may automatically administer insulin, it is possible to provide a steady or periodic drip of insulin. It may be impractical for a subject using injection therapy to administer insulin manually on similar short increments. Instead, a user might administer therapy on a less regular basis (e.g., once every roughly 4-5 hours or 6-8 hours, prior to mealtimes, after waking, and/or before sleeping, etc.). Accordingly, the backup therapy protocol for a pump and for injection may differ. Further, the type of insulin used or identified in the backup protocol may differ. For example, the backup protocol may call for use of long-acting insulin, such as, for example, insulin glargine, or intermediate-acting insulin, such as, for example human recombinant insulin.

In some cases, the backup pump therapy protocol may be used to manually refine pump settings for a replacement glucose level control system to be used by the subject. In other cases, the replacement glucose level control system may automatically configure itself based on the backup therapy protocol. For example, a user may cause the backup therapy protocol to be provided to the replacement glucose level control system, which may use the information to self-calibrate.

Regardless of whether a backup protocol is generated or needed, collecting and analyzing therapy data for therapy provided by the automated glucose level control system can be useful for helping to manage a subject's condition. For example, therapy data may be useful in determining whether the subject is satisfied with therapy provided by the automated glucose level control system or whether the glucose level control system is configured in a way that best matches the subject's lifestyle or therapy preferences (subjective or otherwise). One way to determine whether the glucose level control system is providing desired therapy, or therapy at a desired rate, is to determine the frequency and/or magnitude of modifications made by the subject, or other user that may help manage a subject's therapy, to therapy provided by the automated glucose level control system.

The automated glucose level control system disclosed herein can track user modifications to a control parameter over a tracking period. The tracking period may include any time period described above for tracking therapy to generate a backup protocol. Further, the control parameter may include any type of control parameter that may affect the administering of therapy. For example, the control parameter may relate to a quantity of therapy, a timing of delivered therapy, a rate that therapy is delivered, or a trigger of when or whether to deliver therapy, among other control parameters. Moreover, the control parameters may directly affect the delivery of therapy (e.g., specify a time to deliver the medicament or a quantity of medicament to deliver) or may indirectly affect therapy (e.g., adjust a setpoint range to maintain blood glucose or a rate of insulin accumulation in the subject, which may be used to modify a control algorithm for administering therapy).

The user modifications may include any change to the control parameter or settings of the automated glucose level control system. For example, the automated glucose level control system may track each instance and/or the rate or percentage of times a user reduces or increases a control parameter (e.g., an amount of administered insulin). Further, tracking changes to the control parameter may including tracking how often a user pauses therapy or temporarily adjusted a target blood glucose range, or other control parameter. In addition, tracking changes to the control parameter may include tracking when a user makes changes to the control parameter. For example, the user may generally modify the control parameter at night, but leave the daytime parameter unchanged, or vice versa. In some cases, the automated glucose level control system may track a subject's weight over time. The weight may be provided by a user and may affect the glucose control (e.g., an amount of insulin administered may be related to a subject's weight).

The automated glucose level control system may generate a report that tracks user modifications to the control parameter. The report may comprise a measure of the frequency of increases and decreases from the stored control parameter value. Further, the report may include an indicator of a percentage of times a user modified a control parameter higher or lower than the stored control parameter value of the automated glucose level control system over the tracking period. In some cases, the report indicates the number of times that the infusion of insulin is paused over the tracking period, or the speed (e.g., aggressiveness) that insulin is delivered to the subject.

Using this report, a clinician or other healthcare provider can determine whether modifications should be made to a control parameter to better manage a subject's therapy. For example, if it is determined that a subject is raising a blood glucose target level 4-5 times a week during an evening time or nighttime, the clinician may determine that the target setpoint for the evening should be adjusted to reduce the number of occurrences that a user manually adjusts therapy, or control parameter settings for therapy, provided by the automated glucose level control system. In some cases, the subject may be adjusted therapy based on subjective reasons. In some such cases, the therapy report may enable the clinician or healthcare provider to train the subject on controlling his or her disease. In other cases, the clinician may determine that the subject has a different tolerance for blood glucose than initially determined or than an average subject and may adjust one or more control parameters of the automated glucose level control system accordingly.

In some implementations, the automated glucose level control system may automatically adjust one or more control parameters over time based on the report. For example, if the automated glucose level control system determines that over a course of a month the subject adjusted lower a daytime target glucose range 20 out of 30 days, the automated glucose level control system may modify a control parameter to have a lower setpoint range. In some cases, the automated glucose level control system may communicate the change to a user, such as the subject, a parent or guardian, or a healthcare provider.

Example Backup Therapy Protocol Generation Process

Figure 61:
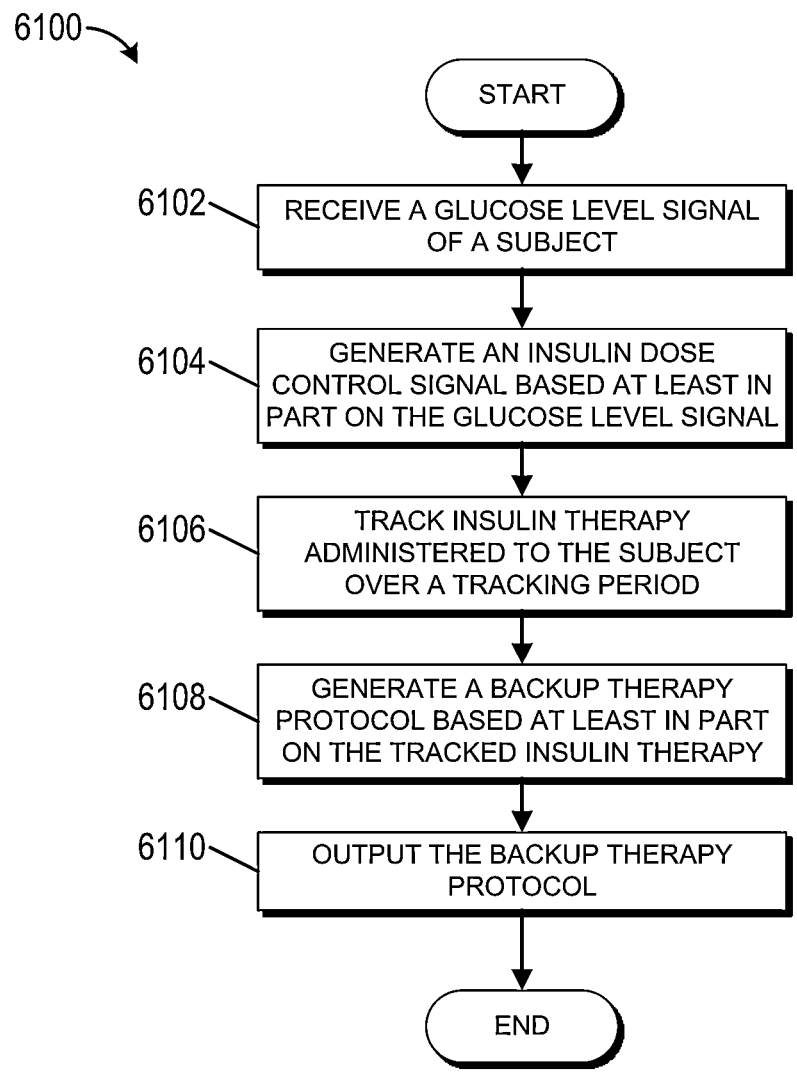
FIG. 61 presents a flowchart of an example backup therapy protocol generation process in accordance with certain embodiments.

FIG. 61 presents a flowchart of an example backup therapy protocol generation process 6100 in accordance with certain embodiments. The process 6100 may be performed by any system that can track medicament therapy (e.g., insulin therapy) provided to a subject over time and generate a backup therapy protocol that may be used if a glucose level control system 5802 becomes unavailable. For example, the process 6100 may be performed by one or more elements of the glucose level control system 5802. In some cases, at least certain operations of the process 6100 may be performed by a separate computing system that receives indications of medicament therapy provided to the subject 5804 from the glucose level control system 5802. Although one or more different systems may perform one or more operations of the process 6100, to simplify discussions and not to limit the present disclosure, the process 6100 is described with respect to particular systems.

The process 6100 begins at block 6102 where the glucose level control system 5802 receives a glucose level of a subject 5804. Receiving the glucose level may include receiving and/or determining a glucose level signal corresponding to a glucose level of the subject. The glucose level signal may be received from the glucose sensor 5808 (e.g., a CGM sensor). Alternatively, or in addition, the glucose level may be received from a user that provides the glucose level to the glucose level control system 5802 via a user interface, such as a user interface generated by the processor 5820 that may be output on a touchscreen by a touchscreen controller 5828. The glucose level received from the user may be a glucose level measured using an alternative sensor or measurement mechanism (e.g., diabetes measurement strips) that may be used in place of the glucose sensor 5808.

At block 6104, the glucose level control system 5802 generates an insulin dose control signal based at least in part on the glucose level signal. In some cases, the insulin dose control signal may be a medicament control signal configured to control a medicament pump to administer medicament (e.g., insulin, counter-regulatory agent, or other medicament) to a subject 5804. The dose control signal may be generated using a control algorithm configured to autonomously determine doses of insulin to be administered to or infused into the subject for the purpose of controlling blood glucose of the subject based at least in part on the glucose level or glucose level signal determined at the block 6102.

At block 6106, the glucose level control system 5802 tracks insulin therapy administered to the subject 5804 over a tracking period. The tracking period is typically at least one day and may be longer. For example, the tracking period may be 1 day, 2 days, a week, a month, several months, a year, any length of time between the foregoing examples, or even longer. In some cases, the tracking period may be continuous from a point in time when tracking begins. For example, the tracking period may encompass the entire usage lifetime of the glucose level control system 5802 by the subject 5804. In cases where the tracking period is set for a defined period of time (which may be modified for different iterations of the process 6100), the process 6100 may be repeated periodically, upon request, or upon a triggering event using a new tracking period, of equal or different length. The triggering event may include any event that may render a prior generated backup therapy protocol potentially out-of-date. For example, the triggering event may include a change in medicament type (e.g., different insulin or counter-regulatory agent formulations), a change in physiological characteristics of the subject 5804 (e.g., a change in weight, or sensitivity to different glucose levels or medicament), or a change in average activity level of the subject 5804.

Although the tracking period is typically at least one day enabling the glucose level control system 5802 to determine a backup protocol based on data from a full cycle (e.g., waking and sleeping hours) of glucose level control system 5802 use, in some cases, the tracking period may at least initially be less than a day. For example, an initial backup therapy protocol may be generated after a half-day's activity. This initial backup therapy protocol may be updated as more data becomes available throughout the day's (and, in some cases, subsequent day's) use of the glucose level control system 5802.

In some cases, the tracking period may be defined by or based on a particular number of insulin administering events. For example, the tracking period may be defined by at least ten instances of generating an insulin dose based on a glucose level signal. As another example, the tracking period may be defined by a minimum number of meal events, correction dose events, and/or basal dose events. For instance, the tracking period may require 3 meals, or 3 meals of each meal type to occur, 2 correction doses, and/or 100 basal doses. It should be understood that the aforementioned number of doses is just an example, and the tracking period may include more or fewer dose amounts. Moreover, the tracking period may be defined or specified as a combination of time and occurrences of a particular number of doses of insulin.

In some cases, the tracking period may be variable. For example, if the glucose level control system 5802 determines that the insulin dose therapy is inconsistent or erratic over the tracking period (e.g., due to inconsistent exercise or eating habits), the tracking period may be extended.

Tracking the insulin therapy may include storing the insulin dose control signal generated based at least in part on the glucose level signal at the block 6104. Alternatively, or in addition, tracking the insulin therapy may include storing an indication of a quantity of insulin (or other medicament) corresponding to the insulin (or another medicament) dose control signal. The insulin dose control signal and/or the indication of the quantity of insulin may correspond to a dose of insulin delivered to the subject 5804 as a basal insulin dose, a correction bolus of insulin, and/or as a mealtime bolus of insulin.

Storing the insulin dose control signal and/or the indication of the quantity of insulin may include storing the insulin dose control signal and/or the indication of the quantity of insulin in a therapy log or any other type of data structure in the memory 540 of the glucose level control system 5802. Alternatively, or in addition, the glucose level control system 5802 may store the insulin dose control signal and/or the indication of the quantity of insulin at a remote data store. This remote data store may be a local computing system with which the glucose level control system 5802 may communicate (e.g., a laptop, desktop, smartphone, or other computing device of the subject 5804 or a user). The glucose control system 5802 may provide the insulin dose control signal data or the indication of the quantity of insulin to the local computing system via Bluetooth® or other near field communication services, or via a local network. Alternatively, or in addition, the remote data store may be a remote computing system that the glucose level control system 5802 may communicate with over a wide area network, such as a wireless area network, a cellular network using IoT based communication technology, cellular communication technology, or any other communication network. In some cases, the wide area network may include the Internet. The glucose level control system 5802 may include a wireless radio that enables it to communicate with the local or remote computing system. Further, the remote computing system may be a computing system of a data center or a cloud computing environment.

Whether a local or remote computing system, the glucose level control system 5802 may establish a communication channel with the computing system. This communication channel may be an encrypted channel. Further the communication channel may be a direct end-to-end connection between the glucose level control system 5802 and the computing system. Once the communication channel is established, the glucose level control system 5802 may transmit the insulin dose control signal data or the indication of the quantity of insulin to the computing system.

Generally, the operations associated with the blocks 6102-6106 may be repeated multiple times throughout the course of the tracking period. For example, in some cases, an insulin dose control system associated with basal insulin may be generated up to 288 times a day. Accordingly, tracking the insulin therapy may include storing insulin does control signals and/or corresponding indications of quantities of insulin for a plurality of autonomously determined doses of insulin infused into the subject 5804 throughout the tracking period.

Generally, counter-regulatory agent therapy includes administering a counter-regulatory agent (e.g., glucagon) when there is a risk or occurrence of hypoglycemia. Usually, the counter-regulatory agent is not supplied on periodic or daily basis. However, it can be useful to understand the amount and frequency that counter-regulatory agent is administered to the subject 5804. For example, it may help a healthcare worker or user guide or adjust care for the subject 5804. Further, tracking counter-regulatory agent use may help determine a minimum quantity of counter-regulatory agent that should be accessible to the subject 5804, either in a bi-hormonal pump or for use in injection therapy. In some cases, the block 6106 may include tracking the counter-regulatory agent administered during the tracking period. Tracking the counter-regulatory agent therapy may include storing an indication of autonomously determined doses of counter-regulatory agent delivered to the subject 5804 responsive to the glucose level signal obtained at the block 6102.

At block 6108, the glucose level control system 5802 generates a backup therapy protocol based at least in part on the tracked insulin therapy. The backup therapy protocol may be determined based on an average quantity or rate of insulin administered to the user over the tracking period, over different portions (e.g., breakfast, lunch, and dinner, or waking and sleeping hours, etc.) of the tracking period, or in response to particular events (e.g., when eating, when blood glucose level exceeds a threshold level, etc.). The backup therapy protocol may include a backup injection protocol and/or a backup pump therapy protocol. The backup injection protocol may provide a user (e.g., the subject 5804, a parent or guardian, or other caretaker for the subject 5804) with quantities of insulin that may be administered to the subject 5804 via injection. Further, the backup injection therapy may indicate times that the insulin may be administered. For example, the backup injection therapy may indicate quantities of insulin to be administered at particular mealtimes. Further, the backup injection therapy may indicate an effect that a unit of insulin may have on the subject 5804 enabling a user to calculate how much insulin to administer to the subject 5804 when a blood glucose reading indicates that the glucose level of the subject 5804 is too high (e.g., above a desired setpoint range).

Similar to the backup injection therapy protocol, the backup pump therapy protocol may provide a user (e.g., the subject 5804, a parent or guardian, or other caretaker for the subject 5804) with quantities of insulin that may be administered to the subject 5804 via a medicament pump. Using the backup pump therapy protocol, a user may configure the medicament pump to administer the quantities of insulin identified. The backup pump therapy protocol may be used to configure the medicament pump when access to a CGM sensor is unavailable (e.g., the subject 5804 does not possess a CGM sensor, or the medicament pump or CGM sensor has a fault, etc.). Further, the backup pump therapy protocol may be useful for providing an initial configuration to a replacement glucose level control system.

In some cases, the backup injection therapy protocol and the backup pump therapy protocol may be the same. However, often at least the recommended basal therapy settings may differ. It is generally not practicable for insulin to be administered to a subject 5804 more than a few times a day via injection therapy. Thus, the backup injection therapy protocol may identify long acting insulin units or doses that may be administered on a limited basis (e.g., once or twice a day). However, the medicament pump may more easily administer insulin on a more than limited basis (e.g., every hour, every half hour, every 5 minutes, etc.). Thus, the backup pump therapy protocol may identify a basal rate of insulin that may be administered once every time unit (e.g., once per hour or once per 15 minutes, or once per five minutes), or continuously at a particular rate (e.g., 0.5 or 0.6 units) per time unit (e.g., per hour). Moreover, the backup pump therapy protocol may identity different rates for different portions of a day (e.g., one rate each half of the day, one rate each quarter of the day, or one rate during typical waking hours and one rate during typical sleeping hours for the subject, etc.).

In some cases, an initial backup therapy protocol may be generated at the block 6108. The initial backup therapy protocol may be updated over time as additional insulin therapy data is obtained.

Generating the backup therapy protocol may include determining a number of long acting insulin units based at least in part on an average total basal insulin provided to the subject 5804 per day over the tracking period. The average total basal insulin provided per day may be included in a backup injection therapy protocol as a single dose of long acting insulin that is configured to help maintain the basal insulin level of the subject 5804 throughout the day. In some cases, the averaged total basal insulin provided per day may be included in a backup injection therapy protocol as multiple doses of insulin (e.g., 2 or 3 doses throughout the day).

Alternatively, or in addition, the basal insulin may be included in the backup therapy protocol, such as in a backup pump therapy protocol, as a dosage rate that may be supplied to a pump to provide a rate of basal insulin throughout the day. Further, in some cases, each day of the tracking period may be divided into a plurality of sub-periods. For example, each day of the tracking period may be divided into two, three, four, or more time periods, or equal or different length. In some such cases, generating the backup therapy protocol may include determining an hourly basal rate for each sub-period of the plurality of sub-periods. This hourly basal rate may be determined by averaging the corresponding sub-periods for each day of the tracking period. For example, if each day of the tracking period is divided into two sub-periods (e.g., noon to midnight, and midnight to noon), the basal rate supplied during the first sub-period throughout the tracking period may be averaged and the basal rate supplied during the second sub-period throughout the tracking period may be averaged to determine two basal rates for inclusion in the backup therapy protocol. The basal rate may be determined on an hourly rate or based on any other time period. Alternatively, the basal rate may be determined based on an amount of time that a particular quantity (e.g., one unit) of insulin is recommended to be administered to the subject 5804 as part of the backup therapy protocol. For example, if the glucose level control system 5802 determines that the subject 5804 is receiving one unit of insulin every 1.125 hours, the backup therapy protocol may indicate the basal rate to be one unit every 1.125 hours. Alternatively, or in addition, the backup therapy protocol may indicate a basal rate of 0.89 units per hour.

In addition, generating the backup therapy protocol may include determining an average correction bolus provided to the subject per day over the tracking period. The average correction bolus may be determined by adding the total amount of correction doses administered each data and dividing by the number of days in the tracking period. The average correction bolus may be included in the backup therapy protocol as guidance for the user. However, generally, the correction bolus is supplied in response to a determination that a subject's blood glucose level is spiking or exceeding a threshold, and not necessarily as a daily dose of insulin. Accordingly, the average correction bolus may be included as part of the backup therapy protocol to facilitate the user understanding an amount of insulin that is likely to be required during an average day, which may be useful for the user (e.g., the subject) to determine how much insulin to have accessible to use, for example, in injection therapy. In some cases, one or more days, or time periods, of the tracking period may be omitted when determining the average correction bolus because, for example, the one or more days or time periods may be determined to be outliers. The outliers may be omitted to provide a more accurate understanding of average insulin needs or consumption.

In some implementations, the glucose level control system 5802 may determine an average change in blood glucose at least partially attributable to a unit of insulin provided as a correction bolus to the subject during the tracking period. In some cases, the glucose level control system 5802 may correlate each correction bolus applied during the tracking period to a change in the blood glucose level of the subject 5804.

Generating the backup therapy protocol may include determining, for each mealtime of a plurality of mealtimes per day, an average mealtime bolus of insulin provided to the subject over the tracking period. In some cases, the average mealtime bolus may be determined for particular meals (e.g., breakfast, lunch, and dinner), while other periods of food intake (e.g., snacks or teatime) may be omitted or ignored. Further, the average mealtime boluses may be associated with particular meal sizes as identified by a user. For example, the glucose level control system 5802 may determine an average mealtime bolus for a small and a large meal, or for a small, a medium, and a large meal. The average mealtime bolus may be determined by averaging an amount of insulin the glucose level control system 5802 determines should be administered to the subject 5804 using a control algorithm of the glucose level control system 5802 for each mealtime and identified meal size.

In some cases, the backup therapy protocol may include data relating to the administering of counter-regulatory agent. For example, the backup therapy protocol may include an indication of total counter-regulatory agent and/or daily counter-regulatory agent provided to the subject over the tracking period.

At block 6110, the glucose level control system 5802 outputs the backup therapy protocol. Outputting the backup therapy protocol may include displaying the backup therapy protocol on a display enabling a user to implement the backup therapy protocol. Alternatively, or in addition, outputting the backup therapy protocol may include transmitting the backup therapy protocol to a computing device of a user for display and/or storage. In some cases, the backup therapy protocol may be stored at the glucose level control system 5802 and may be accessed in response to a user interaction with a user interface of the glucose level control system 5802.

In some cases, the process 6100 can be combined at least in part with the process 6200 described below. Thus, in some cases, the backup therapy protocol may further include a record of user modifications to one or more control parameters used by the control algorithm of the glucose level control system 5802 to autonomously determine doses of insulin to be infused into or administered to the subject. This record of user modifications may include an identity of instances of user modification to the control parameter and/or a percentage of times a user modified the control parameter during each day of the tracking period and/or during the entire tracking period.

Figure 62:
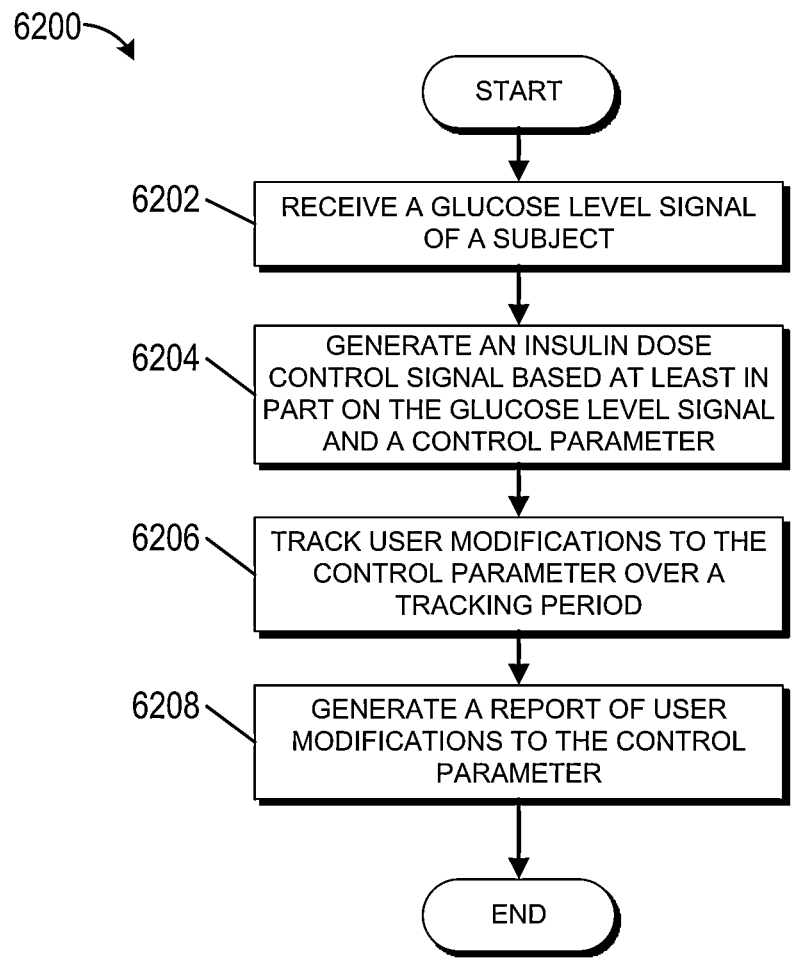
FIG. 62 presents a flowchart of an example control parameter modification tracking process in accordance with certain embodiments.

FIG. 62 presents a flowchart of a control parameter modification tracking process 6200 in accordance with certain embodiments. The process 6200 may be performed by any system that can track user interactivity with glucose level control system 5802, and more specifically, occurrences of a user modifying a control parameter used by the glucose level control system 5802 to help control medicament delivery to the subject 5804. For example, the process 6200 may be performed by one or more elements of the glucose level control system 5802. In some cases, at least certain operations of the process 6200 may be performed by a separate computing system that receives indications of changes to control parameter settings of the glucose level control system 5802 from the glucose level control system 5802 and/or from user interaction with a user interface at the separate computing system prior to transmitting the modification to the glucose level control system 5802. Although one or more different systems may perform one or more operations of the process 6200, to simplify discussions and not to limit the present disclosure, the process 6200 is described with respect to particular systems.

The process 6200 begins at block 6202 where the glucose level control system 5802 receives a glucose level of a subject 5804. The block 6202 can include one or more of the embodiments previously described with respect to the block 6102.

At block 6204, the glucose level control system 5802 generates an insulin dose control signal based at least in part on the glucose level signal and a control parameter. The insulin dose control signal may be generated based on a control algorithm that enables the glucose level control system 5802 to autonomously determine doses of insulin to be infused into or administered to the subject to control the blood glucose level of the subject. The control algorithm may determine the doses of insulin based at least in part on the control parameter. The control parameter may include any parameter that can affect the operation or output of the control algorithm, or the operation of the glucose level control system 5802, and that is modifiable by a user (e.g., the subject 5804 or a user that is at least partially responsible for care of the subject 5804 (e.g., a parent or guardian)). In some cases, the control parameter may be, or may correspond to, a target setpoint for the glucose level of the subject 5804. In other cases, the control parameter may correspond to whether the glucose level control system 5802 is to generate the insulin dose control signal for at least a period of time. For example, the control parameter may relate to whether at least some operation of the glucose level control system 5802 is paused or active. The block 6204 can include one or more of the embodiments previously described with respect to the block 6104.

At block 6206, the glucose level control system 5802 tracks one or more user modifications to the control parameter over a tracking period. The tracking period may be one day, less than a day, or it may be longer than one day (e.g., 2 days, 3 days, a week, a month, etc.). Further, the tracking period may include one or more periods of time as previously described with respect to the process 6100. The user may be the subject 5804 or any other user (e.g., a parent or guardian, or a healthcare provider) that may be permitted to modify a control parameter of the glucose level control system 5802.

The user may modify the control parameter using a user interface that may be generated and/or output by the glucose level control system 5802. Alternatively, or in addition, the user interface may be generated and/or output by a computing system that can communicate with and/or modify the control parameter at the glucose level control system 5802. For example, the computing system may be a smartphone, a smartwatch, a laptop, or desktop computer, or any other type of computing device that may be used to configure the glucose level control system 5802. The user interface may be output on a touchscreen with which the user may interface to modify the control parameter. The user may interact with a control parameter selection element or other user interface element to select and/or modify the control parameter. In some cases, the user may provide the control parameter with any value supported by the glucose level control system 5802. In other cases, the user may be limited to selecting particular values for the control parameter, which may be less than the supported capability of the glucose level control system 5802 or less than what other users are permitted to select. For example, a clinician may be granted a greater modification range than a parent for modifying the control parameter.

Tracking the one or more user modifications may include storing in the one or more user modifications in a therapy log, database, or other data structure. Further, tracking the one or more user modifications may include tracking or storing whether each of the user modifications comprises an increase or a decrease in the control parameter. The determination of whether the control parameter has been increased or decreased may be determined based on whether a value for the control parameter has been increased or decreased relative to a reference value. The reference value may include a current value of the control parameter, a default value, a clinical value supplied to the glucose level control system 5802, and/or a value determined by the glucose level control system 5802. Further, tracking the one or more user modifications may include storing a time and/or one or more conditions under which the control parameter is modified. For example, the glucose level control system 5802 may store a time of day, an activity level of the subject 5804 as determined from one or more physiological sensors and/or as identified by a user, a meal being consumed or not consumed, and the like. Moreover, tracking the insulin therapy may include storing an indication of the autonomously determined doses of insulin delivered or administered to the subject 5804.

In some cases, the tracking period may be divided into a plurality of sub-periods. The sub-periods may correspond to different portions of a day within the tracking period. For example, each day of the tracking period may be divided into two equal halves corresponding roughly to day and night, or into 3 or 4 different periods corresponding to a particular number of hours in the day. The sub-periods may be of equal or unequal length. Tracking the one or more user modifications may include tracking the occurrence of modifications to the control parameter within the sub-periods of the tracking period. Further, the occurrence of modifications within a sub-period of a day within the tracking period may be combined with the occurrence of modifications within a corresponding sub-period of another day within the tracking period. In other words, each occurrence of a modification of a control parameter in a sub-period defined from 9:00-21:00 may be aggregated across days of the tracking period.

In some cases, a different reference value may be determined for the control parameter for each sub-period. In some such cases, tracking the one or more user modifications may include tracking modifications to the control parameter value with respect to the reference value for the sub-period.

At block 6208, the glucose level control system 5802 generates a report of user modifications to the control parameter. Alternatively, or in addition, the repot may be generated by another computing system, such as a cloud computing system or a computing system of a healthcare provider based on data (e.g., occurrences of user modification of the control parameter value) received from the glucose level control system 5802.

The report may include a measure of frequency of increases and decreases from the stored control parameter value. Further, the report may indicate a number of times that operation of one or more features of the glucose level control system 5802 has been paused or suspended, or a percentage of the tracking period that operation of one or more features of the glucose level control system 5802 has been paused or suspended. Moreover, the report may indicate a magnitude of the modification to each control parameter for each occurrence, in total, and/or on average. In some cases, the report may indicate a percentage of user modifications that are higher or lower than the reference value over the tracking period. Further, cases where the tracking period, or each day of the tracking period, is divided into a sub-period, the report may include a measure of frequency of increases and decreases from a reference value for the control parameter for each sub-period of the tracking period. In some cases, the report may include an identity of user activity that occurred when, or within a threshold time period, of a user modification to a value of the control parameter. For example, the report may identify whether a user was exercising (e.g., swimming, running, dancing, etc.) when a user modification to the control parameter value was made.

In some embodiments, the block 6208 may include storing the generated report at the glucose level control system 5802 (e.g., in the memory 5830) and/or at a storage of another computing device. In some cases, the computing device may be a computing device of the subject 5804 (or parent or guardian). Further, the computing device can be a computing device of a healthcare provider. In some cases, the computing device may be a computing device of a cloud computing service.

The report may be obtained from the glucose level control system 5802 by a wired connection (e.g., a USB cable). Alternatively, or in addition, the report may be obtained via a wireless connection to the glucose level control system 5802. For example, the glucose level control system 5802 may establish an encrypted connection to a computing system of a healthcare provider, which may receive the report from the glucose level control system 5802. Alternatively, or in addition, the glucose level control system 5802 may establish an encrypted communication channel with a cloud computing provider, which can receive the report from the glucose level control system 5802. This report may then be accessed by any authorized users.

Advantageously, in certain embodiments, a healthcare provider can use the report to help manage care of the subject 5804. For example, if the healthcare provider determines that a user is modifying the control parameter more than a threshold number of times or during particular time periods, the healthcare provider may use this information to modify the care being provided to the subject 5804 and/or to educate the subject 5804 on optimal care. For example, the rate of therapy may need to be modified or the amount of insulin may be too low for the subject's comfort. For example, in some cases, a subject 5804 may have a different tolerance to a blood glucose level than the average user leading the user to modify a setpoint range. Understanding this information can help the healthcare provider manage care of the subject 5804 (e.g., adjusting the initial setpoint range, or modifying a type of insulin prescribed).

Further, as indicated above, the process 6200 may be combined with the process 6100. In other words, a report may be generated that includes both backup therapy protocols and a record of the number of times a user may a modification to one or more control parameters of the glucose level control system 5802. In other cases, the processes 6100 and 6200 may be triggered and/or performed independently.

Example Backup Therapy Reports

Figure 65:
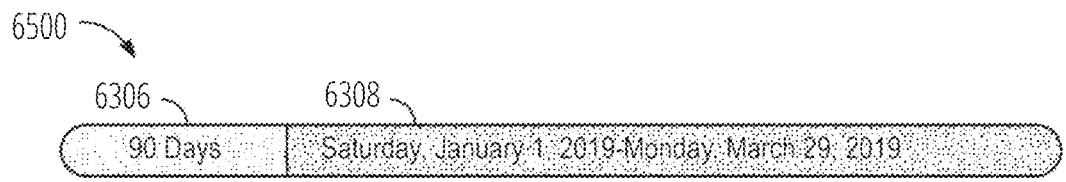
FIG. 65 illustrates an example meal selection report that may be included as part of some implementations of the control parameter modification report of FIG. 11 in accordance with certain embodiments.

FIG. 63-FIG. 65 illustrate one non-limiting example of a backup therapy report, or a set of reports, that may be generated using one or more of the embodiments disclosed herein. In other words, the reports of FIG. 63-FIG. 65 may be portions of a single report generated by the glucose level control system 5802, or may be separate reports that are concurrently generated or that are generated based on different data and/or over different tracking periods. The report may be generated by the automated glucose level control system 5802, or by another computing system that may receive therapy data from the automated glucose level control system. Further, FIG. 63-FIG. 65 represent just one non-limiting example of a report or set of reports that may be generated. It is possible for other reports to be generated that include more or less data. For example, the backup injection therapy protocol and the backup pump therapy protocol illustrated in FIG. 63 may be separated into two separate reports that may be separately generated and/or accessed.

FIG. 63 illustrates a backup therapy protocol report 6300 in accordance with certain embodiments. The amount of insulin recommended under different ties and/or conditions may be displayed in units. In some cases, the backup therapy protocol report 6300 may identify the quantity of insulin included in a unit and/or the type of insulin. Further, in some cases, the backup therapy protocol report 6300 may be an interactive report that enables a user to modify a type of insulin or a unit size of insulin. In some such cases, the table 6302 may update the recommended number of units of insulin to administer under particular times or conditions based on the type of insulin and or unit size of insulin selected.

The backup therapy protocol report 6300 may identify the length of the tracking period 6306 used to determine the backup therapy protocol. Further, the report 6300 may identify the time or date range 6308 during which the tracking period 6306 occurred. Advantageously, knowing the tracking period 6306 may help determine an amount of trust to place in the recommendations included in the backup therapy protocols. The longer the tracking period, the more likely that the recommendations are accurate. A shorter tracking period is more susceptible to less accurate recommendations because, for example, the tracking period may encompass more days that are outliers for the subject's typical condition or activity level. For example, a tracking period of one day that occurs on a day when a subject consumed larger than normal meals or exercised significantly more than normal may result in backup therapy recommendations that do not match the subject's typical lifestyle. Further, knowing when the tracking period occurred may be useful to determine how current the recommendations are and whether they are a reliable indicator of an amount of insulin a subject should administer. For example, if the date range 6308 of the tracking period 6306 is a year old, and the subject has gained or lost significant weight over the year, the backup therapy protocol may no longer be a reliable indication of recommended injection therapy. In such cases, a user may adjust the recommendation and/or trigger a new occurrence of the backup therapy protocol generation process 6100.

The table 6302 illustrates an example backup injection therapy protocol, which may indicate various insulin doses that may be administered to the subject 5804 at various times or under various conditions using injection therapy. The table 6302 identifies an amount of insulin the subject 5804 may inject when consuming a usual-sized meal for breakfast, lunch, or dinner. The usual-sized meal may refer to the size of a meal that the particular subject 5804 usually consumes or has been advised to consume by a healthcare provider. The units of insulin specified may refer to an amount of insulin that the automated glucose level control system 5802 provides the subject 5804 on average when the user consumes the identified usual size meal. In some cases, the table 6302 may further include recommended insulin doses for different size meals. For example, each breakfast may illustrate three different values (e.g., 5 units, 6 units, and 8 units) corresponding to light or smaller than usual breakfast, usual size breakfast, and heavy or larger than usual size breakfast.

It should be understood that the amount of insulin delivered may vary over time and/or based on the condition of the patient at a particular time. Thus, as indicated at the top of the report 6300, the recommendations in the backup therapy protocols are suggested for temporary use for a particular quantity of time (e.g., up to 72 hours in the illustrated example). The quantity of time for which the recommendations are valid may vary based on the subject 5804, the amount of historical data collected (e.g., the size of the tracking period), the amount of daily variation in the subject's blood glucose level, or any number of other factors that may affect the amount of time that the backup therapy protocol can be safely followed.

As illustrated by table 6302, the backup injection therapy protocol may further identify an amount of long-lasting insulin a subject 5804 is recommended to administer each day (or at certain times throughout the day). This long-lasting insulin may be used in place of the basal insulin that the glucose level control system 5802 may provide on a periodic basis.

In addition, the table 6302 identifies the reduction in glucose level attributable to one unit of insulin. For example, as illustrated in the table 6302, the automated glucose level control system 5802 has determined that one unit of insulin (e.g., $1/100^{th}$ of a milliliter of insulin) may reduce a subject's 5804 blood glucose level by 9 mg/dL. Accordingly, a user implementing injection therapy may measure a subject's 5804 blood glucose level, determine a difference between the measured blood glucose level and a desired setpoint or threshold glucose level, and divide the difference by 9 to determine a number of units of insulin to inject in response to a determination that a correction dose is warranted (e.g., that blood glucose is outside of a desired setpoint range).

The table 6304 of the report 6300 provides an example of a backup pump therapy protocol. As illustrated, the backup pump therapy protocol may have the same therapy information as the backup injection therapy protocol for mealtimes and for the correction factor. However, because a pump may be capable of providing periodic basal therapy, the long acting insulin units of the injection therapy may be replaced with a basal rate indicating a rate at which the backup or replacement pump should administer insulin to the subject. As illustrated, the basal rate may vary over time. In the illustrated example, a basal rate is supplied for four different time periods constituting a 24-hour day. However, the basal rate may be divided into a fewer (e.g., 2 twelve-hour blocks) or greater (e.g., every four hours) number of periods, with each time period potentially having a different basal rate as determined based on the historical therapy data provided by an automated glucose level control system.

In some cases, the report 6300 may include additional data that may be tracked over the tracking period. This additional data may include any data that may facilitate care of the subject 5804 and/or maintenance of the automated glucose level control system 5802. Some non-limiting examples of additional data that may be tracked and included in a report using, for example, the process 6100 or 6200 are illustrated in chart 6310 of the report 6300. For example, as illustrated in the chart 6310, the report may include the average blood glucose level of the subject 5804 over the tracking period and/or the corresponding estimated A1C percentage. Further, the report 6300 may indicate the amount or percentage of time that the subject's blood glucose level is within a desired setpoint range and/or is above the desired setpoint range. Similarly, the report 6300 may indicate the amount or percentage of time that the subject's blood glucose level is below a threshold blood glucose level.

In addition, the report 6300 may indicate the average number of meal announcements per day. As illustrated in the chart 6310, the subject 5804 from which the example report 6300 was generated made an average of 4.2 meal announcements indicating that on average, the subject consumed more than 3 meals a day. In some cases, the report may further indicate the types of meals announced (e.g., two breakfasts, one lunch, and one dinner). The second breakfast may be a large snack that is roughly equivalent in size to a small breakfast for the subject. Thus, the subject may have made an additional breakfast meal announcement. In some cases, the automated glucose level control system 5802 may support a separate snack or other meal announcement option.

The report 6300 may further include the total amount of insulin administered to the subject per day, and/or the total amount of counter-regulatory agent (e.g., glucagon) administered to the subject per day. In addition, the report 6300 may indicate the amount of percentage of time that the automated glucose level control system 5802 is able to connect or communicate with the CGM sensor over the tracking period, which may correspond to the amount of time that the automated glucose level control system 5802 functions in an online mode during the tracking period.

FIG. 64 illustrates a control parameter modification report 6400 in accordance with certain embodiments. As previously stated, the report 6400 may be a separate report generated using, for example, the process 6200. Or the report 6400 may be included as a second within the report 6300.

The report 6400 may generally provide an indication of the number or percentage of times that a user modified one or more control parameters of the automated glucose level control system 5802 during a tracking period. Further, as with the report 6300, the report 6400 may identify the time or date range 6308 during which the tracking period 6306 occurred. In some cases, a user may interact with the report 6400 to determine the number of percentage of times that the user modified one or more control parameters during a subset of the tracking period. Similarly, the user may filter or narrow the date range to view other data described herein for a subset (e.g., a selected data range) of the tracking period.

The report 6400 may include a graph 6402 that illustrates the subject's blood glucose level with respect to the desired target setpoint range over the course of a day during the tracking period. This day can be an average of the values obtained for each day over the tracking period, or it can illustrate a particular selected day.

Further, the report 6400 may include a table 6404 that indicates the percentage of times that a user modified the blood glucose target during specific time periods. In the table 6402 of the non-limiting example report 6400 indicates two time-periods, daytime and nighttime. However, it should be understood that the table 6404 may indicate fewer or more time periods. Further, the time periods may indicate specific times (e.g., from 9:00 to 21:00 and from 21:00 to 9:00) for the time periods.

As illustrated, the table 6404 may indicate the percentage of times that a user increased or decreased glucose target setpoints. In addition, the report may indicate the percentage of times that the user did not modify, or left as usual, the glucose target setpoint. This target setpoint indicated in the table 6404 may refer to a single target value (e.g., 108 mg/dL, 125 mg/dL, 130 mg/dL, etc.), or may refer to a target setpoint range (e.g., 70-180 mg/dL).

In addition, the report 6400 may indicate the number of times that a user set a temporary glucose target during the tracking period (the temporary target count 6406) or a selected data range. The report may also indicate a number of times that the user paused therapy during the tracking period (e.g., the paused insulin therapy count 6408) and/or the selected date range.

The blood glucose of a subject may be affected by a subject's weight. Accordingly, the subject may provide updates of weight to the automated glucose level control system. In some such cases, the report may indicate a change in weight and when the weight parameter was modified (e.g., body weight data 6410). In some cases, the report 6400 may be filtered to show data before and after a weight change separately. The body weight data may be helpful for the healthcare provider to, for example, determine whether weight change may at least in part have been a basis for user modifications to target glucose levels. Generally, the automated glucose level control system 5802 (e.g., using blood glucose readings) will automatically account for the effect weight changes may have on glucose control. However, the subject 5804 may feel differently. The ability to collect the modification data relating to a user's modification of the automated glucose level control system 5802 and to correlate the data with weight changes can assist a healthcare provider in better treating the subject 5804 by, for example, adjusting settings of the automated glucose level control system 5802, changing insulin prescriptions, educating the subject 5804, or any other action that may improve care of the subject 5804.

In some cases, the report may omit changes to blood glucose target settings that are below a threshold. In other words, minor changes that may be statistical noise may be ignored. Further, in some cases, the report may indicate when control parameters (e.g., at bedtime, with respect to a particular meal, such as dinner, etc.) are modified. In some cases, the report may also indicate the duration of the change to the glucose target setpoint, or other control parameter.

FIG. 65 illustrates a meal selection report 6500 that may be included as part of some implementations of the control parameter modification report 6400 of FIG. 64 in accordance with certain embodiments. The meal selection report 6500 may include a table 6502 identifying the average number of times per day that a user (e.g., the subject 5804) announces each meal type. Typically, a user will announce a meal 0 or 1 times a day. However, in some cases, a user may announce a particular mealtime more than 1 time to account, for example, for large snacks that may be similar in size to a particular meal. Smaller snacks often may be handled by the control algorithm of the automated glucose level control system 5802 (e.g., by the corrective insulin controller 5906) without a meal announcement.

Further, the table 6502 may identify the number of times over the tracking period, or selected time period within the tracking period, that meals of particular sizes are announced by a user. For example, the table 6502 may indicate the number of times that a usual size meal is announced, a smaller than usual size meal is announce, or a larger than usual size meal is announced.

Automated Glucose Control Refinement

An ambulatory medical device (AMD) may include a control system that autonomously provides therapy to a subject, for example, based on a health condition of a subject (e.g., determined based on one or more measured physiological indicators or parameters of the subject). In some examples, the control system may determine the therapy time and/or the intensity of the therapy during each therapy delivery based on one or more measured physiological parameters (e.g., using one or more subject sensors, such as a CGM sensor) and according to a predictive model that may include one or more control parameters. In some examples, the predictive model may be used to estimate a physiological effect of the therapy in order to adjust the therapy delivery according to an intended physiological effect. It is desirable to adaptively adjust the values of the control parameters to optimize the therapy delivery to a subject in the presence of time varying and subject specific factors that may influence the physiological effects of a therapy delivery on the subject. In some cases, the AMD may be an ambulatory medicament device that regulates the level of an analyte in subject's blood. An example of such ambulatory medicament device is an automated glucose level control system (e.g., the glucose level control system 5802) that may automatically provide insulin and/or a counter-regulatory agent (e.g., Glucagon) to a subject 5804 to help control the blood glucose level (BGL) of the subject 5804. Generally, a control algorithm may be implemented by the automated blood level glucose level control system 5802 to determine when to deliver insulin and/or how much insulin to provide to the subject 5804. Further, the control algorithm may control both an ongoing or periodic delivery of insulin (e.g., a basal dose), and a correction bolus that may be provided to adjust a subject's blood glucose level to within a desired range. The control algorithm may use blood glucose level readings obtained from a subject sensor (e.g., a sensor measuring one or more physiological parameters of the subject in real time), such as a continuous glucose monitoring (CGM) sensor, that obtains automated blood glucose measurements from the subject. Moreover, in some cases, the control algorithm may deliver a bolus of insulin in response to an indication of a meal to be consumed or being consumed by the subject 5804.

Insulin may be administered subcutaneously into blood of a subject 5804. For example, the glucose level control system may subcutaneously deliver a medicament (e.g., insulin, glucagon) via an infusion set connected to a site on subject's body. There is often a delay, referred to as pharmacokinetic (PK) delay, between when the insulin is provided and when the amount of insulin in the subject's blood plasma reaches a particular concentration level, such as maximum concentration. This amount of time may vary based on the type of insulin and/or on the physiology of the particular subject. For example, with a fast-acting insulin, it may take approximately 65 minutes for a bolus of insulin to reach maximum concentration in the blood plasma of one subject, but 60, 64, or 70 minutes for another subject. For some other types of insulin, it may take anywhere from 3-5 hours to reach maximum concentration in the blood plasma of the subject. Additionally, there might be a delay, referred to as pharmacodynamic (PD) delay, between variation of the amount of insulin in the subject's blood plasma and the resulting variation of glucose level in the subject's blood. In some examples, the value of pharmacodynamic (PD) delay may be used to estimate BGL based on an estimated concertation of insulin in patient's blood.

In some cases, the glucose level control system may implement a predictive algorithm based on a pharmacokinetic (PK) model to estimate the accumulation of insulin in the blood plasma of the subject over time, following the subcutaneous administration of insulin to a subject. In some examples, the PK delay may be subject specific and/or change overtime. Accordingly, in these examples, the PK model may include one or more parameters, referred to as control parameters, that may be subject specific and/or change overtime. Examples of factors and parameters that may influence the PK delay and/or the control parameters of the PK model may include, type of insulin, blood glucose level (e.g., at the insulin administration time), physiological characteristics of the subject, health condition of the subject, one or more physiological parameters of the subject, time of the administration, location at which the infusion set is placed, the amount of insulin administered and the like. The physiological characteristics may include characteristics shared among large portions of the population (e.g., weight, gender, age, etc.) as well as characteristics that may be unique or specific to the subject, or shared among few people (e.g., characteristics related to genetics). Differences between the physiologies of different subjects may result in differences in the optimal blood glucose range for each subject, or some subset of subjects. Further, the differences in physiologies may also affect the absorption of insulin into the blood plasma. In other words, different physiologies of different subjects may result in insulin absorption taking different amounts of time for different subjects. Thus, while the maximum concentration of glucose in blood plasma may occur 65 minutes after delivery of a bolus of fast-acting insulin for one subject, it may be 60 minutes or 70 minutes for another subject.

Accordingly, in some such examples, the blood glucose level control system 5802 (e.g., the glucose level control system of an AMD) may implement a method to adaptively change the one or more control parameters in of the PK model used in its control algorithm to modify its predictions, in order to maintain the BGL within a desired range. For example, the glucose level control system may use readings from one or more subject sensors (e.g., a CGM) and/or information received from the subject (e.g., using a user interface of the AMD), to modify one or more control parameters.

As indicated above, a blood glucose system, such as an automated blood glucose level control system 5802, may control delivery or administering of insulin, or a counter-regulatory agent, based on a PK model and one or more blood glucose level measurements of the subject. In some examples, the PK model can be a bi-exponential PK model that may be used to estimate or determine the absorption or accumulation of subcutaneously administered insulin into blood and/or a decay rate of the insulin level in the subject's blood for a given value of delivered dose of insulin. In some examples, the absorption of insulin over time according to a bi-exponential PK model may be represented by the following equation:

$$p(t) = KU_0(e^{-\alpha_1 t} - e^{-\alpha_2 t}) \qquad (2)$$

where $U_0$ is the subcutaneous dose in units (U), K is a scaling constant, and $\alpha_1$ and $\alpha_2$ are time constants that may be used as the control parameters of the model. In some examples, the peak time of absorption of insulin, starting from the time that subcutaneous dose ($U_0$) is administered, may be referred to as Tmax and can be determined based on the following equation:

$$\frac{\log\left(\frac{\alpha_2}{\alpha_1}\right)}{(\alpha_2 - \alpha_1)} \qquad (3)$$

In some examples, $\alpha_1$ and $\alpha_2$ can be related (e.g., through an equation such as $\alpha_2 = 1.5\,\alpha_1$ or any other linear or nonlinear mathematical relations). In some such examples, Tmax alone may be used as the control parameter of the bi-exponential PK model. In some cases, Tmax may be referred to the time at which the concentration of insulin in subject's blood reaches a maximum level (e.g., starting from the time that subcutaneous dose is administered). In some other examples, the bi-exponential PK model may be used to estimate or determine the accumulation of counter-regulatory agent or hormone (e.g., glucagon) in subject's blood. Equation 2 may be used to calculate the pending effect of the accumulated amount of insulin in the subcutaneously administered dose, as that can be taken to be the difference between the total area ($\int_0^\infty p(t)dt$, which can describe a measure of the total amount of hormone (e.g., insulin) that can be absorbed due to a dose $U_0$) and $\int_0^t p(t)dt$, which can represent a measure of the expended portion of $U_0$ at time t.

Often, the glucose level control system is configured to maintain a subject's blood glucose within a particular range (e.g., a normal range). As blood glucose rises or falls, the glucose level control system may administer particular amounts of insulin or counter-regulatory agent to the subject to bring the blood glucose level of the subject back to within a desired range or closer to a desired setpoint. As explained above, it may take some non-infinitesimal amount of time for the medicament to be absorbed into the subject's blood stream. Thus, a PK model (e.g., the bi-exponential PK model), may be used to determine how much insulin or counter-regulatory agent should be provided to the subject in order to maintain the subject's blood glucose within a particular range. In some examples, the PK model (e.g., the bi-exponential PK model) may be used to predict the concentration of insulin blood glucose level of the subject over time as insulin or counter-regulatory agent is administered. In some cases, the control parameter values of the PK model may be set by a healthcare provider based on default values obtained through clinical trials and/or based an individualized treatment plan for the subject as may be determined based on clinical tests of the subject and/or on the healthcare provider's evaluation of the subject, which may be determined based on tests of the subject.

However, as previously indicated, the pharmacokinetic delay and the control parameters of the PK model, may be subject specific and/or change overtime due to various factors. Thus, although clinical data may determine optimal or recommended values of the control parameters for an average subject through one or more trials, the determined data may not be optimal for a particular subject. Moreover, individualized treatment plans are typically based on point-in-time measurements. These point-in-time measurements may provide a good guideline for treatment, but the optimal values of the control parameters for a subject may vary at different times of day, due to different activities, due to changes in the subject over his or her lifetime, or for any other number of reasons.

The glucose level control system 5802 of the present disclosure can implement a method or process to autonomously and/or automatically modify one or more control parameters of a control algorithm, or the model used by the control algorithm, to modify therapy provided to the subject using the glucose level control system 5802. The method may be performed by a hardware separate processor 5820 and/or a controller 5810 that controls the administering of therapy. The system can provide therapy (e.g., insulin) to a subject in response to a determination of a blood glucose level of the subject. The blood glucose level may be determined based at least in part on a glucose level signal obtained from a glucose level sensor that is operatively connected to a subject. The determination of the therapy (e.g., an amount of insulin or counter-regulatory agent) may be based at least in part on the blood glucose level and/or the bi-exponential model. Moreover, the determination of therapy may be based at least in part on a value or setting of one or more control parameters of the glucose level control system. The one or more control parameters may be, or may correspond to, one or more parameters of the bi-exponential PK model, or any other model or control algorithm used to control the administering of therapy to the subject.

As mentioned above, the glucose level control system 5802 may provide the therapy based on the value or setting of the one or more control parameters. The value or setting of the one or more control parameters may be based on an initial configuration of the glucose level control system 5802 by a healthcare provider, subject, or other user. Further, the initial configuration may be based on clinical data or data obtained that is specific to the subject. In some cases, a control parameter may be a time constant used by a control algorithm of the glucose level control system (e.g., Tmax in a bi-exponential PK model). This time constant may be used in a calculation of an accumulation of insulin in the subject by the control algorithm. Further, the control parameter may be used to control an insulin dosing response of the control algorithm to a blood glucose excursion in the subject as indicated by a glucose level signal obtained from a glucose level sensor. In some cases, the control parameter may be, or may be related to, Tmax (e.g., defined by equation 2). For example, the control parameter may be an estimate of Tmax or a fraction (e.g., 0.5) of Tmax. As previously explained, Tmax may be the peak time of absorption of insulin, or the amount of time until the concentration of insulin from an insulin dose reaches maximum concentration in the blood of the subject.

Moreover, the control parameter may be associated with a setpoint or target blood glucose level, or a blood glucose range. For example, the control parameter could relate to a point in time when an estimated amount of "insulin on board" (e.g., an amount of insulin in the subject as determined by a model of insulin accumulation and/or utilization in the subject) falls below a threshold value. As another example, the control parameter can be a clearance time for insulin boluses (e.g., an estimate of an amount of time for an administered bolus of insulin to be utilized by the subject). In some cases, the control parameter may relate to $T\frac{1}{2}$, which corresponds to a time when the concentration of insulin in the blood plasma reaches half of the maximum concentration in the blood plasma. In some cases, the control parameter may be a parameter that can be used to calculate Tmax or $T\frac{1}{2}$.

In some examples, the glucose level control system 5802 may determine an effect of the supplied therapy (herein referred to as therapy effect or effect). For example, the therapy effect may be determined by analyzing a glycemic control of blood glucose (e.g., variation of BGL or supplied therapy over a measurement period) in the subject's blood as indicated by the glucose level signal received from the glucose sensor (e.g., a CGM sensor). In some cases, the control system may measure or determine the effect of the supplied therapy over time. In some such cases, the therapy effect may be determined based on variation of BGL and/or the amount of therapy delivered over time. Moreover, in some cases, the system may continue to supply therapy to the subject over several therapy delivery times or instances and may average or otherwise aggregate the measured or determined effects of the therapy over the several therapy delivery times or instances. In some other examples, the glucose level control system 5802 may determine the therapy effect based at least in part on an input received from the subject. The input received from the subject may include a subjective or objective effect. The input received from the subject may include manual blood glucose level measurements obtained using, for example, test strips. Another example of input may be an indication of light-headedness, difficulty breathing, headaches, or any other objective or subjective effect identified by the subject.

Based at least in part on the provided therapy and the measured or determined effects of the therapy (e.g., the changes in blood glucose level attributed to the therapy), the glucose level control system 5802 may autonomously determine a modification to one or more control parameters. For example, the control system may modify Tmax value used by the control algorithm (or the PK model used in the control algorithm), for example, to improve the effect of a subsequent therapy that may be provided to the subject. As such, the directional modification (e.g., increase or decrease) of a control parameter value may depend on the measured or determined effect of the therapy provided based on the initial or prior value of a control parameter. Moreover, the directional modification of the control parameter value may depend on a difference between the determined or measured effect of the blood glucose therapy and an expected effect of the blood glucose therapy (e.g., calculated based on PK model). In some examples, the directional modification of a control parameter may be determined based on the amount of therapy doses provided and/or measured BGL of the subject, during and between one or more previous therapy deliveries.

In some examples, the pharmacodynamic delay for a subject may be a known value. In these examples, the amount of absorbed insulin in the subject's blood may be estimated based on the measured value of BGL received from a glucose sensor. In some such examples, the directional modification may depend on the difference between calculated value of absorbed insulin based on a PK model (e.g., bi-exponential PK model) with a selected value of Tmax, and the estimated value of the absorbed insulin based on the measured value of BGL received from a glucose sensor.

Using the modified control parameter, the glucose level control system 5802 may determine therapy to deliver to the subject 5804 at a therapy delivery time. As with the initial control parameter, therapy may be delivered during one or more therapy delivery times based on the modified control parameter. The system may determine the effect of the therapy delivered based on the modified control parameter using one or more of the embodiments previously described with respect to the therapy delivered using the initial control parameter.

In some examples, the control system can compare the measured, determined or reported effects (e.g., physiological effects) from the therapy delivered using the initial value of a control parameter and those from the therapy delivered using the modified value of the control parameter. Based on the comparison, the control system may determine which values of the control parameter is preferable for the subject. In some examples, the comparison may be performed in real-time, or substantially in real-time. Further, the comparison may be performed by the glucose level control system 5802 without user interaction. The comparison may be performed using a comparison method and based on one or more comparison criteria.

The comparison method may be based on finite number of therapy effects determined or measured at discrete times or based on continuous temporal variations of an effect over a period. In some examples the comparison method may involve statistical analysis of the measured or determined effects resulting from usage of the initial value and modified value of the control parameter. The comparison criterion may be based on the effects or based on the temporal variations of the effects over a period. For example, the preferable control parameter value can be a value that causes the blood glucose level of the subject to stay within a desired range or closer to a setpoint level for the subject. Accordingly, the system can set or maintain the control parameter to have the value that generated blood glucose levels that are closer to the desired range or setpoint for the subject for subsequent therapy.

In some cases, the glucose level control system 5802 may repeat the process for different control parameter values enabling the system to refine the glucose control for the subject over time. In subsequent performances of the process, the initial control parameter value may not be an initial value but may be the most recent selected value for the control parameter based on the determined effects of the control parameter.

In some cases, the determination of a second or modified value for a control parameter, or the modification of the control parameter may be triggered based on a glucose level of the subject not satisfying a threshold. Alternatively, or in addition, a process of modifying a control parameter value may be triggered based on a difference between an expected glucose value of a subject and an expected glucose value of a subject after the administering of therapy exceeding a threshold.

Using the embodiments described herein, the value of a control parameter may be autonomously modified without interaction by a subject or user with the glucose level control system. In other words, the glucose level control system can automatically adjust and/or refine a control parameter used by a control algorithm for glycemic control of the subject.

As previously described, the glucose level control system may provide both insulin therapy and counter-regulatory agent therapy to a subject. In some cases, the glucose level control system may only provide insulin therapy. In some such cases, the glucose level control system 5802 may output an indication of an amount of counter-regulatory agent that may or should be administered to the subject based on a detected condition of the subject.

The active control parameter value used by the control parameter may remain active until a subsequent occurrence of the therapy modification process. In some cases, performance of the therapy modification process is continuously performed with the control parameter value being modified based at least in part on a determined effect of the prior control parameter value. In other cases, the therapy modification process is performed until the determined effect of the therapy satisfies a desired threshold (e.g., when the detected blood glucose level is within a threshold of a setpoint or median setpoint value). In some cases, the therapy modification process is performed a set amount of times and the control parameter value that provides the best outcome (e.g., closes to desired blood glucose level) is set as the active control parameter for subsequent therapy. In some cases, providing therapy at different sites on the subject's body (e.g., back, stomach, leg, or arm) may result in different blood glucose absorption rates (associated with different PK delays). Thus, in some such cases, the therapy modification process may be performed each time the infusion set used to deliver the therapy is moved to a different site on the subject.

Example Automated Glucose Control Refinement Process

Figure 66:
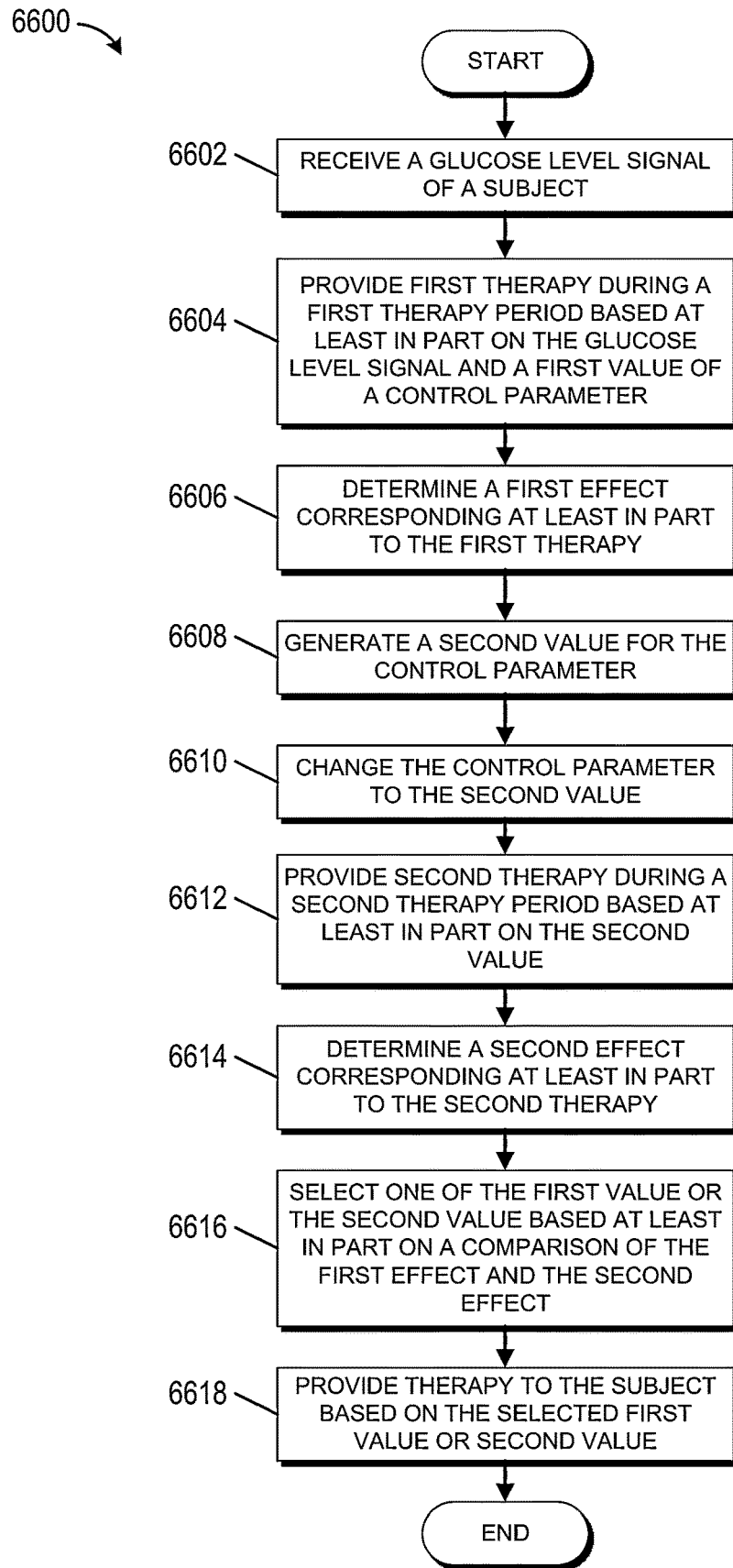
FIG. 66 presents a flowchart of an example automated glucose control refinement process in accordance with certain embodiments.

FIG. 66 presents a flowchart of an example automated glucose control refinement process 6600 in accordance with certain embodiments. The process 6600 may be performed by any system that can autonomously and/or automatically modify a control algorithm and/or a control parameter that affects execution of the control algorithm based on feedback (e.g., from a blood glucose signal) relating to therapy administered to a subject 5804. For example, the process 6600 may be performed by one or more elements of the glucose level control system 5802. In some cases, at least certain operations of the process 6600 may be performed by a separate computing system that receives blood glucose data from the glucose level control system 5802. Although one or more different systems may perform one or more operations of the process 6600, to simplify discussions and not to limit the present disclosure, the process 6600 is described with respect to particular systems.

The process 6600 may be performed automatically and without user interaction. In some cases, a user may trigger the process 6600 via a command or interaction with a user interface. However, once the process 6600 is triggered, the process 6600 may be performed automatically. Further, the process 6600 may be performed continuously, periodically, or in response to a trigger. The trigger may be time based and/or based on a measurement of the glucose level of the subject. For example, the trigger may correspond to a determination that a glucose level of a subject differs by more than a threshold from a predicted glucose level that is predicted by a glucose level control algorithm based on the administering of medicament. Further, the trigger may be based on the activation or first time use of the glucose level control system 5802 by the subject 5804.

The process 6600 begins at block 6602 where the glucose level control system 5802 receives a glucose level signal corresponding to the glucose level of a subject 5804. The glucose level signal may be received from a glucose sensor capable of measuring the level of glucose in the blood of the subject. For example, the sensor may be a continuous glucose monitoring (CGM) sensor. The block 6602 can include one or more of the embodiments previously described with respect to the block 6102 or 6202.

At block 6604, the glucose level control system 5802 provides a first therapy during a first therapy period to the subject 5804. The first therapy may be based at least in part on the glucose level signal and a first value of a control parameter. The control parameter may include any control parameter that affects operation of the glucose level control system 5802 and/or performance of a control algorithm of the glucose level control system 5802. The control algorithm may include any control algorithm used to determine a dose of medicament (e.g., insulin) to administer to the subject 5804. In other words, the controller 5810 or the separate processor 5820 may use the control algorithm to generate a dose control signal based at least in part on a value (e.g., the first value of the block 6604) of the control parameter to cause the delivery device(s) 5806 to administer a dose of insulin or other medicament.

In some cases, the control algorithm may be based on the PK model (equation 2). Further, in some cases, the control parameter may be Tmax, which may be calculated using equation 3. In other cases, the control parameter may be $T_{1/2}$, which may relate to the amount of time for the dose of insulin in the blood stream to drop to ½ of the maximum concentration in the blood attributable to the dose administered to the subject 5804. In some cases, the control parameter corresponds to a time until insulin within blood plasma of the subject reaches a particular concentration level subsequent to administration of an insulin dose. Moreover, in some cases, the control parameter may be a parameter that affects the determination of Tmax, such as one or more of the time constants α1 and α2. In some implementations, the control parameter may be used by the control algorithm to account for and/or determine an accumulation of insulin (or other medicament) in the subject 5804 and/or a rate of diminishment of the insulin (or other medicament) in the subject 5804. In some cases, the control parameter may be used to control an insulin dosing response of the control algorithm to a blood glucose excursion in the subject as indicated by the glucose level signal received at the block 6602.

In some instances, the control parameter may relate to at least one time constant used in a calculation of an accumulation of insulin in the subject by the control algorithm, such as one or more of the time constants $α_1$ and $α_2$ that may be used in the calculation of Tmax. In some cases, the control parameter may correspond to a rate of insulin diminishment in the subject 5804. In some cases, the control parameter may relate to a target setpoint or a target setpoint range for maintaining or attempting to maintain the subject's 5804 blood glucose level.

The first therapy may correspond to a single administering of insulin to the subject 5804. This single administering of insulin may be any type of insulin administered for any reason. For example, the insulin dose may be a basal insulin dose, a priming dose, a dose supplied in response to a meal announcement, or a correction dose of insulin. Moreover, the first therapy may be medicament other than insulin, such as counter-regulatory agent (e.g., glucagon). In some cases, the first therapy may be a plurality of medicament (e.g., insulin and/or counter-regulatory agent) doses supplied or administered to the subject 5804 over the first therapy period. Further, the plurality of medicament doses may include a variety of types of medicament doses, such as one or more basal doses, one or more meal doses associated with one or more meal announcements, one or more corrective doses, etc.

The first therapy period may be a time period that corresponds to a single medicament dose. Alternatively, the first therapy period may be a time period that encompasses a plurality of medicament doses. Further, the time first therapy period may be a time period associated with a defined length of time. Alternatively, or in addition, the first therapy period may be defined based on a number of medicament delivery periods. In other words, the time period may vary based on the amount of time it takes to deliver or administer a specified number of doses of medicament (of any type or of a particular type).

The first value may be selected based on a prior therapy or a prior performance of the process 6600. In some cases, the first value is selected based on a baseline value. The baseline value may be associated with clinical data, or it may be determined based on initial operation of the glucose level control system 5802 for some period of time before performance of the process 6600. Alternatively, or in addition, the first value may be selected based on clinical data or a particular prescription for the subject 5804. In some cases, the first value may be based on clinical data for average users or average users that share certain physiological data with the subject 5804. In some cases, the first value is determined based on a healthcare provider's assessment of the subject 5804. Further, the first value may be determined based on an infusion site (e.g., back, stomach, leg, etc.) for the glucose level control system 5802. In some cases, the first value may be selected based on demographics or characteristics of the subject 5804. For example, the first value may be based on the subject's 5804 gender, weight, body mass, or age.

At block 6606, the glucose level control system 5802 determines a first effect corresponding, or attributable, at least in part to the first therapy. Determining the first effect may include receiving a glucose level signal from the glucose level sensor operatively connected to the subject. This glucose level signal may be a subsequent or updated glucose reading that is more recent than the glucose level signal received at the block 6602. The glucose level signal received at the block 6602 may be used to determine therapy to administer to the subject 5804 and the glucose level signal received at the block 6606 may be used to determine a result of the administered therapy. It should be understood that glucose level signals may be received continuously or periodically and can be used to both determine therapy to administer and to determine the effect of the administered therapy.

In some cases, determining the first effect may include analyzing glycemic control of blood glucose in the subject as indicated by the glucose level signal. Analyzing the glycemic control of the blood glucose in the subject may include tracking the blood glucose level of the subject 5804 over time. Further, analyzing the glycemic control of the blood glucose in the subject may include comparing the blood glucose level of the subject 5804 over time to a predicted blood glucose for the subject 5804 over time as predicted based on the PK model used in the control algorithm using the selected value for the control parameter. As mentioned above, in some examples, the measured blood glucose level of the subject 5804 over time may be used to calculate the accumulation and/or diminishment of the insulin level in subject's blood. In these examples, analyzing the glycemic control of the blood glucose in the subject may include determining whether, or to what degree, the calculated accumulation and/or diminishment of insulin (or other medicament) using the PK model (e.g., bi-exponential PK model) and the control parameter values used in the control algorithm matches the accumulation or diminishment of insulin (or other medicament) estimated based on the measured blood glucose level (e.g., obtained from the CGM sensor). In some cases, the first effect may, at least partially, be determined by analyzing one or more signals received from one or more subject sensors that measure one or more physiological parameters of the subject (e.g., heart rate, temperature and the like).

In yet other examples, the first effect may be determined based on an input received from the subject (e.g., using a user interface of the AMD). In some cases, the first effect may be determined based at least in part on an assessment or input provided by the subject 5804 (e.g., using a user interface) with respect to the first value or the first effect. For example, if the subject 5804 feels woozy, dizzy, lightheaded, nauseous, or otherwise uncomfortable during the first therapy period, the subject 5804 may, via, for example, a touchscreen display of the AMD, indicate how the subject 5804 is feeling.

At block 6608, the glucose level control system 5802 obtains a second value for the control parameter. This second value may be autonomously determined. Further, in some cases, the second value may be automatically determined. In some cases, the second value is determined based at least in part on a user triggering the glucose control refinement process 6600. In some such cases the control system may determine the second value and present it to the user via a user interface user interface 5824 of the glucose level control system 5802.

In some other examples, the second value may be obtained from a user interface 5824 of the glucose level control system 5802 (e.g., in response to a user interaction with the user interface). In some examples, the second value may be obtained from a computing system that is connected to or otherwise in communication with the glucose level control system. The communication connection may be a wired or wireless connection. Further, the wireless connection may be a direct connection (e.g., via Bluetooth or other near-field communication technologies) or a connection over a network (e.g., a local area network, a wide area network, a cellular network, etc.). The user interface user interface 5824 can be implemented in the form of a graphical user-interface configured to output information and receive information via user interaction.

The second value may be an increase or decrease of the control parameter compared to the first value. The second value may be limited to a particular maximum change from the first value. Further, the second value may be selected based at least in part on the first effect. For example, if the first effect corresponding to the first value results in blood glucose being near an upper range of the setpoint range, the second value may be selected in an attempt to being the blood glucose level closer to the middle of the setpoint range. Further, the second value may be selected based at least in part on characteristics of the subject 5804, such as age, weight, gender, or any other characteristics that may affect blood glucose management. In some examples, the second value may be selected based at least in part on the first effect determined based on an assessment provided by the subject 5804, in an attempt to reduce the symptoms felt by the subject 5804.

In some cases, the second value of the control parameter may be generated based at least in part on a baseline value of the control parameter and an output of a function defined based on glycemic control of the subject. In some examples, the glycemic control of the subject may include the measured value of the glucose level in subject's blood (e.g., provided by the CGM) and/or the amount of therapy (e.g., dose of insulin or counter-regulatory hormone) provided during the first therapy period. The baseline value of the control parameter may correspond to the first value used to provide therapy at the block 6604. This baseline value may be a last known optimal value for the subject prior to any changes to the subject (e.g., change in weight, insulin type, or metabolism changes, etc.). Alternatively, or in addition, the baseline value may be a value determined by a healthcare provider. In some cases, the second value of the control parameter is based at least in part on glycemic control indicated by the glucose level signal.

In some cases, the second value may be a modification to Tmax or $T_{1/2}$. It should be understood that Tmax and/or $T_{1/2}$ may, at least in part, be based on the physiology or biochemistry of the subject 5804. Thus, the setting of either Tmax or $T_{1/2}$ for the setting of the first value and the second value may refer to setting a parameter of the control algorithm or the PK model used by the control algorithm, representative of or corresponding to Tmax and/or $T_{1/2}$. For example, the setting of the first value and the second value may include setting one or more control parameters that may be used to determined or estimate Tmax and/or $T_{1/2}$ for the subject 5804. However, the set value may differ from the actual value of Tmax and/or $T_{1/2}$ for the subject 5804. Further, as Tmax and/or $T_{1/2}$ may vary for different subjects, it is not always possible to explicitly set or determine Tmax and/or $T_{1/2}$ for a subject. Instead, Tmax and/or $T_{1/2}$ may be estimated or determined by comparing the effects and/or blood glucose levels determined for different control parameter values that correspond, at least in part, to Tmax and/or $T_{1/2}$. Using the process 6600, the control parameter may iteratively approach the actual Tmax and/or $T_{1/2}$ for the subject 5804, or within a threshold of the actual Tmax and/or $T_{1/2}$ for the subject 5804. Alternatively, using the process 6600, the control parameter (such as one or more of the time constants $\alpha_1$ and $\alpha_2$) may iteratively approach a value that corresponds to the actual Tmax and/or $T_{1/2}$ for the subject 5804.

At block 6610, the glucose level control system 5802 changes the control parameter to the second value. Changing the control parameter to the second value causes a change in the operation or execution of the control algorithm. This change in the execution of the control algorithm may result in a change in one or more factors associated with the provisioning of therapy to the subject 5804. For example, the changing in the execution of the control algorithm may result in a change in an amount of medicament delivered, a timing of the delivery of the medicament, a rate at which a dose of medicament is delivered to the subject 5804, a target setpoint or target range for the blood glucose of the subject, a threshold used in determining whether to deliver medicament (e.g., a threshold difference from the target setpoint), or any other factor that may affect therapy delivered to the subject 5804.

At block 6612, the glucose level control system 5802 provides second therapy during a second therapy period to the subject 5804. The second therapy is based at least in part on the updated control parameter that is updated to the second value at the block 6610. As with the first therapy, the second therapy may refer to one or a plurality of medicament doses. Further, the second therapy period may refer to a specific amount of time, an amount of time to deliver a particular number of medicament doses, or a particular number of medicament doses. In some cases, the block 6612 may include one or more of the embodiments described with respect to the block 6604 but using the second value for the control parameter over the second therapy period. In some examples, the duration of the second therapy period may be equal to the duration of the first period. In some other examples, the number of therapies delivered during the second therapy period may be equal to the number of therapies delivered during the first second therapy period.

At block 6614, the glucose level control system 5802 determines a second effect corresponding at least in part to the second therapy. The block 6614 may include one or more of the embodiments described with respect to the block 6606, but with respect to the second therapy.

At block 6616, the glucose level control system 5802 selects one of the first value or the second value based at least in part on a comparison of the first effect and the second effect. The comparison of the first effect and the second effect may be performed autonomously without action by a user. The glucose level control system 5802 may select the one of the first value or the second value to be a current or active value for the control parameter based on whether the first effect or the second effect results in improved care (e.g., closer to a desired setpoint for a greater period of time, or less volatility in blood glucose values, or any other factor that a healthcare provider may use to evaluate the success of diabetes management) for the subject 5804. In some cases, the glucose level control system 5802 selects a third value to the current or active value for the control parameter. The third value may be selected based on the comparison of the first effect and the second effect. For example, if it is determined that the first effect is preferable to the second effect, the third value may be selected based on a change to the first value in the opposite direction as the change made to the first value to obtain the second value. For instance, if in the prior example, where it is determined that the first effect is preferable to the second effect, the first value corresponded to a Tmax of 60 minutes, and the second value was selected to correspond to a Tmax of a longer time period (e.g., 65 or 70 minutes), the third value may be selected to correspond to a Tmax of a shorter time period (e.g., 50 or 55 minutes).

Comparing the first effect and the second effect may include determining whether the first value or the second value brought the subject's 5804 glucose level closer to a target setpoint and/or maintained the subject's 5804 glucose level within a target range for a longer period of time. In some cases, comparing the first effect and the second effect may include determining whether the first value or the second value resulted in a more stable blood glucose level for the subject 5804 or less volatility in the blood glucose level of the subject 5804. In some cases, comparing the first effect and the second effect may include determining whether the first value or the second value resulted in more and/or greater excursions of the subject's 5804 blood glucose level from a target blood glucose range.

Comparison of the first effect and the second effect may be performed in real-time or substantially in real-time accounting for the processing speed of the hardware separate processor 5820 or the glucose level control system 5802. Thus, in some cases, the comparison of the first effect and the second effect may be performed upon determination of the second effect.

In some embodiments, the comparison of the first effect and the second effect may include a statistical comparison or statistical analysis of the first effect and the second effect. In some cases, the comparison of the first and second effects may include determining whether the second therapy produced a statistically significant improvement in therapy (e.g., glycemic control) compared to the first therapy. A statistically significant improvement may vary depending on the subject or the condition of the subject. The comparison can also include a determination of whether there was a statistically significant increase in risk factors (e.g., hypoglycemia) during the second therapy period compared to the first therapy period. In some embodiments, a statistically significant improvement may be an improvement determined based on a first statistical analysis of a set of data associated with the first effect and a second statistical analysis associated with the second set of data associated with the second effect. For examples, the first and second statistical analysis may include calculating the mean and variance of the blood glucose levels measured during the first and second therapy periods, respectively. In some examples, an improvement may be determined by comparing the mean value and the variance of the blood glucose levels measured during the first and second therapy periods. In some examples, an improvement may be determined by comparing the mean value and the variance of the blood glucose levels measured during the first and second therapy periods with one or more reference values. The reference values may be values provided by a health care provider or a user and may be stored in the memory 5830 of the glucose level control system 5802. In some examples, the first and second therapy period may be long enough to include a plurality of therapy deliveries (e.g., infusion of glucose and/or glucagon) during each period. In some embodiments, an improvement may be determined by comparing by other statistical quantities calculated at least in part based on the blood glucose levels measured during the first and second therapy periods. In some such embodiments the statistical quantities may be specific statistical quantities defined for comparing the effects of a therapy (e.g., medicament delivery for controlling the blood glucose level in a subject).

In some cases, the first and/or second may be output to user (e.g., the subject or a parent) via a user interface of the glucose level control system and/or a computing system (e.g., a smartphone, laptop, personal computer, or the like). In some examples, the user may use the determined effect to adjust the value of a control parameter.

In some cases, the value that better manages the subject's 5804 blood glucose may be output to a user (e.g., the subject or a parent). The user may then configure the glucose level control system 5802 based on the selected control parameter value. Alternatively, or in addition, the glucose level control system 5802 may automatically modify the value of the control parameter. In some cases, the user may be provided with an opportunity to confirm the modification. In other cases, the modification may occur automatically without confirmation. However, the modification may be presented to the user (e.g., the subject or a healthcare provider) and/or logged in a therapy log.

In some cases, the comparison is performed by another computing system that is in communication with the glucose level control system 5802. For example, the glucose level control system 5802 may transmit the glucose level signal, data determined from the glucose level signal, and/or the assessment received from the subject, indicative of the effect of the glucose control, to another computing system, such as a local computing system, a smartphone, or a cloud-based computing system. Further, the glucose level control system 5802 may transmit data associated with the control parameters values and the administering of medicament to the subject 5804 to the computing system. The computing system may determine the value of the control parameter that better manages the subject's 5804 blood glucose level. The computing system may configure the glucose level control system 5802 with the selected value. Alternatively, or in addition, the selected value may be output to a user who can configure the glucose level control system 5802 with the selected value.

At block 6618, the glucose level control system 5802 provides therapy to the subject 5804 based on the selected value for the control parameter that is selected at the block 6616. The therapy provided at the block 6618 may be provided during a third therapy period that is at some point after the first and second therapy periods. Thus, during the first two time periods, the first and second values may be used, respectively, for the control parameter to determine the value that results in the better outcome or improved care for the subject 5804. During subsequent time periods, the value that resulted in the better outcome for the subject 5804 may be used to provide future care for the subject 5804. Alternatively, a new value that is neither the first or second value may be used to provide subsequent care in an attempt to find a value for the control parameter that may provide a better or improved level of care (e.g., closer to a desired target glucose level for a longer period of time) for the subject 5804.

In some examples, providing therapy to the subject, may include generating a dose control signal to a delivery device (s) 5806 (e.g., infusion pump coupled by catheter to a subcutaneous space of the subject 5804) that delivers an amount of a medicament (e.g., insulin or a counter-regulatory agent) to the subject wherein the amount may be determined by the dose signal.

Providing therapy to the subject 5804 based on the selected value may include configuring the glucose level control system 5802 to provide therapy to the subject 5804 during a third therapy period based at least in part on the active control parameter value. In some cases, configuring the glucose level control system 5802 to provide therapy to the subject 5804 based at least in part on the active control parameter value may end the process 6600. In other cases, the automated glucose control refinement process 6600 may be repeated. Repeating the automated glucose control refinement process 6600 may include using the selected value (e.g., the first or second value from a prior iteration of the automated glucose control refinement process 6600) as the first value when performing the operations associated with the block 6604. The second value generated at the block 6608 may be a new value not used during the prior iteration of the process 6600.

The process 6600 may be repeated until a difference between the first effect and the second effect is less than a threshold difference. Alternatively, or in addition, the process 6600 may be repeated a particular number of iterations, periodically, in response to a command, or in response to determining that the subject's 5804 blood glucose does not satisfy a particular threshold for a particular amount of time.

In some examples, the process 6600 may be used to modify more than one control parameters of a glucose system (or a control algorithm used by the control system). In some such examples, the process 6600 may be used to adjust a first control parameter during a first modification period starting from block 6602 and ending at block 6618, and to adjust a second control parameter during a second modification period again starting from block 6602 and ending at block 6618. The second modification period may be immediately after the first modification period or delayed by a particular time. In some example, the control system may determine when a second control parameter should be modified following the modification of a first parameter. In some examples, the delay may be determined at least in part based on the measured glycemic control based on the glucose signal (e.g., received from a CGM sensor). In some other examples, the delay may be determined based on input received from a user. In some examples, the modification of the second control parameter may be at least partially determined based on the determined modification of the first control parameter.

In some examples, a third control parameter may be adjusted during a third time period after adjusting the first and the second control parameters. The adjustment of the third control parameter may immediately follow the adjustment of the second control parameter or may occur after a delay. The delay may be determined at least in part based on the glycemic control of the subject after the second control parameter is adjusted. In some examples, the glucose level control system may be configured to sequentially adjust the first and second, or the first, second and third control parameters when the glycemic control of the subject satisfies one or more threshold conditions. In some examples, the duration of the time period during which a control parameter is adjusted may defer from that of the other parameters.

In some embodiments, a modified version of the process 6600 may be used to determine a value (e.g., an optimal value) of a control parameter. In some such examples, after determining the second effect at block 6614, the control system may skip block 6616 and block 6618, and instead obtain a third value for the control parameter. In some examples, this third value may be determined at least in part based on the determined second effect at block 6614. In some examples, this third value may be autonomously determined. Further, in some cases, the third value may be automatically determined. In some cases, the third value is determined based at least in part on a user triggering the glucose control refinement process 6600. In some such cases the control system may determine the third value and present it to the user via a user interface 5824 of the glucose level control system 5802. In some examples, the third value may be provided by a user via a user interface 5824 of the glucose level control system 5802. In some examples, after obtaining the third value, the system may provide therapy to the subject based on the third value. This modified version of process 6600 may be repeated several times. In some examples, this modified version may be repeated until a difference between the last two subsequent effects is less than a threshold difference. Alternatively, or in addition, the modified version of the process 6600 may be repeated a particular number of iterations, periodically, in response to a command, or in response to determining that the subject's 5804 blood glucose does not satisfy a particular threshold for a particular amount of time.

As described, the process 6600 may be used to modify one or more control parameters that affect the delivery of insulin. However, the process 6600 is not limited as such and may be used to modify one or more control parameters that affect the delivery of other medicaments, such as counter-regulatory agent (e.g., glucagon, dextrose, etc.). In some cases, the process 6600 may be used to recommend a change in insulin and/or counter-regulatory agent delivery without modifying the delivery. This can be advantageous for generating recommendations regarding counter-regulatory agent in a single hormone glucose level control system 5802 that does not support counter-regulatory agent, or that supports the use of counter-regulatory agent, but does not have the counter-regulatory agent available.

Moreover, in cases where the process 6600 is used to modify multiple control parameters, the at least two or more of the control parameters may be related to each other. For example, if the control parameters include the time constants α1 and α2, there may be a relationship between α1 and $α_2$ such that modifying al may cause a modification to α2. For instance, $α_2$ may equal 1.5 times $α_1$ The value for the control parameter set as the active parameter (e.g., the first value or the second value) at the block 6616 may be used by the control algorithm to provide therapy to the subject 5804 for a particular period of time or until the process 6600 is repeated. As previously explained, in some cases, the process 6600 is repeated periodically and/or in response to a trigger, such as a blood glucose value or an average blood glucose value over a time period, or an indicate of a site change for the connection of the glucose level control system 5802 to the subject 5804 (e.g., a change in the location of the infusion set used to provide the subcutaneous dose).

Hypothetical Example

As previously described, the peak time of absorption of insulin may be referred to as Tmax. Different types of insulin may result in different amounts of time until peak absorption into the subject's blood or for different subjects. For example, in one hypothetical example, the aggregate Tmax among subjects for the fast-acting insulin lispro and insulin aspart may be determined to be approximately 65 minutes, while the aggregate Tmax among subjects using ultra-fast-acting insulin, such as, for example, the insulin aspart injection marketed under the Fiasp brand, which has a formulation to decrease time to peak absorption, may be determined to be approximately 40 minutes. When using an automated blood glucose level control system (such as the glucose level control system 5802) with a control parameter corresponding to Tmax set to 65 minutes, there may be no statistically significant improvement in the average glucose level or the frequency of hypoglycemia when using the ultra-fast-acting insulin compared to using the fast-acting insulin. In this comparison, Tmax is held constant while varying the type of insulin used.

When adjusting the value of the control parameter for the automated blood glucose level control system to use different Tmax settings, in a hypothetical example, mean glucose drops when Tmax is lowered when using the ultra-fast acting insulin. In this example, three cohorts of subjects employ control algorithms that use modified Tmax values when using a glucose level control system with ultra-fast-acting insulin such as Fiasp. The first cohort uses a blood glucose level control system configured with a Tmax of 65 minutes for a first week of therapy and a lower Tmax (such as, for example, 50 minutes) for a subsequent week of therapy. The second cohort uses the blood glucose level control system configured with a Tmax of 65 minutes for the first week of therapy and an even lower Tmax (such as, for example, 40 minutes) for a subsequent week of therapy. The third cohort uses the blood glucose level control system configured with a Tmax of 65 minutes for the first week of therapy and a sharply lower Tmax (such as, for example, 30 minutes) for a subsequent week of therapy. Comparison of the change in Tmax within each cohort and across cohorts demonstrates that the mean glucose level drops when Tmax is lowered, and there is no statistically significant increase or decrease in hypoglycemia.

When Tmax is shorter than physiological insulin absorption peak time, there is an increased risk of hypoglycemia because the blood glucose level control system may stack or administer multiple doses of insulin within a time period. This may occur because the blood glucose level control system may incorrectly identify a lower blood glucose concentration as a maximum blood glucose level concentration when Tmax is set below the actual peak insulin absorption time.

By using the process 6600 to compare the effect of different Tmax settings, it is possible to optimize the Tmax setting for a subject and/or a particular type of insulin. In some examples the comparison may be based on one or more statistical methods. For example, using the glucose concentration data collected during a therapy period (e.g., using a CGM sensor), the control system may determine whether there is a statistically significant difference in mean glucose level during a later period using a different Tmax value compared to an earlier evaluation period. If the subsequent or newer value used for Tmax results in an improved effect, Tmax or a control parameter of the blood glucose level control system 5802 corresponding to Tmax may be set to the newer value, where the change in the control parameter value may occur automatically upon determination of a statistically significant improvement or may occur after generating a notification of the potential improvement and receiving confirmation that the change in control parameter value should occur. After collecting glucose signals of the subject 5804 for a period of time at a default or prior value for Tmax, the value for Tmax may be lowered by a significant amount from the initial Tmax. For example, the control algorithm may automatically change Tmax or an associated time constant to reflect a Tmax reduction of at least 10 minutes, at least 5 minutes, at least 2 minutes, no more than 15 minutes, no more than 20 minutes, no more than 30 minutes, or by a change within a range spanning between any two of the preceding values in this sentence, where the preceding values are included in the range. The system can perform a statistical analysis between the prior data set associated with the higher Tmax, and the current data set associated with the lower Tmax. If the controller of the blood glucose level control system determines that there is a significant or statistically significant improvement (e.g., more than a threshold improvement) in the mean glucose level for the subject with little or no increase in hypoglycemia events or risk events, the system can adopt or recommend the lower Tmax value as the preferred Tmax. This process can be repeated using additional reductions in Tmax. In some cases, each reduction in Tmax may be smaller than the previous reduction. Moreover, if it is determined that there is a not an improvement in the mean glucose level for the subject and/or if there is an increase in hypoglycemia or hypoglycemia risk events, the system may use the prior Tmax or may select a Tmax between the new Tmax and the prior Tmax. Thus, using the process 6600, the system can iteratively modify Tmax to find an optimal value for the subject and/or the selected insulin type.

Moreover, by performing real-time analysis and optimization of one or more control parameters, maintenance of the subject's diabetes can be improved faster and more accurately compared to delayed analysis that may occur during clinical testing. Clinical testing may be less accurate as physiological changes in the subject may not be captured in real time.

In some cases, the real-time process and statistical analysis described above can be used to analyze other types of biomedical data obtained by one or more subject sensors (e.g., measuring one or more physiological parameters). In some such cases, the additional biomedical data, such as data may be received from a smartwatch (e.g., blood pressure, heart rate), from a weight sensor, or any other type of biomedical sensor. By adapting the process 6600 to perform statistical analysis of the additional biomedical data, it is possible to perform a quantitatively objective analysis of biometric data, which can be used by a healthcare provider to care for a subject.

Further, the outcomes of the comparative analysis described above may be used to make additional recommendations to the subject. For example, if it is determined that the actual Tmax for a particular type of insulin is higher than expected for the subject, it may be recommended that the subject modify his or her diet in a particular manner while using that particular type of insulin.

Example Simulations

Embodiments of an automated glucose level control system 5802 that can be adapted for use with embodiments of the present disclosure are described in International Publication No. WO 2015/116524, published on Aug. 6, 2015; U.S. Pat. No. 9,833,570, issued on Dec. 5, 2017; and U.S. Pat. No. 7,806,854, issued on Oct. 5, 2010, the disclosures of each of which are hereby incorporated by reference in their entirety for all purposes.

The automated glucose level control system 5802 can autonomously administer insulin doses and account for online accumulation of insulin doses ("insulin on board") due to the finite rate of utilization of the insulin. The rate the insulin absorption, and in turn accumulation, of insulin doses may be modeled by a pharmacokinetic (PK) model (e.g., the bi-exponential PK model represented by equation 2 with preset values of time constants $\alpha 1$ and $\alpha 2$). Of significant clinical significance in relation to the PK model is the time it takes for an insulin dose (e.g., administered subcutaneously) to be absorbed in subject's blood. In some examples, the peak time for insulin absorption in blood is referred to as Tmax. In some other examples. In some other examples, Tmax may be the time at which the concentration of insulin reaches its maximum value following the delivery of a specific dose of insulin. In some such examples, Tmax may be measured from the time that insulin is provided to the subject (e.g., subcutaneously using an infusion set).

In some examples, setting the time constants in the PK model (e.g., $\alpha_1$ and $\alpha_2$ in equation 2) may be equivalent to setting Tmax that is inherently assumed by the model; conversely, setting Tmax may set the time constants of the PK model. Since the values of the time constants may be used to determine the online calculation of the accumulation of insulin by a control system, the value of the time constants may consequently control the control system's insulin dosing response to a given blood glucose level excursion. Thus, varying Tmax or time constants associated with Tmax controls the aggressiveness of the control system's insulin doses.

In certain embodiments, the control system implements a method to adapt the control system's PK model's Tmax (hence time constants) setting online. This method may be performed either by the control system periodically making online assessments and calculations that produce recommendations of modifications in Tmax or by the control system autonomously modulating Tmax online. In either case, the calculations may be based on the control system's performance over some time period. In some cases, adaptations to Tmax online, whether autonomously occurring or issued as recommendations can be based on the glucose-control performance by the control system over some time interval, including trends in glucose level, mean glucose level, or extent and/or duration of low glucose level (hypoglycemia) and/or high glucose level (hyperglycemia) occurrence. Alternatively, the calculation can be based on the usage of a counter-regulatory agent, the otherwise intended usage of a counter-regulatory agent had it been available (e.g., in insulin-only systems or in cases where the counter-regulatory agent or its delivery channel are temporarily unavailable). The method can impose upper and/or lower (static or dynamic) bounds for the range over which the Tmax can vary. The degree of adaptation in Tmax for a given situation can be different depending, for example, on the specific insulin being administered by the control system.

In certain embodiments, the described method may be applicable regardless of whether the continuous glucose monitor (which can provide the input glucose signal to the control system) is online or offline. For example, the method disclosed herein can be applied to system described in International Publication No. WO 2015/116524. Further, the described method can coexist with other aspects of the system being activated or not, such as, but not limited to, having a glucose target that is adapted automatically by the system, e.g., as in the system described in International Publication No. WO 2017/027459, published on Feb. 16, 2017, which is hereby incorporated by reference herein for all purposes.

As previously described, the absorption of subcutaneously administered insulin into blood may be governed by the bi-exponential PK model of equation 2. Setting the time constants in the PK model may set a measure of the pending effect of the accumulated amount of insulin in the subcutaneously administered dose, as that can be taken to be the difference between the total area ($\int_0^\infty p(t)dt$, which can describe a measure of the total action over time due to a dose $U_0$) and $\int_0^t p(t)dt$, which can represent a measure of the expended portion of U0. The peak time, Tmax, of the absorption of insulin doses into blood may be given by equation 3. Thus, setting Tmax may set the PK model time constants, which can directly govern the magnitude (e.g., aggressive or conservative) of the control system's online insulin dosing response to a given glucose profile. Although not limited as such, for simplicity, assume that $\alpha_1$ and $\alpha_2$ are related, e.g. $\alpha_2 = 1.5\ \alpha_1$.

Figure 67A:
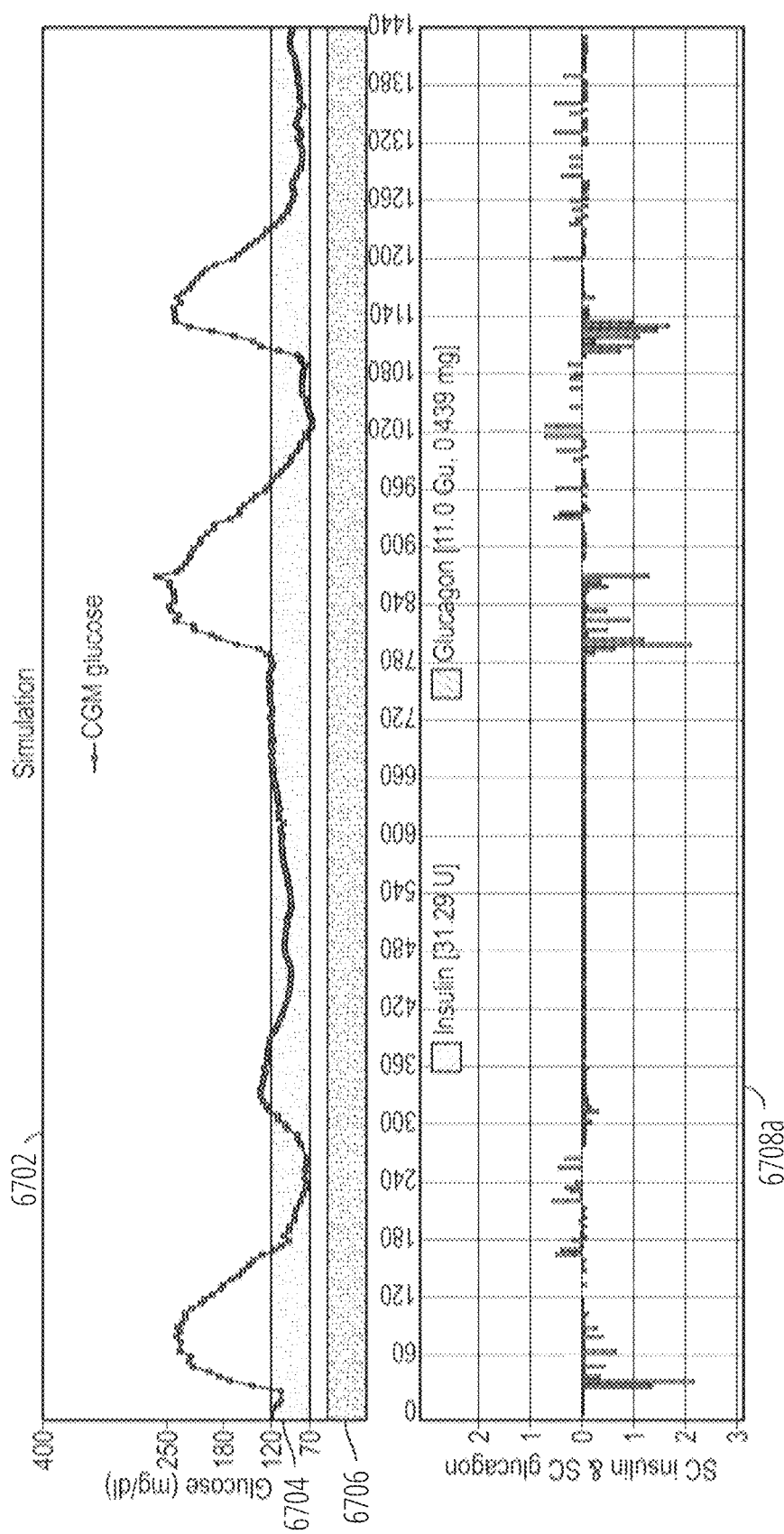
FIG. 67A illustrates a simulation of glucose control of a subject with Tmax set to 65 minutes.
Figure 67B:
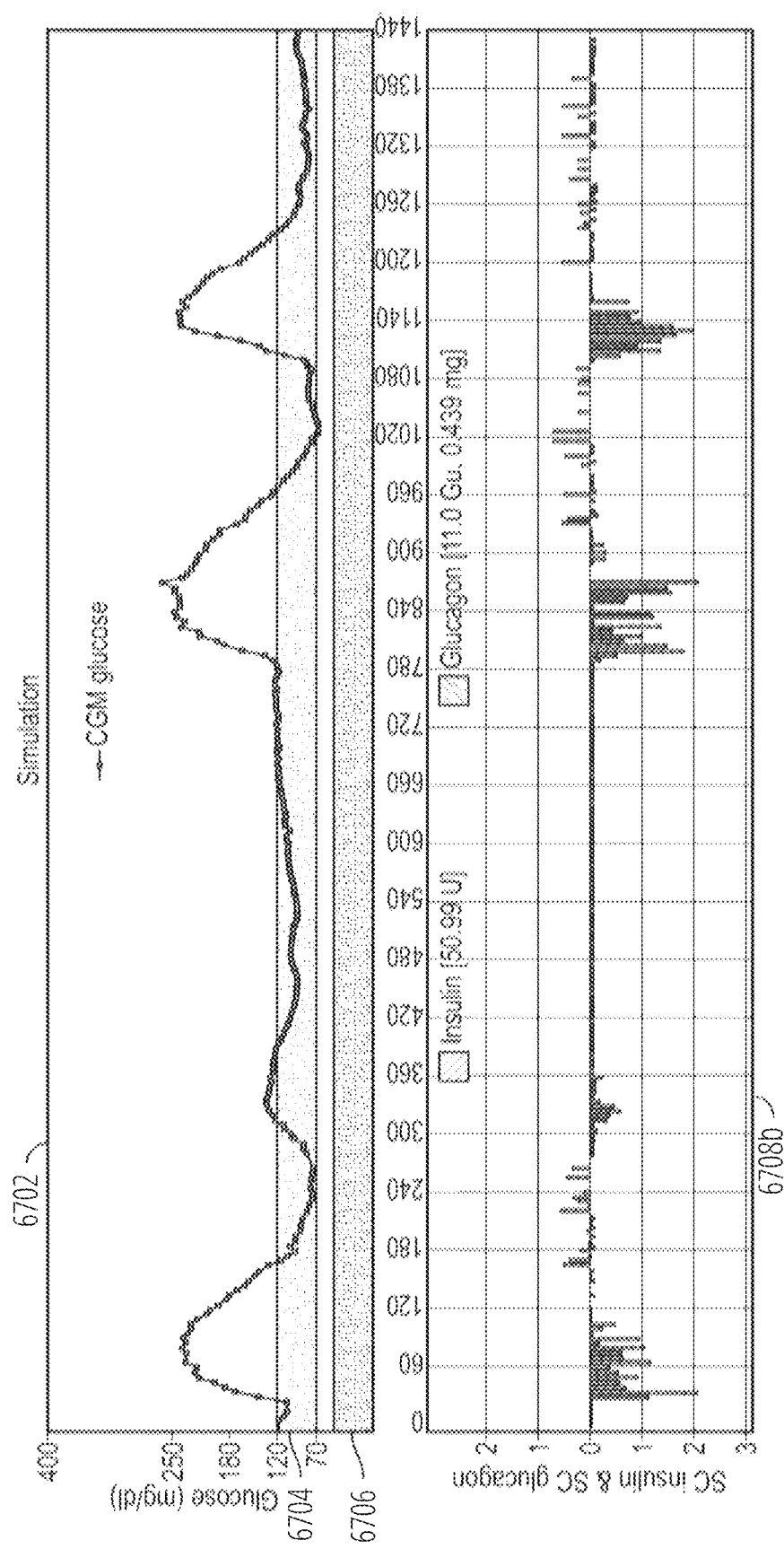
FIG. 67B illustrates a simulation of glucose control of a subject with Tmax set to 15 minutes.
Figure 67C:
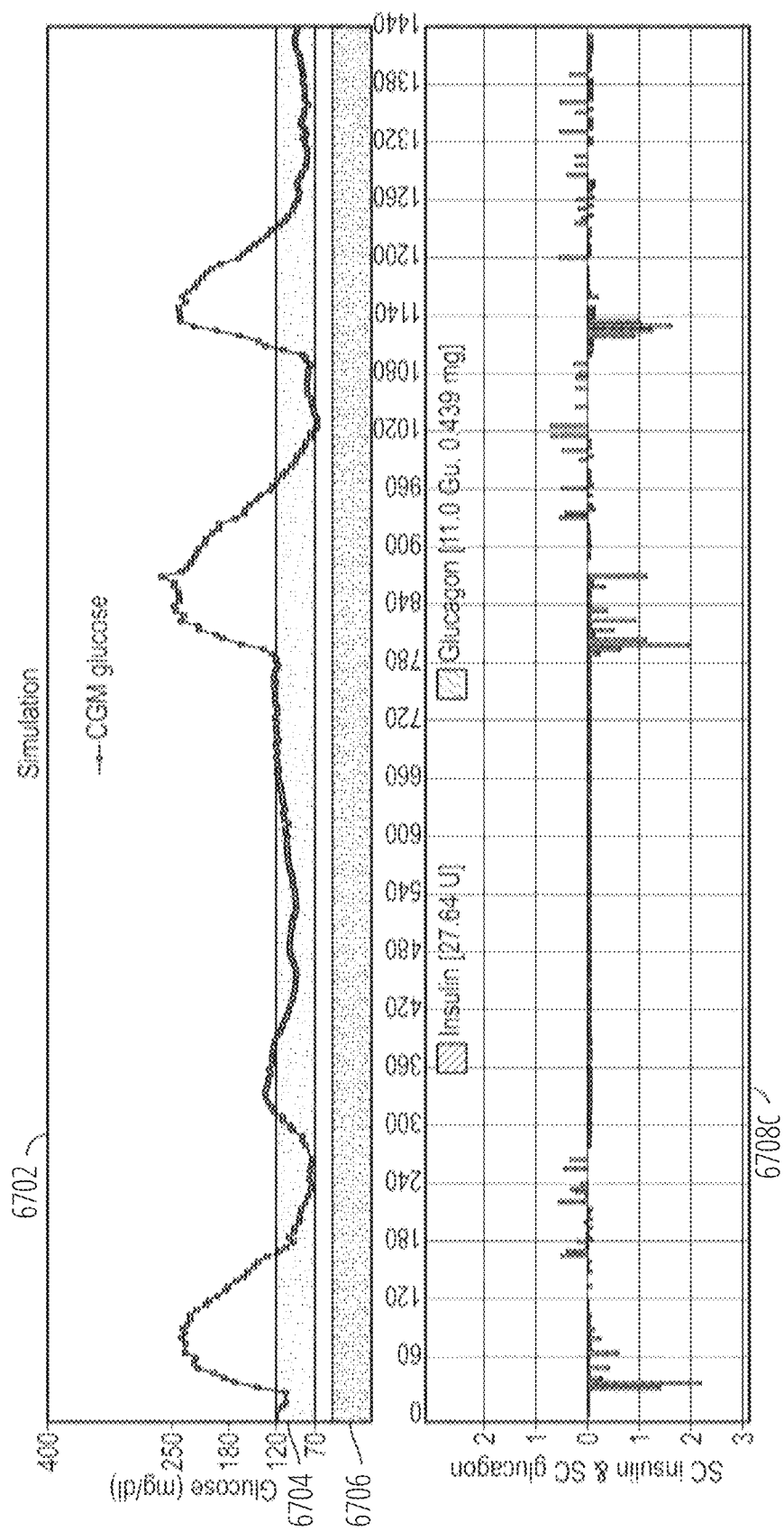
FIG. 67C illustrates a simulation of glucose control of a subject with Tmax set to 130 minutes.

The bi-exponential PK model may be used to simulate the relation between a glucose profile and the medicament (e.g., insulin or glucagon) doses delivered to a subject. FIG. 67A-FIG. 67C illustrate a simulation demonstrating an effect that increasing or decreasing the Tmax setting, or value for a control parameter corresponding to Tmax, may have on the glucose level control system's glucose level control system 5802 online insulin and glucagon dosing response to a given glucose profile (e.g., temporal variation of blood glucose level over 24 hours).

FIG. 67A illustrates a simulation of glucose control of a subject with Tmax set to 65 minutes. The graph 6702 illustrates the variation of blood glucose level (BGL) of a subject over 24 hours. The range 6704 indicates the desired target setpoint range (e.g., between 70 and 120 mg/dL) for the subject's blood glucose level. Further, the range 6706 indicates the range in glucose level (e.g., below 60 mg/dL) for the subject that is associated with hypoglycemia or a risk of hypoglycemia. The graph 6708a illustrates the administering of medicament (insulin or glucagon) to the subject over the same 24-hour time period as graph 6702 based at least in part on the blood glucose level variation illustrated in the graph 6702.

FIG. 67B illustrates a simulation of glucose control of a subject with Tmax set to 15 minutes. The graph 6708b corresponds to the graph 6708a, but with Tmax set to 15 minutes instead of 65 minutes. As illustrated by comparing the graph 6708b to 6708a, reducing Tmax to 15 minutes may result in an increase in insulin dosing required to maintain the given glucose profile 1400.

FIG. 67C illustrates a simulation of glucose control of a subject with Tmax set to 130 minutes. The graph and 6708c corresponds to the graph 6708a, but with Tmax set to 130 minutes instead of 65 minutes. As illustrated by comparing the graph 6708c to 6708a, increasing Tmax to 130 minutes may result in a decrease in insulin dosing required to maintain the given glucose profile 1400.

Even if the glucose profile of a subject is unchanged, increasing or decreasing insulin (or counter-regulatory agent) dosing may affect care of the subject 5804. For example, the subject may experience different degrees of symptoms (e.g., dizziness, nausea, etc.) attributable to maintenance of the subject's diabetes. Advantageously, autonomous optimization of one or more control parameters of a glucose level control system, may reduce the amount and/or frequency of the medicament doses required to maintain a normal glucose profile.

The simulations illustrated in FIG. 67A-FIG. 67C illustrate one non-limiting example of the impact of modifying a control parameter of a glucose level control system. In some cases, different dosing may subsequently lead to different blood glucose excursions which in turn may vary the determined insulin-glucagon doses subsequently. Nonetheless, the simulations shown in FIG. 67A-FIG. 67C, demonstrate the correlation between Tmax as a control parameter and the determined medicament doses by the glucose level control system 5802 for each therapy. Further these simulations demonstrate that the determined therapy doses may be used as a feedback to adjust Tmax as descried below.

Example Automated Glucose Control Refinement Process

In some implementations, the value of Tmax can be varied automatically online based on glycemic control in a receding time period. For example, Tmax can be described using the following the equation:

$$T_{max}(k) = T_{max}^{\circ} + f(y_k, g_k), \quad (4)$$

where $T_{max}^{\circ}$ is a baseline value of Tmax, $f(y_k, g_k)$ is a parameter control adjustment function (herein referred to as adjustment function), based on glycemic control of the glucose signal, $y_k$, and/or the amount of counter-regulatory dosing, $g_k$, that is computed by the control system (whether delivered or not). Evaluation of $f(y_k, g_k)$ could be over a time period (e.g., one week, two weeks, four weeks or other time intervals). For example, $f(y_k, g_k) = \Sigma_{k-N}^{k} f(y_k, g_k)$. In some examples, k may represent a current therapy period and N may indicate a receding time period that may include one or more therapy periods.

The parameter control adjustment function $f(y_k, g_k)$ can cause an increase in $T_{max}(k)$ relative to $T_{max}^{\circ}$ for an increase in hypoglycemia (in severity and/or duration) or impending hypoglycemia in glycemic control of the glucose signal, $y_k$, over the receding time period (that may include one or more therapy periods) and, conversely, can cause a decrease in $T_{max}(k)$ relative to $T_{max}^{\circ}$ for an increase in hyperglycemia (in severity and/or duration) in glycemic control of the glucose signal, $y_k$, over the receding time period. Moreover, $f(y_k, g_k)$ can cause an increase or decrease $T_{max}(k)$ in relative to $T_{max}$ respectively for an increase or decrease in amount of counter-regulatory dosing, $g_k$, over the receding time period. The adjustment $f(y_k, g_k)$ to $T_{max}(k)$ can be evaluated and effected at discrete times, which can be at scheduled periodic intervals (e.g., once every 24 hours, once every three days, once a week, etc.), in response to a user command, or based on a physiological measurement of the subject. Alternatively, or in addition, adjustments can be evaluated and effected online when some metric satisfies a threshold or meets certain criteria within the current computation window (e.g., a week, a month, etc.). This criterion can include when hypoglycemia in $y_k$ reaches or crosses a certain threshold or the level of counter-regulatory dosing in $g_k$ reaches or crosses a certain threshold. Alternatively, or in addition, the adjustment can be effected after some evaluation related to the glucose signal $y_k$ (e.g., mean value) in the current computation window has attained a statistically significant difference from its evaluation in a preceding computation window (e.g., the week before). These described implementations allow for having dynamic instances that are mathematically determined online as to when $T_{max}(k)$ gets adjusted and/or the magnitude by which it is adjusted.

In some examples, therapy periods can be scheduled regular or periodic time intervals (e.g., 24 hour periods, two day periods, one week periods, etc.), based on a user command, or based on a physiological measurement of the subject. In some other examples, therapy periods may be defined as the time interval between two subsequent therapy deliveries, and each therapy period may be identified based on the therapy delivery time that marks the beginning of the therapy period. In either case, $f(y_k, g_k)$ may be the adjustment to $T_{max}$ for the $k^{th}$ therapy period and $f(y_k, g_k)$ may be evaluated based on the equation $f(y_k, g_k) = \Sigma_{k-N}^{k} f(y_n, g_n)$ wherein $y_n$ is the glucose signal measured during the $n^{th}$ therapy period, $g_n$ is the computed dose of a counter-regulatory hormone for the $n^{th}$ therapy period and N indicates the receding time period that may include one or more therapy periods. In some examples, N may be the number of the therapy periods receding the $k^{th}$ therapy period.

Figure 68:
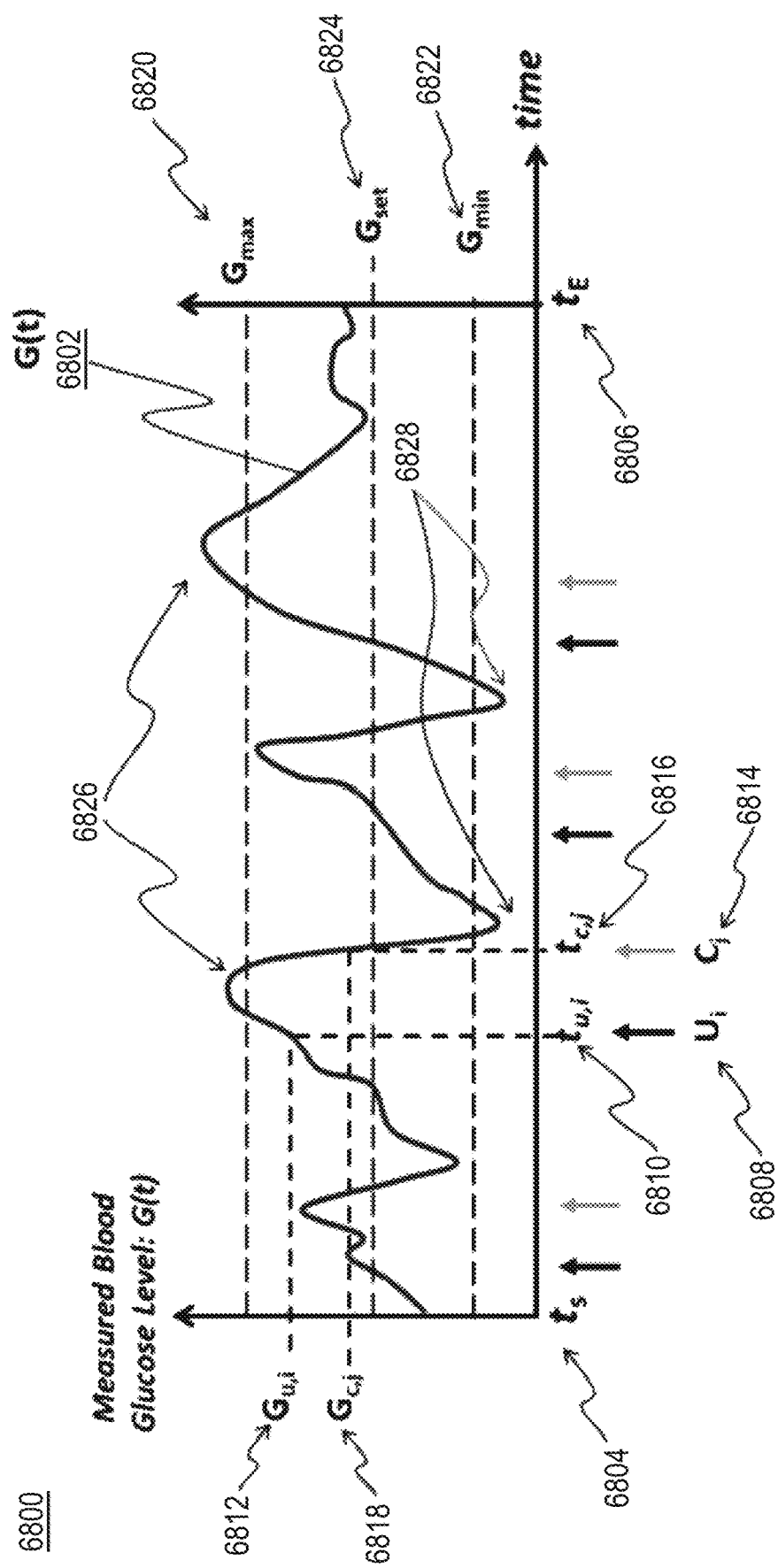
FIG. 68 illustrates an example of blood glucose level signal (CGM trace) and some of the parameters associated with glycemic control using a glucose level control system.

FIG. 68 illustrates a graph 6800 of an example of blood glucose level signal G(t) 6802 (e.g., a CGM trace received from a CGM sensor) over a therapy period (starting from $t_S$ 6804 and ending at $t_E$ 6806) during which one or several doses of insulin and/or a counter-regulatory agent (e.g., glucagon) are determined and/or administered by the glucose level control system 5802. For example, an insulin dose of $U_i$ 6808 units may be provided at time $t_{u,i}$ 6810 at a measured glucose level of $G_{u,i}$ 6812 (where i varies from 1 to the number of insulin deliveries between $t_S$ 6804 and at $t_E$ 6806). Similarly, the control system may have calculated a dose of $C_j$ 6814 units, that may have been administered or not, a glucose level $G_{c,j}$ 6818 at which glucagon may have been delivered and the time $t_{c,j}$ 6816, at which glucagon may have been delivered, (where j varies from 1 to the number of glucagon deliveries between $t_S$ 6804 and at $t_E$ 6806). The control system may be configured to provide therapy in order to maintain the BGL within a normal range defined by an upper bound G. 6820 and a lower bound $G_{min}$ 6822 and close to a $G_{set}$ 6824. In some examples, the glucose levels above upper bound $G_{max}$ 6820 may indicate hyperglycemia and glucose levels below lower bound $G_{min}$ 6822 may be considered hypoglycemia. For example, during the therapy period shown in FIG. 68, two instances of hyperglycemia 6826 and two instances of hypoglycemia 6828 may be identified by the control system. In some examples, during each therapy period the control system may store blood glucose level signal G(t) 6802, $t_{u,i}$ 6810, $t_{c,j}$ 6816, $U_i$ 6808 and $C_j$ 6814, for all therapy deliveries (all values of i and j). In some examples, the value of one or more control parameters (e.g., Tmax, $G_{set}$) may not change during the therapy period between $t_S$ 6804 and $t_E$ 6806.

Figure 69:
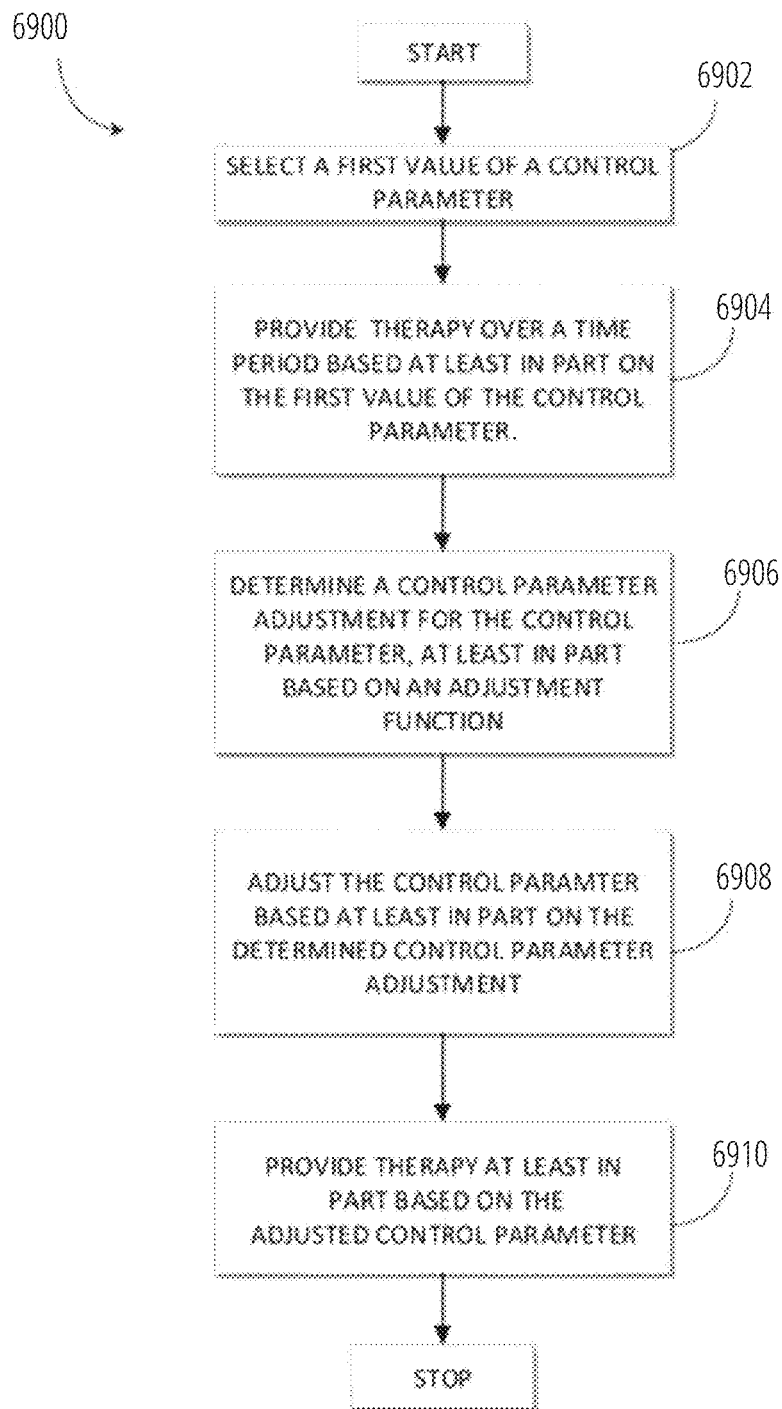
FIG. 69 presents a flowchart of an example automated glucose control refinement process based on an adjustment function in accordance with certain embodiments.

FIG. 69 presents a flowchart of an example automated blood glucose refinement process 6900 that may use the above-mentioned modification method to control Tmax and/or other control parameters of a glucose level control system. The process 6900 may be performed by any system that can autonomously and/or automatically modify a control algorithm and/or a control parameter that affects execution of the control algorithm based on feedback (e.g., from a blood glucose signal) relating to therapy administered to a subject 5804. For example, the process 6900 may be performed by one or more elements of the glucose level control system 5802. In some cases, at least certain operations of the process 6900 may be performed by a separate computing system that receives blood glucose data from the glucose level control system 5802. Although one or more different systems may perform one or more operations of the process 6900, to simplify discussion and not to limit the present disclosure, the process 6900 is described with respect to particular systems.

The process 6900 may be performed automatically and without user interaction. In some cases, a user may trigger the process 6900 via a command or interaction with a user interface. However, once the process 6900 is triggered, the process 6900 may be performed automatically. Further, the process 6900 may be performed continuously, periodically, or in response to a trigger. The trigger may be time based and/or based on a measurement of the glucose level of the subject. For example, the trigger may correspond to a determination that a glucose level of a subject differs by more than a threshold from a predicted glucose level that is predicted by a glucose level control algorithm based on the administering of medicament. Further, the trigger may be based on the activation or first time use of the glucose level control system 5802 by the subject 5804.

The process 6900 begins at block 6902 where a first value is selected for a control parameter (e.g., a control parameter that may be adaptively modified) of the glucose level control system 5802. For example, the control parameter can be a Tmax value used in the control algorithm of the glucose level control system 5802. In some examples, Tmax may be related to one or more parameters in a PK model used by the control algorithm. As another example, the control parameter can be a setpoint (e.g., $G_{set}$ 6824 in FIG. 68) or the target value for the measured value of the blood glucose concentration of a subject 5804 (e.g., measured using a CGM sensor).

The first value of the control parameter may be selected based on a baseline value. The baseline value may be associated with clinical data, may be determined based on operation of the glucose level control system 5802 for some period of time before performance of the process 6900, or may be determined from a prior performance of the process 6900. Alternatively, or in addition, the baseline value may be selected based on clinical data or a particular prescription for the subject 5804. In some cases, the baseline value may be based on clinical data for average users or average users that share certain physiological data with the subject 5804. In some cases, the baseline value is determined based on a healthcare provider's assessment of the subject 5804. Further, the baseline value may be determined based on an infusion site (e.g., back, stomach, leg, etc.) for the glucose level control system 5802. In some cases, the baseline value may be selected based on demographics or characteristics of the subject 5804.

At block 6904, the glucose level control system 5802 provides therapy over a time period to the subject 5804. based at least in part on the first value of the control parameter. Further, the therapy may be provided based at least in part on one or more glucose signals received during the time period. The glucose signals may be received from a glucose sensor (e.g., a CGM) and may correspond to a glucose level of the subject. In some cases, the time period may include one or more therapy periods. In some examples, the number of therapy periods included in the time period may be equal or unequal therapy periods. A therapy period may be a time period that corresponds to a single delivered medicament dose, which may include an instantaneous delivery or a delivery of the medicament dose over a period of time. Alternatively, a therapy period may be a time period that encompasses a plurality of medicament dose deliveries. Further, a therapy period may be a time period associated with a defined length of time. Alternatively, or in addition, the therapy period may be defined based on a number of medicament periods. In other words, the time period may vary based on the amount of time it takes to deliver or administer a specified number of doses of medicament (of any type or of a particular type).

In some examples, the time of delivery and dose of the plurality of therapies may be based at least in part on the glucose level signal and the first value of a control parameter of the control algorithm used by the glucose level control system 5802. The control parameter may include any control parameter that affects operation of the glucose level control system 5802 and/or performance of a control algorithm of the glucose level control system 5802.

For example, the control parameter can be Tmax, $T_{1/2}$, speed of delivery of a medicament dose, a setpoint for the glucose level, a blood glucose range, a threshold value of blood glucose level (e.g., a maximum or minimum value) and the like. The control algorithm may include any control algorithm and/or PK model used to determine a dose of medicament (e.g., insulin) to administer to the subject 5804. In other words, the controller 5810 or the processor 5820 may use the control algorithm to generate a dose control signal based at least in part on a value (e.g., the first value selected at the block 6902) of the control parameter to cause the delivery device(s) 5806 to administer a dose of insulin or other medicament.

Each therapy of the plurality of the therapies provided over the time period, may correspond to a single administering of insulin to the subject 5804. This single administering of insulin may be any type of insulin that may be administered for any reason. For example, the insulin dose may be a basal insulin dose, a priming dose, a dose supplied in response to a meal announcement, or a correction dose of insulin. Moreover, each therapy provided may be a medicament other than insulin, such as counter-regulatory agent (e.g., glucagon). In some cases, each therapy delivery may include a plurality of medicament (e.g., insulin and/or counter-regulatory agent) doses supplied or administered to the subject 5804 over a therapy period. Further, the plurality of medicament doses may include different types of medicament doses, such as one or more basal doses, one or more meal doses associated with one or more meal announcements, one or more corrective doses, etc.

In some examples, the value of the control parameter that is being adjusted may change from one therapy period to another therapy period during the time window. For example, the value of the control parameter may change by a given amount in the beginning of each therapy period or group of therapy periods. In some other examples, the value of the control parameter may change by a given amount after certain number of therapies. In some examples, the amount by which the control parameter is changed may be determined based on one or more receding therapy periods in the time window. In some cases, the block 6904 may include one or more of the embodiments described with respect to the process 6600.

In some examples, during the therapy period or one or more therapy periods of the plurality of therapy periods included in the time period, therapy data may be obtained and/or stored. With reference to FIG. 68, in some examples, therapy data may include the glucose signal blood glucose level signal G(t) 6802, the calculated or actual delivery time ($t_{c,j}$ 6816) and the estimated or delivered amount of a counter-regulatory agent ($C_j$ 6814). This therapy data may be stored in the memory 5830 of the glucose level control system 5802. Further, the therapy data may include a total amount of the counter-regulatory hormone administered during a therapy period. Alternatively, or in addition, other parameters and data associated with each therapy period may be stored in the memory 5830. For example, the total amount of insulin administered, an amounts of insulin delivered ($U_i$ 6808), a delivery time ($t_{u,i}$ 6810) of the insulin delivered during each therapy period, data received from other sensors that may measure one or more physiological parameters of the subject, data received from the subject or user (e.g., via a user interface), and the like.

At block 6906, the glucose level control system 5802 determines a control parameter adjustment for the control parameter. The control parameter adjustment may be based at least partially on the therapy data. In some embodiments, the adjustment may be determined using an adjustment function. For example, the adjustment function may be the function $f(y_k, g_k)$ for modifying Tmax according to equation 4. In some examples, the control parameter adjustment may be determined by analyzing glycemic control of blood glucose in the subject as indicated by the glucose level signal (e.g., G(t) 6802 or the CGM trace). Analyzing the glycemic control of the blood glucose in the subject may include tracking the blood glucose level of the subject 5804 over time. Further, analyzing the glycemic control of the blood glucose in the subject may include comparing the blood glucose level of the subject 5804 over time to a predicted blood glucose for the subject 5804 over time estimated based on the PK model and control parameter values used in the control algorithm. In some examples, the value of the adjustment function $f(y_k, g_k)$ may be calculated at least in part using the estimated or actual values of $t_{c,j}$ 6816, $C_j$ 6814, and glucose level $G_{c,j}$ 6818, (where j varies from 1 to the number of counter-regulatory provided during the time period). In some other examples, determination of the adjustment function $f(y_k, g_k)$ may include a statistical analysis based on the estimated or actual values of $t_{c,j}$ 6816, $C_j$ 6814, and glucose level $G_{c,j}$ 6818, (where j varies from 1 to the number of counter-regulatory provided during the time period). In some such examples, the statistical analysis may be based on statistical quantities and/or the analytical tools described below.

In some cases, the adjustment to the control parameter may be determined based on the number of hypoglycemia 6828 and/or hyperglycemia 6826 events and/or duration of each event. In some examples, the adjustment to the control parameter may be determined based on the difference between measured glucose level and the setpoint ($G_{set}$ 6824). In some examples, the adjustment may be determined based on the time intervals during which the glucose level stays within a target range (e.g., between upper bound $G_{max}$ 6820 and lower bound $G_{min}$ 6822). In some cases, the adjustment may be determined based on the stability of the measured blood glucose level for the subject 5804 or less volatility in the blood glucose level of the subject 5804. For example, a statistical analysis may be performed to determine the distribution rate of change for G(t) beyond one or more threshold rates.

In some cases, the adjustment to the control parameter may, at least partially, be determined by analyzing one or more signals received from one or more subject sensors that measure one or more physiological parameters of the subject (e.g., heart rate, temperature and the like). In yet other examples, the adjustment to the control parameter may be determined based on an assessment or input received from the subject 5804 (e.g., using a user interface of the AMD). For example, if the subject 5804 feels woozy, dizzy, light-headed, nauseous, or otherwise uncomfortable during one or a plurality of therapy periods, the subject 5804 may, via, for example, a touchscreen user interface or other interface of the AMD, indicate how the subject 5804 is feeling.

The adjustment may be determined in real-time or substantially in real-time accounting for the processing speed of the hardware separate processor 5820, the glucose level control system 5802, or the time for the subject to provide an assessment of his or her condition to the glucose level control system 5802. In some cases, the adjustment to the control parameter may be determined by a computing system that is in communication with the glucose level control system 5802. For example, the glucose level control system 5802 may transmit the therapy data, to another computing system, such as a local computing system, a smartphone, or a cloud-based computing system. Further, the glucose level control system 5802 may transmit the therapy data and data associated with the control parameters values to the computing system. The computing system may determine the adjustment that better manages the subject's 5804 blood glucose level in the next time period.

At block 6908, the glucose level control system 5802 adjusts the control parameter using the control parameter adjustment determined at the block 6906. In some examples, the adjustment may be performed autonomously or automatically. In some other examples, the control parameter adjustment determined at block 6906 may be presented to the subject or other user (e.g., parent, guardian, clinician, etc.) via a user interface (e.g., a touchscreen display). In some such cases, the subject or other user may be able to confirm or modify the control parameter adjustment. In other cases, the display of the control parameter adjustment may be presented for informational purposes and may not be adjustable by a user. In some cases, the control parameter may be adjusted only after receiving the user confirmation (e.g., a user interaction with a user interface). In some other examples, where the adjustment is determined by a computing system, the adjustment value may be presented to user via a user interface of the glucose level control system or a user interface of the computing system. In some cases, the user may adjust the control parameter of the glucose level control system using the adjustment value received from or presented by the computer system.

The adjustment at block 6908 may cause a change in the operation or execution of the control algorithm. This change in the execution of the control algorithm may result in a change in one or more factors associated with the provisioning of therapy to the subject 5804. For example, the change in the execution of the control algorithm may result in a change in an amount of medicament delivered, a timing of the delivery of the medicament, a rate at which a dose of medicament is delivered to the subject 5804, a target setpoint or target range for the blood glucose of the subject, a threshold used in determining whether to deliver medicament (e.g., a threshold difference from the target setpoint), or any other factor that may affect therapy delivered to the subject 5804.

In some cases, the adjusted value of the control parameter may be output to a user (e.g., the subject or a parent). The user may then configure the glucose level control system 5802 based on the selected control parameter value. Alternatively, or in addition, the glucose level control system 5802 may automatically adjust the value of the control parameter. In some cases, the user may be provided with an opportunity to confirm the adjustment. In other cases, the adjustment may occur automatically without confirmation. However, the adjustment may be presented to the user (e.g., the subject or a healthcare provider) and/or logged in a therapy log.

At block 6910, the glucose level control system 5802 provides therapy based at least in part on the updated control parameter that is updated at the block 6908. The new value of the control parameter may be maintained during a second time period. The second time period may refer to a specific amount of time, an amount of time to deliver a particular number of medicament doses, or a particular number of medicament doses.

The process 6900 may be repeated during subsequent time periods. In some examples, the process may be repeated periodically (every 24 hours, every two days, every week, or other time intervals). In some cases, the time period may be provided by the subject or a user. Further, the process may be repeated in response to a command. In some cases, the process may be repeated in response to determining that the subject's 5804 blood glucose level does not satisfy one or more criteria for a particular amount of time. For example, the process may be repeated when a statistically significant difference between the measured mean value of the BGL and a target BGL exceeds a threshold, or a number of hypoglycemia and/or hyperglycemia detected exceeds a threshold number during a specific amount of time.

In some examples, the process 6900 may be used to adjust several control parameters that affect the therapy delivery by the glucose level control system. In some such examples, the process 6900 may be used to adjust a first control parameter during a time period and to adjust a second control parameter during a second time period. The second time period may be immediately after the first time period or delayed by a particular time. In some implementations, the glucose level control system 5802 may determine when to adjust the control parameter. In some examples, a delay between periods of control parameter adjustment may be determined at least in part on the glycemic control of the glucose signal. In some cases, the delay may be determined based on input received from a user. Further, the adjustment of the second control parameter may be at least partially determined based on the determined adjustment for the first control parameter.

In some embodiments, a third control parameter may be adjusted during a third time period. The adjustment of the third control parameter may immediately follow the adjustment of the second control parameter or may occur after a delay. The delay may be determined at least in part based on the glycemic control of the subject after the second control parameter is adjusted. In some cases, the glucose level control system may be configured to sequentially adjust the first and second, or the first, second, and third control parameters when the glycemic control of the subject satisfies one or more threshold conditions. In some examples, the duration of the time period during which a control parameter is adjusted may differ from that of the first and second control parameters.

As described above, the process 6900 may be used to adjust one or more control parameters that affect the delivery of insulin. However, the process 6900 is not limited as such and may be used to modify one or more control parameters that affect the delivery of other medicaments, such as a counter-regulatory agent (e.g., glucagon). In some cases, the process 6900 may be used to recommend a change in insulin and/or counter-regulatory agent delivery without modifying the delivery. This can be advantageous for generating recommendations regarding counter-regulatory agent in a non-bi-hormonal glucose level control system 5802 that does not support counter-regulatory agent, or that supports the use of counter-regulatory agent, but does not have the counter-regulatory agent available.

Implementation of Statistical Analysis in Automated Glucose Control Refinement

As described above, a value (e.g., a baseline value or optimal clinical value) of one or more control parameters of a PK model and/or control algorithm used by a glucose level control system 5802 may be determined by statistical analysis of therapy data sets (e.g., glycemic control information) collected from multiple cohorts of subjects (e.g., 20, 50, 100, 200 subjects) during a clinical study. In some examples, the control parameter (e.g., Tmax) may be directly measured for the subjects within each cohort (e.g., based on results of blood analysis following manual or automated medicament administrations). These measurements may be used to determine an optimal value of a control parameter (e.g., Tmax) to be used in a glucose level control system. In some cases, the blood glucose level (BGL) of the subjects may be controlled and recorded for a given period (e.g., one week, two weeks, one months, or other periods) using identical or nearly identical glucose level control systems. The subjects in each cohort may use the same values for a control parameter of the glucose level control system while the subjects in different cohorts may use different values of the same control parameter. Subsequently, the measured therapy data sets, (e.g., comprising measured and/or determined glycemic control information for the subjects) over the given period may be compared using statistical analysis to evaluate an optimal value of the control parameter. For example, the measured glycemic control of subjects in a first cohort in response to setting Tmax to a first value, may be compared to the measured glycemic control of subjects in a second cohort in response to setting Tmax to a second value. Such comparison may include various statistical analysis that can reveal statistically significant differences between measured glycemic controls. For example, the mean value, variance and/or standard deviation of the measured blood glucose level data obtained from the first and second cohort, may be compared to a set of reference values that may be obtained from a third cohort of subjects with normal blood glucose level (e.g., nondiabetic subjects). To generate accurate results, such clinical studies often require several cohorts each comprising a large number of subjects (e.g., large enough to produce enable statistical analysis) and therefore large number of identical glucose level control systems. For example, in some studies 10, 20, 50, or 100 subjects and glucose systems may be required. As such, determining the optimal value of one or more control parameters based on clinical studies can be expensive and time consuming. Moreover, clinical studies typically cannot capture unique physiological characteristics of and real-time physiological changes of a subject (even studies include several large cohorts).

A portable glucose level control system that monitors the BGL in real time and autonomously or automatically provides medicament to a subject, may collect and store therapy data sets that, similar to those collected in clinical studies, may include sufficient number data points for a statistical analysis. In some examples, therapy data may include glycemic control information (e.g., received from a CGM sensor), other physiological effects of the therapy (e.g., obtained from subject sensors or the subject), an amount and type of medicament delivered, medicament delivery times, and the like. Advantageously, these therapy data sets may be used to determine an optimal value of one or more control parameters of the glucose level control system or a value for the one or more control parameters of the glucose level control system that provides improved diabetes management compared to a default value, baseline value, or initial clinically determined value. The optimal or improved values may be determined based on statistical analysis, including the type of statistical analysis that may be used in clinical studies. In some embodiments, the statistical analysis may include calculating one or more statistical quantities such as mean, variance, standard deviation, various statistical distributions (e.g., those described with respect to FIG. 70 below) and the like. On board and real-time (or near real-time) evaluation of values of one or more control parameters of a glucose level control system based on therapy data collected during one or more therapy periods eliminates the need for expensive and time consuming clinical studies and may improve the maintenance of a subject's diabetes by, for example, taking into account unique physiological characteristics of and real-time physiological changes of a subject. Moreover, on board evaluation of control parameter values provides for faster and more accurate diabetes evaluation and management compared to clinical testing. Some of the embodiments described herein may be used to determine optimal values of one or more control parameters that may be used by a user to adjust the control parameters via a user interface of the glucose level control system. In some cases, the glucose level control system may autonomously adjust one or more control parameters using the determined optical values.

The therapy data collected by a glucose level control system may include glycemic control information, information related to medicament delivery times, doses of medicament provided, the BGL level at the time of medicament delivery (e.g., measured based on a glucose signal obtained from a CGM sensor), the physiological effects of the medicament on a subject (e.g., BGL in a time period after medicament delivery, subjects assessment and the like), and any the type of data that may be determined from therapy provided to the subject. In some embodiments, the glucose level control system may collect therapy data during one or more therapy periods. With reference to FIG. 68, the collected and stored therapy data during each therapy period (e.g., a period starting at is 6804 and ending at $t_E$ 6806) may include, but is not limited to: a Blood glucose level signal G(t) 6802, delivered doses ($U_i$ 6808) and delivery times (time $t_{u,i}$) of insulin, delivered or determined doses ($C_j$ 6814) and delivery times ($t_{c,j}$ 6816), of a counter-regulatory agent (e.g., glucagon) and the like. The therapy data may be stored in a memory (e.g., a flash drive, a solid-state drive, a hard disk, or any other type of non-volatile memory) of the glucose level control system as one or more data sets. Each data set may be associated with one or more categories of therapy data or a specific therapy period during which the therapy data was collected. In some cases, the value of the one or more control parameters may change from one therapy period to another therapy period. For example, the value of the control parameter may change by a given amount in the beginning of a therapy period or a group of therapy periods. The value of the control parameter may be changed automatically by the glucose level control system 5802 or by a user via a user interface. In some cases, the control parameter may be changed by a given amount after certain number of therapy periods. The amount by which the control parameter is changed may be determined based on therapy data collected during one or more preceding therapy periods. Alternatively, or in addition, the amount by which the control parameter is changed may be provided by a user via a user interface. In some cases, the duration of one or more therapy periods is selected such that the measured or determined data sets are sufficiently large for statistical analysis. In some examples, an uncertainty associated with an optimal or improved value of a control parameter determined using statistical analysis may depend on the size of the data set used for the analysis.

In some embodiments, the process 6600 may be used to determine a value (e.g., an optimal value) of a control parameter using statistical analysis. For example, statistical analysis may be used to determine the therapy effects at block 6606, block 6614, or to compare the therapy effects resulting from different control parameter values at step 1316. In some such examples, at block 6608, the second value of the control parameter may be provided by the user (e.g., the subject or the guardian) based at least in part on the first effect and outcomes of the statistical analysis performed on the therapy data collected and/or stored during the first therapy period (block 6604). In some examples, at block 6616, a statistical analysis may be performed based at least in part on the first effect and the second effect to obtain a comparative assessment. The comparative assessment may be used to determine whether one of a pair or set of values of a control parameter results in an improved glycemic control of the subject compared to the other values used for the control parameter. In some embodiments, the determined value of the control parameter at block 6616 may be provided to the subject, a guardian or a healthcare provider via a user interface of the glucose level control system 5802 and/or a computing system (e.g., a smartphone, a notebook a personal computer and the like) connected to the glucose level control system (e.g., via a wireless link). In some such embodiments, the subject, the guardian or the healthcare provider may change the value of the corresponding control parameter to the determined value by an interaction with a user interface before the next therapy period (e.g., at block 6618). Alternatively, or in addition, the glucose level control system 5802 may automatically change value of the control parameter to the determined value and proceed to block 6618. In some such cases, the user may be provided with an opportunity to confirm the modification. In other cases, the modification may occur automatically without confirmation.

However, the modification may be presented to the user (e.g., the subject or a healthcare provider) and/or logged in a therapy log.

In some examples, the first and second therapy provided to the subject during the first (block 6604) and second (block 6612) therapy periods, may include a plurality of therapy deliveries. During the first (block 6604) and second (block 6612) therapy periods, a first and second first therapy data may be obtained by the glucose level control system 5802. In some such cases, the therapy data may comprise glycemic control information that at least includes the glucose signal received during the corresponding therapy period. Determining the first effect may include calculating statistical characteristics of the therapy data collected during the plurality of therapies provided during each period. For example, the control system 5802 may calculate the mean value, deviation from mean value, and the variance of the measured BGL. In some cases, the glucose level control system 5802 may calculate one or more quantities (e.g., statistical quantities) to quantify the average blood glucose level and its deviation from a baseline level. In some embodiments, the glucose level control system 5802 may determine one or more quantities (e.g., statistical quantities) to evaluate the variability of glycemic control and the associated risks (e.g., risk of hypoglycemia or hyperglycemia) or quantify the average blood glucose level and its deviations from a baseline (e.g., normal) level. In some cases, the duration of the second period may be equal to the duration of the first period. Alternatively, or in addition, the duration of each period may be selected such that each period includes the same number of therapies provided to the subject. In some embodiments, the duration of each period may be selected such that the number of times therapy is administered during the time period is large enough to enable statistically significant assessments. In some cases, at block 6616, the comparison between the first effect and the second effect, may include statistical analysis of statistical data generated based on the data collected during the first and second period.

In some examples, in addition to the optimal values of one or more control parameters, the control system may generate a control parameter optimization report that may include the statistical quantities calculated during the optimization process. Further, the report may include a graphical representation of the therapy data and related risk assessments. In some such examples, this report may be used by the subject or a healthcare provider to make decisions related to selecting a determined optimal parameter value. Additionally, the control parameter optimization report may include information that may be used by the subject or a healthcare provider to modify the overall strategy for managing the subject's glycemic control. For example, modifying the mealtime, content or amount of meal consumed by the subject, and the like.

Figure 70:
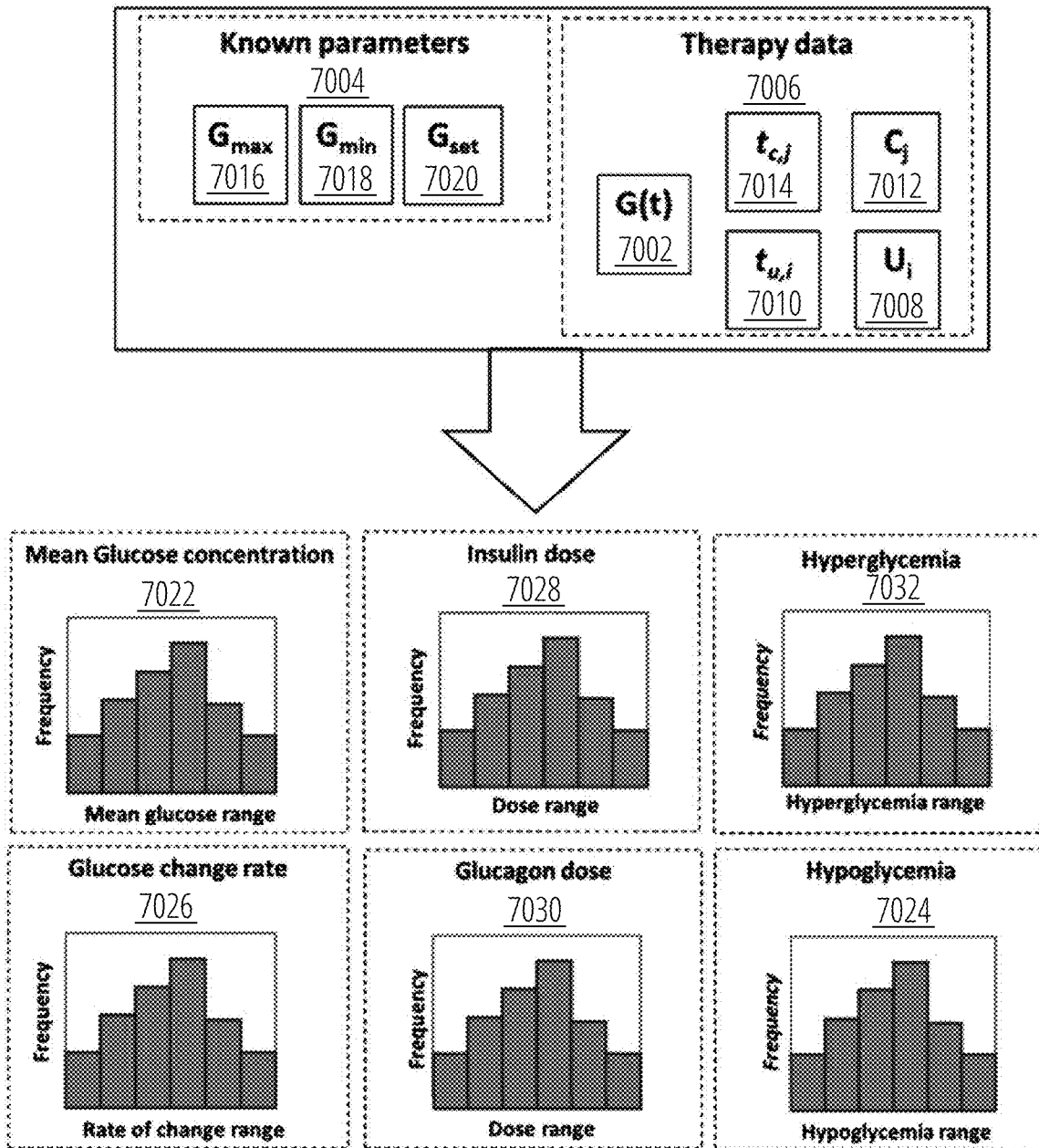
FIG. 70 illustrates some examples of statistical quantities that may be generated and utilized by the glucose level control system as part of statistical analysis.

FIG. 70 illustrates some examples of statistical quantities that may be generated and utilized at blocks 6606 and 6614 of the process 6600, using the therapy data 7006 during a therapy period, and known parameters of the control system 7004. In some embodiments, during the therapy period the value of certain control parameter may be fixed and/or selected based on baseline values (e.g., outcomes of previous clinical studies) or a previously determined value (e.g., by a different control parameter modification and/or optimization process). With reference to FIG. 68, in the example shown in FIG. 70, $G_{min}$ 7018 (lower bound for normal BGL), $G_{max}$ 7016 (upper bound for normal BGL) and $G_{set}$ 7020 (target BGL) are assumed to be known values provided by the subject, the user, a health care provider or determined by a computing system based on a set of clinical data. For example, $G_{min}$ 7018 may between 65 mg/dL and 75 mg/dL, $G_{max}$ 7016 may be between 175 mg/dL and 185 mg/dL and $G_{set}$ 7020 may be between 70 mg/dL and 180 mg/dL. In some examples, $G_{set}$ 7020 may be a value (e.g., an optimal) determined by a previous optimization process (e.g., the process 6600). G(t) 7002 (the CGM trance or the measured glycemic control), $U_i$'s 7008, $t_{u,i}$'s 7010, $C_j$'s 7012 and $t_{c,i}$'s 7014 may be included in the therapy data collected during the therapy period. In some examples, the therapy data 7006 may be used to generate various types of statistical quantities. For example, the therapy data 7006 may be used to generate probability distributions (e.g., discrete or continuous) and/or frequency distributions (e.g., absolute, relative, or cumulative) for certain measured or determined values. For example, the distributions associated with the glucose concentration 7022 (e.g., portions of the therapy period during which the glucose signal was within selected ranges), glucose change rate 7026 (e.g., portions of the therapy period during which the glucose change rate signal was within selected ranges rates), insulin dose 7028 (percent of insulin doses provided within selected dose ranges), glucagon dose 7030 (percent of glucagon doses provided within selected dose ranges), hyperglycemia 7032 (percent of hyperglycemia events detected wherein the glucose signal was above G. by an amount within selected ranges), hypoglycemia 7024 (percent of hypoglycemia events detected wherein the glucose signal was below $G_{min}$ by an amount within selected ranges) and the like. In some examples, one or more characteristic of these statistical distributions (mean, variance, deviation from mean, and the like) or a specific combination of some characteristics of these statistical distributions, may be used to determine (e.g., quantify) the effect of a therapy. In some examples the therapy data considered to generate certain statistical data (e.g., a histogram) may be filtered to exclude the data points collected during certain events. For example, during a mealtime, during exercise, and the like. In some examples, time bins associated with these events may be specified by a user through a user interface.

In some embodiments, the statistical analysis may comprise analytical methods and tools that can compare the effect of different control parameter values. Some examples of analytical methods and tools that can be used with one or more of the embodiments described herein are described in the article "*Statistical Tools to Analyze Continuous Glucose Monitor Data*" (W. Clarke et al., Diabetes Technology and Therapeutics, vol. 11, S45-S54, 2009), which is hereby incorporated by reference in its entirety herein. Examples of methods and tools that may facilitate extraction of information from complex and voluminous measured glycemic control information during therapy periods, are discussed herein. In some cases, the therapy data used for statistical analysis includes the glucose trace of the subject or G(t). In some examples, G(t) may be a time-stamped series of glycemic data received from a CGM sensor (see FIG. 70). In some examples, the glucose signal obtained from CGM may represent blood glucose level as a discrete time series that approximates G(t) in steps determined by the resolution of the particular device (e.g., a reading every 2 min, 5 min, 10 min and the like). In some examples, statistical analysis may be performed on the therapy data (e.g., the glucose signal received from a CGM sensor) to provide an assessment (e.g., a comparative assessment) related to: (1) average blood glucose level and deviations from normal glycemic control (sometimes referred to as normoglycemia), (2) variability and risk assessment, and (3) clinical events, such as post-meal glucose excursions and hypoglycemic episodes. In some embodiments, the assessment may be made based on two sets of therapy data collected during two time periods. In some such examples, the assessment may be used by the glucose level control system 5802 to determine whether the glycemic control for a subject has been improved from a first therapy period to a second therapy period. In some examples, the assessment may be used by a health care provider to evaluate the glycemic control of a subject during one or more time periods.

In some cases, the glucose level control system may determine three values of average blood glucose: the mean value (e.g., computed for the entire G(t) measured during a therapy period or part of a therapy period), a pre-meal mean value (e.g., computed for the time window of 60-120 min after the meal), and post-meal mean value (e.g., computed for the time window of 0-60 min before meal). Computing of pre- and post-meal averages and the difference between the averages can serve as an indication of the overall effectiveness of pre-meal bolus timing and bolus amount. In some examples, deviation from target or normoglycemia may be evaluated by determining percentages of time spent within, below, or above preset target limits (e.g., $G_{min}$=70 and $G_{max}$=180 mg/dL). In some examples, the percentage of time within each range may be calculated via linear interpolation between consecutive glucose readings. In some other examples, percentage of time within additional ranges can be computed. In some such examples, the probability of occurrence of extreme hypoglycemia and hyperglycemia may be also evaluated. To quantify variability of blood glucose level, in some examples, standard deviation and variance may be used to compute variability of BGL. In some cases, a risk index may be defined that can serve as a measure of overall glucose variability when focusing of the relationship between glucose variability and risks for hypo- and hyperglycemia. In some examples, an individual function may be calculated to split the overall glucose variation into two independent sections related to excursions into hypo- and hyperglycemia, and at the same time equalize the amplitude of these excursions with respect to the risk they carry. For example, a BGL transition from 180 to 250 mg/dL may appear threefold larger than a transition from 70 to 50 mg/dL, whereas if converted into risk, these fluctuations would appear equal. In some cases, analysis of BGL rate of change (e.g., measured in mg/dL/min) may be used to evaluate the dynamics of BGL fluctuations on the time scale of minutes. In other words, this is an evaluation of the "local" properties of the system as opposed to "global" properties discussed above. In some examples the local properties may be assessed at a neighborhood of any point in time by the value BGL, its first or, sometimes, second derivatives (acceleration).

In some examples, in addition to statistical analysis of the therapy data, in the blocks 6606, 6614, and 6616 of the process 6600, a statistical analysis of the user inputs provided during the first or second therapy period may be used in determining or comparing the therapy effects. For example, the number of times and time of the day that the subject has indicated certain symptoms, may be used to determining therapy effects.

In some cases, in addition to the statistical analysis of the therapy data in the blocks 6606, 6614, and 6616 of the process 6600, a statistical analysis of the biomedical or physiological data received from one or more subject sensors (e.g., a smart watch, weight sensor, etc.) may be used in determining or comparing the therapy effects. For example,
subject's temperature, blood pressure, heart rate), from a weight sensor, or any other type of biomedical sensor.

In some examples, the process 6600 may be modified to determine the optimal value of Tmax, or a value of Tmax that provides improved maintenance of the subject's diabetes, by reducing Tmax (increasing the aggressiveness of the therapy) after each therapy period in a series of therapy periods, until a statistical assessment shows that further reduction of the Tmax does not improve the mean glucose level without increasing the probability of hypoglycemia. Improved maintenance of the subject's diabetes may include maintaining a mean glucose level closer to a setpoint glucose level range or reducing fluctuations in mean glucose level over time compared to prior control value (e.g., Tmax) settings. It should be understood that other metrics may be used to measure an improvement of maintenance of the subject's diabetes, such as reduction in hypoglycemia risk events or reduction in administration of insulin without increasing diabetic effects or corresponding risks.

Figure 71:
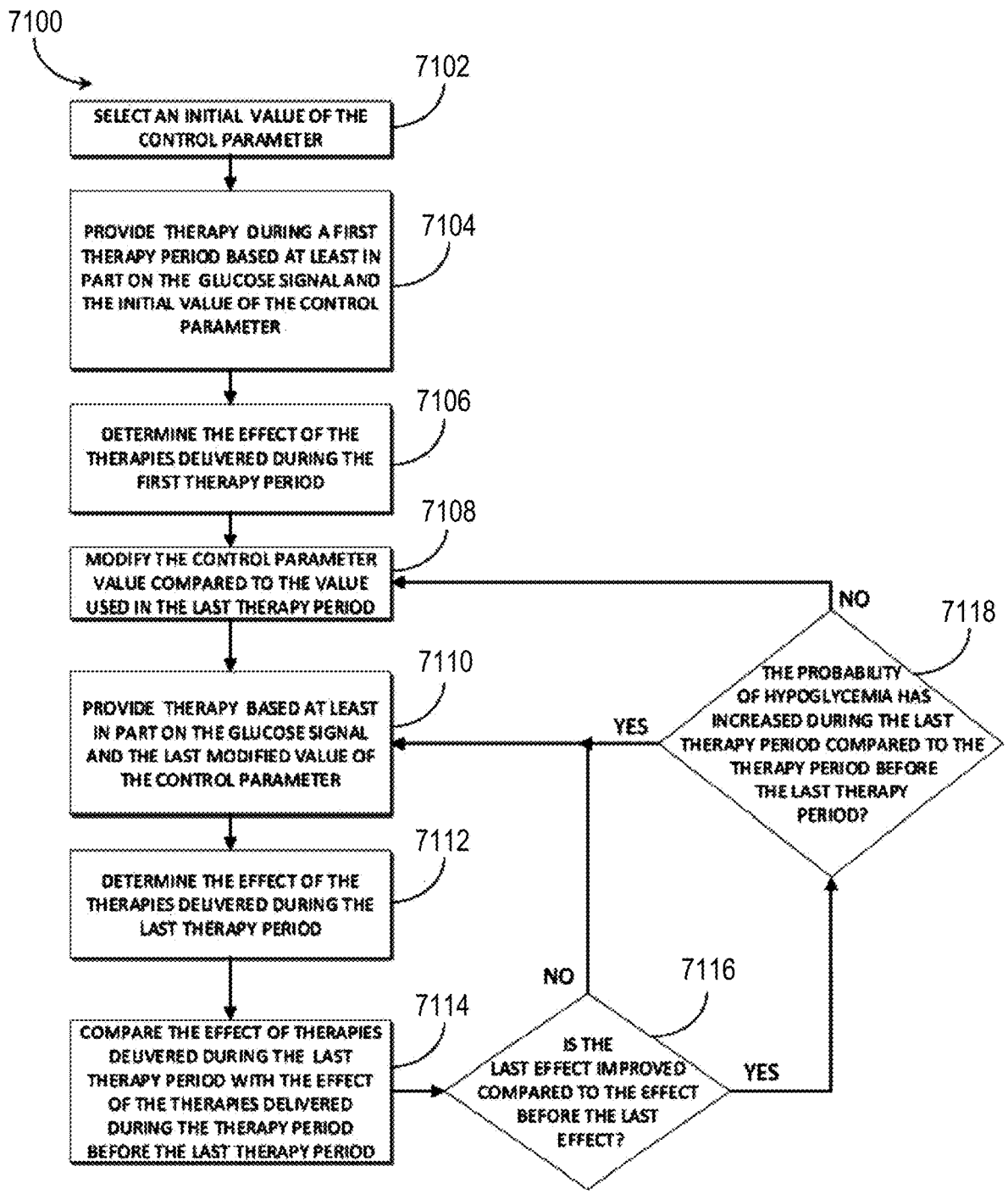
FIG. 71 presents a flowchart of an example automated glucose control refinement process in accordance with certain embodiments.

FIG. 71 presents a flowchart of an example automated control parameter refinement process 7100 in accordance with certain embodiments. The process 7100 may be performed by any system that can autonomously and/or automatically modify a control algorithm and/or a control parameter that affects execution of the control algorithm based on feedback (e.g., from a blood glucose signal) relating to therapy administered to a subject 5804. For example, the process 7100 may be performed by one or more elements of the glucose level control system 5802. In some cases, at least certain operations of the process 7100 may be performed by a separate computing system that receives blood glucose data from the glucose level control system 5802. Although one or more different systems may perform one or more operations of the process 7100, to simplify discussions and not to limit the present disclosure, the process 7100 is described with respect to particular systems.

The process 7100 may be performed automatically and without user interaction. In some cases, a user may trigger the process 7100 via a command or interaction with a user interface. However, once the process 7100 is triggered, the process 7100 may be performed automatically. Further, the process 7100 may be performed continuously, periodically, or in response to a trigger. The trigger may be time based and/or based on a measurement of the glucose level of the subject. For example, the trigger may correspond to a determination that a glucose level of a subject differs by more than a threshold from a predicted glucose level that is predicted by a glucose level control algorithm based on the administering of medicament. Further, the trigger may be based on the activation or first time use of the glucose level control system 5802 by the subject 5804.

In some embodiments, the glucose level control system 5802 may perform the process 7100 in order to adjust one or more control parameters of the glucose level control system 5802 to improve the glycemic control of a subject. The control parameter may include any control parameter that affects operation of the glucose level control system 5802 and/or performance of a control algorithm of the glucose level control system 5802. In some such embodiments, in addition to improving the glycemic control of the subject, the process 7100 may take into account the risk of hypoglycemia in the subject. In some embodiments, the process 7100 may include one or more of the embodiments previously described with respect to the process 6600.

The process 7100 begins at block 7102 where an initial value is selected for a control parameter of the glucose level control system (e.g., Tmax or other control parameters of the glucose level control system selected to be optimized). The control parameter can be a control parameter of a pharmacokinetic (PK) model used by a control algorithm PK of the glucose level control system 5802. In some examples, the control parameter may be a time until insulin within blood plasma of the subject reaches a particular concentration level subsequent to administration of an insulin dose. In some cases, the initial value of the control parameter may be based on therapy delivered during a time period prior to the first therapy period, a clinical value, or a body mass of the subject.

In some examples, the initial value of the control parameter may be selected using one or more of the embodiments described with respect to the block 6604 of the process 6600. In some embodiments, the control parameter may be a control parameter used by the control algorithm of the glucose level control system to account for accumulation of insulin in a subject. In some embodiments the control parameter may be used to control an insulin dosing response of the control algorithm to a blood glucose excursion in the subject based on a glucose level signal received from a glucose level sensor (e.g., a SGM sensor).

At block 7104, the glucose level control system 5802 may provide therapy during a first therapy period based at least in part on the glucose level signal and the initial value of the control parameter. In certain embodiments, the block 7104 can include one or more of the embodiments previously described with respect to the block 6604 of the process 6600. In some embodiments, the first therapy data may include glycemic control information resulting from the delivery of the first therapy. In some examples, the system may store all or some of the therapy data generated during the first therapy period in a memory of the glucose level control system 5802. In some examples, the therapy provided at block 7104, may comprise a plurality of medicament deliveries.

At block 7106, the glucose level control system 5802 may determine the therapy effect of the therapy provided during the first therapy period using statistical analysis of the first therapy data collected and stored at block 7104. In some examples, the statistical analysis may include calculating the statistical quantities discussed above and with reference to FIG. 70. In some cases, the statistical analysis may include regression analysis between certain measured and/or calculated parameters at block 7104. In some such examples the regression analysis may include determining an autoregression model. In some examples, the glucose level control system 5802 may determine the therapy effect using one or more of the embodiments described with respect to the block 6606 of the process 6600.

At block 7108, the glucose level control system 5802 may modify the value of the control parameter compared to the initial value selected at block 7102 or the value used in the last therapy period. In some examples, the modified value may be a value that makes the therapy more aggressive (e.g., aggressive by a significant amount). For example, when the control parameter is Tmax, at block 7108 the value of Tmax may be reduced to an amount less (e.g., 5, 10, 15 minutes, or more) than the value used in a previous therapy period (e.g., the initial value or the last modified value). In some examples, the modified value of the control parameter may be received from a user interface of the glucose level control system responsive to a user interaction with the user interface. The previous therapy period may be the first therapy period or any earlier therapy period. In some examples, the value for Tmax may be lowered by a significant amount (e.g., 10 minutes, 15 minutes, or other values). Further, the amount by which Tmax is reduced may be smaller than a previous reduction during a previous iteration of the process 7100. In some embodiments, the control parameter may be modified automatically without action by a user. In some cases, modifying the control parameter may change a timing, a dosage size, or a speed of injection of insulin administered to the subject.

At block 7110, the glucose level control system 5802 provides therapy to the subject based at least in part on the glucose signal and the modified value of the control parameter received from block 7108. In some examples, the duration of the therapy period (at block 7110), may be equal to the duration of one or more previous therapy periods. In some other examples, the duration of the therapy period may be determined based on the determined therapy effects of the therapies delivered during one or more previous therapy periods. In some examples, at block 7110 the system may store all or some of the therapy data generated during the therapy period. In some examples, the therapy provided at block 7110, may comprise a plurality of medicament deliveries. In some cases, the therapy data may include glycemic control information resulting from the delivery of the therapy.

At block 7112, the glucose level control system 5802 determines the therapy effect of the therapy provided at block 7110 during the last therapy period. In some examples, the therapy effects may be determined based at least in part on the therapy data obtained and stored at block 7110. In some examples, the glucose level control system 5802 may determine the therapy effect using one or more of the embodiments described with respect to the block 6606 of the process 6600.

At block 7114, the glucose level control system 5802 performs a statistical analysis based at least in part in the determined therapy effect of the therapies provided and stored during the last therapy period and the therapy period before the last therapy period to obtain a comparative assessment. In some such examples the comparative assessment may be based on statistical analysis of determined effects and the therapy data collected during the corresponding therapy periods. In some examples, the statistical analysis may include generating statistical quantities (e.g., distributions shown in FIG. 70) using the therapy data. In some examples, the statistical analysis may include the analytical method described above. In some examples, one or more characteristics of the statistical data may be used to compare the therapy effects. In some examples, the statistical analysis may include calculating one or more of a mean, a median, a mode, a standard deviation, a rate, a ratio, or a probability based on the therapy data obtained in the last two therapy periods or the determined effects of the therapies provided during the last two periods.

At the decision block 7116, the glucose level control system 5802, based at least in part on the comparative assessment received from block 7114, the glucose level control system 5802 may determine whether the value of the control parameter used during the last therapy period has improved the glycemic control for the subject compared to the therapy period before the last therapy period. In some embodiments, the glucose level control system 5802 may determine whether the modified value for the control parameter has resulted in statistically significant improvement in glycemic control. In some embodiments, the glucose level control system 5802 may determine whether the modified value for the control parameter has resulted in an improvement of a physiological parameter of the subject. In these embodiments, the physiological parameter may be determined based at least in part on the glucose level signal received from a glucose level sensor.

If the glucose level control system 5802 determines at the decision block 7116 that the glycemic control for the subject is not improved, the glucose level control system 5802 may return to the block 7110 and continue providing therapy to the subject based on the last modified value of the control parameter without any further modification.

If at the decision block 7116 the glucose level control system 5802 determines that the value of the control parameter used during the last therapy period has improved the glycemic control for the subject compared to the therapy period before the last therapy period, the glucose level control system 5802 proceeds to decision block 7118. In some cases, the improvement in the glycemic control should be larger than a threshold level before the glucose level control system 5802 proceeds to decision block 7118. In some cases, the control system proceeds to decision block 7118 if the modified value of the control parameter results in a reduced occurrence of blood glucose excursions compared to the first value of the control parameter.

At decision block 7118 the glucose level control system 5802 may determine whether the frequency and/or severity of hypoglycemia events is increased during the last therapy period compared to the therapy period before the last therapy period. In some examples, if the glucose level control system 5802 determines that the frequency and/or severity of hypoglycemia events is increased (e.g., beyond a threshold number or amount) during the last therapy period, the glucose level control system 5802 may return to the block 7110 and continue providing therapy to the subject based on the last modified value of the control parameter without any further modification. If at decision block 7118, the control system determines that the change in frequency and/or severity of hypoglycemia events is negligible (e.g., below a threshold number or amount), the control system may proceed to the block 7108 where the glucose level control system 5802 modifies the value of the control parameter. In some examples, the modified value may be a value that results in more aggressive therapy (e.g., the value of Tmax may be reduced). In some such examples, the amount by which the control parameter is changed may be smaller than a reduction amount in one or more previous modifications.

In some examples, at the decision block 7118 the control system may determine risks or the frequency and severity of one or more events other than hypoglycemia. For example, the control system may determine that in spite of an improvement in glycemic control for the subject, the rate and magnitude of glucose concentration has increased beyond threshold value. In some such examples, these additional risk determinations may be used to determine whether to keep or modify the last value of the control parameter.

In some embodiments, a modified version of the process 7100 may be used by the glucose level control system wherein the process stops at decision block 7116 and the control system continues providing therapy based on the last modified value of the control parameter until a user input is received. In some such examples, the last value of the control parameter (modified at block 7108), the results of the comparative assessment generated based on the comparison performed at block 7114 (e.g., whether a statistically significant improvement in subject's glycemic control resulted from the last control parameter change), may be output to the subject, a guardian or a healthcare provider via a user interface of the glucose level control system 5802 and/or a computing system (e.g., a smartphone, a notebook a personal computer and the like) connected to the glucose level control system (e.g., via a wireless link). In some such embodiments, at least in part based on the outcomes of the comparative assessment, the subject, the guardian or the healthcare provider may change the value of the corresponding control parameter (e.g., an interaction with a user interface) before the next therapy period.

In some examples, the statistical analysis used to determine the therapy effects (e.g., at blocks 6606 and 6612 in the process 6600, and block 7106 and 7112 in the process 7100) or to compare between therapy effects (e.g., at block 6616 in the process 6600 and block 7114 in the process 7100), may include regression analysis. In some examples, regression analysis may be used to find a relation between parameters calculated and/or measured during the therapy period. For example, with reference to FIG. 70, a regression analysis may be used to find a relation between $U_i$ and the rate of glucose concentration change (e.g., using G(t) near $t_i$) for a plurality of therapies provided during a therapy period. In some cases, the outcomes of one or more regression analysis may be used in the optimization process to determine a value of the control parameter.

In some examples, the therapy data captured and stored during one or more therapy periods may be divided to equal time intervals wherein each time interval starts and ends at substantially the same specific start and end times within a 24 period. In some such examples, an autoregression model may be derived for the glycemic control over the time interval between the specific start and end times. Subsequently, the resulting autoregression model may be used to determine whether the glycemic control has been improved compared to a previous therapy period. In some cases, the resulting autoregression model may be used to make additional adjustments to one or more control parameters in the subsequent therapy periods (after therapy periods following the period in which an autoregression model is determined).

In some examples, the outcome of the statistical analysis of therapy data may be used to evaluate the accuracy glucose signal generated by a CGM sensor.

As mentioned above in some examples the glucose level control system may generate a control parameter optimization report that may include some or all of the statistical quantities calculated during the optimization process, outcomes of the statistical analysis and graphical representation of the therapy data and related risk assessments. In some such examples, a Control Variability-Grid Analysis (CVGA) may be included in the control parameter optimization report, to visualize the variability of CGM data at a group level from a glucose-control point of view. In some examples the graphs may comprise distinctive groups of graphs, for example, to visualize average glycemia and deviations from target values, visualize variability and risk assessment, and event-based clinical characteristics. In some other examples, the graphical data may represent average glycemia and deviations from target glucose trace and aggregated glucose trace representing the time spent below, within or above the preset target range and visualizing the crossing of glycemic thresholds. In yet other examples, the control parameter optimization report may include graphs representing variability and risk assessment data. For example, a risk trace may be presented to highlighting essential variance (e.g., by equalizing the size of glucose deviations towards hypo- and hyperglycemia, emphasizing large glucose excursions, and suppress fluctuation within target range). In some other examples, histogram of blood glucose rate of change may be included in the report to presented, for example, the spread and range of glucose transitions. In yet other examples, Poincare' plots may be included in the report to visualize the stability of the glucose signal during different therapy periods that may be also associated with different values of a control parameter.

Embodiments of High Dose Mode

An automated glucose level control system, such as the glucose level control system 5802, can adjust a subject's glucose level over time by administering medicament, such as insulin or a counter-regulatory agent (e.g., glucagon). It is generally desirable that the glucose level be maintained within a setpoint range that is optimal for maintaining the subject's health or controlling the subject's disease (e.g., diabetes). Using one or more of the 510, the glucose level control system 5802 can adjust the subject's glucose level to be within the desired glucose setpoint range. In certain embodiments, the control algorithm used by the one or more controllers 5810 may adapt over time to control the subject's glucose level more smoothly or such that there is less dynamic range in the subject's glucose level. In other words, the control algorithm can be adapted over time so that the subject's glucose level is maintained within a more consistent range. It is typically desirable to not only maintain the subject's glucose level within a desired setpoint range, but to also limit fluctuations or large fluctuations in glucose level. It should be understood that some fluctuations may occur even in a completely healthy individual as meals and daily life (e.g., sleep, exercise, etc.) may affect glucose level of a subject. However, it is typically desirable to limit fluctuations of glucose level that go beyond that of a healthy or disease-free subject. The ability of the glucose level control system 5802 to adapt the control algorithm for administering medicament helps maintain the subject's glucose level within the desired setpoint range. A number of control algorithms that can be implemented by the glucose level control system 5802 described herein are described in the following patents that are hereby incorporated by reference herein in their entirety and made a part of this application: U.S. Pat. No. 7,806,854, issued Oct. 5, 2010; U.S. Pat. No. 9,833,570, issued Dec. 5, 2017; U.S. Pat. No. 10,543,313, issued Jan. 28, 2020; U.S. Pat. No. 10,842,934, issued Nov. 24, 2020; and U.S. Pat. No. 10,940,267, issued Mar. 9, 2021. It should be understood that the glucose level control system 5802 may implement other control algorithms instead of or in addition to the control algorithms described in the aforementioned patents.

However, there are times when the amount of time to adapt a subject's glucose level is less than ideal. In some cases, the control algorithms that control the administering of medicament may take longer to adapt for subjects with higher insulin per body mass or weight (e.g., per kg) requirements. Further, there are times when an adapted control algorithm is no longer applicable or well-adapted to the subject. In other words, there are times when the glucose level of the subject may be less consistent and may include more fluctuations. For example, a subject whose body is going through significant physiological changes (e.g., puberty, large or rapid weight change, sickness, etc.) may result in larger glucose level fluctuations or for an adapted control algorithm to no longer be well-adapted to the subject. As another example, unusual activity (e.g., a heavy or significant exercise session for a subject that usually does not exercise) may result in fluctuations in glucose level of the subject. Over time, the control algorithm will adapt to the physiological changes or other causes of glucose level fluctuations in the subject. However, while the control algorithm is adapting, glucose control may fluctuate more and/or maintenance of the subject's disease may be suboptimal.

In certain embodiments, providing different operating modes for one or more of the glucose level controllers 5810 that provide for different dosing modes and/or adaptation ranges for the glucose control algorithm of the ambulatory medical device A can reduce the time to adapt the control algorithm used to control administering of medicament to the subject. In other words, while a one size fits all may take varying amounts of time to adapt glucose control for different subjects, the use of different operating modes that may be selected based on one or more physiological characteristics (e.g., weight, sex, age, sensitivity to insulin, sensitivity to glucose, etc.) of the subject can reduce the adaptation time of the control algorithm for certain subjects. Further, the use of different operating modes can reduce fluctuations in glucose level of the subject. Having different operating modes with different adaptation modes enables the glucose level control system to narrow or widen the adaptation range based on one or more characteristics of the subject, which may be determined by the ambulatory medical device, a healthcare provider, a subject, or other user. In some cases, adjusting the adaptation range may adjust the quantity of dosing, the timing of dosing, the frequency of dosing, or any other factor associated with the administering of medicament to the subject. For example, one operating mode may be a high dose mode that results in larger doses of medicament being administered with each bolus of medicament and/or within a particular time period compared to a normal or non high dose mode.

In some embodiments, providing different operating modes for the glucose level controllers 5810 may include providing different adaptation ranges and/or different levels of aggressiveness for adjusting one or more control parameters of a control algorithm that generates control signals for controlling the administration of medicament to the subject. In some cases, the operating mode may be adjusted from an operating mode associated with a particular adaptation range or aggressiveness to another operating mode associated with a different adaptation range or aggressiveness. For instance, if a physician or healthcare provider knows that a subject needs on average more insulin than a particular threshold, the ambulatory medical device may be configured (e.g., by the healthcare provider) to permit a user to adjust the mode of operation to limit or adjust the range of the aggressiveness control parameter (e.g., by eliminating half of the adaptation range). The mode can be activated by interacting with a user interface element of the ambulatory medical device (e.g., by selecting a switch, pushing a button, interacting with a touch screen, causing a command to be transmitted to the ambulatory medical device from another electronic device, etc.).

Further, in some cases, statistical analysis of glycemic control can be used to determine whether a particular operating mode, such as a high dose mode is appropriate. In some such cases, the ambulatory medical device may be able to monitor one or more control parameters and recommend high dose mode, or a non high dose mode, based at least in part on the adapted values for the one or more control parameters.

In some instances, a subject or user may desire to invoke an operating mode (e.g., a high dose mode) for a subset of available controllers. For example, the subject or other user may desire to invoke a high dose mode for a model predictive controller (e.g., the corrective insulin corrective insulin controller 5906) that controls correction boluses while maintaining a basal controller (e.g., the basal insulin controller 5904) and/or meal controller (e.g., the priming insulin controller 5908) in a normal or non high dose mode. In certain embodiments, the subject or user may separately set operating modes for each controller of the glucose level controllers 5810. Further, in instances where operating modes are set automatically, the ambulatory medical device AMD may separately set the operating mode for each controller of the glucose level controllers 5810. In other words, one or more controllers that control administering correction doses, basal doses, and/or meal doses may individually or collectively be configured to operate in high dose mode or non high dose mode.

Configuration Code

The learning aspects of the adaptive control algorithms for medicament administration can be built up over an extended period of time. This learning can be lost if the glucose level control system becomes disabled, unusable, or a subject otherwise needs to begin therapy using a different glucose level control system. While a subsequent glucose level control system can include the ability to re-learn the physiological responses of the subject and the resulting therapy parameters, as described above, this process can take time. Accordingly, it can be advantageous to capture some or all of the glucose level control system parameters (GLCSP) provided to a subject by a previously used glucose level control system. The GLCSP parameters can be provided as initial therapy parameters to subsequently used glucose level control systems. The provided therapy parameters can "jump start" at least initial therapy provided by the subsequent glucose level control system.

The GLCSP, which may include dosing parameters, setting parameters, and/or control parameters of the adaptive algorithm, can be generated by the glucose level control system in the form of a configuration code. The GLCSP can generally include any configuration or setting of the glucose level control system (e.g., control parameters such as weight that influence correction factor, carb ratio, basal rate, etc.). The configuration code can be used when a glucose level control system is replaced with another glucose level control system. The configuration code can customizes at least initial therapy provided by a glucose level control system.

Figure 72:
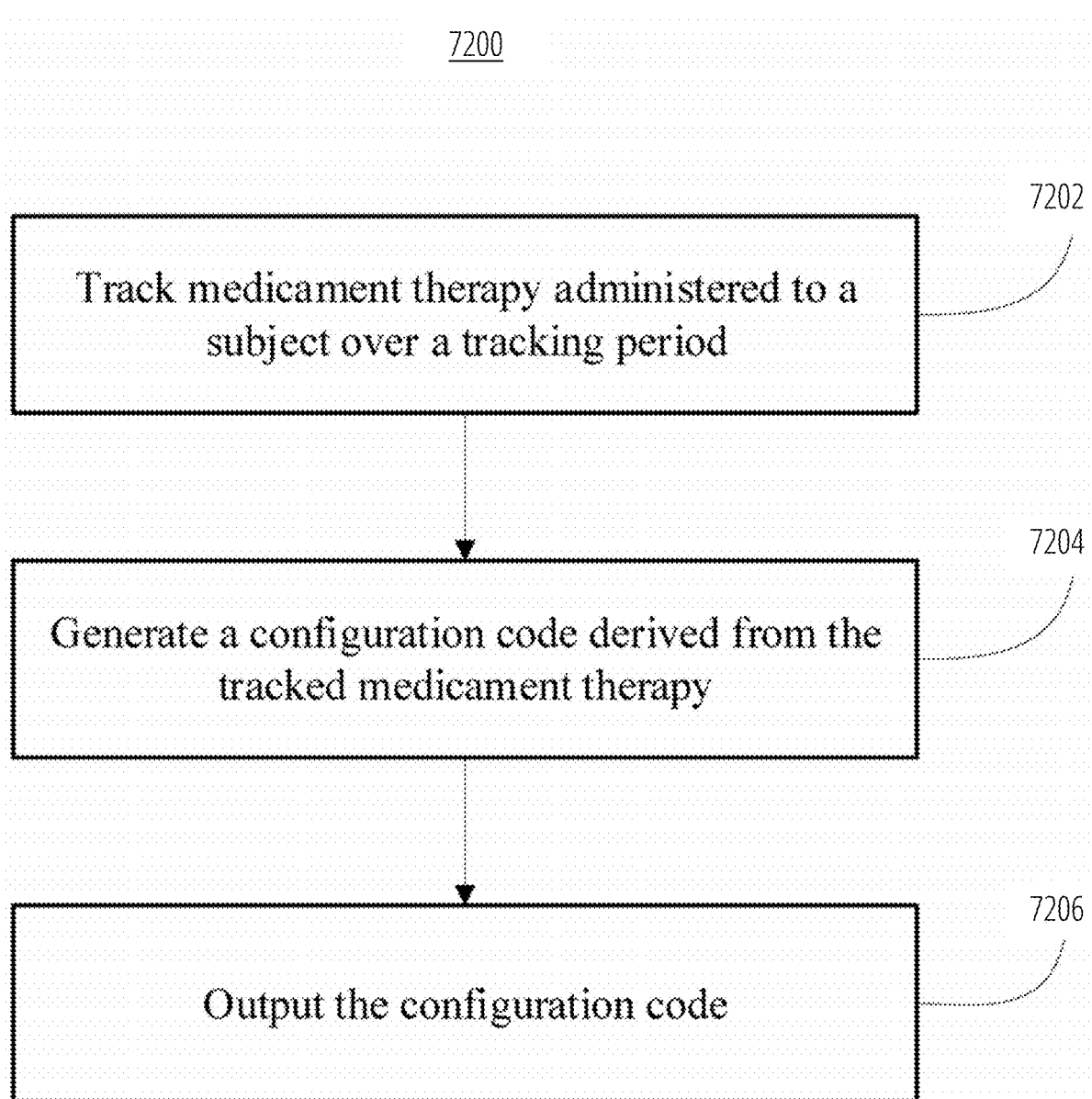
FIG. 72 presents a flowchart of an example configuration code generation process for customizing a glucose level control system.

FIG. 72 presents a flowchart of an example configuration code generation process 7200 in accordance with certain embodiments. The process 7200 may be performed by any system that can track medicament therapy (e.g., insulin or glycogon therapy) provided to a subject over time or system with access to data based on the tracked medicament therapy. The process 7200 generates a configuration code that may be used if a glucose level control system (e.g., glucose level control system 5802) requires customization for a subject (e.g., because the becomes an existing glucose level control system unavailable). For example, the process 7200 may be performed by one or more elements of the glucose level control system 5802.

In some cases, at least certain operations of the process 7200 may be performed by a separate computing system that receives indications of medicament therapy provided to the subject 5804 from the glucose level control system 5802. Although one or more different systems may perform one or more operations of the process 7200, to simplify discussions and not to limit the present disclosure, the process 7200 is described with respect to a glucose level control system 5802. However, other systems, such as cloud-based or other type of remote computing systems may perform the process 7200 to generate and output the configuration code.

At block 7202, the glucose level control system 5802 tracks medicament therapy administered to the subject 5804 over a tracking period. The tracking period is typically at least one day and may be longer. For example, the tracking period may be 1 day, 2 days, a week, a month, several months, a year, any length of time between the foregoing examples, or even longer. In some cases, the tracking period may be continuous from a point in time when tracking begins. For example, the tracking period may encompass the entire usage lifetime of the glucose level control system 5802 by the subject 5804. In cases where the tracking period is set for a defined period of time (which may be modified for different iterations of the process 7200), the process 7200 may be repeated periodically, upon request, or upon a triggering event using a new tracking period, of equal or different length. The triggering event may include any event that may render a prior generated configuration code potentially out-of-date. For example, the triggering event may include a change in medicament type (e.g., different medicament or counter-regulatory agent formulations), a change in physiological characteristics of the subject 5804 (e.g., a change in weight, or sensitivity to different glucose levels or medicament), or a change in average activity level of the subject 5804.

In some cases, the tracking period may be defined by or based on a particular number of medicament administering events. For example, the tracking period may be defined by at least ten instances of generating an medicament dose based on a glucose level signal. As another example, the tracking period may be defined by a minimum number of meal events, correction dose events, and/or basal dose events. For instance, the tracking period may require 3 meals, or 3 meals of each meal type to occur, 2 correction doses, and/or basal doses. It should be understood that the aforementioned number of doses is just an example, and the tracking period may include more or fewer dose amounts. Moreover, the tracking period may be defined or specified as a combination of time and occurrences of a particular number of doses of medicament.

In some cases, the tracking period may be variable. For example, if the glucose level control system 5802 determines that the medicament dose therapy is inconsistent or erratic over the tracking period (e.g., due to inconsistent exercise or eating habits), the tracking period may be extended.

Tracking the medicament therapy includes storing an indication of doses of medicament delivered to the subject as correction boluses of medicament, as food intake boluses of medicament, as basal doses of medicament, and/or other parameters such as those described below. The correction boluses can include regulatory or counter-regulatory agents and can be generated using a model-predictive control (MPC) algorithm such as the one disclosed in the Controller Disclosures described above. The meal boluses can include a regulatory agent and can be generated using a meal control algorithm such as disclosed in the Controller Disclosures. The basal doses can include a regulatory agent and can be generated using a basal control algorithm such as disclosed in the Controller Disclosures. Storing the medicament dose control signal and/or the indication of the quantity of medicament may include storing the medicament dose control signal and/or the indication of the quantity of medicament in a therapy log or any other type of data structure in the memory 5830 of the glucose level control system 5802.

Tracking the medicament therapy may include storing the medicament dose control signal generated based at least in part on a glucose level signal. The glucose level control system 5802 can receive a glucose level of a subject 5804, which may include receiving and/or determining a glucose level signal corresponding to a glucose level of the subject. The glucose level signal may be received from the glucose sensor 5808 (e.g., a CGM sensor). Alternatively, or in addition, the glucose level may be received from a user that provides the glucose level to the glucose level control system 5802 via a user interface, such as a user interface generated by the separate processor 5820 that may be output on a touchscreen by the touchscreen controller 5828. The glucose level received from the user may be a glucose level measured using an alternative sensor or measurement mechanism (e.g., diabetes measurement strips) that may be used in place of the glucose sensor 5808. The glucose level control system 5802 generates an medicament dose control signal based at least in part on the glucose level signal. In some cases, the medicament dose control signal may be a medicament control signal configured to control a medicament pump to administer medicament (e.g., medicament, counter-regulatory agent, or other medicament) to a subject 5804. The dose control signal may be generated using a control algorithm configured to autonomously determine doses of medicament to be administered to or infused into the subject for the purpose of controlling blood glucose of the subject based at least in part on the glucose level or glucose level signal.

Alternatively, or in addition, the glucose level control system 5802 may store the medicament dose control signal and/or the indication of the quantity of medicament at a remote data store location. This remote data store may be a computing system with which the glucose level control system 5802 may communicate (e.g., a laptop, desktop, smartphone, or other computing device of the subject 5804 or a user). The glucose level control system 5802 may provide the medicament dose control signal data or the indication of the quantity of medicament to the local computing system via Bluetooth®, near field communication services, or via a local network. Alternatively, or in addition, the remote data store may be a remote computing system that the glucose level control system 5802 may communicate with over a wide area network, such as a wireless area network, a cellular network using IoT based communication technology, cellular communication technology, or any other communication network. In some cases, the wide area network may include the Internet. The glucose level control system 5802 may include a wireless radio that enables it to communicate with the local or remote computing system. Further, the remote computing system may be a computing system of a data center or a cloud computing environment.

Whether a local or remote computing system, the glucose level control system 5802 may establish a communication channel with the computing system. This communication channel may be an encrypted channel. Further the communication channel may be a direct end-to-end connection between the glucose level control system 5802 and the computing system. Once the communication channel is established, the glucose level control system 5802 may transmit the medicament dose control signal data or the indication of the quantity of medicament to the computing system.

Generally, the operations associated with the block 7202 may be repeated multiple times throughout the course of the tracking period. For example, in some cases, an medicament dose control system associated with basal medicament may be generated up to 288 times a day. Accordingly, tracking the medicament therapy may include storing medicament does control signals and/or corresponding indications of quantities of medicament for a plurality of autonomously determined doses of medicament infused into the subject throughout the tracking period.

Generally, counter-regulatory agent therapy includes administering a counter-regulatory agent (e.g., glucagon) when there is a risk or occurrence of hypoglycemia. Usually, the counter-regulatory agent is not supplied on periodic or daily basis. However, it can be useful to understand the amount and frequency that counter-regulatory agent is administered to the subject. For example, it may help a healthcare worker or user guide or adjust care for the subject. Further, tracking counter-regulatory agent use may help determine a minimum quantity of counter-regulatory agent that should be accessible to the subject, either in a bi-hormonal pump or for use in injection therapy. The block 7202 may include tracking the counter-regulatory agent administered during the tracking period. Tracking the counter-regulatory agent therapy may include storing an indication of autonomously determined doses of counter-regulatory agent delivered to the subject responsive to the glucose level signal obtained.

At block 7204, a configuration code can be generated based on data from the tracked medicament therapy. The data can be based on the tracked medicament therapy provided in block 7202. The data can be stored locally (e.g., on the glucose level control system 5802) or remotely on a remote computing device. The configuration code can be generated by the glucose level control system 5802. Alternatively, the configuration code can be generated by a remote computing device provided access to the data.

The configuration code can include one or more of a plurality of encoded GLCSP. The encoded GLCSP can be determined based on one or more dosing parameters, setting parameters, and/or control parameters.

The encoded dosing parameters can include a correction dosing parameter. The correction dosing parameter can be based on some or all of the correction boluses of medicament administered during the tracking period. For example, the correction dosing parameter can be based on a moving average of correction boluses administered to the subject.

The correction dosing parameter may include determining an average correction bolus provided to the subject per day over the tracking period. The average correction bolus may be determined by adding the total amount of correction doses administered each day and dividing by the number of days in the tracking period. In some cases, one or more days, or time periods, of the tracking period may be omitted when determining the average correction bolus because, for example, the one or more days or time periods may be determined to be outliers. The outliers may be omitted to provide a more accurate understanding of average insulin needs or consumption. While, a correction bolus is often supplied in response to a determination that a subject's blood glucose level is spiking or exceeding a threshold, and not necessarily as a regular dose of insulin, correction dosing parameters based on an average correction bolus can provide an initial starting point for a glucose level control system.

Alternatively, or in addition, the correction dosing parameter can be the moving average of correction doses in combination with a rate of change of blood glucose from a unit of insulin provided during correction therapy. The correction factor can be based on receiving glucose level data of the subject obtained during a specified time duration; causing the ambulatory medicament pump to deliver the first specified doses of insulin information stored in the to the subject for a predetermined time duration; determining from the glucose level data a decrease in the glucose level of the subject during the specified time duration; calculating an effective correction factor for the subject based on the decrease in the glucose level and an amount of the first specified insulin correction bolus; and adjusting the first specified doses of insulin in consideration of the effective correction factor.

The encoded dosing parameters can include a food intake dosing parameter. The food intake dosing parameter can be based on some or all of the food intake boluses of medicament provided during the tracking period. Generating the food intake dosing parameter may include determining, for each period of food intake of a plurality of food intake times per day (e.g., snacks or mealtimes), an average food intake bolus of insulin provided to the subject over the tracking period. In some cases, the average food intake bolus may be determined for particular meals (e.g., breakfast, lunch, and dinner), while other periods of food intake (e.g., snacks or teatime) may be omitted or ignored. Further, the average food intake boluses may be associated with particular meal sizes as identified by a user. For example, the glucose level control system 5802 may determine an average mealtime bolus for a small and a large meal, or for a small, a medium, and a large meal. The average food intake bolus may be determined by averaging an amount of insulin the glucose level control system 5802 determines should be administered to the subject using a control algorithm of the glucose level control system 5802 for each mealtime and identified meal size. A food intake bolus size used to generate the food intake boluses of medicament can be adapted over time based at least in part on one or more glucose level signals received from a glucose sensor configured to determine glucose levels in the subject. The encoded dosing parameters can be determined based on food intake parameters of the subject. The food intake dosing parameter can include a plurality of calculated food intake dose amounts. One calculated food intake dose amount can correspond to a segment of a day different from at least one other calculated food intake dose amount of the plurality of calculated food intake dose amounts.

The encoded dosing parameters can include a basal dosing parameter. The basal dosing parameter can be based on some or all of the basal doses of medicament provided during the tracking period. The basal dosing parameter can be based the moving average of the nominal basal doses over the tracking period. For example, the tracked medicament therapy may include determining a moving average of the past 7 days of nominal basal doses during each dosing interval. The basal dosing parameter may include determining a number of long acting medicament units based at least in part on an average total basal medicament provided to the subject per day over the tracking period. The averaged total basal medicament provided per day may be included in the basal dosing parameter as a single dose of long acting medicament that is configured to help maintain the basal medicament level of the subject throughout the day.

Alternatively, or in addition, the basal dosing parameter may be based on a rate of basal medicament provided within one or more sub-periods of the tracking period. In some cases, each day of the tracking period may be divided into a plurality of sub-periods. For example, each day of the tracking period may be divided into two, three, four, or more time periods, or equal or different length. In some such cases, basal dosing parameter may include determining an hourly basal rate for each sub-period of the plurality of sub-periods. This hourly basal rate may be determined by averaging the corresponding sub-periods for each day of the tracking period. The basal rate may be determined on an hourly rate or based on any other time period.

The encoded dosing parameters can include on one or more demographic parameters. The demographic parameters may include characteristics shared among large portions of a population (e.g., weight, gender, age, etc.) as well as characteristics that may be unique or specific to the subject, or shared among few people (e.g., characteristics related to genetics).

The encoded dosing parameters can be determined based on a carbohydrate ratio. The carbohydrate ratio can be calculated based on medicaments provided during the tracking period.

The encoded dosing parameters can be determined based on a glucagon rate information. A glucagon dosing parameter can be based on at least some glucagon doses administered during the tracking period.

The encoded dosing parameters can be determined based on one or more physiological parameters can include using one or more subject sensors, such as a CGM sensor, weight, heart rate, etc.

The configuration code can be further based on a control parameter. The configuration code can include the encoded control parameter. The control parameter can be based on execution of a control algorithm during the tracking period. In some examples, the time of delivery and dose of the plurality of therapies may be based at least in part on the glucose level signal and the first value of a control parameter of the control algorithm used by the glucose level control system 5802. The control parameter may include any control parameter that affects operation of the glucose level control system 5802 and/or performance of a control algorithm of the glucose level control system 5802. For example, the control parameter can be Tmax, $T_{1/2}$, speed of delivery of a medicament dose, a setpoint for the glucose level, a blood glucose range, a threshold value of blood glucose level (e.g., a maximum or minimum value) and the like. The control algorithm may include any control algorithm and/or PK model used to determine a dose of medicament (e.g., insulin) to administer to the subject. In other words, the controller 5810 or the separate processor 5820 may use the control algorithm to generate a dose control signal based at least in part on a value of the control parameter to cause the delivery device(s) 5806 to administer a dose of insulin or other medicament.

The configuration code can be further based on a setting parameter. The configuration code can include the encoded setting parameter. The setting parameter may be used by the glucose level control system in identifying the subject and/or configuring the glucose level control system during the tracking period. The setting parameters can include a subject identifier. The setting parameter can be used by the glucose level control system in identifying a subject during the tracking period. The subject identifier can include the name or personal identification number of the subject. The setting parameters can include a user identifier and/or a user associated with the subject. The customer identification can include information regarding ownership, safe-access level settings or rights, or other customer related information. The setting parameters can include information for identifying the medicament pump, such as serial identification information. The setting parameters can include medicament pump settings. The setting parameters can include operating system information, such as the version number, update date, etc. The setting parameters can include alert settings (e.g., for the ambulatory pump), such as delivery preferences for sending the alert to the user, outputting an alert on a display, transmitting an alert to an account or device of the user, generating an audio alert or a visual alert, or any other type of alert. The setting parameters can include user interface settings such as menu options, passwords or related settings. The setting parameter may contain a plurality of pump parameters that reproduce part of or all of a "state" or comprehensive pump configuration or glucose level control system. In some cases, the configuration code may be used to refine pump settings for a replacement glucose level control system to be used by the subject. In other cases, the replacement glucose level control system may be manually configured based on the configuration code or the configuration data encoded in the configuration code.

The configuration code generated by the process 7200 can be a string of characters (e.g., alphanumeric), link or reference, QR code, machine readable code, or other type of code. The configuration code can be a predetermined length (e.g., 16 bytes or 16 characters or more). Generating or receiving the configuration code at block 7204 can include generating a checksum for checking an error in a generation of the configuration code. The configuration code can include a time-based parameter. The time-based parameter can include a timestamp indicating an age of the configuration code, age of data derived during the tracking period, or an expiration date of the configuration code.

The configuration code can include a subject identification. The subject identification can include the name or personal identification number of the subject. The configuration code may be based on or include a unique personal identification of the subject, making each configuration code unique to a specific subject. The configuration code may be single-use (e.g., usable only once for a particular glucose level control system). Re-use of the same code my trigger a rejection of the configuration code. The configuration code may be a personal passcode for a new glucose level control system. The glucose level control system may require a confirmation code for initial use.

Generating the configuration code at block 7204 can include a safety check, such as an information checksum. The checksum and verify whether the pump parameters are within threshold parameters (e.g., based on the tracked medicament therapy administered to the subject). The threshold parameters can be preset for the subject (e.g., based on weight). The threshold parameters can be determined based on history of therapy stored in the cloud-based server and associated with the subject identifier. Generating the configuration code at block 7204 can include a step of communicating with a healthcare provider via a data interface to enter parameters, verify parameters, safety check, generate an encrypted source code, verify subject, or other verifications.

At block 7206, the glucose level control system 5802 or remote computing device outputs the configuration code. Outputting (or generating) the configuration code may include encrypting the configuration code and outputting the encrypted configuration code. Outputting the configuration code may include displaying the configuration code on a display or user interface (e.g., a QR code or alphanumeric code). Outputting the configuration code may include may be in response to a request by a user of the user interface. Outputting the configuration code may include may be in response to an automated backup protocol or an input from a remote source (e.g., a command indicating that a new glucose level control system is being implemented). The user interface 5824 can be implemented in the ambulatory medicament pump in the form of a graphical user-interface configured to output the configuration code and/or backup therapy protocol. In some cases, the configuration code may be stored at the glucose level control system 5802 and may be accessed in response to a user interaction with a user interface of the glucose level control system 5802. Outputting the configuration code may be part of or used in conjunction with display of a backup therapy protocol. Alternatively, or in addition, outputting the configuration code may include transmitting the configuration code to a computing device of a user for display and/or storage.

Outputting the configuration code can include transmitting the configuration code to a second glucose level control system or to an electronic device in communication with the glucose level control system (e.g., wired or wirelessly through networked communication). The second glucose lever control system can generate a checksum to check for errors in the transmission of the configuration code.

The glucose level control system 5802 can output a link to the configuration code and/or the configuration data encoded in the generated configuration code stored at a remote computing location. When customizing another glucose level control system (e.g., initializing the system) the link can be input through the user interface manually or by an automatic process, as described further below. The glucose level control system can use the link to identify, access, and download the encoded configuration data and/or the configuration code. In certain implementations, the configuration code can include the link to the remote computing location. When initializing another glucose level control system the configuration code can be input and the glucose level control system can use the linked configuration code to access and download the configuration data.

The configuration code may also be updated over time as additional medicament therapy data is obtained. The configuration code may also be updated by repeating blocks 7202 and 7204 continuously or at intervals (e.g., in response to a request) as additional medicament therapy data is obtained. In one example, the configuration code can be updated based on a generation request from a user (e.g., through the user interface). In another example, the configuration code can be automatically calculated and/or output in response to startup or shutdown of the glucose level control system 5802.

Similar to the backup therapy protocol discussed above, some implementations of the configuration code generated can be configured to produce a "conservative" approach to therapy (e.g., at least during initial stages of therapy followed by use of the adaptive control algorithm).

Figure 73:
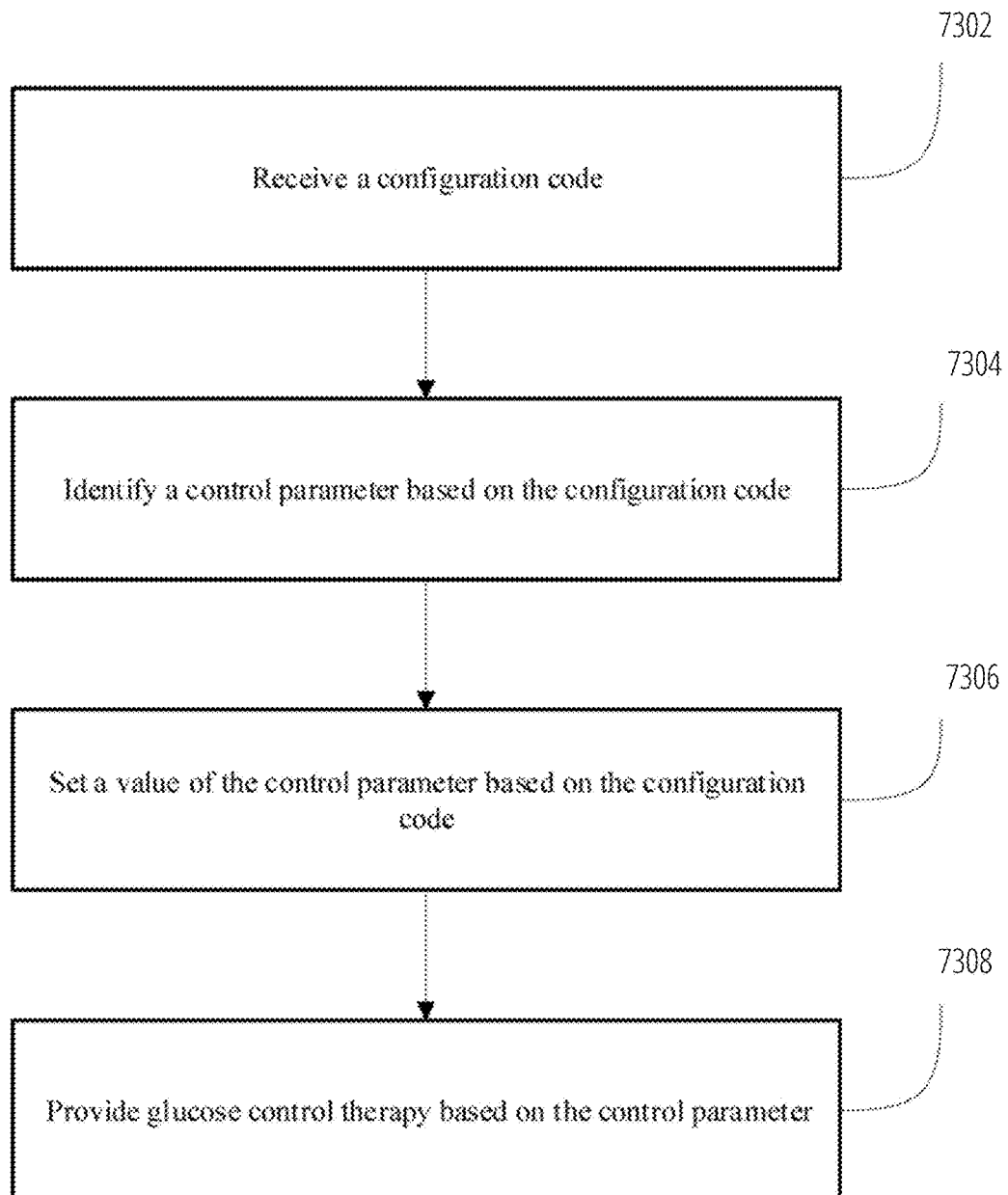
FIG. 73 presents a flowchart of an example configuration process for customizing a glucose level control system based on a received configuration code.

FIG. 73 presents a flowchart of a process 7300 for receiving a configuration code and setting parameters on a glucose level control system based on the configuration code. A configuration code, as output by the configuration code generation process 7200, can be used in conjunction with another glucose level control system. The configuration code customizes therapy (e.g., initial therapy) provided by the second glucose level control system. The original glucose level control system can also include the capacity to receive a configuration code or utilize the generated configuration code.

At block 7302, the glucose level control system 5802 receives a configuration code. The configuration code can be entered at the user interface. The user interface can include a prompt on first-time startup to enter a configuration code. The user interface can alternatively provide a menu location for entering the configuration code. Alternatively, the glucose level control system 5802 can be shipped including the configuration code pre-loaded. In another alternative, the configuration code can be entered through a networked connection with an electronic device.

Alternatively, the second configuration code is received from an electronic computing device in communication with the glucose level control system (e.g., automatically). The configuration code can be received from the electronic computing device in response to a request from the glucose level control system.

At block 7304, the glucose level control system 5802 identifies a control parameter based on the received configuration code. The control parameter can be a parameter that influences a control algorithm that generates control signals for controlling the administration of medicament to the subject. Control parameters can include weight, the correction factor, the carb ratio, the basal rate, food intake bolus size, etc. Identifying the control parameter can include decrypting the encoded dosing parameter of the configuration code and/or using a lookup table based on the configuration code. In certain implementations, the configuration code can identify multiple control parameters.

At block 7306, the glucose level control system 5802 sets an identified control parameter to a value based on the received configuration code. The configuration code can also include a value (or range) for the control parameter. Identifying the value of the control parameter can include decrypting the encoded dosing parameter of the configuration code. In certain implementations, the value comprises an initial value for the control parameter. The control parameter can be adapted over time based at least in part on the medicament therapy administered over the tracking period. Where multiple control parameters are identified, each can include a value (or range).

The glucose level control system 5802 can verify a checksum of the configuration code. Setting the control parameter to the value can be performed in response to successfully verifying the checksum of the configuration code. The glucose level control system 5802 can also include a check to verify that the glucose level control system 5802 is the intended recipient of the configuration code. The glucose level control system 5802 can determine a first reference code associated with the configuration code and determine a second reference code associated with the glucose level control system. If the first reference code matches the second reference code, setting the control parameter to the value can be performed. The first reference code and the second reference code can correspond to one or more versions of control software capable of being executed by the glucose level control system 5802. Where the first reference code and the second reference code do not correspond, the value of the control parameter can remain at an initial or default level. Alternatively, where the first reference code and the second reference code do not correspond, the value of the control parameter can be set based at least in part on a modified version of the second configuration code. For example, the value can be modified to stay within a safe range (e.g., min and/or max) for the control parameter.

The glucose level control system 5802 can determine whether the value of the identified control parameter is safe for the subject by determining whether the value is within a threshold range (e.g., safety maximum and/or minimum, as described above) or a historical value for the control parameter. The historical value can include an average value over a particular time period or a most recent value of the control parameter. The historical value can be obtained based on a history of medicament therapy stored at the glucose level control system. The historical value can be obtained based on a history of medicament therapy stored at an electronic device in communication with the glucose level control system.

At block 7308, the glucose level control system 5802 can provide glucose level therapy based on the value set on the identified control parameter. After initializing the control parameter, the control algorithm can provide tracked medicament therapy to the subject. The initial period may be 1 day, 1 hour, or other time frame. Any necessary updates to the control parameter can be based on the adaptive control algorithm used by the one or more controllers described above and which may adapt over time to control the subject's glucose levels.

Figure 74:
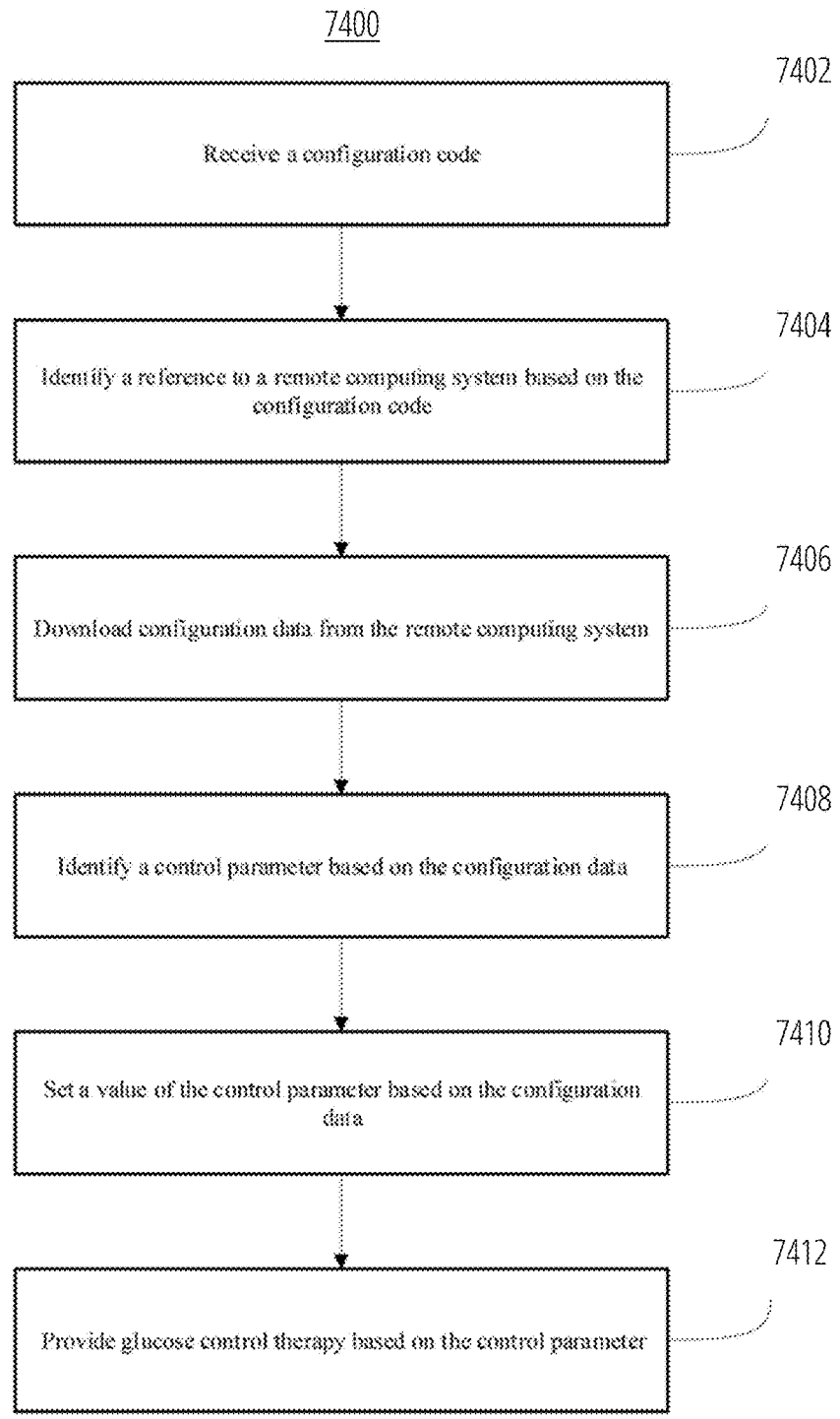
FIG. 74 presents a flowchart of an example configuration process for customizing a glucose level control system based on a received configuration code that includes a reference or link to downloadable configuration data.

FIG. 74 presents a flowchart of a process 7400 for receiving a link to access a configuration code (or a configuration code comprising a link or reference) stored in a remote computing system and setting parameters on a glucose level control system based on the configuration data retrieved from the remote computing system. A configuration code or configuration data based on the configuration code (e.g., as output by the configuration code generation process 7200 to a remote computing location) can be used to customize therapy provided with another glucose level control system. The configuration code customizes at least initial therapy provided by the second glucose level control system.

At block 7402, the glucose level control system 5802 receives a link or reference to a remote computing location. The remote computing location can include configuration data including the dosing parameters and/or the configuration code. The link can be manually or automatically entered through a user interface, as described above.

At block 7404, the glucose level control system 5802 identifies a reference to a remote computing system based on the link. The remote computing system can be accessed through a networked connection. The remote computing system can include the stored configuration code and/or configuration data, such as the dosing parameters.

At block 7406, the glucose level control system 5802 downloads the configuration data from the remote computing system. The configuration data can be downloaded through a networked connection.

At block 7408, the glucose level control system 5802 identifies a control parameter based on the downloaded configuration data. Identifying the value of the control parameter can include decrypting the encoded dosing parameter of the configuration code. Alternatively, the glucose level control system 5802 identifies the control parameter at the remote storage location and downloads the identified control parameter. In certain implementations, the configuration code can identify multiple control parameters.

At block 7410, the glucose level control system 5802 sets the identified control parameter to a value based on the downloaded configuration data. Setting the identified control parameter to a value can include one or more safety checksums, such as those described above in blocks 7306 and 7204. In certain implementations, the value comprises an initial value for the control parameter. The control parameter can be adapted over time based at least in part on the medicament therapy administered over the tracking period. Where multiple control parameters are identified, each can include a value (or range).

At block 7412, the glucose level control system 5802 can provide glucose level therapy based on the value set on the identified control parameter. After initializing the control parameter, the control algorithm can provide tracked medicament therapy to the subject. The initial period may be 1 day, 1 hour, or other time frame. Any necessary updates to the control parameter can be based on the adaptive control algorithm used by the one or more controllers described above and which may adapt over time to control the subject's glucose levels.

Modular Blood Glucose Control Systems

Blood glucose control therapy generally requires the coordination of many elements within a system. For example, a blood glucose control therapy system can broadly include a medicament delivery system (e.g., a medicament pump, a patch pump, a medicament pen, a hospital infusion pump) and a glucose sensor (e.g., a continuous glucose monitor (CGM)), and each of those elements may include one or more sub-elements. In order for the blood glucose control therapy to be properly dosed and delivered, the various elements must be able to properly communicate with one another. For example, the glucose sensor and the medicament delivery system must be able to communicate with one another. This need to communicate often demands that the medicament delivery system and the glucose sensor be specially configured to communicate with each other. Thus, modern systems do not generally allow for a medicament delivery system to communicate with a plurality of glucose sensors, or for a glucose sensor to communicate with a plurality of medicament delivery systems. However, systems and methods described herein help solve this deficiency.

Although any medicament delivery system may be used in the systems and methods described herein, for convenience reference will be made to a medicament pump below. A modular blood glucose control therapy system can provide interoperability between a medicament pump and a plurality of different glucose sensors (e.g., glucose sensors made by a plurality of sensor manufacturers), and/or interoperability between a glucose sensor and a plurality of different medicament pumps (e.g., medicament pumps made by a plurality of pump manufacturers).

The modular blood glucose control therapy system can include a data interface that is configured to transmit a dose control signal to a pump controller and to receive a glucose level signal from a glucose sensor. The glucose level signal received from the glucose sensor may include encoded data that can be read only by one or more medicament pumps. The modular blood glucose control therapy system can be configured to decode the encoded data. The glucose level signal may include, for example, first encoded data corresponding to a glucose level of the subject and/or second encoded data corresponding to an indication of a glucose trend. The glucose trend may indicate one or more signals, such as a predicted change in the glucose level of a subject.

One way to allow interoperability among different medicament pumps and different glucose sensors is to include a plurality of encoding profiles and/or decoding profiles. The modular blood glucose control therapy system can therefore include a plurality of dose control signal encoding profiles and/or glucose level signal decoding profiles. Each of the plurality of dose control signal encoding profiles may correspond to at least one of a plurality of pump controllers of associated medicament pumps. Each dose control signal encoding profile can be configured to encode a dose control signal for transmission to the corresponding pump controller. The modular blood glucose control therapy system can be configured to select the dose control signal encoding profile that corresponds to the pump controller operatively coupled to the subject. If a subject changes medicament pumps, the modular blood glucose control therapy system can modify which dose control signal encoding profile(s) it uses to communicate with the medicament pump (if necessary), according to some embodiments. Additionally or alternatively, each of the plurality of glucose level signal decoding profiles can correspond to at least one of a plurality of glucose sensors, wherein each glucose level signal decoding profile is configured to decode at least the first encoded data and the second encoded data of the glucose level signal, and wherein the selected glucose level signal decoding profile corresponds to the glucose sensor operatively coupled to the subject.

The modular blood glucose control therapy system may be self-contained within a small modular component, such as within a chip. The system can comprise a system on a module (SOM), which can allow the module to be disposed within a number of medical devices, such as a medicament pump (e.g., an ambulatory medicament pump), a glucose sensor (e.g., a continuous glucose monitor (CGM)), or other medical device. The modular blood glucose control therapy system can be able to include a data interface to communicate with other electronic devices, such as a remote network (e.g., cloud, server), a medicament pump, a glucose sensor, and/or a computing device (e.g., a laptop, cell phone, smartphone, Personal Diabetes Manager (PDM), tablet, wearable electronic device, etc.). The data interface can include a wired data interface and/or a wireless data interface. The data interface may refer to a plurality of data interfaces. Each data interface of the plurality of data interfaces may be configured to communicate with a different electronic device.

The modular blood glucose control therapy system can include one or more algorithms stored thereon, such as the control algorithm described above. The system can output a dosing recommendation to a pump controller via a wired and/or wireless data interface. The system can integrate cellular wireless and/or GPS radio module(s) as well. The dosing recommendation can include a command or instruction to the pump controller. Additionally or alternatively the recommendation may include a displayed recommendation but no command for some reason (e.g., that the medicament pump or a component thereof), and feedback can be accepted (e.g., in case the user performs a manual injection)

The system can include one or more computing components, including a microprocessor, a Bluetooth Low Energy (BLE) wireless modem, a clock, and/or non-volatile memory to independently operate and maintain a wireless connection and/or calculate dosing results. As described in more detail below, the system can save and restore algorithm states data and other data on the module. Additionally or alternatively, the system can receive remote software upgrade services and provide them to a target pump controller or other associated medical device. Because of the benefits of the system (e.g., the small form factor), the system can be part of a digital infrastructure that provides interactivity among multiple electronic devices, such as a mobile device, wearable device (e.g., smart watch), cloud network, and/or third-party services. The system may include a hardware and/or software validation package that satisfies public standards, such as, for example, FCC, EMC/EMI, IEC 62304, or other validation standard. In some examples, the system can be coupled directly to an infusion pump, such as a pump in a hospital room.

The modular blood glucose control therapy system may receive one or more inputs from a user and/or from another device. For example, the system may receive glucose sensor pairing information. The pairing information can include credentials that allow it to pair with the glucose sensor, which may be remote from the modular system. As described below, the modular system can include pairing information for a plurality of glucose sensors. The various credentials (e.g., encoding and/or decoding profiles) may be stored on the modular system. Thus, in some embodiments, the modular system can communicate with a plurality of models and/or glucose sensors from a plurality of manufacturers.

The modular system can receive various details related to a subject receiving therapy. For example, the system may receive a body weight and/or blood glucose control parameters from a remote device and/or from a directly coupled medical device. In some embodiments, the modular system can receive meal announcement requests and/or a pump status. Additional details are provided below.

The modular blood glucose control therapy system can receive indications of the status of the pump controller. For example, the modular system can receive an indication that the pump controller is available and/or that it is not available for delivery of therapy. In some embodiments, the modular system may receive a delivery report. The delivery report may indicate how much therapy was delivered since a previous time (e.g., since a most recent status request). The delivery report can include a recommendation for future therapy. The recommendation may include a command to deliver the recommended therapy.

As described in more detail below, the modular system may have the ability to receive pass-through data and route that data to a target device. Pass-through data may include data that is unrelated to a dose control signal and/or not used in a calculation of a dose control signal. The pass-through data may include an alert related to a third-party system. For example, the pass-through data may include an indication that a pump cartridge has a volume of medicament below a threshold volume or that a supply of medicament is below a threshold supply. The indication may include a charge level associated with a battery of the ambulatory medicament pump and/or that an associated glucose sensor has exceeded a threshold performance period. In some embodiments, the data may include an indication that a new pump cartridge has been installed in the ambulatory medicament pump. In some embodiments, the modular system can receive information (e.g., the pass-through data) from a third-party pump element for display on a user interface. The user interface may include a personal computing device, such as a smartphone, a PDM, a tablet, and/or another display device.

The modular system can receive software upgrades for the modular system via a data interface (e.g., a wireless data interface). The data interface can include a Bluetooth module (e.g., BLE) and/or a wireless modem (e.g., an LTE-M). in some embodiments, the modular system receives an indication from the medicament pump which medicament(s) (e.g., U100, U200, glucagon, etc.) will be delivered by the pump. The system may receive an indication from the medicament pump when delivered insulin reaches a point of maximum concentration within the blood of the subject (e.g., $T_{max}$). The $T_{max}$ value may be updated by the medicament pump at regular or periodic intervals. The system may receive a target blood glucose level, a setpoint level, the $T_{max}$, and/or other blood glucose control parameters.

The modular system may receive other signals. For example, the modular system can receive instructions to control the medicament pump. These instructions can include a pause in insulin, a duration of such a pause, a resume signal, an updated rate of insulin delivery (e.g., increase, decrease), and/or other instructions.

The modular blood glucose control therapy system may be able to provide one or more of a variety of outputs. These outputs may be to an associated medicament pump in some embodiments. Additionally or alternatively, the outputs may be to a glucose sensor and/or to another element within a blood glucose control therapy system. The system may output a dose control signal. The dose control signal can include whether insulin only should be delivered to the subject or whether additional therapy should be provided (e.g., bihoromonal therapy, insulin and glucagon, etc.). The system may output a total number of units to be delivered of each therapy and/or a speed at which that therapy is to be delivered. The system can encode the instructions to be readable by one or more of a plurality of pump controllers and/or glucose sensors. As discussed below, the encoding profiles for each of the plurality of pump controllers and/or glucose sensors may be stored within the modular blood glucose control therapy system.

In some embodiments, the system can output to a medicament pump a status and/or reading from an associated glucose sensor. Additionally or alternatively, the system may output a status of an algorithm, such as the control algorithm described herein. For example, the system may alert a user that the algorithm has encountered a problem.

The modular blood glucose control therapy system can output a warning, an error, an alarm, or other indication configured to draw urgent attention by a user. The system can output a basal rate, one or more blood glucose control parameters, an amount of insulin on board, a meal announcement status or availability, and/or a command to pause and/or resume delivery of therapy. Additionally or alternatively, as noted above, the modular system can route received pass-through data to one or more target devices. The pass-through data may be received from any device, such as a pump controller, a glucose sensor, and/or from a separate electronic device (e.g., a user device). In some embodiments, the system can receive encoded glucose sensor signal comprising second pass-through data and/or encoded source device signal comprising third pass-through data. The second and/or third pass-through data can be routed to a corresponding second and/or third target electronic device. This data may be received and/or transmitted wirelessly, such as through a BLE and/or LTE-M. Additional details are provided below with reference to individual figures. The blood glucose control parameters may be determined at least in part on a glycemic response of the subject over a therapy interval. The therapy interval may be on the order of hours, days, weeks, months, or years. In some embodiments, the therapy interval is between about 10 seconds and 10 minutes. Additionally or alternatively, the blood glucose control parameters may be determined at least in part based on glycemic response of the subject to a medicament bolus delivered by the medicament pump.

The blood glucose control system may determine the blood glucose control parameters may be determined by learning the blood glucose control parameters during online operation of an automated blood glucose control system. For example, the modular system may generate the blood glucose control parameters by calculating a size of a correction bolus of insulin of the regular correction boluses at a time of receiving an isolated glucose measurement from the glucose sensor. Additionally or alternatively, the system may generate the blood glucose control parameters by calculating a size of a meal bolus of insulin. The blood glucose control parameters may be determined by use of the control algorithm described above.

Figure 75:
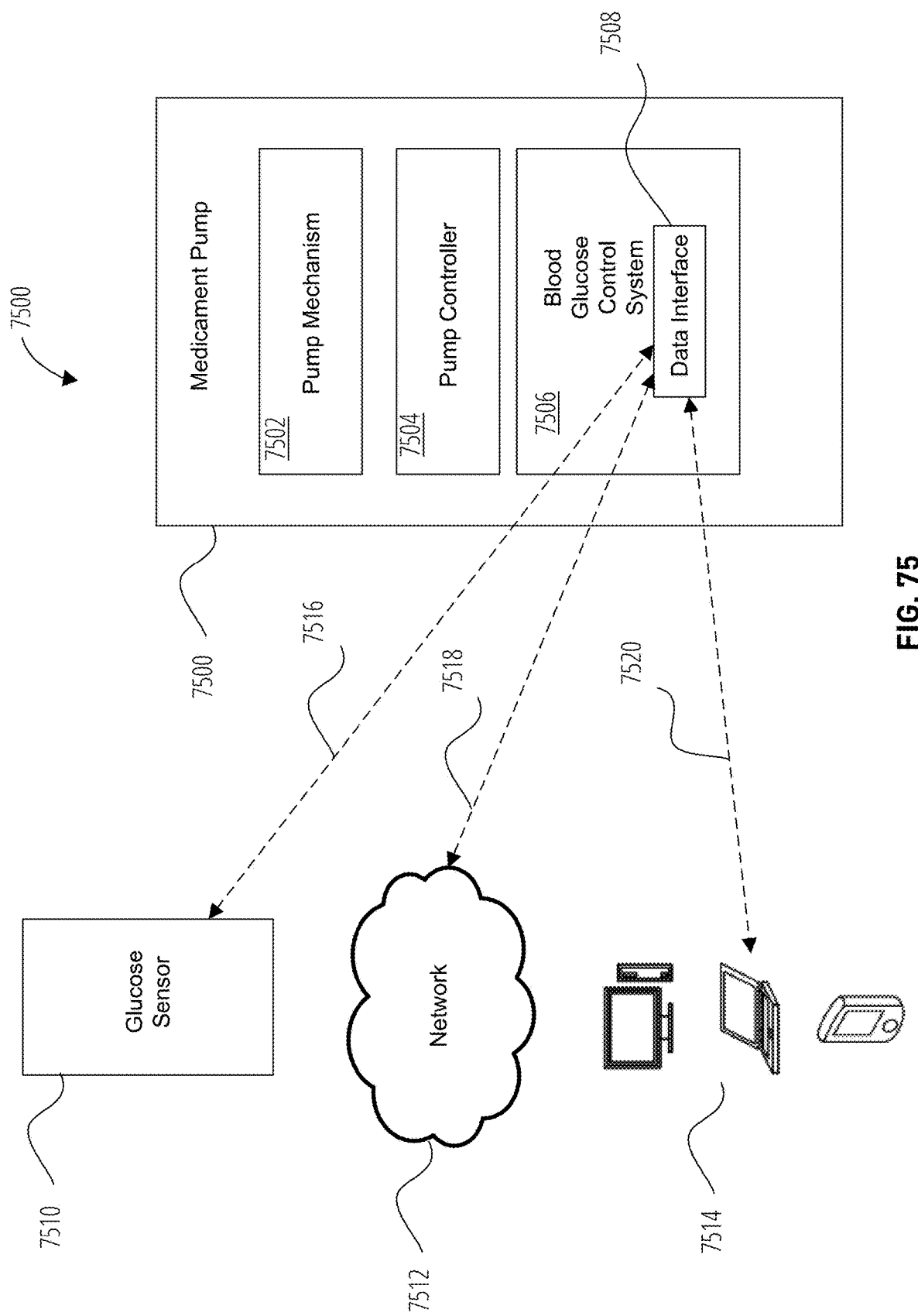
FIG. 75 shows a blood glucose control system disposed within a medicament pump operatively coupled to the subject.

FIG. 75 shows a blood glucose control system 7506 disposed within a medicament pump 7500 operatively coupled to the subject. The medicament pump 7500 includes a pump mechanism 7502, a pump controller 7504, and the blood glucose control system 7506. The blood glucose control system 7506 includes a data interface 7508. As mentioned above, the data interface 7508 may include a wireless and/or wired data interface. The blood glucose control system 7506 an include a short-range wireless data interface.

The medicament pump 7500 may be any medicament pump described herein, such as the pump 100 and/or pump 212. The pump controller 7504 is configured to direct medicament from a medicament reservoir to the subject using the pump mechanism 7502.

The data interface 7508 may be in communication (e.g., wired, wireless) with one or more of a glucose sensor 7510 (e.g., via a glucose sensor connection 7516), with a network 7512 (e.g., via a network connection 7518), and/or a user device connection 7520 (e.g., via a user device connection 7520). Each of the connections 7516, 7518, 7520 may be one-way or two-way. The data interface 7508 may also be in communication with other elements of the medicament pump 7500, such as the pump mechanism 7502 and/or the pump controller 7504. The communication with the other elements of the medicament pump 7500 may be via a wired connection.

The data interface 7508 may be configured to interface with a plurality of glucose sensors. For example, the blood glucose control system 7506 may store a plurality of decoding profiles, such as glucose level signal decoding profiles that are configured to correspond to one or more glucose sensors. In some examples, the blood glucose control system 7506 can select a glucose level signal decoding profile from a plurality of glucose level signal decoding profiles. Each glucose level signal decoding profile is configured to decode encoded data of a glucose level signal. The selected glucose level signal decoding profile can correspond to the glucose sensor 7510 that is operatively coupled to the subject.

The network 7512 may include any wired network, wireless network, or combination thereof. For example, the network 7512 may be a personal area network, local area network, wide area network, over-the-air broadcast network (e.g., for radio or television), cable network, satellite network, cellular telephone network, or combination thereof. As a further example, the network 7512 may be a publicly accessible network of linked networks, possibly operated by various distinct parties, such as the Internet. In some implementations, the network 7512 may be a private or semi-private network, such as a corporate or university intranet. The network 7512 may include one or more wireless networks, such as a Global System for Mobile Communications (GSM) network, a Code Division Multiple Access (CDMA) network, a Long Term Evolution (LTE) network, or any other type of wireless network. The network 7512 can use protocols and components for communicating via the Internet or any of the other aforementioned types of networks. For example, the protocols used by the network 7512 may include Hypertext Transfer Protocol (HTTP), HTTP Secure (HTTPS), Message Queue Telemetry Transport (MQTT), Constrained Application Protocol (CoAP), and the like. Protocols and components for communicating via the Internet or any of the other aforementioned types of communication networks are well known to those skilled in the art and, thus, are not described in more detail herein. The network 7512 may comprise the "cloud." The network 7512 may include a remote computing environment.

Various example user devices 7514 are shown in FIG. 75, including a desktop computer, a laptop, and a mobile phone, each provided by way of illustration. In general, the user devices 7514 can be any computing device such as a desktop, laptop or tablet computer, personal computer, tablet computer, wearable computer, server, personal digital assistant (PDA), PDM, hybrid PDA/mobile phone, mobile phone, smartphone, set top box, voice command device, digital media player, and the like. A user device 7514 may execute an application (e.g., a browser, a stand-alone application) that allows a user to access and interact with interactive graphical user interfaces as described herein.

The glucose sensor 7510 may be configured to transmit data to the medicament pump 7500 via the data interface 7508. The data may be encoded based on the make of the glucose sensor 7510 and/or based on another characteristic. The encoded data may comprise a glucose level signal. The glucose level signal can include first encoded data and/or second encoded data. The first encoded data may correspond to a glucose level of the subject, and the second encoded data may include an indication of a glucose trend. The glucose trend indicates at least a predicted change in the glucose level of the subject.

The blood glucose control system 7506 may include a processor that is configured to execute instructions. The blood glucose control system 7506 can receive, via the data interface 7508, a glucose level signal from the glucose sensor 7510. The glucose sensor 7510 may be operatively coupled to the subject. The blood glucose control system 7506 can decode the first and second encoded data of the glucose level signal to obtain the glucose level of the subject and the indication of the glucose trend. Based on the decoded data, the blood glucose control system 7506 can calculate a dose control signal using a control algorithm that is configured to calculate regular correction boluses of glucose control agent in response to at least the glucose level of the subject. The control algorithm may include features described elsewhere herein.

In some embodiments, the blood glucose control system 7506 can be configured to communicate with one or more of a plurality of pump controllers. In such embodiments, the blood glucose control system 7506 may be configured to select a dose control signal encoding profile from a plurality of dose control signal encoding profiles. Each of the plurality of dose control signal encoding profiles may correspond to at least one of a plurality of pump controllers, including the pump controller 7504. The selected dose control signal encoding profile corresponds to the pump controller operatively coupled to the subject.

The blood glucose control system 7506 may encode the received dose control signal using the selected dose control signal encoding profile such that the pump controller 7504 can read the dose control signal. Once encoded, the dose control signal may be transmitted to the pump controller 7504 of the medicament pump 7500. The dose control signal may be configured to command the medicament pump 7500 to administer glucose control therapy via infusion of the glucose control agent into the subject. The glucose control agent may include insulin, glucagon, and/or other agent disclosed herein.

In some embodiments, the blood glucose control system 7506 can transmit via the data interface 7508 data to a graphical user interface. For example, the blood glucose control system 7506 may transmit one or more of the glucose level of the subject and/or the indication of the glucose trend to the graphical user interface. Additionally or alternatively, the glucose level may be transmitted to a remote device, such as a user device 7514 and/or the network 7512, via a corresponding connection 7518, 7520.

As noted above, the blood glucose control system 7506 can output one or more blood glucose control parameters to the one or more devices, such as the user device 7514 and/or the network 7512. As described above, example blood glucose control parameters may include: an insulin decay rate constant associated with a decay rate of insulin at a subcutaneous depot of the subject and/or a clearance time associated with an estimate of an amount of time for a bolus of insulin to be utilized by the subject. The blood glucose control parameters may additionally or alternatively include an insulin rise rate constant associated with a rise rate of insulin in blood of the subject after a bolus of insulin and/or a value (e.g., half-life value) associated with when a concentration of insulin in blood plasma of the subject reaches a threshold (e.g., half of a maximum) concentration in the blood plasma. In some embodiments, the blood glucose control parameters may include a sensitivity constant associated with the subject's sensitivity to a glucose level or bolus of medicament. Other parameters may be included, such as those with reference to the control algorithm above.

The blood glucose control system 7506 can receive various data from the glucose sensor 7510 and/or from the user device 7514. For example, the blood glucose control system 7506 may receive, via the data interface 7508, an amount of insulin on board and/or a value used in a pharmacokinetic (PK) model of the control algorithm described above. The blood glucose control system 7506 may be configured to execute the control algorithm.

In some embodiments, the blood glucose control system 7506 can communicate with one or more of a plurality of glucose sensors, including the glucose sensor 7510. Each glucose sensor can transmit glucose level signals in an encoded form (e.g., format), and the blood glucose control system 7506 can have a corresponding glucose level signal decoding profile for each glucose sensor. The blood glucose control system 7506 may have each glucose level signal decoding profile for each glucose sensor stored thereon. In some embodiments, the blood glucose control system 7506 can select a glucose level signal decoding profile from the plurality of glucose level signal decoding profiles. Each glucose level signal decoding profile may be configured to decode at least a glucose level of the subject and an indication of a glucose trend, which may indicate at least a predicted change in the glucose level of the subject. The selected glucose level signal decoding profile can correspond to the glucose sensor 7510 that is operatively coupled to the subject. Using the selected glucose level signal decoding profile, the blood glucose control system 7506 can decode the glucose level of the subject and/or the indication of the glucose trend of the glucose level signal.

Another benefit of some embodiments of the blood glucose control system 7506 is it can be configured to store historical data thereon. In this way, the data may not be lost and can be preserved for a future medicament pump 7500. For example, the medicament pump 7500 may be disposed of, and a user or other individual may be interested in the stored historical data on the blood glucose control system 7506. Such historical data can include a therapy delivery history, one or more blood glucose control parameters, and/or other data that may be stored over time on the blood glucose control system 7506. The blood glucose control system 7506 can calculate a dose control signal for use in the medicament pump 7500 in some embodiments. Over time, the generated dose control signal(s) may be stored on the blood glucose control system 7506.

Once stored, the blood glucose control system 7506 may be configured to transmit the stored data to a remote electronic device (e.g., the glucose sensor 7510, the network 7512, the user device 7514) once a triggering condition is satisfied. The triggering condition can include one or more of a variety of triggering conditions. These conditions may indicate or reflect a change that is occurring on the medicament pump 7500 and/or on the blood glucose control system 7506. For example, the triggering condition may include a sensory alarm that alerts a user that the blood glucose control parameters are ready for transmission. The sensory alarm may prompt a user to cause the blood glucose control system 7506 to transmit the data to the remote electronic device. The triggering condition may include a determination that a level of medicament in an associated medicament reservoir is below a threshold level. The medicament reservoir may be included in the medicament pump 7500 (not shown in FIG. 75). Additionally or alternatively, the triggering condition can include a signal received from the remote electronic device requesting transmission of the blood glucose control parameters. In some embodiments, the triggering condition includes a user-generated indication to replace the disposable ambulatory medicament pump. Other conditions are possible and these are listed by way of illustration only.

In embodiments where the triggering condition includes a sensory alarm, the sensory alarm may be configured to regularly and/or periodically alert the user and/or subject until the blood glucose control parameters are transferred to the remote electronic device. For example, the sensory alarm can include a visual, audible, haptic, and/or other alarm. in some embodiments, the sensory alarm includes a beep, a tone, and/or other audible alarm. The alarm may include a vibration and/or flashing light. The sensory alarm may be configured to be annoying to a user so that the user is motivated to provide instructions for the blood glucose control system 7506 to send the stored data to the remote electronic device.

In some embodiments, the blood glucose control system 7506 can receive and route pass-through data to another device, such as a remote electronic device. Pass-through data can include data that is unrelated to a glucose level signal and/or data that is not used in a calculation of a dose control signal. The pass-through data may be encoded data. The data may be encoded by the pump controller 7504. In some embodiments, the data is received from and encoded by the glucose sensor 7510 or some other remote device, such as the user device 7514. The blood glucose control system 7506 can receive, via the blood glucose control system 7506, an encoded pump controller signal (e.g., from the pump controller 7504) via a digital data connection. The encoded pump controller signal can include an encoded medicament delivery signal corresponding to an amount of medicament dosed to the subject. Additionally or alternatively, the encoded pump controller signal includes encoded pass-through data, which may include one or more signals, such as encoded pump controller alert data. The blood glucose control system 7506 can also receive the glucose level signal from the glucose sensor 7510. The system can additionally or alternatively receive encoded glucose sensor signal comprising second pass-through data and/or encoded source device signal comprising third pass-through data. The second and/or third pass-through data can be routed to a corresponding second and/or third target electronic device The blood glucose control system 7506 can decode the encoded medicament delivery signal and the encoded pass-through data to obtain the amount of medicament dosed to the subject and the data unrelated to a glucose level signal. Based on this decoded information, the blood glucose control system 7506 can calculate (e.g., automatically) the dose control signal using the control algorithm configured to calculate regular correction boluses of glucose control agent in response to at least the glucose level of the subject and the amount of medicament dosed to the subject. The blood glucose control system 7506 can route the data unrelated to the glucose level signal to the target electronic device. The target electronic device may include a remote electronic device, such as the user device 7514. For example, the pass-through data may be generated for display on the user device 7514 and/or for storage in and/or re-routing by the network 7512.

The pass-through data can include various data. For example, the pass-through data may include an indication that a pump cartridge has a volume of medicament below a threshold volume, an indication that a supply of medicament is below a threshold supply, a charge level associated with a battery of the ambulatory medicament pump, an indication that the glucose sensor has exceeded a threshold performance period, an indication (e.g., reminder) to wirelessly couple a new glucose sensor with the ambulatory medicament pump, and/or an indication that a new pump cartridge has been installed in the ambulatory medicament pump. Other pass-through data can be use, and these are listed as examples only.

In some embodiments, the blood glucose control system 7506 can determine that the pass-through data is unrelated to the calculation of the dose control signal. Based on the determination that the pass-through data is unrelated to the calculation of the dose control signal, the blood glucose control system 7506 route the status alert to the target electronic device.

Figure 76:
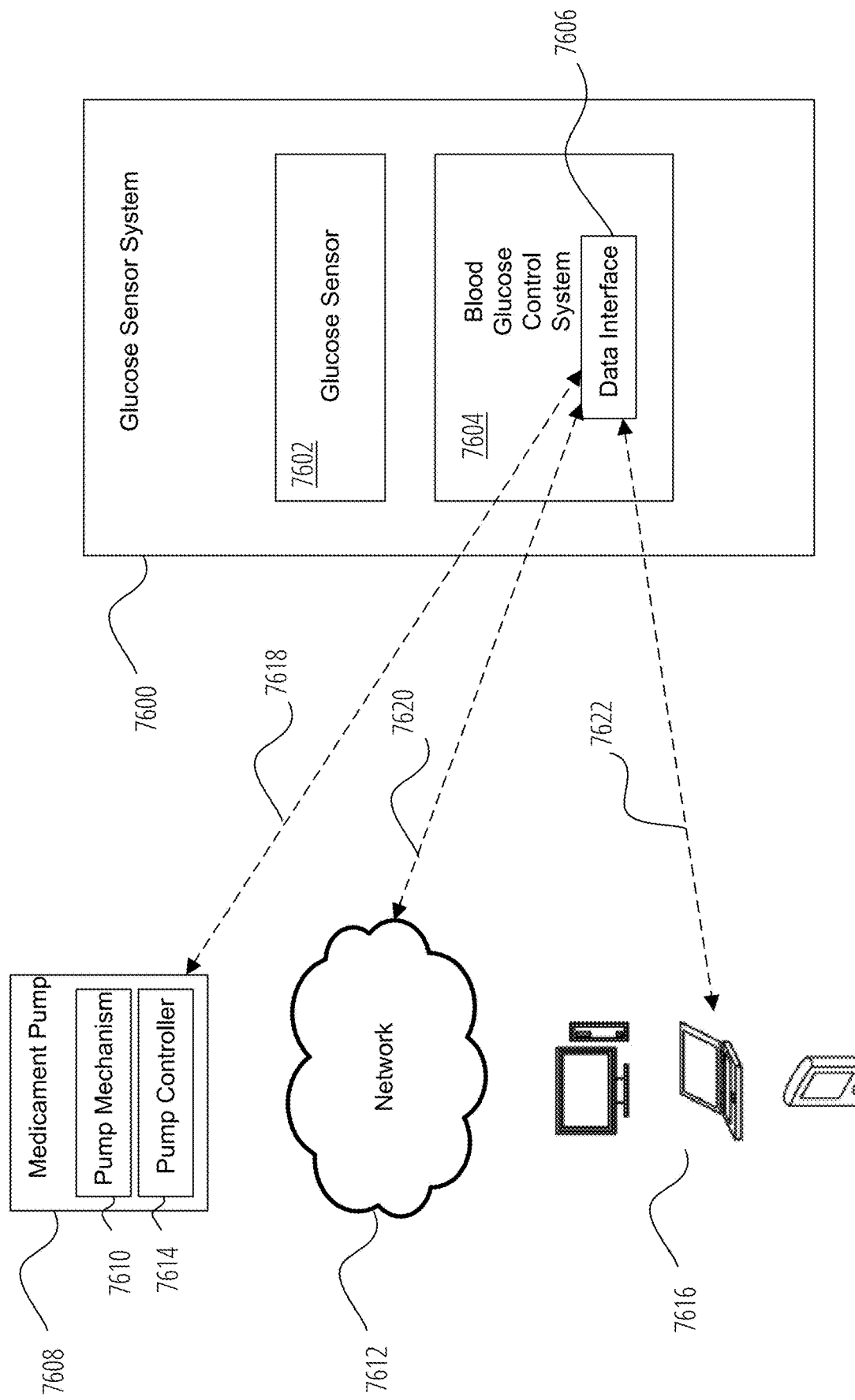
FIG. 76 shows a blood glucose control system that is disposed within a glucose sensor system.

FIG. 76 shows a blood glucose control system 7604 that is disposed within a glucose sensor system 7600. As shown, the glucose sensor system 7600 includes a glucose sensor 7602 and the blood glucose control system 7604. The blood glucose control system 7604 can include a data interface 7606. The blood glucose control system 7604 may include functionality described above with respect to the data interface 7508. For example, the data interface 7606 may be able to communicate (e.g., wirelessly, via wired connection) with a medicament pump 7608, a network 7612, and/or a user device 7616 via respective connections 7618, 7620, 7622. The network 7612 may share one or more details with the network 7512 described above. Additionally or alternatively, the user device 7616 may be the user device 7514 described above.

As shown, the blood glucose control system 7604 can be in direct connection with other elements of the glucose sensor system 7600. For example, the blood glucose control system 7604 may be installed within the glucose sensor system 7600. The data interface 7606 can communicate with the medicament pump 7608, such as via a wireless connection. The medicament pump 7608 can include a pump mechanism 7610 and a pump controller 7614. In some embodiments, the data interface 7606 communicates with the pump controller 7614 of the medicament pump 7608.

The blood glucose control system 7604 may be configured to be operable with one or more of a plurality of glucose sensor systems. For example, the blood glucose control system 7604 may be configured to store a plurality of pump controller decoding profiles corresponding to respective pump controllers. The blood glucose control system 7604 can be configured to select a pump controller decoding profile from a plurality of pump controller decoding profiles.

The blood glucose control system 7604 can be configured to determine a status of the medicament pump 7608, such as a status of the pump controller 7614. The blood glucose control system 7604 can receive, via the data interface 7606, an encoded pump status signal from the pump controller 7614. The encoded pump status signal can include data corresponding to an availability of the ambulatory medicament pump to deliver medicament to the subject. The blood glucose control system 7604 can additionally or alternatively receive an encoded medicament delivery signal from the pump controller pump controller 7614. The encoded medicament delivery signal can include data corresponding to an amount of medicament dosed to the subject.

Each pump controller decoding profile can be configured to decode at least an encoded pump status signal and an encoded medicament delivery signal. The selected pump controller decoding profile can correspond to the pump controller pump controller 7614 that is operatively coupled to the medicament pump medicament pump 7608. Using the selected pump controller decoding profile(s), the blood glucose control system 7604 can decode the glucose level signal to obtain a glucose level of the subject and an indication of a glucose trend. The blood glucose control system 7604 can calculate the dose control signal using a control algorithm (described above) that is configured to calculate regular correction boluses of glucose control agent in response to at least the glucose level of the subject.

In some embodiments, in order to properly transmit the decoded data to the pump controller 7614 (e.g., for instructions on delivering blood glucose control therapy), the blood glucose control system 7604 can proceed to encode the data so that it can be read by the pump controller 7614. Like with the pump controller decoding profiles, the blood glucose control system 7604 may have stored thereon one or more of a plurality of pump controller encoding profiles. The blood glucose control system 7604 can select a pump controller encoding profile from the plurality of pump controller encoding profiles. The selected pump controller encoding profile can correspond to the pump controller 7614. The pump controller encoding profile can be configured to encode at least the dose control signal and any other data that may be transmitted to the pump controller 7614.

Based on the encoded pump status signal, The blood glucose control system 7604 can determine that the medicament pump 7608 is available to deliver medicament to the subject. The blood glucose control system 7604 can encode the dose control signal such that the pump controller 7614 can read the dose control signal. The blood glucose control system 7604 can then transmit the encoded dose control signal to the pump controller 7614. The dose control signal can command the medicament pump 7608 to administer glucose control therapy (e.g., using the pump mechanism 7610) via infusion of glucose control agent into the subject. Thus, the blood glucose control system 7604 can be instrumental in communicating with the medicament pump 7608 and improving interoperability between the medicament pump 7608 and the glucose sensor system 7600.

The blood glucose control system 7604 may have additional functionality, such as that described above with respect to the blood glucose control system 7506 above. For example, the blood glucose control system 7604 may be configured to communicate with a plurality of pump controllers, store and transmit historical data stored on the blood glucose control system 7604 in response to a triggering condition, and receiving and routing pass-through data. Those details are not described again here in order to reduce multiplicity of words.

Figure 77:
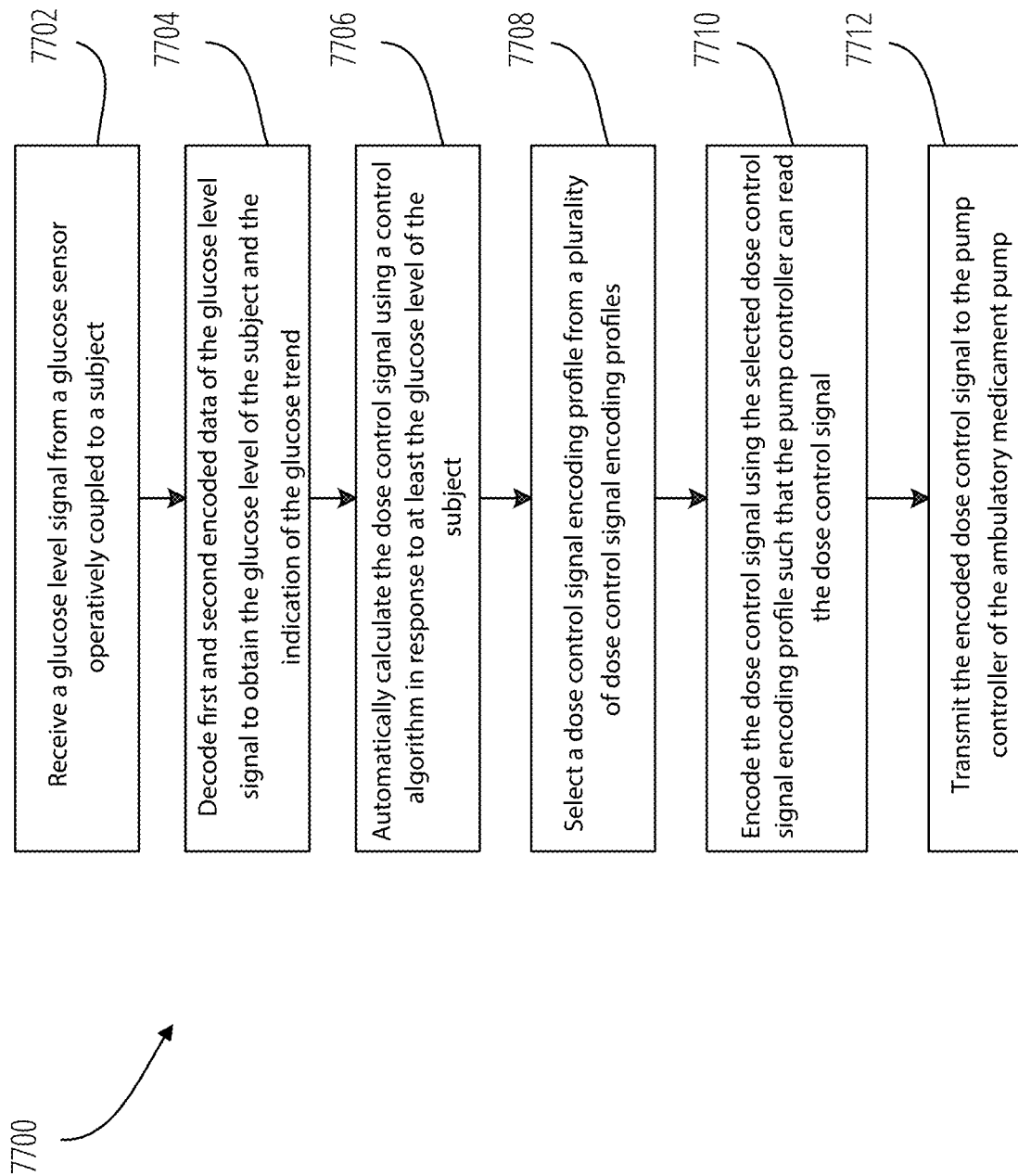
FIG. 77 shows a flow diagram illustrating an example method that may be used by a blood glucose control system to calculate a dose control signal for commanding administration of glucose control therapy to a subject.

FIG. 77 shows a flow diagram illustrating an example method 7700 that may be used by a blood glucose control system (e.g., the blood glucose control system 7506, the blood glucose control system 7604) to calculate a dose control signal for commanding administration of glucose control therapy to a subject. The system can receive a glucose level signal from a glucose sensor operatively coupled to a subject at block 7702. At block 7704 the system decodes first and second encoded data of the glucose level signal to obtain the glucose level of the subject and the indication of the glucose trend. At block 7706, the system calculate (e.g., automatically) the dose control signal using a control algorithm in response to at least the glucose level of the subject. At block 7708, the system selects a dose control signal encoding profile from a plurality of dose control signal encoding profiles. At block 7710 the system encodes the dose control signal using the selected dose control signal encoding profile such that the pump controller can read the dose control signal. At block 7712, the system can transmit the encoded dose control signal to the pump controller of the ambulatory medicament pump.

In some embodiments, the system can transmit, via a data interface to the graphical user interface, one or more of the glucose level of the subject or the indication of the glucose trend. The method 7700 may further include transmitting the glucose level of the subject and/or the indication of the glucose trend to a remote electronic device. Additionally or alternatively, the system may receive, from the glucose sensor, via the data interface, blood glucose control parameters. The blood glucose control parameters can include one or more of the blood glucose control parameters described above. In some embodiments, the system can receive, via the data interface, at least one of an amount of insulin on board or a value used in a pharmacokinetic (PK) model of the control algorithm.

In some embodiments, the method 7700 includes selecting a glucose level signal decoding profile from a plurality of glucose level signal decoding profiles. Each of the plurality of glucose level signal decoding profiles can correspond to at least one of a plurality of glucose sensors. Each glucose level signal decoding profile may be configured to decode at least the first encoded data and the second encoded data of the glucose level signal. The selected glucose level signal decoding profile can correspond to the glucose sensor operatively coupled to the subject. The system may decode the first and second encoded data of the glucose level signal using the selected glucose level signal decoding profile.

Figure 78:
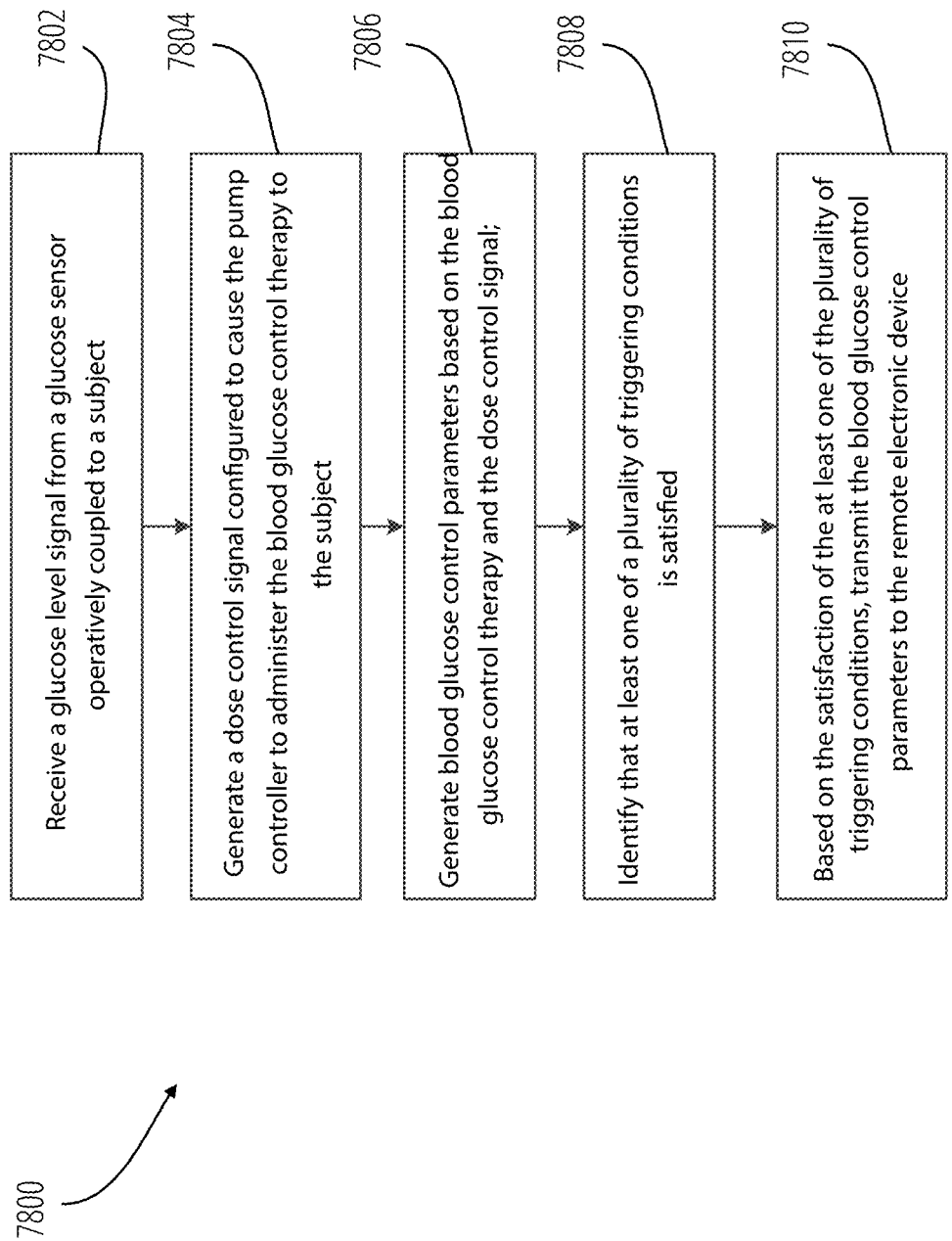
FIG. 78 shows a flow diagram illustrating an example method that may be used by a blood glucose control system to transmit blood glucose control parameters to a remote electronic device in response to an identification of a triggering condition.

FIG. 78 shows a flow diagram illustrating an example method 7800 that may be used by a blood glucose control system (e.g., the blood glucose control system 7506, the blood glucose control system 7604) to transmit blood glucose control parameters to a remote electronic device in response to an identification of a triggering condition. At block 7802, the system can receive, via a data interface, a glucose level signal from a glucose sensor operatively coupled to the subject. At block 7804, the system generates the blood glucose control parameters based on trends in the blood glucose control therapy and the glucose level signal using a control parameter selection process over a therapy period spanning at least hours to days. Examples of blood glucose control parameters are described and listed above. At block 7806, the system generates, based on at least the glucose level signal and the blood glucose control parameters, a dose control signal configured to cause the pump controller to administer the blood glucose control therapy to the subject. At block 7808, the system identifies that at least one of a plurality of triggering conditions is satisfied. Each of the triggering conditions can be configured to prompt transmission of the blood glucose control parameters to the remote electronic device. Examples of triggering conditions are described and listed above. At block 7810, the system transmits the blood glucose control parameters to the remote electronic device based on the satisfaction of the at least one of the plurality of triggering conditions.

In some embodiments, the system transmits, based on the satisfaction of the at least one of the plurality of triggering conditions, at least one of an amount of insulin on board or a value used in a pharmacokinetic (PK) model of a control algorithm. Additionally or alternatively, the system generates the blood glucose control parameters further based on a glycemic response of the subject over a therapy interval. In some embodiments, the system generates the blood glucose control parameters further based on glycemic response of the subject to a medicament bolus. Additionally or alternatively, the system generates the blood glucose control parameters by learning the blood glucose control parameters during online operation of an automated blood glucose control system. Generating the blood glucose control parameters can include calculating a size of a correction bolus of insulin of the regular correction boluses at a time of receiving an isolated glucose measurement from the glucose sensor. Additionally or alternatively, generating the blood glucose control parameters can include calculating a size of a meal bolus of insulin. In some embodiments, the system generates the blood glucose control parameters using a control algorithm (e.g., the control algorithm described above).

Figure 79:
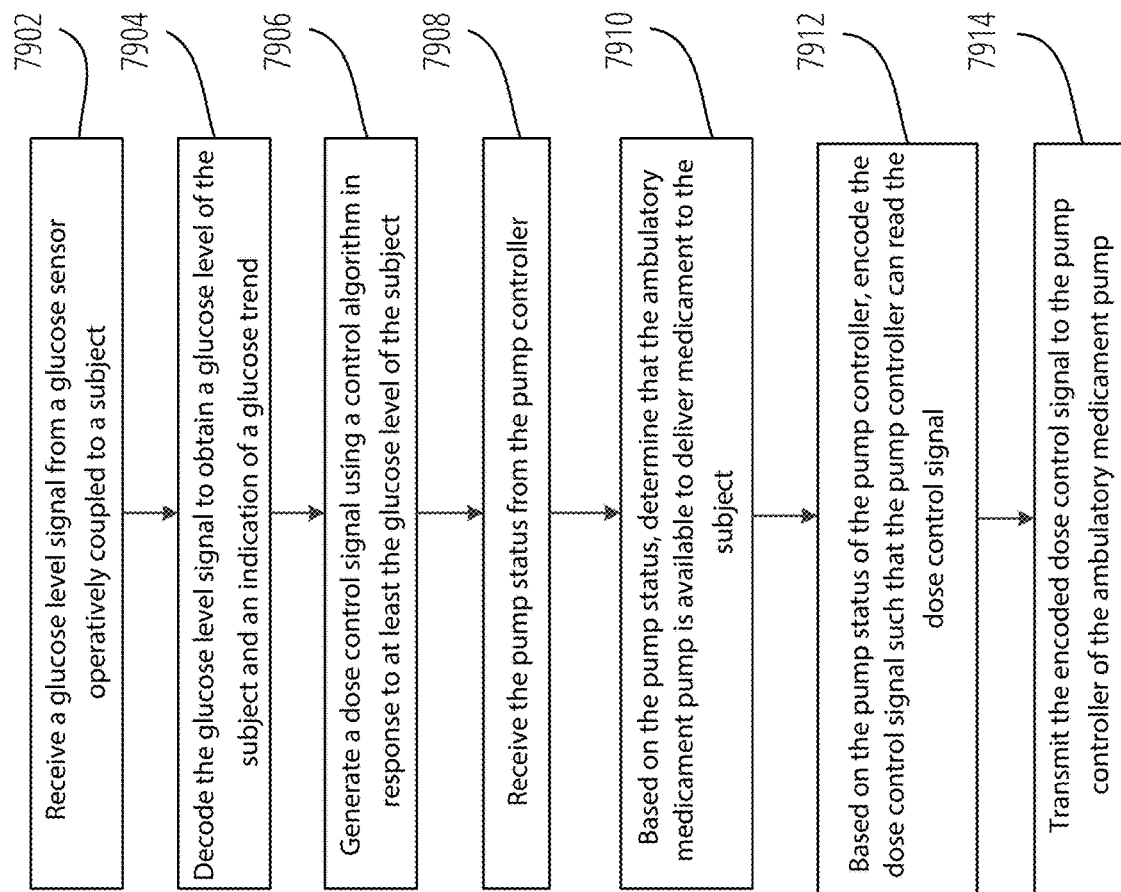
FIG. 79 shows a flow diagram illustrating an example method that may be used by a blood glucose control system receive an encoded pump status signal and an encoded medicament delivery signal from a pump controller.

FIG. 79 shows a flow diagram illustrating an example method 7900 that may be used by a blood glucose control system (e.g., the blood glucose control system 7506, the blood glucose control system 7604) receive an encoded pump status signal and an encoded medicament delivery signal from a pump controller.

At block 7902, the system receives, via a data interface, a glucose level signal from the glucose sensor. At block 7904, the system decodes the glucose level signal to obtain a glucose level of the subject and an indication of a glucose trend. At block 7906, the system generates the dose control signal using a control algorithm configured to calculate regular correction boluses of glucose control agent in response to at least the glucose level of the subject. At block 7908, the system receives, via the data interface, an encoded pump status signal from the pump controller. The encoded pump status signal can include data corresponding to an availability of the ambulatory medicament pump to deliver medicament to the subject. The system selects a pump controller decoding profile from a plurality of pump controller decoding profiles. Each of the plurality of pump controller decoding profiles corresponds to at least one of a plurality of pump controllers. Each pump controller decoding profile can be configured to decode at least the encoded pump status signal and the encoded medicament delivery signal. The selected pump controller decoding profile corresponds to the pump controller operatively coupled to the ambulatory medicament pump.

The system decodes the encoded pump status signal and the encoded medicament delivery signal using the selected pump controller decoding profile. The system can select a pump controller encoding profile from a plurality of pump controller encoding profiles. The selected pump controller encoding profile corresponds to the pump controller operatively coupled to the ambulatory medicament pump. The pump controller encoding profile is configured to encode at least the dose control signal.

At block 7910, the system determines, based on the encoded pump status signal, that the ambulatory medicament pump is available to deliver medicament to the subject and at block 7912 encodes the dose control signal such that the pump controller can read the dose control signal.

At block 7914, the system transmits the encoded dose control signal to the pump controller of the ambulatory medicament pump. The dose control signal commands the ambulatory medicament pump to administer glucose control therapy via infusion of the glucose control agent into the subject.

Figure 80:
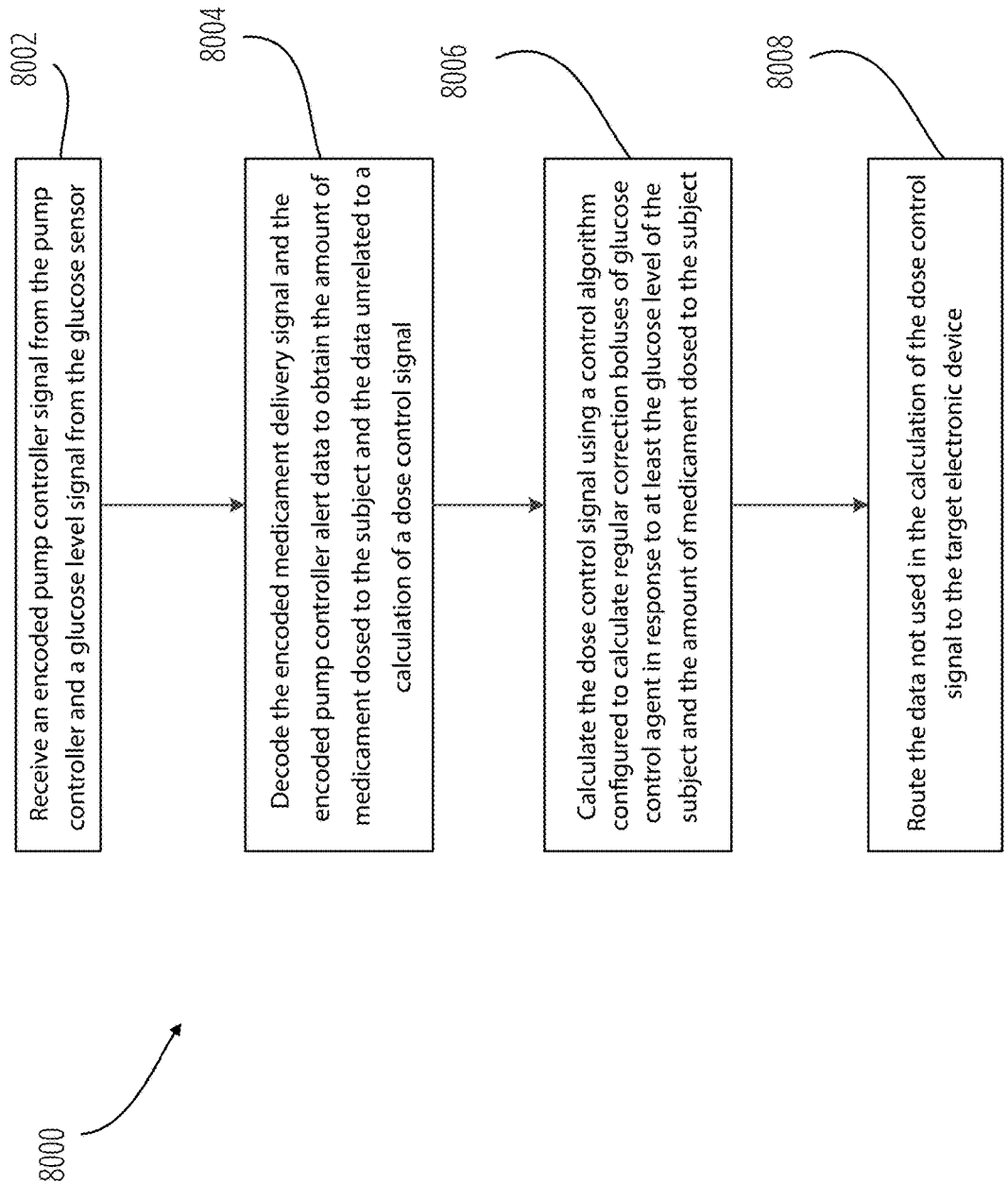
FIG. 80 shows a flow diagram illustrating an example method that may be used by a blood glucose control system to route pass-through data unrelated to a glucose level signal to a target electronic device

FIG. 80 shows a flow diagram illustrating an example method 8000 that may be used by a blood glucose control system (e.g., the blood glucose control system 7506, the blood glucose control system 7604) to route pass-through data unrelated to a glucose level signal to a target electronic device. At block 8002, the system can receive, via a data interface, an encoded pump controller signal from the pump controller via a digital data connection and the glucose level signal from the glucose sensor. The encoded pump controller signal can include an encoded medicament delivery signal corresponding to an amount of medicament dosed to the subject and pass-through data that includes encoded pump controller alert data corresponding to data unrelated to a calculation of a dose control signal.

At block 8004 the system decodes the encoded medicament delivery signal and the encoded pass-through data to obtain the amount of medicament dosed to the subject and the data unrelated to a calculation of a dose control signal. At block 8006 the system calculates the dose control signal using a control algorithm configured to calculate regular correction boluses of glucose control agent in response to at least the glucose level of the subject and the amount of medicament dosed to the subject. At block 8008 the system routes the data unrelated to the glucose level signal to the target electronic device. The system can additionally or alternatively receive encoded glucose sensor signal comprising second pass-through data and/or encoded source device signal comprising third pass-through data. The second and/or third pass-through data can be routed to a corresponding second and/or third target electronic device.

In some embodiments, the system determines that the pass-through data is unrelated to the calculation of the dose control signal. Based on the determination that the pass-through data is unrelated to the calculation of the dose control signal, the system can route the status alert to the target electronic device.

Example Embodiments

Further embodiments of glucose level control systems that can be combined with the features disclosed herein can be found in: U.S. Pat. App. No. 63/169,112 filed on Mar. 31, 2021; PCT. Pub. No. WO 2021/067856 filed on Oct. 2, 2020; U.S. Pat. Pub. No. 2021/0213200 filed on Mar. 25, 2021; and PCT Pub. No. WO 2021/067767 filed on Oct. 2, 2020, which are all hereby incorporated by reference in their entireties herein for all purposes.

Some additional nonlimiting examples of embodiments discussed above are provided below. These should not be read as limiting the breadth of the disclosure in any way.

In a 1st example, a system for transferring historical pump data from a first ambulatory medicament pump to a second ambulatory medicament pump, the system comprising: a data interface configured to receive the historical pump data from the first ambulatory medicament pump, wherein the historical pump data comprises: first encoded data corresponding to therapy data associated with delivery of glucose control therapy delivered by the first ambulatory medicament pump to the subject; and second encoded data corresponding to a glucose control parameter used by the first ambulatory medicament pump in calculating a dose control signal; a non-transitory memory configured to store specific computer-executable instructions ambulatory medicament pump; and an electronic processor in communication with the non-transitory memory and configured to execute the specific computer-executable instructions to at least: receive, via the data interface, the historical pump data from the first ambulatory medicament pump; decode the first and second encoded data of the historical pump data to obtain the therapy data and the glucose control parameter; determine that at least one of a plurality of pairing conditions is satisfied to connect the data interface to the second ambulatory medicament pump, wherein the plurality of pairing conditions comprises: a user request to pair the system to the second ambulatory medicament pump; a user input initiating a replacement process for the first ambulatory medicament pump; an indication that the second ambulatory medicament pump is ready to deliver medicament to the subject; a sensory alarm configured to alert a user that the historical pump data is ready for transmission; an alert indicating a malfunction associated with the first ambulatory medicament pump; a determination that a level of medicament in a medicament reservoir of the first ambulatory medicament pump is below a threshold level; and a signal received from a remote electronic device requesting transmission of at least one of the therapy data associated with the delivery of the glucose control therapy or the glucose control parameter; transmit, via the data interface, a pairing signal to the second ambulatory medicament pump; receive, via the data interface, a confirmation signal from the second ambulatory medicament pump; and in response to receiving the confirmation signal, transmit, via the data interface, at least one of the therapy data associated with the delivery of the glucose control therapy or the glucose control parameter.

In a 2nd example, the system of example 1, wherein the electronic processor is further configured to execute the specific computer-executable instructions to at least: generate, based on at least the therapy data associated with the delivery of the glucose control therapy and the glucose control parameter, a dose control signal configured to cause a pump controller of the first ambulatory medicament pump to deliver the medicament to the subject.

In a 3rd example, the system of example 2, wherein generating the dose control signal comprises calculating regular correction boluses of glucose control agent in response to at least the glucose control parameter.

In a 4th example, the system of any of examples 1-3, wherein the electronic processor is further configured to execute the specific computer-executable instructions to at least: receive third and fourth encoded data, the third encoded data corresponding to a glucose level of a subject, and the fourth encoded data corresponding to an indication of a glucose trend, wherein the glucose trend indicates at least a predicted change in the glucose level of the subject.

In a 5th example, the system of any of examples 1-4, wherein the electronic processor is further configured to execute the specific computer-executable instructions to at least: estimate a second glucose control parameter based on at least one of an amount of glucose control therapy, a time of the glucose control therapy, and/or an amount of insulin on board.

In a 6th example, the system of any of examples 1-5, wherein the electronic processor is further configured to execute the specific computer-executable instructions to at least: receive, via the data interface, a glucose level signal from a glucose sensor operatively coupled to the subject; and estimate a second glucose control parameter based on the glucose level signal received from the glucose sensor.

In a 7th example, the system of any of examples 1-6, further comprising a graphical user interface configured to display at least the glucose level of the subject or the indication of the glucose trend, wherein the instructions, when executed by the hardware processor, are further configured to: transmit to the graphical user interface, via the data interface, one or more of the amount of the therapy data or the glucose control parameter.

In an 8th example, the system of any of examples 1-7, wherein the instructions, when executed by the hardware processor, are further configured to: transmit to the remote electronic device, one or more of the therapy data or the glucose control parameter.

In a 9th example, the system of example 8, wherein the remote electronic device comprises at least one of a mobile device or a remote computing environment.

In a 10th example, the system of any of examples 1-9, wherein the glucose control parameter comprises at least one of: an insulin decay rate constant associated with a decay rate of insulin at a subcutaneous depot of the subject; a clearance time associated with an estimate of an amount of time for a bolus of insulin to be utilized by the subject; an insulin rise rate constant associated with a rise rate of insulin in blood of the subject after a bolus of insulin; a half-life value associated with when a concentration of insulin in blood plasma of the subject reaches half of a maximum concentration in the blood plasma; a weight of the subject; an age of the subject; a learned parameter; glucose level data; a model parameter associated with a pharmacokinetic (PK) model; a health state of the subject; a parameter associated with an activity level of the subject; an aspect of a diet of the subject; a basal rate of insulin delivery to the subject; a correction factor; a carbohydrate ratio associated with the subject; a glucagon control parameter; demographic information associated with the subject; and a sensitivity constant associated with the subject's sensitivity to a glucose level or bolus of medicament.

In a 11th example, the system of any of examples 1-10, wherein the instructions, when executed by the hardware processor, are further configured to: receive, via the data interface, at least one of an amount of insulin on board or a value used in a pharmacokinetic (PK) model of a control algorithm.

In a 12th example, the system of any of examples 1-11, further comprising the first ambulatory medicament pump.

In a 13th example, the system of any of examples 1-12, wherein the data interface comprises a short-range wireless data interface.

In a 14th example, the system of any of examples 1-13, wherein the data interface comprises a plurality of data interfaces.

In a 15th example, the system of any of examples 1-14, wherein the instructions, when executed by the hardware processor, are configured to: transmit to the second ambulatory medicament pump, in response to the confirmation signal, at least one of an amount of insulin on board or a value used in a pharmacokinetic (PK) model of a control algorithm.

In a 16th example, the system of any of examples 1-15, wherein the instructions, when executed by the hardware processor, are further configured to: determine that at least one of a plurality of data retrieval conditions is satisfied to connect the data interface to the first ambulatory medicament pump, wherein the plurality of data retrieval conditions comprises: an occurrence of a scheduled time; a transmission of a meal announcement; a user request to pair the system to the first ambulatory medicament pump; the user input initiating a replacement process for the first ambulatory medicament pump; an indication that the first ambulatory pump is to be replaced; the indication that the second ambulatory medicament pump is ready to deliver medicament to the subject; the sensory alarm configured to alert a user that the historical pump data is ready for transmission; the alert indicating a malfunction associated with the first ambulatory medicament pump; the determination that a level of medicament in a medicament reservoir of the first ambulatory medicament pump is below a threshold level; and the signal received from a remote electronic device requesting transmission of at least one of the therapy data or the glucose control parameter.

In a 17th example, the system of any of examples 16, wherein the instructions, when executed by the hardware processor, are further configured to: in response to determining that the at least one of a plurality of data retrieval conditions is satisfied, receive from the first ambulatory medicament pump, via the data interface, at least one of the therapy data or the glucose control parameter.

In an 18th example, the system of any of examples 1-17, wherein the malfunction associated with the first ambulatory medicament pump comprises at least one of an occlusion, a low battery power, an electrical malfunction, a controller malfunction, or a pump malfunction.

In a 19th example, the system of any of examples 1-18, wherein the therapy data comprises at least one of an amount of insulin on board, a time of a delivery of glucose control therapy, or an amount of delivery of glucose control therapy.

In a 20th example, the system of any of examples 1-19, wherein the therapy data comprises version data comprising at least one of: a timestamp corresponding to a time associated with an update of the therapy data; an indicator of an ordering within a sequence of delivery of the glucose control therapy; or a version code comprising encoded time data associated with delivery of the glucose control therapy.

In a 21st example, the system of any of examples 1-20, wherein the confirmation signal indicates that the second ambulatory medicament pump is in a ready state and that the first ambulatory medicament pump is not in a ready state.

In a 22nd example, the system of any of examples 1-21, wherein the instructions, when executed by the hardware processor, are further configured to: in response to receiving the confirmation signal, turn off a ready state of the first ambulatory medicament pump.

In a 23rd example, a method for transferring historical pump data from a first ambulatory medicament pump to a second ambulatory medicament pump, the method comprising: by an electronic processor of a system executing instructions stored on non-transitory memory connected to the electronic processor: receiving, via a data interface, the historical pump data from the first ambulatory medicament pump, wherein the historical pump data comprises: first encoded data corresponding to therapy data associated with delivery of glucose control therapy delivered by the first ambulatory medicament pump to the subject; and second encoded data corresponding to a version data associated with the therapy data; decoding the first and second encoded data of the historical pump data to obtain the therapy data and the glucose control parameter; determining that at least one of a plurality of pairing conditions is satisfied to connect the data interface to the second ambulatory medicament pump, wherein the plurality of pairing conditions comprises: a user request to pair the system to the second ambulatory medicament pump; a user input initiating a replacement process for the first ambulatory medicament pump; an indication that the second ambulatory medicament pump is ready to deliver medicament to the subject; a sensory alarm configured to alert a user that the historical pump data is ready for transmission; an alert indicating a malfunction associated with the first ambulatory medicament pump; a determination that a level of medicament in a medicament reservoir of the first ambulatory medicament pump is below a threshold level; and a signal received from a remote electronic device requesting transmission of at least one of the therapy data or the glucose control parameter; transmitting, via the data interface, a pairing signal to the second ambulatory medicament pump; receiving, via the data interface, a confirmation signal from the second ambulatory medicament pump; and in response to receiving the confirmation signal, transmitting, via the data interface, at least one of the therapy data or the glucose control parameter.

In a 24th example, the method of example 23, further comprising: generating, based on at least the therapy data and the glucose control parameter, a dose control signal configured to cause a pump controller of the first ambulatory medicament pump to deliver the medicament to the subject.

In a 25th example, the method of example 24, wherein generating the dose control signal comprises calculating regular correction boluses of glucose control agent in response to at least the glucose control parameter.

In a 26th example, the method of any of examples 23-25, further comprising: receiving third and fourth encoded data, the third encoded data corresponding to a glucose level of a subject, and the fourth encoded data corresponding to an indication of a glucose trend, wherein the glucose trend indicates at least a predicted change in the glucose level of the subject.

In a 27th example, the method of any of examples 23-26, further comprising: estimating a second glucose control parameter based on at least one of the therapy data.

In a 28th example, the method of any of examples 23-27, further comprising: receiving, via the data interface, a glucose level signal from a glucose sensor operatively coupled to the subject; and estimating a second glucose control parameter based on the glucose level signal received from the glucose sensor.

In a 29th example, the method of any of examples 23-28, further comprising transmitting to a graphical user interface, via the data interface, one or more of the therapy data or the glucose control parameter.

In a 30th example, the method of any of examples 23-29, wherein the instructions, when executed by the hardware processor, are further configured to: transmitting to the remote electronic device, one or more of the therapy data or the glucose control parameter.

In a 31st example, the method of example 30, wherein the remote electronic device comprises at least one of a mobile device or a remote computing environment.

In a 32nd example, the method of any of examples 23-31, wherein the glucose control parameter comprises at least one of: an insulin decay rate constant associated with a decay rate of insulin at a subcutaneous depot of the subject; a clearance time associated with an estimate of an amount of time for a bolus of insulin to be utilized by the subject; an insulin rise rate constant associated with a rise rate of insulin in blood of the subject after a bolus of insulin; a half-life value associated with when a concentration of insulin in blood plasma of the subject reaches half of a maximum concentration in the blood plasma; a weight of the subject; an age of the subject; a learned parameter; glucose level data; a model parameter associated with a pharmacokinetic (PK) model; a health state of the subject; a parameter associated with an activity level of the subject; an aspect of a diet of the subject; a basal rate of insulin delivery to the subject; a correction factor; a carbohydrate ratio associated with the subject; a glucagon control parameter; demographic information associated with the subject; and a sensitivity constant associated with the subject's sensitivity to a glucose level or bolus of medicament.

In a 33rd example, the method of any of examples 23-32, wherein the instructions, when executed by the hardware processor, are further configured to: receive, via the data interface, at least one of an amount of insulin on board or a value used in a pharmacokinetic (PK) model of a control algorithm.

In a 34th example, the method of any of examples 23-33, further comprising: transmitting to the second ambulatory medicament pump, in response to the confirmation signal, at least one of an amount of insulin on board or a value used in a pharmacokinetic (PK) model of a control algorithm.

In a 35th example, the method of any of examples 23-34, further comprising: determining that at least one of a plurality of data retrieval conditions is satisfied to connect the data interface to the first ambulatory medicament pump, wherein the plurality of data retrieval conditions comprises: an occurrence of a scheduled time; a transmission of a meal announcement; a user request to pair the system to the first ambulatory medicament pump; the user input initiating a replacement process for the first ambulatory medicament pump; an indication that the first ambulatory pump is to be replaced; the indication that the second ambulatory medicament pump is ready to deliver medicament to the subject; the sensory alarm configured to alert a user that the historical pump data is ready for transmission; the alert indicating a malfunction associated with the first ambulatory medicament pump; the determination that a level of medicament in a medicament reservoir of the first ambulatory medicament pump is below a threshold level; and the signal received from a remote electronic device requesting transmission of at least one of the therapy data or the glucose control parameter.

In a 36th example, the method of example 35, further comprising: in response to determining that the at least one of a plurality of data retrieval conditions is satisfied, receiving from the first ambulatory medicament pump, via the data interface, at least one of therapy data or the glucose control parameter.

In a 37th example, the method of any of examples 23-36, wherein the malfunction associated with the first ambulatory medicament pump comprises at least one of an occlusion, a low battery power, an electrical malfunction, a controller malfunction, or a pump malfunction.

In a 38th example, the method of any of examples 23-37, wherein the therapy data comprises at least one of an amount of insulin on board, a time of a delivery of glucose control therapy, or an amount of delivery of glucose control therapy.

In a 39th example, the method of any of examples 23-38, wherein the version data comprises at least one of: a timestamp corresponding to a time associated with an update of the therapy data; an indicator of an ordering within a sequence of delivery of the glucose control therapy; or a version code comprising encoded time data associated with delivery of the glucose control therapy.

In a 40th example, the method of any of examples 23-39, wherein the confirmation signal indicates that the second ambulatory medicament pump is in a ready state and that the first ambulatory medicament pump is not in a ready state.

In a 41st example, the method of any of examples 23-40, further comprising: in response to receiving the confirmation signal, turning off a ready state of the first ambulatory medicament pump.

In a 42nd example, an ambulatory medicament pump configured to store one or more of a plurality of glucose control parameters and glucose control therapy data on a removable data module configured to be readable by a second ambulatory medicament pump, the ambulatory medicament pump comprising: a pump controller configured to direct medicament from a medicament reservoir to a subject; a module interface configured to receive the removable data module; a non-transitory memory configured to store specific computer-executable instructions; and an electronic processor in communication with the non-transitory memory and configured to execute the specific computer-executable instructions to at least: determine the glucose control therapy data comprising at least one of an amount of insulin on board, a time of a delivery of glucose control therapy, or an amount of delivery of glucose control therapy; generate the one or more of the plurality of glucose control parameters, wherein the plurality of glucose control parameters comprises: an insulin decay rate constant associated with a decay rate of insulin at a subcutaneous depot of the subject; a clearance time associated with an estimate of an amount of time for a bolus of insulin to be utilized by the subject; an insulin rise rate constant associated with a rise rate of insulin in blood of the subject after a bolus of insulin; a half-life value associated with when a concentration of insulin in blood plasma of the subject reaches half of a maximum concentration in the blood plasma; a weight of the subject; an age of the subject; a learned parameter; glucose level data; a model parameter associated with a pharmacokinetic (PK) model; a health state of the subject; a parameter associated with an activity level of the subject; an aspect of a diet of the subject; a basal rate of insulin delivery to the subject; a correction factor; a carbohydrate ratio associated with the subject; a glucagon control parameter; demographic information associated with the subject; and a sensitivity constant associated with the subject's sensitivity to a glucose level or bolus of medicament; determine that the removable data module has been removed from the module interface; and in response to determining that the removable data module has been removed, transmit an indication that the data module has been removed.

In a 43rd example, the ambulatory medicament pump of example 42, further comprising a data interface configured to receive a glucose level signal from a glucose sensor operatively coupled to the subject, wherein the glucose level signal comprises: first encoded data corresponding to the glucose level of the subject; and second encoded data corresponding to an indication of a glucose trend, wherein the glucose trend indicates at least a predicted change in the glucose level of the subject.

In a 44th example, the ambulatory medicament pump of example 43, wherein the electronic processor is further configured to execute the specific computer-executable instructions to at least: receive, via the data interface, the glucose level signal from the glucose sensor; and decode the first and second encoded data of the glucose level signal to obtain the glucose level of the subject and the indication of the glucose trend.

In a 45th example, the ambulatory medicament pump of any of examples 42-44, wherein the electronic processor is further configured to execute the specific computer-executable instructions to at least: transmit to a user control element, via the data interface, an indication that the removable data module is ready for removal.

In a 46th example, the ambulatory medicament pump of any of examples 42-45, wherein the electronic processor is further configured to execute the specific computer-executable instructions to at least: generate, based on at least the one or more of the plurality of glucose control parameters, a dose control signal configured to cause the pump controller of the ambulatory medicament pump to deliver medicament to the subject.

In a 47th example, the ambulatory medicament pump of example 46, wherein generating the dose control signal comprises calculating regular correction boluses of glucose control agent in response to at least the one or more of the plurality of glucose control parameters.

In a 48th example, the ambulatory medicament pump of any of examples 46-47, wherein the instructions, when executed by the hardware processor, are further configured to: transmit to a remote electronic device, one or more of the glucose control therapy data or the glucose control parameter.

In a 49th example, the ambulatory medicament pump of example 48, wherein the remote electronic device comprises at least one of a mobile device or a remote computing environment.

In a 50th example, the ambulatory medicament pump of any of examples 42-49, further comprising a graphical user interface configured to display at least one of the one or more of the plurality of glucose control parameters or the glucose control therapy data.

In a 51st example, the ambulatory medicament pump of any of examples 42-50, wherein the instructions, when executed by the hardware processor, are further configured to: receive, via the data interface, at least one of an amount of insulin on board or a value used in a pharmacokinetic (PK) model of a control algorithm.

In a 52nd example, the ambulatory medicament pump of any of examples 42-51, wherein the data interface comprises a short-range wireless data interface.

In a 53rd example, the ambulatory medicament pump of any of examples 42-52, wherein the data interface comprises a plurality of data interfaces.

In a 54th example, the ambulatory medicament pump of any of examples 42-53, wherein the sensitivity constant comprises an indication of a date of diagnosis.

In a 55th example, the ambulatory medicament pump of any of examples 42-54, wherein the instructions, when executed by the hardware processor, are further configured to: execute, in response to transmitting the indication that the data module has been removed, a pump deactivation process configured to deactivate the ambulatory medicament pump.

In a 56th example, the ambulatory medicament pump of any of examples 42-55, wherein the glucose control therapy data comprises version data comprising at least one of: a timestamp corresponding to a time associated with an update of the glucose control therapy data; an indicator of an ordering within a sequence of delivery of the glucose control therapy; or a version code comprising encoded time data associated with delivery of the glucose control therapy.

In a 57th example, a method for storing one or more of a plurality of glucose control parameters and glucose control therapy data on a removable data module of a first ambulatory medicament pump configured to be readable by a second ambulatory medicament pump, the method comprising: by an electronic processor of the ambulatory medicament pump executing instructions stored on non-transitory memory connected to the electronic processor: determining the glucose control therapy data comprising at least one of an amount of insulin on board, a time of a delivery of glucose control therapy, or an amount of delivery of glucose control therapy; generating the one or more of the plurality of glucose control parameters, wherein the plurality of glucose control parameters comprises: an insulin decay rate constant associated with a decay rate of insulin at a subcutaneous depot of the subject; a clearance time associated with an estimate of an amount of time for a bolus of insulin to be utilized by the subject; an insulin rise rate constant associated with a rise rate of insulin in blood of the subject after a bolus of insulin; a half-life value associated with when a concentration of insulin in blood plasma of the subject reaches half of a maximum concentration in the blood plasma; a weight of the subject; an age of the subject; a learned parameter; glucose level data; a model parameter associated with a pharmacokinetic (PK) model; a health state of the subject; a parameter associated with an activity level of the subject; an aspect of a diet of the subject; a basal rate of insulin delivery to the subject; a correction factor; a carbohydrate ratio associated with the subject; a glucagon control parameter; demographic information associated with the subject; and a sensitivity constant associated with the subject's sensitivity to a glucose level or bolus of medicament; determining that the removable data module has been removed from the module interface; and in response to determining that the removable data module has been removed, transmitting an indication that the data module has been removed.

In a 58th example, the method of example 57, further comprising: receiving, via the data interface, a glucose level signal from the glucose sensor, wherein the glucose level signal comprises: first encoded data corresponding to the glucose level of the subject; and second encoded data corresponding to an indication of a glucose trend, wherein the glucose trend indicates at least a predicted change in the glucose level of the subject; and decoding the first and second encoded data of the glucose level signal to obtain the glucose level of the subject and the indication of the glucose trend.

In a 59th example, the method of any of examples 57-58, further comprising: transmitting to a user control element, via the data interface, an indication that the removable data module is ready for removal.

In a 60th example, the method of any of examples 57-59, further comprising: generating, based on at least the one or more of the plurality of glucose control parameters, a dose control signal configured to cause the pump controller of the ambulatory medicament pump to deliver medicament to the subject.

In a 61st example, the method of example 60, wherein generating the dose control signal comprises calculating regular correction boluses of glucose control agent in response to at least the one or more of the plurality of glucose control parameters.

In a 62nd example, the method of any of examples 57-61, further comprising: transmitting to a remote electronic device, one or more of the glucose control therapy data or the one or more of the plurality of glucose control parameters.

In a 63rd example, the method of example 62, wherein the remote electronic device comprises at least one of a mobile device or a remote computing environment.

In a 64th example, the method of any of examples 57-63, further comprising displaying at least one of the one or more of the plurality of glucose control parameters or the glucose control therapy data.

In a 65th example, the method of any of examples 57-64, further comprising: receiving, via the data interface, at least one of an amount of insulin on board or a value used in a pharmacokinetic (PK) model of a control algorithm.

In a 66th example, the method of any of examples 57-65, wherein the sensitivity constant comprises an indication of a date of diagnosis.

In a 67th example, the method of any of examples 57-66, further comprising: executing, in response to transmitting the indication that the data module has been removed, a pump deactivation process configured to deactivate the first ambulatory medicament pump.

In a 68th example, the method of any of examples 57-67, wherein the glucose control therapy data comprises version data comprising at least one of: a timestamp corresponding to a time associated with an update of the glucose control therapy data; an indicator of an ordering within a sequence of delivery of the glucose control therapy; or a version code comprising encoded time data associated with delivery of the glucose control therapy.

In a 69th example, an ambulatory medicament pump configured to wirelessly transmit one or more of a plurality of glucose control parameters and glucose control therapy data to a second ambulatory medicament pump, the ambulatory medicament pump comprising: a pump controller configured to direct medicament from a medicament reservoir to a subject; a data interface comprising a wireless data interface configured to transmit the one or more of the plurality of glucose control parameters and the glucose control therapy data to the second ambulatory medicament pump; a non-transitory memory configured to store specific computer-executable instructions; and an electronic processor in communication with the non-transitory memory and configured to execute the specific computer-executable instructions to at least: determine the glucose control therapy data comprising at least one of an amount of insulin on board, a time of a delivery of glucose control therapy, or an amount of delivery of glucose control therapy; generate the one or more of the plurality of glucose control parameters, wherein the plurality of glucose control parameters comprises: an insulin decay rate constant associated with a decay rate of insulin at a subcutaneous depot of the subject; a clearance time associated with an estimate of an amount of time for a bolus of insulin to be utilized by the subject; an insulin rise rate constant associated with a rise rate of insulin in blood of the subject after a bolus of insulin; a half-life value associated with when a concentration of insulin in blood plasma of the subject reaches half of a maximum concentration in the blood plasma; a weight of the subject; an age of the subject; a learned parameter; glucose level data; a model parameter associated with a pharmacokinetic (PK) model; a health state of the subject; a parameter associated with an activity level of the subject; an aspect of a diet of the subject; a basal rate of insulin delivery to the subject; a correction factor; a carbohydrate ratio associated with the subject; a glucagon control parameter; demographic information associated with the subject; and a sensitivity constant associated with the subject's sensitivity to a glucose level or bolus of medicament; determine that at least one of a plurality of pairing conditions is satisfied to couple the ambulatory medicament pump to the second ambulatory medicament pump, wherein the plurality of pairing conditions comprises: an occurrence of a scheduled time; a transmission of a meal announcement; a user request to pair the ambulatory medicament pump to a remote electronic device; a user input initiating a replacement process for the ambulatory medicament pump; an indication that the ambulatory medicament pump is to be replaced; an indication that the second ambulatory medicament pump is ready to deliver medicament to the subject; a sensory alarm configured to alert a user that historical pump data is ready for transmission; an alert indicating a malfunction associated with the ambulatory medicament pump; a determination that a level of medicament in a medicament reservoir of the ambulatory medicament pump is below a threshold level; a determination that an amount of available medicament of the ambulatory medicament pump is insufficient for a subject's medicament needs; and a signal received from the remote electronic device requesting transmission of at least one of the glucose control therapy data or the one or more of the plurality of glucose control parameters; in response to determining that the at least one of the plurality of pairing conditions is satisfied, wirelessly transmit, via the wireless data interface, the one or more of the plurality of glucose control parameters and the glucose control therapy data to the second ambulatory medicament pump.

In a 70th example, the ambulatory medicament pump of example 69, wherein the electronic processor is further configured to execute the specific computer-executable instructions to at least: transmit, via the wireless data interface, a pairing request signal to the second ambulatory medicament pump.

In a 71st example, the ambulatory medicament pump of any of examples 69-70, wherein the electronic processor is further configured to execute the specific computer-executable instructions to at least: receive, via the wireless data interface, a pairing confirmation signal from the second ambulatory medicament pump.

In a 72nd example, the ambulatory medicament pump of any of examples 69-71, wherein the data interface is further configured to receive a glucose level signal from a glucose sensor operatively coupled to the subject, wherein the glucose level signal comprises: first encoded data corresponding to the glucose level of the subject; and second encoded data corresponding to an indication of a glucose trend, wherein the glucose trend indicates at least a predicted change in the glucose level of the subject.

In a 73rd example, the ambulatory medicament pump of example 72, wherein the electronic processor is further configured to execute the specific computer-executable instructions to at least: receive, via the data interface, the glucose level signal from the glucose sensor; and decode the first and second encoded data of the glucose level signal to obtain the glucose level of the subject and the indication of the glucose trend.

In a 74th example, the ambulatory medicament pump of any of examples 69-73, wherein the electronic processor is further configured to execute the specific computer-executable instructions to at least: transmit to a user control element, via the data interface, an indication that the second ambulatory medicament pump is ready to be paired with the ambulatory medicament pump.

In a 75th example, the ambulatory medicament pump of any of examples 69-74, wherein the electronic processor is further configured to execute the specific computer-executable instructions to at least: generate, based on at least the one or more of the plurality of glucose control parameters, a dose control signal configured to cause the pump controller of the ambulatory medicament pump to deliver medicament to the subject.

In a 76th example, the ambulatory medicament pump of example 75, wherein generating the dose control signal comprises calculating regular correction boluses of glucose control agent in response to at least the one or more of the plurality of glucose control parameters.

In a 77th example, the ambulatory medicament pump of any of examples 69-76, wherein the instructions, when executed by the hardware processor, are further configured to: transmit to a remote electronic device, one or more of the glucose control therapy data or the one or more of the plurality of glucose control parameters.

In a 78th example, the ambulatory medicament pump of example 77, wherein the remote electronic device comprises at least one of a mobile device or a remote computing environment.

In a 79th example, the ambulatory medicament pump of any of examples 69-78, further comprising a graphical user interface configured to display at least one of the glucose control therapy data or the one or more of the plurality of glucose control parameters.

In an 80th example, the ambulatory medicament pump of any of examples 69-79, wherein the instructions, when executed by the hardware processor, are further configured to: receive, via the data interface, at least one of an amount of insulin on board or a value used in a pharmacokinetic (PK) model of a control algorithm.

In an 81st example, the ambulatory medicament pump of any of examples 69-80, wherein the wireless data interface comprises a short-range wireless data interface.

In an 82nd example, the ambulatory medicament pump of any of examples 69-81, wherein the data interface comprises a plurality of data interfaces.

In an 83rd example, the ambulatory medicament pump of any of examples 69-82, wherein the instructions, when executed by the hardware processor, are configured to: transmit to the second ambulatory medicament pump, in response to determining that the at least one of the plurality of pairing conditions is satisfied, at least one of an amount of insulin on board or a value used in a pharmacokinetic (PK) model of a control algorithm.

In an 84th example, the ambulatory medicament pump of any of examples 69-83, wherein the instructions, when executed by the hardware processor, are further configured to: in response to determining that the at least one of the plurality of pairing conditions is satisfied, receive from the remote electronic device, via the wireless data interface, at least one glucose control parameter.

In an 85th example, the ambulatory medicament pump of any of examples 69-84, wherein the malfunction associated with the first ambulatory medicament pump comprises at least one of an occlusion, a low battery power, an electrical malfunction, a controller malfunction, or a pump malfunction.

In an 86th example, the ambulatory medicament pump of any of examples 69-85, wherein the sensitivity constant comprises an indication of a date of diagnosis.

In an 87th example, the ambulatory medicament pump of any of examples 69-86, wherein the instructions, when executed by the hardware processor, are configured to: execute, in response to transmitting the one or more of the plurality of glucose control parameters and the glucose control therapy data to the second ambulatory medicament pump, a pump deactivation process configured to deactivate the first ambulatory medicament pump.

In an 88th example, the ambulatory medicament pump of any of examples 69-87, wherein the glucose control therapy data comprises version data comprising at least one of: a timestamp corresponding to a time associated with an update of the glucose control therapy data; an indicator of an ordering within a sequence of delivery of the glucose control therapy; or a version code comprising encoded time data associated with delivery of the glucose control therapy.

In an 89th example, a method for wirelessly transmitting from an ambulatory medicament pump one or more of a plurality of glucose control parameters and glucose control therapy data to a second ambulatory medicament pump, the method comprising: by an electronic processor of the ambulatory medicament pump executing instructions stored on non-transitory memory connected to the electronic processor: determining the glucose control therapy data comprising at least one of an amount of insulin on board, a time of a delivery of glucose control therapy, or an amount of delivery of glucose control therapy; generating the one or more of the plurality of glucose control parameters, wherein the plurality of glucose control parameters comprises: an insulin decay rate constant associated with a decay rate of insulin at a subcutaneous depot of the subject; a clearance time associated with an estimate of an amount of time for a bolus of insulin to be utilized by the subject; an insulin rise rate constant associated with a rise rate of insulin in blood of the subject after a bolus of insulin; a half-life value associated with when a concentration of insulin in blood plasma of the subject reaches half of a maximum concentration in the blood plasma; a weight of the subject; an age of the subject; a learned parameter; glucose level data; a model parameter associated with a pharmacokinetic (PK) model; a health state of the subject; a parameter associated with an activity level of the subject; an aspect of a diet of the subject; a basal rate of insulin delivery to the subject; a correction factor; a carbohydrate ratio associated with the subject; a glucagon control parameter; demographic information associated with the subject; and a sensitivity constant associated with the subject's sensitivity to a glucose level or bolus of medicament; determining that at least one of a plurality of pairing conditions is satisfied to couple the ambulatory medicament pump to the second ambulatory medicament pump, wherein the plurality of pairing conditions comprises: an occurrence of a scheduled time; a transmission of a meal announcement; a user request to pair the ambulatory medicament pump to a remote electronic device; a user input initiating a replacement process for the ambulatory medicament pump; an indication that the ambulatory medicament pump is to be replaced; an indication that the second ambulatory medicament pump is ready to deliver medicament to the subject; a sensory alarm configured to alert a user that historical pump data is ready for transmission; an alert indicating a malfunction associated with the ambulatory medicament pump; a determination that a level of medicament in a medicament reservoir of the ambulatory medicament pump is below a threshold level; a determination that an amount of available medicament of the ambulatory medicament pump is insufficient for a subject's medicament needs; and a signal received from the remote electronic device requesting transmission of at least one of the glucose control therapy data or the one or more of the plurality of glucose control parameters; in response to determining that the at least one of the plurality of pairing conditions is satisfied, wirelessly transmitting, via a wireless data interface, the one or more of the plurality of glucose control parameters and the glucose control therapy data to the second ambulatory medicament pump.

In a 90th example, the method of example 89, further comprising: transmitting, via the wireless data interface, a pairing request signal to the second ambulatory medicament pump.

In a 91st example, the method of any of examples 89-90, further comprising: receiving, via the wireless data interface, a pairing confirmation signal from the second ambulatory medicament pump.

In a 92nd example, the method of any of examples 89-91, further comprising: receiving a glucose level signal from a glucose sensor operatively coupled to the subject, wherein the glucose level signal comprises: first encoded data corresponding to the glucose level of the subject; and second encoded data corresponding to an indication of a glucose trend, wherein the glucose trend indicates at least a predicted change in the glucose level of the subject; and decoding the first and second encoded data of the glucose level signal to obtain the glucose level of the subject and the indication of the glucose trend.

In a 93rd example, the method of any of examples 89-92, further comprising: transmitting to a user control element, via the data interface, an indication that the second ambulatory medicament pump is ready to be paired with the ambulatory medicament pump.

In a 94th example, the method of any of examples 89-93, further comprising: generating, based on at least the one or more of the plurality of glucose control parameters, a dose control signal configured to cause the pump controller of the ambulatory medicament pump to deliver medicament to the subject.

In a 95th example, the method of example 94, wherein generating the dose control signal comprises calculating regular correction boluses of glucose control agent in response to at least the one or more of the plurality of glucose control parameters.

In a 96th example, the method of any of examples 89-95, further comprising: transmitting to a remote electronic device, one or more of the glucose control therapy data or the one or more of the plurality of glucose control parameters.

In a 97th example, the method of example 96, wherein the remote electronic device comprises at least one of a mobile device or a remote computing environment.

In a 98th example, the method of any of examples 89-97, further comprising displaying at least one of the glucose control therapy data or the one or more of the plurality of glucose control parameters.

In a 99th example, the method of any of examples 89-98, further comprising: receiving, via the data interface, at least one of an amount of insulin on board or a value used in a pharmacokinetic (PK) model of a control algorithm.

In a 100th example, the method of any of examples 89-99, further comprising: transmitting to the second ambulatory medicament pump, in response to determining that the at least one of the plurality of pairing conditions is satisfied, at least one of an amount of insulin on board or a value used in a pharmacokinetic (PK) model of a control algorithm.

In a 101st example, the method of any of examples 89-100, further comprising: in response to determining that the at least one of the plurality of pairing conditions is satisfied, receiving from the remote electronic device, via the wireless data interface, at least one glucose control parameter.

In a 102nd example, the method of any of examples 89-101, wherein the malfunction associated with the first ambulatory medicament pump comprises at least one of an occlusion, a low battery power, an electrical malfunction, a controller malfunction, or a pump malfunction.

In a 103rd example, the method of any of examples 89-102, wherein the sensitivity constant comprises an indication of a date of diagnosis.

In a 104th example, the method of any of examples 89-103, further comprising: executing, in response to transmitting the one or more of the plurality of glucose control parameters and the glucose control therapy data to the second ambulatory medicament pump, a pump deactivation process configured to deactivate the first ambulatory medicament pump.

In a 105th example, the method of any of examples 89-104, wherein the glucose control therapy data comprises version data comprising at least one of: a timestamp corresponding to a time associated with an update of the glucose control therapy data; an indicator of an ordering within a sequence of delivery of the glucose control therapy; or a version code comprising encoded time data associated with delivery of the glucose control therapy.

In a 106th example, a glucose level control system configured to generate a configuration code derived from medicament therapy administered to a subject, the configuration code configured to customize glucose level control therapy, the glucose level control system comprising: a medicament delivery interface configured to operatively connect to an ambulatory medicament pump for infusing medicament into the subject; a non-transitory memory configured to store specific computer-executable instructions; and an electronic processor in communication with the non-transitory memory and configured to execute the specific computer-executable instructions to at least: track medicament therapy administered to the subject over a tracking period by the glucose level control system, wherein tracking the medicament therapy comprises storing an indication of doses of medicament delivered to the subject as correction boluses of medicament, as food intake boluses of medicament, or as basal doses of medicament; generate the configuration code comprising at least one of a plurality of encoded dosing parameters, wherein the plurality of encoded dosing parameters comprises: a correction dosing parameter based on at least some of the correction boluses of medicament administered during the tracking period; a food intake dosing parameter comprising an indication of a food intake bolus size of medicament based on one or more food intake boluses provided during the tracking period; and a basal dosing parameter based on at least some of the basal doses of medicament administered during the tracking period; and output the configuration code as determined by the glucose level control system for the purpose of being used when the glucose level control system is replaced with a second glucose level control system, wherein the configuration code customizes at least initial therapy provided by the second glucose level control system.

In a 107th example, the glucose level control system of example 106, wherein the electronic processor is further configured to execute the specific computer-executable instructions to at least receive glucose level data from a sensor operatively configured to determine glucose levels in the subject.

In a 108th example, the glucose level control system of example 107, wherein the at least one of the plurality of encoded dosing parameters is based on at least the glucose level data received during the tracking period.

In a 109th example, the glucose level control system of any of examples 106-108, wherein the at least one of the plurality of encoded dosing parameters comprises the basal dosing parameter and the food intake dosing parameter.

In a 1200th example, the glucose level control system of any of examples 106-109, wherein the at least one of the plurality of encoded dosing parameters comprises the basal dosing parameter, the correction dosing parameter, and the food intake dosing parameter.

In a 111th example, the glucose level control system of any of examples 106-110, wherein the configuration code further comprises a subject identifier.

In a 112th example, the glucose level control system of any of examples 106-111, wherein the configuration code further comprises a time-based parameter.

In a 113th example, the glucose level control system of example 112, wherein the time-based parameter comprises a timestamp indicating at least one of an age of the configuration code, an age of the tracking period, or an expiration date of the configuration code.

In a 114th example, the glucose level control system of any of examples 106-113, wherein the doses of medicament are determined based on at least one of physiological parameters, demographic parameters, or food intake parameters of the subject.

In a 115th example, the glucose level control system of any of examples 106-114, wherein the food intake dosing parameter includes a plurality of calculated food intake dose amounts, and wherein at least one calculated food intake dose amount corresponds to a segment of a day different from at least one other calculated food intake dose amount of the plurality of calculated food intake dose amounts.

In a 116th example, the glucose level control system of any of examples 106-115, wherein a basal rate used to generate the basal doses of medicament is adapted over time based at least in part on one or more glucose level signals received from a sensor operatively configured to determine glucose levels in the subject.

In a 117th example, the glucose level control system of any of examples 106-116, wherein a food intake bolus size used to generate the food intake boluses of medicament is adapted over time based at least in part on one or more glucose level signals received from a sensor operatively configured to determine glucose levels in the subject.

In a 118th example, the glucose level control system of any of examples 106-117, wherein a length of the configuration code is 16 characters or more.

In a 119th example, the glucose level control system of any of examples 106-118, wherein a length of the configuration code is 16 bytes or more.

In a 120th example, the glucose level control system of any of examples 106-119, wherein outputting the configuration code comprises transmitting the configuration code to the second glucose level control system or to an electronic device in communication with the glucose level control system.

In a 121st example, the glucose level control system of example 120, wherein the electronic processor is further configured to execute the computer-executable instructions to at least generate a checksum for checking an error in the transmission of the configuration code.

In a 122nd example, the glucose level control system of any of examples 120-121, wherein the electronic processor is further configured to execute the specific computer-executable instructions to at least wirelessly transmit the configuration code to the second glucose level control system or to the electronic device.

In a 123rd example, the glucose level control system of any of examples 106-122, wherein outputting the configuration code comprises outputting the configuration code on a user interface of the glucose level control system.

In a 124th example, the glucose level control system of any of examples 106-123, wherein the configuration code is output as part of a backup therapy protocol.

In a 125th example, the glucose level control system of any of examples 106-124, wherein the electronic processor is further configured to execute the specific computer-executable instructions to at least receive a second configuration code comprising an encoded dosing parameter.

In a 126th example, the glucose level control system of example 125, wherein the electronic processor is further configured to execute the specific computer-executable instructions to at least: determine, based on the encoded dosing parameter, a value for a control parameter used by a control algorithm that generates dose control signals to provide medicament therapy to the subject; and configure the control parameter based on the value determined from the encoded dosing parameter.

In a 127th example, the glucose level control system of example 126, wherein the electronic processor is further configured to determine the value for the control parameter by at least decrypting the encoded dosing parameter.

In a 128th example, the glucose level control system of any of examples 126-127, wherein electronic processor is further configured to configure the control parameter by setting the control parameter to the value determined from the encoded dosing parameter.

In a 129th example, the glucose level control system of any of examples 126-128, wherein the value comprises an initial value for the control parameter, and wherein the control parameter is adapted over time based at least in part on the medicament therapy administered over the tracking period.

In a 130th example, the glucose level control system of any of examples 125-129, wherein the electronic processor is further configured to execute the specific computer-executable instructions to at least: verify a checksum of the second configuration code; and responsive to successfully verifying the checksum of the second configuration code, configure a control parameter based at least in part on the second configuration code, wherein the control parameter used by a control algorithm that generates dose control signals to provide medicament therapy to the subject.

In a 131st example, the glucose level control system of any of examples 125-130, wherein electronic processor is further configured to generate the configuration code by updating the second configuration code based at least in part on the tracked medicament therapy.

In a 132nd example, the glucose level control system of any of examples 125-131, wherein the electronic processor is further configured to execute the specific computer-executable instructions to at least: determine a first reference code associated with the second configuration code; determine a second reference code associated with the glucose level control system; and responsive to determining that the first reference code matches the second reference code, configure a control parameter based at least in part on the second configuration code, wherein the control parameter used by a control algorithm that generates dose control signals to provide medicament therapy to the subject.

In a 133rd example, the glucose level control system of example 132, wherein the first reference code and the second reference code correspond to one or more versions of control software capable of being executed by one or more glucose level control systems.

In a 134th example, the glucose level control system of any of examples 132-133, wherein, responsive to determining that the first reference code does not match the second reference code, the electronic processor is further configured to execute the specific computer-executable instructions to at least maintain an existing value of the control parameter.

In a 135th example, the glucose level control system of any of examples 132-134, wherein, responsive to determining that the first reference code does not match the second reference code, the electronic processor is further configured to execute the specific computer-executable instructions to at least configure the control parameter based at least in part on a modified version of the second configuration code.

In a 136th example, the glucose level control system of any of examples 125-135, wherein the electronic processor is further configured to execute the specific computer-executable instructions to at least: determine, based on the encoded dosing parameter, a value for a control parameter used by a control algorithm that generates dose control signals to provide medicament therapy to the subject; determine whether the value is safe for the subject; and responsive to determining that the value is safe for the subject, configure the control parameter based on the value determined from the encoded dosing parameter.

In a 137th example, the glucose level control system of example 136, wherein the electronic processor is further configured to determine whether the value is safe for the subject by determining whether the value is within a threshold range for a historical value for the control parameter.

In a 138th example, the glucose level control system of example 137, wherein the historical value comprises an average value over a particular time period or a most recent value of the control parameter.

In a 139th example, the glucose level control system of any of examples 137-138, wherein the historical value is obtained based on a history of medicament therapy stored at the glucose level control system.

In a 140th example, the glucose level control system of any of examples 137-139, wherein the historical value is obtained based on a history of medicament therapy stored at an electronic device in communication with the glucose level control system.

In a 141st example, the glucose level control system of any of examples 125-140, wherein the second configuration code is received in response to a user interaction with a user interface of the glucose level control system.

In a 142nd example, the glucose level control system of any of examples 125-141, wherein the second configuration code is received from an electronic computing device in communication with the glucose level control system.

In a 143rd example, the glucose level control system of example 142, wherein the second configuration code is received from the electronic computing device in response to a request from the glucose level control system.

In a 144th example, the glucose level control system of any of examples 106-143, wherein the electronic processor is further configured to execute the specific computer-executable instructions to at least encrypt the configuration code, and wherein outputting the configuration code comprises outputting the encrypted configuration code.

In a 145th example, the glucose level control system of any of examples 106-144, wherein the configuration code is associated with a serial number corresponding to the glucose level control system.

In a 146th example, a computer-implemented method of generating a configuration code derived from medicament therapy administered to a subject, the configuration code configured to customize glucose level control therapy, the computer-implemented method comprising: by a hardware processor of a glucose level control system configured to provide medicament therapy to the subject, tracking the medicament therapy administered to the subject over a tracking period by the glucose level control system, wherein tracking the medicament therapy comprises storing an indication of doses of medicament delivered to the subject as correction boluses of medicament, as food intake boluses of medicament, or as basal doses of medicament; generating the configuration code comprising at least one of a plurality of encoded dosing parameters, wherein the plurality of encoded dosing parameters comprises: a correction dosing parameter based on at least some of the correction boluses of medicament administered during the tracking period; a food intake dosing parameter comprising an indication of a food intake bolus size of medicament based on one or more food intake boluses provided during the tracking period; a basal dosing parameter based on at least some of the basal doses of medicament administered during the tracking period; a carbohydrate ratio comprising an indication of a quantity of medicament to administer per quantity of carbohydrates consumed or to be consumed; a correction factor comprising an indication of how much a quantity of medicament will affect or is predicted to affect a glucose level of the subject; a basal rate comprising an indication of a rate of medicament to administer over a time period; a counter-regulatory agent dosing parameter comprising an indication of a quantity of a counter-regulatory agent based on one or more counter-regulatory agent boluses administered during the tracking period; a control parameter based on execution of a control algorithm during the tracking period; and a setting parameter used by the glucose level control system in identifying the subject or configuring the glucose level control system during the tracking period; and outputting the configuration code as determined by the glucose level control system for the purpose of being used when the glucose level control system is replaced with a second glucose level control system, wherein the configuration code customizes at least initial therapy provided by the second glucose level control system.

In a 147th example, the computer-implemented method of example 146, wherein the setting parameter comprises a subject identifier of the subject, an alert setting, a medicament pump setting, a user interface setting, a security setting, a safe-access level setting, state data of the glucose level control system, or a user identifier of a user associated with the subject.

In a 148th example, the computer-implemented method of any of examples 146-147, wherein the counter-regulatory agent comprises glucagon.

In a 149th example, the computer-implemented method of any of examples 146-148, wherein the food intake dosing parameter corresponds to a particular meal.

In a 150th example, a glucose level control system configured to modify control parameters based on a configuration code generated based on prior medicament therapy administered to a subject, the configuration code configured to customize glucose level control therapy, the glucose level control system comprising: a medicament delivery interface configured to operatively connect to an ambulatory medicament pump for infusing medicament into the subject; a non-transitory memory configured to store specific computer-executable instructions; and an electronic processor in communication with the non-transitory memory and configured to execute the specific computer-executable instructions to at least: receive the configuration code comprising at least one of a plurality of encoded dosing parameters, wherein the plurality of encoded dosing parameters correspond to a set of dosing parameters comprising: a correction dosing parameter used by a control algorithm to determine a correction bolus of medicament to administer to the subject; a food intake dosing parameter used by the control algorithm to determine a food intake bolus size of medicament to administer to the subject; and a basal dosing parameter used by the control algorithm to determine a basal rate of medicament to administer to the subject; decode the configuration code to identify a dosing parameter and a value of the dosing parameter, wherein the dosing parameter is one of the set of dosing parameters; and configure a control parameter of the control algorithm corresponding to the dosing parameter based on the value of the dosing parameter.

In a 151st example, the glucose level control system of example 150, wherein the electronic processor is further configured to decode the configuration code by decrypting the configuration code.

In a 152nd example, the glucose level control system of any of examples 150-151, wherein the electronic processor is further configured to configure the control parameter by setting the control parameter to the value identified from the configuration code.

In a 153rd example, the glucose level control system of any of examples 150-152, wherein the value comprises an initial value for the control parameter, and wherein the control parameter is adapted over a time period based at least in part on medicament therapy administered over the time period.

In a 154th example, the glucose level control system of any of examples 150-153, wherein the electronic processor is further configured to execute the specific computer-executable instructions to at least verify a checksum of the configuration code prior to decoding the configuration code.

In a 155th example, the glucose level control system of any of examples 150-154, wherein the electronic processor is further configured to execute the specific computer-executable instructions to at least: update the configuration code based on medicament therapy provided over a tracking period; and output the updated configuration code enabling a second glucose level control system to be configured based at least in part on the updated configuration code.

In a 156th example, the glucose level control system of any of examples 150-155, wherein the electronic processor is further configured to execute the specific computer-executable instructions to at least verify that a reference code of the glucose level control system matches a reference code of the configuration code prior to configuring the control parameter of the control algorithm.

In a 157th example, the glucose level control system of example 156, wherein the reference code of the glucose level control system comprises: a serial number, a software version number, or a model number.

In a 158th example, the glucose level control system of any of examples 150-157, wherein the electronic processor is further configured to identify the value of the control parameter by at least: determining a reference to a server from the configuration code; and accessing the server to obtain the value of the control parameter.

In a 159th example, the glucose level control system of example 158, wherein the server stores one or more values of one or more dosing parameters associated with the subject or a demographic that includes the subject.

In a 160th example, the glucose level control system of any of examples 150-159, wherein the configuration code is received in response to a user interaction with a user interface of the glucose level control system.

In a 161st example, the glucose level control system of any of examples 150-160, wherein the configuration code is received from an electronic device in communication with the glucose level control system.

In a 162nd example, the glucose level control system of example 161, wherein the electronic processor is further configured to execute the specific computer-executable instructions to at least access an account of the subject at the electronic device, and wherein the configuration code is associated with the account of the subject.

In a 163rd example, the glucose level control system of example 162, wherein the account comprises an electronic health record of the subject.

In a 164th example, the glucose level control system of any of examples 150-163, wherein the configuration code is associated with the subject or a demographic that includes the subject.

In a 165th example, the glucose level control system of any of examples 150-164, wherein the electronic processor is further configured to execute the specific computer-executable instructions to at least determine whether the value of the dosing parameter is safe for the subject.

In a 166th example, the glucose level control system of example 165, wherein the electronic processor determines whether the value of the dosing parameter is safe for the subject be at least determining a probability that the value of the dosing parameter will cause a hypoglycemic or hyperglycemic event.

In a 167th example, the glucose level control system of any of examples 150-166, wherein the configuration code is received during an initialization process of the glucose level control system.

In a 168th example, the glucose level control system of any of examples 150, wherein the configuration code is received from the non-transitory memory.

In a 169th example, a computer-implemented method of modifying control parameters based on a configuration code generated based on prior medicament therapy administered to a subject, the configuration code configured to customize glucose level control therapy, the computer-implemented method comprising: by a hardware processor of a glucose level control system configured to provide medicament therapy to the subject, receiving the configuration code comprising at least one of a plurality of encoded dosing parameters, wherein the plurality of encoded dosing parameters correspond to a set of dosing parameters comprising: a correction dosing parameter used by a control algorithm to determine a correction bolus of medicament to administer to the subject; a food intake dosing parameter used by the control algorithm to determine a food intake bolus size of medicament to administer to the subject; and a basal dosing parameter used by the control algorithm to determine a basal rate of medicament to administer to the subject; decoding the configuration code to identify a dosing parameter and a value of the dosing parameter, wherein the dosing parameter is one of the set of dosing parameters; and configuring a control parameter of the control algorithm corresponding to the dosing parameter based on the value of the dosing parameter.

In a 170th example, an electronic device configured to generate a configuration code derived from medicament therapy administered to a subject, the configuration code configured to customize glucose level control therapy, the electronic device comprising: a network interface configured to receive medicament therapy data; and a non-transitory memory configured to store specific computer-executable instructions; and an electronic processor in communication with the non-transitory memory and configured to execute the specific computer-executable instructions to at least: receive medicament therapy data from a glucose level control system configured to administer medicament therapy to a subject, wherein the medicament therapy data corresponds to the medicament therapy administered to the subject over a tracking period, and wherein the medicament therapy data comprises an indication of doses of medicament delivered to the subject as correction boluses of medicament, as food intake boluses of medicament, or as basal doses of medicament; generate the configuration code comprising at least one of a plurality of encoded dosing parameters, wherein the plurality of encoded dosing parameters comprises: a correction dosing parameter based on at least some of the correction boluses of medicament administered during the tracking period; a food intake dosing parameter comprising an indication of a food intake bolus size of medicament based on one or more food intake boluses provided during the tracking period; and a basal dosing parameter based on at least some of the basal doses of medicament administered during the tracking period; and transmit the configuration code to a second glucose level control system enabling the second glucose level control system to be customized with an initial configuration based at least in part on the configuration code.

In a 171st example, the electronic device of example 170, wherein the electronic device comprises a server of a networked computing environment.

In a 172nd example, the electronic device of any of examples 170-171, wherein the electronic device comprises a distributed computing system.

In a 173rd example, the electronic device of any of examples 170-172, wherein generating the configuration code further comprises generating a checksum to include with the configuration code.

In a 174th example, the electronic device of any of examples 170-173, wherein the medicament therapy data is received by the network interface over a wireless or cellular network.

In a 175th example, a computer-implemented method of generating a configuration code derived from medicament therapy administered to a subject, the configuration code configured to customize glucose level control therapy, the computer-implemented method comprising: by a hardware processor of an electronic device that communicates over a network with a glucose level control system configured to provide medicament therapy to the subject, receiving medicament therapy data from the glucose level control system configured to administer medicament therapy to a subject, wherein the medicament therapy data corresponds to the medicament therapy administered to the subject over a tracking period, and wherein the medicament therapy data comprises an indication of doses of medicament delivered to the subject as correction boluses of medicament, as food intake boluses of medicament, or as basal doses of medicament; generating the configuration code comprising at least one of a plurality of encoded dosing parameters, wherein the plurality of encoded dosing parameters comprises: a correction dosing parameter based on at least some of the correction boluses of medicament administered during the tracking period; a food intake dosing parameter comprising an indication of a food intake bolus size of medicament based on one or more food intake boluses provided during the tracking period; and a basal dosing parameter based on at least some of the basal doses of medicament administered during the tracking period; and transmitting the configuration code to a second glucose level control system enabling the second glucose level control system to be customized with an initial configuration based at least in part on the configuration code.

In a 176th example, a blood glucose control system configured to receive a glucose level signal from a glucose sensor operatively coupled to the subject and to calculate a dose control signal for commanding administration of glucose control therapy to a subject via a pump controller of an ambulatory medicament pump operatively coupled to the subject, the blood glucose control system comprising: a data interface configured to transmit the dose control signal to the pump controller and to receive the glucose level signal from the glucose sensor, wherein the glucose level signal comprises: first encoded data corresponding to a glucose level of the subject; and second encoded data corresponding to an indication of a glucose trend, wherein the glucose trend indicates at least a predicted change in the glucose level of the subject; a non-transitory memory configured to store specific computer-executable instructions; and an electronic processor in communication with the non-transitory memory and configured to execute the specific computer-executable instructions to at least: receive, via the data interface, the glucose level signal from the glucose sensor operatively coupled to the subject; decode the first and second encoded data of the glucose level signal to obtain the glucose level of the subject and the indication of the glucose trend; calculate the dose control signal using a control algorithm configured to calculate regular correction boluses of glucose control agent in response to at least the glucose level of the subject; select a dose control signal encoding profile from a plurality of dose control signal encoding profiles, wherein each of the plurality of dose control signal encoding profiles corresponds to at least one of a plurality of pump controllers, wherein each dose control signal encoding profile is configured to encode the dose control signal for transmission to the pump controller, and wherein the selected dose control signal encoding profile corresponds to the pump controller operatively coupled to the subject; encode the dose control signal using the selected dose control signal encoding profile such that the pump controller can read the dose control signal; and transmit the encoded dose control signal to the pump controller of the ambulatory medicament pump, wherein the dose control signal commands the ambulatory medicament pump to administer glucose control therapy via infusion of the glucose control agent into the subject.

In a 177th example, the blood glucose control system of example 176, further comprising a graphical user interface configured to display the glucose level of the subject or the indication of the glucose trend, wherein the instructions, when executed by the hardware processor, are further configured to: transmit, via the data interface to the graphical user interface, one or more of the glucose level of the subject or the indication of the glucose trend.

In a 178th example, the blood glucose control system of any of examples 176-177, wherein the instructions, when executed by the hardware processor, are further configured to transmit the glucose level of the subject or the indication of the glucose trend to a remote electronic device.

In a 179th example, the blood glucose control system of example 178, wherein the remote electronic device comprises at least one of a mobile device or a remote computing environment.

In a 180th example, the blood glucose control system of any of examples 176-179, wherein the instructions, when executed by the hardware processor, are further configured to receive, from the glucose sensor, via the data interface, blood glucose control parameters comprising at least one of: an insulin decay rate constant associated with a decay rate of insulin at a subcutaneous depot of the subject; a clearance time associated with an estimate of an amount of time for a bolus of insulin to be utilized by the subject; an insulin rise rate constant associated with a rise rate of insulin in blood of the subject after a bolus of insulin; a time value associated with when a concentration of insulin in blood plasma of the subject reaches a threshold concentration in the blood plasma; or a sensitivity constant associated with the subject's sensitivity to a glucose level or bolus of medicament.

In a 181st example, the blood glucose control system of any of examples 176-180, wherein the instructions, when executed by the hardware processor, are further configured to: receive, via the data interface, at least one of an amount of insulin on board or a value used in a pharmacokinetic (PK) model of the control algorithm.

In a 182nd example, the blood glucose control system of any of examples 176-181, further comprising the ambulatory medicament pump and the pump controller.

In a 183rd example, the blood glucose control system of any of examples 176-182, wherein the instructions, when executed by the hardware processor, are configured to execute the control algorithm.

In a 184th example, the blood glucose control system of any of examples 176-183, wherein the data interface comprises a short-range wireless data interface.

In a 185th example, the blood glucose control system of any of examples 176-184, wherein the instructions, when executed by the hardware processor, are further configured to: select a glucose level signal decoding profile from a plurality of glucose level signal decoding profiles, wherein each of the plurality of glucose level signal decoding profiles corresponds to at least one of a plurality of glucose sensors, wherein each glucose level signal decoding profile is configured to decode at least the first encoded data and the second encoded data of the glucose level signal, and wherein the selected glucose level signal decoding profile corresponds to the glucose sensor operatively coupled to the subject; and decode the first and second encoded data of the glucose level signal using the selected glucose level signal decoding profile.

In a 186th example, the blood glucose control system of any of examples 176-185, wherein the data interface comprises a plurality of data interfaces.

In a 187th example, a disposable ambulatory medicament pump configured to administer blood glucose control therapy to a subject and to transmit blood glucose control parameters to a remote electronic device in response to an identification of a triggering condition, the disposable ambulatory medicament pump comprising: a medicament reservoir configured to store medicament to be delivered through a cannula into a subcutaneous depot of the subject as at least a portion of the blood glucose control therapy; a pump controller configured to direct the medicament from the medicament reservoir to the subject via the disposable ambulatory medicament pump; a data interface configured to receive a glucose level signal from a glucose sensor and to transmit the blood glucose control parameters to the remote electronic device; a non-transitory memory configured to store specific computer-executable instructions and the blood glucose control parameters; and an electronic processor in communication with the non-transitory memory and configured to execute the specific computer-executable instructions to at least: receive, via the data interface, the glucose level signal from the glucose sensor operatively coupled to the subject; generate the blood glucose control parameters based on trends in the blood glucose control therapy and the glucose level signal using a control parameter selection process over a therapy period spanning at least hours to days; generate, based on at least the glucose level signal and the blood glucose control parameters, a dose control signal configured to cause the pump controller to administer the blood glucose control therapy to the subject; identify that at least one of a plurality of triggering conditions is satisfied, the at least one of the plurality of triggering conditions configured to prompt transmission of the blood glucose control parameters to the remote electronic device, the plurality of triggering conditions comprising: a sensory alarm configured to alert a user that the blood glucose control parameters are ready for transmission; a determination that a level of medicament in the medicament reservoir is below a threshold level; a signal received from the remote electronic device requesting transmission of the blood glucose control parameters; and a user-generated indication to replace the disposable ambulatory medicament pump; and based on the satisfaction of the at least one of the plurality of triggering conditions, transmit the blood glucose control parameters to the remote electronic device.

In a 188th example, the disposable ambulatory medicament pump of example 187, wherein the blood glucose control parameters comprise at least one of a glucose level or an indication of a glucose trend of the subject.

In a 189th example, the disposable ambulatory medicament pump of any of examples 187-188, wherein the blood glucose control parameters comprise at least one of: an insulin decay rate constant associated with a decay rate of insulin at a subcutaneous depot of the subject; a clearance time associated with an estimate of an amount of time for a bolus of insulin to be utilized by the subject; an insulin rise rate constant associated with a rise rate of insulin in blood of the subject after a bolus of insulin; a time value associated with when a concentration of insulin in blood plasma of the subject reaches a threshold concentration in the blood plasma; or a sensitivity constant associated with the subject's sensitivity to a glucose level or bolus of medicament.

In a 190th example, the disposable ambulatory medicament pump of any of examples 187-189, wherein the instructions, when executed by the hardware processor, are further configured to: transmit, based on the satisfaction of the at least one of the plurality of triggering conditions, at least one of an amount of insulin on board or a value used in a pharmacokinetic (PK) model of a control algorithm.

In a 191st example, the disposable ambulatory medicament pump of any of examples 187-190, wherein the triggering condition comprises the sensory alarm configured to alert a user that the blood glucose control parameters are ready for transmission.

In a 192nd example, the disposable ambulatory medicament pump of example 191, wherein the sensory alarm is configured to regularly or periodically alert the user until the blood glucose control parameters are transferred to the remote electronic device.

In a 193rd example, the disposable ambulatory medicament pump of any of examples 187-192, wherein the instructions, when executed by the hardware processor, are configured to: generate the blood glucose control parameters further based on a glycemic response of the subject over a therapy interval.

In a 194th example, the disposable ambulatory medicament pump of any of examples 187-193, wherein the therapy interval comprises between about 10 seconds and 10 minutes.

In a 195th example, the disposable ambulatory medicament pump of any of examples 187-194, wherein the instructions, when executed by the hardware processor, are configured to: generate the blood glucose control parameters further based on glycemic response of the subject to a medicament bolus.

In a 196th example, the disposable ambulatory medicament pump of any of examples 187-195, wherein the instructions, when executed by the hardware processor, are configured to: generate the blood glucose control parameters by learning the blood glucose control parameters during online operation of an automated blood glucose control system.

In a 197th example, the disposable ambulatory medicament pump of any of examples 196-196, wherein generating the blood glucose control parameters comprises at least one of: calculating a size of a correction bolus of insulin of the regular correction boluses at a time of receiving an isolated glucose measurement from the glucose sensor.

In a 198th example, the disposable ambulatory medicament pump of any of examples 196-197, wherein generating the blood glucose control parameters comprises at least one of: calculating a size of a meal bolus of insulin.

In a 199th example, the disposable ambulatory medicament pump of any of examples 187-198, wherein the instructions, when executed by the hardware processor, are configured to: generating the blood glucose control parameters using a control algorithm.

In a 200th example, the disposable ambulatory medicament pump of any of examples 187-199, wherein the remote electronic device comprises a mobile device.

In a 201st example, the disposable ambulatory medicament pump of any of examples 187-200, wherein the remote electronic device comprises a remote computing environment.

In a 202nd example, the disposable ambulatory medicament pump of any of examples 187-201, wherein the data interface comprises a short-range wireless data interface.

In a 203rd example, a method for administering blood glucose control therapy to a subject and transmitting blood glucose control parameters to a remote electronic device in response to an identification of a triggering condition, the method comprising: by an electronic processor of a blood glucose control system executing instructions stored on non-transitory memory connected to the electronic processor: receiving, via a data interface, a glucose level signal from a glucose sensor operatively coupled to the subject; calculating, based on the glucose level signal, a dose control signal configured to cause a pump controller to administer at least a portion of blood glucose control therapy into a subcutaneous depot of the subject; generating the blood glucose control parameters based on the blood glucose control therapy and the dose control signal; identifying that at least one of a plurality of triggering conditions is satisfied, the at least one of the plurality of triggering conditions configured to prompt transmission of the blood glucose control parameters to the remote electronic device, the plurality of triggering conditions comprising: a sensory alarm configured to alert a user that the blood glucose control parameters are ready for transmission; a determination that a level of medicament in the medicament reservoir is below a threshold level; a signal received from the remote electronic device requesting transmission of the blood glucose control parameters; and a user-generated indication to replace the disposable ambulatory medicament pump; and based on the satisfaction of the at least one of the plurality of triggering conditions, transmitting the blood glucose control parameters to the remote electronic device.

In a 204th example, the method of example 203, wherein the glucose level signal comprises at least one of a glucose level or an indication of a glucose trend of the subject.

In a 205th example, the method of any of examples 203-204, wherein the blood glucose control parameters comprise at least one of: an insulin decay rate constant associated with a decay rate of insulin at a subcutaneous depot of the subject; a clearance time associated with an estimate of an amount of time for a bolus of insulin to be utilized by the subject; an insulin rise rate constant associated with a rise rate of insulin in blood of the subject after a bolus of insulin; a time value associated with when a concentration of insulin in blood plasma of the subject reaches a threshold concentration in the blood plasma; or a sensitivity constant associated with the subject's sensitivity to a glucose level or bolus of medicament.

In a 206th example, the method of any of examples 203-205, further comprising: transmitting, based on the satisfaction of the at least one of the plurality of triggering conditions, at least one of an amount of insulin on board or a value used in a pharmacokinetic (PK) model.

In a 207th example, the method of any of examples 203-206, wherein the triggering condition comprises the sensory alarm configured to alert a user that the blood glucose control parameters are ready for transmission.

In a 208th example, the method of example 207, wherein the sensory alarm is configured to regularly or periodically alert the user until the blood glucose control parameters are transferred to the remote electronic device.

In a 209th example, the method of any of examples 203-208, further comprising: generating the blood glucose control parameters further based on glycemic response of the subject to a medicament bolus.

In a 210th example, a blood glucose control system configured to receive an encoded pump status signal and an encoded medicament delivery signal from a pump controller operatively coupled to an ambulatory medicament pump and to calculate a dose control signal for commanding administration of glucose control therapy to a subject via the ambulatory medicament pump, the blood glucose control system comprising: a data interface configured to receive: the encoded pump status signal from the pump controller, wherein the encoded pump status signal comprises data corresponding to an availability of the ambulatory medicament pump to deliver medicament to the subject; the encoded medicament delivery signal from the pump controller, wherein the encoded medicament delivery signal comprises data corresponding to an amount of medicament dosed to the subject; and a glucose level signal from a glucose sensor operatively coupled to the subject; a non-transitory memory configured to store specific computer-executable instructions; and an electronic processor in communication with the non-transitory memory and configured to execute the specific computer-executable instructions to at least: receive, via the data interface, the glucose level signal from the glucose sensor; decode the glucose level signal to obtain a glucose level of the subject and an indication of a glucose trend; calculate the dose control signal using a control algorithm configured to calculate regular correction boluses of glucose control agent in response to at least the glucose level of the subject; receive, via the data interface, the encoded pump status signal from the pump controller; select a pump controller decoding profile from a plurality of pump controller decoding profiles, wherein each of the plurality of pump controller decoding profiles corresponds to at least one of a plurality of pump controllers, wherein each pump controller decoding profile is configured to decode at least the encoded pump status signal and the encoded medicament delivery signal, and wherein the selected pump controller decoding profile corresponds to the pump controller operatively coupled to the ambulatory medicament pump; decode the encoded pump status signal and the encoded medicament delivery signal using the selected pump controller decoding profile; select a pump controller encoding profile from a plurality of pump controller encoding profiles, wherein the selected pump controller encoding profile corresponds to the pump controller operatively coupled to the ambulatory medicament pump, wherein the pump controller encoding profile is configured to encode at least the dose control signal; based on the encoded pump status signal, determine that the ambulatory medicament pump is available to deliver medicament to the subject and encode the dose control signal such that the pump controller can read the dose control signal; and transmit the encoded dose control signal to the pump controller of the ambulatory medicament pump, wherein the dose control signal commands the ambulatory medicament pump to administer glucose control therapy via infusion of the glucose control agent into the subject.

In a 211th example, a blood glucose control system configured to receive an encoded pump controller signal from a pump controller operatively coupled to an ambulatory medicament pump and to route pass-through data not used in a calculation of a dose control signal to a target electronic device, the blood glucose control system comprising: a data interface configured to receive the encoded pump controller signal from the pump controller via a digital data connection and to receive the glucose level signal from the glucose sensor, the encoded pump controller signal comprising: an encoded medicament delivery signal corresponding to an amount of medicament dosed to the subject, and pass-through data comprising encoded pump controller alert data, wherein the pass-through data is not used in the calculation of the dose control signal; a non-transitory memory configured to store specific computer-executable instructions; and an electronic processor in communication with the non-transitory memory and configured to execute the specific computer-executable instructions to at least: receive, via the data interface, the encoded pump controller signal from the pump controller via the digital data connection and the glucose level signal from the glucose sensor; decode the encoded medicament delivery signal and the encoded pump controller alert data to obtain the amount of medicament dosed to the subject and the data not used in the calculation of the dose control signal; calculate the dose control signal using a control algorithm configured to calculate regular correction boluses of glucose control agent in response to at least the glucose level of the subject and the amount of medicament dosed to the subject; and route the data not used in the calculation of the dose control signal to the target electronic device.

In a 212th example, the blood glucose control system of example 211, wherein the pass-through data comprises at least one of: an indication that a pump cartridge has a volume of medicament below a threshold volume; an indication that a supply of medicament is below a threshold supply; a charge level associated with a battery of the ambulatory medicament pump; an indication that the glucose sensor has exceeded a threshold performance period; an indication to wirelessly couple a new glucose sensor with the ambulatory medicament pump; and an indication that a new pump cartridge has been installed in the ambulatory medicament pump.

In a 213th example, the blood glucose control system of any of examples 211-212, wherein the instructions, when executed by the hardware processor, are configured to: determine that the pass-through data is unrelated to the calculation of the dose control signal; and based on the determination that the pass-through data is not used in the dose control signal, route the status alert to the target electronic device.

In a 214th example, the blood glucose control system of any of examples 211-213, wherein the data interface is further configured to receive encoded glucose sensor signal comprising second pass-through corresponding to second data not used in the calculation of the dose control signal, and wherein the instructions, when executed by the hardware processor, are configured to: receive the encoded glucose sensor signal comprising the second pass-through data; decode the encoded glucose sensor signal to obtain the second data not used in the calculation of the dose control signal; and route the second data not used in the calculation of the dose control signal to a second target electronic device.

In a 215th example, the blood glucose control system of any of examples 211-214, wherein the data interface is further configured to receive encoded source device signal comprising third pass-through corresponding to third data not used in the calculation of the dose control signal, and wherein the instructions, when executed by the hardware processor, are configured to: receive the encoded source device signal comprising the third pass-through data; and decode the encoded source device signal to obtain the third data not used in the calculation of the dose control signal; and route the third data not used in the calculation of the dose control signal to a third target electronic device.

In a 216th example, an ambulatory medicament pump configured to enable therapy change controls associated with a selected safe access level for a user of an ambulatory medicament pump configured to provide medicament therapy to a subject, the ambulatory medicament pump comprising: a pump controller configured to receive a dose control signal configured to cause the ambulatory medicament pump to infuse a medicament from a medicament reservoir into the subject; a data interface configured to communicate with an electronic access device; a non-transitory memory configured to store specific computer-executable instructions and a plurality of safe access level profiles, each safe access level profile specifying therapy change controls associated with a safe access level, wherein the therapy change controls comprise a control for selecting a medicament therapy setting that affects administration of medicament therapy by the ambulatory medicament pump; and an electronic processor in communication with the non-transitory memory and configured to execute the specific computer-executable instructions to at least: receive, via the data interface, an access signal from the electronic access device, wherein the access signal is configured to enable one or more therapy change controls associated with the selected safe access level; and in response to receiving the access signal, enable the one or more therapy change controls associated with the selected safe access level, wherein selecting a medicament therapy setting using the one or more therapy change controls causes modification of a control parameter used by a control algorithm to affect the administration of medicament therapy by the ambulatory medicament pump.

In a 217th example, the ambulatory medicament pump of example 216, wherein the ambulatory medicament pump is configured to provide medicament therapy to control a blood glucose level in the subject.

In a 218th example, the computer-implemented method of example 217, wherein the medicament therapy comprises insulin therapy.

In a 219th example, the computer-implemented method of example 218, wherein the one or more therapy change controls comprise a control for selecting a type of the insulin therapy from a plurality of insulin therapy types.

In a 220th example, the ambulatory medicament pump of example 219, wherein the type of insulin therapy comprises U100 insulin therapy, U200 insulin therapy, ultra-rapid insulin therapy, or fast-acting insulin therapy.

In a 221st example, the ambulatory medicament pump of any of examples 216-220, wherein the control parameter is used by the control algorithm to account for an accumulation of insulin in the subject.

In a 222nd example, the ambulatory medicament pump of any of examples 216-221, wherein the one or more therapy change controls associated with the selected safe access level are enabled during a validity period.

In a 223rd example, the ambulatory medicament pump of example 222, wherein the validity period is one hour, one day, or one week.

In a 224th example, the ambulatory medicament pump of any of examples 222-223, wherein the validity period expires when the subject associated with the ambulatory medicament pump changes.

In a 225th example, the ambulatory medicament pump of any of examples 222-224, wherein the validity period is modified from a first period to a second period in response to a user interaction with a user interface of the ambulatory medicament pump.

In a 226th example, the ambulatory medicament pump of any of examples 216-225, wherein the data interface is configured to communicate with the electronic access device via a wired or a wireless communication connection.

In a 227th example, the ambulatory medicament pump of example 226, wherein the wireless communication connection comprises: a Long-Term Evolution wireless connection, a Wi-Fi network connection, a 5G communication network connection, a wide area network connection, a near-field communication network connection, or a short-range wireless connection.

In a 228th example, the ambulatory medicament pump of any of examples 216-227, wherein the electronic access device comprises a personal computer, a mobile phone, a dedicated electronic access device, a cloud server, or a passcode server.

In a 229th example, the ambulatory medicament pump of any of examples 216-228, wherein the electronic access device comprises an electronic device associated with a healthcare provider or a trainer of the user or the subject.

In a 230th example, the ambulatory medicament pump of any of examples 216-229, wherein the selected safe access level is associated with a therapy history of the subject, or a training level of the subject or the user.

In a 231st example, the ambulatory medicament pump of any of examples 216-230, wherein the selected safe access level is associated with a medicament prescription of the subject.

In a 232nd example, the ambulatory medicament pump of any of examples 216-231, wherein the electronic processor is further configured to enable the one or more therapy change controls associated with the selected safe access level by displaying therapy change control elements on a user interface wherein the therapy change control elements enable modification of control parameter values corresponding to the one or more therapy change controls.

In a 233rd example, the ambulatory medicament pump of any of examples 216-232, wherein the electronic processor is further configured to enable the one or more therapy change controls associated with the selected safe access level by unlocking therapy change control elements in a menu displayed on a user interface wherein the therapy change control elements enable modification of control parameter values corresponding to the one or more therapy change controls.

In a 234th example, the ambulatory medicament pump of any of examples 216-233, wherein the electronic processor is further configured to execute the specific computer-executable instructions to at least: receive, responsive to a user interaction with a user interface, a request to restore the control parameter to a previous value; and restore the control parameter to the previous value.

In a 235th example, the ambulatory medicament pump of any of examples 216-234, wherein the access signal comprises a time-based passcode associated with the safe access level, wherein the time-based passcode is configured to expire after a validity period, and wherein in response to receiving the access signal, the electronic processor is further configured to execute the specific computer-executable instructions to at least: receive a user passcode in response to user interaction with a passcode entry interface; determine that the user passcode matches the time-based passcode and that the user passcode is received during the validity period; and in response to determining that the user passcode matches the time-based passcode and that the passcode attempt is received during the validity period, enable the therapy change controls associated with the safe access level.

In a 236th example, the ambulatory medicament pump of any of examples 216-235, wherein the user is the subject receiving medicament therapy from the ambulatory medicament pump.

In a 237th example, a computer-implemented method of enabling therapy change controls associated with a selected safe access level for a user of an ambulatory medicament pump configured to provide medicament therapy to a subject, wherein the medicament therapy comprises infusing a medicament to the subject, the computer-implemented method comprising: by an electronic processor of the ambulatory medicament pump, wherein the electronic processor is configured to execute specific computer-executable instructions stored in a non-transitory memory in communication with the electronic processor, receiving, via a digital data interface, an access signal from the electronic access device, wherein the access signal is configured to enable one or more therapy change controls associated with the selected safe access level, wherein the selected safe access level is associated with at least one of a plurality of safe access level profiles, each safe access level profile specifying therapy change controls associated with a safe access level, and wherein the one or more therapy change controls affect administration of medicament therapy by the ambulatory medicament pump; and in response to receiving the access signal, enabling the one or more therapy change controls associated with the safe access level, wherein selecting a medicament therapy setting using the one or more therapy change controls causes modification of a control parameter used by a control algorithm to affect administration of the medicament therapy by the ambulatory medicament pump.

In a 238th example, the computer-implemented method of example 237, wherein the ambulatory medicament pump is configured to provide medicament therapy to control a glucose level in the subject.

In a 239th example, the computer-implemented method of example 238, wherein the medicament therapy comprises insulin therapy.

In a 240th example, the computer-implemented method of example 239, wherein the one or more therapy change controls comprise a control for selecting a type of the insulin therapy from a plurality of insulin therapy types.

In a 241st example, the ambulatory medicament pump of example 240, wherein the type of insulin therapy comprises U100 insulin therapy, U200 insulin therapy, ultra-rapid insulin therapy, or fast-acting insulin therapy.

In a 242nd example, the computer-implemented method of any of examples 237-241, wherein the control parameter is used by the control algorithm to account for an accumulation of insulin in the subject.

In a 243rd example, the computer-implemented method of any of examples 237-242, wherein the one or more therapy change controls associated with the selected safe access level are enabled during a validity period.

In a 244th example, the computer-implemented method of any of examples 243-243, wherein the validity period is one hour, one day, or one week.

In a 245th example, the computer-implemented method of any of examples 243-244, wherein the validity period expires when the subject associated with the ambulatory medicament pump changes.

In a 246th example, the computer-implemented method of any of examples 242-245, wherein the validity period is modified from a first period to a second period in response to a user interaction with user interface of the ambulatory medicament pump.

In a 247th example, the computer-implemented method of any of examples 237-246, wherein the data interface is configured to communicate with the electronic access device via a wired or a wireless communication connection.

In a 248th example, the computer-implemented method of example 247, wherein the wireless communication connection comprises a Long-Term Evolution wireless connection, a Wi-Fi network connection, a 5G communication network connection, a wide area network connection, a near-field communication network connection, or a short-range wireless connection.

In a 249th example, the computer-implemented method of any of examples 237-248, wherein the electronic access device comprises a computer, a mobile phone, a cloud server, or a dedicated electronic access device.

In a 250th example, the computer-implemented method of any of examples 237-249, wherein the electronic access device comprises an electronic device that is associated with a healthcare provider or a trainer of the subject.

In a 251st example, the computer-implemented method of any of examples 237-250, wherein the safe access level is associated with a therapy history or a training level of the subject.

In a 252nd example, the computer-implemented method of any of examples 237-251, wherein the safe access level is selected based at least in part on a medicament prescription of the subject.

In a 253rd example, the computer-implemented method of any of examples 237-252, wherein enabling the one or more therapy change controls associated with the selected safe access level comprises displaying therapy change control elements on a user interface, and wherein the therapy change control elements enable modification of control parameter values corresponding to the therapy change controls.

In a 254th example, the computer-implemented method of any of examples 237-253, wherein enabling the one or more therapy change controls associated with the selected safe access level comprises unlocking therapy change control elements in a menu displayed on a user interface, and wherein the therapy change control elements enable modification of control parameter values corresponding to the therapy change controls.

In a 255th example, the computer-implemented method of any of examples 237-254, further comprising: receiving, responsive to user interaction with a user interface, a request to restore the control parameter to a previous value; and restoring the control parameter to the previous value.

In a 256th example, the computer-implemented method of any of examples 237-255, wherein the access signal corresponds to a time-based passcode associated with the safe access level, wherein the time-based passcode is configured to expire after a validity period, and wherein the computer-implemented method further comprises: receiving a user passcode in response to user interaction with a passcode entry interface; determining that the user passcode matches the time-based passcode and that the user passcode is received during the validity period; and in response to determining that the user passcode matches the time-based passcode and that the passcode attempt is received during the validity period, enabling the therapy change controls associated with the safe access level.

In a 257th example, the computer-implemented method of any of examples 237-256, wherein the user is the subject receiving medicament therapy from the ambulatory medicament pump.

In a 258th example, a computer-implemented method of managing access to therapy change controls of an ambulatory medicament pump configured to provide medicament therapy to a subject, the computer-implemented method comprising: by an electronic processor of an electronic evaluation device, wherein the electronic processor is configured to execute specific computer-executable instructions stored in the electronic evaluation device to determine a safe access level from a plurality of safe access levels: receiving, from an electronic device in communication with the electronic evaluation device, evaluation data associated with the subject, wherein the evaluation data comprises therapy data corresponding to glycemic control of the subject by the ambulatory medicament pump; determining a safe access level for a user of the ambulatory medicament pump based at least in part on the evaluation data, wherein the safe access level is associated with a plurality of therapy change controls of the ambulatory medicament pump, and wherein the plurality of therapy change controls comprise a control for selecting a medicament therapy setting that affects administration of medicament therapy by the ambulatory medicament pump; determining, based at least in part on the evaluation data, a validity period during which the plurality of change controls are enabled; generating an access signal that, when received by the ambulatory medicament pump, is configured to cause the plurality of therapy change controls to be enabled during the validity period; and transmitting the access signal to the ambulatory medicament pump via a data connection.

In a 259th example, the computer-implemented method of example 258, wherein the electronic evaluation device is a personal electronic device of the user or subject, an electronic device used by a healthcare provider or a trainer, or a cloud server.

In a 260th example, the computer-implemented method of any of examples 258-259, wherein the electronic device is the ambulatory medicament pump.

In a 261st example, the computer-implemented method of any of examples 258-260, wherein the electronic device is an electronic device used by a physician or a trainer or a personal electronic device of a physician or a trainer.

In a 262nd example, the computer-implemented method of any of examples 258-261, wherein the data connection is a wired or wireless connection.

In a 263rd example, the computer-implemented method of example 262, wherein the wireless connection comprises a Long-Term Evolution network connection, a Wi-Fi network connection, a 5G communication network connection, a wide area network connection, a near-field communication network connection, or a short-range wireless network connection.

In a 264th example, the computer-implemented method of any of examples 258-263, wherein the validity period comprises one hour, one day, or one week.

In a 265th example, the computer-implemented method of any of examples 258-264, wherein the ambulatory medicament pump is configured to provide medicament therapy to control a glucose level in the subject.

In a 266th example, the computer-implemented method of example 265, wherein the medicament comprises insulin.

In a 267th example, the computer-implemented method of example 266, wherein the plurality of therapy change controls comprise a control for selecting a type of insulin.

In a 268th example, the computer-implemented method of example 267, wherein at least one of the one or more control parameters is used by the control algorithm to account for an accumulation of insulin in the subject.

In a 269th example, the computer-implemented method of any of examples 267-268, wherein the type of insulin comprises U100 insulin, U200 insulin, ultra-rapid insulin, or fast-acting insulin.

In a 270th example, the computer-implemented method of any of examples 258-269, wherein the safe access level is selected based at least in part on a medicament prescription of the subject.

In a 271st example, the computer-implemented method of any of examples 258-270, wherein the validity period expires when the subject associated with the ambulatory medicament pump changes.

In a 272nd example, the computer-implemented method of any of examples 258-271, wherein the validity period is extendable or renewable in response to receiving an extension or renewal request.

In a 273rd example, the computer-implemented method of any of examples 258-272, wherein the user is the subject receiving medicament therapy from the ambulatory medicament pump.

In a 274th example, the computer-implemented method of any of examples 258-273, wherein generating the access signal comprises generating a time-based passcode associated with the safe access level, and wherein receipt of a user passcode that matches the time-based passcode, by the ambulatory medicament pump from the user, causes the ambulatory medicament pump to enable the therapy change controls associated with the safe access level.

In a 275th example, a computer-implemented method of enabling therapy change controls associated with a safe access level for a user of an ambulatory medicament pump configured to provide medicament therapy to a subject wherein the medicament therapy comprises infusing a medicament into the subject, the computer-implemented method comprising: by an electronic processor of the ambulatory medicament pump, wherein the electronic processor is configured to execute specific computer-executable instructions stored in a non-transitory memory connected to the electronic processor: receiving, via a therapy change control request interface, a request to access therapy change controls associated with the safe access level, wherein the safe access level is associated with at least one of a plurality of safe access level profiles, each safe access level profile specifying one or more therapy change controls associated with the selected safe access level, and wherein the one or more therapy change controls affect administration of medicament therapy by the ambulatory medicament pump; and in response to receiving the request to access the therapy change controls associated with the safe access level: establishing a data connection with an electronic passcode device; sending a passcode request to an electronic passcode device wherein the passcode request comprises a device identifier, wherein the device identifier is usable to uniquely identify the ambulatory medicament pump; receiving a user passcode attempt via user interaction with a passcode entry interface, wherein the user passcode is generated by the electronic passcode device upon receiving the passcode request; determining that the passcode attempt matches the device passcode; and in response to determining that the passcode attempt matches a device passcode, enabling the one or more therapy change controls associated with the safe level access.

In a 276th example, the computer-implemented method of example 275, wherein the user of the ambulatory medicament pump is the subject receiving medicament therapy provided by the ambulatory medicament pump.

In a 277th example, the computer-implemented method of any of examples 275-276, wherein the ambulatory medicament pump is configured to provide medicament therapy to control a glucose level in the subject.

In a 278th example, the computer-implemented method of example 277, wherein the medicament therapy comprises insulin therapy.

In a 279th example, the computer-implemented method of example 278, wherein the one or more therapy change controls comprise a control for selecting a type of the insulin therapy from a plurality of insulin therapy types.

In a 280th example, the ambulatory medicament pump of example 279, wherein the type of the insulin therapy comprises U100 insulin therapy, U200 insulin therapy, ultra-rapid insulin therapy, or fast-acting insulin therapy.

In a 281st example, the computer-implemented method of any of examples 278-280, wherein the control parameter is used by the control algorithm to account for an accumulation of insulin in the subject.

In a 282nd example, the computer-implemented method of any of examples 275-281, further comprising generating the device passcode using a shared passcode algorithm, wherein the shared passcode algorithm comprises the same passcode algorithm used by the electronic passcode device to generate the user passcode.

In a 283rd example, the computer-implemented method of any of examples 275-282, further comprising: by an electronic processor of the electronic passcode device, wherein the electronic processor of the electronic passcode device is configured to execute specific computer-executable passcode generation instructions stored in a second non-transitory memory connected to the electronic processor of the electronic passcode device: receiving the device identifier; verifying eligibility of the user for the safe access level; and in response to verifying eligibility of the user for the safe access level, generating the user passcode using a shared passcode algorithm and the device identifier.

In a 284th example, the computer-implemented method of example 283, wherein said verifying eligibility of the user for the safe access level comprises receiving eligibility data from an electronic evaluation device.

In a 285th example, the computer-implemented method of example 284, wherein said receiving eligibility data from an electronic evaluation device comprises receiving a validity period, and wherein the user passcode is a time-based user passcode usable for enabling the one or more therapy change controls associated with the safe level access during the validity period.

In a 286th example, the computer-implemented method of example 285, wherein said determining that the passcode attempt matches the device passcode comprises determining that the passcode is received during the validity period.

In a 287th example, the computer-implemented method of any of examples 285-286, wherein said enabling the therapy change controls comprises enabling the one or more therapy change controls during the validity period.

In a 288th example, the computer-implemented method of example 287, wherein the validity period is one hour, one day or one week.

In a 289th example, the computer-implemented method of any of examples 285-288, further comprising extending or renewing the validity period in response to an extension or renewal request to extend or renew access to the one or more therapy change controls associated with the safe level access.

In a 290th example, the computer-implemented method of any of examples 275-289, wherein the data connection is a wired or wireless connection.

In a 291st example, the computer-implemented method of example 290, wherein the wireless connection comprises a Long-Term Evolution connection, a Wi-Fi network connection, a 5G communication network connection, a wide area network connection, a near-field communication network connection, or a short-range wireless connection.

In a 292nd example, the computer-implemented method of any of examples 275-291, wherein the user passcode is output to the user by the electronic passcode device via a text message.

In a 293rd example, the computer-implemented method of any of examples 284-292, wherein the electronic evaluation device is the electronic device of a healthcare provider or a trainer.

In a 294th example, the computer-implemented method of any of examples 275-293, wherein the device identifier comprises an IP address, a MAC address, or a serial number.

In a 295th example, a glucose level control system configured to modify or enable modification of a control algorithm of the glucose level control system based on a safe access level for a user of an ambulatory medicament pump configured to provide medicament therapy to a subject, the glucose level control system comprising: a non-transitory memory configured to store specific computer-executable instructions; and a hardware processor in communication with the non-transitory memory and configured to execute the specific computer-executable instructions to at least: receive a first access code via an access code entry interface, wherein the first access code comprises first safe access level data and a first unique identifier; validate the first access code to determine whether to enable a second glucose level therapy control configuration, wherein the second glucose level therapy control configuration is different from a first glucose level therapy control configuration of the glucose level control system; and enable the second glucose level therapy control configuration responsive to validating the first access code, wherein the second glucose level therapy control configuration modifies or enables modification of execution of a control algorithm that generates a dose control signal to cause the ambulatory medicament pump to administer a quantity of medicament from a medicament reservoir into the subject.

In a 296th example, the glucose level control system of example 295, wherein the first access code comprises an encrypted access code, and wherein the hardware processor is configured to validate the first access code by at least: decrypting the encrypted access code to access the first unique identifier and the first safe access level data; and verifying that the first unique identifier matches a second unique identifier corresponding to the glucose level control system.

In a 297th example, the glucose level control system of example 296, wherein the first access code further comprises a first time-based value, and wherein the hardware processor is further configured to validate the first access code by at least determining whether the first time-based value is valid or expired.

In a 298th example, the glucose level control system of example 297, wherein the first time-based value corresponds to a period of time during which the first access code is valid.

In a 299th example, the glucose level control system of any of examples 297-298, wherein the hardware processor is further configured to determine whether the first time-based value is valid or expired by at least comparing the first time-based value to a second time-based value generated at the glucose level control system.

In a 300th example, the glucose level control system of example 299, wherein the first time based-value and the second time based-value are generated based on a seed value, the seed value being the same value used to generate both the first time based-value and the second time based-value, and wherein the first time based-value and the second time based-value are scheduled to expire at the same time.

In a 301st example, the glucose level control system of any of examples 296-300, wherein the second unique identifier is stored in the non-transitory memory.

In a 302nd example, the glucose level control system of any of examples 295-301, wherein the hardware processor is further configured to execute the specific computer-executable instructions to at least receive an indication of second safe access level data.

In a 303rd example, the glucose level control system of example 302, wherein the first access code is a first hashed value, and wherein the hardware processor is configured to validate the first access code by at least: hashing the second safe access level data and a second unique identifier corresponding to the glucose level control system to obtain a second hashed value; and comparing the first hashed value to the second hashed value.

In a 304th example, the glucose level control system of example 303, wherein the hardware processor is further configured to execute the specific computer-executable instructions to at least determine that the first access code is valid when the first hashed value matches the second hashed value.

In a 305th example, the glucose level control system of any of examples 303-304, wherein the first access code further comprises a first time based-value, and wherein a second time based-value is hashed with the second safe access level data and the second unique identifier to obtain the second hashed value.

In a 306th example, the glucose level control system of example 305, wherein the first time based-value and the second time based-value are generated based on a seed value, the seed value being the same value used to generate both the first time based-value and the second time based-value, and wherein the first time based-value and the second time based-value are scheduled to expire at the same time.

In a 307th example, the glucose level control system of any of examples 305-306, wherein the first time-based value corresponds to a period of time during which the first access code is valid.

In a 308th example, the glucose level control system of any of examples 303-307, wherein the second unique identifier is stored in the non-transitory memory.

In a 309th example, the glucose level control system of any of examples 295-308, wherein the first safe access level data identifies one or more of: a new therapy control interface, a control parameter to include in a therapy control interface, the control parameter to enable in the therapy control interface, a control parameter value for the control parameter, or a new control algorithm functionality for the control parameter.

In a 310th example, the glucose level control system of any of examples 295-309, wherein the access code entry interface comprises a user interface that enables the user to enter the first access code.

In a 311th example, the glucose level control system of any of examples 295-310, wherein the access code entry interface comprises a wired or wireless network connection to a computing device configured to transmit the first access code to the glucose level control system.

In a 312th example, the glucose level control system of any of examples 295-311, wherein the second glucose level therapy control configuration enables access to a control parameter, and wherein the control parameter affects glycemic control of the subject.

In a 313th example, the glucose level control system of any of examples 295-312, wherein the hardware processor is further configured to enable the second glucose level therapy control configuration by permitting the user to access a new therapy control interface that enables the user to modify one or more control parameters used by the control algorithm.

In a 314th example, the glucose level control system of example 313, wherein the new therapy control interface is not accessible by the user prior to the first access code being validated.

In a 315th example, the glucose level control system of any of examples 295-314, wherein the hardware processor is further configured to execute the specific computer-executable instructions to at least disable a feature of the glucose level control system associated with the second glucose level therapy control configuration.

In a 316th example, the glucose level control system of example 315, wherein the hardware processor is further configured to disable the feature of the glucose level control system associated with the second glucose level therapy control configuration responsive to validating a second access code.

In a 317th example, the glucose level control system of any of examples 315-316, wherein the hardware processor is further configured to disable the feature of the glucose level control system associated with the second glucose level therapy control configuration by reverting the glucose level control system to the first glucose level therapy control configuration.

In a 318th example, the glucose level control system of any of examples 295-317, wherein the second glucose level therapy control configuration is associated with an expiration value.

In a 319th example, the glucose level control system of example 318, wherein the glucose level control system automatically reverts to the first glucose level therapy control configuration upon the expiration value being satisfied.

In a 320th example, the glucose level control system of any of examples 318-319, wherein the expiration value comprises one or more of a time, a date, or a number of administrations of medicament.

In a 321st example, the glucose level control system of any of examples 295-320, wherein the first access code further comprises an error-detection code.

In a 322nd example, the glucose level control system of example 321, wherein the hardware processor is further configured to execute the specific computer-executable instructions to at least use the error-detection code to confirm that the first access code is error free or can be recovered from a detected error.

In a 323rd example, the glucose level control system of any of examples 321-322, wherein the error-detection code comprises a checksum, a cyclic redundancy check, a hash value, an error correction code, or a parity bit.

In a 324th example, the glucose level control system of any of examples 295-323, wherein enabling the second glucose level therapy control configuration comprises downloading an update to the control algorithm of the glucose level control system and/or downloading an update to the specific computer-executable instructions from a computing system separate from the glucose level control system.

In a 325th example, a computer-implemented method of modifying or enabling modification of execution of a control algorithm of a glucose level control system based on a safe access level for a user of an ambulatory medicament pump configured to provide medicament therapy to a subject and controlled by the glucose level control system, the computer-implemented method comprising: by a hardware processor of the glucose level control system, receiving a first access code via an access code entry interface, wherein the first access code comprises first safe access level data and a first unique identifier; validating the first access code to determine whether to enable a second glucose level therapy control configuration, wherein the second glucose level therapy control configuration is different from a first glucose level therapy control configuration of the glucose level control system; and enabling the second glucose level therapy control configuration responsive to validating the first access code, wherein the second glucose level therapy control configuration modifies or enables modification of execution of a control algorithm that generates a dose control signal to cause the ambulatory medicament pump to administer a quantity of medicament from a medicament reservoir into the subject.

In a 326th example, the computer-implemented method of example 325, wherein the first access code comprises an encrypted access code, and wherein said validating the first access code comprises: decrypting the encrypted access code to access the first unique identifier and the first safe access level data; and verifying that the first unique identifier matches a second unique identifier corresponding to the glucose level control system.

In a 327th example, the computer-implemented method of example 326, wherein the first access code further comprises a first time-based value, and wherein said validating the first access code further comprises determining whether the first time-based value is valid or expired.

In a 328th example, the computer-implemented method of example 327, wherein the first time-based value corresponds to a period of time during which the first access code is valid.

In a 329th example, the computer-implemented method of any of examples 327-328, wherein said determining whether the first time-based value is valid or expired comprises comparing the first time-based value to a second time-based value generated at the glucose level control system.

In a 330th example, the computer-implemented method of example 329, wherein the first time based-value and the second time based-value are generated based on a seed value, the seed value being the same value used to generate both the first time based-value and the second time based-value, and wherein the first time based-value and the second time based-value are scheduled to expire at the same time.

In a 331st example, the computer-implemented method of any of examples 326-330, wherein the second unique identifier is stored at the glucose level control system.

In a 332nd example, the computer-implemented method of any of examples 325-331, further comprising receiving an indication of second safe access level data.

In a 333rd example, the computer-implemented method of example 332, wherein the first access code is a first hashed value, and wherein said validating the first access code comprises: hashing the second safe access level data and a second unique identifier corresponding to the glucose level control system to obtain a second hashed value; and comparing the first hashed value to the second hashed value.

In a 334th example, the computer-implemented method of example 333, further comprising determining that the first access code is valid when the first hashed value matches the second hashed value.

In a 335th example, the computer-implemented method of any of examples 333-334, wherein the first access code further comprises a first time based-value, and wherein a second time based-value is hashed with the second safe access level data and the second unique identifier to obtain the second hashed value.

In a 336th example, the computer-implemented method of example 335, wherein the first time based-value and the second time based-value are generated based on a seed value, the seed value being the same value used to generate both the first time based-value and the second time based-value, and wherein the first time based-value and the second time based-value are scheduled to expire at the same time.

In a 337th example, the computer-implemented method of any of examples 335-336, wherein the first time-based value corresponds to a period of time during which the first access code is valid.

In a 338th example, the computer-implemented method of any of examples 333-337, wherein the second unique identifier is stored at the glucose level control system.

In a 339th example, the computer-implemented method of any of examples 325-338, wherein the first safe access level data identifies one or more of: a new therapy control interface, a control parameter to include in a therapy control interface, the control parameter to enable in the therapy control interface, a control parameter value for the control parameter, or a new control algorithm functionality for the control parameter.

In a 340th example, the computer-implemented method of any of examples 325-339, wherein the access code entry interface comprises a user interface that enables the user to enter the first access code.

In a 341st example, the computer-implemented method of any of examples 325-340, wherein the access code entry interface comprises a wired or wireless network connection to a computing device configured to transmit the first access code to the glucose level control system.

In a 342nd example, the computer-implemented method of any of examples 325-341, wherein the second glucose level therapy control configuration enables access to a control parameter, and wherein the control parameter affects glycemic control of the subject.

In a 343rd example, the computer-implemented method of any of examples 325-342, wherein said enabling the second glucose level therapy control configuration comprises permitting the user to access a new therapy control interface that enables the user to modify one or more control parameters used by the control algorithm.

In a 344th example, the computer-implemented method of example 343, wherein the new therapy control interface is not accessible by the user prior to the first access code being validated.

In a 345th example, the computer-implemented method of any of examples 325-344, further comprising disabling a feature of the glucose level control system associated with the second glucose level therapy control configuration.

In a 346th example, the computer-implemented method of example 345, further comprising validating a second access code, wherein the feature of the glucose level control system associated with the second glucose level therapy control configuration is disabled responsive to the second access code being validated.

In a 347th example, the computer-implemented method of any of examples 345-346, wherein disabling the feature of the glucose level control system associated with the second glucose level therapy control configuration comprises reverting the glucose level control system to the first glucose level therapy control configuration.

In a 348th example, the computer-implemented method of any of examples 325-347, wherein the second glucose level therapy control configuration is associated with an expiration value.

In a 349th example, the computer-implemented method of example 348, further comprising automatically reverting to the first glucose level therapy control configuration upon the expiration value being satisfied.

In a 350th example, the computer-implemented method of any of examples 348-349, wherein the expiration value comprises one or more of a time, a date, or a number of administrations of medicament.

In a 351st example, the computer-implemented method of any of examples 325-350, wherein the first access code further comprises an error-detection code.

In a 352nd example, the computer-implemented method of example 351, further comprising confirm that the first access code is error free or can be recovered from a detected error based at least in part on the error-detection code.

In a 353rd example, the computer-implemented method of any of examples 351-352, wherein the error-detection code comprises a checksum, a cyclic redundancy check, a hash value, an error correction code, or a parity bit.

In a 354th example, the computer-implemented method of any of examples 325-353, wherein enabling the second glucose level therapy control configuration comprises downloading an update to the control algorithm of the glucose level control system from a computing system separate from the glucose level control system.

In a 355th example, an electronic configuration device configured to modify or enable modification, at a glucose level control system, of a control algorithm based on a selected safe access level for a user of an ambulatory medicament pump controlled by the glucose level control system, the electronic configuration device comprising: a non-transitory memory configured to store specific computer-executable instructions; and a hardware processor in communication with the non-transitory memory and configured to execute the specific computer-executable instructions to at least: receive an indication to modify a glucose level therapy control configuration of the glucose level control system to a second glucose level therapy control configuration that differs from a first glucose level therapy control configuration of the glucose level control system, wherein modifying the glucose level therapy control configuration modifies or enables modification of execution of the control algorithm that generates a dose control signal to cause the ambulatory medicament pump to administer a quantity of medicament from a medicament reservoir into a subject; receive a first unique identifier associated with the glucose level control system; validate the user's capability to safely use the glucose level control system with the second glucose level therapy control configuration; responsive to validating the user's capability to safely use the glucose level control system with the second glucose level therapy control configuration, generate a first access code comprising safe access level data and the first unique identifier, wherein the safe access level data corresponds to the second glucose level therapy control configuration; and output the first access code, wherein the first access code is useable to cause the glucose level therapy control configuration of the glucose level control system to be modified from the first glucose level therapy control configuration to the second glucose level therapy control configuration.

In a 356th example, the electronic configuration device of example 355, wherein the hardware processor is further configured to execute the specific computer-executable instructions to at least encrypt the first access code to obtain an encrypted access code, and wherein outputting the first access code comprises outputting the encrypted access code.

In a 357th example, the electronic configuration device of any of examples 355-356, wherein the hardware processor is further configured to execute the specific computer-executable instructions to at least hash the first access code to obtain a hashed access code, and wherein outputting the first access code comprises outputting the hashed access code.

In a 358th example, the electronic configuration device of any of examples 355-357, wherein the hardware processor is further configured to output the first access code on a display of the electronic passcode device.

In a 359th example, the electronic configuration device of any of examples 355-358, wherein the hardware processor is further configured to output the first access code by transmitting the first access code over a wired or wireless network connection to the glucose level control system.

In a 360th example, the electronic configuration device of any of examples 355-359, wherein the hardware processor is further configured to receive the indication to modify the glucose level therapy control configuration of the glucose level control system to the second glucose level therapy control configuration in response to a first user interacting with a user interface of the electronic passcode device.

In a 361st example, the electronic configuration device of example 360, wherein the hardware processor is further configured to output the first access code by transmitting the first access code over a wired or wireless network connection to a computing device of a second user enabling the computing device to: output the first access code on a user interface of the computing device; or to communicate the first access code to the glucose level control system.

In a 362nd example, the electronic configuration device of any of examples 355-361, wherein the hardware processor is further configured to execute the specific computer-executable instructions to at least generate a first time-based value.

In a 363rd example, the electronic configuration device of example 362, wherein the hardware processor is further configured to include the first time-based value as part of the first access code when generating the first access code.

In a 364th example, the electronic configuration device of any of examples 362-363, wherein the first time-based value corresponds to a period of time during which the first access code is valid.

In a 365th example, the electronic configuration device of any of examples 362-364, wherein the first time based-value is generated based on a seed value, the seed value being the same value used to generate a second time based-value at the glucose level control system.

In a 366th example, the electronic configuration device of example 365, wherein the first time based-value and the second time based-value are scheduled to expire at the same time.

In a 367th example, the electronic configuration device of any of examples 355-366, wherein the safe access level data identifies one or more of: a new therapy control interface, a control parameter to include in a therapy control interface, the control parameter to enable in the therapy control interface, a control parameter value for the control parameter, or a new control algorithm functionality for the control parameter.

In a 368th example, the electronic configuration device of any of examples 355-367, wherein the hardware processor is configured to validate the user's capability to safely use the glucose level control system with the second glucose level therapy control configuration by at least accessing training data associated with the user and confirming that the training data satisfies a training threshold.

In a 369th example, the electronic configuration device of any of examples 355-368, wherein the hardware processor is configured to validate the user's capability to safely use the glucose level control system with the second glucose level therapy control configuration by at least accessing a prescription associated with the subject, the prescription corresponding to the safe access level data.

In a 370th example, the electronic configuration device of any of examples 355-369, wherein the hardware processor is configured to validate the user's capability to safely use the glucose level control system with the second glucose level therapy control configuration by at least: outputting a set of queries for display to the user, wherein the set of queries correspond to one or more use cases of the glucose level control system; receiving a set of responses to the set of queries; evaluating the set of responses to obtain an evaluation score; and determining based at least in part on the evaluation score whether the user is capable of safely using the glucose level control system with the second glucose level therapy control.

In a 371st example, the electronic configuration device of any of examples 355-370, wherein the hardware processor is configured to validate the user's capability to safely use the glucose level control system with the second glucose level therapy control configuration by at least evaluating use of the glucose level control system over an evaluation time period.

In a 372nd example, a computer-implemented method of modifying or enabling modification, at a glucose level control system, of a control algorithm based on a selected safe access level for a user of an ambulatory medicament pump controlled by the glucose level control system, the computer-implemented method comprising: by a hardware processor of an electronic configuration device separate from the glucose level control system, receiving an indication to modify a glucose level therapy control configuration of the glucose level control system to a second glucose level therapy control configuration that differs from a first glucose level therapy control configuration of the glucose level control system, wherein modifying the glucose level therapy control configuration modifies or enables modification of execution of the control algorithm that generates a dose control signal to cause the ambulatory medicament pump to administer a quantity of medicament from a medicament reservoir into a subject; receiving a first unique identifier associated with the glucose level control system; validating the user's capability to safely use the glucose level control system with the second glucose level therapy control configuration; responsive to validating the user's capability to safely use the glucose level control system with the second glucose level therapy control configuration, generating a first access code comprising safe access level data and the first unique identifier, wherein the safe access level data corresponds to the second glucose level therapy control configuration; and outputting the first access code, wherein the first access code is useable to cause the glucose level therapy control configuration of the glucose level control system to by modified from the first glucose level therapy control configuration to the second glucose level therapy control configuration.

In a 373rd example, the computer-implemented method of example 372, further comprising encrypting the first access code to obtain an encrypted access code, wherein outputting the first access code comprises outputting the encrypted access code.

In a 374th example, the computer-implemented method of any of examples 372-373, further comprising hashing the first access code to obtain a hashed access code, wherein outputting the first access code comprises outputting the hashed access code.

In a 375th example, the computer-implemented method of any of examples 372-374, wherein outputting the first access code comprises outputting the first access code on a display of the electronic passcode device.

In a 376th example, the computer-implemented method of any of examples 372-375, wherein outputting the first access code comprises transmitting the first access code over a wired or wireless network connection to the glucose level control system.

In a 377th example, the computer-implemented method of any of examples 372-376, wherein said receiving the indication to modify the glucose level therapy control configuration of the glucose level control system to the second glucose level therapy control configuration occurs in response to a first user interacting with a user interface of the electronic passcode device.

In a 378th example, the computer-implemented method of example 377, wherein said outputting the first access code comprises transmitting the first access code over a wired or wireless network connection to a computing device of a second user enabling the computing device to: output the first access code on a user interface of the computing device; or to communicate the first access code to the glucose level control system.

In a 379th example, the computer-implemented method of any of examples 372-378, further comprising generating a first time-based value.

In a 380th example, the computer-implemented method of example 379, wherein said generating the first access code includes incorporating the first time-based value as part of the first access code.

In a 381st example, the computer-implemented method of any of examples 379-380, wherein the first time-based value corresponds to a period of time during which the first access code is valid.

In a 382nd example, the computer-implemented method of any of examples 379-381, wherein the first time based-value is generated based on a seed value, the seed value being the same value used to generate a second time based-value at the glucose level control system.

In a 383rd example, the computer-implemented method of example 382, wherein the first time based-value and the second time based-value are scheduled to expire at the same time.

In a 384th example, the computer-implemented method of any of examples 372-383, wherein the safe access level data identifies one or more of: a new therapy control interface, a control parameter to include in a therapy control interface, the control parameter to enable in the therapy control interface, a control parameter value for the control parameter, or a new control algorithm functionality for the control parameter.

In a 385th example, the computer-implemented method of any of examples 372-384, wherein said validating the user's capability to safely use the glucose level control system with the second glucose level therapy control configuration comprises accessing training data associated with the user and confirming that the training data satisfies a training threshold.

In a 386th example, the computer-implemented method of any of examples 372-385, wherein said validating the user's capability to safely use the glucose level control system with the second glucose level therapy control configuration comprises accessing a prescription associated with the subject, the prescription corresponding to the safe access level data.

In a 387th example, the computer-implemented method of any of examples 372-386, wherein said validating the user's capability to safely use the glucose level control system with the second glucose level therapy control configuration comprises: outputting a set of queries for display to the user, wherein the set of queries correspond to one or more use cases of the glucose level control system; receiving a set of responses to the set of queries; evaluating the set of responses to obtain an evaluation score; and determining based at least in part on the evaluation score whether the user is capable of safely using the glucose level control system with the second glucose level therapy control.

In a 388th example, the computer-implemented method of any of examples 372-387, wherein said validating the user's capability to safely use the glucose level control system with the second glucose level therapy control configuration comprises evaluating use of the glucose level control system over an evaluation time period.

Terminology

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more computers or processors. The code modules may be stored in any type of non-transitory computer-readable medium or other computer storage device. Some or all the methods may be embodied in specialized computer hardware. Further, the computing system may include, be implemented as part of, or communicate with an automated blood glucose system, an ambulatory medicament system, or an ambulatory medical device.

Many other variations than those described herein will be apparent from this disclosure. For example, depending on the embodiment, certain acts, events, or functions of any of the algorithms described herein can be performed in a different sequence, can be added, merged, or left out altogether (for example, not all described acts or events are necessary for the practice of the algorithms). Moreover, in certain embodiments, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. Although described herein primarily with respect to digital technology, a processor may also include primarily analog components. A computing environment can include any type of computer system, including, but not limited to, a computer system based on a microprocessor, a mainframe computer, a digital signal processor, a portable computing device, a device controller, or a computational engine within an appliance, to name a few.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is otherwise understood with the context as used in general to present that an item, term, etc., may be either X, Y, or Z, or any combination thereof (for example, X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

Many variations and modifications may be made to the above-described embodiments, the elements of which are to be understood as being among other acceptable examples. All such modifications and variations are intended to be included herein within the scope of this disclosure.

What is claimed is:

1. An ambulatory medicament pump configured to wirelessly transmit one or more of a plurality of glucose control parameters and glucose control therapy data to a second ambulatory medicament pump, the ambulatory medicament pump comprising:
    a pump controller configured to command to direct medicament from a medicament reservoir to a subject;
    a data interface comprising a wireless data interface configured to transmit one or more of a plurality of glucose control parameters and glucose control therapy data to a second ambulatory medicament pump;
    a non-transitory memory configured to store specific computer-executable instructions; and
    a hardware processor in communication with the non-transitory memory and configured to execute the specific computer-executable instructions to at least:
        determine the glucose control therapy data comprising at least one of an amount of insulin on board, a time of a delivery of glucose control therapy, or an amount of delivery of glucose control therapy;
        generate the one or more of the plurality of glucose control parameters, wherein the plurality of glucose control parameters comprises:
            an insulin decay rate constant associated with a decay rate of insulin at a subcutaneous depot of the subject;
            a clearance time associated with an estimate of an amount of time for a bolus of insulin to be utilized by the subject;
            an insulin rise rate constant associated with a rise rate of insulin in blood of the subject after a bolus of insulin;
            a half-life value associated with when a concentration of insulin in blood plasma of the subject reaches half of a maximum concentration in the blood plasma;
            a weight of the subject;
            an age of the subject;
            a learned parameter;
            glucose level data;
            a model parameter associated with a pharmacokinetic (PK) model;
            a health state of the subject;
            a parameter associated with an activity level of the subject;
            an aspect of a diet of the subject;
            a basal rate of insulin delivery to the subject;
            a correction factor;
            a carbohydrate ratio associated with the subject;
            a glucagon control parameter;
            demographic information associated with the subject; and
            a sensitivity constant associated with the sensitivity of the subject to a glucose level or bolus of medicament;
        determine that at least one of a plurality of pairing conditions is satisfied to couple the ambulatory medicament pump to the second ambulatory medicament pump, wherein the plurality of pairing conditions comprises:
            an occurrence of a scheduled time;
            a transmission of a meal announcement;
            a user request to pair the ambulatory medicament pump to a remote electronic device;
            a user input initiating a replacement process for the ambulatory medicament pump;
            an indication that the ambulatory medicament pump is to be replaced;
            an indication that the second ambulatory medicament pump is ready to deliver medicament to the subject;
            a sensory alarm configured to alert a user that historical pump data is ready for transmission;
            an alert indicating a malfunction associated with the ambulatory medicament pump;
            a determination that a level of medicament in the medicament reservoir of the ambulatory medicament pump is below a threshold level;
            a determination that an amount of available medicament of the ambulatory medicament pump is insufficient for a medicament requirement of the subject; and
            a signal received from the remote electronic device requesting transmission of at least one of the glucose control therapy data or the one or more of the plurality of glucose control parameters; and
        in response to determining that the at least one of the plurality of pairing conditions is satisfied, wirelessly transmit, via the wireless data interface, the one or more of the plurality of glucose control parameters and the glucose control therapy data to the second ambulatory medicament pump.

2. The ambulatory medicament pump of claim 1, wherein the hardware processor is further configured to execute the specific computer-executable instructions to at least:
    transmit, via the wireless data interface, a pairing request signal to the second ambulatory medicament pump; and receive, via the wireless data interface, a pairing confirmation signal from the second ambulatory medicament pump.

3. The ambulatory medicament pump of claim 1, wherein the wireless data interface is further configured to receive a glucose level signal from a glucose sensor operatively coupled to the subject, wherein the glucose level signal comprises encoded data corresponding to the glucose level of the subject, and wherein the hardware processor is further configured to execute the specific computer-executable instructions to at least:
decode the encoded data of the glucose level signal to obtain the glucose level of the subject.

4. The ambulatory medicament pump of claim 1, wherein the hardware processor is further configured to execute the specific computer-executable instructions to at least:
receive, via the wireless data interface, encoded data corresponding to an indication of a glucose trend, wherein the glucose trend indicates at least a predicted change in the glucose level of the subject; and
decode the encoded data to obtain the indication of the glucose trend.

5. The ambulatory medicament pump of claim 1, wherein the hardware processor is further configured to execute the specific computer-executable instructions to at least:
transmit to a user control element, via the wireless data interface, an indication that the second ambulatory medicament pump is ready to be paired with the ambulatory medicament pump.

6. The ambulatory medicament pump of claim 1, wherein the hardware processor is further configured to execute the specific computer-executable instructions to at least:
generate a dose control signal based on at least the one or more of the plurality of glucose control parameters, wherein the pump controller of the ambulatory medicament pump is configured to cause administration of medicament to the subject based on the dose control signal.

7. The ambulatory medicament pump of claim 1, wherein the hardware processor is further configured to execute the specific computer-executable instructions to at least:
transmit to the remote electronic device, one or more of the glucose control therapy data or the one or more of the plurality of glucose control parameters.

8. The ambulatory medicament pump of claim 1, further comprising a graphical user interface configured to display at least one of the glucose control therapy data or the one or more of the plurality of glucose control parameters.

9. The ambulatory medicament pump of claim 1, wherein the hardware processor is further configured to execute the specific computer-executable instructions to at least:
receive, via the wireless data interface, at least one of an amount of insulin on board or a value used in a pharmacokinetic (PK) model of a control algorithm.

10. The ambulatory medicament pump of claim 1, wherein the wireless data interface comprises a short-range wireless data interface configured to wirelessly communicate with the second ambulatory medicament pump.

11. The ambulatory medicament pump of claim 1, wherein the hardware processor is further configured to execute the specific computer-executable instructions to at least:
transmit to the second ambulatory medicament pump, in response to determining that the at least one of the plurality of pairing conditions is satisfied, at least one of an amount of insulin on board or a value used in a pharmacokinetic (PK) model of a control algorithm.

12. The ambulatory medicament pump of claim 1, wherein the hardware processor is further configured to execute the specific computer-executable instructions to at least:
in response to determining that the at least one of the plurality of pairing conditions is satisfied, receive from the remote electronic device, via the wireless data interface, at least one glucose control parameter.

13. The ambulatory medicament pump of claim 1, wherein the hardware processor is further configured to execute the specific computer-executable instructions to at least:
execute, in response to transmitting the one or more of the plurality of glucose control parameters and the glucose control therapy data to the second ambulatory medicament pump, a pump deactivation process configured to deactivate the ambulatory medicament pump.

14. The ambulatory medicament pump of claim 1, wherein the glucose control therapy data comprises version data comprising at least one of:
a timestamp corresponding to a time associated with an update of the glucose control therapy data;
an indicator of an ordering within a sequence of delivery of the glucose control therapy; or
a version code comprising encoded time data associated with delivery of the glucose control therapy.

15. A method for transmitting from a first ambulatory medicament pump one or more of a plurality of glucose control parameters and glucose control therapy data to a second ambulatory medicament pump, the method comprising:
by a hardware processor of a first ambulatory medicament pump executing instructions stored on non-transitory memory connected to the hardware processor:
determining glucose control therapy data comprising at least one of an amount of insulin on board, a time of a delivery of glucose control therapy, or an amount of delivery of glucose control therapy;
generating one or more of a plurality of glucose control parameters, wherein the plurality of glucose control parameters comprises:
an insulin decay rate constant associated with a decay rate of insulin at a subcutaneous depot of a subject;
a clearance time associated with an estimate of an amount of time for a bolus of insulin to be utilized by the subject;
an insulin rise rate constant associated with a rise rate of insulin in blood of the subject after a bolus of insulin;
a half-life value associated with when a concentration of insulin in blood plasma of the subject reaches half of a maximum concentration in the blood plasma;
a weight of the subject;
an age of the subject;
a learned parameter;
glucose level data;
a model parameter associated with a pharmacokinetic (PK) model;
a health state of the subject;
a parameter associated with an activity level of the subject;
an aspect of a diet of the subject;
a basal rate of insulin delivery to the subject;
a correction factor;
a carbohydrate ratio associated with the subject;

a glucagon control parameter;
demographic information associated with the subject; and
a sensitivity constant associated with the sensitivity of the subject to a glucose level or bolus of medicament;
determining that at least one of a plurality of pairing conditions is satisfied to couple the first ambulatory medicament pump to a second ambulatory medicament pump, wherein the plurality of pairing conditions comprises:
an occurrence of a scheduled time;
a transmission of a meal announcement;
a user request to pair the first ambulatory medicament pump to a remote electronic device;
a user input initiating a replacement process for the first ambulatory medicament pump;
an indication that the first ambulatory medicament pump is to be replaced;
an indication that the second ambulatory medicament pump is ready to deliver medicament to the subject;
a sensory alarm configured to alert a user that historical pump data is ready for transmission;
an alert indicating a malfunction associated with the first ambulatory medicament pump;
a determination that a level of medicament in a medicament reservoir of the first ambulatory medicament pump is below a threshold level;
a determination that an amount of available medicament of the first ambulatory medicament pump is insufficient for a medicament requirement of the subject; and
a signal received from the remote electronic device requesting transmission of at least one of the glucose control therapy data or the one or more of the plurality of glucose control parameters; and
in response to determining that the at least one of the plurality of pairing conditions is satisfied, transmitting the one or more of the plurality of glucose control parameters and the glucose control therapy data to the second ambulatory medicament pump.

16. The method of claim 15, further comprising:
transmitting a pairing request signal to the second ambulatory medicament pump; and
receiving a pairing confirmation signal from the second ambulatory medicament pump.

17. The method of claim 15, further comprising:
receiving:
a glucose level signal from a glucose sensor operatively coupled to the subject, wherein the glucose level signal comprises first encoded data corresponding to the glucose level of the subject; and
second encoded data corresponding to an indication of a glucose trend, wherein the glucose trend indicates at least a predicted change in the glucose level of the subject; and
decoding the first and second encoded data to obtain the glucose level of the subject and the indication of the glucose trend.

18. The method of claim 15, further comprising:
transmitting to a user control element an indication that the second ambulatory medicament pump is ready to be paired with the first ambulatory medicament pump.

19. The method of claim 15, further comprising:
generating a dose control signal based on at least the one or more of the plurality of glucose control parameters, wherein a pump controller of the first ambulatory medicament pump is configured to cause administration of medicament to the subject.

20. The method of claim 15, further comprising:
transmitting to the remote electronic device, one or more of the glucose control therapy data or the one or more of the plurality of glucose control parameters.

21. The method of claim 15, further comprising displaying at least one of the glucose control therapy data or the one or more of the plurality of glucose control parameters.

22. The method of claim 15, further comprising:
receiving at least one of an amount of insulin on board or a value used in a pharmacokinetic (PK) model of a control algorithm.

23. The method of claim 15, further comprising:
transmitting to the second ambulatory medicament pump, in response to determining that the at least one of the plurality of pairing conditions is satisfied, at least one of an amount of insulin on board or a value used in a pharmacokinetic (PK) model of a control algorithm.

24. The method of claim 15, further comprising:
in response to determining that the at least one of the plurality of pairing conditions is satisfied, receiving from the remote electronic device at least one glucose control parameter.

25. The method of claim 15, further comprising:
executing, in response to transmitting the one or more of the plurality of glucose control parameters and the glucose control therapy data to the second ambulatory medicament pump, a pump deactivation process configured to deactivate the first ambulatory medicament pump.

26. The method of claim 15, wherein the glucose control therapy data comprises version data comprising at least one of:
a timestamp corresponding to a time associated with an update of the glucose control therapy data;
an indicator of an ordering within a sequence of delivery of the glucose control therapy; or
a version code comprising encoded time data associated with delivery of the glucose control therapy.

27. A glucose level control system configured to generate a dose output for administration of medicament to a subject and wirelessly transmit one or more of a plurality of glucose control parameters and glucose control therapy data to a second glucose level control system, the glucose level control system comprising:
a data interface comprising a wireless data interface configured to transmit one or more of a plurality of glucose control parameters and glucose control therapy data to a second glucose level control system;
a memory configured to store specific computer-executable instructions and an application that generates a dose output for administration of medicament to a subject; and
a hardware processor in communication with the memory and configured to execute the specific computer-executable instructions to at least:
determine the glucose control therapy data comprising at least one of an amount of insulin on board, a time of a delivery of glucose control therapy, or an amount of delivery of glucose control therapy;
generate one or more of the plurality of glucose control parameters, wherein the plurality of glucose control parameters comprises:

an insulin decay rate constant associated with a decay rate of insulin at a subcutaneous depot of a subject;
a clearance time associated with an estimate of an amount of time for a bolus of insulin to be utilized by the subject;
an insulin rise rate constant associated with a rise rate of insulin in blood of the subject after a bolus of insulin;
a half-life value associated with when a concentration of insulin in blood plasma of the subject reaches half of a maximum concentration in the blood plasma;
a weight of the subject;
an age of the subject;
a learned parameter;
glucose level data;
a model parameter associated with a pharmacokinetic (PK) model;
a health state of the subject;
a parameter associated with an activity level of the subject;
an aspect of a diet of the subject;
a basal rate of insulin delivery to the subject;
a correction factor;
a carbohydrate ratio associated with the subject;
a glucagon control parameter;
demographic information associated with the subject; and
a sensitivity constant associated with the sensitivity of the subject to a glucose level or bolus of medicament;
determine that at least one of a plurality of pairing conditions is satisfied to couple the glucose level control system to the second glucose level control system, wherein the plurality of pairing conditions comprises:
an occurrence of a scheduled time;
a transmission of a meal announcement;
a user request to pair the glucose level control system to a remote electronic device;
a user input initiating a replacement process for the glucose level control system;
an indication that the glucose level control system is to be replaced;
an indication that the second glucose level control system is ready to deliver medicament to the subject;
a sensory alarm configured to alert a user that historical pump data is ready for transmission;
an alert indicating a malfunction associated with the glucose level control system;
a determination that a level of medicament in a medicament reservoir is below a threshold level;
a determination that an amount of available medicament is insufficient for a medicament requirement of the subject; and
a signal received from the remote electronic device requesting transmission of at least one of the glucose control therapy data or the one or more of the plurality of glucose control parameters; and
in response to determining that the at least one of the plurality of pairing conditions is satisfied, wirelessly transmit, via the wireless data interface, the one or more of the plurality of glucose control parameters and the glucose control therapy data to the second glucose level control system.

28. The glucose level control system of claim 27, wherein the hardware processor is further configured to execute the specific computer-executable instructions to at least:
transmit, via the wireless data interface, a pairing request signal to the second glucose level control system; and
receive, via the wireless data interface, a pairing confirmation signal from the second glucose level control system.

29. The glucose level control system of claim 27, wherein the hardware processor is further configured to execute the specific computer-executable instructions to at least:
transmit to a user control element, via the wireless data interface, an indication that the second glucose level control system is ready to be paired with the glucose level control system.

30. The glucose level control system of claim 27, wherein the hardware processor is further configured to execute the specific computer-executable instructions to at least:
transmit to the remote electronic device, one or more of the glucose control therapy data or the one or more of the plurality of glucose control parameters.

* * * * *